US012485162B2

(12) United States Patent
Chan et al.

(10) Patent No.: US 12,485,162 B2
(45) Date of Patent: *Dec. 2, 2025

(54) DETERMINANTS OF CANCER RESPONSE TO IMMUNOTHERAPY BY PD-1 BLOCKADE

(71) Applicant: Memorial Sloan Kettering Cancer Center, New York, NY (US)

(72) Inventors: Timothy A. Chan, Cortlandt Manor, NY (US); Naiyer A. Rizvi, New York, NY (US); Matthew D. Hellmann, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 309 days.

This patent is subject to a terminal disclaimer.

(21) Appl. No.: 17/202,173

(22) Filed: Mar. 15, 2021

(65) Prior Publication Data

US 2021/0308241 A1 Oct. 7, 2021

Related U.S. Application Data

(63) Continuation of application No. 16/283,555, filed on Feb. 22, 2019, now Pat. No. 10,993,998, which is a continuation of application No. 15/528,385, filed as application No. PCT/US2015/062208 on Nov. 23, 2015, now abandoned.

(60) Provisional application No. 62/132,381, filed on Mar. 12, 2015, provisional application No. 62/083,088, filed on Nov. 21, 2014.

(51) Int. Cl.

| | |
|---|---|
| ***A61K 39/00*** | (2006.01) |
| ***A61P 35/00*** | (2006.01) |
| ***A61P 35/02*** | (2006.01) |
| ***A61P 35/04*** | (2006.01) |
| ***C07K 14/47*** | (2006.01) |
| ***C07K 16/28*** | (2006.01) |
| ***C12Q 1/68*** | (2018.01) |
| ***C12Q 1/6886*** | (2018.01) |

(52) U.S. Cl.

CPC .......... *A61K 39/0011* (2013.01); *A61P 35/00* (2018.01); *A61P 35/02* (2018.01); *A61P 35/04* (2018.01); *C07K 14/4748* (2013.01); *C07K 16/2818* (2013.01); *C12Q 1/68* (2013.01); *C12Q 1/6886* (2013.01); *A61K 2039/505* (2013.01); *A61K 2039/55* (2013.01); *C07K 2317/21* (2013.01); *C07K 2317/24* (2013.01); *C07K 2317/76* (2013.01); *C12Q 2600/106* (2013.01); *C12Q 2600/156* (2013.01)

(58) Field of Classification Search

None

See application file for complete search history.

(56) References Cited

U.S. PATENT DOCUMENTS

| | | | | |
|---|---|---|---|---|
| 10,993,998 | B2 * | 5/2021 | Chan | C07K 14/4748 |
| 11,230,599 | B2 * | 1/2022 | Chan | C12Q 1/6886 |
| 2004/0033497 | A1 | 2/2004 | Alarcon-Riquelme et al. | |
| 2010/0233202 | A1 | 9/2010 | Yoshida et al. | |
| 2011/0293637 | A1 | 12/2011 | Hacohen et al. | |
| 2013/0225433 | A1 * | 8/2013 | Chinnaiyan | C12Q 1/6886 435/7.1 |
| 2013/0295110 | A1 | 11/2013 | Binder et al. | |
| 2016/0326597 | A1 | 11/2016 | Chan et al. | |
| 2017/0313775 | A1 * | 11/2017 | Diaz | C07K 16/2818 |
| 2018/0291074 | A1 | 10/2018 | Chan et al. | |
| 2020/0040049 | A1 | 2/2020 | Chan et al. | |

FOREIGN PATENT DOCUMENTS

| | | | |
|---|---|---|---|
| CN | 102905721 | A | 1/2013 |
| WO | WO-2011/113819 | A2 | 9/2011 |
| WO | WO-2014/052707 | A2 | 4/2014 |
| WO | WO-2015/103037 | A2 | 7/2015 |
| WO | WO-2016/077553 | A1 | 5/2016 |
| WO | WO-2016/081947 | A2 | 5/2016 |

OTHER PUBLICATIONS

Abaan, O. et al., The exomes of the NCI-60 panel: a genomic resource for cancer biology and systems pharmacology, Cancer Research, 73(14):4372-4382 (2013).
Adzhubei, I. et al., A method and server for predicting damaging missense mutations, Nature Methods, 7(4):248-249 (2010).
Alexandrov, L. et al., Signatures of mutational processes in human cancer, Nature, 500:415-421 (2013).
Andersen, R. et al., Parallel detection of antigen-specific T cell responses by combinatorial encoding of MHC multimers, Nature Protocols, 7(5):891-902 (2012).
Ansell, S. et al., PD-1 blockade with nivolumab in relapsed or refractory Hodgkin's lymphoma, N Engl J Med., 372(4):311-319 (2015).
Bei, R. and Scardino, A., TAA polyepitope DNA-based vaccines: a potential tool for cancer therapy, J. Biomed. Biotechnol., 2010:102758 (2010).
Berzofsky, J.A. et al., Progress on new vaccine strategies for the immunotherapy and prevention of cancer, J. Clin. Invest., 113(11):1515-25 (2004).
Brown, S.D., et. al., Neo-antigens predicted by tumor genome meta-analysis correlate with increased patient survival, Genome Research, 24:743-750 (2014).
Callahan, M. K. et al, At the Bedside: CTLA-4- and PD-1-blocking antibodies in cancer immunotherapy, Journal of Leukocyte Biology, 94: 41-53 (2013).

(Continued)

*Primary Examiner* — Peter J Reddig

(74) *Attorney, Agent, or Firm* — ArentFox Schiff LLP; Daniel W. Clarke; Shawn P. Foley, Esq.

(57) ABSTRACT

Molecular determinants of cancer response to immunotherapy are described, as are systems and tools for identifying and/or characterizing cancers likely to respond to immunotherapy.

8 Claims, 306 Drawing Sheets

Specification includes a Sequence Listing.

(56) References Cited

OTHER PUBLICATIONS

Castle, J. et al., Exploiting the mutanome for tumor vaccination, Cancer Research, 72(5):1081-1091 (2012).
Champiat, S. et al, Exomics and immunogenics: Bridging mutational load and immune checkpoints efficacy, Oncoiummonology, 3(1): e27817 (2014).
Charen, A. et al., The neoantigen landscape underlying clinical response to ipilimumab, J Clin Oncol, 31(15): Abstract 3003 (2014).
Cibulskis, K. et al., Sensitive detection of somatic point mutations in impure and heterogeneous cancer samples, Nat. Biotechnol., 31(3):213-219 (2013).
Coley, W., The treatment of malignant tumors by repeated inoculations of erysipelas. With a report of ten original cases, Clinical Orthopaedics and Related Research, 262: 3-11 (1991).
De Baets, G. et al., SNPeffect 4.0: on-line prediction of molecular and structural effects of protein-coding variants, Nucleic Acids Res, 40:D935-939 (2012).
Depristo, M. et al., A framework for variation discovery and genotyping using next-generation DNA sequencing data, Nature Genetics, 43(5):491-498 (2011).
Dogan, S. et al., Molecular epidemiology of EGFR and KRAS mutations in 3,026 lung adenocarcinomas: higher susceptibility of women to smoking-related KRAS-mutant cancers, Clinical Cancer Research, 18(22):6169-6177 (2012).
Duan, F. et al., Genomic and bioinformatic profiling of mutational neoepitopes reveals new rules to predict anticancer immunogenicity, J Exp Med., 211(11):2231-2248 (2014).
Garon, E. et al., Antitumor activity of pembrolizumab (pembro; mk-3475) and correlation with programmed death ligand 1 (pd-l1) expression in a pooled analysis of patients (pts) with advanced non-small cell lung carcinoma (NSCLC)., Annals of Oncology, 25(Supp. 25): V1-V41, Abstract LBA43 (2014).
Goodwin, J. & Knudsen, K., Beyond DNA Repair: DNA-PK Function in Cancer, Cancer Discovery, 4:1126-1139 (2014).
Govindan, R. et al., Genomic Landscape of Non-Small Cell Lung Cancer in Smokers and Never-Smokers, Cell, 150:1121-1134 (2012).
Gubin, M. et al., Checkpoint blockade cancer immunotherapy targets tumour-specific mutant antigens, Nature, 515:577-581 (2014).
Hamid, O. et al., Safety and Tumor Responses with Lambrolizumab (Anti-PD-1) in Melanoma, New England Journal of Medicine, 369(2): 134-144 (2013).
Hammerman, P. et al., Comprehensive genomic characterization of squamous cell lung cancers, Nature, 489:519-525 (2012).
Herbst, R. et al., Predictive correlates of response to the anti-PD-L1 antibody MPDL3280A in cancer patients, Nature, 515(7528):563-567 (2014).
Hindges, R. et al., DNA polymerase delta, an essential enzyme for DNA transactions, Biological Chemistry, 378:345-362 (1997).
Ho, A. et al., The mutational landscape of adenoid cystic carcinoma, Nature Genetics, 45(7):791-798 (2013).
Hodi, F. et al., Improved survival with ipilimumab in patients with metastatic melanoma, The New England Journal of Medicine, 363(8):711-723 (2010).
Hoffman, D. et al., The less harmful cigarette: a controversial issue. a tribute to Ernst L. Wynder, Chemical Research in Toxicology, 14(7):767-790 (2001).
Imielinski, M. et al., Mapping the hallmarks of lung adenocarcinoma with massively parallel sequencing, Cell, 150(6):1107-1120 (2012).
International Search Report for PCT/US2015/062208, 4 pages (Jun. 2, 2016).
Koboldt, D. et al., VarScan 2: somatic mutation and copy number alteration discovery in cancer by exome sequencing, Genome Res., 22:568-576 (2012).
Kreiter, S. et al, Mutant MHC class II epitopes drive therapeutic immune response to cancer, Nature, 520(7549): 692-696 and Erratum (2015).
Kumar, P. et al., Predicting the effects of coding non-synonymous variants on protein function using the SIFT algorithm, Nat. Protoc., 4(8):1073-1081 (2009).
Larson, D. et al., SomaticSniper: identification of somatic point mutations in whole genome sequencing data, Bioinformatics, 28(3):311-317 (2012).
Lawrence, M. et al., Mutational heterogeneity in cancer and the search for new cancer-associated genes, Nature, 499:214-218 (2013).
Li, H. & Durbin, R., Fast and accurate short read alignment with Burrows-Wheeler transform, Bioinformatics, 25(14):1754-1760 (2009).
Linnemann, C. et al., High-throughput epitope discovery reveals frequent recognition of neo-antigens by CD4+ T cells in human melanoma, Nat Med., 21(1):81-85 (2015).
Liu, C. et al., ATHLATES: accurate typing of human leukocyte antigen through exome sequencing, Nucleic Acids Research, 41(14):e142 (2013).
Liu, X. et al., dbNSFP v2.0: a database of human non-synonymous SNVs and their functional predictions and annotations, Human Mutation, 34(9):E2393-2402 (2013).
Lundegaard, C. et al., Accurate approximation method for prediction of class I MHC affinities for peptides of length 8, 10 and 11 using prediction tools trained on 9mers, Bioinformatics, 24(11):1397-1398 (2008).
Lundegaard, C. et al., NetMHC-3.0: accurate web accessible predictions of human, mouse and monkey MHC class I affinities for peptides of length 8-11, Nucleic Acids Research, 36:W509-512 (2008).
Matsushita, H. et al., Cancer exome analysis reveals a T-cell-dependent mechanism of cancer immunoediting, Nature, 482(7385):400-404 (2012).
Matsutake, T. & Srivastava, P., The immunoprotective MHC II epitope of a chemically induced tumor harbors a unique mutation in a ribosomal protein, Proceedings of the National Academy of Sciences of the United States of America, 98(7):3992-3997 (2001).
Nielsen, M. et al., Improved prediction of MHC class I and class II epitopes using a novel Gibbs sampling approach, Bioinformatics, 20(9):1388-1397 (2004).
Nielsen, M. et al., Reliable prediction of T-cell epitopes using neural networks with novel sequence representations, Protein Science, 12:1007-1017 (2003).
Nielsen, M. et al., The role of the proteasome in generating cytotoxic T-cell epitopes: insights obtained from improved predictions of proteasomal cleavage, Immunogenetics, 57:33-41 (2005).
Palles, C. et al., Germline mutations affecting the proofreading domains of POLE and POLD1 predispose to colorectal adenomas and carcinomas, Nature Genetics, 45(2):136-144 (2013).
Pfeifer, G. et al., Mutations induced by ultraviolet light, Mutation Research, 571:19-31 (2005).
Pfeifer, G. et al., Tobacco smoke carcinogens, DNA damage and p53 mutations in smoking-associated cancers, Oncogene, 21:7435-7451 (2002).
Philippidis, A., Merck Melanoma Drug is First PD-1 Inhibitor OK'd by FDA, Genetic Engineering & Biotechnology News, 3 pages (2014).
Powles, T. et al., MPDL3280A (anti-PD-L1) treatment leads to clinical activity in metastatic bladder cancer, Nature, 515:558-562 (2014).
Raedler, L. A., Keytruda (Pembrolizumab): First PD-1 Inhibitor Approved for Previously Treated Unresectable or Metastatic Melanoma, AMerican Health & Drug Benefits, 8(Special Feature): 96-100 (2015).
Rajasagi, M. et al., Systematic identification of personal tumor-specific neoantigens in chronic lymphocytic leukemia, Blood, 124(3):453-462 (2014).
Rizvi, N. A. et al, Supplementary Materials for Mutational lanscape determines sensitivity to PD-1 blockade in non-small cell lung cancer, Science, 1-31 (2015).
Rizvi, N.A., et al., Mutational landscape determines sensitivity to PD-1 blockade in non-small cell lung cancer, Science, 348(6230):124-128 (2015).
Robbins, P. et al., Mining exomic sequencing data to identify mutated antigens recognized by adoptively transferred tumor-reactive T cells, Nature Medicine, 19:747-752 (2013).

(56) References Cited

OTHER PUBLICATIONS

Robert, C. et al., Anti-programmed-death-receptor-1 treatment with pembrolizumab in ipilimumab-refractory advanced melanoma: a randomised dose-comparison cohort of a phase 1 trial, Lancet, 384:1109-1117 (2014).
Robinson, J. et al., Integrative genomics viewer, Nature Biotechnology, 29(1):24-26 (2011).
Rodenko, B. et al., Generation of peptide-MHC class I complexes through UV-mediated ligand exchange, Nature Protocols, 1(3):1120-1132 (2006).
Rooney, M. et al., Molecular and genetic properties of tumors associated with local immune cytolytic activity, Cell, 160(1-2):48-61 (2015).
Saunders, C. et al., Strelka: accurate somatic small-variant calling from sequenced tumor-normal sample pairs, Bioinformatics, 28(14):1811-1817 (2012).
Schreiber, R. et al., Cancer immunoediting: integrating immunity's roles in cancer suppression and promotion, Science, 331:1565-1570 (2011).
Schumacher, T. et al., A vaccine targeting mutant IDH1 induces antitumour immunity, Nature 512:324-327 (2014).
Sherry, S. et al., dbSNP-database for single nucleotide polymorphisms and other classes of minor genetic variation, Genome Research, 9:677-679 (1999).
Snyder, A. et al, Genetic Basis for Clinical Response to CTLA-4 Blockade in Melanoma, New England Journal of Medicine, 371(23): 2189-2199 (2014).
Taube, J. et al., Association of PD-1, PD-1 Ligands, and Other Features of the Tumor Immune Microenvironment with Response to Anti-PD-1 Therapy, Clinical Cancer Research, 20(19):5064-5074 (2014).
The Cancer Genome Atlas Research Network, Comprehensive molecular profiling of lung adenocarcinoma, Nature, 511(7511): 543-550 (2014).
Toebes, M. et al., Design and use of conditional MHC class I ligands, Nature Medicine, 12(2):246-251 (2006).
Topalian, S. et al., Safety, Activity, and Immune Correlates of Anti-PD-1 Antibody in Cancer, The New England Journal of Medicine, 366(26):2443-2454 (2012).
Tran, E. et al., Cancer immunotherapy based on mutation-specific CD4+ T cells in a patient with epithelial cancer, Science, 344:641-645 (2014).
Tumeh, P. et al., PD-1 blockade induces responses by inhibiting adaptive immune resistance, Nature, 515(7528):568-571 (2014).
Van Rooij, N. et al., Tumor exome analysis reveals neoantigen-specific T-cell reactivity in an ipilimumab-responsive melanoma, J Clin Oncol, 31(32):439-442 (2013).
Vareki, S. M., High and low mutational burden tumors versus immunologically hot and cold tumors and response to immune checkpoint inhibitors, Journal for ImmunoTherapy of Cancer, 6(1): 1-5 (2018).
Via, M., The 1000 Genomes Project: new opportunities for research and social challenges, Genome Medicine, 2:3 (2010).
Vogelstein, B. et al., Cancer genome landscapes, Science, 339(6127):1546-1558 (2013).
Wang, X. et al., Genomic instability and endoreduplication triggered by RAD17 deletion, Genes & Development, 17:965-970 (2003).
Wolchok, J. et al., Guidelines for the evaluation of immune therapy activity in solid tumors: immune-related response criteria, Clinical Cancer Research, 15(23):7412-7420 (2009).
Wolchok, J. et al., Nivolumab plus ipilimumab in advanced melanoma, The New England Journal of Medicine, 369(2):122-133 (2013).
Written Opinion for PCT/US2015/062208, 6 pages (Jun. 2, 2016).
Yadav, M. et al., Predicting immunogenic tumour mutations by combining mass spectrometry and exome sequencing, Nature, 515:572-576 (2014).
Yuan, J. et al., CTLA-4 blockade enhances polyfunctional NY-ESO-1 specific T cell responses in metastatic melanoma patients with clinical benefit, Proceedings of the National Academy of Sciences of the United States of America, 105(51):20410-20415 (2008).

* cited by examiner

| StudyID | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 |
|---|---|---|---|---|---|---|---|---|---|---|---|---|---|---|---|---|---|---|---|---|---|---|---|---|---|---|---|---|---|---|---|---|---|---|
| Cohort | V | D | D | V | V | D | V | V | D | D | V | D | D | V | V | V | D | D | V | V | D | D | D | V | V | V | D | V | V | V | D | V | D | D |
| Objective Response | PR | PR | POD | SD | PR | PR | POD | SD | PR | PR | PR | SD | POD | PR | SD | POD | POD | PR | PR | PR | SD | SD | POD | POD | POD | POD | POD | SD | SD | PR | SD | POD | POD | SD |
| PFS (months) | 8.4 | 14.7 | 2.1 | 8.3 | 14.6 | 16.6 | 1.9 | 4.0 | 14.5 | 12.6 | 4.2 | 8.1 | 1.8 | 4.4 | 8.4 | 3.3 | 3.4 | 9.8 | 27.3 | 10.4 | 8.3 | 6.5 | 1.9 | 1.9 | 1.4 | 1.9 | 2.1 | 3.5 | 6.3 | 8.3 | 4.1 | 1.9 | 1.8 | 6.3 |
| Ongoing response | ++ | ++ | | | ++ | ++ | | ++ | | ++ | ++ | | | ++ | ++ | | | ++ | ++ | ++ | | | | | | | | | | | | | | |
| Smoking signature | TH | TH | TH | TL | TH | TH | TL | TH | TH | TH | TH | TH | TH | TH | TH | TL | TL | TH | TL | TL | TH | TL | TH | TL | TL | TL | TL | TL | TL | TL | TL | TL | TL | TL |

Figure 5: Coverage and depth of target exome sequence. Coverage and depth of sequenced exomes is similar in discovery compared to validation cohorts and is similar in those with durable clinical benefit (DCB) compared to those with no durable benefit (NDB).

Figure 6. Exome analysis pipeline.

| | Pembrolizumab Cohort | TCGA Lung Adenocarcinoma [16] | TCGA Lung Squamous Cell Carcinoma [17] |
|---|---|---|---|
| Number of values | 34 | 236 | 178 |
| Minimum | 11 | 11 | 0 |
| 25% Percentile | 118.8 | 93.5 | 163.5 |
| Median | 199.5 | 188 | 222.5 |
| 75% Percentile | 335 | 387.8 | 298.5 |
| Maximum | 1192 | 2402 | 2508 |

Figure 7A: Median and interquartile range of mutations in the current study and in published series of NSCLC (13, 14). (A) Somatic nonsynonymous mutation burden.

| | Pembrolizumab Cohort | TCGA Lung Adenocarcinoma | TCGA Lung Squamous Cell Carcinoma |
|---|---|---|---|
| Number of values | 34 | 236 | 178 |
| Minimum | 94 | 22 | 3 |
| 25% Percentile | 235.3 | 131 | 219.5 |
| Median | 420 | 264.5 | 296 |
| 75% Percentile | 602.3 | 546 | 409.8 |
| Maximum | 2219 | 3306 | 3889 |

Figure 7B: Median and interquartile range of mutations in the current study and in published series of NSCLC (13, 14). (B) Total exonic mutations.

Figure 8: Pattern of nucleotide changes in tumors sequenced. The spectrum and frequency of nucleotide changes in the pembrolizumab-treated NSCLCs is typical of non-small cell lung cancers.

Figure 9: Distribution of nucleotide alterations in nonsynonymous mutations. Across the overall set of sequenced NSCLCs treated with pembrolizumab, C>A transversions are more frequent in those with DCB, while C>T transitions are more frequent in those with NDB (* denotes p=0.01).

Figure 10. Neoantigen analysis pipeline. ^\All steps are executed for predicted wild type and mutant. *MHC Class I prediction by NetMHCv3.4

Figure 11: HLA type and benefit to pembrolizumab. There was no evident association between the presence of any specific HLA allele and benefit from pembrolizumab.

Figure 12: Neoantigens and best objective response. The absolute quantity of predicted neoantigens correlates with best overall response (Spearman p -0.43, 95% CI -0.68- -0.10, p=0.01), but the frequency of neoantigens/nonsynonymous mutation does not (Spearman p -0.04, 95% CI -0.39-0.30, p=0.78).

Figure 13A:Following expansion, stimulation of peripheral blood mononuclear cells with wild type or mutant peptide versus no stimulation control shows a polyfunctional CD8+ T cell response to the mutant peptide only. (A) Neoantigen-induced IFNγ production by CD3+CD8+ T-cells at day 63 and day 297 after initiation of therapy.

Figure 13B: Following expansion, stimulation of peripheral blood mononuclear cells with wild type or mutant peptide versus no stimulation control shows a polyfunctional CD8+ T cell response to the mutant peptide only. (B) Co-staining of CD107a in CD3+CD8+IFNγ+ cells when stimulated with mutant peptide versus no stimulation or wild type.

Figure 13C:Following expansion, stimulation of peripheral blood mononuclear cells with wild type or mutant peptide versus no stimulation control shows a polyfunctional CD8+ T cell response to the mutant peptide only. (C) Co-staining of MIP-1 β in CD3+CD8+IFNγ+ cells when stimulated with mutant peptide versus no stimulation or wild type.

Figure 13D: Following expansion, stimulation of peripheral blood mononuclear cells with wild type or mutant peptide versus no stimulation control shows a polyfunctional CD8+ T cell response to the mutant peptide only. (D) Co-staining of TNF-α in CD3+CD8+IFNγ+ cells when stimulated with mutant peptide versus no stimulation or wild type.

| | All patients | Discovery Cohort | Validation Cohort |
|---|---|---|---|
| *n* | 34 | 16 | 18 |
| Age (median, range) | 63 years (41-80) | 62 (56-73) | 63 (41-80) |
| Gender (n,%) | | | |
| Male | 16 (47) | 8 (50) | 8 (44) |
| Female | 18 (53) | 8 (50) | 10 (56) |
| Smoking status (n,%) | | | |
| Current | 7 (21) | 5 (31) | 2 (11) |
| Former | 21 (62) | 10 (63) | 11 (61) |
| Never | 6 (17) | 1 (6) | 5 (28) |
| Histology (n,%) | | | |
| Adenocarcinoma | 29 (85) | 15 (94) | 14 (78) |
| Squamous | 4 (12) | 1 (6) | 3 (17) |
| NSCLCNOS | 1 (3) | 0 (0) | 1 (6) |
| Driver oncogenes (n,%) | | | |
| KRAS mutant | 8 (24) | 5 (31) | 3 (17) |
| EGFR mutant | 2 (6) | 1 (6) | 1 (6) |
| ALK re-arranged | 1 (3) | 0 (0) | 1 (6) |
| MK3475 as *n* line of therapy (n,%) | | | |
| 1st | 9 (26) | 5 (31) | 4 (22) |
| 2nd | 11 (33) | 6 (38) | 5 (28) |
| 3rd | 5 (15) | 1 (6) | 4 (22) |
| 4th and beyond | 9 (26) | 4 (25) | 5 (28) |

Figure 15

| | | | |
|---|---|---|---|
| PDL1 expression (n,%) | | | |
| ≥1% | 31 (91) | 15 (94) | 16 (88) |
| <1% | 2 (6) | 1 (6) | 1 (6) |
| unknown | 1 (3) | 0 (0) | 1 (6) |
| Dose of pembrolizumab (n,%) | | | |
| 2mg/kg | 5 (15) | 0 (0) | 5 (28) |
| 10mg/kg | 29 (85) | 16 (100) | 13 (72) |
| Confirmed objective response by irRC | | | |
| Partial response | 12 (35) | 5 (31) | 7 (39) |
| Stable disease | 9 (26) | 5 (31) | 5 (28) |
| Progressive disease | 13 (39) | 6 (38) | 6 (33) |
| Durable clinical benefit (PR/SD)>6 months | | | |
| Yes | 14 (41) | 7 (44) | 7 (39) |
| No | 17 (50) | 9 (56) | 8 (44) |
| Not yet reached 6 month follow up | 3 (9) | 0 | 3 (17) |
| Somatic non-synonymous mutation burden (median, range) | 200 (11-1192) | 207 (11-746) | 200 (35-1192) |
| Total somatic exonic mutation burden (median, range) | 327 (45-1732) | 309 (45-1011) | 322 (85-1732) |

Figure 15 (Cont.)

Figure 15: Summary of clinical genomic characteristics.

| Mutations quantified | Patient population | *n* | Median # mutations/ sample (range) | ORR (n,%) |
|---|---|---|---|---|
| Nonsynonymous mutations | Disc. Cohort: high burden | 8 | 313 (228-746) | 5 (63) |
| | Disc. Cohort: low burden | 8 | 127 (11-190) | 0 (0) |
| | Valid. Cohort: high burden | 9 | 368 (201-1192) | 5 (56) |
| | Valid. Cohort: low burden | 9 | 122 (35-198) | 2 (22) |
| | | | | |
| Nonsynonymous mutations | All patients: high burden | 17 | 324 (201-1192) | 10 (59) |
| | All patients: low burden | 17 | 122 (11-198) | 2 (12) |
| | | | | |
| Total exonic mutations | All patients: high burden | 17 | 494 (328-1732) | 8 |
| | All patients: low burden | 17 | 190 (45-326) | 4 |

Figure 16

| Fisher's Exact *P* | DCB (n of x patients evaluable at 6 months,%) | Fisher's Exact *P* | Median PFS (months) | Log-rank *P* | HR for PFS (95% CI) |
|---|---|---|---|---|---|
| 0.03 | 6 of 8 (75) | 0.04 | 14.5 | 0.01 | 0.19 (0.05-0.70) |
| | 1 of 8 (13) | | 3.7 | | |
| 0.33 | 5 of 6^ (83) | 0.04 | Not reached | 0.006 | 0.15 (0.04-0.59) |
| | 2 of 9 (22) | | 3.4 | | |
| | | | | | |
| 0.01 | 11 of 14^ (79) | 0.0011 | Not reached | 0.0004 | 0.19 (0.08-0.47) |
| | 3 of 17 (18) | | 3.4 | | |
| | | | | | |
| 0.28 | 9 of 14^ | 0.08 | 14.5 | 0.045 | 0.40 (0.17-0.98) |
| | 5 of 17 | | 4.1 | | |

Figure 16 (Cont.)

| # | Study ID | Cohort (Discovery, Validation) | Histology | Age (years) | Sex | Smok.^ | Pack-years | PD-L1* | Priors^ |
|---|---|---|---|---|---|---|---|---|---|
| 1 | SA9755 | Valid | NSCLCNOS | 63 | F | Former | 36 | P | 1 |
| 2 | HE3202 | Disc | Adeno | 63 | F | Former | 58 | P | 3 |
| 3 | TU0428 | Disc | Adeno | 66 | M | Current | 48 | P | 0 |
| 4 | Y2087 | Valid | Adeno | 68 | F | Never | 0 | P | 5 |
| 5 | M4945 | Valid | Adeno | 66 | M | Former | 40 | P | 3 |
| 6 | RI1933 | Disc | Adeno | 60 | F | Former | 21 | P | 1 |
| 7 | ZA6505 | Valid | Adeno | 76 | F | Never | 0 | P | 6 |
| 8 | CU9061 | Valid | Squam | 57 | M | Former | 39 | P | 1 |
| 9 | CA9903 | Disc | Adeno | 57 | M | Former | 80 | P | 3 |
| 10 | SC0899 | Disc | Adeno | 64 | F | Current | 25 | P | 0 |
| 11 | FR9547 | Valid | Adeno | 65 | F | Current | 25 | P | 1 |
| 12 | KA3947 | Disc | Adeno | 64 | F | Former | 52.5 | P | 0 |
| 13 | MA7027 | Disc | Adeno | 56 | M | Former | 37.5 | P | 1 |
| 14 | ZA6965 | Valid | Adeno | 57 | F | Former | 25 | P | 1 |
| 15 | AL4602 | Valid | Adeno | 59 | M | Former | 34 | P | 0 |
| 16 | JB112852 | Disc | Adeno | 60 | M | Never | 0 | N | 5 |
| 17 | SR070761 | Valid | Squam | 51 | F | Former | 2.5 | P | 4 |
| 18 | DI6359 | Disc | Adeno | 61 | F | Current | 60 | P | 6 |
| 19 | SB010944 | Valid | Squam | 68 | M | Never | 0 | U | 2 |
| 20 | RH090935 | Valid | Adeno | 78 | F | Former | 60 | P | 0 |
| 21 | SC6470 | Disc | Adeno | 59 | M | Current | 15 | P | 0 |
| 22 | BL3403 | Disc | Adeno | 73 | F | Former | 43.75 | P | 1 |
| 23 | GR4788 | Disc | Squam | 59 | M | Current | 45 | P | 0 |
| 24 | DM123062 | Valid | Adeno | 50 | M | Never | 0 | N | 6 |
| 25 | R7495 | Valid | Adeno | 63 | M | Former | 73.5 | P | 2 |
| 26 | WA7899 | Valid | Adeno | 49 | M | Never | 0 | P | 2 |
| 27 | RO3338 | Disc | Adeno | 71 | M | Former | 20 | P | 1 |
| 28 | LO3793 | Valid | Adeno | 62 | F | Former | 6 | P | 2 |
| 29 | LO5004 | Valid | Adeno | 56 | F | Former | 8 | P | 0 |
| 30 | GR0134 | Valid | Adeno | 80 | M | Former | 56 | P | 0 |
| 31 | VA1330 | Disc | Adeno | 71 | F | Former | 0.5 | P | 1 |
| 32 | NI9507 | Valid | Adeno | 41 | F | Current | 2.25 | P | 1 |
| 33 | AU5884 | Disc | Adeno | 64 | M | Former | 10 | P | 2 |
| 34 | VA7859 | Disc | Adeno | 57 | F | Former | 3.15 | P | 1 |

*PDL-1 expersion. P ,>/=1% membraneous staining, N, <1% membraneous staining, U, unknown.
**Pembrolizumab dosed every 2 or 3 weeks as indicated.

Figure 17

Figure 17: Detailed clinical and genomic characteristics of individual patients

| Dose (mg/kg) | Sched.* * | PFS (mos) | Event ^^^ | Resp ^^^^ | Durable Clinical Benefit | Nonsyn. | Smok Sig. ^^^^^ | Neoant. | Total exonic |
|---|---|---|---|---|---|---|---|---|---|
| 10 | 3 | 8.4 | 0 | PR | DCB | 1192 | TH | 576 | 1732 |
| 10 | 3 | 14.7 | 0 | PR | DCB | 746 | TH | 610 | 1011 |
| 10 | 3 | 2.1 | 1 | POD | NDB | 626 | TH | 446 | 992 |
| 10 | 3 | 8.3 | 1 | SD | DCB | 507 | TL | 358 | 914 |
| 10 | 2 | 14.6 | 0 | PR | DCB | 427 | TH | 300 | 685 |
| 10 | 3 | 16.6 | 0 | PR | DCB | 473 | TH | 228 | 622 |
| 10 | 3 | 1.9 | 1 | POD | NDB | 378 | TL | 209 | 558 |
| 2 | 3 | 4.0 | 0 | SD | NR | 368 | TH | 271 | 552 |
| 10 | 3 | 14.5 | 1 | PR | DCB | 324 | TH | 226 | 494 |
| 10 | 3 | 12.6 | 0 | PR | DCB | 296 | TH | 191 | 450 |
| 2 | 3 | 4.2 | 0 | PR | NR | 290 | TH | 208 | 441 |
| 10 | 3 | 8.1 | 1 | SD | DCB | 302 | TH | 114 | 426 |
| 10 | 2 | 1.8 | 1 | POD | NDB | 292 | TH | 90 | 396 |
| 2 | 3 | 4.4 | 0 | PR | NR | 223 | TH | 111 | 342 |
| 10 | 3 | 8.4 | 0 | SD | DCB | 244 | TH | 148 | 341 |
| 10 | 2 | 3.3 | 1 | POD | NDB | 190 | TL | 118 | 341 |
| 10 | 2 | 3.4 | 1 | POD | NDB | 184 | TL | 50 | 328 |
| 10 | 3 | 9.8 | 0 | PR | DCB | 228 | TH | 215 | 326 |
| 10 | 3 | 27.3 | 0 | PR | DCB | 198 | TL | 80 | 316 |
| 10 | 3 | 10.4 | 0 | PR | DCB | 201 | TL | 135 | 305 |
| 10 | 2 | 8.3 | 1 | SD | DCB | 185 | TH | 100 | 292 |
| 10 | 2 | 6.5 | 1 | SD | NDB | 148 | TL | 99 | 261 |
| 10 | 2 | 1.9 | 1 | POD | NDB | 170 | TH | 51 | 255 |
| 10 | 2 | 1.9 | 1 | POD | NDB | 134 | TL | 99 | 209 |
| 2 | 3 | 1.4 | 1 | POD | NDB | 122 | TL | 83 | 199 |
| 10 | 3 | 1.9 | 1 | POD | NDB | 127 | TL | 58 | 190 |
| 10 | 3 | 2.1 | 1 | POD | NDB | 106 | TL | 112 | 167 |
| 2 | 3 | 3.5 | 1 | SD | NDB | 109 | TL | 74 | 145 |
| 10 | 2 | 6.3 | 1 | SD | NDB | 79 | TL | 87 | 140 |
| 10 | 3 | 8.3 | 1 | PR | DCB | 56 | TL | 30 | 94 |
| 10 | 3 | 4.1 | 1 | SD | NDB | 22 | TL | 11 | 88 |
| 10 | 3 | 1.9 | 1 | POD | NDB | 35 | TL | 18 | 85 |
| 10 | 2 | 1.8 | 1 | POD | NDB | 34 | TL | 27 | 80 |
| 10 | 3 | 6.3 | 1 | SD | NDB | 11 | TL | 8 | 45 |

Figure 17 (Cont.)

Figure 18: Quality Metrics for All Samples

N denotes corresponding normal. T denotes tumor DNA.

| Sample | Target Regions | Bases in Target Region | Bases Sequenced (after quality filtering) | Bases Mapped to Genome | Bases Mapped to Targeted Region | Mean Target Coverage | Targeted bases with at least 10 reads (%) |
|---|---|---|---|---|---|---|---|
| AL4602_N | 189894 | 32950014 | 122241930 | 97695214 | 4164823498 | 127.910427 | 0.947177 |
| AL4602_T | 189894 | 32950014 | 174485170 | 120860811 | 5253119108 | 161.46365 | 0.929297 |
| AU5884_N | 189894 | 32950014 | 66835458 | 55734427 | 2304570612 | 70.843604 | 0.921004 |
| AU5884_T | 189894 | 32950014 | 118497954 | 94583875 | 4170777521 | 128.058385 | 0.944011 |
| BL3403_N | 189894 | 32950014 | 136844124 | 108868175 | 4629994777 | 142.309651 | 0.948924 |
| BL3403_T | 189894 | 32950014 | 193969718 | 129204954 | 5821496526 | 178.814652 | 0.948857 |
| CA9903_N | 189894 | 32950014 | 64979750 | 54918581 | 2330210601 | 71.664856 | 0.922207 |
| CA9903_T | 189894 | 32950014 | 168826212 | 86438802 | 3863459107 | 118.675283 | 0.935412 |
| CU9061_N | 189894 | 32950014 | 117298618 | 94106296 | 3899679871 | 119.727027 | 0.943262 |
| CU9061_T | 189894 | 32950014 | 201703716 | 150891200 | 6320749651 | 193.970315 | 0.948994 |
| DI6359_N | 189894 | 32950014 | 68049462 | 56550125 | 2407997050 | 74.122135 | 0.925119 |
| DI6359_T | 189894 | 32950014 | 168308292 | 111211926 | 5019682373 | 154.345326 | 0.93995 |
| DM123062_N | 189894 | 32950014 | 124307148 | 98892833 | 4144985321 | 127.271345 | 0.940088 |
| DM123062_T | 189894 | 32950014 | 204623226 | 144255724 | 6221869654 | 190.844881 | 0.957608 |
| FR9547_N | 189894 | 32950014 | 101950654 | 84261089 | 3503354252 | 107.733974 | 0.937841 |
| FR9547_T | 189894 | 32950014 | 289002628 | 183741554 | 8143266088 | 249.718474 | 0.961299 |
| GR0134_N | 189894 | 32950014 | 104653358 | 85484969 | 3605380860 | 110.734625 | 0.940999 |
| GR0134_T | 189894 | 32950014 | 171945148 | 119503807 | 5065491487 | 155.356158 | 0.958604 |
| GR4788_N | 189894 | 32950014 | 130304080 | 105883167 | 4296757787 | 131.869851 | 0.946906 |
| GR4788_T | 189894 | 32950014 | 132101358 | 99136708 | 4175677808 | 128.244339 | 0.937001 |

Figure 18

| | | | | | | | |
|---|---|---|---|---|---|---|---|
| HE3202_N | 189894 | 32950014 | 82775862 | 67786929 | 2899161034 | 89.139081 | 0.937354 |
| HE3202_T | 189894 | 32950014 | 210311958 | 146137890 | 6177199349 | 189.705252 | 0.953064 |
| JB112852_N | 189894 | 32950014 | 134678418 | 105188597 | 4282340768 | 131.38132 | 0.948069 |
| JB112852_T | 189894 | 32950014 | 230739280 | 144875778 | 6466021163 | 198.480088 | 0.948037 |
| KA3947_N | 189894 | 32950014 | 77056996 | 63313850 | 2663182054 | 81.930577 | 0.930997 |
| KA3947_T | 189894 | 32950014 | 155786088 | 120766066 | 5290255334 | 162.673575 | 0.945223 |
| LO3793_N | 189894 | 32950014 | 132239512 | 105621709 | 4373397268 | 134.371784 | 0.947441 |
| LO3793_T | 189894 | 32950014 | 232306320 | 156548630 | 6447683860 | 197.894255 | 0.953127 |
| LO5004_N | 189894 | 32950014 | 144552248 | 114238356 | 4967705952 | 152.779572 | 0.945465 |
| LO5004_T | 189894 | 32950014 | 165443838 | 118709865 | 5123970335 | 157.417225 | 0.948988 |
| M4945_N | 189894 | 32950014 | 173996666 | 120449383 | 4973895139 | 152.876338 | 0.944888 |
| M4945_T | 189894 | 32950014 | 142673104 | 98036127 | 4379381020 | 134.605136 | 0.937004 |
| MA7027_N | 189894 | 32950014 | 83057034 | 68260266 | 2709982859 | 83.373941 | 0.927823 |
| MA7027_T | 189894 | 32950014 | 150331376 | 97286744 | 4207985362 | 129.24121 | 0.942497 |
| NI9507_N | 189894 | 32950014 | 81283298 | 67141865 | 2773039135 | 85.307115 | 0.934554 |
| NI9507_T | 189894 | 32950014 | 87518556 | 72125675 | 3122392732 | 96.15003 | 0.921913 |
| R7495_2_N | 189894 | 32950014 | 61239422 | 47497172 | 2068983168 | 63.709224 | 0.905356 |
| R7495_2_T | 189894 | 32950014 | 232334688 | 166758347 | 7041823600 | 216.094387 | 0.954393 |
| RH090935_N | 189894 | 32950014 | 142939372 | 110822654 | 4593839588 | 141.086216 | 0.947859 |
| RH090935_T | 189894 | 32950014 | 231189894 | 158799965 | 6670585461 | 204.845435 | 0.945123 |
| RI1933_N | 189894 | 32950014 | 61514952 | 51634672 | 2214858840 | 68.188206 | 0.921412 |
| RI1933_T | 189894 | 32950014 | 181659848 | 126801454 | 5374555898 | 164.985052 | 0.952561 |
| RO3338_N | 189894 | 32950014 | 114933782 | 92345228 | 3941073553 | 121.010249 | 0.945127 |
| RO3338_T | 189894 | 32950014 | 136807956 | 96927640 | 4122322714 | 126.57824 | 0.942479 |

Figure 18 (Cont.)

| | | | | | | | |
|---|---|---|---|---|---|---|---|
| HE3202_N | 189894 | 32950014 | 82775862 | 67786929 | 2899161034 | 89.139081 | 0.937354 |
| HE3202_T | 189894 | 32950014 | 210311958 | 146137890 | 6177199349 | 189.705252 | 0.953064 |
| JB112852_N | 189894 | 32950014 | 134678418 | 105188597 | 4282340768 | 131.38132 | 0.948069 |
| JB112852_T | 189894 | 32950014 | 230739280 | 144875778 | 6466021163 | 198.480088 | 0.948037 |
| KA3947_N | 189894 | 32950014 | 77056996 | 63313850 | 2663182054 | 81.930577 | 0.930997 |
| KA3947_T | 189894 | 32950014 | 155786088 | 120766066 | 5290255334 | 162.673575 | 0.945223 |
| LO3793_N | 189894 | 32950014 | 132239512 | 105621709 | 4373397268 | 134.371784 | 0.947441 |
| LO3793_T | 189894 | 32950014 | 232306320 | 156548630 | 6447683860 | 197.894255 | 0.953127 |
| LO5004_N | 189894 | 32950014 | 144552248 | 114238356 | 4967705952 | 152.779572 | 0.945465 |
| LO5004_T | 189894 | 32950014 | 165443838 | 118709865 | 5123970335 | 157.417225 | 0.948988 |
| M4945_N | 189894 | 32950014 | 173996666 | 120449383 | 4973895139 | 152.876338 | 0.944888 |
| M4945_T | 189894 | 32950014 | 142673104 | 98036127 | 4379381020 | 134.605136 | 0.937004 |
| MA7027_N | 189894 | 32950014 | 83057034 | 68260266 | 2709982859 | 83.373941 | 0.927823 |
| MA7027_T | 189894 | 32950014 | 150331376 | 97286744 | 4207985362 | 129.24121 | 0.942497 |
| NI9507_N | 189894 | 32950014 | 81283298 | 67141865 | 2773039135 | 85.307115 | 0.934554 |
| NI9507_T | 189894 | 32950014 | 87518556 | 72125675 | 3122392732 | 96.15003 | 0.921913 |
| R7495_2_N | 189894 | 32950014 | 61239422 | 47497172 | 2068983168 | 63.709224 | 0.905356 |
| R7495_2_T | 189894 | 32950014 | 232334688 | 166758347 | 7041823600 | 216.094387 | 0.954393 |
| RH090935_N | 189894 | 32950014 | 142939372 | 110822654 | 4593839588 | 141.086216 | 0.947859 |
| RH090935_T | 189894 | 32950014 | 231189894 | 158799965 | 6670585461 | 204.845435 | 0.945123 |
| RI1933_N | 189894 | 32950014 | 61514952 | 51634672 | 2214858840 | 68.188206 | 0.921412 |
| RI1933_T | 189894 | 32950014 | 181659848 | 126801454 | 5374555898 | 164.985052 | 0.952561 |
| RO3338_N | 189894 | 32950014 | 114933782 | 92345228 | 3941073553 | 121.010249 | 0.945127 |
| RO3338_T | 189894 | 32950014 | 136807956 | 96927640 | 4122322714 | 126.57824 | 0.942479 |

Figure 18 (Cont.)

| | | | | | | | |
|---|---|---|---|---|---|---|---|
| SA9755_N | 189894 | 32950014 | 212193658 | 155714066 | 6280943203 | 192.855379 | 0.955406 |
| SA9755_T | 189894 | 32950014 | 337403682 | 147938917 | 6738028155 | 206.866007 | 0.954466 |
| SB010944_N | 189894 | 32950014 | 130379650 | 101376126 | 4127460552 | 126.687776 | 0.943184 |
| SB010944_T | 189894 | 32950014 | 203661878 | 128276989 | 5703056939 | 175.015936 | 0.953241 |
| SC0899_N | 189894 | 32950014 | 88196986 | 70871472 | 3026465969 | 93.073728 | 0.939313 |
| SC0899_T | 189894 | 32950014 | 127991220 | 100522435 | 4377068882 | 134.579314 | 0.945167 |
| SC6470_N | 189894 | 32950014 | 55732342 | 47099900 | 1993400576 | 61.39547 | 0.911818 |
| SC6470_T | 189894 | 32950014 | 135739362 | 105861548 | 4692875686 | 144.26427 | 0.94648 |
| SR070761_N | 189894 | 32950014 | 158234930 | 124099331 | 5182991030 | 159.200373 | 0.949353 |
| SR070761_T | 189894 | 32950014 | 292050470 | 131933890 | 6207870162 | 190.519262 | 0.956545 |
| TU0428_N | 189894 | 32950014 | 127303050 | 101189405 | 4235332792 | 130.048835 | 0.947366 |
| TU0428_T | 189894 | 32950014 | 173450270 | 86584996 | 3689714094 | 113.278032 | 0.937217 |
| VA1330_N | 189894 | 32950014 | 65827552 | 55120033 | 2312376779 | 71.166279 | 0.922597 |
| VA1330_T | 189894 | 32950014 | 135610336 | 96504297 | 4088027942 | 125.711679 | 0.934442 |
| VA7859_N | 189894 | 32950014 | 63607140 | 53269713 | 2284415774 | 70.285595 | 0.924709 |
| VA7859_T | 189894 | 32950014 | 148703334 | 111998475 | 4935762628 | 151.640293 | 0.950753 |
| WA7899_N | 189894 | 32950014 | 160212294 | 123379606 | 4393264721 | 134.733791 | 0.948183 |
| WA7899_T | 189894 | 32950014 | 279269126 | 182085921 | 7605022449 | 233.266847 | 0.957596 |
| Y2087_N | 189894 | 32950014 | 122411904 | 90118304 | 3743922360 | 114.936891 | 0.940341 |
| Y2087_T | 189894 | 32950014 | 231934998 | 82257541 | 3928385204 | 120.578421 | 0.942763 |
| ZA6505_N | 189894 | 32950014 | 109178546 | 89123821 | 3725962819 | 114.531038 | 0.943478 |
| ZA6505_T | 189894 | 32950014 | 121363396 | 82900539 | 3440391275 | 105.85472 | 0.927032 |
| ZA6965_N | 189894 | 32950014 | 203920638 | 151245038 | 6220321627 | 190.965368 | 0.956287 |
| ZA6965_T | 189894 | 32950014 | 295234318 | 170201302 | 7363403623 | 226.270477 | 0.940573 |

Figure 18 (Cont.)

Figure 21: Immunogenic mutations, HLA Types, neoantigens, and predicted MHC binding

Chr=chromosome. Position=location of mutation.

Ref=reference nucleotide (hg37 build). Alt=mutation.

Allele=HLA Class I allele predicted to bind mutant peptide

Mut Score=predicted MHC Class I binding score by NetMHC. Only those with a score ≤500nM are included.

WT Score=predicted MHC Class I binding score by NetMHC of wild type peptide corresponding to mutant.

Mut peptide=nonamer within a 17-amino acid sequence with centrally positioned mutant amino acid predicted to bind to the patient's MHC Class I.

WT peptide=wild type nonamer corresponding to the Mut peptide above.

| Sample | Gene | Chr | Position | Ref | Alt | HLA I Type | Allele | Mut Score | WT Score | Mut peptide | WT peptide |
|---|---|---|---|---|---|---|---|---|---|---|---|
| AL4602 | VWA1 | 1 | 1374587 | C | A | A0301,A3201,B0801,B5101,C0702,C1502 | B0801 | 430 | 4159 | Qgaarrqql | Pgaarrqql |
| AL4602 | CASZ1 | 1 | 10699817 | C | T | A0301,A3201,B0801,B5101,C0702,C1502 | A0301 | 103 | 195 | Mlddfkrfk | Vlddfkrfk |
| AL4602 | ATP13A2 | 1 | 17318822 | C | A | A0301,A3201,B0801,B5101,C0702,C1502 | A3201 | 98 | 368 | alqrmsvvL | alqrmsvvV |
| AL4602 | ATP13A2 | 1 | 17318822 | C | A | A0301,A3201,B0801,B5101,C0702,C1502 | C0702 | 490 | 411 | qrmsvvLaw | qrmsvvVaw |
| AL4602 | SH2D5 | 1 | 21049266 | C | T | A0301,A3201,B0801,B5101,C0702,C1502 | A0301 | 424 | 626 | qvfmhlSr | qvfmhlGr |
| AL4602 | SH2D5 | 1 | 21049266 | C | T | A0301,A3201,B0801,B5101,C0702,C1502 | A0301 | 373 | 1185 | hlSrycleh | hlGrycleh |
| AL4602 | SH2D5 | 1 | 21049266 | C | T | A0301,A3201,B0801,B5101,C0702,C1502 | C0702 | 355 | 448 | vfmhlSry | vfmhlGry |
| AL4602 | HSPG2 | 1 | 22198776 | G | A | A0301,A3201,B0801,B5101,C0702,C1502 | C1502 | 385 | 21971 | ltgeftveL | ltgeftveP |
| AL4602 | ZNF683 | 1 | 26694272 | C | T | A0301,A3201,B0801,B5101,C0702,C1502 | C1502 | 471 | 571 | qvfsacKpl | qvfsacRpl |
| AL4602 | ARID1A | 1 | 27023633 | G | A | A0301,A3201,B0801,B5101,C0702,C1502 | A0301 | 372 | 581 | gaaaaTgsk | gaaaaAgsk |

Figure 21

| | | | | | | | | | | | |
|---|---|---|---|---|---|---|---|---|---|---|---|
| AL4602 | PPAP2B | 1 | 56990069 | C | A | A0301,A3201,B0801,B5101,C0702,C1502 | B0801 | 165 | 305 | iVrlrphfl | iGrlrphfl |
| AL4602 | HRNR | 1 | 152192039 | C | A | A0301,A3201,B0801,B5101,C0702,C1502 | C1502 | 210 | 73 | ssnVphgsv | ssnGphgsv |
| AL4602 | NPR1 | 1 | 153652095 | G | A | A0301,A3201,B0801,B5101,C0702,C1502 | A3201 | 68 | 118 | klgdfvaTl | klgdfvaAl |
| AL4602 | NPR1 | 1 | 153652095 | G | A | A0301,A3201,B0801,B5101,C0702,C1502 | A3201 | 218 | 6745 | aTlhrrlgw | aAlhrrlgw |
| AL4602 | CD1A | 1 | 158227298 | G | T | A0301,A3201,B0801,B5101,C0702,C1502 | A3201 | 284 | 547 | alwfrkLcf | alwfrkRcf |
| AL4602 | OR6P1 | 1 | 158532614 | G | A | A0301,A3201,B0801,B5101,C0702,C1502 | A0301 | 127 | 139 | tlftyaWpr | tlftyaRpr |
| AL4602 | OR6P1 | 1 | 158532614 | G | A | A0301,A3201,B0801,B5101,C0702,C1502 | A3201 | 28 | 11403 | sstlftyaW | sstlftyaR |
| AL4602 | OR6P1 | 1 | 158532614 | G | A | A0301,A3201,B0801,B5101,C0702,C1502 | C0702 | 151 | 239 | ftyaWpram | ftyaRpram |
| AL4602 | OR6P1 | 1 | 158532614 | G | A | A0301,A3201,B0801,B5101,C0702,C1502 | C1502 | 32 | 30 | ftyaWpram | ftyaRpram |
| AL4602 | OR6P1 | 1 | 158532614 | G | A | A0301,A3201,B0801,B5101,C0702,C1502 | C1502 | 59 | 141 | yaWpramyt | yaRpramyt |
| AL4602 | OR10J1 | 1 | 159410378 | C | G | A0301,A3201,B0801,B5101,C0702,C1502 | C1502 | 42 | 41 | nSrehdqli | nTrehdqli |
| AL4602 | MARC2 | 1 | 220922141 | G | T | A0301,A3201,B0801,B5101,C0702,C1502 | A0301 | 345 | 20238 | glrsgnlrY | glrsgnlrD |
| AL4602 | MARC2 | 1 | 220922141 | G | T | A0301,A3201,B0801,B5101,C0702,C1502 | A3201 | 23 | 916 | rsgnlrYrf | rsgnlrDrf |
| AL4602 | MARC2 | 1 | 220922141 | G | T | A0301,A3201,B0801,B5101,C0702,C1502 | B0801 | 10 | 24 | nlrYrfwlv | nlrDrfwlv |
| AL4602 | TRIM67 | 1 | 231349643 | G | T | A0301,A3201,B0801,B5101,C0702,C1502 | A3201 | 59 | 11745 | htltffinW | htltffinG |
| AL4602 | IRF2BP2 | 1 | 234744526 | C | A | A0301,A3201,B0801,B5101,C0702,C1502 | B0801 | 77 | 106 | gahkrpSsv | gahkrpAsv |
| AL4602 | IRF2BP2 | 1 | 234744526 | C | A | A0301,A3201,B0801,B5101,C0702,C1502 | C1502 | 486 | 666 | gahkrpSsv | gahkrpAsv |
| AL4602 | IRF2BP2 | 1 | 234744526 | C | A | A0301,A3201,B0801,B5101,C0702,C1502 | C1502 | 78 | 128 | Ssvsssaav | Asvsssaav |
| AL4602 | OR2M3 | 1 | 248367272 | C | A | A0301,A3201,B0801,B5101,C0702,C1502 | A0301 | 89 | 36 | raLmkilgk | raFmkilgk |
| AL4602 | OR2M3 | 1 | 248367272 | C | A | A0301,A3201,B0801,B5101,C0702,C1502 | C1502 | 327 | 241 | evtraLmki | evtraFmki |
| AL4602 | PSAP | 10 | 73579374 | C | T | A0301,A3201,B0801,B5101,C0702,C1502 | A0301 | 460 | 442 | ltvhMtqpk | ltvhVtqpk |
| AL4602 | TCERG1L | 10 | 132902598 | C | A | A0301,A3201,B0801,B5101,C0702,C1502 | A0301 | 40 | 130 | vsafstLek | vsafstWek |

Figure 21 (Cont.)

| | | | | | | | | | | | |
|---|---|---|---|---|---|---|---|---|---|---|---|
| AL4602 | TCERG1L | 10 | 132902598 | C | A | A0301,A3201,B0801,B5101,C0702,C1502 | A0301 | 212 | 189 | stLekelhk | stWekelhk |
| AL4602 | OR4C15 | 11 | 55322010 | G | T | A0301,A3201,B0801,B5101,C0702,C1502 | C1502 | 222 | 341 | nvHeivfvv | nvQeivfvv |
| AL4602 | OR8K1 | 11 | 56114447 | A | T | A0301,A3201,B0801,B5101,C0702,C1502 | A0301 | 359 | 670 | alkrtFtnr | alkrtLtnr |
| AL4602 | OR8K1 | 11 | 56114447 | A | T | A0301,A3201,B0801,B5101,C0702,C1502 | A3201 | 14 | 36 | rtFtnrfki | rtLtnrfki |
| AL4602 | OR8K1 | 11 | 56114447 | A | T | A0301,A3201,B0801,B5101,C0702,C1502 | A3201 | 377 | 104 | Ftnrfkipi | Ltnrfkipi |
| AL4602 | OR8K1 | 11 | 56114447 | A | T | A0301,A3201,B0801,B5101,C0702,C1502 | C1502 | 154 | 136 | rtFtnrfki | rtLtnrfki |
| AL4602 | OR8K1 | 11 | 56114447 | A | T | A0301,A3201,B0801,B5101,C0702,C1502 | C1502 | 78 | 148 | Ftnrfkipi | Ltnrfkipi |
| AL4602 | SLC22A9 | 11 | 63137761 | C | A | A0301,A3201,B0801,B5101,C0702,C1502 | C1502 | 452 | 310 | isiQldsnm | isiPldsnm |
| AL4602 | SLC22A20 | 11 | 64981692 | C | T | A0301,A3201,B0801,B5101,C0702,C1502 | C1502 | 164 | 30 | Csvfpstiv | Rsvfpstiv |
| AL4602 | TENM4 | 11 | 78440432 | G | A | A0301,A3201,B0801,B5101,C0702,C1502 | A3201 | 5 | 4 | kvfglLeaf | kvfglSeaf |
| AL4602 | PCF11 | 11 | 82878199 | C | T | A0301,A3201,B0801,B5101,C0702,C1502 | C1502 | 178 | 17298 | qvdehskpL | qvdehskpP |
| AL4602 | B3GAT1 | 11 | 134252876 | C | A | A0301,A3201,B0801,B5101,C0702,C1502 | A3201 | 10 | 10 | rvsLwpvaf | rvsVwpvaf |
| AL4602 | B3GAT1 | 11 | 134252876 | C | A | A0301,A3201,B0801,B5101,C0702,C1502 | B0801 | 17 | 35 | mrstrrvsL | mrstrrvsV |
| AL4602 | B3GAT1 | 11 | 134252876 | C | A | A0301,A3201,B0801,B5101,C0702,C1502 | C1502 | 231 | 221 | vsLwpvafv | vsVwpvafv |
| AL4602 | RAD51AP1 | 12 | 4662254 | A | T | A0301,A3201,B0801,B5101,C0702,C1502 | A0301 | 89 | 19358 | vMvkspvek | vKvkspvek |
| AL4602 | RAD51AP1 | 12 | 4662254 | A | T | A0301,A3201,B0801,B5101,C0702,C1502 | A0301 | 155 | 99 | Mvkspvekk | Kvkspvekk |
| AL4602 | SLCO1B3 | 12 | 21007975 | C | T | A0301,A3201,B0801,B5101,C0702,C1502 | A0301 | 24 | 27 | Vlsfsyiak | Alsfsyiak |
| AL4602 | SLCO1B3 | 12 | 21007975 | C | T | A0301,A3201,B0801,B5101,C0702,C1502 | A3201 | 3 | 4 | kmflaVlsf | kmflaAlsf |
| AL4602 | SLCO1B3 | 12 | 21007975 | C | T | A0301,A3201,B0801,B5101,C0702,C1502 | B5101 | 282 | 295 | laVlsfsyi | laAlsfsyi |
| AL4602 | SLCO1B3 | 12 | 21051402 | T | C | A0301,A3201,B0801,B5101,C0702,C1502 | A3201 | 125 | 75 | aTgfqsmvi | aMgfqsmvi |
| AL4602 | SLCO1B3 | 12 | 21051402 | T | C | A0301,A3201,B0801,B5101,C0702,C1502 | C1502 | 181 | 49 | laTgfqsmv | laMgfqsmv |
| AL4602 | SLCO1B3 | 12 | 21051402 | T | C | A0301,A3201,B0801,B5101,C0702,C1502 | C1502 | 79 | 2826 | aTgfqsmvi | aMgfqsmvi |
| AL4602 | KRAS | 12 | 25398285 | C | T | A0301,A3201,B0801,B5101,C0702,C1502 | A0301 | 217 | 410 | vvgaSgvgk | vvgaGgvgk |

Figure 21 (Cont.)

| | | | | | | | | | | | |
|---|---|---|---|---|---|---|---|---|---|---|---|
| AL4602 | KRT75 | 12 | 52820621 | C | A | A0301,A3201,B0801,B5101,C0702,C1502 | C1502 | 238 | 771 | lsgeVvspv | lsgeGvspv |
| AL4602 | KRT75 | 12 | 52820621 | C | A | A0301,A3201,B0801,B5101,C0702,C1502 | C1502 | 364 | 2091 | Vvspvnisv | Gvspvnisv |
| AL4602 | GRIP1 | 12 | 66788093 | T | A | A0301,A3201,B0801,B5101,C0702,C1502 | A0301 | 127 | 527 | aiiytvVlk | aiiytvElk |
| AL4602 | GRIP1 | 12 | 66788093 | T | A | A0301,A3201,B0801,B5101,C0702,C1502 | A0301 | 33 | 69 | iiytvVlkr | iiytvElkr |
| AL4602 | GRIP1 | 12 | 66788093 | T | A | A0301,A3201,B0801,B5101,C0702,C1502 | B0801 | 86 | 38 | Vlkryggpl | Elkryggpl |
| AL4602 | NAP1L1 | 12 | 76453955 | C | A | A0301,A3201,B0801,B5101,C0702,C1502 | B0801 | 131 | 165 | dleMkyavl | dleRkyavl |
| AL4602 | KSR2 | 12 | 117914279 | A | T | A0301,A3201,B0801,B5101,C0702,C1502 | C0702 | 227 | 142 | skhsdvlal | skhsdvFal |
| AL4602 | ATP6V0A2 | 12 | 124220082 | C | T | A0301,A3201,B0801,B5101,C0702,C1502 | C0702 | 58 | 74 | cyYchvypy | cyHchvypy |
| AL4602 | PCNX | 14 | 71514552 | G | T | A0301,A3201,B0801,B5101,C0702,C1502 | A0301 | 38 | 28 | lmitvaClk | lmitvaGlk |
| AL4602 | PCNX | 14 | 71514552 | G | T | A0301,A3201,B0801,B5101,C0702,C1502 | B0801 | 44 | 214 | Clkllrssf | Glkllrssf |
| AL4602 | PLD4 | 14 | 105395734 | T | C | A0301,A3201,B0801,B5101,C0702,C1502 | C1502 | 135 | 42 | rtPtdlqvl | rtStdlqvl |
| AL4602 | JAG2 | 14 | 105615331 | C | T | A0301,A3201,B0801,B5101,C0702,C1502 | B0801 | 144 | 2327 | qpRgnfsci | qpGgnfsci |
| AL4602 | ATP10A | 15 | 25932909 | C | A | A0301,A3201,B0801,B5101,C0702,C1502 | A3201 | 21 | 369 | rlliihWhw | rlliihGhw |
| AL4602 | ATP10A | 15 | 25932909 | C | A | A0301,A3201,B0801,B5101,C0702,C1502 | C0702 | 332 | 3781 | hWhwcysrl | hGhwcysrl |
| AL4602 | CHST14 | 15 | 40763569 | T | A | A0301,A3201,B0801,B5101,C0702,C1502 | A3201 | 226 | 733 | aTsglllmi | aSsglllmi |
| AL4602 | CHST14 | 15 | 40763569 | T | A | A0301,A3201,B0801,B5101,C0702,C1502 | C1502 | 59 | 48 | aTsglllmi | aSsglllmi |
| AL4602 | SPTBN5 | 15 | 42163599 | C | A | A0301,A3201,B0801,B5101,C0702,C1502 | B0801 | 158 | 17 | lvrqrqqdl | Mvrqrqqdl |
| AL4602 | FAM192A | 16 | 57188221 | G | C | A0301,A3201,B0801,B5101,C0702,C1502 | A3201 | 17 | 13 | ssifrtnSf | ssifrtnTf |
| AL4602 | FAM192A | 16 | 57188221 | G | C | A0301,A3201,B0801,B5101,C0702,C1502 | B0801 | 425 | 1411 | ssifrtnSf | ssifrtnTf |
| AL4602 | LCAT | 16 | 67973956 | G | T | A0301,A3201,B0801,B5101,C0702,C1502 | C0702 | 334 | 223 | grqpqpvNl | grqpqpvHl |
| AL4602 | OR1E2 | 17 | 3336201 | C | A | A0301,A3201,B0801,B5101,C0702,C1502 | C1502 | 339 | 23691 | rdmkgaleM | rdmkgaleR |
| AL4602 | HGS | 17 | 79660723 | G | C | A0301,A3201,B0801,B5101,C0702,C1502 | C1502 | 216 | 493 | talqeeQel | talqeeEel |

Figure 21 (Cont.)

| | | | | | | | | | | | |
|---|---|---|---|---|---|---|---|---|---|---|---|
| AL4602 | LRRC45 | 17 | 79981688 | G | A | A0301,A3201,B0801,B5101,C0702,C1502 | A0301 | 74 | 22340 | algkllprK | algkllprE |
| AL4602 | LRRC45 | 17 | 79981688 | G | A | A0301,A3201,B0801,B5101,C0702,C1502 | A3201 | 266 | 13404 | Ktlctelvl | Etlctelvl |
| AL4602 | LRRC45 | 17 | 79981688 | G | A | A0301,A3201,B0801,B5101,C0702,C1502 | C1502 | 42 | 145 | Ktlctelvl | Etlctelvl |
| AL4602 | HRH4 | 18 | 22057240 | T | C | A0301,A3201,B0801,B5101,C0702,C1502 | B0801 | 104 | 89 | lPrarrlak | lLrarrlak |
| AL4602 | HRH4 | 18 | 22057240 | T | C | A0301,A3201,B0801,B5101,C0702,C1502 | C0702 | 318 | 1836 | velPrarrl | velLrarrl |
| AL4602 | INSR | 19 | 7122909 | G | A | A0301,A3201,B0801,B5101,C0702,C1502 | B0801 | 487 | 39 | dlksylrFl | dlksylrSl |
| AL4602 | ZNF560 | 19 | 9577668 | C | A | A0301,A3201,B0801,B5101,C0702,C1502 | A0301 | 19 | 15 | hlrthtVyk | hlrthtGyk |
| AL4602 | ZNF560 | 19 | 9577668 | C | A | A0301,A3201,B0801,B5101,C0702,C1502 | A3201 | 122 | 310 | rthtVykpy | rthtGykpy |
| AL4602 | LPHN1 | 19 | 14272252 | C | T | A0301,A3201,B0801,B5101,C0702,C1502 | C0702 | 126 | 77 | trQppapnl | trRppapnl |
| AL4602 | AP1M1 | 19 | 16344422 | G | A | A0301,A3201,B0801,B5101,C0702,C1502 | B5101 | 88 | 65 | ipyfttsDi | ipyfttsGi |
| AL4602 | LGI4 | 19 | 35624607 | G | T | A0301,A3201,B0801,B5101,C0702,C1502 | A3201 | 325 | 421 | glshMqylf | glshLqylf |
| AL4602 | LGI4 | 19 | 35624607 | G | T | A0301,A3201,B0801,B5101,C0702,C1502 | C1502 | 306 | 501 | lshMqylfi | lshLqylfi |
| AL4602 | KCNH7 | 2 | 163361083 | G | A | A0301,A3201,B0801,B5101,C0702,C1502 | A3201 | 6 | 17 | kiLqltlnf | kiPqltlnf |
| AL4602 | KCNH7 | 2 | 163361083 | G | A | A0301,A3201,B0801,B5101,C0702,C1502 | C1502 | 188 | 1222 | stinkiLql | stinkiPql |
| AL4602 | ERBB4 | 2 | 212495306 | C | A | A0301,A3201,B0801,B5101,C0702,C1502 | B5101 | 331 | 321 | tpliSagvi | tpliAagvi |
| AL4602 | ERBB4 | 2 | 212495306 | C | A | A0301,A3201,B0801,B5101,C0702,C1502 | C1502 | 242 | 286 | rtpliSagv | rtpliAagv |
| AL4602 | PAK7 | 20 | 9546965 | C | A | A0301,A3201,B0801,B5101,C0702,C1502 | A0301 | 342 | 428 | dtyprCpak | dtyprGpak |
| AL4602 | DZANK1 | 20 | 18393435 | C | A | A0301,A3201,B0801,B5101,C0702,C1502 | C1502 | 234 | 17663 | kSdigtqtv | kRdigtqtv |
| AL4602 | JPH2 | 20 | 42744639 | T | A | A0301,A3201,B0801,B5101,C0702,C1502 | C0702 | 137 | 141 | srepVvaly | srepEvaly |
| AL4602 | GNAS | 20 | 57429964 | G | C | A0301,A3201,B0801,B5101,C0702,C1502 | B0801 | 148 | 1110 | llrgllaPl | llrgllaRl |
| AL4602 | ZDHHC8 | 22 | 20119484 | C | G | A0301,A3201,B0801,B5101,C0702,C1502 | B0801 | 10 | 1020 | mprsRgtrl | mprsPgtrl |
| AL4602 | ZDHHC8 | 22 | 20119484 | C | G | A0301,A3201,B0801,B5101,C0702,C1502 | B0801 | 299 | 29 | sRgtrlkpa | sPgtrlkpa |
| AL4602 | SCARF2 | 22 | 20791890 | C | T | A0301,A3201,B0801,B5101,C0702,C1502 | C1502 | 495 | 909 | elnprgHnv | elnprgRnv |

Figure 21 (Cont.)

| | | | | | | | | | | | |
|---|---|---|---|---|---|---|---|---|---|---|---|
| AL4602 | CDC42EP1 | 22 | 37964115 | G | T | A0301,A3201,B0801,B5101,C0702,C1502 | C1502 | 20 | 5392 | stdghssyV | stdghssyG |
| AL4602 | SEMA3G | 3 | 52476882 | G | T | A0301,A3201,B0801,B5101,C0702,C1502 | A0301 | 47 | 19031 | rsaiflgpK | rsaiflgpQ |
| AL4602 | SEMA3G | 3 | 52476882 | G | T | A0301,A3201,B0801,B5101,C0702,C1502 | C0702 | 480 | 440 | iflgpKgsl | iflgpQgsl |
| AL4602 | ROBO1 | 3 | 78710282 | C | A | A0301,A3201,B0801,B5101,C0702,C1502 | A0301 | 121 | 653 | svvipYlrk | svvipDlrk |
| AL4602 | SLC26A1 | 4 | 983192 | A | T | A0301,A3201,B0801,B5101,C0702,C1502 | B0801 | 234 | 1126 | tqrprtaQl | tqrprtaLl |
| AL4602 | OTP | 5 | 76926156 | C | A | A0301,A3201,B0801,B5101,C0702,C1502 | B0801 | 249 | 2428 | wLgtsiasl | wRgtsiasl |
| AL4602 | PCDH12 | 5 | 141336680 | T | A | A0301,A3201,B0801,B5101,C0702,C1502 | C1502 | 154 | 3485 | aVsslalei | aEsslalei |
| AL4602 | GABRP | 5 | 170239030 | G | A | A0301,A3201,B0801,B5101,C0702,C1502 | A0301 | 334 | 249 | ssissfkQk | ssissfkRk |
| AL4602 | GABRP | 5 | 170239030 | G | A | A0301,A3201,B0801,B5101,C0702,C1502 | A3201 | 149 | 158 | ssfkQkisf | ssfkRkisf |
| AL4602 | GABRP | 5 | 170239030 | G | A | A0301,A3201,B0801,B5101,C0702,C1502 | B0801 | 470 | 212 | sfkQkisfa | sfkRkisfa |
| AL4602 | GPRIN1 | 5 | 176026256 | C | T | A0301,A3201,B0801,B5101,C0702,C1502 | C1502 | 129 | 210 | eilgkgNpv | eilgkgDpv |
| AL4602 | RANBP9 | 6 | 13711284 | T | C | A0301,A3201,B0801,B5101,C0702,C1502 | B0801 | 143 | 29 | elqrrlErl | elqrrlKrl |
| AL4602 | RANBP9 | 6 | 13711284 | T | C | A0301,A3201,B0801,B5101,C0702,C1502 | B0801 | 328 | 53 | rrlErlypa | rrlKrlypa |
| AL4602 | HLA-DRB5 | 6 | 32489882 | T | A | A0301,A3201,B0801,B5101,C0702,C1502 | C0702 | 386 | 241 | vrflLrdiy | vrflHrdiy |
| AL4602 | CUL9 | 6 | 43153826 | G | T | A0301,A3201,B0801,B5101,C0702,C1502 | B0801 | 495 | 4819 | sLgqrelef | sRgqrelef |
| AL4602 | PAPOLB | 7 | 4899715 | G | A | A0301,A3201,B0801,B5101,C0702,C1502 | C1502 | 276 | 502 | atefFlqqv | atefSlqqv |
| AL4602 | TNRC18 | 7 | 5415693 | A | G | A0301,A3201,B0801,B5101,C0702,C1502 | B0801 | 399 | 368 | Selqrsaql | Lelqrsaql |
| AL4602 | SEMA3E | 7 | 82997239 | G | T | A0301,A3201,B0801,B5101,C0702,C1502 | A0301 | 312 | 23007 | tvehsfvhK | tvehsfvhT |
| AL4602 | SEMA3E | 7 | 82997239 | G | T | A0301,A3201,B0801,B5101,C0702,C1502 | A0301 | 37 | 24 | hsfvhKvrk | hsfvhTvrk |
| AL4602 | SEMA3E | 7 | 82997239 | G | T | A0301,A3201,B0801,B5101,C0702,C1502 | C1502 | 42 | 180 | Kvrkitlev | Tvrkitlev |
| AL4602 | AP4M1 | 7 | 99701067 | G | A | A0301,A3201,B0801,B5101,C0702,C1502 | C1502 | 80 | 133 | yvqttstel | yvqttsteM |
| AL4602 | CTTNBP2 | 7 | 117407155 | C | A | A0301,A3201,B0801,B5101,C0702,C1502 | C1502 | 92 | 614 | kcnrtvhYv | kcnrtvhDv |

Figure 21 (Cont.)

| | | | | | | | | | | | |
|---|---|---|---|---|---|---|---|---|---|---|---|
| AL4602 | OR2F1 | 7 | 143657664 | G | T | A0301,A3201,B0801,B5101,C0702,C1502 | C1502 | 43 | 23 | ssnevtimL | ssnevtimV |
| AL4602 | OR2F1 | 7 | 143657664 | G | T | A0301,A3201,B0801,B5101,C0702,C1502 | C1502 | 45 | 38 | vtimLssiv | vtimVssiv |
| AL4602 | STAR | 8 | 38001823 | C | T | A0301,A3201,B0801,B5101,C0702,C1502 | B0801 | 219 | 1129 | hlrkrlKsh | hlrkrlEsh |
| AL4602 | STAR | 8 | 38001823 | C | T | A0301,A3201,B0801,B5101,C0702,C1502 | B0801 | 133 | 6157 | rkrlKshpa | rkrlEshpa |
| AL4602 | IDO2 | 8 | 39836608 | T | A | A0301,A3201,B0801,B5101,C0702,C1502 | A0301 | 189 | 63 | pllscqYlk | pllscqFlk |
| AL4602 | IDO2 | 8 | 39836608 | T | A | A0301,A3201,B0801,B5101,C0702,C1502 | B0801 | 367 | 454 | mpllscqYl | mpllscqFl |
| AL4602 | IDO2 | 8 | 39836608 | T | A | A0301,A3201,B0801,B5101,C0702,C1502 | B5101 | 345 | 421 | mpllscqYl | mpllscqFl |
| AL4602 | NDUFAF6 | 8 | 96037306 | C | T | A0301,A3201,B0801,B5101,C0702,C1502 | C0702 | 168 | 269 | crWpplgly | crRpplgly |
| AL4602 | OXR1 | 8 | 107705038 | C | A | A0301,A3201,B0801,B5101,C0702,C1502 | A3201 | 286 | 2958 | stYeeeeaf | stSeeeeaf |
| AL4602 | OXR1 | 8 | 107705038 | C | A | A0301,A3201,B0801,B5101,C0702,C1502 | C1502 | 354 | 2146 | stYeeeeaf | stSeeeeaf |
| AL4602 | MROH5 | 8 | 142484263 | G | A | A0301,A3201,B0801,B5101,C0702,C1502 | C1502 | 147 | 259 | Ltadelhfl | Ptadelhfl |
| AL4602 | COMMD5 | 8 | 146076346 | C | A | A0301,A3201,B0801,B5101,C0702,C1502 | C1502 | 315 | 375 | lvgdFasvv | lvgdLasvv |
| AL4602 | SUSD1 | 9 | 114820943 | G | A | A0301,A3201,B0801,B5101,C0702,C1502 | A3201 | 372 | 9775 | ssyqvlvlL | ssyqvlvlP |
| AL4602 | SUSD1 | 9 | 114820943 | G | A | A0301,A3201,B0801,B5101,C0702,C1502 | A3201 | 289 | 25378 | lLlalqstf | lPlalqstf |
| AL4602 | SUSD1 | 9 | 114820943 | G | A | A0301,A3201,B0801,B5101,C0702,C1502 | C0702 | 174 | 73 | syqvlvlLl | syqvlvlPl |
| AL4602 | SUSD1 | 9 | 114820943 | G | A | A0301,A3201,B0801,B5101,C0702,C1502 | C1502 | 63 | 12344 | ssyqvlvlL | ssyqvlvlP |
| AL4602 | ASTN2 | 9 | 119976922 | C | T | A0301,A3201,B0801,B5101,C0702,C1502 | C1502 | 37 | 38 | Tsteathei | Asteathei |
| AL4602 | C9orf50 | 9 | 132382765 | G | A | A0301,A3201,B0801,B5101,C0702,C1502 | A0301 | 200 | 116 | rssdLrlpk | rssdPrlpk |
| AL4602 | C9orf50 | 9 | 132382765 | G | A | A0301,A3201,B0801,B5101,C0702,C1502 | C0702 | 65 | 82 | frrssdLrl | frrssdPrl |
| AL4602 | ABCA2 | 9 | 139908302 | G | T | A0301,A3201,B0801,B5101,C0702,C1502 | C1502 | 29 | 31 | vamtvaMsv | vamtvaLsv |
| AL4602 | DPP7 | 9 | 140008360 | C | T | A0301,A3201,B0801,B5101,C0702,C1502 | B0801 | 212 | 187 | llralrrNl | llralrrDl |
| AL4602 | KLHL34 | X | 21675269 | A | C | A0301,A3201,B0801,B5101,C0702,C1502 | B0801 | 397 | 2070 | erRahctel | erLahctel |
| AL4602 | PCDH19 | X | 99551442 | G | T | A0301,A3201,B0801,B5101,C0702,C1502 | C1502 | 240 | 228 | pardMeqyv | pardLeqyv |

Figure 21 (Cont.)

| | | | | | | | | | | | |
|---|---|---|---|---|---|---|---|---|---|---|---|
| AL4602 | PLXNB3 | X | 153041663 | G | T | A0301,A3201,B0801,B5101,C0702,C1502 | A3201 | 257 | 706 | svhalYlew | svhalDlew |
| AL4602 | PLXNB3 | X | 153041663 | G | T | A0301,A3201,B0801,B5101,C0702,C1502 | C0702 | 143 | 4684 | lYlewrsgl | lDlewrsgl |
| AL4602 | PLXNB3 | X | 153041663 | G | T | A0301,A3201,B0801,B5101,C0702,C1502 | C1502 | 333 | 3251 | rpsvhalYl | rpsvhalDl |
| AU5884 | LRRIQ3 | 1 | 74506967 | G | T | A0201,A2402,B1302,B5101,C0602,C1502 | A0201 | 305 | 321 | vlkeksMiv | vlkeksLiv |
| AU5884 | LRRIQ3 | 1 | 74506967 | G | T | A0201,A2402,B1302,B5101,C0602,C1502 | C1502 | 52 | 137 | ksMivkqkl | ksLivkqkl |
| AU5884 | KIF20B | 10 | 91518521 | A | G | A0201,A2402,B1302,B5101,C0602,C1502 | C0602 | 55 | 20 | wreGrdqlv | wreErdqlv |
| AU5884 | ABCB9 | 12 | 123414607 | C | T | A0201,A2402,B1302,B5101,C0602,C1502 | C1502 | 269 | 129 | vvldkgrlv | vvldkgrVv |
| AU5884 | CLMN | 14 | 95670049 | G | A | A0201,A2402,B1302,B5101,C0602,C1502 | A0201 | 68 | 1238 | fqikvnlml | fqikvnlmT |
| AU5884 | NFE2L1 | 17 | 46136777 | G | T | A0201,A2402,B1302,B5101,C0602,C1502 | A0201 | 8 | 146 | lllLekvefl | llRekvefl |
| AU5884 | NFE2L1 | 17 | 46136777 | G | T | A0201,A2402,B1302,B5101,C0602,C1502 | C0602 | 98 | 11095 | qrdkarllL | qrdkarllR |
| AU5884 | NFE2L1 | 17 | 46136777 | G | T | A0201,A2402,B1302,B5101,C0602,C1502 | C1502 | 265 | 390 | karllLekv | karllRekv |
| AU5884 | SIGLEC5 | 19 | 52132769 | G | A | A0201,A2402,B1302,B5101,C0602,C1502 | A0201 | 23 | 1975 | wMgnalspl | wTgnalspl |
| AU5884 | MYO1B | 2 | 192160895 | C | T | A0201,A2402,B1302,B5101,C0602,C1502 | B5101 | 314 | 323 | lpiyLpekv | lpiySpekv |
| AU5884 | SON | 21 | 34948684 | G | A | A0201,A2402,B1302,B5101,C0602,C1502 | C0602 | 55 | 237 | frvlrnEal | frvlrnGal |
| AU5884 | SON | 21 | 34948684 | G | A | A0201,A2402,B1302,B5101,C0602,C1502 | C1502 | 262 | 1277 | Ealtrpncm | Galtrpncm |
| AU5884 | SON | 21 | 34948686 | G | A | A0201,A2402,B1302,B5101,C0602,C1502 | C0602 | 73 | 237 | frvlrngTl | frvlrngAl |
| AU5884 | SON | 21 | 34948686 | G | A | A0201,A2402,B1302,B5101,C0602,C1502 | C1502 | 480 | 1277 | gTltrpncm | gAltrpncm |
| AU5884 | FANCD2 | 3 | 10108913 | G | T | A0201,A2402,B1302,B5101,C0602,C1502 | C0602 | 341 | 1382 | fcHetspem | fcQetspem |
| AU5884 | BFSP2 | 3 | 133191330 | G | T | A0201,A2402,B1302,B5101,C0602,C1502 | C0602 | 264 | 437 | qqqerShll | qqqerAhll |
| AU5884 | BFSP2 | 3 | 133191330 | G | T | A0201,A2402,B1302,B5101,C0602,C1502 | C1502 | 428 | 558 | qqqerShll | qqqerAhll |
| AU5884 | BCHE | 3 | 165548427 | G | A | A0201,A2402,B1302,B5101,C0602,C1502 | A0201 | 364 | 23836 | kLknatvli | kPknatvli |
| AU5884 | DND1 | 5 | 140052407 | G | A | A0201,A2402,B1302,B5101,C0602,C1502 | A0201 | 182 | 40 | qliLlfqrv | qliPlfqrv |

Figure 21 (Cont.)

| | | | | | | | | | | | |
|---|---|---|---|---|---|---|---|---|---|---|---|
| AU5884 | DND1 | 5 | 140052407 | G | A | A0201,A2402,B1302,B5101,C0602,C1502 | A0201 | 252 | 7397 | Llfqrvgrl | Plfqrvgrl |
| AU5884 | DND1 | 5 | 140052407 | G | A | A0201,A2402,B1302,B5101,C0602,C1502 | C1502 | 197 | 21649 | dvyehqliL | dvyehqliP |
| AU5884 | TFEC | 7 | 115614304 | C | A | A0201,A2402,B1302,B5101,C0602,C1502 | A0201 | 240 | 3091 | aqwhmeYvi | aqwhmeDvi |
| AU5884 | TFEC | 7 | 115614304 | C | A | A0201,A2402,B1302,B5101,C0602,C1502 | A0201 | 21 | 12574 | Yviediigm | Dviediigm |
| AU5884 | TFEC | 7 | 115614304 | C | A | A0201,A2402,B1302,B5101,C0602,C1502 | C1502 | 74 | 694 | naqwhmeYv | naqwhmeDv |
| AU5884 | CPXCR1 | X | 88009020 | T | A | A0201,A2402,B1302,B5101,C0602,C1502 | C0602 | 30 | 35 | frrpsrEhy | frrpsrVhy |
| AU5884 | CPXCR1 | X | 88009020 | T | A | A0201,A2402,B1302,B5101,C0602,C1502 | C0602 | 226 | 41 | rrpsrEhyy | rrpsrVhyy |
| AU5884 | NKAP | X | 119065974 | T | A | A0201,A2402,B1302,B5101,C0602,C1502 | C1502 | 436 | 132 | Maeepsdli | Kaeepsdli |
| BL3403 | GPR88 | 1 | 101004563 | G | A | A0201,A2601,B3501,B4402,C0401,C0501 | C0501 | 143 | 24739 | ttDgslllll | ttGgslllll |
| BL3403 | HRNR | 1 | 152185879 | C | G | A0201,A2601,B3501,B4402,C0401,C0501 | A2601 | 118 | 769 | sstgHsssy | sstgQsssy |
| BL3403 | HRNR | 1 | 152185879 | C | G | A0201,A2601,B3501,B4402,C0401,C0501 | B3501 | 64 | 248 | sstgHsssy | sstgQsssy |
| BL3403 | PROX1 | 1 | 214171319 | C | T | A0201,A2601,B3501,B4402,C0401,C0501 | A0201 | 18 | 57 | stfChpfpl | stfRhpfpl |
| BL3403 | PROX1 | 1 | 214171319 | C | T | A0201,A2601,B3501,B4402,C0401,C0501 | B3501 | 418 | 1825 | ttstfChpf | ttstfRhpf |
| BL3403 | CYP26C1 | 10 | 94828338 | G | A | A0201,A2601,B3501,B4402,C0401,C0501 | B3501 | 53 | 4 | lTtpafpam | lAtpafpam |
| BL3403 | USH1C | 11 | 17531178 | G | A | A0201,A2601,B3501,B4402,C0401,C0501 | A0201 | 481 | 13469 | Svlplsghv | Pvlplsghv |
| BL3403 | USH1C | 11 | 17531178 | G | A | A0201,A2601,B3501,B4402,C0401,C0501 | B3501 | 20 | 74 | vpapSvlpl | vpapPvlpl |
| BL3403 | FRMD8 | 11 | 65164490 | G | T | A0201,A2601,B3501,B4402,C0401,C0501 | B3501 | 16 | 13 | lpfyWcaff | lpfyGcaff |
| BL3403 | BEST3 | 12 | 70087510 | G | A | A0201,A2601,B3501,B4402,C0401,C0501 | A0201 | 400 | 1113 | lllifrLvst | lllifrSvst |
| BL3403 | POC1B-GALNT4 | 12 | 89919707 | G | A | A0201,A2601,B3501,B4402,C0401,C0501 | B3501 | 333 | 2074 | lpsplrvpS | lpsplrvpP |
| BL3403 | EXOC3L4 | 14 | 103569099 | G | A | A0201,A2601,B3501,B4402,C0401,C0501 | A0201 | 6 | 3 | illdwaanl | illdwaanV |
| BL3403 | EXOC3L4 | 14 | 103569099 | G | A | A0201,A2601,B3501,B4402,C0401,C0501 | B3501 | 139 | 79 | lldwaanly | lldwaanVy |
| BL3403 | EXOC3L4 | 14 | 103569099 | G | A | A0201,A2601,B3501,B4402,C0401,C0501 | C0501 | 51 | 31 | lldwaanly | lldwaanVy |
| BL3403 | HBZ | 16 | 204060 | G | A | A0201,A2601,B3501,B4402,C0401,C0501 | A0201 | 12 | 12 | klselhTyi | klselhAyi |

Figure 21 (Cont.)

| | | | | | | | | | | | |
|---|---|---|---|---|---|---|---|---|---|---|---|
| BL3403 | HBZ | 16 | 204060 | G | A | A0201,A2601,B3501,B4402,C0401,C0501 | A0201 | 173 | 115 | elhTyilrv | elhAyilrv |
| BL3403 | CACNA1H | 16 | 1268591 | C | T | A0201,A2601,B3501,B4402,C0401,C0501 | B3501 | 395 | 889 | vpasaShpr | vpasaPhpr |
| BL3403 | BAIAP3 | 16 | 1396452 | G | T | A0201,A2601,B3501,B4402,C0401,C0501 | A2601 | 265 | 24751 | hltskmvgY | hltskmvgD |
| BL3403 | ITGAM | 16 | 31309111 | C | G | A0201,A2601,B3501,B4402,C0401,C0501 | B3501 | 487 | 691 | Epwgrfgaa | Qpwgrfgaa |
| BL3403 | GAS8 | 16 | 90102977 | C | T | A0201,A2601,B3501,B4402,C0401,C0501 | A0201 | 227 | 483 | itlnnlaFi | itlnnlaLi |
| BL3403 | GAS8 | 16 | 90102977 | C | T | A0201,A2601,B3501,B4402,C0401,C0501 | B3501 | 334 | 3888 | ditlnnlaF | ditlnnlaL |
| BL3403 | GGT6 | 17 | 4461888 | G | A | A0201,A2601,B3501,B4402,C0401,C0501 | B4402 | 272 | 202 | aeqlSvpqg | aeqlPvpqg |
| BL3403 | GGT6 | 17 | 4461888 | G | A | A0201,A2601,B3501,B4402,C0401,C0501 | C0501 | 380 | 5495 | lSvpqgilf | lPvpqgilf |
| BL3403 | TP53 | 17 | 7578190 | T | C | A0201,A2601,B3501,B4402,C0401,C0501 | A0201 | 350 | 343 | vvpCeppev | vvpYeppev |
| BL3403 | SARM1 | 17 | 26708758 | C | T | A0201,A2601,B3501,B4402,C0401,C0501 | A0201 | 194 | 1115 | llFsnrlea | llDsnrlea |
| BL3403 | AATF | 17 | 35306433 | G | A | A0201,A2601,B3501,B4402,C0401,C0501 | B3501 | 44 | 41 | maEpqplal | maGpqplal |
| BL3403 | AATF | 17 | 35306433 | G | A | A0201,A2601,B3501,B4402,C0401,C0501 | C0501 | 15 | 618 | maEpqplal | maGpqplal |
| BL3403 | MED24 | 17 | 38176135 | G | A | A0201,A2601,B3501,B4402,C0401,C0501 | A0201 | 111 | 17960 | ilgsrtagL | ilgsrtagP |
| BL3403 | ETV4 | 17 | 41622971 | C | T | A0201,A2601,B3501,B4402,C0401,C0501 | B4402 | 460 | 263 | merrIkagy | merrMkagy |
| BL3403 | ST6GALNAC2 | 17 | 74581812 | A | G | A0201,A2601,B3501,B4402,C0401,C0501 | A0201 | 10 | 8 | llfalHfsa | llfalYfsa |
| BL3403 | SLC16A3 | 17 | 80195221 | T | C | A0201,A2601,B3501,B4402,C0401,C0501 | A0201 | 51 | 54 | lllnccAca | lllnccVca |
| BL3403 | SLC16A3 | 17 | 80195221 | T | C | A0201,A2601,B3501,B4402,C0401,C0501 | A0201 | 479 | 93 | llnccAcaa | llnccVcaa |
| BL3403 | POLRMT | 19 | 622354 | G | T | A0201,A2601,B3501,B4402,C0401,C0501 | B4402 | 284 | 962 | pepclQrqy | pepclPrqy |
| BL3403 | ZBTB7A | 19 | 4054707 | G | A | A0201,A2601,B3501,B4402,C0401,C0501 | A0201 | 233 | 428 | slppVaaaa | slppAaaaa |
| BL3403 | ZBTB7A | 19 | 4054707 | G | A | A0201,A2601,B3501,B4402,C0401,C0501 | B3501 | 473 | 326 | npmnslppV | npmnslppA |
| BL3403 | ZBTB7A | 19 | 4054707 | G | A | A0201,A2601,B3501,B4402,C0401,C0501 | B3501 | 306 | 92 | lppVaaaaa | lppAaaaaa |
| BL3403 | ZBTB7A | 19 | 4054707 | G | A | A0201,A2601,B3501,B4402,C0401,C0501 | B3501 | 229 | 280 | ppVaaaaaa | ppAaaaaaa |

Figure 21 (Cont.)

| | | | | | | | | | | | |
|---|---|---|---|---|---|---|---|---|---|---|---|
| BL3403 | ZBTB7A | 19 | 4054707 | G | A | A0201,A2601,B3501,B4402,C0401,C0501 | B3501 | 9 | 20 | Vaaaaaasf | Aaaaaaasf |
| BL3403 | LOC100131094 | 19 | 4683767 | C | A | A0201,A2601,B3501,B4402,C0401,C0501 | B3501 | 380 | 234 | wlagspMsf | wlagspLsf |
| BL3403 | LOC100131094 | 19 | 4683767 | C | A | A0201,A2601,B3501,B4402,C0401,C0501 | B3501 | 327 | 2455 | Msfqalltl | Lsfqalltl |
| BL3403 | KDM4B | 19 | 5144311 | G | A | A0201,A2601,B3501,B4402,C0401,C0501 | A2601 | 90 | 349 | itknHngly | itknRngly |
| BL3403 | HSD11B1L | 19 | 5685078 | G | T | A0201,A2601,B3501,B4402,C0401,C0501 | A0201 | 37 | 3509 | yaLlgshlv | yaRlgshlv |
| BL3403 | HSD11B1L | 19 | 5685078 | G | T | A0201,A2601,B3501,B4402,C0401,C0501 | A0201 | 108 | 23567 | aLlgshlvl | aRlgshlvl |
| BL3403 | HSD11B1L | 19 | 5685078 | G | T | A0201,A2601,B3501,B4402,C0401,C0501 | A2601 | 48 | 86 | elayhyaLl | elayhyaRl |
| BL3403 | HSD11B1L | 19 | 5685078 | G | T | A0201,A2601,B3501,B4402,C0401,C0501 | B4402 | 353 | 4909 | eelayhyaL | eelayhyaR |
| BL3403 | ZNF414 | 19 | 8577545 | C | T | A0201,A2601,B3501,B4402,C0401,C0501 | B3501 | 57 | 58 | fpslrdlaq | fpsVrdlaq |
| BL3403 | FKRP | 19 | 47259298 | T | A | A0201,A2601,B3501,B4402,C0401,C0501 | A0201 | 385 | 306 | aldgEavvl | aldgDavvl |
| BL3403 | FKRP | 19 | 47259298 | T | A | A0201,A2601,B3501,B4402,C0401,C0501 | C0501 | 119 | 90 | aldgEavvl | aldgDavvl |
| BL3403 | KCNC3 | 19 | 50823531 | G | A | A0201,A2601,B3501,B4402,C0401,C0501 | A0201 | 10 | 14 | flpdlnVna | flpdlnAna |
| BL3403 | KCNC3 | 19 | 50823531 | G | A | A0201,A2601,B3501,B4402,C0401,C0501 | B3501 | 205 | 155 | lpdlnVnaa | lpdlnAnaa |
| BL3403 | POLD1 | 19 | 50919698 | T | A | A0201,A2601,B3501,B4402,C0401,C0501 | B3501 | 80 | 30 | lpidtqNyl | lpidtqYyl |
| BL3403 | PPP2R1A | 19 | 52714607 | C | T | A0201,A2601,B3501,B4402,C0401,C0501 | B3501 | 138 | 182 | spFdleahf | spSdleahf |
| BL3403 | ZNF480 | 19 | 52826068 | G | A | A0201,A2601,B3501,B4402,C0401,C0501 | A0201 | 67 | 180 | kafsHisyl | kafsRisyl |
| BL3403 | APCDD1L | 20 | 57036139 | G | A | A0201,A2601,B3501,B4402,C0401,C0501 | A0201 | 451 | 3388 | plglWlphv | plglRlphv |
| BL3403 | APCDD1L | 20 | 57036139 | G | A | A0201,A2601,B3501,B4402,C0401,C0501 | A0201 | 29 | 52 | Wlphveyel | Rlphveyel |
| BL3403 | APCDD1L | 20 | 57036139 | G | A | A0201,A2601,B3501,B4402,C0401,C0501 | B3501 | 17 | 54 | lplglWlph | lplglRlph |
| BL3403 | UMODL1 | 21 | 43531056 | G | T | A0201,A2601,B3501,B4402,C0401,C0501 | A0201 | 86 | 148 | glVtgtaal | glGtgtaal |
| BL3403 | MYO18B | 22 | 26247463 | C | T | A0201,A2601,B3501,B4402,C0401,C0501 | C0501 | 10 | 13 | yadhmgltC | yadhmgltR |
| BL3403 | CHEK2 | 22 | 29091840 | T | C | A0201,A2601,B3501,B4402,C0401,C0501 | A2601 | 82 | 14101 | Eilgetslm | Kilgetslm |
| BL3403 | CHEK2 | 22 | 29091840 | T | C | A0201,A2601,B3501,B4402,C0401,C0501 | C0501 | 2 | 6 | itdfghsEi | itdfghsKi |

Figure 21 (Cont.)

| | | | | | | | | | | | |
|---|---|---|---|---|---|---|---|---|---|---|---|
| BL3403 | PPP6R2 | 22 | 50882314 | C | T | A0201,A2601,B3501,B4402,C0401,C0501 | A0201 | 84 | 180 | Wllspacpa | Rllspacpa |
| BL3403 | SBF1 | 22 | 50904902 | T | A | A0201,A2601,B3501,B4402,C0401,C0501 | A0201 | 221 | 788 | rqlgitlvl | rqlgitNvl |
| BL3403 | DHX30 | 3 | 47890437 | G | A | A0201,A2601,B3501,B4402,C0401,C0501 | A0201 | 259 | 2159 | sSsdhlafv | sGsdhlafv |
| BL3403 | DHX30 | 3 | 47890437 | G | A | A0201,A2601,B3501,B4402,C0401,C0501 | B3501 | 70 | 257 | dsSsdhlaf | dsGsdhlaf |
| BL3403 | PLXNA1 | 3 | 126707449 | C | T | A0201,A2601,B3501,B4402,C0401,C0501 | B3501 | 202 | 2586 | lpSrslqvl | lpPrslqvl |
| BL3403 | MUC4 | 3 | 195513112 | G | A | A0201,A2601,B3501,B4402,C0401,C0501 | B3501 | 206 | 195 | lpvlglssa | lpvTglssa |
| BL3403 | ID4 | 6 | 19838367 | G | T | A0201,A2601,B3501,B4402,C0401,C0501 | B3501 | 50 | 35 | hpSgtcpaa | hpAgtcpaa |
| BL3403 | RIMS1 | 6 | 72962515 | G | C | A0201,A2601,B3501,B4402,C0401,C0501 | A2601 | 376 | 7707 | dAigvvppv | dGigvvppv |
| BL3403 | RIMS1 | 6 | 72962515 | G | C | A0201,A2601,B3501,B4402,C0401,C0501 | C0501 | 55 | 8 | evddAigvv | evddGigvv |
| BL3403 | GPRC6A | 6 | 117113765 | T | C | A0201,A2601,B3501,B4402,C0401,C0501 | A2601 | 44 | 51 | fifafkgRy | fifafkgKy |
| BL3403 | GPRC6A | 6 | 117113765 | T | C | A0201,A2601,B3501,B4402,C0401,C0501 | B3501 | 189 | 202 | fifafkgRy | fifafkgKy |
| BL3403 | INTS1 | 7 | 1510311 | G | A | A0201,A2601,B3501,B4402,C0401,C0501 | A0201 | 6 | 7 | vlFhraflv | vlLhraflv |
| BL3403 | INTS1 | 7 | 1510311 | G | A | A0201,A2601,B3501,B4402,C0401,C0501 | B3501 | 320 | 368 | aavlFhraf | aavlLhraf |
| BL3403 | RADIL | 7 | 4839876 | C | T | A0201,A2601,B3501,B4402,C0401,C0501 | B3501 | 240 | 100 | sssteNfcy | sssteDfcy |
| BL3403 | RADIL | 7 | 4839876 | C | T | A0201,A2601,B3501,B4402,C0401,C0501 | C0501 | 251 | 85 | steNfcyvf | steDfcyvf |
| BL3403 | SAMD9 | 7 | 92733498 | G | A | A0201,A2601,B3501,B4402,C0401,C0501 | A0201 | 50 | 5158 | rllpsiglL | rllpsiglS |
| BL3403 | SAMD9 | 7 | 92733498 | G | A | A0201,A2601,B3501,B4402,C0401,C0501 | B3501 | 326 | 359 | lpsiglLtv | lpsiglStv |
| BL3403 | CHD7 | 8 | 61775123 | C | T | A0201,A2601,B3501,B4402,C0401,C0501 | B3501 | 114 | 79 | mggamVppm | mggamAppm |
| BL3403 | NAPRT1 | 8 | 144660329 | A | G | A0201,A2601,B3501,B4402,C0401,C0501 | B3501 | 6 | 5 | cpfggaLal | cpfggaFal |
| BL3403 | ADCK5 | 8 | 145618266 | C | A | A0201,A2601,B3501,B4402,C0401,C0501 | A0201 | 476 | 255 | slvppaeel | slvppaeeL |
| BL3403 | ADCK5 | 8 | 145618266 | C | A | A0201,A2601,B3501,B4402,C0401,C0501 | B3501 | 388 | 539 | lvppaeely | lvppaeeLy |
| BL3403 | ADCK5 | 8 | 145618266 | C | A | A0201,A2601,B3501,B4402,C0401,C0501 | B3501 | 45 | 55 | ppaeelyqy | ppaeeLyqy |

Figure 21 (Cont.)

| | | | | | | | | | | | |
|---|---|---|---|---|---|---|---|---|---|---|---|
| BL3403 | ZNF34 | 8 | 146002947 | C | T | A0201,A2601,B3501,B4402,C0401,C0501 | C0501 | 15 | 24423 | paDpkpgvi | paGpkpgvi |
| BL3403 | ERMP1 | 9 | 5832814 | G | A | A0201,A2601,B3501,B4402,C0401,C0501 | A0201 | 27 | 116 | glsevCaal | glsevRaal |
| BL3403 | ERMP1 | 9 | 5832814 | G | A | A0201,A2601,B3501,B4402,C0401,C0501 | B3501 | 42 | 316 | Caalglaly | Raalglaly |
| BL3403 | ERMP1 | 9 | 5832814 | G | A | A0201,A2601,B3501,B4402,C0401,C0501 | B4402 | 50 | 419 | sevCaalgl | sevRaalgl |
| BL3403 | CNTFR | 9 | 34552193 | C | T | A0201,A2601,B3501,B4402,C0401,C0501 | A0201 | 317 | 986 | tlalaTaaa | tlalaAaaa |
| BL3403 | CNTFR | 9 | 34552193 | C | T | A0201,A2601,B3501,B4402,C0401,C0501 | A0201 | 268 | 165 | alaTaaata | alaAaaata |
| BL3403 | CNTFR | 9 | 34552193 | C | T | A0201,A2601,B3501,B4402,C0401,C0501 | B3501 | 80 | 65 | vpitlalaT | vpitlalaA |
| BL3403 | CNTFR | 9 | 34552193 | C | T | A0201,A2601,B3501,B4402,C0401,C0501 | B3501 | 423 | 192 | lalaTaaat | lalaAaaat |
| BL3403 | CNTFR | 9 | 34552193 | C | T | A0201,A2601,B3501,B4402,C0401,C0501 | B3501 | 185 | 78 | laTaaatas | laAaaatas |
| BL3403 | CNTFR | 9 | 34552193 | C | T | A0201,A2601,B3501,B4402,C0401,C0501 | B3501 | 140 | 1099 | Taaatassl | Aaaatassl |
| BL3403 | KCNT1 | 9 | 138678262 | A | T | A0201,A2601,B3501,B4402,C0401,C0501 | A2601 | 163 | 5853 | Fsqqrlsly | Isqqrlsly |
| BL3403 | KCNT1 | 9 | 138678262 | A | T | A0201,A2601,B3501,B4402,C0401,C0501 | B4402 | 94 | 54 | aewFsqqrl | aewIsqqrl |
| BL3403 | RNF208 | 9 | 140114887 | T | C | A0201,A2601,B3501,B4402,C0401,C0501 | B3501 | 20 | 33 | nplsacsVm | nplsacsIm |
| BL3403 | MID1 | X | 10427815 | C | T | A0201,A2601,B3501,B4402,C0401,C0501 | B3501 | 428 | 1060 | Ipnikqnhy | Vpnikqnhy |
| BL3403 | CASK | X | 41712385 | G | A | A0201,A2601,B3501,B4402,C0401,C0501 | A2601 | 163 | 9985 | dvakftssL | dvakftssP |
| BL3403 | WNK3 | X | 54319707 | T | A | A0201,A2601,B3501,B4402,C0401,C0501 | B3501 | 178 | 32 | tsCqpsvay | tsSqpsvay |
| BL3403 | PLXNB3 | X | 153040204 | G | A | A0201,A2601,B3501,B4402,C0401,C0501 | A0201 | 473 | 905 | kvlMqlesl | kvlVqlesl |
| CA9903 | TAS1R2 | 1 | 19166269 | C | A | A0201,A1101,B1801,B5108,C0701,C1602 | A0201 | 21 | 22 | fmsSysgvl | fmsAysgvl |
| CA9903 | TAS1R2 | 1 | 19166269 | C | A | A0201,A1101,B1801,B5108,C0701,C1602 | A1101 | 73 | 91 | slctfmsSy | slctfmsAy |
| CA9903 | TAS1R2 | 1 | 19166269 | C | A | A0201,A1101,B1801,B5108,C0701,C1602 | C0701 | 368 | 676 | fmsSysgvl | fmsAysgvl |
| CA9903 | TMCO4 | 1 | 20072046 | A | T | A0201,A1101,B1801,B5108,C0701,C1602 | A1101 | 51 | 32 | vtgRlasgk | vtgWlasgk |
| CA9903 | SRRM1 | 1 | 24978938 | G | A | A0201,A1101,B1801,B5108,C0701,C1602 | A1101 | 33 | 55 | tsdilkIpk | tsdilkVpk |
| CA9903 | INADL | 1 | 62550226 | G | T | A0201,A1101,B1801,B5108,C0701,C1602 | A0201 | 43 | 400 | svdpatFpi | svdpatCpi |

Figure 21 (Cont.)

| | | | | | | | | | | | |
|---|---|---|---|---|---|---|---|---|---|---|---|
| CA9903 | DNAJB4 | 1 | 78478867 | G | A | A0201,A1101,B1801,B5108,C0701,C1602 | B1801 | 67 | 192 | feiffgrQm | feiffgrRm |
| CA9903 | MCOLN2 | 1 | 85462501 | C | T | A0201,A1101,B1801,B5108,C0701,C1602 | A1101 | 464 | 12489 | sSvfrltvr | sGvfrltvr |
| CA9903 | NTNG1 | 1 | 107867043 | C | A | A0201,A1101,B1801,B5108,C0701,C1602 | C0701 | 358 | 22412 | kHlqvnitl | kPlqvnitl |
| CA9903 | S100A12 | 1 | 153346398 | C | G | A0201,A1101,B1801,B5108,C0701,C1602 | C0701 | 95 | 10769 | lHanqdeqv | lDanqdeqv |
| CA9903 | OR6N2 | 1 | 158746857 | T | A | A0201,A1101,B1801,B5108,C0701,C1602 | A0201 | 200 | 466 | slacMdtsa | slacKdtsa |
| CA9903 | ATP1A4 | 1 | 160136781 | G | T | A0201,A1101,B1801,B5108,C0701,C1602 | A0201 | 43 | 8973 | Ytwfmlari | Dtwfmlari |
| CA9903 | ATP1A4 | 1 | 160136781 | G | T | A0201,A1101,B1801,B5108,C0701,C1602 | A1101 | 103 | 1951 | ssYtwfmla | ssDtwfmla |
| CA9903 | ATP1A4 | 1 | 160136781 | G | T | A0201,A1101,B1801,B5108,C0701,C1602 | A1101 | 292 | 5238 | sYtwfmlar | sDtwfmlar |
| CA9903 | ATP1A4 | 1 | 160136781 | G | T | A0201,A1101,B1801,B5108,C0701,C1602 | C0701 | 437 | 1717 | tkssYtwfm | tkssDtwfm |
| CA9903 | NOS1AP | 1 | 162313652 | G | T | A0201,A1101,B1801,B5108,C0701,C1602 | A0201 | 43 | 233 | rtLgqafev | rtVgqafev |
| CA9903 | DUSP27 | 1 | 167095803 | G | T | A0201,A1101,B1801,B5108,C0701,C1602 | A1101 | 66 | 119 | stwdSwner | stwdAwner |
| CA9903 | PAPPA2 | 1 | 176525894 | G | T | A0201,A1101,B1801,B5108,C0701,C1602 | A0201 | 59 | 28 | llgdddSyl | llgdddAyl |
| CA9903 | ASPM | 1 | 197070277 | G | T | A0201,A1101,B1801,B5108,C0701,C1602 | A1101 | 151 | 505 | iqsfyrmNr | iqsfyrmHr |
| CA9903 | ASPM | 1 | 197070277 | G | T | A0201,A1101,B1801,B5108,C0701,C1602 | A1101 | 262 | 189 | sfyrmNrak | sfyrmHrak |
| CA9903 | CR2 | 1 | 207641886 | T | A | A0201,A1101,B1801,B5108,C0701,C1602 | B1801 | 313 | 204 | leSpalpmi | leCpalpmi |
| CA9903 | KCNH1 | 1 | 210857395 | G | T | A0201,A1101,B1801,B5108,C0701,C1602 | A0201 | 35 | 83 | lilpQdhpv | lilpPdhpv |
| CA9903 | KCNH1 | 1 | 210857395 | G | T | A0201,A1101,B1801,B5108,C0701,C1602 | B1801 | 22 | 436 | neaplilpQ | neaplilpP |
| CA9903 | PROX1 | 1 | 214171100 | C | A | A0201,A1101,B1801,B5108,C0701,C1602 | C0701 | 224 | 125 | fhtanqSlq | fhtanqRlq |
| CA9903 | GPR137B | 1 | 236341907 | T | C | A0201,A1101,B1801,B5108,C0701,C1602 | A0201 | 37 | 20 | kmPlaniyl | kmSlaniyl |
| CA9903 | EDARADD | 1 | 236577563 | G | T | A0201,A1101,B1801,B5108,C0701,C1602 | A0201 | 332 | 1921 | fnmsYkypi | fnmsDkypi |
| CA9903 | EDARADD | 1 | 236577563 | G | T | A0201,A1101,B1801,B5108,C0701,C1602 | A1101 | 15 | 6397 | stlsfnmsY | stlsfnmsD |
| CA9903 | EDARADD | 1 | 236577563 | G | T | A0201,A1101,B1801,B5108,C0701,C1602 | A1101 | 16 | 86 | tlsfnmsYk | tlsfnmsDk |

Figure 21 (Cont.)

| | | | | | | | | | | | |
|---|---|---|---|---|---|---|---|---|---|---|---|
| CA9903 | EDARADD | 1 | 236577563 | G | T | A0201,A1101,B1801,B5108,C0701,C1602 | A1101 | 92 | 670 | lsfnmsYky | lsfnmsDky |
| CA9903 | RYR2 | 1 | 237617843 | T | A | A0201,A1101,B1801,B5108,C0701,C1602 | A1101 | 39 | 26 | kqnrlraQk | kqnrlraLk |
| CA9903 | RYR2 | 1 | 237801694 | G | T | A0201,A1101,B1801,B5108,C0701,C1602 | A0201 | 17 | 25 | glqsFqmlv | glqsCqmlv |
| CA9903 | RYR2 | 1 | 237801694 | G | T | A0201,A1101,B1801,B5108,C0701,C1602 | A1101 | 27 | 68 | qsFqmlvsk | qsCqmlvsk |
| CA9903 | MLLT10 | 10 | 21845663 | G | A | A0201,A1101,B1801,B5108,C0701,C1602 | C0701 | 408 | 592 | casphpQcl | casphpRcl |
| CA9903 | PARD3 | 10 | 34420482 | C | A | A0201,A1101,B1801,B5108,C0701,C1602 | C0701 | 126 | 21 | snhdLiqrl | snhdRiqrl |
| CA9903 | MYPN | 10 | 69961673 | G | T | A0201,A1101,B1801,B5108,C0701,C1602 | A0201 | 15 | 19 | Lvigmpppv | Rvigmpppv |
| CA9903 | MYPN | 10 | 69961673 | G | T | A0201,A1101,B1801,B5108,C0701,C1602 | C0701 | 279 | 13281 | ghpvrlecL | ghpvrlecR |
| CA9903 | AIFM2 | 10 | 71883672 | C | A | A0201,A1101,B1801,B5108,C0701,C1602 | A1101 | 18 | 23 | asLetgfak | asVetgfak |
| CA9903 | AIFM2 | 10 | 71883672 | C | A | A0201,A1101,B1801,B5108,C0701,C1602 | A1101 | 192 | 42 | sLetgfakk | sVetgfakk |
| CA9903 | LRIT1 | 10 | 85992587 | G | A | A0201,A1101,B1801,B5108,C0701,C1602 | C0701 | 23 | 17 | shldFgdyi | shldSgdyi |
| CA9903 | DUSP5 | 10 | 112269893 | G | T | A0201,A1101,B1801,B5108,C0701,C1602 | A0201 | 231 | 244 | rlkDafdyi | rlkEafdyi |
| CA9903 | WDR11 | 10 | 122662647 | C | A | A0201,A1101,B1801,B5108,C0701,C1602 | A1101 | 22 | 16 | ksDsttapk | ksAsttapk |
| CA9903 | ACADSB | 10 | 124810613 | A | G | A0201,A1101,B1801,B5108,C0701,C1602 | B1801 | 6 | 12 | leaaGllty | leaaRllty |
| CA9903 | OR10A3 | 11 | 7960443 | C | A | A0201,A1101,B1801,B5108,C0701,C1602 | A0201 | 14 | 12 | ilivmFpfl | ilivmVpfl |
| CA9903 | OR10A3 | 11 | 7960443 | C | A | A0201,A1101,B1801,B5108,C0701,C1602 | A0201 | 75 | 141 | livmFpfll | livmVpfll |
| CA9903 | OR10A3 | 11 | 7960443 | C | A | A0201,A1101,B1801,B5108,C0701,C1602 | A0201 | 325 | 613 | ivmFpflli | ivmVpflli |
| CA9903 | OR10A3 | 11 | 7960443 | C | A | A0201,A1101,B1801,B5108,C0701,C1602 | A0201 | 11 | 29 | vmFpfllil | vmVpfllil |
| CA9903 | LRRC4C | 11 | 40136052 | G | T | A0201,A1101,B1801,B5108,C0701,C1602 | A1101 | 36 | 28 | hlnQynsyk | hlnHynsyk |
| CA9903 | LRRC4C | 11 | 40136052 | G | T | A0201,A1101,B1801,B5108,C0701,C1602 | B1801 | 12 | 22 | iehehlnQy | iehehlnHy |
| CA9903 | OR4A5 | 11 | 51412022 | C | A | A0201,A1101,B1801,B5108,C0701,C1602 | A0201 | 47 | 755 | aiFkplhyl | aiCkplhyl |
| CA9903 | OR8K1 | 11 | 56114142 | G | T | A0201,A1101,B1801,B5108,C0701,C1602 | A0201 | 58 | 254 | ilifsCcnl | ilifsGcnl |
| CA9903 | OR8K1 | 11 | 56114142 | G | T | A0201,A1101,B1801,B5108,C0701,C1602 | A0201 | 78 | 128 | lifsCcnll | lifsGcnll |

Figure 21 (Cont.)

| | | | | | | | | | | | |
|---|---|---|---|---|---|---|---|---|---|---|---|
| CA9903 | OR9Q2 | 11 | 57958288 | C | T | A0201,A1101,B1801,B5108,C0701,C1602 | A0201 | 4 | 5 | flftffaFi | flftffaSi |
| CA9903 | OR9Q2 | 11 | 57958288 | C | T | A0201,A1101,B1801,B5108,C0701,C1602 | A0201 | 99 | 772 | faFidcyll | faSidcyll |
| CA9903 | OR9Q2 | 11 | 57958288 | C | T | A0201,A1101,B1801,B5108,C0701,C1602 | A0201 | 8 | 59 | Fidcyllai | Sidcyllai |
| CA9903 | OR9Q2 | 11 | 57958288 | C | T | A0201,A1101,B1801,B5108,C0701,C1602 | B1801 | 451 | 11841 | fflftffaF | fflftffaS |
| CA9903 | GLYATL1 | 11 | 58711064 | G | A | A0201,A1101,B1801,B5108,C0701,C1602 | C0701 | 4 | 5 | Trsehgryl | Arsehgryl |
| CA9903 | CCDC88B | 11 | 64112394 | G | A | A0201,A1101,B1801,B5108,C0701,C1602 | A0201 | 81 | 1172 | rlQeaveaa | rlReaveaa |
| CA9903 | OR8B8 | 11 | 124310402 | C | A | A0201,A1101,B1801,B5108,C0701,C1602 | A0201 | 3 | 6 | yLnelvvfv | yVnelvvfv |
| CA9903 | PRDM10 | 11 | 129782029 | T | A | A0201,A1101,B1801,B5108,C0701,C1602 | C0701 | 275 | 136 | qhaiqvLhi | qhaiqvQhi |
| CA9903 | VWF | 12 | 6155892 | G | C | A0201,A1101,B1801,B5108,C0701,C1602 | A1101 | 165 | 257 | ssplshGsk | ssplshRsk |
| CA9903 | PIK3C2G | 12 | 18719941 | C | G | A0201,A1101,B1801,B5108,C0701,C1602 | C0701 | 439 | 968 | rrfrdVnhy | rrfrdLnhy |
| CA9903 | KRAS | 12 | 25398285 | C | A | A0201,A1101,B1801,B5108,C0701,C1602 | A1101 | 69 | 107 | vvgaCgvgk | vvgaGgvgk |
| CA9903 | POP5 | 12 | 121018918 | C | T | A0201,A1101,B1801,B5108,C0701,C1602 | A1101 | 70 | 4141 | aStirtcqk | aGtirtcqk |
| CA9903 | LATS2 | 13 | 21549285 | C | T | A0201,A1101,B1801,B5108,C0701,C1602 | A0201 | 50 | 381 | yvptishpl | yvptishpM |
| CA9903 | UPF3A | 13 | 115047496 | G | C | A0201,A1101,B1801,B5108,C0701,C1602 | A1101 | 370 | 221 | alskLvirr | alskVvirr |
| CA9903 | UPF3A | 13 | 115047496 | G | C | A0201,A1101,B1801,B5108,C0701,C1602 | C0701 | 388 | 591 | krtalskLv | krtalskVv |
| CA9903 | TGM1 | 14 | 24730916 | G | A | A0201,A1101,B1801,B5108,C0701,C1602 | B1801 | 6 | 37 | yessdritF | yessdritL |
| CA9903 | BCL11B | 14 | 99641604 | G | T | A0201,A1101,B1801,B5108,C0701,C1602 | C0701 | 37 | 55 | rhhesEpsl | rhhesDpsl |
| CA9903 | MTA1 | 14 | 105929881 | C | T | A0201,A1101,B1801,B5108,C0701,C1602 | A1101 | 22 | 24 | qvyiSnynk | qvyiPnynk |
| CA9903 | HERC1 | 15 | 63948325 | G | A | A0201,A1101,B1801,B5108,C0701,C1602 | A1101 | 17 | 18 | asnaSsaak | asnaPsaak |
| CA9903 | SLC9A3R2 | 16 | 2087885 | C | T | A0201,A1101,B1801,B5108,C0701,C1602 | A0201 | 442 | 798 | hlspMaaea | hlspTaaea |
| CA9903 | DNAH3 | 16 | 21151969 | A | G | A0201,A1101,B1801,B5108,C0701,C1602 | A1101 | 321 | 274 | tsStfpgsr | tsLtfpgsr |
| CA9903 | DNAH3 | 16 | 21151969 | A | G | A0201,A1101,B1801,B5108,C0701,C1602 | B1801 | 117 | 63 | kevktsStf | kevktsLtf |

Figure 21 (Cont.)

| | | | | | | | | | | | |
|---|---|---|---|---|---|---|---|---|---|---|---|
| CA9903 | MMP2 | 16 | 55518075 | G | T | A0201,A1101,B1801,B5108,C0701,C1602 | B1801 | 5 | 3 | Cehgdgypf | Wehgdgypf |
| CA9903 | VPS53 | 17 | 526807 | C | A | A0201,A1101,B1801,B5108,C0701,C1602 | A0201 | 87 | 20112 | kLfsgctlt | kRfsgctlt |
| CA9903 | VPS53 | 17 | 526807 | C | A | A0201,A1101,B1801,B5108,C0701,C1602 | B1801 | 65 | 267 | fegflakLf | fegflakRf |
| CA9903 | ATP2A3 | 17 | 3832738 | C | T | A0201,A1101,B1801,B5108,C0701,C1602 | C0701 | 189 | 114 | slsenqsll | sVsenqsll |
| CA9903 | PELP1 | 17 | 4576733 | G | A | A0201,A1101,B1801,B5108,C0701,C1602 | A0201 | 3 | 8 | rlhdlvFpl | rlhdlvLpl |
| CA9903 | PELP1 | 17 | 4576733 | G | A | A0201,A1101,B1801,B5108,C0701,C1602 | A0201 | 20 | 25 | lvFplvmgv | lvLplvmgv |
| CA9903 | SLC2A4 | 17 | 7187403 | G | A | A0201,A1101,B1801,B5108,C0701,C1602 | A0201 | 23 | 18 | illTqvlgl | illAqvlgl |
| CA9903 | TP53 | 17 | 7578394 | T | C | A0201,A1101,B1801,B5108,C0701,C1602 | C0701 | 337 | 431 | rrcphRerc | rrcphHerc |
| CA9903 | CTC1 | 17 | 8136328 | G | T | A0201,A1101,B1801,B5108,C0701,C1602 | A1101 | 72 | 41 | gvlvDsshk | gvlvAsshk |
| CA9903 | MYOCD | 17 | 12655927 | C | T | A0201,A1101,B1801,B5108,C0701,C1602 | A0201 | 22 | 538 | yqsssstsV | yqsssstsA |
| CA9903 | MYOCD | 17 | 12655927 | C | T | A0201,A1101,B1801,B5108,C0701,C1602 | A1101 | 36 | 190 | sVlsngfyh | sAlsngfyh |
| CA9903 | TMEM98 | 17 | 31263385 | G | A | A0201,A1101,B1801,B5108,C0701,C1602 | A0201 | 51 | 216 | tltekIval | tltekIvaM |
| CA9903 | TMEM98 | 17 | 31263385 | G | A | A0201,A1101,B1801,B5108,C0701,C1602 | A1101 | 140 | 212 | altmgsgak | aMtmgsgak |
| CA9903 | TMEM98 | 17 | 31263385 | G | A | A0201,A1101,B1801,B5108,C0701,C1602 | B1801 | 36 | 29 | teklvaltm | teklvaMtm |
| CA9903 | LHX1 | 17 | 35297786 | G | T | A0201,A1101,B1801,B5108,C0701,C1602 | A1101 | 21 | 53 | ylsnssFak | ylsnssVak |
| CA9903 | KRT14 | 17 | 39739912 | C | T | A0201,A1101,B1801,B5108,C0701,C1602 | A0201 | 393 | 6418 | kteelnHev | kteelnRev |
| CA9903 | CDC27 | 17 | 45247329 | C | A | A0201,A1101,B1801,B5108,C0701,C1602 | A0201 | 488 | 2811 | fCdsacftl | fGdsacftl |
| CA9903 | CDC27 | 17 | 45247329 | C | A | A0201,A1101,B1801,B5108,C0701,C1602 | B1801 | 34 | 17 | tefCdsacf | tefGdsacf |
| CA9903 | PRAC1 | 17 | 46799723 | G | T | A0201,A1101,B1801,B5108,C0701,C1602 | A1101 | 94 | 10796 | gQahlttsk | gPahlttsk |
| CA9903 | TRIM37 | 17 | 57125098 | G | A | A0201,A1101,B1801,B5108,C0701,C1602 | A0201 | 120 | 2189 | qldgssssV | qldgssssA |
| CA9903 | INTS2 | 17 | 59975056 | A | T | A0201,A1101,B1801,B5108,C0701,C1602 | A0201 | 59 | 37 | mvvwlswKi | mvvwlswMi |
| CA9903 | INTS2 | 17 | 59975056 | A | T | A0201,A1101,B1801,B5108,C0701,C1602 | A1101 | 288 | 20377 | lmvvwlswK | lmvvwlswM |
| CA9903 | INTS2 | 17 | 59975056 | A | T | A0201,A1101,B1801,B5108,C0701,C1602 | A1101 | 176 | 19 | vvwlswKik | vvwlswMik |

Figure 21 (Cont.)

| | | | | | | | | | | | |
|---|---|---|---|---|---|---|---|---|---|---|---|
| CA9903 | BPTF | 17 | 65890224 | G | T | A0201,A1101,B1801,B5108,C0701,C1602 | A0201 | 15 | 84 | alaileFav | alaileCav |
| CA9903 | BPTF | 17 | 65890224 | G | T | A0201,A1101,B1801,B5108,C0701,C1602 | A0201 | 313 | 235 | ileFavkpv | ileCavkpv |
| CA9903 | BPTF | 17 | 65890224 | G | T | A0201,A1101,B1801,B5108,C0701,C1602 | A1101 | 242 | 1500 | laileFavk | laileCavk |
| CA9903 | BPTF | 17 | 65890224 | G | T | A0201,A1101,B1801,B5108,C0701,C1602 | B1801 | 24 | 133 | leFavkpvv | leCavkpvv |
| CA9903 | ABCA6 | 17 | 67075130 | T | A | A0201,A1101,B1801,B5108,C0701,C1602 | A0201 | 282 | 26088 | tmrwkllpL | tmrwkllpH |
| CA9903 | SDK2 | 17 | 71398257 | C | A | A0201,A1101,B1801,B5108,C0701,C1602 | C0701 | 36 | 3268 | eHeeevtmv | eQeeevtmv |
| CA9903 | PIEZO2 | 18 | 10696494 | G | A | A0201,A1101,B1801,B5108,C0701,C1602 | A0201 | 87 | 1434 | Fihpeysav | Lihpeysav |
| CA9903 | PIEZO2 | 18 | 10696494 | G | A | A0201,A1101,B1801,B5108,C0701,C1602 | A1101 | 167 | 489 | kqffynFih | kqffynLih |
| CA9903 | MUC16 | 19 | 9002632 | C | A | A0201,A1101,B1801,B5108,C0701,C1602 | A1101 | 143 | 783 | rvdavFthr | rvdavCthr |
| CA9903 | OR7G1 | 19 | 9225670 | C | G | A0201,A1101,B1801,B5108,C0701,C1602 | A0201 | 21 | 1101 | slfygtafA | slfygtafG |
| CA9903 | OR7G1 | 19 | 9225670 | C | G | A0201,A1101,B1801,B5108,C0701,C1602 | A0201 | 146 | 3144 | fAvyissav | fGvyissav |
| CA9903 | ZNF675 | 19 | 23836812 | C | A | A0201,A1101,B1801,B5108,C0701,C1602 | C0701 | 203 | 15327 | tthkkihtV | tthkkihtG |
| CA9903 | ZNF675 | 19 | 23836812 | C | A | A0201,A1101,B1801,B5108,C0701,C1602 | C0701 | 250 | 58 | ihtVeqpyi | ihtGeqpyi |
| CA9903 | ZNF226 | 19 | 44679169 | G | T | A0201,A1101,B1801,B5108,C0701,C1602 | A0201 | 99 | 344 | lllyYlaqt | lllyDlaqt |
| CA9903 | ZNF226 | 19 | 44679169 | G | T | A0201,A1101,B1801,B5108,C0701,C1602 | A1101 | 183 | 17569 | lvkalllyY | lvkalllyD |
| CA9903 | C5AR1 | 19 | 47823770 | G | T | A0201,A1101,B1801,B5108,C0701,C1602 | A0201 | 64 | 60 | ktlkvvCav | ktlkvvVav |
| CA9903 | LILRB3 | 19 | 54725905 | G | T | A0201,A1101,B1801,B5108,C0701,C1602 | A0201 | 487 | 945 | sqkgyQhfv | sqkgyHhfv |
| CA9903 | LILRB3 | 19 | 54725905 | G | T | A0201,A1101,B1801,B5108,C0701,C1602 | A1101 | 63 | 83 | gyQhfvlmk | gyHhfvlmk |
| CA9903 | NLRP7 | 19 | 55450270 | G | T | A0201,A1101,B1801,B5108,C0701,C1602 | B1801 | 116 | 82 | mdfelEief | mdfelDief |
| CA9903 | NLRP7 | 19 | 55450270 | G | T | A0201,A1101,B1801,B5108,C0701,C1602 | B1801 | 474 | 1478 | felEiefes | felDiefes |
| CA9903 | NLRP7 | 19 | 55450270 | G | T | A0201,A1101,B1801,B5108,C0701,C1602 | C0701 | 286 | 1482 | nymdfelEi | nymdfelDi |
| CA9903 | NLRP11 | 19 | 56303739 | C | A | A0201,A1101,B1801,B5108,C0701,C1602 | A0201 | 126 | 16885 | rqldlcvnL | rqldlcvnR |

Figure 21 (Cont.)

| | | | | | | | | | | | |
|---|---|---|---|---|---|---|---|---|---|---|---|
| CA9903 | NLRP11 | 19 | 56303739 | C | A | A0201,A1101,B1801,B5108,C0701,C1602 | A0201 | 448 | 765 | qldlcvnLl | qldlcvnRl |
| CA9903 | DQX1 | 2 | 74750345 | C | A | A0201,A1101,B1801,B5108,C0701,C1602 | C0701 | 249 | 120 | lrsFynpri | lrsVynpri |
| CA9903 | SEMA4C | 2 | 97527324 | C | A | A0201,A1101,B1801,B5108,C0701,C1602 | A1101 | 72 | 43 | gicnlrglk | gicnlrgSk |
| CA9903 | MYO7B | 2 | 128390864 | G | A | A0201,A1101,B1801,B5108,C0701,C1602 | A0201 | 196 | 250 | kqpphqMev | kqpphqVev |
| CA9903 | WDR33 | 2 | 128471571 | T | A | A0201,A1101,B1801,B5108,C0701,C1602 | C0701 | 108 | 93 | srgppnLhm | srgppnHhm |
| CA9903 | LRP1B | 2 | 141533727 | G | T | A0201,A1101,B1801,B5108,C0701,C1602 | C0701 | 143 | 275 | lrnktsgvv | Lrnktsgvv |
| CA9903 | GALNT5 | 2 | 158142604 | G | T | A0201,A1101,B1801,B5108,C0701,C1602 | C0701 | 318 | 304 | lrlkerhCl | lrlkerhGl |
| CA9903 | TTN | 2 | 179612473 | T | A | A0201,A1101,B1801,B5108,C0701,C1602 | A0201 | 31 | 9573 | emietsfsL | emietsfsQ |
| CA9903 | TTN | 2 | 179612473 | T | A | A0201,A1101,B1801,B5108,C0701,C1602 | A1101 | 10 | 11 | tsfsLnipk | tsfsQnipk |
| CA9903 | TTN | 2 | 179654796 | G | A | A0201,A1101,B1801,B5108,C0701,C1602 | A0201 | 63 | 108 | kvivVtpkv | kvivAtpkv |
| CA9903 | ALS2 | 2 | 202591214 | C | T | A0201,A1101,B1801,B5108,C0701,C1602 | A1101 | 56 | 17266 | sgmfrnglK | sgmfrnglE |
| CA9903 | ALS2 | 2 | 202591214 | C | T | A0201,A1101,B1801,B5108,C0701,C1602 | C0701 | 356 | 677 | frnglKdgy | frnglEdgy |
| CA9903 | CD28 | 2 | 204594440 | G | T | A0201,A1101,B1801,B5108,C0701,C1602 | A0201 | 96 | 526 | wvlvvvVgv | wvlvvvGgv |
| CA9903 | ITM2C | 2 | 231729855 | G | A | A0201,A1101,B1801,B5108,C0701,C1602 | B1801 | 158 | 218 | teilltpTr | teilltpAr |
| CA9903 | OR6B2 | 2 | 240969313 | G | T | A0201,A1101,B1801,B5108,C0701,C1602 | A0201 | 251 | 449 | vlnhfLcdi | vlnhfFcdi |
| CA9903 | OR6B2 | 2 | 240969313 | G | T | A0201,A1101,B1801,B5108,C0701,C1602 | A0201 | 5 | 3107 | fLcdispil | fFcdispil |
| CA9903 | APMAP | 20 | 24952097 | T | A | A0201,A1101,B1801,B5108,C0701,C1602 | C0701 | 221 | 280 | evnpwNrev | evnpwKrev |
| CA9903 | KCNG1 | 20 | 49626764 | C | A | A0201,A1101,B1801,B5108,C0701,C1602 | A1101 | 110 | 173 | qaikgSfyr | qaikgAfyr |
| CA9903 | KCNG1 | 20 | 49626764 | C | A | A0201,A1101,B1801,B5108,C0701,C1602 | A1101 | 224 | 511 | aikgSfyrr | aikgAfyrr |
| CA9903 | KCNG1 | 20 | 49626764 | C | A | A0201,A1101,B1801,B5108,C0701,C1602 | A1101 | 121 | 587 | gSfyrraqr | gAfyrraqr |
| CA9903 | KCNG1 | 20 | 49626764 | C | A | A0201,A1101,B1801,B5108,C0701,C1602 | C0701 | 236 | 678 | Sfyrraqrl | Afyrraqrl |
| CA9903 | TSHZ2 | 20 | 51870152 | A | T | A0201,A1101,B1801,B5108,C0701,C1602 | B1801 | 328 | 516 | Veletgpeq | Eeletgpeq |
| CA9903 | SMTN | 22 | 31484745 | C | T | A0201,A1101,B1801,B5108,C0701,C1602 | C0701 | 21 | 19 | irrvWaqei | irrvRaqei |

Figure 21 (Cont.)

| | | | | | | | | | | | |
|---|---|---|---|---|---|---|---|---|---|---|---|
| CA9903 | INPP5J | 22 | 31520945 | G | A | A0201,A1101,B1801,B5108,C0701,C1602 | A1101 | 151 | 17648 | aamsasseR | aamsasseG |
| CA9903 | KCNJ4 | 22 | 38823622 | C | A | A0201,A1101,B1801,B5108,C0701,C1602 | A1101 | 44 | 34 | fmigtilak | fmigtiMak |
| CA9903 | KCNJ4 | 22 | 38823622 | C | A | A0201,A1101,B1801,B5108,C0701,C1602 | A1101 | 252 | 99 | gtilakmar | gtiMakmar |
| CA9903 | KCNJ4 | 22 | 38823622 | C | A | A0201,A1101,B1801,B5108,C0701,C1602 | A1101 | 80 | 124 | ilakmarpk | iMakmarpk |
| CA9903 | SREBF2 | 22 | 42266968 | A | T | A0201,A1101,B1801,B5108,C0701,C1602 | A0201 | 81 | 70 | vLaavqnpa | vMaavqnpa |
| CA9903 | ITGA9 | 3 | 37670769 | C | T | A0201,A1101,B1801,B5108,C0701,C1602 | A0201 | 303 | 2762 | elLpltpvl | elPpltpvl |
| CA9903 | BSN | 3 | 49689586 | G | T | A0201,A1101,B1801,B5108,C0701,C1602 | A1101 | 20 | 20 | atsVrglak | atsGrglak |
| CA9903 | STAB1 | 3 | 52551123 | A | T | A0201,A1101,B1801,B5108,C0701,C1602 | A0201 | 17 | 4600 | ymgdgelcL | ymgdgelcQ |
| CA9903 | VGLL3 | 3 | 87027729 | T | A | A0201,A1101,B1801,B5108,C0701,C1602 | A0201 | 101 | 25233 | algqaitlL | algqaitlH |
| CA9903 | BOC | 3 | 112968688 | G | T | A0201,A1101,B1801,B5108,C0701,C1602 | A0201 | 310 | 4892 | gmSpevtla | gmRpevtla |
| CA9903 | SIDT1 | 3 | 113330984 | G | T | A0201,A1101,B1801,B5108,C0701,C1602 | A0201 | 9 | 44 | vifsaihFl | vifsaihVl |
| CA9903 | SIDT1 | 3 | 113330984 | G | T | A0201,A1101,B1801,B5108,C0701,C1602 | A0201 | 282 | 504 | saihFlasl | saihVlasl |
| CA9903 | SIDT1 | 3 | 113330984 | G | T | A0201,A1101,B1801,B5108,C0701,C1602 | A0201 | 42 | 489 | Flaslalst | Vlaslalst |
| CA9903 | SIDT1 | 3 | 113330984 | G | T | A0201,A1101,B1801,B5108,C0701,C1602 | C0701 | 50 | 457 | ihFlaslal | ihVlaslal |
| CA9903 | PDIA5 | 3 | 122873818 | G | T | A0201,A1101,B1801,B5108,C0701,C1602 | A0201 | 47 | 17692 | tlvmfyapL | tlvmfyapW |
| CA9903 | SHOX2 | 3 | 157815905 | C | A | A0201,A1101,B1801,B5108,C0701,C1602 | A1101 | 28 | 37 | vvaaSaaak | vvaaAaaak |
| CA9903 | SHOX2 | 3 | 157815905 | C | A | A0201,A1101,B1801,B5108,C0701,C1602 | A1101 | 42 | 68 | Saaakttsk | Aaaakttsk |
| CA9903 | WDR49 | 3 | 167277886 | C | A | A0201,A1101,B1801,B5108,C0701,C1602 | A0201 | 191 | 433 | aldanetLl | aldanetRl |
| CA9903 | WDR49 | 3 | 167277886 | C | A | A0201,A1101,B1801,B5108,C0701,C1602 | B1801 | 456 | 1943 | netLlltgs | netRlltgs |
| CA9903 | WDR49 | 3 | 167277886 | C | A | A0201,A1101,B1801,B5108,C0701,C1602 | C0701 | 294 | 11496 | maldanetL | maldanetR |
| CA9903 | JAKMIP1 | 4 | 6107622 | A | G | A0201,A1101,B1801,B5108,C0701,C1602 | A1101 | 30 | 26 | htaHiselk | htaYiselk |
| CA9903 | JAKMIP1 | 4 | 6107622 | A | G | A0201,A1101,B1801,B5108,C0701,C1602 | C0701 | 9 | 11 | rhtaHisel | rhtaYisel |

Figure 21 (Cont.)

| | | | | | | | | | | | |
|---|---|---|---|---|---|---|---|---|---|---|---|
| CA9903 | APBB2 | 4 | 40827923 | T | A | A0201,A1101,B1801,B5108,C0701,C1602 | A0201 | 6 | 24 | vqylgmFpv | vqylgmLpv |
| CA9903 | APBB2 | 4 | 40827923 | T | A | A0201,A1101,B1801,B5108,C0701,C1602 | A0201 | 27 | 43 | gmFpvdkpv | gmLpvdkpv |
| CA9903 | APBB2 | 4 | 40827923 | T | A | A0201,A1101,B1801,B5108,C0701,C1602 | C0701 | 170 | 26 | fhvqylgmF | fhvqylgmL |
| CA9903 | GABRB1 | 4 | 47322211 | C | A | A0201,A1101,B1801,B5108,C0701,C1602 | B1801 | 167 | 402 | deqnctMei | deqnctLei |
| CA9903 | EGF | 4 | 110862211 | G | A | A0201,A1101,B1801,B5108,C0701,C1602 | A1101 | 72 | 102 | iIdfhynek | iMdfhynek |
| CA9903 | UGT8 | 4 | 115597231 | G | T | A0201,A1101,B1801,B5108,C0701,C1602 | A0201 | 415 | 878 | isfcHyfll | isfcQyfll |
| CA9903 | UGT8 | 4 | 115597231 | G | T | A0201,A1101,B1801,B5108,C0701,C1602 | A1101 | 427 | 9022 | avhqisfcH | avhqisfcQ |
| CA9903 | UGT8 | 4 | 115597231 | G | T | A0201,A1101,B1801,B5108,C0701,C1602 | B1801 | 398 | 835 | Hyflldiaf | Qyflldiaf |
| CA9903 | ZNF827 | 4 | 146770524 | C | A | A0201,A1101,B1801,B5108,C0701,C1602 | A0201 | 55 | 15 | nlflqdisv | nlfSqdisv |
| CA9903 | ZNF827 | 4 | 146770524 | C | A | A0201,A1101,B1801,B5108,C0701,C1602 | A0201 | 145 | 6730 | flqdisvkm | fSqdisvkm |
| CA9903 | TENM3 | 4 | 183603095 | C | A | A0201,A1101,B1801,B5108,C0701,C1602 | B1801 | 178 | 49 | dqcsgNgty | dqcsgHgty |
| CA9903 | CTNND2 | 5 | 11159732 | C | G | A0201,A1101,B1801,B5108,C0701,C1602 | C0701 | 34 | 2148 | iHlhssqvl | iQlhssqvl |
| CA9903 | SPEF2 | 5 | 35704717 | C | G | A0201,A1101,B1801,B5108,C0701,C1602 | A1101 | 38 | 17123 | isqrvaaeK | isqrvaaeN |
| CA9903 | RASGRF2 | 5 | 80375978 | G | T | A0201,A1101,B1801,B5108,C0701,C1602 | A0201 | 4 | 370 | flheifhqV | flheifhqG |
| CA9903 | RASGRF2 | 5 | 80375978 | G | T | A0201,A1101,B1801,B5108,C0701,C1602 | C0701 | 182 | 427 | lheifhqVl | lheifhqGl |
| CA9903 | RASGRF2 | 5 | 80375978 | G | T | A0201,A1101,B1801,B5108,C0701,C1602 | C0701 | 215 | 58 | fhqVlkari | fhqGlkari |
| CA9903 | TMED7-TICAM2 | 5 | 114916850 | T | C | A0201,A1101,B1801,B5108,C0701,C1602 | C0701 | 171 | 5535 | sRksedlsl | sKksedlsl |
| CA9903 | ARSI | 5 | 149677904 | C | T | A0201,A1101,B1801,B5108,C0701,C1602 | A1101 | 23 | 15750 | gvcgfdlhK | gvcgfdlhE |
| CA9903 | KIF13A | 6 | 17837806 | G | T | A0201,A1101,B1801,B5108,C0701,C1602 | A1101 | 51 | 19518 | gsninkslK | gsninkslT |
| CA9903 | SLC17A3 | 6 | 25850739 | A | G | A0201,A1101,B1801,B5108,C0701,C1602 | A1101 | 180 | 424 | stmAvyipt | stmVvyipt |
| CA9903 | HIST1H2BJ | 6 | 27100417 | T | A | A0201,A1101,B1801,B5108,C0701,C1602 | A1101 | 18 | 19 | esFsiyvyk | esYsiyvyk |
| CA9903 | HIST1H2BJ | 6 | 27100417 | T | A | A0201,A1101,B1801,B5108,C0701,C1602 | B1801 | 15 | 16 | kesFsiyvy | kesYsiyvy |
| CA9903 | FOXP4 | 6 | 41545819 | G | T | A0201,A1101,B1801,B5108,C0701,C1602 | A0201 | 434 | 587 | kqsasavHv | kqsasavQv |

Figure 21 (Cont.)

| | | | | | | | | | | | |
|---|---|---|---|---|---|---|---|---|---|---|---|
| CA9903 | FOXP4 | 6 | 41545819 | G | T | A0201,A1101,B1801,B5108,C0701,C1602 | C0701 | 241 | 9947 | vHvpvsvam | vQvpvsvam |
| CA9903 | RPL7L1 | 6 | 42852473 | C | T | A0201,A1101,B1801,B5108,C0701,C1602 | A0201 | 111 | 50 | mlriveLyv | mlrivePyv |
| CA9903 | RPL7L1 | 6 | 42852473 | C | T | A0201,A1101,B1801,B5108,C0701,C1602 | A1101 | 307 | 342 | kmlriveLy | kmlrivePy |
| CA9903 | RPL7L1 | 6 | 42852473 | C | T | A0201,A1101,B1801,B5108,C0701,C1602 | B1801 | 6 | 36 | veLyvtwgf | vePyvtwgf |
| CA9903 | FAM83B | 6 | 54806671 | A | C | A0201,A1101,B1801,B5108,C0701,C1602 | A1101 | 105 | 29 | atLgnsygr | atMgnsygr |
| CA9903 | MYO6 | 6 | 76624595 | G | C | A0201,A1101,B1801,B5108,C0701,C1602 | C0701 | 130 | 206 | trkrgPeil | trkrgAeil |
| CA9903 | DOPEY1 | 6 | 83840101 | G | C | A0201,A1101,B1801,B5108,C0701,C1602 | A1101 | 76 | 163 | iaeNteffk | iaeKteffk |
| CA9903 | ZNF292 | 6 | 87967981 | C | T | A0201,A1101,B1801,B5108,C0701,C1602 | C0701 | 382 | 7555 | lhtvchpnl | lhtvchpnT |
| CA9903 | CCR6 | 6 | 167550402 | G | T | A0201,A1101,B1801,B5108,C0701,C1602 | A0201 | 74 | 114 | ffipllfmi | ffiplMfmi |
| CA9903 | IGFBP1 | 7 | 45931537 | T | G | A0201,A1101,B1801,B5108,C0701,C1602 | C0701 | 131 | 91 | Grielyrvv | Crielyrvv |
| CA9903 | ABCA13 | 7 | 48556373 | G | T | A0201,A1101,B1801,B5108,C0701,C1602 | A0201 | 213 | 4293 | rifsssYva | rifsssDva |
| CA9903 | ABCA13 | 7 | 48556373 | G | T | A0201,A1101,B1801,B5108,C0701,C1602 | A0201 | 93 | 637 | fsssYvafi | fsssDvafi |
| CA9903 | ABCA13 | 7 | 48556373 | G | T | A0201,A1101,B1801,B5108,C0701,C1602 | A1101 | 21 | 160 | ssYvafisy | ssDvafisy |
| CA9903 | ABCA13 | 7 | 48556373 | G | T | A0201,A1101,B1801,B5108,C0701,C1602 | C0701 | 151 | 967 | srifsssYv | srifsssDv |
| CA9903 | ABCA13 | 7 | 48556373 | G | T | A0201,A1101,B1801,B5108,C0701,C1602 | C0701 | 399 | 1527 | fsssYvafi | fsssDvafi |
| CA9903 | GRM3 | 7 | 86479774 | T | C | A0201,A1101,B1801,B5108,C0701,C1602 | A1101 | 21 | 28 | hiiPfqpqk | hiiLfqpqk |
| CA9903 | PNPLA8 | 7 | 108154667 | G | C | A0201,A1101,B1801,B5108,C0701,C1602 | C0701 | 312 | 876 | lrrttdRkl | lrrttdPkl |
| CA9903 | CPA4 | 7 | 129938639 | G | T | A0201,A1101,B1801,B5108,C0701,C1602 | B1801 | 129 | 411 | deiskllql | deisklSql |
| CA9903 | ATG9B | 7 | 150718318 | C | A | A0201,A1101,B1801,B5108,C0701,C1602 | A1101 | 451 | 15752 | yLdiqvfyr | yWdiqvfyr |
| CA9903 | CHPF2 | 7 | 150933647 | C | T | A0201,A1101,B1801,B5108,C0701,C1602 | B1801 | 128 | 523 | leleWayse | leleRayse |
| CA9903 | TRPA1 | 8 | 72951978 | A | G | A0201,A1101,B1801,B5108,C0701,C1602 | C0701 | 102 | 47 | nhpvckeHl | nhpvckeYl |
| CA9903 | DCAF4L2 | 8 | 88885945 | C | A | A0201,A1101,B1801,B5108,C0701,C1602 | C0701 | 473 | 1111 | tntdHlftv | tntdQlftv |

Figure 21 (Cont.)

| | | | | | | | | | | | |
|---|---|---|---|---|---|---|---|---|---|---|---|
| CA9903 | SLC39A4 | 8 | 145637974 | C | A | A0201,A1101,B1801,B5108,C0701,C1602 | A0201 | 83 | 96 | gllgVwtvl | gllgGwtvl |
| CA9903 | SLC39A4 | 8 | 145637974 | C | A | A0201,A1101,B1801,B5108,C0701,C1602 | A0201 | 70 | 21 | llgVwtvll | llgGwtvll |
| CA9903 | SLC39A4 | 8 | 145637974 | C | A | A0201,A1101,B1801,B5108,C0701,C1602 | A0201 | 74 | 3629 | gVwtvllll | gGwtvllll |
| CA9903 | SLC39A4 | 8 | 145637974 | C | A | A0201,A1101,B1801,B5108,C0701,C1602 | C0701 | 404 | 18749 | lhnvgllgV | lhnvgllgG |
| CA9903 | SLC39A4 | 8 | 145637975 | C | T | A0201,A1101,B1801,B5108,C0701,C1602 | A0201 | 119 | 96 | gllgSwtvl | gllgGwtvl |
| CA9903 | SLC39A4 | 8 | 145637975 | C | T | A0201,A1101,B1801,B5108,C0701,C1602 | A0201 | 17 | 21 | llgSwtvll | llgGwtvll |
| CA9903 | KCNV2 | 9 | 2718284 | T | C | A0201,A1101,B1801,B5108,C0701,C1602 | C0701 | 463 | 3998 | rrfPeelgy | rrfLeelgy |
| CA9903 | FREM1 | 9 | 14859259 | G | T | A0201,A1101,B1801,B5108,C0701,C1602 | C0701 | 196 | 275 | trlpaNgqm | trlpaHgqm |
| CA9903 | FRMPD1 | 9 | 37735582 | G | T | A0201,A1101,B1801,B5108,C0701,C1602 | A0201 | 19 | 136 | llFgakygi | llVgakygi |
| CA9903 | FRMPD1 | 9 | 37735582 | G | T | A0201,A1101,B1801,B5108,C0701,C1602 | A1101 | 70 | 140 | yiallFgak | yiallVgak |
| CA9903 | FRMPD1 | 9 | 37735582 | G | T | A0201,A1101,B1801,B5108,C0701,C1602 | B1801 | 82 | 6289 | resyiallF | resyiallV |
| CA9903 | CNTNAP3 | 9 | 39171536 | C | T | A0201,A1101,B1801,B5108,C0701,C1602 | B1801 | 51 | 264 | Eedkvsvtf | Gedkvsvtf |
| CA9903 | SPATA31D1 | 9 | 84607496 | G | A | A0201,A1101,B1801,B5108,C0701,C1602 | C0701 | 112 | 78 | rrwglpHri | rrwglpRri |
| CA9903 | SPATA31D1 | 9 | 84607496 | G | A | A0201,A1101,B1801,B5108,C0701,C1602 | C0701 | 252 | 258 | Hriheslsl | Rrihesl sl |
| CA9903 | TDRD7 | 9 | 100222479 | G | T | A0201,A1101,B1801,B5108,C0701,C1602 | A1101 | 385 | 12664 | sVgqdllly | sGgqdllly |
| CA9903 | FAM47B | X | 34961252 | G | T | A0201,A1101,B1801,B5108,C0701,C1602 | A0201 | 4 | 4 | Slfselspv | Alfselspv |
| CA9903 | KLHL4 | X | 86919804 | C | G | A0201,A1101,B1801,B5108,C0701,C1602 | A1101 | 28 | 36 | tvapVsvpr | tvapLsvpr |
| CA9903 | ARHGAP36 | X | 130220395 | G | T | A0201,A1101,B1801,B5108,C0701,C1602 | C0701 | 67 | 38 | irrmlrNi | irrmlrKi |
| CU9061 | TTLL10 | 1 | 1118412 | C | G | A0101,A2902,B3801,B4403,C1601,C1203 | C1203 | 84 | 101 | frgpqGrvv | frgpqArvv |
| CU9061 | DVL1 | 1 | 1271541 | A | G | A0101,A2902,B3801,B4403,C1601,C1203 | C1203 | 451 | 1526 | mgnpceSfv | mgnpceFfv |
| CU9061 | DVL1 | 1 | 1271541 | A | G | A0101,A2902,B3801,B4403,C1601,C1203 | C1203 | 269 | 122 | npceSfvdi | npceFfvdi |
| CU9061 | NPHP4 | 1 | 6007239 | C | T | A0101,A2902,B3801,B4403,C1601,C1203 | B4403 | 500 | 341 | pelvghpaf | peMvghpaf |
| CU9061 | SLC2A7 | 1 | 9083069 | C | T | A0101,A2902,B3801,B4403,C1601,C1203 | C1203 | 492 | 1828 | atfmdgkll | atfmdgklM |

Figure 21 (Cont.)

| | | | | | | | | | | | |
|---|---|---|---|---|---|---|---|---|---|---|---|
| CU9061 | SLC2A7 | 1 | 9083069 | C | T | A0101,A2902,B3801,B4403,C1601,C1203 | C1203 | 160 | 198 | fmdgklllll | fmdgklMll |
| CU9061 | SLC2A7 | 1 | 9083069 | C | T | A0101,A2902,B3801,B4403,C1601,C1203 | C1203 | 179 | 116 | lllllwsctv | Mlllwsctv |
| CU9061 | ARHGEF19 | 1 | 16528297 | T | A | A0101,A2902,B3801,B4403,C1601,C1203 | C1203 | 219 | 302 | spqedkVvi | spqedkEvi |
| CU9061 | SPOCD1 | 1 | 32258884 | C | T | A0101,A2902,B3801,B4403,C1601,C1203 | C1203 | 340 | 593 | rllqalptv | rlVqalptv |
| CU9061 | AGO3 | 1 | 36432575 | G | C | A0101,A2902,B3801,B4403,C1601,C1203 | C1203 | 64 | 25 | mLqhfkvti | mVqhfkvti |
| CU9061 | GRIK3 | 1 | 37270593 | C | T | A0101,A2902,B3801,B4403,C1601,C1203 | C1203 | 127 | 240 | Kqrsfcstv | Eqrsfcstv |
| CU9061 | EPS15 | 1 | 51860085 | G | A | A0101,A2902,B3801,B4403,C1601,C1203 | C1203 | 28 | 19 | dpfaLggtv | dpfaPggtv |
| CU9061 | EPS15 | 1 | 51860085 | G | A | A0101,A2902,B3801,B4403,C1601,C1203 | C1203 | 26 | 95 | faLggtvva | faPggtvva |
| CU9061 | DDX20 | 1 | 112303368 | G | T | A0101,A2902,B3801,B4403,C1601,C1203 | A2902 | 10 | 10 | qmlSvsaty | qmlAvsaty |
| CU9061 | DDX20 | 1 | 112303368 | G | T | A0101,A2902,B3801,B4403,C1601,C1203 | C1203 | 372 | 359 | qmlSvsaty | qmlAvsaty |
| CU9061 | GATAD2B | 1 | 153789964 | A | G | A0101,A2902,B3801,B4403,C1601,C1203 | C1203 | 148 | 387 | hmlmPqrvi | hmlmSqrvi |
| CU9061 | NTRK1 | 1 | 156843526 | A | T | A0101,A2902,B3801,B4403,C1601,C1203 | A2902 | 183 | 25216 | apslrwlfY | apslrwlfN |
| CU9061 | ETV3L | 1 | 157062713 | G | A | A0101,A2902,B3801,B4403,C1601,C1203 | C1203 | 467 | 152 | illSgprsl | illPgprsl |
| CU9061 | FMO1 | 1 | 171254428 | C | A | A0101,A2902,B3801,B4403,C1601,C1203 | C1203 | 215 | 140 | yinakpKlf | yinakpNlf |
| CU9061 | FMO1 | 1 | 171254428 | C | A | A0101,A2902,B3801,B4403,C1601,C1203 | C1203 | 115 | 54 | nakpKlfsm | nakpNlfsm |
| CU9061 | TNR | 1 | 175324727 | C | G | A0101,A2902,B3801,B4403,C1601,C1203 | B4403 | 432 | 1975 | sevtTqsal | sevtRqsal |
| CU9061 | CFH | 1 | 196682918 | C | G | A0101,A2902,B3801,B4403,C1601,C1203 | A0101 | 284 | 124 | fisesEyty | fisesQyty |
| CU9061 | CFH | 1 | 196682918 | C | G | A0101,A2902,B3801,B4403,C1601,C1203 | A2902 | 26 | 10 | fisesEyty | fisesQyty |
| CU9061 | CFH | 1 | 196682918 | C | G | A0101,A2902,B3801,B4403,C1601,C1203 | B4403 | 79 | 60 | sesEytyal | sesQytyal |
| CU9061 | CFH | 1 | 196682918 | C | G | A0101,A2902,B3801,B4403,C1601,C1203 | B4403 | 372 | 18919 | sEytyalke | sQytyalke |
| CU9061 | CFH | 1 | 196682918 | C | G | A0101,A2902,B3801,B4403,C1601,C1203 | C1203 | 58 | 54 | fisesEyty | fisesQyty |
| CU9061 | SOX13 | 1 | 204093838 | G | T | A0101,A2902,B3801,B4403,C1601,C1203 | A2902 | 201 | 1138 | lsLqhleky | lsRqhleky |

Figure 21 (Cont.)

| | | | | | | | | | | | |
|---|---|---|---|---|---|---|---|---|---|---|---|
| CU9061 | SOX13 | 1 | 204093838 | G | T | A0101,A2902,B3801,B4403,C1601,C1203 | C1203 | 172 | 181 | qarlsLqhl | qarlsRqhl |
| CU9061 | SOX13 | 1 | 204093838 | G | T | A0101,A2902,B3801,B4403,C1601,C1203 | C1203 | 309 | 551 | lsLqhleky | lsRqhleky |
| CU9061 | SLC30A10 | 1 | 220091782 | G | A | A0101,A2902,B3801,B4403,C1601,C1203 | A2902 | 32 | 34 | vviMaiify | vviTaiify |
| CU9061 | SLC30A10 | 1 | 220091782 | G | A | A0101,A2902,B3801,B4403,C1601,C1203 | C1203 | 475 | 430 | vvvviMaii | vvvviTaii |
| CU9061 | EPRS | 1 | 220198569 | G | C | A0101,A2902,B3801,B4403,C1601,C1203 | C1203 | 245 | 379 | kaaVlnqhy | kaaLlnqhy |
| CU9061 | RYR2 | 1 | 237947175 | C | T | A0101,A2902,B3801,B4403,C1601,C1203 | C1203 | 9 | 15 | kamesYkhy | kamesHkhy |
| CU9061 | OR2T12 | 1 | 248458091 | T | A | A0101,A2902,B3801,B4403,C1601,C1203 | C1203 | 124 | 203 | Wstnhdkvv | Rstnhdkvv |
| CU9061 | OR2T12 | 1 | 248458277 | C | A | A0101,A2902,B3801,B4403,C1601,C1203 | A2902 | 61 | 651 | amyiccLlm | amyiccVlm |
| CU9061 | OR2T12 | 1 | 248458277 | C | A | A0101,A2902,B3801,B4403,C1601,C1203 | C1203 | 230 | 105 | namyiccLl | namyiccVl |
| CU9061 | OR2T12 | 1 | 248458277 | C | A | A0101,A2902,B3801,B4403,C1601,C1203 | C1203 | 330 | 303 | yiccLlmll | yiccVlmll |
| CU9061 | MCM10 | 10 | 13246296 | G | T | A0101,A2902,B3801,B4403,C1601,C1203 | B3801 | 20 | 42 | whdgvNrff | whdgvKrff |
| CU9061 | PRTFDC1 | 10 | 25160950 | C | T | A0101,A2902,B3801,B4403,C1601,C1203 | C1203 | 363 | 1048 | iggdNlstl | iggdDlstl |
| CU9061 | NRAP | 10 | 115405604 | C | A | A0101,A2902,B3801,B4403,C1601,C1203 | C1203 | 229 | 192 | qaqsLnklv | qaqsVnklv |
| CU9061 | BBOX1 | 11 | 27148867 | G | T | A0101,A2902,B3801,B4403,C1601,C1203 | A2902 | 213 | 3521 | itfdnwLll | itfdnwRll |
| CU9061 | BBOX1 | 11 | 27148867 | G | T | A0101,A2902,B3801,B4403,C1601,C1203 | A2902 | 152 | 266 | tfdnwLllh | tfdnwRllh |
| CU9061 | BBOX1 | 11 | 27148867 | G | T | A0101,A2902,B3801,B4403,C1601,C1203 | A2902 | 172 | 1131 | Lllhgrrsy | Rllhgrrsy |
| CU9061 | BBOX1 | 11 | 27148867 | G | T | A0101,A2902,B3801,B4403,C1601,C1203 | C1203 | 25 | 23 | itfdnwLll | itfdnwRll |
| CU9061 | NR1H3 | 11 | 47290170 | G | A | A0101,A2902,B3801,B4403,C1601,C1203 | B3801 | 277 | 212 | vhsKqvfal | vhsEqvfal |
| CU9061 | OR4C15 | 11 | 55322235 | G | T | A0101,A2902,B3801,B4403,C1601,C1203 | B4403 | 187 | 188 | fegclmqlf | fegcMmqlf |
| CU9061 | OR5AP2 | 11 | 56409662 | G | A | A0101,A2902,B3801,B4403,C1601,C1203 | C1203 | 111 | 10962 | asysssvtL | asysssvtP |
| CU9061 | OR5AP2 | 11 | 56409662 | G | A | A0101,A2902,B3801,B4403,C1601,C1203 | C1203 | 77 | 142 | ysssvtLkm | ysssvtPkm |
| CU9061 | GLYAT | 11 | 58478118 | G | T | A0101,A2902,B3801,B4403,C1601,C1203 | C1203 | 65 | 192 | takeltTfl | takeltPfl |
| CU9061 | ZBTB3 | 11 | 62521122 | T | G | A0101,A2902,B3801,B4403,C1601,C1203 | C1203 | 140 | 246 | fpDhsqqll | fpEhsqqll |

Figure 21 (Cont.)

| | | | | | | | | | | | |
|---|---|---|---|---|---|---|---|---|---|---|---|
| CU9061 | BACE1 | 11 | 117160430 | G | A | A0101,A2902,B3801,B4403,C1601,C1203 | A0101 | 80 | 90 | qtdeLtlmt | qtdeStlmt |
| CU9061 | BACE1 | 11 | 117160430 | G | A | A0101,A2902,B3801,B4403,C1601,C1203 | C1203 | 156 | 10148 | ynipqtdeL | ynipqtdeS |
| CU9061 | BACE1 | 11 | 117160430 | G | A | A0101,A2902,B3801,B4403,C1601,C1203 | C1203 | 349 | 1044 | Ltlmtiayv | Stlmtiayv |
| CU9061 | ARHGAP32 | 11 | 128842745 | G | A | A0101,A2902,B3801,B4403,C1601,C1203 | C1203 | 426 | 19683 | fldqdqspL | fldqdqspP |
| CU9061 | OLR1 | 12 | 10321718 | G | A | A0101,A2902,B3801,B4403,C1601,C1203 | C1203 | 367 | 177 | laaatlgvF | laaatlgvL |
| CU9061 | OLR1 | 12 | 10321718 | G | A | A0101,A2902,B3801,B4403,C1601,C1203 | C1203 | 380 | 2022 | gvFclglvv | gvLclglvv |
| CU9061 | OLR1 | 12 | 10321718 | G | A | A0101,A2902,B3801,B4403,C1601,C1203 | C1203 | 20 | 138 | Fclglvvti | Lclglvvti |
| CU9061 | LRMP | 12 | 25257316 | G | C | A0101,A2902,B3801,B4403,C1601,C1203 | B3801 | 63 | 585 | kHsehrpsl | kQsehrpsl |
| CU9061 | ITPR2 | 12 | 26580911 | T | C | A0101,A2902,B3801,B4403,C1601,C1203 | C1203 | 296 | 445 | rpflvsVml | rpflvsIml |
| CU9061 | ITPR2 | 12 | 26580911 | T | C | A0101,A2902,B3801,B4403,C1601,C1203 | C1203 | 55 | 37 | Vmlrsiyti | Imlrsiyti |
| CU9061 | ASUN | 12 | 27069110 | C | A | A0101,A2902,B3801,B4403,C1601,C1203 | C1203 | 36 | 32 | fllngLsvl | fllngRsvl |
| CU9061 | ASUN | 12 | 27069111 | G | T | A0101,A2902,B3801,B4403,C1601,C1203 | C1203 | 40 | 32 | fllngSsvl | fllngRsvl |
| CU9061 | GXYLT1 | 12 | 42523633 | C | A | A0101,A2902,B3801,B4403,C1601,C1203 | A0101 | 62 | 93 | fslFywnpy | fslCywnpy |
| CU9061 | GXYLT1 | 12 | 42523633 | C | A | A0101,A2902,B3801,B4403,C1601,C1203 | A2902 | 300 | 876 | rckdfslFy | rckdfslCy |
| CU9061 | GXYLT1 | 12 | 42523633 | C | A | A0101,A2902,B3801,B4403,C1601,C1203 | A2902 | 11 | 24 | fslFywnpy | fslCywnpy |
| CU9061 | GXYLT1 | 12 | 42523633 | C | A | A0101,A2902,B3801,B4403,C1601,C1203 | A2902 | 40 | 2632 | lFywnpywm | lCywnpywm |
| CU9061 | GXYLT1 | 12 | 42523633 | C | A | A0101,A2902,B3801,B4403,C1601,C1203 | C1203 | 52 | 28 | fslFywnpy | fslCywnpy |
| CU9061 | GXYLT1 | 12 | 42523633 | C | A | A0101,A2902,B3801,B4403,C1601,C1203 | C1203 | 421 | 6735 | Fywnpywml | Cywnpywml |
| CU9061 | SENP1 | 12 | 48457493 | C | A | A0101,A2902,B3801,B4403,C1601,C1203 | A0101 | 481 | 336 | lndDiinfy | lndEiinfy |
| CU9061 | ZBTB39 | 12 | 57396735 | G | A | A0101,A2902,B3801,B4403,C1601,C1203 | A0101 | 171 | 147 | kthLgalmy | kthSgalmy |
| CU9061 | ZBTB39 | 12 | 57396735 | G | A | A0101,A2902,B3801,B4403,C1601,C1203 | A2902 | 9 | 6 | kthLgalmy | kthSgalmy |
| CU9061 | SLC6A15 | 12 | 85266538 | C | A | A0101,A2902,B3801,B4403,C1601,C1203 | C1203 | 126 | 18713 | timkflkmV | timkflkmG |

Figure 21 (Cont.)

| | | | | | | | | | | | |
|---|---|---|---|---|---|---|---|---|---|---|---|
| CU9061 | SLC6A15 | 12 | 85266538 | C | A | A0101,A2902,B3801,B4403,C1601,C1203 | C1203 | 463 | 830 | mkflkmVni | mkflkmGni |
| CU9061 | NAA25 | 12 | 112499013 | C | T | A0101,A2902,B3801,B4403,C1601,C1203 | A2902 | 31 | 16 | vvrellIry | vvrelMlry |
| CU9061 | GCN1L1 | 12 | 120574439 | C | A | A0101,A2902,B3801,B4403,C1601,C1203 | C1203 | 84 | 112 | kalglviLl | kalglviRl |
| CU9061 | CSNK1A1L | 13 | 37678582 | A | G | A0101,A2902,B3801,B4403,C1601,C1203 | A2902 | 490 | 872 | feeApdymy | feeVpdymy |
| CU9061 | CSNK1A1L | 13 | 37678582 | A | G | A0101,A2902,B3801,B4403,C1601,C1203 | B4403 | 388 | 633 | feeApdymy | feeVpdymy |
| CU9061 | SIAH3 | 13 | 46357750 | G | A | A0101,A2902,B3801,B4403,C1601,C1203 | A0101 | 233 | 992 | Ltqadcfty | Ptqadcfty |
| CU9061 | SIAH3 | 13 | 46357750 | G | A | A0101,A2902,B3801,B4403,C1601,C1203 | A2902 | 359 | 1869 | mmligtLtq | mmligtPtq |
| CU9061 | SIAH3 | 13 | 46357750 | G | A | A0101,A2902,B3801,B4403,C1601,C1203 | A2902 | 12 | 98 | Ltqadcfty | Ptqadcfty |
| CU9061 | ARL11 | 13 | 50204855 | C | T | A0101,A2902,B3801,B4403,C1601,C1203 | C1203 | 278 | 350 | yvldsIdea | yvldsTdea |
| CU9061 | CHAMP1 | 13 | 115091376 | G | A | A0101,A2902,B3801,B4403,C1601,C1203 | C1203 | 20 | 33 | ftKekeafi | ftEekeafi |
| CU9061 | NGDN | 14 | 23944783 | G | T | A0101,A2902,B3801,B4403,C1601,C1203 | C1203 | 448 | 320 | tvleklLpl | tvleklRpl |
| CU9061 | NGDN | 14 | 23944783 | G | T | A0101,A2902,B3801,B4403,C1601,C1203 | C1203 | 500 | 571 | Lpldqklky | Rpldqklky |
| CU9061 | VSX2 | 14 | 74727456 | C | T | A0101,A2902,B3801,B4403,C1601,C1203 | C1203 | 266 | 445 | elrensiVv | elrensiAv |
| CU9061 | NPAP1 | 15 | 24922911 | C | A | A0101,A2902,B3801,B4403,C1601,C1203 | C1203 | 109 | 303 | fifhnttTs | fifhnttPs |
| CU9061 | GPR176 | 15 | 40093678 | C | G | A0101,A2902,B3801,B4403,C1601,C1203 | C1203 | 85 | 366 | sadfHakei | sadfQakei |
| CU9061 | GPR176 | 15 | 40093678 | C | G | A0101,A2902,B3801,B4403,C1601,C1203 | C1203 | 215 | 370 | Hakeifstc | Qakeifstc |
| CU9061 | VPS13C | 15 | 62304329 | T | C | A0101,A2902,B3801,B4403,C1601,C1203 | A2902 | 131 | 239 | tsgSippny | tsgNippny |
| CU9061 | VPS13C | 15 | 62304329 | T | C | A0101,A2902,B3801,B4403,C1601,C1203 | A2902 | 21 | 31 | gSippnyqy | gNippnyqy |
| CU9061 | VPS13C | 15 | 62304329 | T | C | A0101,A2902,B3801,B4403,C1601,C1203 | C1203 | 383 | 125 | Sippnyqyi | Nippnyqyi |
| CU9061 | LCTL | 15 | 66857625 | G | A | A0101,A2902,B3801,B4403,C1601,C1203 | A0101 | 51 | 1824 | gsSeeasfy | gsPeeasfy |
| CU9061 | LCTL | 15 | 66857625 | G | A | A0101,A2902,B3801,B4403,C1601,C1203 | A0101 | 10 | 11300 | sSeeasfyy | sPeeasfyy |
| CU9061 | LCTL | 15 | 66857625 | G | A | A0101,A2902,B3801,B4403,C1601,C1203 | A2902 | 151 | 1050 | gsSeeasfy | gsPeeasfy |
| CU9061 | LCTL | 15 | 66857625 | G | A | A0101,A2902,B3801,B4403,C1601,C1203 | A2902 | 273 | 1206 | sSeeasfyy | sPeeasfyy |

Figure 21 (Cont.)

| | | | | | | | | | | | |
|---|---|---|---|---|---|---|---|---|---|---|---|
| CU9061 | HCN4 | 15 | 73659842 | G | A | A0101,A2902,B3801,B4403,C1601,C1203 | A2902 | 11 | 45 | agfwiihLy | agfwiihPy |
| CU9061 | HCN4 | 15 | 73659842 | G | A | A0101,A2902,B3801,B4403,C1601,C1203 | A2902 | 300 | 1030 | gfwiihLys | gfwiihPys |
| CU9061 | HCN4 | 15 | 73659842 | G | A | A0101,A2902,B3801,B4403,C1601,C1203 | A2902 | 159 | 372 | wiihLysdf | wiihPysdf |
| CU9061 | HCN4 | 15 | 73659842 | G | A | A0101,A2902,B3801,B4403,C1601,C1203 | A2902 | 21 | 728 | hLysdfrfy | hPysdfrfy |
| CU9061 | HCN4 | 15 | 73659842 | G | A | A0101,A2902,B3801,B4403,C1601,C1203 | C1203 | 219 | 10193 | sagfwiihL | sagfwiihP |
| CU9061 | HCN4 | 15 | 73659842 | G | A | A0101,A2902,B3801,B4403,C1601,C1203 | C1203 | 303 | 98 | hLysdfrfy | hPysdfrfy |
| CU9061 | IQGAP1 | 15 | 91017318 | A | T | A0101,A2902,B3801,B4403,C1601,C1203 | C1203 | 147 | 5015 | hindiikiL | hindiikiQ |
| CU9061 | IQGAP1 | 15 | 91017318 | A | T | A0101,A2902,B3801,B4403,C1601,C1203 | C1203 | 297 | 465 | Lafiranka | Qafiranka |
| CU9061 | CHD2 | 15 | 93486145 | A | C | A0101,A2902,B3801,B4403,C1601,C1203 | A0101 | 9 | 11661 | eTdegeiqy | eKdegeiqy |
| CU9061 | SYNGR3 | 16 | 2042078 | G | T | A0101,A2902,B3801,B4403,C1601,C1203 | B3801 | 419 | 847 | Frfgvalgl | Crfgvalgl |
| CU9061 | SYNGR3 | 16 | 2042078 | G | T | A0101,A2902,B3801,B4403,C1601,C1203 | C1203 | 52 | 245 | gaFrfgval | gaCrfgval |
| CU9061 | NLRC3 | 16 | 3613038 | G | T | A0101,A2902,B3801,B4403,C1601,C1203 | A0101 | 133 | 824 | qsllTqlly | qsllPqlly |
| CU9061 | NLRC3 | 16 | 3613038 | G | T | A0101,A2902,B3801,B4403,C1601,C1203 | A2902 | 7 | 8 | qsllTqlly | qsllPqlly |
| CU9061 | SEPT12 | 16 | 4833495 | T | G | A0101,A2902,B3801,B4403,C1601,C1203 | C1203 | 407 | 296 | fdedLndki | fdedIndki |
| CU9061 | ZP2 | 16 | 21210936 | G | A | A0101,A2902,B3801,B4403,C1601,C1203 | B3801 | 428 | 1902 | nrlspdsSl | nrlspdsPl |
| CU9061 | CRYM | 16 | 21278893 | G | A | A0101,A2902,B3801,B4403,C1601,C1203 | C1203 | 248 | 186 | kSgahinav | kPgahinav |
| CU9061 | NLRC5 | 16 | 57059933 | G | T | A0101,A2902,B3801,B4403,C1601,C1203 | B4403 | 22 | 27 | aeaSmvhml | aeaAmvhml |
| CU9061 | NLRC5 | 16 | 57059933 | G | T | A0101,A2902,B3801,B4403,C1601,C1203 | C1203 | 424 | 420 | paeaSmvhm | paeaAmvhm |
| CU9061 | FHOD1 | 16 | 67263568 | G | T | A0101,A2902,B3801,B4403,C1601,C1203 | C1203 | 281 | 380 | lskgpglev | Lskgpglev |
| CU9061 | OR1G1 | 17 | 3030327 | C | A | A0101,A2902,B3801,B4403,C1601,C1203 | C1203 | 425 | 73 | lsfcanhDi | lsfcanhEi |
| CU9061 | OR1G1 | 17 | 3030327 | C | A | A0101,A2902,B3801,B4403,C1601,C1203 | C1203 | 305 | 372 | canhDiphf | canhEiphf |
| CU9061 | KIF1C | 17 | 4925705 | C | A | A0101,A2902,B3801,B4403,C1601,C1203 | B4403 | 41 | 41 | aeiealaal | aeiealaaL |

Figure 21 (Cont.)

| | | | | | | | | | | | |
|---|---|---|---|---|---|---|---|---|---|---|---|
| CU9061 | KIF1C | 17 | 4925705 | C | A | A0101,A2902,B3801,B4403,C1601,C1203 | C1203 | 455 | 347 | laaikmrel | laaLkmrel |
| CU9061 | TP53 | 17 | 7579473 | G | C | A0101,A2902,B3801,B4403,C1601,C1203 | C1203 | 408 | 286 | rmpeaapAv | rmpeaapPv |
| CU9061 | WRAP53 | 17 | 7592241 | G | C | A0101,A2902,B3801,B4403,C1601,C1203 | C1203 | 491 | 965 | spselspPi | spselspRi |
| CU9061 | NOS2 | 17 | 26106080 | T | C | A0101,A2902,B3801,B4403,C1601,C1203 | B4403 | 139 | 75 | mehpkCewf | mehpkYewf |
| CU9061 | CDC27 | 17 | 45234357 | G | T | A0101,A2902,B3801,B4403,C1601,C1203 | A2902 | 131 | 25933 | lgtgtsilY | lgtgtsilS |
| CU9061 | SPOP | 17 | 47699411 | A | C | A0101,A2902,B3801,B4403,C1601,C1203 | C1203 | 126 | 1107 | fAymwtinn | fSymwtinn |
| CU9061 | KIF2B | 17 | 51902313 | G | T | A0101,A2902,B3801,B4403,C1601,C1203 | C1203 | 108 | 45 | fciaLslsi | fciaRslsi |
| CU9061 | HELZ | 17 | 65162648 | C | T | A0101,A2902,B3801,B4403,C1601,C1203 | B3801 | 328 | 1212 | drikdnEvl | drikdnGvl |
| CU9061 | BAHCC1 | 17 | 79410450 | C | T | A0101,A2902,B3801,B4403,C1601,C1203 | A2902 | 317 | 85 | samknlMky | samknlLky |
| CU9061 | BAHCC1 | 17 | 79410450 | C | T | A0101,A2902,B3801,B4403,C1601,C1203 | C1203 | 63 | 54 | samknlMky | samknlLky |
| CU9061 | BAHCC1 | 17 | 79410450 | C | T | A0101,A2902,B3801,B4403,C1601,C1203 | C1203 | 213 | 437 | Mkyssqalv | Lkyssqalv |
| CU9061 | NARF | 17 | 80430515 | G | T | A0101,A2902,B3801,B4403,C1601,C1203 | C1203 | 250 | 400 | sqkefvrLy | sqkefvrRy |
| CU9061 | SYT4 | 18 | 40854056 | C | A | A0101,A2902,B3801,B4403,C1601,C1203 | C1203 | 26 | 6332 | fpktnlkpV | fpktnlkpG |
| CU9061 | ST8SIA5 | 18 | 44260450 | C | A | A0101,A2902,B3801,B4403,C1601,C1203 | B4403 | 481 | 3536 | lekwLrpfy | lekwRrpfy |
| CU9061 | ST8SIA5 | 18 | 44260450 | C | A | A0101,A2902,B3801,B4403,C1601,C1203 | C1203 | 127 | 388 | wLrpfyrvl | wRrpfyrvl |
| CU9061 | FSTL3 | 19 | 681368 | T | G | A0101,A2902,B3801,B4403,C1601,C1203 | C1203 | 423 | 542 | cprpqAcvv | cprpqScvv |
| CU9061 | FUT5 | 19 | 5866821 | C | T | A0101,A2902,B3801,B4403,C1601,C1203 | C1203 | 185 | 67 | lppdafihM | lppdafihV |
| CU9061 | FUT5 | 19 | 5866821 | C | T | A0101,A2902,B3801,B4403,C1601,C1203 | C1203 | 458 | 328 | dafihMddf | dafihVddf |
| CU9061 | VMAC | 19 | 5909136 | T | C | A0101,A2902,B3801,B4403,C1601,C1203 | C1203 | 183 | 62 | qpavLgttv | qpavFgttv |
| CU9061 | MUC16 | 19 | 9068646 | G | T | A0101,A2902,B3801,B4403,C1601,C1203 | C1203 | 159 | 306 | dmdKnlepv | dmdTnlepv |
| CU9061 | CEACAM3 | 19 | 42301806 | T | C | A0101,A2902,B3801,B4403,C1601,C1203 | A0101 | 25 | 84 | vtqndTgfy | vtqndIgfy |
| CU9061 | CEACAM3 | 19 | 42301806 | T | C | A0101,A2902,B3801,B4403,C1601,C1203 | A2902 | 106 | 120 | vtqndTgfy | vtqndIgfy |
| CU9061 | GLTSCR1 | 19 | 48197849 | A | G | A0101,A2902,B3801,B4403,C1601,C1203 | C1203 | 106 | 1049 | pApppthl | pTppptlhl |

Figure 21 (Cont.)

| | | | | | | | | | | | |
|---|---|---|---|---|---|---|---|---|---|---|---|
| CU9061 | BCAT2 | 19 | 49303285 | C | G | A0101,A2902,B3801,B4403,C1601,C1203 | C1203 | 224 | 855 | vpdPagtsl | vpdAagtsl |
| CU9061 | ZNF616 | 19 | 52619315 | G | A | A0101,A2902,B3801,B4403,C1601,C1203 | C1203 | 27 | 18 | kafrhrsnF | kafrhrsnL |
| CU9061 | PRPF31 | 19 | 54621804 | A | T | A0101,A2902,B3801,B4403,C1601,C1203 | C1203 | 35 | 22 | lsgdsvMti | lsgdsvKti |
| CU9061 | KIR2DL3 | 19 | 55253465 | C | T | A0101,A2902,B3801,B4403,C1601,C1203 | C1203 | 313 | 545 | llahpgLlv | llahpgPlv |
| CU9061 | NLRP7 | 19 | 55451170 | G | T | A0101,A2902,B3801,B4403,C1601,C1203 | B4403 | 73 | 304 | Eedqamraf | Dedqamraf |
| CU9061 | EML4 | 2 | 42508025 | C | A | A0101,A2902,B3801,B4403,C1601,C1203 | C1203 | 19 | 40 | kmfmrgrTi | kmfmrgrPi |
| CU9061 | EML4 | 2 | 42508025 | C | A | A0101,A2902,B3801,B4403,C1601,C1203 | C1203 | 21 | 28 | fmrgrTitm | fmrgrPitm |
| CU9061 | RAB11FIP5 | 2 | 73302653 | T | A | A0101,A2902,B3801,B4403,C1601,C1203 | C1203 | 48 | 6211 | lqippgppl | lqippgppK |
| CU9061 | TLX2 | 2 | 74742781 | G | T | A0101,A2902,B3801,B4403,C1601,C1203 | A2902 | 45 | 43 | Vtrrighpy | Gtrrighpy |
| CU9061 | TLX2 | 2 | 74742781 | G | T | A0101,A2902,B3801,B4403,C1601,C1203 | C1203 | 113 | 70 | spfsVtrri | spfsGtrri |
| CU9061 | EIF2AK3 | 2 | 88874369 | T | C | A0101,A2902,B3801,B4403,C1601,C1203 | A2902 | 257 | 81 | pGspkvyly | pSspkvyly |
| CU9061 | XIRP2 | 2 | 168101413 | A | G | A0101,A2902,B3801,B4403,C1601,C1203 | C1203 | 14 | 23 | feAenldsi | feTenldsi |
| CU9061 | DYNC1I2 | 2 | 172582501 | A | G | A0101,A2902,B3801,B4403,C1601,C1203 | B4403 | 220 | 367 | eeflsffGh | eeflsffDh |
| CU9061 | DYNC1I2 | 2 | 172582501 | A | G | A0101,A2902,B3801,B4403,C1601,C1203 | C1203 | 218 | 76 | ffGhstriv | ffDhstriv |
| CU9061 | HOXD3 | 2 | 177036808 | G | A | A0101,A2902,B3801,B4403,C1601,C1203 | C1203 | 448 | 217 | mapTsgpvf | mapAsgpvf |
| CU9061 | TTN | 2 | 179483045 | A | T | A0101,A2902,B3801,B4403,C1601,C1203 | C1203 | 155 | 75 | raesSeftv | raesCeftv |
| CU9061 | TTN | 2 | 179529195 | G | T | A0101,A2902,B3801,B4403,C1601,C1203 | B4403 | 291 | 600 | aevvHvkvh | aevvPvkvh |
| CU9061 | TTN | 2 | 179529195 | G | T | A0101,A2902,B3801,B4403,C1601,C1203 | C1203 | 262 | 84 | raevvHvkv | raevvPvkv |
| CU9061 | TTN | 2 | 179593305 | G | T | A0101,A2902,B3801,B4403,C1601,C1203 | A2902 | 212 | 66 | vmkKdsgqy | vmkQdsgqy |
| CU9061 | C2orf62 | 2 | 219227539 | A | G | A0101,A2902,B3801,B4403,C1601,C1203 | C1203 | 339 | 40 | Gvmawrrmv | Rvmawrrmv |
| CU9061 | RBM44 | 2 | 238727007 | G | A | A0101,A2902,B3801,B4403,C1601,C1203 | C1203 | 224 | 175 | Katsarpsv | Ratsarpsv |
| CU9061 | SIRPD | 20 | 1517882 | A | T | A0101,A2902,B3801,B4403,C1601,C1203 | C1203 | 214 | 126 | dahtSlsal | dahtClsal |

Figure 21 (Cont.)

| | | | | | | | | | | | |
|---|---|---|---|---|---|---|---|---|---|---|---|
| CU9061 | NCAM2 | 21 | 22664458 | G | T | A0101,A2902,B3801,B4403,C1601,C1203 | C1203 | 127 | 379 | mlannnlHi | mlannnlQi |
| CU9061 | NCAM2 | 21 | 22664458 | G | T | A0101,A2902,B3801,B4403,C1601,C1203 | C1203 | 17 | 14 | lannnlHil | lannnlQil |
| CU9061 | EIF4ENIF1 | 22 | 31859039 | G | C | A0101,A2902,B3801,B4403,C1601,C1203 | C1203 | 261 | 581 | yteeepewL | yteeepewF |
| CU9061 | SH3BP1 | 22 | 38051297 | C | A | A0101,A2902,B3801,B4403,C1601,C1203 | C1203 | 104 | 91 | rpapDrptm | rpapArptm |
| CU9061 | CCDC134 | 22 | 42205893 | G | A | A0101,A2902,B3801,B4403,C1601,C1203 | C1203 | 386 | 1467 | psleiykkl | psleiykkM |
| CU9061 | CCDC134 | 22 | 42205893 | G | A | A0101,A2902,B3801,B4403,C1601,C1203 | C1203 | 420 | 513 | eiykklfev | eiykkMfev |
| CU9061 | ULK4 | 3 | 41746602 | C | T | A0101,A2902,B3801,B4403,C1601,C1203 | A2902 | 18 | 138 | sTfeaiiqy | sAfeaiiqy |
| CU9061 | ULK4 | 3 | 41746602 | C | T | A0101,A2902,B3801,B4403,C1601,C1203 | C1203 | 463 | 2235 | fikitlsTf | fikitlsAf |
| CU9061 | ULK4 | 3 | 41746602 | C | T | A0101,A2902,B3801,B4403,C1601,C1203 | C1203 | 254 | 164 | itlsTfeai | itlsAfeai |
| CU9061 | ULK4 | 3 | 41746602 | C | T | A0101,A2902,B3801,B4403,C1601,C1203 | C1203 | 145 | 15 | sTfeaiiqy | sAfeaiiqy |
| CU9061 | TMPRSS7 | 3 | 111775893 | A | T | A0101,A2902,B3801,B4403,C1601,C1203 | A2902 | 54 | 40 | stlgLalkf | stlglalkf |
| CU9061 | TMPRSS7 | 3 | 111775893 | A | T | A0101,A2902,B3801,B4403,C1601,C1203 | A2902 | 468 | 465 | tlgLalkfy | tlglalkfy |
| CU9061 | TMPRSS7 | 3 | 111775893 | A | T | A0101,A2902,B3801,B4403,C1601,C1203 | A2902 | 10 | 13 | gLalkfyny | glalkfyny |
| CU9061 | ACAD11 | 3 | 132358341 | T | C | A0101,A2902,B3801,B4403,C1601,C1203 | C1203 | 70 | 373 | fhpEecrvi | fhpKecrvi |
| CU9061 | CLCN2 | 3 | 184071983 | C | T | A0101,A2902,B3801,B4403,C1601,C1203 | C1203 | 17 | 84 | iavilanTv | iavilanAv |
| CU9061 | CLCN2 | 3 | 184071983 | C | T | A0101,A2902,B3801,B4403,C1601,C1203 | C1203 | 128 | 63 | lanTvaqsl | lanAvaqsl |
| CU9061 | RFC4 | 3 | 186507842 | T | A | A0101,A2902,B3801,B4403,C1601,C1203 | B4403 | 208 | 817 | aevdNclad | aevdKclad |
| CU9061 | IQCG | 3 | 197670669 | C | T | A0101,A2902,B3801,B4403,C1601,C1203 | C1203 | 13 | 12 | vqyeRrqsi | vqyeGrqsi |
| CU9061 | IQCG | 3 | 197670669 | C | T | A0101,A2902,B3801,B4403,C1601,C1203 | C1203 | 452 | 1294 | yeRrqsicv | yeGrqsicv |
| CU9061 | STK32B | 4 | 5170103 | G | C | A0101,A2902,B3801,B4403,C1601,C1203 | C1203 | 451 | 385 | ieSdevrnv | ieRdevrnv |
| CU9061 | RBM47 | 4 | 40440501 | C | A | A0101,A2902,B3801,B4403,C1601,C1203 | B4403 | 344 | 300 | yeiLpgrll | yeiRpgrll |
| CU9061 | RBM47 | 4 | 40440501 | C | A | A0101,A2902,B3801,B4403,C1601,C1203 | C1203 | 187 | 58 | yeiLpgrll | yeiRpgrll |
| CU9061 | PDGFRA | 4 | 55127579 | G | C | A0101,A2902,B3801,B4403,C1601,C1203 | C1203 | 101 | 107 | yiyvpHpdv | yiyvpDpdv |

Figure 21 (Cont.)

| | | | | | | | | | | | |
|---|---|---|---|---|---|---|---|---|---|---|---|
| CU9061 | PDGFRA | 4 | 55127579 | G | C | A0101,A2902,B3801,B4403,C1601,C1203 | C1203 | 208 | 59 | yvpHpdvaf | yvpDpdvaf |
| CU9061 | PDGFRA | 4 | 55127579 | G | C | A0101,A2902,B3801,B4403,C1601,C1203 | C1203 | 45 | 58 | vpHpdvafv | vpDpdvafv |
| CU9061 | TMPRSS11D | 4 | 68688104 | G | T | A0101,A2902,B3801,B4403,C1601,C1203 | A2902 | 86 | 100 | gvyNrvtay | gvyTrvtay |
| CU9061 | TMPRSS11D | 4 | 68688104 | G | T | A0101,A2902,B3801,B4403,C1601,C1203 | C1203 | 104 | 426 | gvyNrvtay | gvyTrvtay |
| CU9061 | ABCG2 | 4 | 89020583 | C | T | A0101,A2902,B3801,B4403,C1601,C1203 | A2902 | 25 | 35 | fiheyisEy | fiheyisGy |
| CU9061 | ABCG2 | 4 | 89020583 | C | T | A0101,A2902,B3801,B4403,C1601,C1203 | B4403 | 69 | 36626 | sEyyrvssy | sGyyrvssy |
| CU9061 | ABCG2 | 4 | 89020583 | C | T | A0101,A2902,B3801,B4403,C1601,C1203 | C1203 | 25 | 115 | fiheyisEy | fiheyisGy |
| CU9061 | ABCG2 | 4 | 89020583 | C | T | A0101,A2902,B3801,B4403,C1601,C1203 | C1203 | 281 | 834 | sEyyrvssy | sGyyrvssy |
| CU9061 | ETNPPL | 4 | 109677623 | G | A | A0101,A2902,B3801,B4403,C1601,C1203 | C1203 | 254 | 109 | eandlalCl | eandlalRl |
| CU9061 | ETNPPL | 4 | 109677623 | G | A | A0101,A2902,B3801,B4403,C1601,C1203 | C1203 | 339 | 255 | lalClarqf | lalRlarqf |
| CU9061 | FSTL5 | 4 | 162841783 | G | A | A0101,A2902,B3801,B4403,C1601,C1203 | A2902 | 279 | 1273 | gfmiqdgLf | gfmiqdgPf |
| CU9061 | FSTL5 | 4 | 162841783 | G | A | A0101,A2902,B3801,B4403,C1601,C1203 | A2902 | 152 | 682 | Lfgscenky | Pfgscenky |
| CU9061 | VEGFC | 4 | 177609049 | T | C | A0101,A2902,B3801,B4403,C1601,C1203 | C1203 | 14 | 69 | tSymwnnhi | tNymwnnhi |
| CU9061 | KIAA0947 | 5 | 5489291 | G | T | A0101,A2902,B3801,B4403,C1601,C1203 | A2902 | 16 | 300 | wgiqlaaLy | wgiqlaaVy |
| CU9061 | CDH18 | 5 | 19483546 | G | T | A0101,A2902,B3801,B4403,C1601,C1203 | C1203 | 43 | 81 | lsssRtlti | lsssStlti |
| CU9061 | C1QTNF3 | 5 | 34043080 | C | A | A0101,A2902,B3801,B4403,C1601,C1203 | C1203 | 318 | 830 | rsCsrrekv | rsGsrrekv |
| CU9061 | C6 | 5 | 41195895 | C | T | A0101,A2902,B3801,B4403,C1601,C1203 | A2902 | 341 | 192 | qlmgnRfhf | qlmgnGfhf |
| CU9061 | PCDHB8 | 5 | 140558636 | G | A | A0101,A2902,B3801,B4403,C1601,C1203 | C1203 | 106 | 111 | dMndhapev | dVndhapev |
| CU9061 | ANXA6 | 5 | 150516820 | C | T | A0101,A2902,B3801,B4403,C1601,C1203 | A2902 | 217 | 38 | qlhqlvaay | qMhqlvaay |
| CU9061 | ANXA6 | 5 | 150516820 | C | T | A0101,A2902,B3801,B4403,C1601,C1203 | C1203 | 170 | 687 | lasrtneql | lasrtneqM |
| CU9061 | PGBD1 | 6 | 28251891 | C | A | A0101,A2902,B3801,B4403,C1601,C1203 | C1203 | 142 | 204 | elKpcvkty | elQpcvkty |
| CU9061 | TNXB | 6 | 32035473 | C | T | A0101,A2902,B3801,B4403,C1601,C1203 | C1203 | 116 | 134 | yglhegQrv | yglhegRrv |

Figure 21 (Cont.)

| | | | | | | | | | | | |
|---|---|---|---|---|---|---|---|---|---|---|---|
| CU9061 | ITPR3 | 6 | 33658760 | C | T | A0101,A2902,B3801,B4403,C1601,C1203 | B3801 | 145 | 1637 | trngCsill | trngRsill |
| CU9061 | ITPR3 | 6 | 33658760 | C | T | A0101,A2902,B3801,B4403,C1601,C1203 | C1203 | 490 | 301 | vtrngCsil | vtrngRsil |
| CU9061 | HS3ST5 | 6 | 114378951 | T | C | A0101,A2902,B3801,B4403,C1601,C1203 | B4403 | 74 | 20747 | yEmnssikl | yKmnssikl |
| CU9061 | HS3ST5 | 6 | 114378951 | T | C | A0101,A2902,B3801,B4403,C1601,C1203 | C1203 | 28 | 84 | riyEmnssi | riyKmnssi |
| CU9061 | HS3ST5 | 6 | 114378951 | T | C | A0101,A2902,B3801,B4403,C1601,C1203 | C1203 | 89 | 155 | yEmnssikl | yKmnssikl |
| CU9061 | KIAA0408 | 6 | 127771400 | A | G | A0101,A2902,B3801,B4403,C1601,C1203 | A2902 | 483 | 135 | kvTesspny | kvIesspny |
| CU9061 | SLC35D3 | 6 | 137243879 | G | T | A0101,A2902,B3801,B4403,C1601,C1203 | C1203 | 395 | 238 | lslpmyLvf | lslpmyVvf |
| CU9061 | SLC35D3 | 6 | 137243879 | G | T | A0101,A2902,B3801,B4403,C1601,C1203 | C1203 | 193 | 233 | Lvfkrclpl | Vvfkrclpl |
| CU9061 | SAMD5 | 6 | 147830446 | C | G | A0101,A2902,B3801,B4403,C1601,C1203 | C1203 | 68 | 112 | ypkVklkim | ypkLklkim |
| CU9061 | SYNE1 | 6 | 152527366 | C | G | A0101,A2902,B3801,B4403,C1601,C1203 | B4403 | 493 | 421 | aeiqDkwks | aeiqEkwks |
| CU9061 | GNA12 | 7 | 2771305 | T | A | A0101,A2902,B3801,B4403,C1601,C1203 | B3801 | 153 | 699 | ehdfviMki | ehdfviKki |
| CU9061 | GNA12 | 7 | 2771305 | T | A | A0101,A2902,B3801,B4403,C1601,C1203 | C1203 | 219 | 1528 | iMkipfkmv | iKkipfkmv |
| CU9061 | PDE1C | 7 | 31918657 | C | G | A0101,A2902,B3801,B4403,C1601,C1203 | C1203 | 195 | 159 | dekpPfksi | dekpRfksi |
| CU9061 | TYW1B | 7 | 72277814 | A | G | A0101,A2902,B3801,B4403,C1601,C1203 | C1203 | 359 | 373 | frawktkLi | frawktkFi |
| CU9061 | MUC17 | 7 | 100686003 | C | A | A0101,A2902,B3801,B4403,C1601,C1203 | B3801 | 380 | 13092 | fHesstpsi | fPesstpsi |
| CU9061 | MUC17 | 7 | 100686003 | C | A | A0101,A2902,B3801,B4403,C1601,C1203 | C1203 | 353 | 71 | fHesstpsi | fPesstpsi |
| CU9061 | PLXNA4 | 7 | 131912238 | C | G | A0101,A2902,B3801,B4403,C1601,C1203 | C1203 | 354 | 755 | paaNevpri | paaKevpri |
| CU9061 | PLXNA4 | 7 | 131912238 | C | G | A0101,A2902,B3801,B4403,C1601,C1203 | C1203 | 20 | 31 | aaNevprii | aaKevprii |
| CU9061 | TRPV6 | 7 | 142575508 | G | T | A0101,A2902,B3801,B4403,C1601,C1203 | A2902 | 33 | 9 | tElhiaaly | tAlhiaaly |
| CU9061 | TRPV6 | 7 | 142575508 | G | T | A0101,A2902,B3801,B4403,C1601,C1203 | B4403 | 24 | 20047 | tElhiaaly | tAlhiaaly |
| CU9061 | TRPV6 | 7 | 142575509 | C | T | A0101,A2902,B3801,B4403,C1601,C1203 | A0101 | 437 | 9314 | tTlhiaaly | tAlhiaaly |
| CU9061 | TRPV6 | 7 | 142575509 | C | T | A0101,A2902,B3801,B4403,C1601,C1203 | A2902 | 3 | 9 | tTlhiaaly | tAlhiaaly |
| CU9061 | OR2A2 | 7 | 143806866 | A | T | A0101,A2902,B3801,B4403,C1601,C1203 | A2902 | 70 | 119 | myfflsLla | myfflsHla |

Figure 21 (Cont.)

| | | | | | | | | | | | |
|---|---|---|---|---|---|---|---|---|---|---|---|
| CU9061 | OR2A2 | 7 | 143806866 | A | T | A0101,A2902,B3801,B4403,C1601,C1203 | A2902 | 15 | 35 | Llaiidmsy | Hlaiidmsy |
| CU9061 | OR2A2 | 7 | 143806866 | A | T | A0101,A2902,B3801,B4403,C1601,C1203 | C1203 | 463 | 198 | pmyfflsLl | pmyfflsHl |
| CU9061 | OR2A2 | 7 | 143806866 | A | T | A0101,A2902,B3801,B4403,C1601,C1203 | C1203 | 77 | 121 | yfflsLlai | yfflsHlai |
| CU9061 | OR2A2 | 7 | 143806866 | A | T | A0101,A2902,B3801,B4403,C1601,C1203 | C1203 | 118 | 55 | fflsLlaii | fflsHlaii |
| CU9061 | NUB1 | 7 | 151064151 | G | C | A0101,A2902,B3801,B4403,C1601,C1203 | C1203 | 473 | 5160 | Faqkcfknc | Laqkcfknc |
| CU9061 | HTR5A | 7 | 154863152 | G | C | A0101,A2902,B3801,B4403,C1601,C1203 | A2902 | 15 | 6 | llfgCgety | llfgWgety |
| CU9061 | HTR5A | 7 | 154863152 | G | C | A0101,A2902,B3801,B4403,C1601,C1203 | C1203 | 42 | 36 | llfgCgety | llfgWgety |
| CU9061 | DLGAP2 | 8 | 1514017 | C | A | A0101,A2902,B3801,B4403,C1601,C1203 | C1203 | 160 | 177 | lpepMlksi | lpepLlksi |
| CU9061 | DEFB134 | 8 | 11851538 | T | C | A0101,A2902,B3801,B4403,C1601,C1203 | B4403 | 92 | 33 | semlvaCcm | semlvaYcm |
| CU9061 | SH2D4A | 8 | 19214752 | G | T | A0101,A2902,B3801,B4403,C1601,C1203 | C1203 | 452 | 148 | mFadsinrm | mLadsinrm |
| CU9061 | KIF13B | 8 | 28929774 | C | A | A0101,A2902,B3801,B4403,C1601,C1203 | C1203 | 127 | 196 | Nicdkpakv | Kicdkpakv |
| CU9061 | PCMTD1 | 8 | 52733138 | G | T | A0101,A2902,B3801,B4403,C1601,C1203 | C1203 | 65 | 65 | rvkKrinty | rvkQrinty |
| CU9061 | CSMD3 | 8 | 113564916 | G | A | A0101,A2902,B3801,B4403,C1601,C1203 | C1203 | 304 | 344 | fkgesLgri | fkgesSgri |
| CU9061 | ASAP1 | 8 | 131127945 | C | A | A0101,A2902,B3801,B4403,C1601,C1203 | A2902 | 180 | 588 | fnphFhvey | fnphVhvey |
| CU9061 | ASAP1 | 8 | 131127945 | C | A | A0101,A2902,B3801,B4403,C1601,C1203 | B3801 | 83 | 317 | Fhveyewnl | Vhveyewnl |
| CU9061 | PIP5K1B | 9 | 71532480 | A | G | A0101,A2902,B3801,B4403,C1601,C1203 | A2902 | 398 | 542 | lesfRimdy | lesfKimdy |
| CU9061 | PIP5K1B | 9 | 71532480 | A | G | A0101,A2902,B3801,B4403,C1601,C1203 | B3801 | 391 | 1581 | fRimdysll | fKimdysll |
| CU9061 | PIP5K1B | 9 | 71532480 | A | G | A0101,A2902,B3801,B4403,C1601,C1203 | C1203 | 128 | 119 | rvlesfRim | rvlesfKim |
| CU9061 | SLC28A3 | 9 | 86909155 | C | A | A0101,A2902,B3801,B4403,C1601,C1203 | A0101 | 13 | 10 | fstvlsmly | fstvMsmly |
| CU9061 | SLC28A3 | 9 | 86909155 | C | A | A0101,A2902,B3801,B4403,C1601,C1203 | A0101 | 37 | 18 | stvlsmlyy | stvMsmlyy |
| CU9061 | SLC28A3 | 9 | 86909155 | C | A | A0101,A2902,B3801,B4403,C1601,C1203 | A2902 | 5 | 6 | fstvlsmly | fstvMsmly |
| CU9061 | SLC28A3 | 9 | 86909155 | C | A | A0101,A2902,B3801,B4403,C1601,C1203 | A2902 | 6 | 4 | stvlsmlyy | stvMsmlyy |

Figure 21 (Cont.)

| | | | | | | | | | | | |
|---|---|---|---|---|---|---|---|---|---|---|---|
| CU9061 | SLC28A3 | 9 | 86909155 | C | A | A0101,A2902,B3801,B4403,C1601,C1203 | C1203 | 135 | 513 | ivvffstvl | ivvffstvM |
| CU9061 | SYK | 9 | 93624510 | G | T | A0101,A2902,B3801,B4403,C1601,C1203 | C1203 | 23 | 23 | rardnnCsy | rardnnGsy |
| CU9061 | SVEP1 | 9 | 113312302 | C | G | A0101,A2902,B3801,B4403,C1601,C1203 | C1203 | 481 | 246 | dpTpiaasl | dpRpiaasl |
| CU9061 | BRINP1 | 9 | 121929645 | A | T | A0101,A2902,B3801,B4403,C1601,C1203 | C1203 | 48 | 194 | nadHlrsav | nadLlrsav |
| CU9061 | NUP188 | 9 | 131733097 | G | T | A0101,A2902,B3801,B4403,C1601,C1203 | B3801 | 92 | 304 | hhapvllSw | hhapvllAw |
| CU9061 | ABO | 9 | 136131365 | C | A | A0101,A2902,B3801,B4403,C1601,C1203 | C1203 | 132 | 391 | ftyerrpls | ftyerrpQs |
| CU9061 | AMELX | X | 11316830 | G | T | A0101,A2902,B3801,B4403,C1601,C1203 | C1203 | 31 | 212 | mpFpgqhsm | mpVpgqhsm |
| CU9061 | ARX | X | 25025270 | G | T | A0101,A2902,B3801,B4403,C1601,C1203 | B4403 | 87 | 29022 | aEvfrhpaf | aAvfrhpaf |
| CU9061 | ARX | X | 25025270 | G | T | A0101,A2902,B3801,B4403,C1601,C1203 | C1203 | 37 | 68 | Evfrhpafi | Avfrhpafi |
| CU9061 | MAGEB16 | X | 35821217 | C | A | A0101,A2902,B3801,B4403,C1601,C1203 | A0101 | 53 | 18368 | yThsfpsqy | yPhsfpsqy |
| CU9061 | MAGEB16 | X | 35821217 | C | A | A0101,A2902,B3801,B4403,C1601,C1203 | A2902 | 6 | 128 | yThsfpsqy | yPhsfpsqy |
| CU9061 | MAGEB16 | X | 35821217 | C | A | A0101,A2902,B3801,B4403,C1601,C1203 | B3801 | 279 | 416 | vhgsyThsf | vhgsyPhsf |
| CU9061 | MAGEB16 | X | 35821217 | C | A | A0101,A2902,B3801,B4403,C1601,C1203 | C1203 | 27 | 35 | yThsfpsqy | yPhsfpsqy |
| CU9061 | ABCB7 | X | 74293779 | C | T | A0101,A2902,B3801,B4403,C1601,C1203 | C1203 | 206 | 807 | Saqfalvtl | Gaqfalvtl |
| CU9061 | DACH2 | X | 86067934 | C | A | A0101,A2902,B3801,B4403,C1601,C1203 | C1203 | 174 | 1096 | Hagfpgpfi | Pagfpgpfi |
| CU9061 | ARMCX3 | X | 100881008 | G | T | A0101,A2902,B3801,B4403,C1601,C1203 | C1203 | 455 | 182 | fqvcadkFl | fqvcadkVl |
| CU9061 | NXF2B | X | 101623751 | G | T | A0101,A2902,B3801,B4403,C1601,C1203 | A2902 | 76 | 20789 | vnhstapyY | vnhstapyS |
| CU9061 | HS6ST2 | X | 132092223 | C | A | A0101,A2902,B3801,B4403,C1601,C1203 | C1203 | 29 | 39 | Nifgpmasv | Kifgpmasv |
| CU9061 | SOX3 | X | 139586109 | C | G | A0101,A2902,B3801,B4403,C1601,C1203 | C1203 | 173 | 58 | mslgpmgsL | mslgpmgsV |
| DI6359 | PTPRU | 1 | 29642003 | A | G | A0301,A1101,B1801,B5101,C1203,C1504 | C1203 | 162 | 101 | lcsrrvSmi | lcsrrvNmi |
| DI6359 | PPCS | 1 | 42922400 | G | T | A0301,A1101,B1801,B5101,C1203,C1504 | C1203 | 234 | 7597 | vplearpvL | vplearpvR |
| DI6359 | LPPR4 | 1 | 99771576 | C | A | A0301,A1101,B1801,B5101,C1203,C1504 | C1203 | 295 | 182 | dpvrrnaRi | dpvrrnaSi |
| DI6359 | SLC22A15 | 1 | 116562272 | G | A | A0301,A1101,B1801,B5101,C1203,C1504 | C1203 | 28 | 26 | fsgvflgvi | fsgvfVgvi |

Figure 21 (Cont.)

| | | | | | | | | | | | |
|---|---|---|---|---|---|---|---|---|---|---|---|
| DI6359 | SETDB1 | 1 | 150902580 | T | C | A0301,A1101,B1801,B5101,C1203,C1504 | B1801 | 390 | 519 | dedddvPsi | dedddvLsi |
| DI6359 | SETDB1 | 1 | 150902580 | T | C | A0301,A1101,B1801,B5101,C1203,C1504 | C1203 | 463 | 256 | dedddvPsi | dedddvLsi |
| DI6359 | CGN | 1 | 151503193 | G | T | A0301,A1101,B1801,B5101,C1203,C1504 | A0301 | 342 | 691 | rllYrtvdr | rllDrtvdr |
| DI6359 | CGN | 1 | 151503193 | G | T | A0301,A1101,B1801,B5101,C1203,C1504 | B1801 | 190 | 17049 | leeqkrllY | leeqkrllD |
| DI6359 | CGN | 1 | 151503193 | G | T | A0301,A1101,B1801,B5101,C1203,C1504 | C1203 | 314 | 4580 | llYrtvdrl | llDrtvdrl |
| DI6359 | TPM3 | 1 | 154164379 | T | A | A0301,A1101,B1801,B5101,C1203,C1504 | C1203 | 34 | 67 | qaeerskLl | qaeerskQl |
| DI6359 | OR10Z1 | 1 | 158576775 | C | A | A0301,A1101,B1801,B5101,C1203,C1504 | C1203 | 111 | 418 | hffcdtpTv | hffcdtpPv |
| DI6359 | OR10Z1 | 1 | 158576775 | C | A | A0301,A1101,B1801,B5101,C1203,C1504 | C1203 | 107 | 190 | ffcdtpTvl | ffcdtpPvl |
| DI6359 | FMO2 | 1 | 171165828 | C | A | A0301,A1101,B1801,B5101,C1203,C1504 | C1203 | 31 | 449 | fsYsgqwkv | fsSsgqwkv |
| DI6359 | SHCBP1L | 1 | 182874684 | C | G | A0301,A1101,B1801,B5101,C1203,C1504 | A1101 | 225 | 844 | tviifpAey | tviifpGey |
| DI6359 | HMCN1 | 1 | 186114963 | G | T | A0301,A1101,B1801,B5101,C1203,C1504 | C1203 | 63 | 70 | Llcdhpvpv | Rlcdhpvpv |
| DI6359 | HHIPL2 | 1 | 222696025 | T | A | A0301,A1101,B1801,B5101,C1203,C1504 | A0301 | 120 | 364 | hvrqgMrrk | hvrqgKrrk |
| DI6359 | GALNT2 | 1 | 230379165 | G | T | A0301,A1101,B1801,B5101,C1203,C1504 | C1203 | 6 | 6 | Laedrtrvv | Vaedrtrvv |
| DI6359 | GALNT2 | 1 | 230415134 | G | T | A0301,A1101,B1801,B5101,C1203,C1504 | C1203 | 46 | 62 | taksgVlsv | taksgGlsv |
| DI6359 | RYR2 | 1 | 237791213 | G | T | A0301,A1101,B1801,B5101,C1203,C1504 | A1101 | 393 | 11913 | amfvllhrH | amfvllhrQ |
| DI6359 | RYR2 | 1 | 237791213 | G | T | A0301,A1101,B1801,B5101,C1203,C1504 | C1203 | 350 | 93 | rHydgiggl | rQydgiggl |
| DI6359 | EXO1 | 1 | 242016683 | A | T | A0301,A1101,B1801,B5101,C1203,C1504 | A0301 | 52 | 518 | rqanllMgk | rqanllKgk |
| DI6359 | EXO1 | 1 | 242016683 | A | T | A0301,A1101,B1801,B5101,C1203,C1504 | A0301 | 124 | 727 | llMgkqllr | llKgkqllr |
| DI6359 | EXO1 | 1 | 242016683 | A | T | A0301,A1101,B1801,B5101,C1203,C1504 | A1101 | 24 | 325 | rqanllMgk | rqanllKgk |
| DI6359 | OR2T33 | 1 | 248436344 | A | G | A0301,A1101,B1801,B5101,C1203,C1504 | A0301 | 29 | 30 | aiftyTrpk | aiftyMrpk |
| DI6359 | OR2T33 | 1 | 248436344 | A | G | A0301,A1101,B1801,B5101,C1203,C1504 | A1101 | 486 | 200 | gaaiftyTr | gaaiftyMr |
| DI6359 | OR2T33 | 1 | 248436344 | A | G | A0301,A1101,B1801,B5101,C1203,C1504 | A1101 | 14 | 13 | aiftyTrpk | aiftyMrpk |

Figure 21 (Cont.)

| | | | | | | | | | | | |
|---|---|---|---|---|---|---|---|---|---|---|---|
| DI6359 | OR2T33 | 1 | 248436344 | A | G | A0301,A1101,B1801,B5101,C1203,C1504 | C1203 | 287 | 230 | ftyTrpksh | ftyMrpksh |
| DI6359 | ITIH2 | 10 | 7751016 | A | G | A0301,A1101,B1801,B5101,C1203,C1504 | C1203 | 13 | 4 | ysCkvqsti | ysYkvqsti |
| DI6359 | TET1 | 10 | 70446123 | T | C | A0301,A1101,B1801,B5101,C1203,C1504 | A1101 | 119 | 50 | stvvctStr | stvvctLtr |
| DI6359 | CHST3 | 10 | 73767570 | G | T | A0301,A1101,B1801,B5101,C1203,C1504 | A1101 | 250 | 541 | vtlaSeacr | vtlaAeacr |
| DI6359 | CPN1 | 10 | 101835811 | G | A | A0301,A1101,B1801,B5101,C1203,C1504 | B1801 | 202 | 76 | nealgCelm | nealgRelm |
| DI6359 | CPN1 | 10 | 101835811 | G | A | A0301,A1101,B1801,B5101,C1203,C1504 | C1203 | 205 | 218 | ealgCelml | ealgRelml |
| DI6359 | OR52M1 | 11 | 4567100 | C | A | A0301,A1101,B1801,B5101,C1203,C1504 | C1203 | 26 | 19 | yvmifrDvm | yvmifrAvm |
| DI6359 | OR52M1 | 11 | 4567227 | G | T | A0301,A1101,B1801,B5101,C1203,C1504 | C1203 | 286 | 233 | lihrfgHcv | lihrfgQcv |
| DI6359 | OR52M1 | 11 | 4567227 | G | T | A0301,A1101,B1801,B5101,C1203,C1504 | C1203 | 280 | 752 | fgHcvpppv | fgQcvpppv |
| DI6359 | OR51G2 | 11 | 4936230 | A | G | A0301,A1101,B1801,B5101,C1203,C1504 | B1801 | 55 | 93 | dsllilfPy | dsllilfSy |
| DI6359 | OR51G2 | 11 | 4936230 | A | G | A0301,A1101,B1801,B5101,C1203,C1504 | C1203 | 410 | 1035 | lilfPyali | lilfSyali |
| DI6359 | OR51G2 | 11 | 4936230 | A | G | A0301,A1101,B1801,B5101,C1203,C1504 | C1203 | 124 | 326 | ilfPyalil | ilfSyalil |
| DI6359 | OR51G2 | 11 | 4936230 | A | G | A0301,A1101,B1801,B5101,C1203,C1504 | C1203 | 140 | 145 | fPyalilrt | fSyalilrt |
| DI6359 | NLRP14 | 11 | 7064290 | G | A | A0301,A1101,B1801,B5101,C1203,C1504 | A0301 | 66 | 226 | yiyqffeNk | yiyqffeDk |
| DI6359 | NLRP14 | 11 | 7064290 | G | A | A0301,A1101,B1801,B5101,C1203,C1504 | A1101 | 16 | 33 | yiyqffeNk | yiyqffeDk |
| DI6359 | NLRP14 | 11 | 7064290 | G | A | A0301,A1101,B1801,B5101,C1203,C1504 | C1203 | 464 | 1566 | yiyqffeNk | yiyqffeDk |
| DI6359 | C11orf16 | 11 | 8953842 | G | T | A0301,A1101,B1801,B5101,C1203,C1504 | A0301 | 467 | 2516 | Kgprmpllk | Tgprmpllk |
| DI6359 | ANO3 | 11 | 26677704 | C | T | A0301,A1101,B1801,B5101,C1203,C1504 | C1203 | 285 | 61 | yvnnslFff | yvnnslSff |
| DI6359 | PRDM11 | 11 | 45204602 | G | T | A0301,A1101,B1801,B5101,C1203,C1504 | C1203 | 307 | 757 | evipNghif | evipKghif |
| DI6359 | OR4A15 | 11 | 55136321 | A | C | A0301,A1101,B1801,B5101,C1203,C1504 | A0301 | 238 | 2010 | ytlknaAmk | ytlknaEmk |
| DI6359 | OR4A15 | 11 | 55136321 | A | C | A0301,A1101,B1801,B5101,C1203,C1504 | A0301 | 36 | 935 | aAmksamrk | aEmksamrk |
| DI6359 | OR4A15 | 11 | 55136321 | A | C | A0301,A1101,B1801,B5101,C1203,C1504 | A1101 | 49 | 97 | ytlknaAmk | ytlknaEmk |
| DI6359 | OR4A15 | 11 | 55136321 | A | C | A0301,A1101,B1801,B5101,C1203,C1504 | A1101 | 16 | 558 | aAmksamrk | aEmksamrk |

Figure 21 (Cont.)

| | | | | | | | | | | | |
|---|---|---|---|---|---|---|---|---|---|---|---|
| DI6359 | OR5T2 | 11 | 56000423 | C | A | A0301,A1101,B1801,B5101,C1203,C1504 | C1203 | 194 | 19121 | aiylftlmV | aiylftlmG |
| DI6359 | OR5T2 | 11 | 56000423 | C | A | A0301,A1101,B1801,B5101,C1203,C1504 | C1203 | 78 | 138 | ylftlmVnl | ylftlmGnl |
| DI6359 | OR5T2 | 11 | 56000423 | C | A | A0301,A1101,B1801,B5101,C1203,C1504 | C1203 | 387 | 3479 | mVnlglilv | mGnlglilv |
| DI6359 | CACNA1C | 12 | 2694542 | G | T | A0301,A1101,B1801,B5101,C1203,C1504 | A1101 | 317 | 5870 | laStaspek | laRtaspek |
| DI6359 | CACNA1C | 12 | 2694542 | G | T | A0301,A1101,B1801,B5101,C1203,C1504 | A1101 | 102 | 16553 | aStaspekk | aRtaspekk |
| DI6359 | PRMT8 | 12 | 3701468 | G | T | A0301,A1101,B1801,B5101,C1203,C1504 | C1203 | 205 | 159 | ltvrrWeei | ltvrrGeei |
| DI6359 | ST8SIA1 | 12 | 22354591 | A | T | A0301,A1101,B1801,B5101,C1203,C1504 | B5101 | 360 | 310 | lpfsgfQam | lpfsgfHam |
| DI6359 | ST8SIA1 | 12 | 22354591 | A | T | A0301,A1101,B1801,B5101,C1203,C1504 | C1203 | 130 | 162 | lpfsgfQam | lpfsgfHam |
| DI6359 | ST8SIA1 | 12 | 22354591 | A | T | A0301,A1101,B1801,B5101,C1203,C1504 | C1203 | 385 | 1300 | fQampeefl | fHampeefl |
| DI6359 | KRAS | 12 | 25398284 | C | T | A0301,A1101,B1801,B5101,C1203,C1504 | A1101 | 194 | 107 | vvgaDgvgk | vvgaGgvgk |
| DI6359 | CNTN1 | 12 | 41316228 | G | T | A0301,A1101,B1801,B5101,C1203,C1504 | B1801 | 7 | 14 | teatlsfVy | teatlsfGy |
| DI6359 | GRIP1 | 12 | 66773190 | T | A | A0301,A1101,B1801,B5101,C1203,C1504 | A0301 | 497 | 18379 | tsfqasgyY | tsfqasgyN |
| DI6359 | GRIP1 | 12 | 66773190 | T | A | A0301,A1101,B1801,B5101,C1203,C1504 | A1101 | 116 | 11963 | tsfqasgyY | tsfqasgyN |
| DI6359 | RFX4 | 12 | 107126804 | C | A | A0301,A1101,B1801,B5101,C1203,C1504 | C1203 | 155 | 221 | evQppsspv | evPppsspv |
| DI6359 | DHX37 | 12 | 125467165 | G | T | A0301,A1101,B1801,B5101,C1203,C1504 | A1101 | 158 | 96 | sqrEemlqk | sqrAemlqk |
| DI6359 | PABPC3 | 13 | 25671609 | C | A | A0301,A1101,B1801,B5101,C1203,C1504 | B5101 | 199 | 2257 | yppsqiarl | yppsqiarL |
| DI6359 | PABPC3 | 13 | 25671609 | C | A | A0301,A1101,B1801,B5101,C1203,C1504 | C1203 | 50 | 177 | yppsqiarl | yppsqiarL |
| DI6359 | RALGAPA1 | 14 | 36097083 | C | A | A0301,A1101,B1801,B5101,C1203,C1504 | A0301 | 333 | 267 | hlvnhlChy | hlvnhlGhy |
| DI6359 | MDGA2 | 14 | 47342794 | C | A | A0301,A1101,B1801,B5101,C1203,C1504 | A1101 | 318 | 1079 | gskeVfymy | gskeGfymy |
| DI6359 | CEP152 | 15 | 49034170 | C | A | A0301,A1101,B1801,B5101,C1203,C1504 | C1203 | 41 | 148 | yyliclqHi | yyliclqQi |
| DI6359 | CEP152 | 15 | 49034170 | C | A | A0301,A1101,B1801,B5101,C1203,C1504 | C1203 | 213 | 193 | yliclqHil | yliclqQil |
| DI6359 | ITGA11 | 15 | 68631894 | C | T | A0301,A1101,B1801,B5101,C1203,C1504 | A1101 | 173 | 205 | kviplHesy | kviplResy |

Figure 21 (Cont.)

| | | | | | | | | | | | |
|---|---|---|---|---|---|---|---|---|---|---|---|
| DI6359 | ADAMTS7 | 15 | 79058418 | C | T | A0301,A1101,B1801,B5101,C1203,C1504 | C1203 | 391 | 1066 | Mdselwptv | Vdselwptv |
| DI6359 | OTOA | 16 | 21739728 | G | T | A0301,A1101,B1801,B5101,C1203,C1504 | C1203 | 487 | 134 | kaavMlkll | kaavRlkll |
| DI6359 | ITGAX | 16 | 31373932 | G | T | A0301,A1101,B1801,B5101,C1203,C1504 | C1203 | 212 | 2494 | dmrdsylVy | dmrdsylGy |
| DI6359 | ITGAX | 16 | 31373932 | G | T | A0301,A1101,B1801,B5101,C1203,C1504 | C1203 | 396 | 3273 | lVystelal | lGystelal |
| DI6359 | ABCA6 | 17 | 67081310 | C | A | A0301,A1101,B1801,B5101,C1203,C1504 | A0301 | 300 | 7417 | kVcssvlgh | kGcssvlgh |
| DI6359 | ABCA6 | 17 | 67081310 | C | A | A0301,A1101,B1801,B5101,C1203,C1504 | A1101 | 261 | 11678 | kVcssvlgh | kGcssvlgh |
| DI6359 | ABCA6 | 17 | 67081310 | C | A | A0301,A1101,B1801,B5101,C1203,C1504 | C1203 | 222 | 19371 | tagevelkV | tagevelkG |
| DI6359 | MISP | 19 | 758424 | A | T | A0301,A1101,B1801,B5101,C1203,C1504 | C1203 | 280 | 598 | cpLanrgvv | cpQanrgvv |
| DI6359 | MISP | 19 | 758424 | A | T | A0301,A1101,B1801,B5101,C1203,C1504 | C1203 | 309 | 503 | Lanrgvvrw | Qanrgvvrw |
| DI6359 | LMNB2 | 19 | 2438524 | T | C | A0301,A1101,B1801,B5101,C1203,C1504 | C1203 | 365 | 466 | Rkregeltv | Kkregeltv |
| DI6359 | ZFR2 | 19 | 3806120 | C | T | A0301,A1101,B1801,B5101,C1203,C1504 | A0301 | 167 | 1054 | hTlrmlafr | hAlrmlafr |
| DI6359 | ZFR2 | 19 | 3806120 | C | T | A0301,A1101,B1801,B5101,C1203,C1504 | A1101 | 57 | 592 | hTlrmlafr | hAlrmlafr |
| DI6359 | ZFR2 | 19 | 3806120 | C | T | A0301,A1101,B1801,B5101,C1203,C1504 | C1203 | 319 | 185 | saqhTlrml | saqhAlrml |
| DI6359 | COLGALT1 | 19 | 17691573 | T | C | A0301,A1101,B1801,B5101,C1203,C1504 | B1801 | 63 | 2052 | nPveadysy | nLveadysy |
| DI6359 | UNC13A | 19 | 17756501 | C | A | A0301,A1101,B1801,B5101,C1203,C1504 | A1101 | 432 | 5166 | mYvwynldk | mDvwynldk |
| DI6359 | RYR1 | 19 | 39034227 | A | T | A0301,A1101,B1801,B5101,C1203,C1504 | B1801 | 366 | 434 | ieeLgkrnf | ieeQgkrnf |
| DI6359 | MAP4K1 | 19 | 39105080 | C | T | A0301,A1101,B1801,B5101,C1203,C1504 | C1203 | 101 | 191 | diyqvtSsl | diyqvtGsl |
| DI6359 | SELV | 19 | 40009784 | G | T | A0301,A1101,B1801,B5101,C1203,C1504 | C1203 | 462 | 13927 | videeikkM | videeikkR |
| DI6359 | IRF3 | 19 | 50165574 | C | G | A0301,A1101,B1801,B5101,C1203,C1504 | B1801 | 72 | 122 | eewefQvta | eewefEvta |
| DI6359 | IRF3 | 19 | 50165574 | C | G | A0301,A1101,B1801,B5101,C1203,C1504 | B1801 | 3 | 2 | wefQvtafy | wefEvtafy |
| DI6359 | IRF3 | 19 | 50165574 | C | G | A0301,A1101,B1801,B5101,C1203,C1504 | C1203 | 354 | 78 | wefQvtafy | wefEvtafy |
| DI6359 | IL4I1 | 19 | 50394689 | C | G | A0301,A1101,B1801,B5101,C1203,C1504 | A0301 | 178 | 101 | algcrkalk | algcrkaMk |
| DI6359 | IL4I1 | 19 | 50394689 | C | G | A0301,A1101,B1801,B5101,C1203,C1504 | C1203 | 16 | 44 | kalgcrkal | kalgcrkaM |

Figure 21 (Cont.)

| | | | | | | | | | | | |
|---|---|---|---|---|---|---|---|---|---|---|---|
| DI6359 | ZNF836 | 19 | 52658275 | T | A | A0301,A1101,B1801,B5101,C1203,C1504 | A0301 | 133 | 100 | hqmihsgDk | hqmihsgEk |
| DI6359 | MYADM | 19 | 54377507 | G | T | A0301,A1101,B1801,B5101,C1203,C1504 | B5101 | 418 | 2961 | ipfpsflsW | ipfpsflsG |
| DI6359 | MYADM | 19 | 54377507 | G | T | A0301,A1101,B1801,B5101,C1203,C1504 | C1203 | 281 | 3892 | ipfpsflsW | ipfpsflsG |
| DI6359 | LILRA3 | 19 | 54802193 | G | T | A0301,A1101,B1801,B5101,C1203,C1504 | C1203 | 151 | 55 | lsvrQgptv | lsvrPgptv |
| DI6359 | ZNF524 | 19 | 56114088 | C | T | A0301,A1101,B1801,B5101,C1203,C1504 | A1101 | 332 | 4554 | yqcpicWlr | yqcpicRlr |
| DI6359 | NT5C1B | 2 | 18765932 | C | T | A0301,A1101,B1801,B5101,C1203,C1504 | C1203 | 147 | 869 | Riypastql | Giypastql |
| DI6359 | APOB | 2 | 21230763 | C | T | A0301,A1101,B1801,B5101,C1203,C1504 | C1203 | 311 | 812 | qsqvNsqhv | qsqvDsqhv |
| DI6359 | APOB | 2 | 21230763 | C | T | A0301,A1101,B1801,B5101,C1203,C1504 | C1203 | 367 | 469 | Nsqhvghsv | Dsqhvghsv |
| DI6359 | NRXN1 | 2 | 51254990 | T | A | A0301,A1101,B1801,B5101,C1203,C1504 | B1801 | 208 | 7911 | veakwvevM | veakwvevK |
| DI6359 | NRXN1 | 2 | 51254990 | T | A | A0301,A1101,B1801,B5101,C1203,C1504 | C1203 | 68 | 240 | Mskrrdmtv | Kskrrdmtv |
| DI6359 | ANKRD36 | 2 | 97877478 | G | A | A0301,A1101,B1801,B5101,C1203,C1504 | A0301 | 266 | 242 | isgtMscqk | isgtVscqk |
| DI6359 | ANKRD36 | 2 | 97877478 | G | A | A0301,A1101,B1801,B5101,C1203,C1504 | A1101 | 61 | 46 | isgtMscqk | isgtVscqk |
| DI6359 | RANBP2 | 2 | 109384632 | G | T | A0301,A1101,B1801,B5101,C1203,C1504 | A1101 | 304 | 337 | Vfsfnaplk | Gfsfnaplk |
| DI6359 | RANBP2 | 2 | 109384632 | G | T | A0301,A1101,B1801,B5101,C1203,C1504 | C1203 | 11 | 50 | fVfsfnapl | fGfsfnapl |
| DI6359 | DPP10 | 2 | 116101477 | G | T | A0301,A1101,B1801,B5101,C1203,C1504 | C1203 | 60 | 2538 | fvlhdpeaL | fvlhdpeaR |
| DI6359 | LRP1B | 2 | 141283442 | C | A | A0301,A1101,B1801,B5101,C1203,C1504 | A1101 | 244 | 10036 | cVdysdelk | cGdysdelk |
| DI6359 | XIRP2 | 2 | 168107506 | G | C | A0301,A1101,B1801,B5101,C1203,C1504 | B5101 | 191 | 291 | cpaPtpvpi | cpaAtpvpi |
| DI6359 | XIRP2 | 2 | 168107506 | G | C | A0301,A1101,B1801,B5101,C1203,C1504 | C1203 | 39 | 46 | ipcpaPtpv | ipcpaAtpv |
| DI6359 | XIRP2 | 2 | 168107506 | G | C | A0301,A1101,B1801,B5101,C1203,C1504 | C1203 | 196 | 629 | cpaPtpvpi | cpaAtpvpi |
| DI6359 | XIRP2 | 2 | 168107506 | G | C | A0301,A1101,B1801,B5101,C1203,C1504 | C1203 | 388 | 215 | paPtpvpiv | paAtpvpiv |
| DI6359 | TTN | 2 | 179428111 | G | T | A0301,A1101,B1801,B5101,C1203,C1504 | C1203 | 104 | 1849 | dtYrssvsl | dtSrssvsl |
| DI6359 | TTN | 2 | 179532034 | G | A | A0301,A1101,B1801,B5101,C1203,C1504 | C1203 | 187 | 9487 | patkepdtI | patkepdtT |

Figure 21 (Cont.)

| | | | | | | | | | | | |
|---|---|---|---|---|---|---|---|---|---|---|---|
| DI6359 | TTN | 2 | 179634660 | T | C | A0301,A1101,B1801,B5101,C1203,C1504 | A0301 | 121 | 133 | tlRitktmk | tlHitktmk |
| DI6359 | TTN | 2 | 179634660 | T | C | A0301,A1101,B1801,B5101,C1203,C1504 | A1101 | 359 | 270 | fvetlRitk | fvetlHitk |
| DI6359 | TTN | 2 | 179634660 | T | C | A0301,A1101,B1801,B5101,C1203,C1504 | C1203 | 178 | 178 | etlRitktm | etlHitktm |
| DI6359 | IQCA1 | 2 | 237406003 | C | A | A0301,A1101,B1801,B5101,C1203,C1504 | A0301 | 99 | 226 | qtlatfyLk | qtlatfyVk |
| DI6359 | IQCA1 | 2 | 237406003 | C | A | A0301,A1101,B1801,B5101,C1203,C1504 | A0301 | 97 | 348 | tlatfyLky | tlatfyVky |
| DI6359 | IQCA1 | 2 | 237406003 | C | A | A0301,A1101,B1801,B5101,C1203,C1504 | A0301 | 389 | 1155 | yLkyvqifr | yVkyvqifr |
| DI6359 | IQCA1 | 2 | 237406003 | C | A | A0301,A1101,B1801,B5101,C1203,C1504 | A1101 | 14 | 19 | qtlatfyLk | qtlatfyVk |
| DI6359 | IQCA1 | 2 | 237406003 | C | A | A0301,A1101,B1801,B5101,C1203,C1504 | A1101 | 139 | 390 | tlatfyLky | tlatfyVky |
| DI6359 | IQCA1 | 2 | 237406003 | C | A | A0301,A1101,B1801,B5101,C1203,C1504 | C1203 | 120 | 57 | latfyLkyv | latfyVkyv |
| DI6359 | IQCA1 | 2 | 237406003 | C | A | A0301,A1101,B1801,B5101,C1203,C1504 | C1203 | 213 | 315 | fyLkyvqif | fyVkyvqif |
| DI6359 | PTPRT | 20 | 40713445 | A | G | A0301,A1101,B1801,B5101,C1203,C1504 | B1801 | 207 | 269 | lqyTgwpay | lqyIgwpay |
| DI6359 | PTPRT | 20 | 40713445 | A | G | A0301,A1101,B1801,B5101,C1203,C1504 | C1203 | 181 | 328 | lqyTgwpay | lqyIgwpay |
| DI6359 | MC3R | 20 | 54823903 | A | C | A0301,A1101,B1801,B5101,C1203,C1504 | C1203 | 43 | 57 | Hascclpsv | Nascclpsv |
| DI6359 | ADAMTS1 | 21 | 28210265 | T | A | A0301,A1101,B1801,B5101,C1203,C1504 | B1801 | 245 | 6278 | Mesfnaipt | Kesfnaipt |
| DI6359 | ADAMTS1 | 21 | 28210265 | T | A | A0301,A1101,B1801,B5101,C1203,C1504 | C1203 | 30 | 1438 | ytyfvkkkM | ytyfvkkkK |
| DI6359 | ADAMTS1 | 21 | 28210265 | T | A | A0301,A1101,B1801,B5101,C1203,C1504 | C1203 | 142 | 498 | fvkkkMesf | fvkkkKesf |
| DI6359 | ADAMTS1 | 21 | 28210265 | T | A | A0301,A1101,B1801,B5101,C1203,C1504 | C1203 | 163 | 599 | kkMesfnai | kkKesfnai |
| DI6359 | KRTAP27-1 | 21 | 31709737 | C | T | A0301,A1101,B1801,B5101,C1203,C1504 | C1203 | 144 | 121 | qsncfpglv | qsncfpgVv |
| DI6359 | KRTAP27-1 | 21 | 31709737 | C | T | A0301,A1101,B1801,B5101,C1203,C1504 | C1203 | 365 | 199 | fpglvqtty | fpgVvqtty |
| DI6359 | BHLHE40 | 3 | 5024689 | A | T | A0301,A1101,B1801,B5101,C1203,C1504 | A0301 | 28 | 74 | llLggtsrk | llQggtsrk |
| DI6359 | BHLHE40 | 3 | 5024689 | A | T | A0301,A1101,B1801,B5101,C1203,C1504 | A1101 | 462 | 578 | llLggtsrk | llQggtsrk |
| DI6359 | ITGA9 | 3 | 37550061 | C | G | A0301,A1101,B1801,B5101,C1203,C1504 | A0301 | 307 | 181 | kvyiLradr | kvyiFradr |
| DI6359 | ITGA9 | 3 | 37550061 | C | G | A0301,A1101,B1801,B5101,C1203,C1504 | A1101 | 122 | 74 | gigkvyiLr | gigkvyiFr |

Figure 21 (Cont.)

| | | | | | | | | | | | |
|---|---|---|---|---|---|---|---|---|---|---|---|
| DI6359 | ITGA9 | 3 | 37550061 | C | G | A0301,A1101,B1801,B5101,C1203,C1504 | A1101 | 319 | 97 | kvyiLradr | kvyiFradr |
| DI6359 | XCR1 | 3 | 46062830 | A | G | A0301,A1101,B1801,B5101,C1203,C1504 | A0301 | 410 | 19002 | lslgiilfR | lslgiilfC |
| DI6359 | XCR1 | 3 | 46062830 | A | G | A0301,A1101,B1801,B5101,C1203,C1504 | A1101 | 60 | 18239 | lslgiilfR | lslgiilfC |
| DI6359 | XCR1 | 3 | 46062830 | A | G | A0301,A1101,B1801,B5101,C1203,C1504 | C1203 | 436 | 382 | iilfRyvei | iilfCyvei |
| DI6359 | XCR1 | 3 | 46062830 | A | G | A0301,A1101,B1801,B5101,C1203,C1504 | C1203 | 108 | 140 | ilfRyveil | ilfCyveil |
| DI6359 | XCR1 | 3 | 46062830 | A | G | A0301,A1101,B1801,B5101,C1203,C1504 | C1203 | 303 | 1603 | Ryveilrtl | Cyveilrtl |
| DI6359 | EPHA3 | 3 | 89498444 | G | C | A0301,A1101,B1801,B5101,C1203,C1504 | A1101 | 96 | 321 | tsasHvwsy | tsasDvwsy |
| DI6359 | EPHA3 | 3 | 89498444 | G | C | A0301,A1101,B1801,B5101,C1203,C1504 | C1203 | 243 | 4028 | rkftsasHv | rkftsasDv |
| DI6359 | CD80 | 3 | 119263433 | G | A | A0301,A1101,B1801,B5101,C1203,C1504 | B1801 | 26 | 890 | Wehlaevtl | Rehlaevtl |
| DI6359 | CD80 | 3 | 119263433 | G | A | A0301,A1101,B1801,B5101,C1203,C1504 | C1203 | 21 | 20 | fkWehlaev | fkRehlaev |
| DI6359 | WDR49 | 3 | 167240216 | T | A | A0301,A1101,B1801,B5101,C1203,C1504 | C1203 | 148 | 155 | lpkrdtnFv | lpkrdtnLv |
| DI6359 | MECOM | 3 | 168840388 | C | G | A0301,A1101,B1801,B5101,C1203,C1504 | C1203 | 12 | 20 | yQcencakv | yEcencakv |
| DI6359 | TACC3 | 4 | 1737528 | G | A | A0301,A1101,B1801,B5101,C1203,C1504 | C1203 | 53 | 291 | dspDrpvpv | dspGrpvpv |
| DI6359 | CABS1 | 4 | 71201795 | G | A | A0301,A1101,B1801,B5101,C1203,C1504 | A1101 | 355 | 1969 | tNntetvpk | tDntetvpk |
| DI6359 | CABS1 | 4 | 71201795 | G | A | A0301,A1101,B1801,B5101,C1203,C1504 | C1203 | 325 | 128 | setNntetv | setDntetv |
| DI6359 | SCD5 | 4 | 83601963 | T | A | A0301,A1101,B1801,B5101,C1203,C1504 | C1203 | 373 | 226 | fffshFgwl | fffshlgwl |
| DI6359 | SCD5 | 4 | 83601963 | T | A | A0301,A1101,B1801,B5101,C1203,C1504 | C1203 | 37 | 61 | fshFgwlfv | fshlgwlfv |
| DI6359 | PPP3CA | 4 | 101947178 | G | T | A0301,A1101,B1801,B5101,C1203,C1504 | A1101 | 192 | 68 | kitsLeeak | kitsFeeak |
| DI6359 | FAT4 | 4 | 126369637 | C | G | A0301,A1101,B1801,B5101,C1203,C1504 | C1203 | 434 | 86 | gsfvfavRv | gsfvfavTv |
| DI6359 | PCDH18 | 4 | 138451064 | C | G | A0301,A1101,B1801,B5101,C1203,C1504 | A0301 | 394 | 1300 | atrcnrQkk | atrcnrEkk |
| DI6359 | DCHS2 | 4 | 155219345 | T | A | A0301,A1101,B1801,B5101,C1203,C1504 | B1801 | 398 | 3877 | dpvleqYpf | dpvleqNpf |
| DI6359 | DCHS2 | 4 | 155219345 | T | A | A0301,A1101,B1801,B5101,C1203,C1504 | C1203 | 92 | 968 | eqYpfdvfl | eqNpfdvfl |

Figure 21 (Cont.)

| | | | | | | | | | | | |
|---|---|---|---|---|---|---|---|---|---|---|---|
| DI6359 | DCHS2 | 4 | 155219345 | T | A | A0301,A1101,B1801,B5101,C1203,C1504 | C1203 | 319 | 3700 | Ypfdvflsp | Npfdvflsp |
| DI6359 | DNAH5 | 5 | 13916517 | C | A | A0301,A1101,B1801,B5101,C1203,C1504 | A0301 | 168 | 60 | kliysishy | kMiysishy |
| DI6359 | DNAH5 | 5 | 13916517 | C | A | A0301,A1101,B1801,B5101,C1203,C1504 | A0301 | 43 | 34 | liysishyy | Miysishyy |
| DI6359 | DNAH5 | 5 | 13916517 | C | A | A0301,A1101,B1801,B5101,C1203,C1504 | A1101 | 294 | 503 | kliysishy | kMiysishy |
| DI6359 | DNAH5 | 5 | 13916517 | C | A | A0301,A1101,B1801,B5101,C1203,C1504 | A1101 | 17 | 14 | liysishyy | Miysishyy |
| DI6359 | DNAH5 | 5 | 13916517 | C | A | A0301,A1101,B1801,B5101,C1203,C1504 | C1203 | 201 | 193 | tlinaikli | tlinaikMi |
| DI6359 | DNAH5 | 5 | 13916517 | C | A | A0301,A1101,B1801,B5101,C1203,C1504 | C1203 | 28 | 32 | naikliysi | naikMiysi |
| DI6359 | DNAH5 | 5 | 13916517 | C | A | A0301,A1101,B1801,B5101,C1203,C1504 | C1203 | 139 | 85 | liysishyy | Miysishyy |
| DI6359 | C6 | 5 | 41199926 | G | A | A0301,A1101,B1801,B5101,C1203,C1504 | A1101 | 48 | 126 | afqpcipFk | afqpcipSk |
| DI6359 | C6 | 5 | 41199926 | G | A | A0301,A1101,B1801,B5101,C1203,C1504 | C1203 | 41 | 1370 | vafqpcipF | vafqpcipS |
| DI6359 | RGS7BP | 5 | 63803656 | G | T | A0301,A1101,B1801,B5101,C1203,C1504 | A1101 | 465 | 464 | rtkVcemar | rtkGcemar |
| DI6359 | ARSB | 5 | 78260384 | G | A | A0301,A1101,B1801,B5101,C1203,C1504 | C1203 | 230 | 7408 | dyyshercI | dyyshercT |
| DI6359 | ARSB | 5 | 78260384 | G | A | A0301,A1101,B1801,B5101,C1203,C1504 | C1203 | 330 | 131 | yyshercIl | yyshercTl |
| DI6359 | ARSB | 5 | 78260384 | G | A | A0301,A1101,B1801,B5101,C1203,C1504 | C1203 | 9 | 7 | yshercIli | yshercTli |
| DI6359 | PCDHB9 | 5 | 140566903 | G | T | A0301,A1101,B1801,B5101,C1203,C1504 | A0301 | 76 | 163 | ktMgfsfpr | ktRgfsfpr |
| DI6359 | PCDHB9 | 5 | 140566903 | G | T | A0301,A1101,B1801,B5101,C1203,C1504 | A1101 | 10 | 34 | ktMgfsfpr | ktRgfsfpr |
| DI6359 | SLIT3 | 5 | 168112795 | C | T | A0301,A1101,B1801,B5101,C1203,C1504 | C1203 | 7 | 11 | faDprcekl | faGprcekl |
| DI6359 | TNXB | 6 | 32020482 | T | C | A0301,A1101,B1801,B5101,C1203,C1504 | A0301 | 343 | 14829 | hlyglhegR | hlyglhegQ |
| DI6359 | TNXB | 6 | 32020482 | T | C | A0301,A1101,B1801,B5101,C1203,C1504 | C1203 | 134 | 116 | yglhegRrv | yglhegQrv |
| DI6359 | UNC5CL | 6 | 40999457 | G | A | A0301,A1101,B1801,B5101,C1203,C1504 | C1203 | 161 | 75 | salIneiiv | salTneiiv |
| DI6359 | UNC5CL | 6 | 40999457 | G | A | A0301,A1101,B1801,B5101,C1203,C1504 | C1203 | 42 | 23 | lIneiivtm | lTneiivtm |
| DI6359 | PREP | 6 | 105776727 | T | A | A0301,A1101,B1801,B5101,C1203,C1504 | B1801 | 58 | 316 | teifyLfts | teifyQfts |
| DI6359 | PREP | 6 | 105776727 | T | A | A0301,A1101,B1801,B5101,C1203,C1504 | C1203 | 241 | 101 | ifyLftsfl | ifyQftsfl |

Figure 21 (Cont.)

| | | | | | | | | | | | |
|---|---|---|---|---|---|---|---|---|---|---|---|
| DI6359 | MLLT4 | 6 | 168299059 | A | C | A0301,A1101,B1801,B5101,C1203,C1504 | C1203 | 338 | 371 | gashvfQfv | gashvfKfv |
| DI6359 | MAGI2 | 7 | 77755074 | T | G | A0301,A1101,B1801,B5101,C1203,C1504 | C1203 | 197 | 384 | reyNmdlyv | reyKmdlyv |
| DI6359 | PLOD3 | 7 | 100853673 | G | A | A0301,A1101,B1801,B5101,C1203,C1504 | B1801 | 45 | 156 | hefgrllaI | hefgrllaT |
| DI6359 | PLOD3 | 7 | 100853673 | G | A | A0301,A1101,B1801,B5101,C1203,C1504 | C1203 | 137 | 8556 | hefgrllaI | hefgrllaT |
| DI6359 | CUX1 | 7 | 101844886 | C | T | A0301,A1101,B1801,B5101,C1203,C1504 | C1203 | 112 | 7672 | islkkpsaV | islkkpsaA |
| DI6359 | GRM8 | 7 | 126173280 | G | T | A0301,A1101,B1801,B5101,C1203,C1504 | C1203 | 9 | 8 | fvvdpHhii | fvvdpPhii |
| DI6359 | GRM8 | 7 | 126173280 | G | T | A0301,A1101,B1801,B5101,C1203,C1504 | C1203 | 84 | 87 | vvdpHhiii | vvdpPhiii |
| DI6359 | CHRM2 | 7 | 136700181 | C | T | A0301,A1101,B1801,B5101,C1203,C1504 | C1203 | 297 | 173 | aavtfgMai | aavtfgTai |
| DI6359 | CHRM2 | 7 | 136700181 | C | T | A0301,A1101,B1801,B5101,C1203,C1504 | C1203 | 289 | 2108 | fgMaiaafy | fgTaiaafy |
| DI6359 | RP1L1 | 8 | 10467730 | G | T | A0301,A1101,B1801,B5101,C1203,C1504 | B1801 | 488 | 15314 | Dentvqeev | Aentvqeev |
| DI6359 | ADAMDEC1 | 8 | 24259478 | G | T | A0301,A1101,B1801,B5101,C1203,C1504 | C1203 | 364 | 663 | rahfeiyll | rahfeRyll |
| DI6359 | DOCK5 | 8 | 25149686 | C | G | A0301,A1101,B1801,B5101,C1203,C1504 | A1101 | 45 | 18767 | vtakidhgK | vtakidhgN |
| DI6359 | CHRNA6 | 8 | 42611226 | T | G | A0301,A1101,B1801,B5101,C1203,C1504 | A1101 | 298 | 644 | Sglarrpak | Rglarrpak |
| DI6359 | PRKDC | 8 | 48777155 | C | A | A0301,A1101,B1801,B5101,C1203,C1504 | A1101 | 74 | 42 | Cvdaidvlk | Vvdaidvlk |
| DI6359 | PRKDC | 8 | 48777155 | C | A | A0301,A1101,B1801,B5101,C1203,C1504 | C1203 | 84 | 179 | fstiCvdai | fstiVvdai |
| DI6359 | PRKDC | 8 | 48777155 | C | A | A0301,A1101,B1801,B5101,C1203,C1504 | C1203 | 416 | 105 | iCvdaidvl | iVvdaidvl |
| DI6359 | FRMPD1 | 9 | 37746438 | T | C | A0301,A1101,B1801,B5101,C1203,C1504 | C1203 | 118 | 277 | lPsscrhvi | lLsscrhvi |
| DI6359 | PPAPDC3 | 9 | 134183375 | G | A | A0301,A1101,B1801,B5101,C1203,C1504 | A0301 | 52 | 20527 | likrrgpyK | likrrgpyE |
| DI6359 | PPAPDC3 | 9 | 134183375 | G | A | A0301,A1101,B1801,B5101,C1203,C1504 | A0301 | 248 | 9971 | Ktspslldy | Etspslldy |
| DI6359 | PPAPDC3 | 9 | 134183375 | G | A | A0301,A1101,B1801,B5101,C1203,C1504 | A1101 | 91 | 20410 | likrrgpyK | likrrgpyE |
| DI6359 | PPAPDC3 | 9 | 134183375 | G | A | A0301,A1101,B1801,B5101,C1203,C1504 | A1101 | 104 | 5004 | Ktspslldy | Etspslldy |
| DI6359 | COL5A1 | 9 | 137726853 | G | A | A0301,A1101,B1801,B5101,C1203,C1504 | A1101 | 97 | 40 | gMvqmtflr | gVvqmtflr |

Figure 21 (Cont.)

| | | | | | | | | | | | |
|---|---|---|---|---|---|---|---|---|---|---|---|
| DI6359 | GLRA2 | X | 14599405 | T | C | A0301,A1101,B1801,B5101,C1203,C1504 | A1101 | 143 | 376 | psmPdsiwk | psmLdsiwk |
| DI6359 | SERPINA7 | X | 105280479 | C | A | A0301,A1101,B1801,B5101,C1203,C1504 | A0301 | 323 | 2249 | vvgliqYlk | vvgliqDlk |
| DI6359 | SERPINA7 | X | 105280479 | C | A | A0301,A1101,B1801,B5101,C1203,C1504 | A1101 | 24 | 68 | vvgliqYlk | vvgliqDlk |
| DI6359 | SERPINA7 | X | 105280479 | C | A | A0301,A1101,B1801,B5101,C1203,C1504 | C1203 | 21 | 101 | iqYlkpnti | iqDlkpnti |
| DI6359 | SERPINA7 | X | 105280479 | C | A | A0301,A1101,B1801,B5101,C1203,C1504 | C1203 | 13 | 117 | Ylkpntimv | Dlkpntimv |
| DI6359 | MAGEC2 | X | 141291382 | G | A | A0301,A1101,B1801,B5101,C1203,C1504 | B1801 | 483 | 6772 | Ldsessfty | Pdsessfty |
| DI6359 | MAGEA4 | X | 151092860 | G | A | A0301,A1101,B1801,B5101,C1203,C1504 | A0301 | 473 | 777 | htvygKprk | htvygEprk |
| DI6359 | MAGEA4 | X | 151092860 | G | A | A0301,A1101,B1801,B5101,C1203,C1504 | A1101 | 221 | 184 | htvygKprk | htvygEprk |
| DI6359 | MAGEA4 | X | 151092860 | G | A | A0301,A1101,B1801,B5101,C1203,C1504 | C1203 | 214 | 247 | tvygKprkl | tvygEprkl |
| DM123062 | ERMAP | 1 | 43296520 | C | G | A0301,A0201,A0321,B1801,B4002,C0202,C0501 | A0301 | 48 | 72 | slwRgtvpk | slwPgtvpk |
| DM123062 | PPIAL4A | 1 | 147955256 | A | G | A0301,A0201,A0321,B1801,B4002,C0202,C0501 | A0301 | 26 | 22 | klfadkiPk | klfadkiLk |
| DM123062 | PPIAL4A | 1 | 147955256 | A | G | A0301,A0201,A0321,B1801,B4002,C0202,C0501 | C0501 | 137 | 856 | fadkiPkta | fadkiLkta |
| DM123062 | NID1 | 1 | 236180468 | G | A | A0301,A0201,A0321,B1801,B4002,C0202,C0501 | A0201 | 8 | 2765 | fLdegtcva | fSdegtcva |
| DM123062 | NID1 | 1 | 236180468 | G | A | A0301,A0201,A0321,B1801,B4002,C0202,C0501 | C0501 | 11 | 5 | fLdegtcva | fSdegtcva |
| DM123062 | SLC25A16 | 10 | 70243327 | C | T | A0301,A0201,A0321,B1801,B4002,C0202,C0501 | A0201 | 241 | 561 | tmrdtlkyv | tmrdtMkyv |
| DM123062 | ERLIN1 | 10 | 101933965 | C | A | A0301,A0201,A0321,B1801,B4002,C0202,C0501 | A0201 | 469 | 936 | gltiHavrv | gltiQavrv |
| DM123062 | ERLIN1 | 10 | 101933965 | C | A | A0301,A0201,A0321,B1801,B4002,C0202,C0501 | A0301 | 84 | 223 | tiHavrvtk | tiQavrvtk |
| DM123062 | OR5M3 | 11 | 56237144 | G | T | A0301,A0201,A0321,B1801,B4002,C0202,C0501 | A0201 | 55 | 51 | kmvavfyNt | kmvavfyTt |
| DM123062 | OR5M3 | 11 | 56237144 | G | T | A0301,A0201,A0321,B1801,B4002,C0202,C0501 | A0201 | 70 | 45 | mvavfyNtv | mvavfyTtv |
| DM123062 | CAND1 | 12 | 67699993 | A | G | A0301,A0201,A0321,B1801,B4002,C0202,C0501 | A0201 | 27 | 103 | slgevghhV | slgevghhl |
| DM123062 | CAND1 | 12 | 67699993 | A | G | A0301,A0201,A0321,B1801,B4002,C0202,C0501 | B4002 | 44 | 52 | gevghhVdl | gevghhIdl |
| DM123062 | TRAFD1 | 12 | 112583390 | G | T | A0301,A0201,A0321,B1801,B4002,C0202,C0501 | A0201 | 105 | 1219 | slsdikVaa | slsdikGaa |
| DM123062 | POLR1D | 13 | 28197374 | A | G | A0301,A0201,A0321,B1801,B4002,C0202,C0501 | C0501 | 166 | 670 | kasmGstf | kasmEstf |

Figure 21 (Cont.)

| | | | | | | | | | | |
|---|---|---|---|---|---|---|---|---|---|---|
| DM123062 MYCBP2 | 13 | 77730266 | C | T | A0301,A0201,A0321,B1801,B4002,C0202,C0501 | A0201 | 172 | 4530 | Ygwpttitv | Cgwpttitv |
| DM123062 AKAP6 | 14 | 33242951 | T | A | A0301,A0201,A0321,B1801,B4002,C0202,C0501 | C0501 | 237 | 110 | Hlddretcn | Llddretcn |
| DM123062 GABRG3 | 15 | 27772665 | C | A | A0301,A0201,A0321,B1801,B4002,C0202,C0501 | A0201 | 20 | 24 | yvtamdlfv | yvtamdLfv |
| DM123062 GABRG3 | 15 | 27772665 | C | A | A0301,A0201,A0321,B1801,B4002,C0202,C0501 | A0201 | 34 | 38 | tamdlfvtv | tamdLfvtv |
| DM123062 SCAPER | 15 | 76641041 | G | A | A0301,A0201,A0321,B1801,B4002,C0202,C0501 | B1801 | 88 | 51 | lelVnrfpq | lelAnrfpq |
| DM123062 SCAPER | 15 | 76641041 | G | A | A0301,A0201,A0321,B1801,B4002,C0202,C0501 | B4002 | 148 | 83 | lelVnrfpq | lelAnrfpq |
| DM123062 PRRT2 | 16 | 29824976 | C | T | A0301,A0201,A0321,B1801,B4002,C0202,C0501 | B1801 | 54 | 4665 | eegpapepY | eegpapepH |
| DM123062 SLC9A5 | 16 | 67286520 | G | A | A0301,A0201,A0321,B1801,B4002,C0202,C0501 | A0201 | 373 | 1099 | llglvlEgi | llglvlGgi |
| DM123062 SLC9A5 | 16 | 67286520 | G | A | A0301,A0201,A0321,B1801,B4002,C0202,C0501 | A0201 | 76 | 248 | lvlEgivla | lvlGgivla |
| DM123062 SLC9A5 | 16 | 67286520 | G | A | A0301,A0201,A0321,B1801,B4002,C0202,C0501 | A0201 | 60 | 27 | vlEgivlav | vlGgivlav |
| DM123062 BANP | 16 | 88105690 | C | A | A0301,A0201,A0321,B1801,B4002,C0202,C0501 | A0201 | 203 | 196 | lqgaKliav | lqgaQliav |
| DM123062 DHX33 | 17 | 5356947 | T | G | A0301,A0201,A0321,B1801,B4002,C0202,C0501 | A0201 | 363 | 8221 | vmlqllamT | vmlqllamK |
| DM123062 DHX33 | 17 | 5356947 | T | G | A0301,A0201,A0321,B1801,B4002,C0202,C0501 | A0201 | 28 | 52 | mlqllamTv | mlqllamKv |
| DM123062 DHX33 | 17 | 5356947 | T | G | A0301,A0201,A0321,B1801,B4002,C0202,C0501 | A0201 | 8 | 9 | llamTvpnv | llamKvpnv |
| DM123062 DHX33 | 17 | 5356947 | T | G | A0301,A0201,A0321,B1801,B4002,C0202,C0501 | C0501 | 374 | 24649 | mTvpnvltf | mKvpnvltf |
| DM123062 DHX33 | 17 | 5356949 | C | T | A0301,A0201,A0321,B1801,B4002,C0202,C0501 | A0201 | 295 | 1296 | svmlqllal | svmlqllaM |
| DM123062 DHX33 | 17 | 5356949 | C | T | A0301,A0201,A0321,B1801,B4002,C0202,C0501 | A0201 | 47 | 52 | mlqllalkv | mlqllaMkv |
| DM123062 DHX33 | 17 | 5356949 | C | T | A0301,A0201,A0321,B1801,B4002,C0202,C0501 | A0201 | 16 | 9 | llalkvpnv | llaMkvpnv |
| DM123062 DHX33 | 17 | 5356949 | C | T | A0301,A0201,A0321,B1801,B4002,C0202,C0501 | A0301 | 67 | 45 | vmlqllalk | vmlqllaMk |
| DM123062 SREBF1 | 17 | 17717594 | G | T | A0301,A0201,A0321,B1801,B4002,C0202,C0501 | A0201 | 27 | 23 | ylqdsMatt | ylqdsLatt |
| DM123062 TEX2 | 17 | 62238232 | T | G | A0301,A0201,A0321,B1801,B4002,C0202,C0501 | A0201 | 13 | 20 | flmtletNm | flmtletKm |
| DM123062 TEX2 | 17 | 62238232 | T | G | A0301,A0201,A0321,B1801,B4002,C0202,C0501 | A0201 | 77 | 464 | mtletNmnl | mtletKmnl |

Figure 21 (Cont.)

| | | | | | | | | | | | |
|---|---|---|---|---|---|---|---|---|---|---|---|
| DM123062 | TEX2 | 17 | 62238232 | T | G | A0301,A0201,A0321,B1801,B4002,C0202,C0501 | A0301 | 250 | 38 | Nmnltklgk | Kmnltklgk |
| DM123062 | TEX2 | 17 | 62238232 | T | G | A0301,A0201,A0321,B1801,B4002,C0202,C0501 | B4002 | 496 | 688 | letNmnltk | letKmnltk |
| DM123062 | RBBP8 | 18 | 20570906 | C | G | A0301,A0201,A0321,B1801,B4002,C0202,C0501 | B1801 | 427 | 246 | eesetEgpm | |
| DM123062 | KCNG2 | 18 | 77623972 | G | A | A0301,A0201,A0321,B1801,B4002,C0202,C0501 | B4002 | 387 | 463 | Hdelaywgi | Rdelaywgi |
| DM123062 | MADCAM1 | 19 | 496508 | C | A | A0301,A0201,A0321,B1801,B4002,C0202,C0501 | B4002 | 329 | 92 | mdLglalll | mdFglalll |
| DM123062 | WDR18 | 19 | 991295 | C | T | A0301,A0201,A0321,B1801,B4002,C0202,C0501 | B1801 | 146 | 419 | delvrlwdv | deTvrlwdv |
| DM123062 | WTIP | 19 | 34986636 | C | T | A0301,A0201,A0321,B1801,B4002,C0202,C0501 | A0201 | 73 | 991 | Fmdrdyhva | |
| DM123062 | WTIP | 19 | 34986636 | C | T | A0301,A0201,A0321,B1801,B4002,C0202,C0501 | B1801 | 21 | 2901 | cettirvvF | cettirvvS |
| DM123062 | WTIP | 19 | 34986636 | C | T | A0301,A0201,A0321,B1801,B4002,C0202,C0501 | B4002 | 82 | 555 | cettirvvF | cettirvvS |
| DM123062 | PAK4 | 19 | 39663564 | G | A | A0301,A0201,A0321,B1801,B4002,C0202,C0501 | A0301 | 31 | 76 | iMrgskgak | iVrgskgak |
| DM123062 | KLK1 | 19 | 51323463 | T | A | A0301,A0201,A0321,B1801,B4002,C0202,C0501 | B4002 | 420 | 7469 | velpteepV | velpteepE |
| DM123062 | ZNF17 | 19 | 57931138 | T | C | A0301,A0201,A0321,B1801,B4002,C0202,C0501 | A0201 | 61 | 17 | slPkdilhl | slLkdilhl |
| DM123062 | A1BG | 19 | 58861808 | A | G | A0301,A0201,A0321,B1801,B4002,C0202,C0501 | C0501 | 219 | 224 | vadsanysR | vadsanysC |
| DM123062 | ASAP2 | 2 | 9490950 | C | T | A0301,A0201,A0321,B1801,B4002,C0202,C0501 | A0301 | 45 | 68 | gtanrpLak | gtanrpPak |
| DM123062 | XIRP2 | 2 | 168102494 | C | A | A0301,A0201,A0321,B1801,B4002,C0202,C0501 | A0301 | 57 | 19700 | ktttwlfeK | ktttwlfeT |
| DM123062 | XIRP2 | 2 | 168102494 | C | A | A0301,A0201,A0321,B1801,B4002,C0202,C0501 | B1801 | 86 | 39 | feKtplhef | feTtplhef |
| DM123062 | XIRP2 | 2 | 168102494 | C | A | A0301,A0201,A0321,B1801,B4002,C0202,C0501 | B4002 | 241 | 168 | feKtplhef | feTtplhef |
| DM123062 | TTN | 2 | 179611639 | C | T | A0301,A0201,A0321,B1801,B4002,C0202,C0501 | B1801 | 11 | 31 | yeiwHsdsf | yeiwRsdsf |
| DM123062 | TTN | 2 | 179611639 | C | T | A0301,A0201,A0321,B1801,B4002,C0202,C0501 | B4002 | 139 | 334 | yeiwHsdsf | yeiwRsdsf |
| DM123062 | PAK7 | 20 | 9561540 | G | A | A0301,A0201,A0321,B1801,B4002,C0202,C0501 | B4002 | 77 | 152 | ketFingll | ketSingll |
| DM123062 | RBM39 | 20 | 34312584 | C | T | A0301,A0201,A0321,B1801,B4002,C0202,C0501 | B1801 | 66 | 556 | Mefvdvssv | Vefvdvssv |
| DM123062 | RBM39 | 20 | 34312584 | C | T | A0301,A0201,A0321,B1801,B4002,C0202,C0501 | B4002 | 27 | 46 | Mefvdvssv | Vefvdvssv |
| DM123062 | ZFP64 | 20 | 50776706 | C | T | A0301,A0201,A0321,B1801,B4002,C0202,C0501 | C0501 | 269 | 324 | yaNmssql | yaSmssql |

Figure 21 (Cont.)

| | | | | | | | | | | | |
|---|---|---|---|---|---|---|---|---|---|---|---|
| DM123062 | SLC16A8 | 22 | 38478021 | A | G | A0301,A0201,A0321,B1801,B4002,C0202,C0501 | C0501 | 427 | 982 | vssiPvtrf | vssiLvtrf |
| DM123062 | CELSR1 | 22 | 46763647 | G | T | A0301,A0201,A0321,B1801,B4002,C0202,C0501 | A0201 | 237 | 93 | alsfhylLa | alsfhylFa |
| DM123062 | CELSR1 | 22 | 46763647 | G | T | A0301,A0201,A0321,B1801,B4002,C0202,C0501 | A0201 | 5 | 5 | ylLaifsgl | ylFaifsgl |
| DM123062 | CELSR3 | 3 | 48678778 | G | A | A0301,A0201,A0321,B1801,B4002,C0202,C0501 | B1801 | 9 | 75 | detslgWaq | detslgRaq |
| DM123062 | CNTN3 | 3 | 74413674 | C | A | A0301,A0201,A0321,B1801,B4002,C0202,C0501 | A0201 | 79 | 3926 | Fiaenkhgl | Ciaenkhgl |
| DM123062 | CNTN3 | 3 | 74413674 | C | A | A0301,A0201,A0321,B1801,B4002,C0202,C0501 | C0501 | 3 | 263 | vtdsgmfqF | |
| DM123062 | CD47 | 3 | 107777256 | C | A | A0301,A0201,A0321,B1801,B4002,C0202,C0501 | A0201 | 443 | 2494 | aigltsfFi | aigltsfVi |
| DM123062 | CD47 | 3 | 107777256 | C | A | A0301,A0201,A0321,B1801,B4002,C0202,C0501 | A0201 | 35 | 26 | gltsfFiai | gltsfViai |
| DM123062 | CD47 | 3 | 107777256 | C | A | A0301,A0201,A0321,B1801,B4002,C0202,C0501 | A0201 | 19 | 134 | Fiailviqv | Viailviqv |
| DM123062 | HEG1 | 3 | 124696730 | C | A | A0301,A0201,A0321,B1801,B4002,C0202,C0501 | A0201 | 421 | 1729 | glllilVia | glllilGia |
| DM123062 | HEG1 | 3 | 124696730 | C | A | A0301,A0201,A0321,B1801,B4002,C0202,C0501 | A0201 | 50 | 179 | lllilVial | lllilGial |
| DM123062 | HEG1 | 3 | 124696730 | C | A | A0301,A0201,A0321,B1801,B4002,C0202,C0501 | A0201 | 73 | 45 | llilViali | llilGiali |
| DM123062 | HEG1 | 3 | 124696730 | C | A | A0301,A0201,A0321,B1801,B4002,C0202,C0501 | A0201 | 430 | 108 | lilVialiv | lilGialiv |
| DM123062 | NPHP3 | 3 | 132402361 | A | T | A0301,A0201,A0321,B1801,B4002,C0202,C0501 | A0301 | 105 | 5158 | ilykkmgkH | ilykkmgkL |
| DM123062 | ZAR1 | 4 | 48492870 | C | T | A0301,A0201,A0321,B1801,B4002,C0202,C0501 | A0201 | 67 | 354 | alCrltafl | alRrltafl |
| DM123062 | FCHO2 | 5 | 72383578 | C | T | A0301,A0201,A0321,B1801,B4002,C0202,C0501 | A0201 | 115 | 1939 | slikkrfal | slikkrfaT |
| DM123062 | DMGDH | 5 | 78359507 | C | T | A0301,A0201,A0321,B1801,B4002,C0202,C0501 | A0201 | 108 | 93 | slayhlTka | slayhlAka |
| DM123062 | DMGDH | 5 | 78359507 | C | T | A0301,A0201,A0321,B1801,B4002,C0202,C0501 | A0301 | 48 | 43 | vslayhlTk | vslayhlAk |
| DM123062 | PCDHGA6 | 5 | 140754269 | G | A | A0301,A0201,A0321,B1801,B4002,C0202,C0501 | A0201 | 482 | 854 | alyrlvlta | aVyrlvlta |
| DM123062 | PCDHGA6 | 5 | 140754269 | G | A | A0301,A0201,A0321,B1801,B4002,C0202,C0501 | B4002 | 38 | 37 | regealyrl | regeaVyrl |
| DM123062 | PCDHGA6 | 5 | 140754269 | G | A | A0301,A0201,A0321,B1801,B4002,C0202,C0501 | B4002 | 29 | 27 | gealyrlvl | geaVyrlvl |
| DM123062 | PCDHGA6 | 5 | 140754269 | G | A | A0301,A0201,A0321,B1801,B4002,C0202,C0501 | C0501 | 138 | 171 | tldregeal | tldregeaV |

Figure 21 (Cont.)

| | | | | | | | | | | | |
|---|---|---|---|---|---|---|---|---|---|---|---|
| DM123062 | ADAMTS2 | 5 | 178555013 | A | G | A0301,A0201,A0321,B1801,B4002,C0202,C0501 | A0301 | 145 | 534 | svAyewalk | svVyewalk |
| DM123062 | ADAMTS2 | 5 | 178555013 | A | G | A0301,A0201,A0321,B1801,B4002,C0202,C0501 | A0301 | 27 | 24 | vAyewalkk | vVyewalkk |
| DM123062 | ADAMTS2 | 5 | 178555013 | A | G | A0301,A0201,A0321,B1801,B4002,C0202,C0501 | B1801 | 494 | 160 | eedsvAyew | eedsvVyew |
| DM123062 | ADAMTS2 | 5 | 178555013 | A | G | A0301,A0201,A0321,B1801,B4002,C0202,C0501 | C0501 | 185 | 168 | vleedsvAy | vleedsvVy |
| DM123062 | SNAP91 | 6 | 84326716 | T | A | A0301,A0201,A0321,B1801,B4002,C0202,C0501 | A0301 | 43 | 43 | hlnSlegkk | hlnTlegkk |
| DM123062 | FBXL4 | 6 | 99365471 | G | C | A0301,A0201,A0321,B1801,B4002,C0202,C0501 | A0201 | 19 | 4 | sVleyytel | sLleyytel |
| DM123062 | MAP7 | 6 | 136693744 | G | C | A0301,A0201,A0321,B1801,B4002,C0202,C0501 | A0301 | 376 | 1559 | iMmpykaah | ilmpykaah |
| DM123062 | CRHR2 | 7 | 30693171 | G | T | A0301,A0201,A0321,B1801,B4002,C0202,C0501 | C0501 | 350 | 695 | wqdhNslrv | wqdhHslrv |
| DM123062 | UBXN8 | 8 | 30618405 | A | T | A0301,A0201,A0321,B1801,B4002,C0202,C0501 | B4002 | 180 | 687 | keFpdlpee | kelpdlpee |
| DM123062 | GOT1L1 | 8 | 37795189 | C | A | A0301,A0201,A0321,B1801,B4002,C0202,C0501 | B4002 | 439 | 451 | kdSrivyii | kdArivyii |
| DM123062 | ZFHX4 | 8 | 77761275 | G | T | A0301,A0201,A0321,B1801,B4002,C0202,C0501 | A0201 | 207 | 273 | svagCtqpl | svagGtqpl |
| DM123062 | ZFHX4 | 8 | 77761275 | G | T | A0301,A0201,A0321,B1801,B4002,C0202,C0501 | A0301 | 303 | 316 | Ctqplllak | Gtqplllak |
| DM123062 | ZFHX4 | 8 | 77764707 | G | T | A0301,A0201,A0321,B1801,B4002,C0202,C0501 | A0301 | 23 | 30 | imNdvpsyk | imKdvpsyk |
| DM123062 | KLF10 | 8 | 103663584 | C | G | A0301,A0201,A0321,B1801,B4002,C0202,C0501 | A0201 | 31 | 1049 | vLqsskppv | vVqsskppv |
| DM123062 | DCSTAMP | 8 | 105361043 | C | T | A0301,A0201,A0321,B1801,B4002,C0202,C0501 | A0201 | 113 | 142 | llvflFcgl | llvflScgl |
| DM123062 | WNK2 | 9 | 96060263 | G | A | A0301,A0201,A0321,B1801,B4002,C0202,C0501 | A0301 | 333 | 15866 | rQrktsksk | rRrktsksk |
| DM123062 | ZNF462 | 9 | 109690335 | T | C | A0301,A0201,A0321,B1801,B4002,C0202,C0501 | B4002 | 71 | 56 | feavsTwdi | feavslwdi |
| DM123062 | LHX6 | 9 | 124976279 | T | A | A0301,A0201,A0321,B1801,B4002,C0202,C0501 | C0501 | 150 | 263 | ladmSglsr | ladmTglsr |
| FR9547 | NBPF1 | 1 | 16891341 | C | G | A2402,A0201,B0801,B1801,C0701, | A0201 | 171 | 54 | lleaQepev | lleaVepev |
| FR9547 | CROCC | 1 | 17285204 | C | A | A2402,A0201,B0801,B1801,C0701, | A0201 | 62 | 73 | rMlkgeasl | rLlkgeasl |
| FR9547 | CROCC | 1 | 17285204 | C | A | A2402,A0201,B0801,B1801,C0701, | B0801 | 219 | 627 | tlglrqrMl | tlglrqrLl |
| FR9547 | MSH4 | 1 | 76288113 | G | T | A2402,A0201,B0801,B1801,C0701, | A0201 | 94 | 60 | tlfCvlnyt | tlfGvlnyt |
| FR9547 | MSH4 | 1 | 76288113 | G | T | A2402,A0201,B0801,B1801,C0701, | C0701 | 34 | 492 | ymnhtlfC | ymnhtlfG |

Figure 21 (Cont.)

| | | | | | | | | | | | |
|---|---|---|---|---|---|---|---|---|---|---|---|
| FR9547 | FRRS1 | 1 | 100174558 | C | A | A2402,A0201,B0801,B1801,C0701, | A0201 | 74 | 742 | ktlafaCqv | ktlafaGqv |
| FR9547 | NTNG1 | 1 | 107867028 | A | T | A2402,A0201,B0801,B1801,C0701, | A2402 | 376 | 3767 | twMeypkpl | twKeypkpl |
| FR9547 | NTNG1 | 1 | 107867028 | A | T | A2402,A0201,B0801,B1801,C0701, | B1801 | 225 | 1236 | wqsatwMey | wqsatwKey |
| FR9547 | NTNG1 | 1 | 107867028 | A | T | A2402,A0201,B0801,B1801,C0701, | C0701 | 130 | 944 | Meypkplqv | Keypkplqv |
| FR9547 | SYCP1 | 1 | 115469129 | C | T | A2402,A0201,B0801,B1801,C0701, | B0801 | 491 | 919 | Vlkkkgtae | Alkkkgtae |
| FR9547 | PDE4DIP | 1 | 145075756 | G | A | A2402,A0201,B0801,B1801,C0701, | C0701 | 487 | 969 | yrsgdVtrt | yrsgdAtrt |
| FR9547 | ARHGEF11 | 1 | 156928609 | A | T | A2402,A0201,B0801,B1801,C0701, | A0201 | 121 | 59 | slygendQl | slygendLl |
| FR9547 | FCER1A | 1 | 159277630 | C | A | A2402,A0201,B0801,B1801,C0701, | A0201 | 266 | 2261 | Kqvtfllki | Qqvtfllki |
| FR9547 | DDR2 | 1 | 162745477 | G | T | A2402,A0201,B0801,B1801,C0701, | A0201 | 341 | 23727 | sLlkdpnii | sRlkdpnii |
| FR9547 | DUSP27 | 1 | 167097360 | G | A | A2402,A0201,B0801,B1801,C0701, | C0701 | 11 | 12 | yheanSnsv | yheanGnsv |
| FR9547 | OR14C36 | 1 | 248512179 | G | T | A2402,A0201,B0801,B1801,C0701, | A0201 | 145 | 141 | ffmlylLtl | ffmlylVtl |
| FR9547 | OR14C36 | 1 | 248512179 | G | T | A2402,A0201,B0801,B1801,C0701, | A0201 | 12 | 14 | fmlylLtlm | fmlylVtlm |
| FR9547 | OR14C36 | 1 | 248512179 | G | T | A2402,A0201,B0801,B1801,C0701, | A0201 | 22 | 87 | ylLtlmgni | ylVtlmgni |
| FR9547 | OR14C36 | 1 | 248512179 | G | T | A2402,A0201,B0801,B1801,C0701, | A2402 | 339 | 638 | ffmlylLtl | ffmlylVtl |
| FR9547 | OR14C36 | 1 | 248512179 | G | T | A2402,A0201,B0801,B1801,C0701, | B0801 | 54 | 104 | ffmlylLtl | ffmlylVtl |
| FR9547 | ITIH5 | 10 | 7657949 | C | A | A2402,A0201,B0801,B1801,C0701, | A0201 | 462 | 9483 | klLqtkdal | klRqtkdal |
| FR9547 | RBP3 | 10 | 48390487 | C | A | A2402,A0201,B0801,B1801,C0701, | A0201 | 160 | 1205 | vlegnvCyl | vlegnvGyl |
| FR9547 | ZWINT | 10 | 58118447 | C | A | A2402,A0201,B0801,B1801,C0701, | A0201 | 9 | 3783 | hlaevsaeV | hlaevsaeG |
| FR9547 | ZWINT | 10 | 58118447 | C | A | A2402,A0201,B0801,B1801,C0701, | A2402 | 436 | 868 | vsaeVkllf | vsaeGkllf |
| FR9547 | PBLD | 10 | 70056708 | C | A | A2402,A0201,B0801,B1801,C0701, | B1801 | 293 | 4851 | Memnlseta | Remnlseta |
| FR9547 | PBLD | 10 | 70056708 | C | A | A2402,A0201,B0801,B1801,C0701, | C0701 | 28 | 21 | mhqkiaMem | mhqkiaRem |
| FR9547 | MARCH5 | 10 | 94109442 | G | T | A2402,A0201,B0801,B1801,C0701, | A2402 | 162 | 4415 | ifpgigcpF | ifpgigcpV |

Figure 21 (Cont.)

| | | | | | | | | | | | |
|---|---|---|---|---|---|---|---|---|---|---|---|
| FR9547 | NEURL1 | 10 | 105330826 | T | C | A2402,A0201,B0801,B1801,C0701, | A0201 | 305 | 20269 | tLsnrpvli | tFsnrpvli |
| FR9547 | NEURL1 | 10 | 105330826 | T | C | A2402,A0201,B0801,B1801,C0701, | C0701 | 204 | 200 | tLsnrpvli | tFsnrpvli |
| FR9547 | TMEM86A | 11 | 18723155 | G | T | A2402,A0201,B0801,B1801,C0701, | A2402 | 360 | 491 | thmfySsaf | thmfyAsaf |
| FR9547 | TMEM86A | 11 | 18723155 | G | T | A2402,A0201,B0801,B1801,C0701, | C0701 | 202 | 294 | thmfySsaf | thmfyAsaf |
| FR9547 | ARL14EP | 11 | 30354528 | C | T | A2402,A0201,B0801,B1801,C0701, | C0701 | 249 | 7244 | rrltknatV | rrltknatA |
| FR9547 | MYEOV | 11 | 69063507 | C | G | A2402,A0201,B0801,B1801,C0701, | A0201 | 116 | 88 | imwGrmdva | imwArmdva |
| FR9547 | MMP10 | 11 | 102643704 | A | T | A2402,A0201,B0801,B1801,C0701, | B1801 | 63 | 16 | neEqagypr | neVqagypr |
| FR9547 | C11orf63 | 11 | 122756722 | G | T | A2402,A0201,B0801,B1801,C0701, | B1801 | 31 | 18 | qeiIchsef | qeiMchsef |
| FR9547 | IQSEC3 | 12 | 247458 | G | A | A2402,A0201,B0801,B1801,C0701, | C0701 | 178 | 208 | ehkyDghlv | ehkyGghlv |
| FR9547 | KCNA5 | 12 | 5155015 | G | T | A2402,A0201,B0801,B1801,C0701, | A2402 | 314 | 5063 | sfckagWtl | sfckagGtl |
| FR9547 | ANO2 | 12 | 5939605 | C | A | A2402,A0201,B0801,B1801,C0701, | C0701 | 99 | 52 | trsLivhei | trsRivhei |
| FR9547 | NOP2 | 12 | 6672816 | G | T | A2402,A0201,B0801,B1801,C0701, | B1801 | 140 | 840 | eeTfvlppa | eePfvlppa |
| FR9547 | ING4 | 12 | 6761483 | C | A | A2402,A0201,B0801,B1801,C0701, | C0701 | 173 | 1931 | Fhqvsygem | Chqvsygem |
| FR9547 | SLC2A3 | 12 | 8083229 | G | T | A2402,A0201,B0801,B1801,C0701, | A0201 | 30 | 8 | ilvaqifgM | ilvaqifgL |
| FR9547 | SLC2A3 | 12 | 8083229 | G | T | A2402,A0201,B0801,B1801,C0701, | A0201 | 277 | 159 | aqifgMefi | aqifgLefi |
| FR9547 | SLC2A3 | 12 | 8083229 | G | T | A2402,A0201,B0801,B1801,C0701, | A0201 | 489 | 384 | qifgMefil | qifgLefil |
| FR9547 | SLC2A3 | 12 | 8083229 | G | T | A2402,A0201,B0801,B1801,C0701, | B1801 | 346 | 1318 | Mefilgsee | Lefilgsee |
| FR9547 | CAPZA3 | 12 | 18891440 | G | T | A2402,A0201,B0801,B1801,C0701, | A2402 | 373 | 983 | nvmgYyrff | nvmgDyrff |
| FR9547 | CAPZA3 | 12 | 18891440 | G | T | A2402,A0201,B0801,B1801,C0701, | C0701 | 300 | 2403 | shhnvmgYy | shhnvmgDy |
| FR9547 | DBX2 | 12 | 45417596 | G | T | A2402,A0201,B0801,B1801,C0701, | C0701 | 101 | 396 | fYedqrkal | fSedqrkal |
| FR9547 | ADCY6 | 12 | 49169202 | C | T | A2402,A0201,B0801,B1801,C0701, | B1801 | 403 | 161 | Nevdeflsr | Devdeflsr |
| FR9547 | KMT2D | 12 | 49431079 | C | A | A2402,A0201,B0801,B1801,C0701, | A0201 | 116 | 6284 | amvsnqWhm | amvsnqGhm |
| FR9547 | SLC26A10 | 12 | 58014868 | C | A | A2402,A0201,B0801,B1801,C0701, | A0201 | 168 | 11 | Elmlgmfvl | Almlgmfvl |

Figure 21 (Cont.)

| | | | | | | | | | | | |
|---|---|---|---|---|---|---|---|---|---|---|---|
| FR9547 | SLC26A10 | 12 | 58014868 | C | A | A2402,A0201,B0801,B1801,C0701, | C0701 | 344 | 1057 | vafgsgElm | vafgsgAlm |
| FR9547 | NUAK1 | 12 | 106460828 | T | A | A2402,A0201,B0801,B1801,C0701, | A0201 | 107 | 78 | vlsCdsfdl | vlsSdsfdl |
| FR9547 | BTBD11 | 12 | 107937819 | G | A | A2402,A0201,B0801,B1801,C0701, | A0201 | 194 | 51 | alywepKal | alywepEal |
| FR9547 | BTBD11 | 12 | 107937819 | G | A | A2402,A0201,B0801,B1801,C0701, | B1801 | 12 | 6 | wepKalytl | wepEalytl |
| FR9547 | ACACB | 12 | 109665243 | G | T | A2402,A0201,B0801,B1801,C0701, | A0201 | 97 | 1336 | rqlpdVtcv | rqlpdGtcv |
| FR9547 | ACACB | 12 | 109665243 | G | T | A2402,A0201,B0801,B1801,C0701, | A0201 | 49 | 74 | qlpdVtcvv | qlpdGtcvv |
| FR9547 | TMEM132B | 12 | 126128721 | T | G | A2402,A0201,B0801,B1801,C0701, | A0201 | 134 | 83 | ftsqVevtv | ftsqFevtv |
| FR9547 | TMEM132B | 12 | 126128721 | T | G | A2402,A0201,B0801,B1801,C0701, | A0201 | 310 | 44 | sqVevtvwa | sqFevtvwa |
| FR9547 | TMEM132B | 12 | 126128721 | T | G | A2402,A0201,B0801,B1801,C0701, | C0701 | 82 | 380 | thqhftsqV | thqhftsqF |
| FR9547 | TMEM132B | 12 | 126128721 | T | G | A2402,A0201,B0801,B1801,C0701, | C0701 | 33 | 60 | qhftsqVev | qhftsqFev |
| FR9547 | TMTC4 | 13 | 101315388 | C | T | A2402,A0201,B0801,B1801,C0701, | C0701 | 171 | 156 | fhpvgfhMv | fhpvgfhVv |
| FR9547 | TMTC4 | 13 | 101315388 | C | T | A2402,A0201,B0801,B1801,C0701, | C0701 | 88 | 525 | fhMvnillh | fhVvnillh |
| FR9547 | ARHGEF7 | 13 | 111926265 | C | G | A2402,A0201,B0801,B1801,C0701, | A0201 | 352 | 44 | rldkyRtll | rldkyPtll |
| FR9547 | ARHGEF7 | 13 | 111926265 | C | G | A2402,A0201,B0801,B1801,C0701, | B0801 | 185 | 348 | mrldkyRtl | mrldkyPtl |
| FR9547 | ARHGEF7 | 13 | 111926265 | C | G | A2402,A0201,B0801,B1801,C0701, | C0701 | 12 | 24 | mrldkyRtl | mrldkyPtl |
| FR9547 | OR4K15 | 14 | 20444659 | C | T | A2402,A0201,B0801,B1801,C0701, | B0801 | 19 | 40 | msklksWyl | msklksRyl |
| FR9547 | TEP1 | 14 | 20852650 | C | A | A2402,A0201,B0801,B1801,C0701, | A2402 | 149 | 500 | rypcewVgv | rypcewGgv |
| FR9547 | MYH7 | 14 | 23899064 | G | T | A2402,A0201,B0801,B1801,C0701, | B0801 | 378 | 7767 | myklKgaim | myklTgaim |
| FR9547 | CBLN3 | 14 | 24898214 | G | T | A2402,A0201,B0801,B1801,C0701, | C0701 | 125 | 45 | lhsHglplv | lhsPglplv |
| FR9547 | RALGAPA1 | 14 | 36097115 | C | A | A2402,A0201,B0801,B1801,C0701, | A0201 | 480 | 1050 | glisiaaLt | glisiaaRt |
| FR9547 | RALGAPA1 | 14 | 36097115 | C | A | A2402,A0201,B0801,B1801,C0701, | A0201 | 29 | 15824 | aLtvithlv | aRtvithlv |
| FR9547 | TMEM229B | 14 | 67940427 | G | T | A2402,A0201,B0801,B1801,C0701, | B0801 | 153 | 354 | ylrlrgrcT | ylrlrgrcP |

Figure 21 (Cont.)

| | | | | | | | | | | | |
|---|---|---|---|---|---|---|---|---|---|---|---|
| FR9547 | TMEM229B | 14 | 67940427 | G | T | A2402,A0201,B0801,B1801,C0701, | B0801 | 57 | 139 | rlrgrcTll | rlrgrcPll |
| FR9547 | TMEM229B | 14 | 67940427 | G | T | A2402,A0201,B0801,B1801,C0701, | C0701 | 74 | 68 | lrgrcTlll | lrgrcPlll |
| FR9547 | VRTN | 14 | 74824097 | G | A | A2402,A0201,B0801,B1801,C0701, | C0701 | 259 | 201 | irpyfnHvi | irpyfnRvi |
| FR9547 | CDC42BPB | 14 | 103432670 | C | A | A2402,A0201,B0801,B1801,C0701, | A0201 | 62 | 272 | ylqalaskl | ylqalaskM |
| FR9547 | CDC42BPB | 14 | 103432670 | C | A | A2402,A0201,B0801,B1801,C0701, | A0201 | 325 | 27 | klteeleal | kMteeleal |
| FR9547 | OR4N4 | 15 | 22382630 | C | T | A2402,A0201,B0801,B1801,C0701, | C0701 | 443 | 639 | irsdLglta | irsdPglta |
| FR9547 | IL16 | 15 | 81571918 | T | A | A2402,A0201,B0801,B1801,C0701, | B0801 | 465 | 624 | qakkglHtl | qakkglLtl |
| FR9547 | MFGE8 | 15 | 89449071 | T | A | A2402,A0201,B0801,B1801,C0701, | A0201 | 90 | 30 | nlfetpvVa | nlfetpvEa |
| FR9547 | MFGE8 | 15 | 89449071 | T | A | A2402,A0201,B0801,B1801,C0701, | B1801 | 9 | 30 | fetpvVaqy | fetpvEaqy |
| FR9547 | SLCO3A1 | 15 | 92647532 | G | T | A2402,A0201,B0801,B1801,C0701, | A2402 | 248 | 24260 | dYprwigaw | dDprwigaw |
| FR9547 | BAIAP3 | 16 | 1394815 | G | A | A2402,A0201,B0801,B1801,C0701, | A0201 | 19 | 27 | ilnvdlftl | ilnvdVftl |
| FR9547 | BAIAP3 | 16 | 1394815 | G | A | A2402,A0201,B0801,B1801,C0701, | C0701 | 313 | 315 | fhsilnvdl | fhsilnvdV |
| FR9547 | SMG1 | 16 | 18849990 | C | A | A2402,A0201,B0801,B1801,C0701, | A0201 | 19 | 202 | Fmsmvgyii | Vmsmvgyii |
| FR9547 | SMG1 | 16 | 18849990 | C | A | A2402,A0201,B0801,B1801,C0701, | A2402 | 163 | 483 | syarstaFm | syarstaVm |
| FR9547 | SMG1 | 16 | 18849990 | C | A | A2402,A0201,B0801,B1801,C0701, | A2402 | 284 | 4219 | aFmsmvgyi | aVmsmvgyi |
| FR9547 | SMG1 | 16 | 18849990 | C | A | A2402,A0201,B0801,B1801,C0701, | B0801 | 440 | 463 | qsyarstaF | qsyarstaV |
| FR9547 | ANKS4B | 16 | 21261957 | T | A | A2402,A0201,B0801,B1801,C0701, | B1801 | 241 | 7237 | hQeeflpif | hLeeflpif |
| FR9547 | WWOX | 16 | 78142341 | G | T | A2402,A0201,B0801,B1801,C0701, | B1801 | 150 | 873 | teektHweh | teektQweh |
| FR9547 | OR1A1 | 17 | 3118931 | A | T | A2402,A0201,B0801,B1801,C0701, | A0201 | 101 | 1761 | nLsstlefi | nQsstlefi |
| FR9547 | OR1A1 | 17 | 3118931 | A | T | A2402,A0201,B0801,B1801,C0701, | C0701 | 405 | 456 | mrennLsst | mrennQsst |
| FR9547 | KCNAB3 | 17 | 7830726 | G | C | A2402,A0201,B0801,B1801,C0701, | A0201 | 302 | 245 | Vtvayehgv | Ltvayehgv |
| FR9547 | KCNAB3 | 17 | 7830726 | G | C | A2402,A0201,B0801,B1801,C0701, | B1801 | 158 | 196 | aedvVtvay | aedvLtvay |
| FR9547 | KCNJ12 | 17 | 21319499 | G | T | A2402,A0201,B0801,B1801,C0701, | B1801 | 164 | 558 | deasplfVi | deasplfGi |

Figure 21 (Cont.)

| | | | | | | | | | | | |
|---|---|---|---|---|---|---|---|---|---|---|---|
| FR9547 | LGALS9 | 17 | 25967713 | G | T | A2402,A0201,B0801,B1801,C0701, | B0801 | 140 | 3317 | Wpeerkthm | Gpeerkthm |
| FR9547 | TBC1D29 | 17 | 28890301 | G | A | A2402,A0201,B0801,B1801,C0701, | C0701 | 309 | 352 | sesNrgpsl | sesSrgpsl |
| FR9547 | SAMD14 | 17 | 48190280 | C | T | A2402,A0201,B0801,B1801,C0701, | B0801 | 33 | 170 | klrrrKqea | klrrrEqea |
| FR9547 | ABCC3 | 17 | 48753888 | C | G | A2402,A0201,B0801,B1801,C0701, | A0201 | 430 | 529 | vvimGstpl | vvimAstpl |
| FR9547 | ABCC3 | 17 | 48753888 | C | G | A2402,A0201,B0801,B1801,C0701, | A2402 | 224 | 205 | vimGstplf | vimAstplf |
| FR9547 | RIT2 | 18 | 40613799 | G | A | A2402,A0201,B0801,B1801,C0701, | A0201 | 11 | 11130 | fLdyhdpti | fPdyhdpti |
| FR9547 | SEMA6B | 19 | 4546284 | G | T | A2402,A0201,B0801,B1801,C0701, | A0201 | 456 | 65 | flspgtrDa | flspgtrAa |
| FR9547 | KEAP1 | 19 | 10600330 | C | A | A2402,A0201,B0801,B1801,C0701, | C0701 | 299 | 86 | irsWagvcv | irsGagvcv |
| FR9547 | SLC25A42 | 19 | 19221390 | G | T | A2402,A0201,B0801,B1801,C0701, | B0801 | 491 | 18340 | slhreysgL | slhreysgR |
| FR9547 | TSHZ3 | 19 | 31768177 | T | A | A2402,A0201,B0801,B1801,C0701, | A0201 | 12 | 12057 | fmsnsplrV | fmsnsplrE |
| FR9547 | TYROBP | 19 | 36398659 | G | T | A2402,A0201,B0801,B1801,C0701, | A0201 | 284 | 1592 | lavsglSpv | lavsglRpv |
| FR9547 | TYROBP | 19 | 36398659 | G | T | A2402,A0201,B0801,B1801,C0701, | A0201 | 324 | 4162 | glSpvqaqa | glRpvqaqa |
| FR9547 | PHLDB3 | 19 | 43979606 | T | A | A2402,A0201,B0801,B1801,C0701, | A0201 | 165 | 111 | wLdvivtaa | wMdvivtaa |
| FR9547 | CCDC61 | 19 | 46509887 | G | A | A2402,A0201,B0801,B1801,C0701, | B0801 | 143 | 259 | slmrkmEg | slmrkmGg |
| FR9547 | KIR3DL3 | 19 | 55246755 | T | C | A2402,A0201,B0801,B1801,C0701, | A0201 | 128 | 119 | vligtPvvi | vligtSvvi |
| FR9547 | ABCG5 | 2 | 44059193 | T | A | A2402,A0201,B0801,B1801,C0701, | A0201 | 399 | 534 | lldaLsgrl | lldaMsgrl |
| FR9547 | NRXN1 | 2 | 50280645 | A | G | A2402,A0201,B0801,B1801,C0701, | B0801 | 492 | 5845 | lPglyyngl | lSglyyngl |
| FR9547 | NRXN1 | 2 | 50758386 | C | T | A2402,A0201,B0801,B1801,C0701, | C0701 | 435 | 3030 | grMkltvnl | grVkltvnl |
| FR9547 | MOGS | 2 | 74692184 | G | A | A2402,A0201,B0801,B1801,C0701, | A0201 | 57 | 540 | gmsgrwvlV | gmsgrwvlA |
| FR9547 | IL1RL2 | 2 | 102805737 | G | T | A2402,A0201,B0801,B1801,C0701, | A0201 | 112 | 13173 | wilflpmeL | wilflpmeW |
| FR9547 | IL1RL2 | 2 | 102805737 | G | T | A2402,A0201,B0801,B1801,C0701, | B1801 | 13 | 8 | meLgdsgvy | meWgdsgvy |
| FR9547 | SLC9A4 | 2 | 103090441 | C | A | A2402,A0201,B0801,B1801,C0701, | A0201 | 447 | 303 | vqipyevtl | vqipyevtL |

Figure 21 (Cont.)

| | | | | | | | | | | | |
|---|---|---|---|---|---|---|---|---|---|---|---|
| FR9547 | SLC9A4 | 2 | 103090441 | C | A | A2402,A0201,B0801,B1801,C0701, | A0201 | 135 | 47 | tlwillasl | tLwillasl |
| FR9547 | SLC9A4 | 2 | 103090441 | C | A | A2402,A0201,B0801,B1801,C0701, | B1801 | 60 | 50 | yevtlwill | yevtLwill |
| FR9547 | TMEM169 | 2 | 216964702 | G | T | A2402,A0201,B0801,B1801,C0701, | C0701 | 179 | 495 | trWkkkgqm | trGkkkgqm |
| FR9547 | SLC23A3 | 2 | 220033426 | C | A | A2402,A0201,B0801,B1801,C0701, | C0701 | 140 | 429 | Shrevaqfc | Ahrevaqfc |
| FR9547 | COL6A3 | 2 | 238287281 | G | A | A2402,A0201,B0801,B1801,C0701, | B1801 | 266 | 5517 | Leskrdilf | Peskrdilf |
| FR9547 | PTK6 | 20 | 62166372 | G | A | A2402,A0201,B0801,B1801,C0701, | C0701 | 16 | 8 | srseavrWl | srseavrRl |
| FR9547 | ZGPAT | 20 | 62340323 | G | A | A2402,A0201,B0801,B1801,C0701, | B1801 | 141 | 470 | deeelsRtk | deeelsGtk |
| FR9547 | TTC3 | 21 | 38572549 | C | G | A2402,A0201,B0801,B1801,C0701, | A0201 | 255 | 209 | algasCcei | algasScei |
| FR9547 | AIRE | 21 | 45712263 | G | T | A2402,A0201,B0801,B1801,C0701, | B0801 | 313 | 2809 | eprpHeppv | eprpQeppv |
| FR9547 | TBC1D5 | 3 | 17550029 | G | T | A2402,A0201,B0801,B1801,C0701, | A0201 | 313 | 47 | slsetrhpM | slsetrhpL |
| FR9547 | PLXNB1 | 3 | 48465147 | C | G | A2402,A0201,B0801,B1801,C0701, | A0201 | 27 | 30 | Llfaafssa | Vlfaafssa |
| FR9547 | PLXNB1 | 3 | 48465147 | C | G | A2402,A0201,B0801,B1801,C0701, | C0701 | 338 | 522 | srevahgeL | srevahgeV |
| FR9547 | STAB1 | 3 | 52537457 | T | A | A2402,A0201,B0801,B1801,C0701, | A0201 | 69 | 11921 | yQgdgmvcl | yHgdgmvcl |
| FR9547 | GOLGB1 | 3 | 121415453 | C | A | A2402,A0201,B0801,B1801,C0701, | A0201 | 324 | 3242 | salqgVtsv | salqgGtsv |
| FR9547 | CLDN18 | 3 | 137717862 | G | A | A2402,A0201,B0801,B1801,C0701, | A0201 | 246 | 831 | yqglwHscv | yqglwRscv |
| FR9547 | TRPC1 | 3 | 142467213 | G | T | A2402,A0201,B0801,B1801,C0701, | A0201 | 15 | 25 | mllkHdvsl | mllkQdvsl |
| FR9547 | TRPC1 | 3 | 142467213 | G | T | A2402,A0201,B0801,B1801,C0701, | B0801 | 9 | 26 | mllkHdvsl | mllkQdvsl |
| FR9547 | ZIC4 | 3 | 147114166 | G | T | A2402,A0201,B0801,B1801,C0701, | C0701 | 219 | 3289 | lheeppqaY | lheeppqaS |
| FR9547 | GMPS | 3 | 155629013 | A | T | A2402,A0201,B0801,B1801,C0701, | B0801 | 368 | 135 | fmrNresqs | fmrKresqs |
| FR9547 | GMPS | 3 | 155629013 | A | T | A2402,A0201,B0801,B1801,C0701, | C0701 | 36 | 69 | mrNresqsv | mrKresqsv |
| FR9547 | KIAA0226 | 3 | 197428713 | G | A | A2402,A0201,B0801,B1801,C0701, | B0801 | 28 | 4746 | mfarkhesL | mfarkhesP |
| FR9547 | KIAA0226 | 3 | 197428713 | G | A | A2402,A0201,B0801,B1801,C0701, | B0801 | 49 | 13 | farkhesLl | farkhesPl |
| FR9547 | KIAA0226 | 3 | 197428713 | G | A | A2402,A0201,B0801,B1801,C0701, | B1801 | 173 | 203 | hesLllvtk | hesPllvtk |

Figure 21 (Cont.)

| | | | | | | | | | | | |
|---|---|---|---|---|---|---|---|---|---|---|---|
| FR9547 | KIAA0226 | 3 | 197428713 | G | A | A2402,A0201,B0801,B1801,C0701, | C0701 | 278 | 3739 | farkhesLl | farkhesPl |
| FR9547 | KIAA0226 | 3 | 197428713 | G | A | A2402,A0201,B0801,B1801,C0701, | C0701 | 125 | 204 | arkhesLll | arkhesPll |
| FR9547 | NDST4 | 4 | 115997409 | G | T | A2402,A0201,B0801,B1801,C0701, | A0201 | 227 | 15 | glhdgiqrv | gLhdgiqrv |
| FR9547 | NDST4 | 4 | 115997409 | G | T | A2402,A0201,B0801,B1801,C0701, | C0701 | 35 | 62 | lhdgiqrvl | Lhdgiqrvl |
| FR9547 | ANKH | 5 | 14756014 | T | A | A2402,A0201,B0801,B1801,C0701, | A2402 | 420 | 428 | illkhkyCf | illkhkySf |
| FR9547 | ANKH | 5 | 14756014 | T | A | A2402,A0201,B0801,B1801,C0701, | B0801 | 58 | 25 | illkhkyCf | illkhkySf |
| FR9547 | ANKH | 5 | 14756014 | T | A | A2402,A0201,B0801,B1801,C0701, | B0801 | 14 | 16 | llkhkyCfl | llkhkySfl |
| FR9547 | CDH10 | 5 | 24491716 | G | C | A2402,A0201,B0801,B1801,C0701, | A0201 | 13 | 31 | alMaillci | allaillci |
| FR9547 | CDH10 | 5 | 24491716 | G | C | A2402,A0201,B0801,B1801,C0701, | A0201 | 173 | 1625 | lMaillcii | llaillcii |
| FR9547 | GPR98 | 5 | 89938854 | C | T | A2402,A0201,B0801,B1801,C0701, | B1801 | 465 | 8437 | Leldehywv | Peldehywv |
| FR9547 | GPR98 | 5 | 89938854 | C | T | A2402,A0201,B0801,B1801,C0701, | C0701 | 28 | 39 | arldgiLel | arldgiPel |
| FR9547 | GPR98 | 5 | 90124879 | G | T | A2402,A0201,B0801,B1801,C0701, | A0201 | 20 | 40 | sqilvyfsv | sqSlvyfsv |
| FR9547 | GPR98 | 5 | 90124879 | G | T | A2402,A0201,B0801,B1801,C0701, | B1801 | 4 | 7 | desqIlvyf | desqSlvyf |
| FR9547 | FBN2 | 5 | 127615930 | C | A | A2402,A0201,B0801,B1801,C0701, | C0701 | 14 | 22 | yrcDcnegf | yrcEcnegf |
| FR9547 | PCDHA1 | 5 | 140166966 | C | T | A2402,A0201,B0801,B1801,C0701, | A0201 | 21 | 13509 | aLlstvial | aPlstvial |
| FR9547 | PCDHA1 | 5 | 140166966 | C | T | A2402,A0201,B0801,B1801,C0701, | A0201 | 28 | 1523 | Llstviali | Plstviali |
| FR9547 | ARAP3 | 5 | 141050949 | C | A | A2402,A0201,B0801,B1801,C0701, | C0701 | 491 | 1476 | Srpnllknm | Arpnllknm |
| FR9547 | ANXA6 | 5 | 150518964 | T | A | A2402,A0201,B0801,B1801,C0701, | C0701 | 316 | 956 | rsYrqrqev | rsNrqrqev |
| FR9547 | STC2 | 5 | 172755129 | C | A | A2402,A0201,B0801,B1801,C0701, | A0201 | 18 | 16971 | vlatfdpaL | vlatfdpaR |
| FR9547 | WRNIP1 | 6 | 2779689 | G | T | A2402,A0201,B0801,B1801,C0701, | B0801 | 304 | 87 | Dglqrshil | Eglqrshil |
| FR9547 | EYS | 6 | 66205160 | G | T | A2402,A0201,B0801,B1801,C0701, | B1801 | 328 | 89 | teKicldfy | teNicldfy |
| FR9547 | HTR1B | 6 | 78172870 | G | C | A2402,A0201,B0801,B1801,C0701, | A0201 | 496 | 225 | klhtpGnyl | klhtpAnyl |

Figure 21 (Cont.)

| | | | | | | | | | | | |
|---|---|---|---|---|---|---|---|---|---|---|---|
| FR9547 | HTR1B | 6 | 78172870 | G | C | A2402,A0201,B0801,B1801,C0701, | C0701 | 64 | 38 | lhtpGnyli | lhtpAnyli |
| FR9547 | GPR6 | 6 | 110301318 | G | A | A2402,A0201,B0801,B1801,C0701, | A0201 | 96 | 5928 | Kiqralwll | Eiqralwll |
| FR9547 | GPR6 | 6 | 110301318 | G | A | A2402,A0201,B0801,B1801,C0701, | A2402 | 15 | 17 | iyafmqKi | iyafmqEi |
| FR9547 | GPR6 | 6 | 110301318 | G | A | A2402,A0201,B0801,B1801,C0701, | A2402 | 224 | 1767 | Kiqralwll | Eiqralwll |
| FR9547 | GPR6 | 6 | 110301318 | G | A | A2402,A0201,B0801,B1801,C0701, | C0701 | 49 | 146 | fmqKiqra | fmqEiqra |
| FR9547 | DDO | 6 | 110714517 | T | A | A2402,A0201,B0801,B1801,C0701, | B0801 | 423 | 991 | tlSrriedl | tlTrriedl |
| FR9547 | KATNA1 | 6 | 149916369 | C | A | A2402,A0201,B0801,B1801,C0701, | B0801 | 137 | 1091 | tnvcrYasl | tnvcrDasl |
| FR9547 | KATNA1 | 6 | 149916369 | C | A | A2402,A0201,B0801,B1801,C0701, | C0701 | 156 | 895 | crYaslmam | crDaslmam |
| FR9547 | ULBP2 | 6 | 150267723 | G | T | A2402,A0201,B0801,B1801,C0701, | A0201 | 132 | 32 | smgYcigwl | smgDcigwl |
| FR9547 | ULBP2 | 6 | 150267723 | G | T | A2402,A0201,B0801,B1801,C0701, | A2402 | 47 | 336 | hyfsmgYci | hyfsmgDci |
| FR9547 | SLC22A3 | 6 | 160858208 | G | T | A2402,A0201,B0801,B1801,C0701, | A0201 | 37 | 14395 | faasnivaV | faasnivaG |
| FR9547 | SLC22A3 | 6 | 160858208 | G | T | A2402,A0201,B0801,B1801,C0701, | A0201 | 441 | 145 | ivaVvaclv | ivaGvaclv |
| FR9547 | TNRC18 | 7 | 5352259 | C | T | A2402,A0201,B0801,B1801,C0701, | C0701 | 98 | 100 | srpkkregl | srpkkregV |
| FR9547 | TNRC18 | 7 | 5352259 | C | T | A2402,A0201,B0801,B1801,C0701, | C0701 | 50 | 53 | lhlpttkel | Vhlpttkel |
| FR9547 | MUC17 | 7 | 100685961 | G | T | A2402,A0201,B0801,B1801,C0701, | A0201 | 199 | 48 | stlVttilv | stlGttilv |
| FR9547 | MUC17 | 7 | 100685961 | G | T | A2402,A0201,B0801,B1801,C0701, | B1801 | 172 | 886 | meistlVtt | meistlGtt |
| FR9547 | DUSP26 | 8 | 33449719 | C | A | A2402,A0201,B0801,B1801,C0701, | A0201 | 9 | 29 | ilLhcavgv | ilVhcavgv |
| FR9547 | POTEA | 8 | 43157139 | G | T | A2402,A0201,B0801,B1801,C0701, | A0201 | 295 | 8795 | avLcgsasi | avRcgsasi |
| FR9547 | KCNB2 | 8 | 73848416 | C | A | A2402,A0201,B0801,B1801,C0701, | A0201 | 5 | 7 | llailTyyv | llailPyyv |
| FR9547 | KCNB2 | 8 | 73848416 | C | A | A2402,A0201,B0801,B1801,C0701, | A0201 | 97 | 56 | ailTyyvti | ailPyyvti |
| FR9547 | KCNB2 | 8 | 73848416 | C | A | A2402,A0201,B0801,B1801,C0701, | A0201 | 111 | 6895 | lTyyvtifl | lPyyvtifl |
| FR9547 | KCNB2 | 8 | 73848416 | C | A | A2402,A0201,B0801,B1801,C0701, | B1801 | 230 | 218 | idllailTy | idllailPy |
| FR9547 | CSMD3 | 8 | 113662524 | C | A | A2402,A0201,B0801,B1801,C0701, | C0701 | 64 | 50 | Lryghdfsi | Rryghdfsi |

Figure 21 (Cont.)

| | | | | | | | | | | | |
|---|---|---|---|---|---|---|---|---|---|---|---|
| FR9547 | TRPM6 | 9 | 77377163 | C | A | A2402,A0201,B0801,B1801,C0701, | A2402 | 337 | 30664 | sikkkwqtF | sikkkwqtC |
| FR9547 | TRPM6 | 9 | 77377163 | C | A | A2402,A0201,B0801,B1801,C0701, | B0801 | 24 | 284 | sikkkwqtF | sikkkwqtC |
| FR9547 | PRUNE2 | 9 | 79320300 | G | A | A2402,A0201,B0801,B1801,C0701, | B1801 | 11 | 13 | seVafdhsf | seAafdhsf |
| FR9547 | PRUNE2 | 9 | 79320301 | C | A | A2402,A0201,B0801,B1801,C0701, | B1801 | 13 | 13 | seSafdhsf | seAafdhsf |
| FR9547 | SPATA31D1 | 9 | 84608596 | A | G | A2402,A0201,B0801,B1801,C0701, | B0801 | 365 | 5239 | tlrrefsdA | tlrrefsdT |
| FR9547 | TLR4 | 9 | 120470841 | G | C | A2402,A0201,B0801,B1801,C0701, | B1801 | 29 | 44 | veLvpnity | veVvpnity |
| FR9547 | TSC1 | 9 | 135801029 | C | A | A2402,A0201,B0801,B1801,C0701, | B0801 | 43 | 4116 | sLkhklsqa | sWkhklsqa |
| FR9547 | SHROOM2 | X | 9841741 | A | T | A2402,A0201,B0801,B1801,C0701, | A0201 | 97 | 26071 | avdkllagV | avdkllagD |
| FR9547 | SHROOM2 | X | 9841741 | A | T | A2402,A0201,B0801,B1801,C0701, | A0201 | 11 | 42 | kllagVeiv | kllagDeiv |
| FR9547 | RBM10 | X | 47038529 | G | C | A2402,A0201,B0801,B1801,C0701, | B0801 | 30 | 72 | nfkrrQkcf | nfkrrEkcf |
| FR9547 | ITIH6 | X | 54777561 | C | A | A2402,A0201,B0801,B1801,C0701, | A0201 | 88 | 969 | ltlrlVpyl | ltlrlGpyl |
| FR9547 | ITIH6 | X | 54777561 | C | A | A2402,A0201,B0801,B1801,C0701, | A0201 | 10 | 19 | rlVpylefl | rlGpylefl |
| FR9547 | ITIH6 | X | 54777561 | C | A | A2402,A0201,B0801,B1801,C0701, | A0201 | 97 | 7934 | lVpyleflv | lGpyleflv |
| FR9547 | HEPH | X | 65409681 | G | T | A2402,A0201,B0801,B1801,C0701, | C0701 | 259 | 290 | hhtdLanif | hhtdVanif |
| FR9547 | CITED1 | X | 71521928 | G | T | A2402,A0201,B0801,B1801,C0701, | C0701 | 327 | 23473 | tHptkppsf | tPptkppsf |
| FR9547 | MAGEE1 | X | 75651039 | C | T | A2402,A0201,B0801,B1801,C0701, | A0201 | 356 | 408 | fvwgpraCl | fvwgpraRl |
| FR9547 | IRS4 | X | 107978317 | G | T | A2402,A0201,B0801,B1801,C0701, | B0801 | 444 | 894 | Srsrravsv | Rrsrravsv |
| FR9547 | IRS4 | X | 107978317 | G | T | A2402,A0201,B0801,B1801,C0701, | C0701 | 47 | 97 | Srsrravsv | Rrsrravsv |
| FR9547 | PGRMC1 | X | 118370465 | C | A | A2402,A0201,B0801,B1801,C0701, | B0801 | 158 | 1700 | fllykivSg | fllykivRg |
| FR9547 | GRIA3 | X | 122538672 | A | C | A2402,A0201,B0801,B1801,C0701, | C0701 | 26 | 51 | vriNyklsi | vriKyklsi |
| FR9547 | FLNA | X | 153578462 | C | T | A2402,A0201,B0801,B1801,C0701, | C0701 | 198 | 416 | Rhggdpglv | Ghggdpglv |
| FR9547 | ATP6AP1 | X | 153660705 | G | T | A2402,A0201,B0801,B1801,C0701, | A0201 | 27 | 1316 | ylqeklWas | ylqeklGas |

Figure 21 (Cont.)

| | | | | | | | | | | | |
|---|---|---|---|---|---|---|---|---|---|---|---|
| FR9547 | ATP6AP1 | X | 153660705 | G | T | A2402,A0201,B0801,B1801,C0701, | A0201 | 9 | 39 | klWasplhv | klGasplhv |
| GR0134 | MPL | 1 | 43814578 | G | A | A0201,A3301,B1302,B1402,C0602,C0802 | A3301 | 350 | 201 | rsryHlqlr | rsryRlqlr |
| GR0134 | MPL | 1 | 43814578 | G | A | A0201,A3301,B1302,B1402,C0602,C0802 | C0602 | 358 | 129 | prsryHlql | prsryRlql |
| GR0134 | MPL | 1 | 43814578 | G | A | A0201,A3301,B1302,B1402,C0602,C0802 | C0602 | 178 | 95 | yHlqlrarl | yRlqlrarl |
| GR0134 | NBPF24 | 1 | 147580910 | T | C | A0201,A3301,B1302,B1402,C0602,C0802 | A0201 | 9 | 8 | lldekGpev | lldekEpev |
| GR0134 | NBPF24 | 1 | 147580910 | T | C | A0201,A3301,B1302,B1402,C0602,C0802 | C0802 | 61 | 1513 | lldekGpev | lldekEpev |
| GR0134 | RYR2 | 1 | 237433822 | C | T | A0201,A3301,B1302,B1402,C0602,C0802 | A0201 | 221 | 320 | vvlqciati | vvlqcTati |
| GR0134 | ZDHHC17 | 12 | 77209663 | C | T | A0201,A3301,B1302,B1402,C0602,C0802 | A0201 | 11 | 5 | lllIlfnvsv | lllTfnvsv |
| GR0134 | ZDHHC17 | 12 | 77209663 | C | T | A0201,A3301,B1302,B1402,C0602,C0802 | A0201 | 75 | 402 | llfnvsvnl | lTfnvsvnl |
| GR0134 | KIAA1199 | 15 | 81166237 | G | T | A0201,A3301,B1302,B1402,C0602,C0802 | A0201 | 10 | 16413 | gMqdflfka | gRqdflfka |
| GR0134 | TANGO6 | 16 | 69074302 | G | T | A0201,A3301,B1302,B1402,C0602,C0802 | A0201 | 65 | 109 | Vlsqkatev | Glsqkatev |
| GR0134 | ENGASE | 17 | 77071054 | C | T | A0201,A3301,B1302,B1402,C0602,C0802 | A3301 | 158 | 310 | vtvtWsatr | vtvtRsatr |
| GR0134 | ENGASE | 17 | 77071054 | C | T | A0201,A3301,B1302,B1402,C0602,C0802 | A3301 | 497 | 6114 | tWsatrrrr | tRsatrrrr |
| GR0134 | SH2D3A | 19 | 6763691 | C | A | A0201,A3301,B1302,B1402,C0602,C0802 | C0602 | 94 | 398 | srHkaeall | srQkaeall |
| GR0134 | MYO9B | 19 | 17303759 | G | A | A0201,A3301,B1302,B1402,C0602,C0802 | C0602 | 83 | 131 | ertqaaMyl | ertqaaVyl |
| GR0134 | LRP3 | 19 | 33697976 | G | C | A0201,A3301,B1302,B1402,C0602,C0802 | A3301 | 72 | 295 | rPlgrlwnr | rRlgrlwnr |
| GR0134 | TMEM87B | 2 | 112813185 | G | A | A0201,A3301,B1302,B1402,C0602,C0802 | A3301 | 195 | 3340 | Hsvagllpr | Rsvagllpr |
| GR0134 | ADAM33 | 20 | 3651716 | C | A | A0201,A3301,B1302,B1402,C0602,C0802 | A0201 | 9 | 11 | glawccyLl | glawccyRl |
| GR0134 | COL7A1 | 3 | 48632550 | G | T | A0201,A3301,B1302,B1402,C0602,C0802 | A0201 | 42 | 138 | glMaeaprv | glLaeaprv |
| GR0134 | COL7A1 | 3 | 48632562 | A | T | A0201,A3301,B1302,B1402,C0602,C0802 | A0201 | 451 | 1033 | rllvaalSa | rllvaalCa |
| GR0134 | COL7A1 | 3 | 48632562 | A | T | A0201,A3301,B1302,B1402,C0602,C0802 | A0201 | 449 | 626 | lvaalSagi | lvaalCagi |
| GR0134 | BMP2K | 4 | 79792166 | C | G | A0201,A3301,B1302,B1402,C0602,C0802 | C0602 | 31 | 37 | Qhhhhhhhl | Hhhhhhhhl |
| GR0134 | C2 | 6 | 31895543 | T | C | A0201,A3301,B1302,B1402,C0602,C0802 | A0201 | 124 | 30 | Tvlfcllfl | Mvlfcllfl |

Figure 21 (Cont.)

| | | | | | | | | | | | |
|---|---|---|---|---|---|---|---|---|---|---|---|
| GR0134 | ZNF76 | 6 | 35248963 | G | T | A0201,A3301,B1302,B1402,C0602,C0802 | A0201 | 19 | 745 | lldgttayv | lSdgttayv |
| GR0134 | ZNF76 | 6 | 35248963 | G | T | A0201,A3301,B1302,B1402,C0602,C0802 | C0802 | 337 | 196 | lldgttayv | lSdgttayv |
| GR0134 | SNAP91 | 6 | 84317434 | C | T | A0201,A3301,B1302,B1402,C0602,C0802 | A0201 | 241 | 251 | atasTavpv | atasAavpv |
| GR0134 | TNRC18 | 7 | 5385303 | C | T | A0201,A3301,B1302,B1402,C0602,C0802 | A0201 | 78 | 154 | llaHfaasa | llaRfaasa |
| GR0134 | SLC26A5 | 7 | 103019706 | T | C | A0201,A3301,B1302,B1402,C0602,C0802 | A3301 | 180 | 283 | dlysSalkr | dlysNalkr |
| GR0134 | ZNF777 | 7 | 149152750 | G | A | A0201,A3301,B1302,B1402,C0602,C0802 | C0602 | 193 | 147 | shsShhqea | shsPhhqea |
| GR0134 | CPXCR1 | X | 88008737 | G | T | A0201,A3301,B1302,B1402,C0602,C0802 | A3301 | 424 | 5507 | vshkplnYr | vshkplnDr |
| GR0134 | MORC4 | X | 106184842 | C | T | A0201,A3301,B1302,B1402,C0602,C0802 | A0201 | 136 | 226 | kltQlrihv | kltRlrihv |
| GR4788 | AGRN | 1 | 983540 | G | T | A0101,A2601,B3501,B3701,C0401,C0602 | B3501 | 17 | 71 | qpvaNttaa | qpvaKttaa |
| GR4788 | MXRA8 | 1 | 1290475 | C | T | A0101,A2601,B3501,B3701,C0401,C0602 | B3501 | 477 | 1375 | lavarDapa | lavarGapa |
| GR4788 | COL9A2 | 1 | 40782848 | G | T | A0101,A2601,B3501,B3701,C0401,C0602 | B3501 | 277 | 191 | maaatasTr | maaatasPr |
| GR4788 | ARHGEF11 | 1 | 156909555 | C | A | A0101,A2601,B3501,B3701,C0401,C0602 | B3501 | 128 | 169 | hpwdpgspV | hpwdpgspG |
| GR4788 | ARHGEF11 | 1 | 156909556 | C | A | A0101,A2601,B3501,B3701,C0401,C0602 | B3501 | 60 | 169 | hpwdpgspW | hpwdpgspG |
| GR4788 | SNAP47 | 1 | 227923184 | C | T | A0101,A2601,B3501,B3701,C0401,C0602 | C0602 | 87 | 9294 | rrrgrlwdL | rrrgrlwdS |
| GR4788 | HK1 | 10 | 71142517 | T | C | A0101,A2601,B3501,B3701,C0401,C0602 | B3501 | 299 | 1116 | avvkmlpPf | avvkmlpSf |
| GR4788 | FBXW4 | 10 | 103454202 | G | T | A0101,A2601,B3501,B3701,C0401,C0602 | C0602 | 241 | 161 | rrftscdMl | rrftscdLl |
| GR4788 | NAALADL1 | 11 | 64815177 | A | T | A0101,A2601,B3501,B3701,C0401,C0602 | A2601 | 167 | 45 | siNdnwiry | siYdnwiry |
| GR4788 | NAALADL1 | 11 | 64815177 | A | T | A0101,A2601,B3501,B3701,C0401,C0602 | B3501 | 219 | 162 | siNdnwiry | siYdnwiry |
| GR4788 | MMP7 | 11 | 102398519 | G | A | A0101,A2601,B3501,B3701,C0401,C0602 | B3501 | 134 | 514 | fpnsSkwts | fpnsPkwts |
| GR4788 | TREH | 11 | 118529026 | G | A | A0101,A2601,B3501,B3701,C0401,C0602 | B3501 | 378 | 352 | laatllpVl | laatllpSl |
| GR4788 | TREH | 11 | 118529026 | G | A | A0101,A2601,B3501,B3701,C0401,C0602 | B3501 | 97 | 197 | lpVlllsll | lpSlllsll |
| GR4788 | PDE3A | 12 | 20766470 | A | T | A0101,A2601,B3501,B3701,C0401,C0602 | A0101 | 33 | 18851 | ladpslppY | ladpslppN |

Figure 21 (Cont.)

| | | | | | | | | | | | |
|---|---|---|---|---|---|---|---|---|---|---|---|
| GR4788 | PDE3A | 12 | 20766470 | A | T | A0101,A2601,B3501,B3701,C0401,C0602 | B3501 | 3 | 4764 | ladpslppY | ladpslppN |
| GR4788 | PDE3A | 12 | 20766470 | A | T | A0101,A2601,B3501,B3701,C0401,C0602 | B3501 | 270 | 443 | lppYvctsl | lppNvctsl |
| GR4788 | MTFMT | 15 | 65321764 | A | T | A0101,A2601,B3501,B3701,C0401,C0602 | B3501 | 80 | 67 | fareaQral | fareaLral |
| GR4788 | MTFMT | 15 | 65321764 | A | T | A0101,A2601,B3501,B3701,C0401,C0602 | C0602 | 369 | 248 | fareaQral | fareaLral |
| GR4788 | MSLN | 16 | 818722 | A | G | A0101,A2601,B3501,B3701,C0401,C0602 | B3501 | 179 | 454 | lalllasAl | lalllasTl |
| GR4788 | NDE1 | 16 | 15790676 | G | T | A0101,A2601,B3501,B3701,C0401,C0602 | C0602 | 306 | 117 | Drrpsstsv | Errpsstsv |
| GR4788 | TRIM72 | 16 | 31235994 | C | T | A0101,A2601,B3501,B3701,C0401,C0602 | B3501 | 15 | 37 | lprpvyLff | lprpvyPff |
| GR4788 | TRIM72 | 16 | 31235994 | C | T | A0101,A2601,B3501,B3701,C0401,C0602 | C0602 | 32 | 5428 | erlprpvyL | erlprpvyP |
| GR4788 | WDR59 | 16 | 74985433 | T | A | A0101,A2601,B3501,B3701,C0401,C0602 | A0101 | 89 | 88 | ssnHrvdly | ssnQrvdly |
| GR4788 | SMG6 | 17 | 1964830 | C | T | A0101,A2601,B3501,B3701,C0401,C0602 | B3501 | 7 | 7 | vplrdipaf | vpVrdipaf |
| GR4788 | SMG6 | 17 | 1964830 | C | T | A0101,A2601,B3501,B3701,C0401,C0602 | C0602 | 141 | 105 | trnvplrdi | trnvpVrdi |
| GR4788 | HEATR6 | 17 | 58137346 | C | A | A0101,A2601,B3501,B3701,C0401,C0602 | B3501 | 200 | 233 | tpfsLmiac | tpfsVmiac |
| GR4788 | TMC6 | 17 | 76113703 | C | A | A0101,A2601,B3501,B3701,C0401,C0602 | B3501 | 83 | 122 | kpsstcCpf | kpsstcGpf |
| GR4788 | TMC6 | 17 | 76113703 | C | A | A0101,A2601,B3501,B3701,C0401,C0602 | B3501 | 15 | 287 | Cpfrtldtm | Gpfrtldtm |
| GR4788 | DUS3L | 19 | 5786768 | G | T | A0101,A2601,B3501,B3701,C0401,C0602 | B3501 | 232 | 206 | qaaspmHlf | qaaspmPlf |
| GR4788 | ZNF568 | 19 | 37487926 | C | T | A0101,A2601,B3501,B3701,C0401,C0602 | C0602 | 203 | 79 | frhqriYtg | frhqriHtg |
| GR4788 | ZNF17 | 19 | 57929304 | G | C | A0101,A2601,B3501,B3701,C0401,C0602 | B3501 | 64 | 76 | mvfedvPlh | mvfedvAlh |
| GR4788 | MAP1LC3A | 20 | 33146689 | C | A | A0101,A2601,B3501,B3701,C0401,C0602 | C0602 | 56 | 9370 | rHfkqrrsf | rPfkqrrsf |
| GR4788 | MROH8 | 20 | 35788539 | G | T | A0101,A2601,B3501,B3701,C0401,C0602 | C0602 | 51 | 3561 | vhtlnvlvL | vhtlnvlvQ |
| GR4788 | DMC1 | 22 | 38951382 | G | C | A0101,A2601,B3501,B3701,C0401,C0602 | A2601 | 41 | 90 | esmGiteaf | esmAiteaf |
| GR4788 | DMC1 | 22 | 38951382 | G | C | A0101,A2601,B3501,B3701,C0401,C0602 | B3501 | 111 | 57 | esmGiteaf | esmAiteaf |
| GR4788 | PCDH10 | 4 | 134073156 | G | A | A0101,A2601,B3501,B3701,C0401,C0602 | C0602 | 438 | 472 | ysiMrgnem | ysiVrgnem |
| GR4788 | PCDH10 | 4 | 134073156 | G | A | A0101,A2601,B3501,B3701,C0401,C0602 | C0602 | 227 | 587 | Mrgnemnlf | Vrgnemnlf |

Figure 21 (Cont.)

| | | | | | | | | | | | |
|---|---|---|---|---|---|---|---|---|---|---|---|
| GR4788 | CTNND2 | 5 | 11236868 | C | A | A0101,A2601,B3501,B3701,C0401,C0602 | B3501 | 17 | 21 | fpsFqsnaa | fpsVqsnaa |
| GR4788 | CTNND2 | 5 | 11236868 | C | A | A0101,A2601,B3501,B3701,C0401,C0602 | B3501 | 255 | 20 | sFqsnaaay | sVqsnaaay |
| GR4788 | RUFY1 | 5 | 179016634 | G | A | A0101,A2601,B3501,B3701,C0401,C0602 | C0602 | 163 | 30 | ersKksvei | ersEksvei |
| GR4788 | PTK7 | 6 | 43109465 | G | A | A0101,A2601,B3501,B3701,C0401,C0602 | A2601 | 39 | 3153 | Mtrddagny | Vtrddagny |
| GR4788 | C7orf26 | 7 | 6631307 | C | A | A0101,A2601,B3501,B3701,C0401,C0602 | A2601 | 20 | 1479 | qlleimcny | qlLeimcny |
| GR4788 | TRIM50 | 7 | 72738510 | G | T | A0101,A2601,B3501,B3701,C0401,C0602 | C0602 | 83 | 30 | vhQmplsl | vhHmplsl |
| GR4788 | CLIP2 | 7 | 73790362 | G | A | A0101,A2601,B3501,B3701,C0401,C0602 | B3501 | 406 | 1096 | hpdaaellQ | hpdaaellR |
| GR4788 | PLXNA4 | 7 | 131866208 | G | T | A0101,A2601,B3501,B3701,C0401,C0602 | B3501 | 279 | 290 | ftyypnTvf | ftyypnPvf |
| GR4788 | PLXNA4 | 7 | 131866208 | G | T | A0101,A2601,B3501,B3701,C0401,C0602 | B3501 | 3 | 3 | ypnTvfeaf | ypnPvfeaf |
| GR4788 | CTAGE4 | 7 | 143964066 | C | A | A0101,A2601,B3501,B3701,C0401,C0602 | B3501 | 6 | 8 | ypprClppy | ypprGlppy |
| GR4788 | EGR3 | 8 | 22548525 | G | A | A0101,A2601,B3501,B3701,C0401,C0602 | B3501 | 427 | 11636 | ndmgsipeY | ndmgsipeH |
| GR4788 | COL14A1 | 8 | 121292197 | G | T | A0101,A2601,B3501,B3701,C0401,C0602 | B3501 | 189 | 1057 | Ladadysel | Vadadysel |
| GR4788 | CXCR3 | X | 70836684 | G | A | A0101,A2601,B3501,B3701,C0401,C0602 | B3501 | 24 | 16 | fpqvgrMal | fpqvgrTal |
| GR4788 | CXCR3 | X | 70836684 | G | A | A0101,A2601,B3501,B3701,C0401,C0602 | C0602 | 265 | 8087 | ynfpqvgrM | ynfpqvgrT |
| HE3202 | SDF4 | 1 | 1159283 | G | A | A2403,A3201,B3801,B4101,C1203,C1701 | C1203 | 76 | 336 | Maehfqeam | Taehfqeam |
| HE3202 | ESPN | 1 | 6508764 | T | A | A2403,A3201,B3801,B4101,C1203,C1701 | C1203 | 260 | 2981 | dssrkpral | dssrkpraF |
| HE3202 | CASP9 | 1 | 15833417 | C | A | A2403,A3201,B3801,B4101,C1203,C1701 | A3201 | 426 | 1399 | sslhfmveL | sslhfmveV |
| HE3202 | CASP9 | 1 | 15833417 | C | A | A2403,A3201,B3801,B4101,C1203,C1701 | C1203 | 457 | 133 | sslhfmveL | sslhfmveV |
| HE3202 | HTR1D | 1 | 23519907 | C | G | A2403,A3201,B3801,B4101,C1203,C1701 | B3801 | 150 | 98 | shsaAsplf | shsaGsplf |
| HE3202 | YARS | 1 | 33272090 | C | A | A2403,A3201,B3801,B4101,C1203,C1701 | A3201 | 328 | 7787 | llsgllypV | llsgllypG |
| HE3202 | YARS | 1 | 33272090 | C | A | A2403,A3201,B3801,B4101,C1203,C1701 | C1203 | 74 | 48 | llypVlqal | llypGlqal |
| HE3202 | CSMD2 | 1 | 34042986 | C | A | A2403,A3201,B3801,B4101,C1203,C1701 | A2403 | 36 | 321 | Cyrlvghsm | Gyrlvghsm |

Figure 21 (Cont.)

| | | | | | | | | | | | |
|---|---|---|---|---|---|---|---|---|---|---|---|
| HE3202 | NRD1 | 1 | 52299696 | G | C | A2403,A3201,B3801,B4101,C1203,C1701 | A2403 | 51 | 31 | yfkeaVdrw | yfkeaLdrw |
| HE3202 | NRD1 | 1 | 52299696 | G | C | A2403,A3201,B3801,B4101,C1203,C1701 | C1203 | 115 | 67 | eaVdrwaqf | eaLdrwaqf |
| HE3202 | JAK1 | 1 | 65349061 | C | A | A2403,A3201,B3801,B4101,C1203,C1701 | C1203 | 276 | 25122 | vnleapepV | vnleapepG |
| HE3202 | JAK1 | 1 | 65349061 | C | A | A2403,A3201,B3801,B4101,C1203,C1701 | C1203 | 25 | 32 | eapepVvev | eapepGvev |
| HE3202 | JAK1 | 1 | 65349061 | C | A | A2403,A3201,B3801,B4101,C1203,C1701 | C1203 | 285 | 151 | apepVvevi | apepGvevi |
| HE3202 | WDR78 | 1 | 67292521 | C | A | A2403,A3201,B3801,B4101,C1203,C1701 | C1203 | 343 | 2104 | iLdlhistl | iWdlhistl |
| HE3202 | SRSF11 | 1 | 70703127 | G | C | A2403,A3201,B3801,B4101,C1203,C1701 | A3201 | 133 | 112 | klnhvaaRl | klnhvaaGl |
| HE3202 | PTGER3 | 1 | 71513107 | C | T | A2403,A3201,B3801,B4101,C1203,C1701 | A2403 | 124 | 505 | Mafpitmll | Vafpitmll |
| HE3202 | PTGER3 | 1 | 71513107 | C | T | A2403,A3201,B3801,B4101,C1203,C1701 | A3201 | 230 | 415 | gsvsMafpi | gsvsVafpi |
| HE3202 | PTGER3 | 1 | 71513107 | C | T | A2403,A3201,B3801,B4101,C1203,C1701 | A3201 | 240 | 1193 | Mafpitmll | Vafpitmll |
| HE3202 | PTGER3 | 1 | 71513107 | C | T | A2403,A3201,B3801,B4101,C1203,C1701 | C1203 | 37 | 112 | vsMafpitm | vsVafpitm |
| HE3202 | PTGER3 | 1 | 71513107 | C | T | A2403,A3201,B3801,B4101,C1203,C1701 | C1203 | 8 | 11 | Mafpitmll | Vafpitmll |
| HE3202 | SLC44A5 | 1 | 75677192 | C | A | A2403,A3201,B3801,B4101,C1203,C1701 | A2403 | 7 | 13 | Fyamcveti | Vyamcveti |
| HE3202 | SLC44A5 | 1 | 75677192 | C | A | A2403,A3201,B3801,B4101,C1203,C1701 | A3201 | 118 | 3742 | liahgffsF | liahgffsV |
| HE3202 | SLC44A5 | 1 | 75677192 | C | A | A2403,A3201,B3801,B4101,C1203,C1701 | C1203 | 21 | 12 | iahgffsFy | iahgffsVy |
| HE3202 | SLC44A5 | 1 | 75677192 | C | A | A2403,A3201,B3801,B4101,C1203,C1701 | C1203 | 15 | 268 | Fyamcveti | Vyamcveti |
| HE3202 | SLC44A5 | 1 | 75683559 | C | A | A2403,A3201,B3801,B4101,C1203,C1701 | C1203 | 147 | 5189 | ivleyldhL | ivleyldhR |
| HE3202 | HFM1 | 1 | 91841101 | G | C | A2403,A3201,B3801,B4101,C1203,C1701 | A2403 | 15 | 11 | mysdEkptl | mysdQkptl |
| HE3202 | HFM1 | 1 | 91841101 | G | C | A2403,A3201,B3801,B4101,C1203,C1701 | C1203 | 8 | 18 | ysdEkptlv | ysdQkptlv |
| HE3202 | BRDT | 1 | 92442922 | A | T | A2403,A3201,B3801,B4101,C1203,C1701 | A2403 | 14 | 96 | yydvvlnpm | yydvvKnpm |
| HE3202 | BRDT | 1 | 92442922 | A | T | A2403,A3201,B3801,B4101,C1203,C1701 | B3801 | 137 | 5555 | lhnyydvvl | lhnyydvvK |
| HE3202 | BRDT | 1 | 92442922 | A | T | A2403,A3201,B3801,B4101,C1203,C1701 | C1203 | 117 | 491 | yydvvlnpm | yydvvKnpm |
| HE3202 | ABCA4 | 1 | 94574166 | C | G | A2403,A3201,B3801,B4101,C1203,C1701 | A3201 | 472 | 2404 | ilsqfmHtl | ilsqfmDtl |

Figure 21 (Cont.)

| | | | | | | | | | | | |
|---|---|---|---|---|---|---|---|---|---|---|---|
| HE3202 | ABCA4 | 1 | 94574166 | C | G | A2403,A3201,B3801,B4101,C1203,C1701 | C1203 | 206 | 321 | ilsqfmHtl | ilsqfmDtl |
| HE3202 | NOTCH2 | 1 | 120508099 | C | A | A2403,A3201,B3801,B4101,C1203,C1701 | C1203 | 78 | 1308 | kcidhpnVy | kcidhpnGy |
| HE3202 | DENND4B | 1 | 153905348 | A | T | A2403,A3201,B3801,B4101,C1203,C1701 | C1203 | 206 | 198 | qtlEsrpsv | qtlDsrpsv |
| HE3202 | FDPS | 1 | 155279585 | C | T | A2403,A3201,B3801,B4101,C1203,C1701 | C1203 | 314 | 2243 | Llsrwlrsv | Plsrwlrsv |
| HE3202 | ATP1A2 | 1 | 160100328 | G | T | A2403,A3201,B3801,B4101,C1203,C1701 | C1203 | 13 | 52 | miYppraav | miDppraav |
| HE3202 | FMO4 | 1 | 171310772 | G | A | A2403,A3201,B3801,B4101,C1203,C1701 | A2403 | 250 | 1419 | qwNrtlkpl | qwDrtlkpl |
| HE3202 | AXDND1 | 1 | 179414169 | A | T | A2403,A3201,B3801,B4101,C1203,C1701 | C1203 | 143 | 86 | skydtlMii | skydtlKii |
| HE3202 | AXDND1 | 1 | 179414169 | A | T | A2403,A3201,B3801,B4101,C1203,C1701 | C1203 | 332 | 199 | dtlMiikhl | dtlKiikhl |
| HE3202 | RGS8 | 1 | 182636094 | C | A | A2403,A3201,B3801,B4101,C1203,C1701 | C1203 | 232 | 10091 | mprrnkgmM | mprrnkgmR |
| HE3202 | ASPM | 1 | 197070788 | C | A | A2403,A3201,B3801,B4101,C1203,C1701 | A3201 | 107 | 22 | rqChsavvi | rqWhsavvi |
| HE3202 | ASPM | 1 | 197070788 | C | A | A2403,A3201,B3801,B4101,C1203,C1701 | C1203 | 39 | 25 | yirqChsav | yirqWhsav |
| HE3202 | ASPM | 1 | 197070788 | C | A | A2403,A3201,B3801,B4101,C1203,C1701 | C1203 | 139 | 132 | rqChsavvi | rqWhsavvi |
| HE3202 | ASPM | 1 | 197070789 | C | A | A2403,A3201,B3801,B4101,C1203,C1701 | A3201 | 40 | 22 | rqLhsavvi | rqWhsavvi |
| HE3202 | ASPM | 1 | 197070789 | C | A | A2403,A3201,B3801,B4101,C1203,C1701 | C1203 | 99 | 25 | yirqLhsav | yirqWhsav |
| HE3202 | ASPM | 1 | 197070789 | C | A | A2403,A3201,B3801,B4101,C1203,C1701 | C1203 | 94 | 132 | rqLhsavvi | rqWhsavvi |
| HE3202 | IGFN1 | 1 | 201185591 | A | T | A2403,A3201,B3801,B4101,C1203,C1701 | C1203 | 452 | 366 | kpVppqgpm | kpDppqgpm |
| HE3202 | IGFN1 | 1 | 201187709 | G | A | A2403,A3201,B3801,B4101,C1203,C1701 | C1203 | 487 | 226 | cqyefQvta | cqyefRvta |
| HE3202 | IGFN1 | 1 | 201187709 | G | A | A2403,A3201,B3801,B4101,C1203,C1701 | C1203 | 304 | 238 | yefQvtava | yefRvtava |
| HE3202 | TAF1A | 1 | 222737428 | C | G | A2403,A3201,B3801,B4101,C1203,C1701 | A3201 | 12 | 43 | klmlQfhtl | klmlEfhtl |
| HE3202 | TAF1A | 1 | 222737428 | C | G | A2403,A3201,B3801,B4101,C1203,C1701 | A3201 | 365 | 381 | lmlQfhtll | lmlEfhtll |
| HE3202 | TAF1A | 1 | 222737428 | C | G | A2403,A3201,B3801,B4101,C1203,C1701 | C1203 | 468 | 129 | lmlQfhtll | lmlEfhtll |
| HE3202 | RAB4A | 1 | 229433362 | T | A | A2403,A3201,B3801,B4101,C1203,C1701 | A3201 | 311 | 1530 | vtfleaTrf | vtfleaSrf |

Figure 21 (Cont.)

| | | | | | | | | | | | |
|---|---|---|---|---|---|---|---|---|---|---|---|
| HE3202 | TTC13 | 1 | 231064818 | G | A | A2403,A3201,B3801,B4101,C1203,C1701 | C1203 | 57 | 2438 | reysrylhV | reysrylhA |
| HE3202 | TTC13 | 1 | 231064818 | G | A | A2403,A3201,B3801,B4101,C1203,C1701 | C1203 | 121 | 134 | ysrylhVhl | ysrylhAhl |
| HE3202 | RYR2 | 1 | 237780733 | G | T | A2403,A3201,B3801,B4101,C1203,C1701 | C1203 | 81 | 93 | qalnmsSal | qalnmsAal |
| HE3202 | RYR2 | 1 | 237947415 | C | A | A2403,A3201,B3801,B4101,C1203,C1701 | A2403 | 4 | 5 | yfqpflgSi | yfqpflgRi |
| HE3202 | RYR2 | 1 | 237947415 | C | A | A2403,A3201,B3801,B4101,C1203,C1701 | C1203 | 28 | 62 | yfqpflgSi | yfqpflgRi |
| HE3202 | RYR2 | 1 | 237947415 | C | A | A2403,A3201,B3801,B4101,C1203,C1701 | C1203 | 232 | 176 | qpflgSiei | qpflgRiei |
| HE3202 | OR2W3 | 1 | 248059315 | G | T | A2403,A3201,B3801,B4101,C1203,C1701 | A3201 | 383 | 274 | rlcrClvsv | rlcrGlvsv |
| HE3202 | OR2W3 | 1 | 248059315 | G | T | A2403,A3201,B3801,B4101,C1203,C1701 | C1203 | 333 | 391 | rlcrClvsv | rlcrGlvsv |
| HE3202 | OR2M2 | 1 | 248343719 | G | C | A2403,A3201,B3801,B4101,C1203,C1701 | A3201 | 11 | 12 | kicgllatf | kicglMatf |
| HE3202 | OR2T12 | 1 | 248458342 | G | C | A2403,A3201,B3801,B4101,C1203,C1701 | A2403 | 307 | 122 | hffceaRvl | hffceaPvl |
| HE3202 | OR2T12 | 1 | 248458342 | G | C | A2403,A3201,B3801,B4101,C1203,C1701 | C1203 | 50 | 40 | ffceaRvlv | ffceaPvlv |
| HE3202 | OR2T34 | 1 | 248737725 | G | T | A2403,A3201,B3801,B4101,C1203,C1701 | A3201 | 115 | 25 | iqmffhltM | iqmffhltL |
| HE3202 | OR2T34 | 1 | 248737725 | G | T | A2403,A3201,B3801,B4101,C1203,C1701 | A3201 | 159 | 459 | ltMagaevf | ltLagaevf |
| HE3202 | OR2T34 | 1 | 248737725 | G | T | A2403,A3201,B3801,B4101,C1203,C1701 | C1203 | 231 | 258 | iqmffhltM | iqmffhltL |
| HE3202 | OR2T34 | 1 | 248737725 | G | T | A2403,A3201,B3801,B4101,C1203,C1701 | C1203 | 300 | 517 | ltMagaevf | ltLagaevf |
| HE3202 | OR2T27 | 1 | 248814155 | C | A | A2403,A3201,B3801,B4101,C1203,C1701 | A2403 | 114 | 1347 | snysvyaYf | snysvyaDf |
| HE3202 | OR2T27 | 1 | 248814155 | C | A | A2403,A3201,B3801,B4101,C1203,C1701 | A2403 | 10 | 22 | nysvyaYfi | nysvyaDfi |
| HE3202 | OR2T27 | 1 | 248814155 | C | A | A2403,A3201,B3801,B4101,C1203,C1701 | A2403 | 5 | 9680 | aYfillglf | aDfillglf |
| HE3202 | OR2T27 | 1 | 248814155 | C | A | A2403,A3201,B3801,B4101,C1203,C1701 | A3201 | 171 | 10321 | qsnysvyaY | qsnysvyaD |
| HE3202 | OR2T27 | 1 | 248814155 | C | A | A2403,A3201,B3801,B4101,C1203,C1701 | C1203 | 492 | 1134 | ysvyaYfil | ysvyaDfil |
| HE3202 | OR2T27 | 1 | 248814155 | C | A | A2403,A3201,B3801,B4101,C1203,C1701 | C1203 | 427 | 373 | svyaYfill | svyaDfill |
| HE3202 | OR2T27 | 1 | 248814155 | C | A | A2403,A3201,B3801,B4101,C1203,C1701 | C1203 | 14 | 158 | yaYfillgl | yaDfillgl |
| HE3202 | AKR1C4 | 10 | 5255064 | G | T | A2403,A3201,B3801,B4101,C1203,C1701 | A2403 | 28 | 165 | ryqlqLgvv | ryqlqRgvv |

Figure 21 (Cont.)

| | | | | | | | | | | | |
|---|---|---|---|---|---|---|---|---|---|---|---|
| HE3202 | AKR1C4 | 10 | 5255064 | G | T | A2403,A3201,B3801,B4101,C1203,C1701 | C1203 | 359 | 13420 | ialryqlqL | ialryqlqR |
| HE3202 | AKR1C4 | 10 | 5255064 | G | T | A2403,A3201,B3801,B4101,C1203,C1701 | C1203 | 14 | 10 | yqlqLgvvv | yqlqRgvvv |
| HE3202 | ALOX5 | 10 | 45936007 | C | G | A2403,A3201,B3801,B4101,C1203,C1701 | A3201 | 452 | 16 | Gthlvsevf | Rthlvsevf |
| HE3202 | JMJD1C | 10 | 64967381 | C | G | A2403,A3201,B3801,B4101,C1203,C1701 | C1203 | 161 | 30 | eagQtgrii | eagEtgrii |
| HE3202 | CTNNA3 | 10 | 68280419 | G | A | A2403,A3201,B3801,B4101,C1203,C1701 | C1203 | 117 | 13 | eVvdditsi | eAvdditsi |
| HE3202 | CDH23 | 10 | 73498312 | G | T | A2403,A3201,B3801,B4101,C1203,C1701 | A3201 | 329 | 1835 | ftsYsavsi | ftsDsavsi |
| HE3202 | CDH23 | 10 | 73498312 | G | T | A2403,A3201,B3801,B4101,C1203,C1701 | C1203 | 104 | 257 | fdftsYsav | fdftsDsav |
| HE3202 | CDH23 | 10 | 73498312 | G | T | A2403,A3201,B3801,B4101,C1203,C1701 | C1203 | 40 | 8 | ftsYsavsi | ftsDsavsi |
| HE3202 | DUPD1 | 10 | 76818104 | C | T | A2403,A3201,B3801,B4101,C1203,C1701 | A2403 | 13 | 10 | qythvnKvw | qythvnEvw |
| HE3202 | DUPD1 | 10 | 76818104 | C | T | A2403,A3201,B3801,B4101,C1203,C1701 | C1203 | 92 | 108 | pqythvnKv | pqythvnEv |
| HE3202 | GRID1 | 10 | 87482802 | A | T | A2403,A3201,B3801,B4101,C1203,C1701 | A2403 | 4 | 3 | sytanHaaf | sytanLaaf |
| HE3202 | GRID1 | 10 | 87482802 | A | T | A2403,A3201,B3801,B4101,C1203,C1701 | C1203 | 19 | 43 | ytanHaafl | ytanLaafl |
| HE3202 | C10orf12 | 10 | 98742071 | G | T | A2403,A3201,B3801,B4101,C1203,C1701 | C1203 | 358 | 1716 | tasslvCpl | tasslvWpl |
| HE3202 | C10orf12 | 10 | 98742071 | G | T | A2403,A3201,B3801,B4101,C1203,C1701 | C1203 | 179 | 170 | lvCplpahl | lvWplpahl |
| HE3202 | ELOVL3 | 10 | 103986396 | G | A | A2403,A3201,B3801,B4101,C1203,C1701 | C1203 | 122 | 161 | dmrpffKey | dmrpffEey |
| HE3202 | SORCS1 | 10 | 108389069 | C | A | A2403,A3201,B3801,B4101,C1203,C1701 | C1203 | 19 | 47 | vsyvnlssl | vsyvnlssM |
| HE3202 | SORCS1 | 10 | 108389069 | C | A | A2403,A3201,B3801,B4101,C1203,C1701 | C1203 | 97 | 43 | siedgikhv | sMedgikhv |
| HE3202 | SORCS1 | 10 | 108389070 | A | T | A2403,A3201,B3801,B4101,C1203,C1701 | C1203 | 355 | 43 | sKedgikhv | sMedgikhv |
| HE3202 | FAM160B1 | 10 | 116606002 | T | G | A2403,A3201,B3801,B4101,C1203,C1701 | A2403 | 324 | 201 | Gllqemvff | Vllqemvff |
| HE3202 | ATRNL1 | 10 | 117061521 | A | C | A2403,A3201,B3801,B4101,C1203,C1701 | C1203 | 167 | 85 | isfpygPcl | isfpygQcl |
| HE3202 | ATRNL1 | 10 | 117061521 | A | C | A2403,A3201,B3801,B4101,C1203,C1701 | C1203 | 115 | 361 | fpygPclew | fpygQclew |
| HE3202 | ATRNL1 | 10 | 117221510 | C | T | A2403,A3201,B3801,B4101,C1203,C1701 | B3801 | 240 | 704 | rhYtainfi | rhHtainfi |

Figure 21 (Cont.)

| | | | | | | | | | | | |
|---|---|---|---|---|---|---|---|---|---|---|---|
| HE3202 | ATRNL1 | 10 | 117221510 | C | T | A2403,A3201,B3801,B4101,C1203,C1701 | C1203 | 86 | 1086 | rhYtainfi | rhHtainfi |
| HE3202 | RAB11FIP2 | 10 | 119805410 | T | C | A2403,A3201,B3801,B4101,C1203,C1701 | C1203 | 426 | 661 | livmhGslv | livmhRslv |
| HE3202 | MCMBP | 10 | 121596409 | G | A | A2403,A3201,B3801,B4101,C1203,C1701 | C1203 | 456 | 166 | lLadcqihl | lPadcqihl |
| HE3202 | TCERG1L | 10 | 133058566 | G | T | A2403,A3201,B3801,B4101,C1203,C1701 | A3201 | 200 | 242 | rhflNlapi | rhflTlapi |
| HE3202 | TCERG1L | 10 | 133058566 | G | T | A2403,A3201,B3801,B4101,C1203,C1701 | C1203 | 218 | 877 | rhflNlapi | rhflTlapi |
| HE3202 | TCERG1L | 10 | 133058566 | G | T | A2403,A3201,B3801,B4101,C1203,C1701 | C1203 | 140 | 332 | flNlapiki | flTlapiki |
| HE3202 | KCNQ1 | 11 | 2591961 | C | A | A2403,A3201,B3801,B4101,C1203,C1701 | C1203 | 65 | 3 | fDrkpisii | fArkpisii |
| HE3202 | ART5 | 11 | 3661341 | C | G | A2403,A3201,B3801,B4101,C1203,C1701 | A2403 | 5 | 10 | vytnssntF | vytnssntL |
| HE3202 | ART5 | 11 | 3661341 | C | G | A2403,A3201,B3801,B4101,C1203,C1701 | A2403 | 184 | 597 | Fyweinqav | Lyweinqav |
| HE3202 | ART5 | 11 | 3661341 | C | G | A2403,A3201,B3801,B4101,C1203,C1701 | C1203 | 107 | 103 | ytnssntFy | ytnssntLy |
| HE3202 | ART5 | 11 | 3661341 | C | G | A2403,A3201,B3801,B4101,C1203,C1701 | C1203 | 52 | 733 | Fyweinqav | Lyweinqav |
| HE3202 | NUP98 | 11 | 3794875 | C | T | A2403,A3201,B3801,B4101,C1203,C1701 | C1203 | 402 | 705 | yeNksleel | yeSksleel |
| HE3202 | OR51A7 | 11 | 4928760 | C | T | A2403,A3201,B3801,B4101,C1203,C1701 | A2403 | 338 | 153 | Llhepmyyf | Slhepmyyf |
| HE3202 | HBD | 11 | 5254280 | C | A | A2403,A3201,B3801,B4101,C1203,C1701 | C1203 | 93 | 39 | lamfCkef | lamfGkef |
| HE3202 | HBD | 11 | 5254280 | C | A | A2403,A3201,B3801,B4101,C1203,C1701 | C1203 | 110 | 282 | fCkeftpqm | fGkeftpqm |
| HE3202 | OR10A6 | 11 | 7949446 | G | T | A2403,A3201,B3801,B4101,C1203,C1701 | A2403 | 105 | 32 | fygtDsmty | fygtAsmty |
| HE3202 | OR10A6 | 11 | 7949446 | G | T | A2403,A3201,B3801,B4101,C1203,C1701 | C1203 | 149 | 967 | ygtDsmtyl | ygtAsmtyl |
| HE3202 | WT1 | 11 | 32456321 | C | A | A2403,A3201,B3801,B4101,C1203,C1701 | C1203 | 375 | 469 | qassCqarm | qassGqarm |
| HE3202 | DGKZ | 11 | 46396582 | C | T | A2403,A3201,B3801,B4101,C1203,C1701 | A2403 | 4 | 383 | gylevigfI | gylevigfT |
| HE3202 | DGKZ | 11 | 46396582 | C | T | A2403,A3201,B3801,B4101,C1203,C1701 | C1203 | 141 | 79 | fImtslaal | fTmtslaal |
| HE3202 | ARFGAP2 | 11 | 47188135 | G | C | A2403,A3201,B3801,B4101,C1203,C1701 | C1203 | 491 | 357 | earsGlqql | earsRlqql |
| HE3202 | TRIM51 | 11 | 55658821 | T | G | A2403,A3201,B3801,B4101,C1203,C1701 | A2403 | 64 | 36 | afgvGnnyw | afgvCnnyw |
| HE3202 | TRIM51 | 11 | 55658821 | T | G | A2403,A3201,B3801,B4101,C1203,C1701 | C1203 | 16 | 24 | wafgvGnny | wafgvCnny |

Figure 21 (Cont.)

| | | | | | | | | | | | |
|---|---|---|---|---|---|---|---|---|---|---|---|
| HE3202 | OR5AS1 | 11 | 55798567 | G | C | A2403,A3201,B3801,B4101,C1203,C1701 | A2403 | 5 | 41 | syfcilitL | syfcilitV |
| HE3202 | OR5AS1 | 11 | 55798567 | G | C | A2403,A3201,B3801,B4101,C1203,C1701 | A2403 | 142 | 118 | yfcilitLI | yfcilitVI |
| HE3202 | OR8H1 | 11 | 56058376 | G | T | A2403,A3201,B3801,B4101,C1203,C1701 | A2403 | 336 | 134 | lqlhtpmyf | lqLhtpmyf |
| HE3202 | OR8H1 | 11 | 56058376 | G | T | A2403,A3201,B3801,B4101,C1203,C1701 | A3201 | 387 | 344 | qlhtpmyff | qLhtpmyff |
| HE3202 | OR8H1 | 11 | 56058376 | G | T | A2403,A3201,B3801,B4101,C1203,C1701 | B3801 | 34 | 39 | lhtpmyffl | Lhtpmyffl |
| HE3202 | OR5M1 | 11 | 56380101 | C | G | A2403,A3201,B3801,B4101,C1203,C1701 | A2403 | 44 | 280 | yslPntdvi | yslRntdvi |
| HE3202 | OR5M1 | 11 | 56380101 | C | G | A2403,A3201,B3801,B4101,C1203,C1701 | C1203 | 5 | 7 | yslPntdvi | yslRntdvi |
| HE3202 | OR5B3 | 11 | 58169991 | C | G | A2403,A3201,B3801,B4101,C1203,C1701 | C1203 | 435 | 2059 | vksPfkkvv | vksAfkkvv |
| HE3202 | MS4A7 | 11 | 60152636 | T | A | A2403,A3201,B3801,B4101,C1203,C1701 | A2403 | 145 | 14 | vfapypshl | vfapypshF |
| HE3202 | MS4A7 | 11 | 60152636 | T | A | A2403,A3201,B3801,B4101,C1203,C1701 | C1203 | 66 | 32 | ypshlnpai | ypshFnpai |
| HE3202 | RPS6KA4 | 11 | 64129169 | C | T | A2403,A3201,B3801,B4101,C1203,C1701 | A3201 | 433 | 1136 | elltgaLpf | elltgaSpf |
| HE3202 | RPS6KA4 | 11 | 64137062 | G | T | A2403,A3201,B3801,B4101,C1203,C1701 | C1203 | 12 | 11 | fmheeaCvv | fmheeaGvv |
| HE3202 | ANO1 | 11 | 69950126 | C | T | A2403,A3201,B3801,B4101,C1203,C1701 | A3201 | 110 | 341 | kmyhinetC | kmyhinetR |
| HE3202 | ANO1 | 11 | 69950126 | C | T | A2403,A3201,B3801,B4101,C1203,C1701 | B3801 | 451 | 2142 | yhinetCgl | yhinetRgl |
| HE3202 | INTS4 | 11 | 77629897 | C | A | A2403,A3201,B3801,B4101,C1203,C1701 | A2403 | 183 | 4520 | qVaqellef | qGaqellef |
| HE3202 | GRM5 | 11 | 88780896 | C | T | A2403,A3201,B3801,B4101,C1203,C1701 | C1203 | 31 | 12 | fsvhhqptM | fsvhhqptV |
| HE3202 | FAT3 | 11 | 92568036 | G | A | A2403,A3201,B3801,B4101,C1203,C1701 | A3201 | 139 | 349 | kinpktEgi | kinpktGgi |
| HE3202 | FAT3 | 11 | 92568036 | G | A | A2403,A3201,B3801,B4101,C1203,C1701 | A3201 | 281 | 287 | ktEgisvse | ktGgisvse |
| HE3202 | DYNC2H1 | 11 | 102988426 | A | T | A2403,A3201,B3801,B4101,C1203,C1701 | A2403 | 309 | 266 | pyFlvkesl | pyYlvkesl |
| HE3202 | CUL5 | 11 | 107923458 | G | T | A2403,A3201,B3801,B4101,C1203,C1701 | C1203 | 315 | 495 | lqdsamNlv | lqdsamKlv |
| HE3202 | SIK3 | 11 | 116744228 | C | A | A2403,A3201,B3801,B4101,C1203,C1701 | C1203 | 397 | 615 | rpLgpsplv | rpRgpsplv |
| HE3202 | TMPRSS13 | 11 | 117776413 | T | C | A2403,A3201,B3801,B4101,C1203,C1701 | C1203 | 420 | 5201 | qAfslnetc | qTfslnetc |

Figure 21 (Cont.)

| | | | | | | | | | | | |
|---|---|---|---|---|---|---|---|---|---|---|---|
| HE3202 | ROBO4 | 11 | 124766519 | C | A | A2403,A3201,B3801,B4101,C1203,C1701 | C1203 | 119 | 35 | qprdmvavL | qprdmvavV |
| HE3202 | GLB1L2 | 11 | 134217265 | G | T | A2403,A3201,B3801,B4101,C1203,C1701 | A2403 | 375 | 195 | tykCfteav | tykGfteav |
| HE3202 | CACNA2D4 | 12 | 1919749 | C | T | A2403,A3201,B3801,B4101,C1203,C1701 | C1203 | 113 | 185 | aatrqcNtv | aatrqcStv |
| HE3202 | KCNA1 | 12 | 5021636 | G | T | A2403,A3201,B3801,B4101,C1203,C1701 | C1203 | 260 | 678 | dafCwavvs | dafWwavvs |
| HE3202 | USP5 | 12 | 6971714 | A | T | A2403,A3201,B3801,B4101,C1203,C1701 | C1203 | 364 | 803 | vpMkldvsi | vpKkldvsi |
| HE3202 | PPFIBP1 | 12 | 27832494 | G | T | A2403,A3201,B3801,B4101,C1203,C1701 | A3201 | 471 | 1492 | kdsqMnspf | kdsqRnspf |
| HE3202 | ERGIC2 | 12 | 29519869 | C | T | A2403,A3201,B3801,B4101,C1203,C1701 | C1203 | 162 | 435 | cqyvgaNvl | cqyvgaDvl |
| HE3202 | ERGIC2 | 12 | 29519869 | C | T | A2403,A3201,B3801,B4101,C1203,C1701 | C1203 | 439 | 1194 | yvgaNvldl | yvgaDvldl |
| HE3202 | ERGIC2 | 12 | 29519869 | C | T | A2403,A3201,B3801,B4101,C1203,C1701 | C1203 | 40 | 51 | Nvldlaetm | Dvldlaetm |
| HE3202 | H3F3C | 12 | 31944741 | C | A | A2403,A3201,B3801,B4101,C1203,C1701 | C1203 | 303 | 1060 | ihakrvtil | ihakrvtiM |
| HE3202 | ABCD2 | 12 | 39947815 | C | G | A2403,A3201,B3801,B4101,C1203,C1701 | C1203 | 480 | 1998 | sqlPgipkm | sqlAgipkm |
| HE3202 | KRT80 | 12 | 52579169 | C | G | A2403,A3201,B3801,B4101,C1203,C1701 | C1203 | 389 | 538 | kveefPiry | kveefRiry |
| HE3202 | KRT80 | 12 | 52579169 | C | G | A2403,A3201,B3801,B4101,C1203,C1701 | C1203 | 82 | 722 | fPiryedei | fRiryedei |
| HE3202 | ITGB7 | 12 | 53591298 | C | T | A2403,A3201,B3801,B4101,C1203,C1701 | A3201 | 49 | 110 | rlqelthsv | rlqeVthsv |
| HE3202 | ITGB7 | 12 | 53591298 | C | T | A2403,A3201,B3801,B4101,C1203,C1701 | A3201 | 205 | 298 | lthsvrigf | Vthsvrigf |
| HE3202 | ITGB7 | 12 | 53591298 | C | T | A2403,A3201,B3801,B4101,C1203,C1701 | C1203 | 244 | 316 | rlqelthsv | rlqeVthsv |
| HE3202 | NCKAP1L | 12 | 54925983 | G | A | A2403,A3201,B3801,B4101,C1203,C1701 | C1203 | 39 | 115 | fsshcpfll | fsshcpflM |
| HE3202 | NCKAP1L | 12 | 54925983 | G | A | A2403,A3201,B3801,B4101,C1203,C1701 | C1203 | 100 | 64 | fllgpiecl | flMgpiecl |
| HE3202 | OR6C6 | 12 | 55688560 | T | A | A2403,A3201,B3801,B4101,C1203,C1701 | A2403 | 25 | 56 | swvtgflFi | swvtgflli |
| HE3202 | OR6C6 | 12 | 55688560 | T | A | A2403,A3201,B3801,B4101,C1203,C1701 | A2403 | 105 | 224 | wvtgflFif | wvtgfllif |
| HE3202 | OR6C6 | 12 | 55688560 | T | A | A2403,A3201,B3801,B4101,C1203,C1701 | A2403 | 37 | 83 | gflFifppl | gfllifppl |
| HE3202 | OR6C6 | 12 | 55688560 | T | A | A2403,A3201,B3801,B4101,C1203,C1701 | A3201 | 152 | 602 | sswvtgflF | sswvtgfll |
| HE3202 | OR6C6 | 12 | 55688560 | T | A | A2403,A3201,B3801,B4101,C1203,C1701 | C1203 | 31 | 128 | flFifpplv | fllifpplv |

Figure 21 (Cont.)

| | | | | | | | | | | | |
|---|---|---|---|---|---|---|---|---|---|---|---|
| HE3202 | OR6C6 | 12 | 55688560 | T | A | A2403,A3201,B3801,B4101,C1203,C1701 | C1203 | 296 | 2742 | Flfpplvmg | lifpplvmg |
| HE3202 | MMP19 | 12 | 56231721 | G | T | A2403,A3201,B3801,B4101,C1203,C1701 | C1203 | 387 | 761 | irfrtgplv | irfrtgpLv |
| HE3202 | MMP19 | 12 | 56231721 | G | T | A2403,A3201,B3801,B4101,C1203,C1701 | C1203 | 325 | 490 | rtgplvpsv | rtgpLvpsv |
| HE3202 | PMEL | 12 | 56350811 | T | C | A2403,A3201,B3801,B4101,C1203,C1701 | C1203 | 211 | 3595 | eAtarelpi | eTtarelpi |
| HE3202 | CCT2 | 12 | 69983338 | C | T | A2403,A3201,B3801,B4101,C1203,C1701 | C1203 | 39 | 886 | Yhkdhftkl | Hhkdhftkl |
| HE3202 | PTPRB | 12 | 70983957 | C | T | A2403,A3201,B3801,B4101,C1203,C1701 | A3201 | 9 | 6 | rmrsllvsw | rmrslVvsw |
| HE3202 | LGR5 | 12 | 71978171 | C | G | A2403,A3201,B3801,B4101,C1203,C1701 | C1203 | 495 | 69 | lRfispevi | lTfispevi |
| HE3202 | GNPTAB | 12 | 102160028 | C | A | A2403,A3201,B3801,B4101,C1203,C1701 | C1203 | 297 | 4783 | yiaggggtW | yiaggggtG |
| HE3202 | KIAA1033 | 12 | 105538614 | G | T | A2403,A3201,B3801,B4101,C1203,C1701 | A2403 | 395 | 617 | ryglvltea | ryglvMtea |
| HE3202 | KIAA1033 | 12 | 105538614 | G | T | A2403,A3201,B3801,B4101,C1203,C1701 | A3201 | 496 | 6178 | atqryglvl | atqryglvM |
| HE3202 | DNAH10 | 12 | 124349233 | G | T | A2403,A3201,B3801,B4101,C1203,C1701 | C1203 | 122 | 135 | ltlanWeri | ltlanGeri |
| HE3202 | IL17D | 13 | 21295803 | A | T | A2403,A3201,B3801,B4101,C1203,C1701 | A2403 | 9 | 2349 | sydparypW | sydparypR |
| HE3202 | IL17D | 13 | 21295803 | A | T | A2403,A3201,B3801,B4101,C1203,C1701 | A2403 | 74 | 66 | rypWylpea | rypRylpea |
| HE3202 | IL17D | 13 | 21295803 | A | T | A2403,A3201,B3801,B4101,C1203,C1701 | A2403 | 5 | 4 | Wylpeaycl | Rylpeaycl |
| HE3202 | IL17D | 13 | 21295803 | A | T | A2403,A3201,B3801,B4101,C1203,C1701 | C1203 | 216 | 212 | ypWylpeay | ypRylpeay |
| HE3202 | GTF3A | 13 | 27998923 | G | A | A2403,A3201,B3801,B4101,C1203,C1701 | A3201 | 68 | 176 | ssltiTdaf | ssltiAdaf |
| HE3202 | CCDC70 | 13 | 52439669 | G | A | A2403,A3201,B3801,B4101,C1203,C1701 | A2403 | 15 | 60 | afHeemkif | afReemkif |
| HE3202 | CCDC70 | 13 | 52439669 | G | A | A2403,A3201,B3801,B4101,C1203,C1701 | C1203 | 18 | 18 | kafHeemki | kafReemki |
| HE3202 | DZIP1 | 13 | 96237023 | C | A | A2403,A3201,B3801,B4101,C1203,C1701 | A2403 | 171 | 116 | hvlnawCaf | hvlnawGaf |
| HE3202 | DZIP1 | 13 | 96237023 | C | A | A2403,A3201,B3801,B4101,C1203,C1701 | A3201 | 177 | 934 | hvlnawCaf | hvlnawGaf |
| HE3202 | IPO5 | 13 | 98642687 | A | G | A2403,A3201,B3801,B4101,C1203,C1701 | C1203 | 185 | 199 | qehpsVrtl | qehpsirtl |
| HE3202 | NALCN | 13 | 101890156 | T | A | A2403,A3201,B3801,B4101,C1203,C1701 | C1203 | 383 | 202 | lvigtSlhv | lvigtTlhv |

Figure 21 (Cont.)

| | | | | | | | | | | | |
|---|---|---|---|---|---|---|---|---|---|---|---|
| HE3202 | FAM155A | 13 | 108518104 | C | G | A2403,A3201,B3801,B4101,C1203,C1701 | A2403 | 433 | 279 | haqekyeQf | haqekyeEf |
| HE3202 | FAM155A | 13 | 108518104 | C | G | A2403,A3201,B3801,B4101,C1203,C1701 | A2403 | 33 | 71 | kyeQfesvl | kyeEfesvl |
| HE3202 | FAM155A | 13 | 108518104 | C | G | A2403,A3201,B3801,B4101,C1203,C1701 | C1203 | 193 | 108 | haqekyeQf | haqekyeEf |
| HE3202 | FAM155A | 13 | 108518104 | C | G | A2403,A3201,B3801,B4101,C1203,C1701 | C1203 | 136 | 102 | ekyeQfesv | ekyeEfesv |
| HE3202 | OR4L1 | 14 | 20528255 | T | A | A2403,A3201,B3801,B4101,C1203,C1701 | C1203 | 260 | 1023 | flgrwelqi | fFgrwelqi |
| HE3202 | SIX4 | 14 | 61180343 | C | G | A2403,A3201,B3801,B4101,C1203,C1701 | C1203 | 52 | 17 | fvqQhrlvl | fvqEhrlvl |
| HE3202 | KCNH5 | 14 | 63269158 | A | T | A2403,A3201,B3801,B4101,C1203,C1701 | C1203 | 349 | 1345 | hSapgdliy | hCapgdliy |
| HE3202 | EXD2 | 14 | 69707693 | G | C | A2403,A3201,B3801,B4101,C1203,C1701 | A3201 | 43 | 704 | slmqlesPw | slmqlesRw |
| HE3202 | EXD2 | 14 | 69707693 | G | C | A2403,A3201,B3801,B4101,C1203,C1701 | C1203 | 407 | 1543 | lesPwrqhf | lesRwrqhf |
| HE3202 | ADAM21 | 14 | 70924572 | C | A | A2403,A3201,B3801,B4101,C1203,C1701 | C1203 | 235 | 71 | yveaaHesl | yveaaPesl |
| HE3202 | ADAM21 | 14 | 70924572 | C | A | A2403,A3201,B3801,B4101,C1203,C1701 | C1203 | 65 | 22 | eaaHeslvv | eaaPeslvv |
| HE3202 | ADAM21 | 14 | 70924572 | C | A | A2403,A3201,B3801,B4101,C1203,C1701 | C1203 | 99 | 374 | aaHeslvvf | aaPeslvvf |
| HE3202 | GALC | 14 | 88429804 | C | A | A2403,A3201,B3801,B4101,C1203,C1701 | A2403 | 3 | 4 | yylktvVhl | yylktvGhl |
| HE3202 | GALC | 14 | 88429804 | C | A | A2403,A3201,B3801,B4101,C1203,C1701 | C1203 | 82 | 137 | yylktvVhl | yylktvGhl |
| HE3202 | TCL1A | 14 | 96178119 | C | A | A2403,A3201,B3801,B4101,C1203,C1701 | C1203 | 486 | 1693 | ikidgvedl | ikidgvedM |
| HE3202 | BEGAIN | 14 | 101004911 | T | A | A2403,A3201,B3801,B4101,C1203,C1701 | A2403 | 123 | 24 | lLppnlwsl | lMppnlwsl |
| HE3202 | POTEB2 | 15 | 21071328 | T | A | A2403,A3201,B3801,B4101,C1203,C1701 | A2403 | 30 | 22 | Wyhvrredl | Ryhvrredl |
| HE3202 | OR4M2 | 15 | 22369155 | C | A | A2403,A3201,B3801,B4101,C1203,C1701 | A2403 | 108 | 18 | tfTeelvmi | tfPeelvmi |
| HE3202 | OR4M2 | 15 | 22369155 | C | A | A2403,A3201,B3801,B4101,C1203,C1701 | C1203 | 381 | 445 | cantfTeel | cantfPeel |
| HE3202 | SNRPN | 15 | 25223057 | C | A | A2403,A3201,B3801,B4101,C1203,C1701 | C1203 | 66 | 28 | ratpTpgim | ratpPpgim |
| HE3202 | UBE3A | 15 | 25620900 | C | G | A2403,A3201,B3801,B4101,C1203,C1701 | B3801 | 421 | 1312 | kraPakhli | kraAakhli |
| HE3202 | GABRB3 | 15 | 26793154 | C | A | A2403,A3201,B3801,B4101,C1203,C1701 | A2403 | 304 | 1779 | qyMkqsmpr | qyRkqsmpr |
| HE3202 | GABRB3 | 15 | 26793154 | C | A | A2403,A3201,B3801,B4101,C1203,C1701 | C1203 | 213 | 9969 | fdnsgiqyM | fdnsgiqyR |

Figure 21 (Cont.)

| | | | | | | | | | | | |
|---|---|---|---|---|---|---|---|---|---|---|---|
| HE3202 | GATM | 15 | 45658597 | C | G | A2403,A3201,B3801,B4101,C1203,C1701 | C1203 | 215 | 2021 | daadfiraA | daadfiraG |
| HE3202 | GATM | 15 | 45658597 | C | G | A2403,A3201,B3801,B4101,C1203,C1701 | C1203 | 420 | 220 | firaArdif | firaGrdif |
| HE3202 | VPS13C | 15 | 62176399 | T | A | A2403,A3201,B3801,B4101,C1203,C1701 | C1203 | 177 | 181 | fsqkqiiFl | fsqkqiiLl |
| HE3202 | VPS13C | 15 | 62234260 | G | A | A2403,A3201,B3801,B4101,C1203,C1701 | A2403 | 3 | 5 | ffmsllnfF | ffmsllnfL |
| HE3202 | VPS13C | 15 | 62234260 | G | A | A2403,A3201,B3801,B4101,C1203,C1701 | A2403 | 58 | 187 | sllnfFnnf | sllnfLnnf |
| HE3202 | VPS13C | 15 | 62234260 | G | A | A2403,A3201,B3801,B4101,C1203,C1701 | A3201 | 18 | 24 | sllnfFnnf | sllnfLnnf |
| HE3202 | VPS13C | 15 | 62234260 | G | A | A2403,A3201,B3801,B4101,C1203,C1701 | C1203 | 448 | 223 | ffmsllnfF | ffmsllnfL |
| HE3202 | SIN3A | 15 | 75684759 | C | A | A2403,A3201,B3801,B4101,C1203,C1701 | A2403 | 4 | 3 | fyvnnnLyi | fyvnnnWyi |
| HE3202 | SIN3A | 15 | 75684759 | C | A | A2403,A3201,B3801,B4101,C1203,C1701 | A2403 | 14 | 13 | yvnnnLyif | yvnnnWyif |
| HE3202 | SIN3A | 15 | 75684759 | C | A | A2403,A3201,B3801,B4101,C1203,C1701 | A3201 | 76 | 248 | yvnnnLyif | yvnnnWyif |
| HE3202 | SIN3A | 15 | 75684759 | C | A | A2403,A3201,B3801,B4101,C1203,C1701 | C1203 | 472 | 2116 | lfyvnnnLy | lfyvnnnWy |
| HE3202 | SIN3A | 15 | 75684759 | C | A | A2403,A3201,B3801,B4101,C1203,C1701 | C1203 | 66 | 275 | fyvnnnLyi | fyvnnnWyi |
| HE3202 | SIN3A | 15 | 75684759 | C | A | A2403,A3201,B3801,B4101,C1203,C1701 | C1203 | 43 | 36 | yvnnnLyif | yvnnnWyif |
| HE3202 | SLCO3A1 | 15 | 92459325 | T | C | A2403,A3201,B3801,B4101,C1203,C1701 | C1203 | 243 | 231 | lalilLvsy | lalilFvsy |
| HE3202 | C16orf13 | 16 | 685337 | G | A | A2403,A3201,B3801,B4101,C1203,C1701 | A2403 | 269 | 15034 | gFfraaghl | gLfraaghl |
| HE3202 | C16orf13 | 16 | 685337 | G | A | A2403,A3201,B3801,B4101,C1203,C1701 | A2403 | 92 | 392 | Ffraaghll | Lfraaghll |
| HE3202 | BAIAP3 | 16 | 1391300 | A | T | A2403,A3201,B3801,B4101,C1203,C1701 | A2403 | 327 | 124 | gfCdpycml | gfSdpycml |
| HE3202 | MGRN1 | 16 | 4738802 | C | G | A2403,A3201,B3801,B4101,C1203,C1701 | C1203 | 170 | 158 | ylpgrAtsm | ylpgrPtsm |
| HE3202 | C16orf54 | 16 | 29755993 | C | T | A2403,A3201,B3801,B4101,C1203,C1701 | A2403 | 338 | 5241 | Nwygsavpl | Dwygsavpl |
| HE3202 | FAM57B | 16 | 30038030 | G | A | A2403,A3201,B3801,B4101,C1203,C1701 | A2403 | 239 | 176 | raLgstwai | raPgstwai |
| HE3202 | FAM57B | 16 | 30038030 | G | A | A2403,A3201,B3801,B4101,C1203,C1701 | A3201 | 31 | 244 | raLgstwai | raPgstwai |
| HE3202 | FAM57B | 16 | 30038030 | G | A | A2403,A3201,B3801,B4101,C1203,C1701 | C1203 | 117 | 614 | raLgstwai | raPgstwai |

Figure 21 (Cont.)

| | | | | | | | | | | | |
|---|---|---|---|---|---|---|---|---|---|---|---|
| HE3202 | PKD1L2 | 16 | 81213294 | G | A | A2403,A3201,B3801,B4101,C1203,C1701 | A3201 | 98 | 19 | stlllnsLf | stlllnsSf |
| HE3202 | GAN | 16 | 81388140 | G | T | A2403,A3201,B3801,B4101,C1203,C1701 | C1203 | 216 | 6420 | aaencigiL | aaencigiR |
| HE3202 | FANCA | 16 | 89836653 | G | A | A2403,A3201,B3801,B4101,C1203,C1701 | A2403 | 250 | 427 | rqgpwValf | rqgpwAalf |
| HE3202 | FANCA | 16 | 89836653 | G | A | A2403,A3201,B3801,B4101,C1203,C1701 | A3201 | 203 | 298 | rqgpwValf | rqgpwAalf |
| HE3202 | FANCA | 16 | 89836653 | G | A | A2403,A3201,B3801,B4101,C1203,C1701 | C1203 | 436 | 788 | rqgpwValf | rqgpwAalf |
| HE3202 | FANCA | 16 | 89836653 | G | A | A2403,A3201,B3801,B4101,C1203,C1701 | C1203 | 127 | 16 | wValfvrtm | wAalfvrtm |
| HE3202 | RAP1GAP2 | 17 | 2921384 | G | T | A2403,A3201,B3801,B4101,C1203,C1701 | C1203 | 475 | 742 | rshsietmv | rshsMetmv |
| HE3202 | ATP2A3 | 17 | 3839634 | C | A | A2403,A3201,B3801,B4101,C1203,C1701 | C1203 | 109 | 340 | fnppdldil | fnppdldiM |
| HE3202 | PMP22 | 17 | 15163987 | A | G | A2403,A3201,B3801,B4101,C1203,C1701 | A3201 | 467 | 228 | lvllLvsti | lvllFvsti |
| HE3202 | PMP22 | 17 | 15163987 | A | G | A2403,A3201,B3801,B4101,C1203,C1701 | C1203 | 316 | 312 | vavlvllLv | vavlvllFv |
| HE3202 | PMP22 | 17 | 15163987 | A | G | A2403,A3201,B3801,B4101,C1203,C1701 | C1203 | 104 | 34 | lvllLvsti | lvllFvsti |
| HE3202 | IGF2BP1 | 17 | 47121332 | G | A | A2403,A3201,B3801,B4101,C1203,C1701 | C1203 | 296 | 152 | fmqTpeqem | fmqApeqem |
| HE3202 | IGF2BP1 | 17 | 47121332 | G | A | A2403,A3201,B3801,B4101,C1203,C1701 | C1203 | 248 | 140 | mqTpeqemv | mqApeqemv |
| HE3202 | SMG8 | 17 | 57292205 | G | C | A2403,A3201,B3801,B4101,C1203,C1701 | A2403 | 19 | 28 | vfypQkqei | vfypEkqei |
| HE3202 | SMG8 | 17 | 57292205 | G | C | A2403,A3201,B3801,B4101,C1203,C1701 | C1203 | 270 | 198 | vfypQkqei | vfypEkqei |
| HE3202 | SMG8 | 17 | 57292205 | G | C | A2403,A3201,B3801,B4101,C1203,C1701 | C1203 | 114 | 141 | ypQkqeitl | ypEkqeitl |
| HE3202 | CLTC | 17 | 57759778 | C | T | A2403,A3201,B3801,B4101,C1203,C1701 | C1203 | 55 | 4166 | fingpnnaY | fingpnnaH |
| HE3202 | MAP2K6 | 17 | 67515522 | G | T | A2403,A3201,B3801,B4101,C1203,C1701 | A3201 | 78 | 316 | smStvdcpf | smRtvdcpf |
| HE3202 | MAP2K6 | 17 | 67515522 | G | T | A2403,A3201,B3801,B4101,C1203,C1701 | C1203 | 101 | 34 | Stvdcpftv | Rtvdcpftv |
| HE3202 | KCNJ16 | 17 | 68129039 | G | T | A2403,A3201,B3801,B4101,C1203,C1701 | A2403 | 456 | 5034 | lyaldrkaL | lyaldrkaV |
| HE3202 | KCNJ16 | 17 | 68129039 | G | T | A2403,A3201,B3801,B4101,C1203,C1701 | C1203 | 24 | 15 | yaldrkaLa | yaldrkaVa |
| HE3202 | KCNJ16 | 17 | 68129039 | G | T | A2403,A3201,B3801,B4101,C1203,C1701 | C1203 | 10 | 12 | Lakdnfeil | Vakdnfeil |
| HE3202 | EVPL | 17 | 74006293 | T | A | A2403,A3201,B3801,B4101,C1203,C1701 | C1203 | 426 | 12386 | qadlevaaL | qadlevaaQ |

Figure 21 (Cont.)

| | | | | | | | | | | | |
|---|---|---|---|---|---|---|---|---|---|---|---|
| HE3202 | SEC14L1 | 17 | 75209484 | G | T | A2403,A3201,B3801,B4101,C1203,C1701 | C1203 | 393 | 549 | caasslpLv | caasslpRv |
| HE3202 | SEC14L1 | 17 | 75209484 | G | T | A2403,A3201,B3801,B4101,C1203,C1701 | C1203 | 253 | 299 | Lvddvlasl | Rvddvlasl |
| HE3202 | HGS | 17 | 79663655 | A | T | A2403,A3201,B3801,B4101,C1203,C1701 | A2403 | 8 | 51 | eylevqWql | eylevqRql |
| HE3202 | HGS | 17 | 79663655 | A | T | A2403,A3201,B3801,B4101,C1203,C1701 | A2403 | 25 | 15252 | qWqlaiqrl | qRqlaiqrl |
| HE3202 | HGS | 17 | 79663655 | A | T | A2403,A3201,B3801,B4101,C1203,C1701 | A3201 | 222 | 24953 | kqeylevqW | kqeylevqR |
| HE3202 | DCXR | 17 | 79995337 | G | T | A2403,A3201,B3801,B4101,C1203,C1701 | A3201 | 407 | 1501 | rtqadldsl | rtqadldsL |
| HE3202 | C17orf62 | 17 | 80405468 | A | G | A2403,A3201,B3801,B4101,C1203,C1701 | A2403 | 16 | 6 | Hysgdslgw | Yysgdslgw |
| HE3202 | EPB41L3 | 18 | 5396220 | T | C | A2403,A3201,B3801,B4101,C1203,C1701 | C1203 | 142 | 126 | vvhtetktV | vvhtetktl |
| HE3202 | EPB41L3 | 18 | 5396220 | T | C | A2403,A3201,B3801,B4101,C1203,C1701 | C1203 | 477 | 720 | htetktVty | htetktlty |
| HE3202 | ALPK2 | 18 | 56203571 | G | T | A2403,A3201,B3801,B4101,C1203,C1701 | C1203 | 84 | 377 | kadDvvpel | kadAvvpel |
| HE3202 | ADNP2 | 18 | 77895757 | C | A | A2403,A3201,B3801,B4101,C1203,C1701 | B3801 | 31 | 393 | Thldfitil | Phldfitil |
| HE3202 | ADNP2 | 18 | 77895757 | C | A | A2403,A3201,B3801,B4101,C1203,C1701 | C1203 | 195 | 36 | llfThldfi | llfPhldfi |
| HE3202 | ADNP2 | 18 | 77895757 | C | A | A2403,A3201,B3801,B4101,C1203,C1701 | C1203 | 28 | 27 | fThldfiti | fPhldfiti |
| HE3202 | ADNP2 | 18 | 77895757 | C | A | A2403,A3201,B3801,B4101,C1203,C1701 | C1203 | 282 | 1392 | Thldfitil | Phldfitil |
| HE3202 | AP3D1 | 19 | 2111328 | C | T | A2403,A3201,B3801,B4101,C1203,C1701 | C1203 | 414 | 558 | eqlppKssy | eqlppEssy |
| HE3202 | KEAP1 | 19 | 10610126 | C | A | A2403,A3201,B3801,B4101,C1203,C1701 | C1203 | 46 | 16210 | ianfaeqiV | ianfaeqiG |
| HE3202 | CD97 | 19 | 14515319 | G | T | A2403,A3201,B3801,B4101,C1203,C1701 | C1203 | 81 | 5913 | Fqcshlssf | Cqcshlssf |
| HE3202 | MAST3 | 19 | 18255471 | C | A | A2403,A3201,B3801,B4101,C1203,C1701 | A2403 | 6 | 9252 | aYvsalsli | aSvsalsli |
| HE3202 | MAST3 | 19 | 18255471 | C | A | A2403,A3201,B3801,B4101,C1203,C1701 | C1203 | 46 | 831 | saYvsalsl | saSvsalsl |
| HE3202 | MAST3 | 19 | 18255471 | C | A | A2403,A3201,B3801,B4101,C1203,C1701 | C1203 | 39 | 2056 | Yvsalslii | Svsalslii |
| HE3202 | PIK3R2 | 19 | 18266889 | G | A | A2403,A3201,B3801,B4101,C1203,C1701 | C1203 | 158 | 1023 | qQgdfpgty | qRgdfpgty |
| HE3202 | ZNF729 | 19 | 22497558 | C | A | A2403,A3201,B3801,B4101,C1203,C1701 | A3201 | 41 | 145 | kafnssstl | kafnssstL |

Figure 21 (Cont.)

| | | | | | | | | | | | |
|---|---|---|---|---|---|---|---|---|---|---|---|
| HE3202 | ZNF729 | 19 | 22497558 | C | A | A2403,A3201,B3801,B4101,C1203,C1701 | C1203 | 3 | 5 | kafnsssti | kafnssstL |
| HE3202 | ZNF728 | 19 | 23170197 | C | G | A2403,A3201,B3801,B4101,C1203,C1701 | C1203 | 19 | 12 | iaPpkpdli | iaApkpdli |
| HE3202 | DPY19L3 | 19 | 32902208 | G | C | A2403,A3201,B3801,B4101,C1203,C1701 | C1203 | 346 | 1377 | lSiglltsv | lCiglltsv |
| HE3202 | LSM14A | 19 | 34685466 | G | T | A2403,A3201,B3801,B4101,C1203,C1701 | C1203 | 124 | 96 | yiifrWsdi | yiifrGsdi |
| HE3202 | LSM14A | 19 | 34685467 | G | T | A2403,A3201,B3801,B4101,C1203,C1701 | C1203 | 76 | 96 | yiifrVsdi | yiifrGsdi |
| HE3202 | GRAMD1A | 19 | 35501077 | A | T | A2403,A3201,B3801,B4101,C1203,C1701 | A2403 | 58 | 75 | nwicfysli | nwicfysNi |
| HE3202 | GRAMD1A | 19 | 35501077 | A | T | A2403,A3201,B3801,B4101,C1203,C1701 | A2403 | 12 | 7 | cfyslifrw | cfysNifrw |
| HE3202 | GRAMD1A | 19 | 35501077 | A | T | A2403,A3201,B3801,B4101,C1203,C1701 | A3201 | 16 | 64 | iifrwetti | Nifrwetti |
| HE3202 | GRAMD1A | 19 | 35501077 | A | T | A2403,A3201,B3801,B4101,C1203,C1701 | C1203 | 13 | 13 | iifrwetti | Nifrwetti |
| HE3202 | NPHS1 | 19 | 36339994 | C | G | A2403,A3201,B3801,B4101,C1203,C1701 | C1203 | 44 | 30 | qavaPsvlv | qavaRsvlv |
| HE3202 | ZNF45 | 19 | 44417720 | C | A | A2403,A3201,B3801,B4101,C1203,C1701 | A3201 | 56 | 33 | kvfsLssyl | kvfsWssyl |
| HE3202 | ZNF45 | 19 | 44417720 | C | A | A2403,A3201,B3801,B4101,C1203,C1701 | C1203 | 269 | 66 | kvfsLssyl | kvfsWssyl |
| HE3202 | TSKS | 19 | 50266391 | C | A | A2403,A3201,B3801,B4101,C1203,C1701 | C1203 | 110 | 206 | lvpeaprSv | lvpeaprRv |
| HE3202 | POLD1 | 19 | 50919066 | G | A | A2403,A3201,B3801,B4101,C1203,C1701 | A2403 | 12 | 8 | Tymksedpl | Aymksedpl |
| HE3202 | POLD1 | 19 | 50919066 | G | A | A2403,A3201,B3801,B4101,C1203,C1701 | C1203 | 20 | 94 | saakgvaTy | saakgvaAy |
| HE3202 | ZNF534 | 19 | 52941209 | G | A | A2403,A3201,B3801,B4101,C1203,C1701 | A2403 | 54 | 76 | ifnnymNf | ifnnymDf |
| HE3202 | NLRP2 | 19 | 55501467 | G | T | A2403,A3201,B3801,B4101,C1203,C1701 | C1203 | 490 | 11886 | Fvnlsdnel | Cvnlsdnel |
| HE3202 | NLRP13 | 19 | 56416366 | C | T | A2403,A3201,B3801,B4101,C1203,C1701 | C1203 | 221 | 104 | lqddSikll | lqddGikll |
| HE3202 | ZFP28 | 19 | 57066694 | C | T | A2403,A3201,B3801,B4101,C1203,C1701 | A2403 | 456 | 800 | Ftsnpvdlf | Stsnpvdlf |
| HE3202 | ZFP28 | 19 | 57066694 | C | T | A2403,A3201,B3801,B4101,C1203,C1701 | C1203 | 44 | 2400 | Ftsnpvdlf | Stsnpvdlf |
| HE3202 | USP29 | 19 | 57640780 | A | G | A2403,A3201,B3801,B4101,C1203,C1701 | A3201 | 421 | 3682 | Rtlnakngl | Qtlnakngl |
| HE3202 | ZNF274 | 19 | 58724230 | A | G | A2403,A3201,B3801,B4101,C1203,C1701 | A2403 | 349 | 579 | rvhsgeGpf | rvhsgeRpf |
| HE3202 | ZNF274 | 19 | 58724230 | A | G | A2403,A3201,B3801,B4101,C1203,C1701 | A3201 | 150 | 38 | rvhsgeGpf | rvhsgeRpf |

Figure 21 (Cont.)

| | | | | | | | | | | | |
|---|---|---|---|---|---|---|---|---|---|---|---|
| HE3202 | NOL10 | 2 | 10811780 | G | A | A2403,A3201,B3801,B4101,C1203,C1701 | A2403 | 440 | 2090 | ryiefYsqs | ryiefHsqs |
| HE3202 | NOL10 | 2 | 10811780 | G | A | A2403,A3201,B3801,B4101,C1203,C1701 | A2403 | 59 | 13522 | fYsqsgfyy | fHsqsgfyy |
| HE3202 | MDH1 | 2 | 63831928 | G | T | A2403,A3201,B3801,B4101,C1203,C1701 | C1203 | 55 | 33 | ypdvnhaNv | ypdvnhaKv |
| HE3202 | ATP6V1B1 | 2 | 71190741 | C | T | A2403,A3201,B3801,B4101,C1203,C1701 | C1203 | 19 | 38 | fiiegqiyv | fiTegqiyv |
| HE3202 | EXOC6B | 2 | 72411292 | C | T | A2403,A3201,B3801,B4101,C1203,C1701 | A3201 | 139 | 875 | iqwNwstyl | iqwDwstyl |
| HE3202 | EXOC6B | 2 | 72411292 | C | T | A2403,A3201,B3801,B4101,C1203,C1701 | C1203 | 43 | 115 | fiqwNwsty | fiqwDwsty |
| HE3202 | EXOC6B | 2 | 72411292 | C | T | A2403,A3201,B3801,B4101,C1203,C1701 | C1203 | 188 | 85 | iqwNwstyl | iqwDwstyl |
| HE3202 | GLI2 | 2 | 121554948 | G | T | A2403,A3201,B3801,B4101,C1203,C1701 | A2403 | 32 | 16060 | sWileaagf | sGileaagf |
| HE3202 | MYO7B | 2 | 128381686 | G | A | A2403,A3201,B3801,B4101,C1203,C1701 | B3801 | 469 | 1430 | Rrdhmmdai | Grdhmmdai |
| HE3202 | POTEE | 2 | 132010557 | A | T | A2403,A3201,B3801,B4101,C1203,C1701 | B3801 | 420 | 799 | thvgfpeYl | thvgfpeNl |
| HE3202 | DARS | 2 | 136678081 | C | T | A2403,A3201,B3801,B4101,C1203,C1701 | A2403 | 4 | 4 | hyhKvmeei | hyhEvmeei |
| HE3202 | DARS | 2 | 136678081 | C | T | A2403,A3201,B3801,B4101,C1203,C1701 | C1203 | 449 | 809 | mafnyhyhK | mafnyhyhE |
| HE3202 | DARS | 2 | 136678081 | C | T | A2403,A3201,B3801,B4101,C1203,C1701 | C1203 | 45 | 49 | fnyhyhKvm | fnyhyhEvm |
| HE3202 | TNFAIP6 | 2 | 152222584 | G | A | A2403,A3201,B3801,B4101,C1203,C1701 | A2403 | 209 | 1274 | gfhvcTagw | gfhvcAagw |
| HE3202 | NEB | 2 | 152500514 | C | A | A2403,A3201,B3801,B4101,C1203,C1701 | A2403 | 23 | 46 | eykkYfekw | eykkDfekw |
| HE3202 | NEB | 2 | 152500514 | C | A | A2403,A3201,B3801,B4101,C1203,C1701 | A2403 | 84 | 10914 | Yfekwktkf | Dfekwktkf |
| HE3202 | GRB14 | 2 | 165358787 | C | A | A2403,A3201,B3801,B4101,C1203,C1701 | A3201 | 196 | 1588 | rsgcisqsi | rsgcSsqsi |
| HE3202 | SCN7A | 2 | 167313540 | A | T | A2403,A3201,B3801,B4101,C1203,C1701 | A2403 | 130 | 66 | iffvvEsfl | iffvvVsfl |
| HE3202 | SCN7A | 2 | 167313540 | A | T | A2403,A3201,B3801,B4101,C1203,C1701 | A2403 | 24 | 15 | ffvvEsflf | ffvvVsflf |
| HE3202 | SCN7A | 2 | 167313540 | A | T | A2403,A3201,B3801,B4101,C1203,C1701 | A3201 | 7 | 4 | miffvvEsf | miffvvVsf |
| HE3202 | SCN7A | 2 | 167313540 | A | T | A2403,A3201,B3801,B4101,C1203,C1701 | A3201 | 93 | 74 | vvEsflfsf | vvVsflfsf |
| HE3202 | SCN7A | 2 | 167313540 | A | T | A2403,A3201,B3801,B4101,C1203,C1701 | C1203 | 275 | 214 | miffvvEsf | miffvvVsf |

Figure 21 (Cont.)

| | | | | | | | | | | | |
|---|---|---|---|---|---|---|---|---|---|---|---|
| HE3202 | FASTKD1 | 2 | 170417062 | C | G | A2403,A3201,B3801,B4101,C1203,C1701 | C1203 | 336 | 283 | IdIdsiTki | IdIdsiSki |
| HE3202 | FASTKD1 | 2 | 170417062 | C | G | A2403,A3201,B3801,B4101,C1203,C1701 | C1203 | 462 | 228 | dsiTkilsv | dsiSkilsv |
| HE3202 | TTN | 2 | 179616107 | C | T | A2403,A3201,B3801,B4101,C1203,C1701 | A2403 | 243 | 155 | dymydKeyl | dymydEeyl |
| HE3202 | FN1 | 2 | 216237060 | G | C | A2403,A3201,B3801,B4101,C1203,C1701 | C1203 | 356 | 620 | hpnVhgpei | hpnLhgpei |
| HE3202 | VIL1 | 2 | 219299357 | G | T | A2403,A3201,B3801,B4101,C1203,C1701 | C1203 | 416 | 432 | fevparSnf | fevparAnf |
| HE3202 | SIRPB1 | 20 | 1592320 | T | A | A2403,A3201,B3801,B4101,C1203,C1701 | C1203 | 52 | 308 | qviqpVksi | qviqpDksi |
| HE3202 | CST2 | 20 | 23807183 | G | T | A2403,A3201,B3801,B4101,C1203,C1701 | C1203 | 292 | 228 | dadInderv | dadLnderv |
| HE3202 | RALGAPB | 20 | 37194116 | C | T | A2403,A3201,B3801,B4101,C1203,C1701 | A2403 | 168 | 21631 | fvvpspveF | fvvpspveS |
| HE3202 | RALGAPB | 20 | 37194116 | C | T | A2403,A3201,B3801,B4101,C1203,C1701 | C1203 | 54 | 3195 | fvvpspveF | fvvpspveS |
| HE3202 | PTPRT | 20 | 41306677 | G | A | A2403,A3201,B3801,B4101,C1203,C1701 | A2403 | 64 | 53 | eyCtttgtw | eyRtttgtw |
| HE3202 | L3MBTL1 | 20 | 42162985 | C | T | A2403,A3201,B3801,B4101,C1203,C1701 | C1203 | 10 | 484 | eavdrmpV | eavdrmpA |
| HE3202 | GDAP1L1 | 20 | 42887136 | C | T | A2403,A3201,B3801,B4101,C1203,C1701 | A2403 | 432 | 16568 | qharvlqyW | qharvlqyR |
| HE3202 | GDAP1L1 | 20 | 42887136 | C | T | A2403,A3201,B3801,B4101,C1203,C1701 | A2403 | 11 | 15 | qyWelldal | qyRelldal |
| HE3202 | PIGT | 20 | 44050034 | G | T | A2403,A3201,B3801,B4101,C1203,C1701 | C1203 | 179 | 212 | Lpflhaqry | Vpflhaqry |
| HE3202 | ZNF335 | 20 | 44578921 | T | G | A2403,A3201,B3801,B4101,C1203,C1701 | C1203 | 421 | 653 | pPqtptqti | pTqtptqti |
| HE3202 | CYP24A1 | 20 | 52773783 | C | G | A2403,A3201,B3801,B4101,C1203,C1701 | C1203 | 224 | 378 | Qmlhsgtlv | Emlhsgtlv |
| HE3202 | CASS4 | 20 | 55033503 | C | G | A2403,A3201,B3801,B4101,C1203,C1701 | A2403 | 64 | 8 | yfgalfkaM | yfgalfkal |
| HE3202 | CASS4 | 20 | 55033503 | C | G | A2403,A3201,B3801,B4101,C1203,C1701 | A3201 | 119 | 92 | alfkaMsaf | alfkalsaf |
| HE3202 | BMP7 | 20 | 55748344 | C | G | A2403,A3201,B3801,B4101,C1203,C1701 | C1203 | 39 | 29 | iapeAyaay | iapeGyaay |
| HE3202 | SON | 21 | 34923641 | A | G | A2403,A3201,B3801,B4101,C1203,C1701 | C1203 | 431 | 80 | lvgetsvAv | lvgetsvTv |
| HE3202 | C2CD2 | 21 | 43373717 | T | A | A2403,A3201,B3801,B4101,C1203,C1701 | A2403 | 15 | 11 | swlgeaLwl | swlgeaQwl |
| HE3202 | C2CD2 | 21 | 43373717 | T | A | A2403,A3201,B3801,B4101,C1203,C1701 | A2403 | 7 | 5 | Lwlalvslf | Qwlalvslf |
| HE3202 | C2CD2 | 21 | 43373717 | T | A | A2403,A3201,B3801,B4101,C1203,C1701 | A3201 | 82 | 148 | aLwlalvsl | aQwlalvsl |

Figure 21 (Cont.)

| | | | | | | | | | | | |
|---|---|---|---|---|---|---|---|---|---|---|---|
| HE3202 | UBASH3A | 21 | 43852239 | G | C | A2403,A3201,B3801,B4101,C1203,C1701 | C1203 | 40 | 19 | varksvlLv | varksvlVv |
| HE3202 | U2AF1 | 21 | 44524456 | G | A | A2403,A3201,B3801,B4101,C1203,C1701 | C1203 | 224 | 6649 | Frlhnkptf | Srlhnkptf |
| HE3202 | DIP2A | 21 | 47957410 | G | T | A2403,A3201,B3801,B4101,C1203,C1701 | C1203 | 10 | 8 | yalmkSnpl | yalmkAnpl |
| HE3202 | TRIM71 | 3 | 32933205 | G | T | A2403,A3201,B3801,B4101,C1203,C1701 | A2403 | 39 | 27 | kfgaqgsCf | kfgaqgsGf |
| HE3202 | PTH1R | 3 | 46935431 | A | T | A2403,A3201,B3801,B4101,C1203,C1701 | B3801 | 361 | 378 | tkeeLifll | tkeeQifll |
| HE3202 | PTH1R | 3 | 46935431 | A | T | A2403,A3201,B3801,B4101,C1203,C1701 | C1203 | 308 | 851 | mtkeeLifl | mtkeeQifl |
| HE3202 | PRKAR2A | 3 | 48884842 | G | T | A2403,A3201,B3801,B4101,C1203,C1701 | C1203 | 200 | 1226 | Qpepgpdrv | Ppepgpdrv |
| HE3202 | USP4 | 3 | 49316276 | C | A | A2403,A3201,B3801,B4101,C1203,C1701 | A2403 | 26 | 693 | wyyfddsnL | wyyfddsnV |
| HE3202 | USP4 | 3 | 49316276 | C | A | A2403,A3201,B3801,B4101,C1203,C1701 | C1203 | 197 | 113 | yfddsnLsl | yfddsnVsl |
| HE3202 | SPCS1 | 3 | 52740182 | C | G | A2403,A3201,B3801,B4101,C1203,C1701 | C1203 | 357 | 245 | daqcqtlAl | daqcqtlPl |
| HE3202 | ITIH1 | 3 | 52817103 | C | T | A2403,A3201,B3801,B4101,C1203,C1701 | C1203 | 78 | 5141 | qaseanlqV | qaseanlqA |
| HE3202 | ITIH1 | 3 | 52817103 | C | T | A2403,A3201,B3801,B4101,C1203,C1701 | C1203 | 160 | 834 | Vaqdfvrgf | Aaqdfvrgf |
| HE3202 | IL17RD | 3 | 57136567 | G | T | A2403,A3201,B3801,B4101,C1203,C1701 | A3201 | 292 | 68 | ravaitvpM | ravaitvpL |
| HE3202 | IL17RD | 3 | 57136567 | G | T | A2403,A3201,B3801,B4101,C1203,C1701 | C1203 | 56 | 65 | ravaitvpM | ravaitvpL |
| HE3202 | IL17RD | 3 | 57136567 | G | T | A2403,A3201,B3801,B4101,C1203,C1701 | C1203 | 39 | 32 | vaitvpMvv | vaitvpLvv |
| HE3202 | ZNF654 | 3 | 88188515 | C | T | A2403,A3201,B3801,B4101,C1203,C1701 | C1203 | 66 | 836 | qaYqkkgsf | qaHqkkgsf |
| HE3202 | EPHA6 | 3 | 97202843 | C | A | A2403,A3201,B3801,B4101,C1203,C1701 | C1203 | 162 | 178 | avNefakei | avHefakei |
| HE3202 | GPR128 | 3 | 100368550 | G | T | A2403,A3201,B3801,B4101,C1203,C1701 | A3201 | 179 | 268 | mtfkNdyqy | mtfkKdyqy |
| HE3202 | GPR128 | 3 | 100368550 | G | T | A2403,A3201,B3801,B4101,C1203,C1701 | C1203 | 452 | 1047 | mtfkNdyqy | mtfkKdyqy |
| HE3202 | KALRN | 3 | 124418854 | C | T | A2403,A3201,B3801,B4101,C1203,C1701 | A2403 | 110 | 162 | slpsepLef | slpsepSef |
| HE3202 | KALRN | 3 | 124418854 | C | T | A2403,A3201,B3801,B4101,C1203,C1701 | C1203 | 66 | 80 | lpsepLefv | lpsepSefv |
| HE3202 | PLXNA1 | 3 | 126741099 | G | C | A2403,A3201,B3801,B4101,C1203,C1701 | C1203 | 341 | 29 | yPtgvlkql | yAtgvlkql |

Figure 21 (Cont.)

| | | | | | | | | | | | |
|---|---|---|---|---|---|---|---|---|---|---|---|
| HE3202 | CLSTN2 | 3 | 140167415 | C | A | A2403,A3201,B3801,B4101,C1203,C1701 | A2403 | 280 | 512 | gsmplfHsi | gsmplfPsi |
| HE3202 | CLSTN2 | 3 | 140167415 | C | A | A2403,A3201,B3801,B4101,C1203,C1701 | A3201 | 253 | 789 | gsmplfHsi | gsmplfPsi |
| HE3202 | CLSTN2 | 3 | 140167415 | C | A | A2403,A3201,B3801,B4101,C1203,C1701 | C1203 | 402 | 718 | gsmplfHsi | gsmplfPsi |
| HE3202 | CLSTN2 | 3 | 140167415 | C | A | A2403,A3201,B3801,B4101,C1203,C1701 | C1203 | 183 | 212 | mplfHsihl | mplfPsihl |
| HE3202 | BCHE | 3 | 165547444 | C | T | A2403,A3201,B3801,B4101,C1203,C1701 | A2403 | 382 | 3367 | Kwmgvmhgy | Ewmgvmhgy |
| HE3202 | SAMD7 | 3 | 169639052 | T | A | A2403,A3201,B3801,B4101,C1203,C1701 | C1203 | 108 | 106 | Dpsqfgssv | Vpsqfgssv |
| HE3202 | AP2M1 | 3 | 183898769 | C | G | A2403,A3201,B3801,B4101,C1203,C1701 | C1203 | 191 | 249 | lmspEgqvl | lmspQgqvl |
| HE3202 | DGKG | 3 | 186015981 | G | T | A2403,A3201,B3801,B4101,C1203,C1701 | A2403 | 196 | 106 | lfmrEylev | lfmrAylev |
| HE3202 | MFSD7 | 4 | 679985 | C | A | A2403,A3201,B3801,B4101,C1203,C1701 | A2403 | 185 | 143 | aflmggqll | aflmggqSl |
| HE3202 | MFSD7 | 4 | 679985 | C | A | A2403,A3201,B3801,B4101,C1203,C1701 | C1203 | 8 | 1046 | faflmggql | faflmggqS |
| HE3202 | SLC26A1 | 4 | 983388 | C | T | A2403,A3201,B3801,B4101,C1203,C1701 | C1203 | 136 | 118 | svlacviMv | svlacviVv |
| HE3202 | SLC26A1 | 4 | 983388 | C | T | A2403,A3201,B3801,B4101,C1203,C1701 | C1203 | 117 | 80 | lacviMvsl | lacviVvsl |
| HE3202 | TLR6 | 4 | 38829068 | C | G | A2403,A3201,B3801,B4101,C1203,C1701 | C1203 | 246 | 380 | iclheTnfv | iclheRnfv |
| HE3202 | TLR6 | 4 | 38829068 | C | G | A2403,A3201,B3801,B4101,C1203,C1701 | C1203 | 311 | 146 | Tnfvpgksi | Rnfvpgksi |
| HE3202 | YIPF7 | 4 | 44638038 | C | A | A2403,A3201,B3801,B4101,C1203,C1701 | A2403 | 316 | 2314 | Cyagqffqp | Gyagqffqp |
| HE3202 | COX7B2 | 4 | 46737056 | C | A | A2403,A3201,B3801,B4101,C1203,C1701 | A2403 | 9 | 6 | afcvStwvf | afcvAtwvf |
| HE3202 | COX7B2 | 4 | 46737056 | C | A | A2403,A3201,B3801,B4101,C1203,C1701 | A3201 | 312 | 371 | Stwvftatq | Atwvftatq |
| HE3202 | COX7B2 | 4 | 46737056 | C | A | A2403,A3201,B3801,B4101,C1203,C1701 | C1203 | 164 | 119 | tafcvStwv | tafcvAtwv |
| HE3202 | SPATA18 | 4 | 52938279 | G | A | A2403,A3201,B3801,B4101,C1203,C1701 | C1203 | 244 | 320 | nlkeKiavl | nlkeEiavl |
| HE3202 | UGT2B17 | 4 | 69434100 | G | A | A2403,A3201,B3801,B4101,C1203,C1701 | A2403 | 6 | 16 | vwpteysYw | vwpteysHw |
| HE3202 | UGT2B17 | 4 | 69434100 | G | A | A2403,A3201,B3801,B4101,C1203,C1701 | A2403 | 11 | 6449 | sYwinmkti | sHwinmkti |
| HE3202 | UGT2B17 | 4 | 69434100 | G | A | A2403,A3201,B3801,B4101,C1203,C1701 | A2403 | 52 | 373 | Ywinmktil | Hwinmktil |
| HE3202 | UGT2B17 | 4 | 69434100 | G | A | A2403,A3201,B3801,B4101,C1203,C1701 | A3201 | 293 | 7865 | lvwpteysY | lvwpteysH |

Figure 21 (Cont.)

| | | | | | | | | | | | |
|---|---|---|---|---|---|---|---|---|---|---|---|
| HE3202 | UGT2B17 | 4 | 69434100 | G | A | A2403,A3201,B3801,B4101,C1203,C1701 | C1203 | 459 | 6732 | ysYwinmkt | ysHwinmkt |
| HE3202 | UGT2A3 | 4 | 69796271 | C | A | A2403,A3201,B3801,B4101,C1203,C1701 | A3201 | 432 | 13883 | ralrtvitY | ralrtvitD |
| HE3202 | UGT2A3 | 4 | 69796271 | C | A | A2403,A3201,B3801,B4101,C1203,C1701 | C1203 | 14 | 4140 | ralrtvitY | ralrtvitD |
| HE3202 | UGT2A3 | 4 | 69796271 | C | A | A2403,A3201,B3801,B4101,C1203,C1701 | C1203 | 245 | 5948 | Yssykenam | Dssykenam |
| HE3202 | GRID2 | 4 | 94343958 | G | C | A2403,A3201,B3801,B4101,C1203,C1701 | C1203 | 445 | 728 | nvlRkpkky | nvlGkpkky |
| HE3202 | SLC9B1 | 4 | 103826692 | C | A | A2403,A3201,B3801,B4101,C1203,C1701 | A2403 | 69 | 74 | Cmpkatvqi | Wmpkatvqi |
| HE3202 | SLC9B1 | 4 | 103826692 | C | A | A2403,A3201,B3801,B4101,C1203,C1701 | C1203 | 15 | 14 | laCmpkatv | laWmpkatv |
| HE3202 | CENPE | 4 | 104062009 | C | A | A2403,A3201,B3801,B4101,C1203,C1701 | B3801 | 348 | 135 | erYqlkesl | erDqlkesl |
| HE3202 | TACR3 | 4 | 104577358 | T | C | A2403,A3201,B3801,B4101,C1203,C1701 | C1203 | 488 | 991 | qlkaRrkvv | qlkaKrkvv |
| HE3202 | TACR3 | 4 | 104577358 | T | C | A2403,A3201,B3801,B4101,C1203,C1701 | C1203 | 42 | 51 | kaRrkvvkm | kaKrkvvkm |
| HE3202 | AIMP1 | 4 | 107246239 | C | G | A2403,A3201,B3801,B4101,C1203,C1701 | A2403 | 159 | 30 | eyVkqqvsl | eyLkqqvsl |
| HE3202 | AIMP1 | 4 | 107246239 | C | G | A2403,A3201,B3801,B4101,C1203,C1701 | C1203 | 47 | 162 | eadqiieyV | eadqiieyL |
| HE3202 | AIMP1 | 4 | 107246239 | C | G | A2403,A3201,B3801,B4101,C1203,C1701 | C1203 | 65 | 169 | yVkqqvsll | yLkqqvsll |
| HE3202 | NDST4 | 4 | 115997651 | G | C | A2403,A3201,B3801,B4101,C1203,C1701 | C1203 | 321 | 57 | fRlnlfnnl | fPlnlfnnl |
| HE3202 | NDST4 | 4 | 115997984 | G | T | A2403,A3201,B3801,B4101,C1203,C1701 | C1203 | 141 | 213 | melktvkHi | melktvkPi |
| HE3202 | NDST4 | 4 | 115998158 | C | A | A2403,A3201,B3801,B4101,C1203,C1701 | A2403 | 30 | 242 | sfLtlivll | sfRtlivll |
| HE3202 | NDST4 | 4 | 115998158 | C | A | A2403,A3201,B3801,B4101,C1203,C1701 | A3201 | 414 | 1156 | klrrsfLtl | klrrsfRtl |
| HE3202 | NDST4 | 4 | 115998158 | C | A | A2403,A3201,B3801,B4101,C1203,C1701 | A3201 | 89 | 52 | rsfLtlivl | rsfRtlivl |
| HE3202 | BBS7 | 4 | 122765084 | C | T | A2403,A3201,B3801,B4101,C1203,C1701 | B3801 | 105 | 380 | sKsndnfll | sEsndnfll |
| HE3202 | TRPC3 | 4 | 122828520 | C | A | A2403,A3201,B3801,B4101,C1203,C1701 | A2403 | 7 | 7 | ffafligmf | ffafMigmf |
| HE3202 | TRPC3 | 4 | 122828520 | C | A | A2403,A3201,B3801,B4101,C1203,C1701 | A2403 | 237 | 84 | afligmfll | afMigmfll |
| HE3202 | TRPC3 | 4 | 122828520 | C | A | A2403,A3201,B3801,B4101,C1203,C1701 | A3201 | 92 | 98 | imvffafli | imvffafMi |

Figure 21 (Cont.)

| | | | | | | | | | | | |
|---|---|---|---|---|---|---|---|---|---|---|---|
| HE3202 | TRPC3 | 4 | 122828520 | C | A | A2403,A3201,B3801,B4101,C1203,C1701 | C1203 | 17 | 41 | fimvffafl | fimvffafM |
| HE3202 | TRPC3 | 4 | 122828520 | C | A | A2403,A3201,B3801,B4101,C1203,C1701 | C1203 | 421 | 402 | imvffafli | imvffafMi |
| HE3202 | TRPC3 | 4 | 122828520 | C | A | A2403,A3201,B3801,B4101,C1203,C1701 | C1203 | 6 | 5 | fafligmfi | fafMigmfi |
| HE3202 | TRPC3 | 4 | 122828520 | C | A | A2403,A3201,B3801,B4101,C1203,C1701 | C1203 | 240 | 97 | fligmfily | fMigmfily |
| HE3202 | KIAA1109 | 4 | 123188029 | C | T | A2403,A3201,B3801,B4101,C1203,C1701 | A2403 | 4 | 4 | myfgehlLf | myfgehlSf |
| HE3202 | KIAA1109 | 4 | 123188029 | C | T | A2403,A3201,B3801,B4101,C1203,C1701 | A3201 | 54 | 10117 | rmyfgehlL | rmyfgehlS |
| HE3202 | KIAA1109 | 4 | 123188029 | C | T | A2403,A3201,B3801,B4101,C1203,C1701 | B3801 | 368 | 176 | ehlLfsgtl | ehlSfsgtl |
| HE3202 | KIAA1109 | 4 | 123188029 | C | T | A2403,A3201,B3801,B4101,C1203,C1701 | C1203 | 260 | 11059 | rmyfgehlL | rmyfgehlS |
| HE3202 | DDX60 | 4 | 169205994 | T | A | A2403,A3201,B3801,B4101,C1203,C1701 | A2403 | 262 | 897 | dyVrsrcqf | dyDrsrcqf |
| HE3202 | SH3RF1 | 4 | 170190248 | C | T | A2403,A3201,B3801,B4101,C1203,C1701 | C1203 | 86 | 420 | fckrcllEi | fckrcllGi |
| HE3202 | WDR17 | 4 | 177056323 | C | T | A2403,A3201,B3801,B4101,C1203,C1701 | C1203 | 12 | 35 | Vsfdgtikv | Asfdgtikv |
| HE3202 | TERT | 5 | 1279563 | A | G | A2403,A3201,B3801,B4101,C1203,C1701 | C1203 | 101 | 1160 | rAkalfsvl | rVkalfsvl |
| HE3202 | ADAMTS16 | 5 | 5187892 | G | A | A2403,A3201,B3801,B4101,C1203,C1701 | C1203 | 160 | 73 | iaiIglill | iaiVglill |
| HE3202 | DNAH5 | 5 | 13708315 | C | T | A2403,A3201,B3801,B4101,C1203,C1701 | A3201 | 217 | 1478 | klaiNgtii | klaiDgtii |
| HE3202 | DNAH5 | 5 | 13708315 | C | T | A2403,A3201,B3801,B4101,C1203,C1701 | C1203 | 14 | 9 | laiNgtiim | laiDgtiim |
| HE3202 | C6 | 5 | 41149516 | T | G | A2403,A3201,B3801,B4101,C1203,C1701 | A2403 | 5 | 6 | yftspacTf | yftspacKf |
| HE3202 | C6 | 5 | 41149516 | T | G | A2403,A3201,B3801,B4101,C1203,C1701 | C1203 | 239 | 1168 | yftspacTf | yftspacKf |
| HE3202 | C6 | 5 | 41149516 | T | G | A2403,A3201,B3801,B4101,C1203,C1701 | C1203 | 54 | 47 | ftspacTfl | ftspacKfl |
| HE3202 | ADAMTS6 | 5 | 64521984 | C | A | A2403,A3201,B3801,B4101,C1203,C1701 | C1203 | 65 | 49 | fyterSpav | fyterApav |
| HE3202 | ADAMTS6 | 5 | 64521984 | C | A | A2403,A3201,B3801,B4101,C1203,C1701 | C1203 | 14 | 13 | yterSpavi | yterApavi |
| HE3202 | MAP1B | 5 | 71495226 | C | A | A2403,A3201,B3801,B4101,C1203,C1701 | C1203 | 424 | 1141 | Nsfpesegy | Tsfpesegy |
| HE3202 | YTHDC2 | 5 | 112899815 | T | A | A2403,A3201,B3801,B4101,C1203,C1701 | A3201 | 294 | 194 | alHrafqaw | alLrafqaw |
| HE3202 | HSPA4 | 5 | 132432907 | G | T | A2403,A3201,B3801,B4101,C1203,C1701 | C1203 | 99 | 91 | daknSveey | daknAveey |

Figure 21 (Cont.)

| | | | | | | | | | | | |
|---|---|---|---|---|---|---|---|---|---|---|---|
| HE3202 | PCDHGB3 | 5 | 140751565 | G | A | A2403,A3201,B3801,B4101,C1203,C1701 | B3801 | 84 | 570 | aHdqgsptl | aRdqgsptl |
| HE3202 | PCDHGB3 | 5 | 140751565 | G | A | A2403,A3201,B3801,B4101,C1203,C1701 | C1203 | 383 | 580 | qaHdqgspt | qaRdqgspt |
| HE3202 | NDST1 | 5 | 149900856 | G | C | A2403,A3201,B3801,B4101,C1203,C1701 | A2403 | 384 | 151 | hLspqavlf | hVspqavlf |
| HE3202 | NMUR2 | 5 | 151784173 | C | A | A2403,A3201,B3801,B4101,C1203,C1701 | A2403 | 213 | 119 | rilCivwgf | rilGivwgf |
| HE3202 | NMUR2 | 5 | 151784173 | C | A | A2403,A3201,B3801,B4101,C1203,C1701 | A3201 | 11 | 5 | rilCivwgf | rilGivwgf |
| HE3202 | NMUR2 | 5 | 151784173 | C | A | A2403,A3201,B3801,B4101,C1203,C1701 | C1203 | 21 | 18 | ralrilCiv | ralrilGiv |
| HE3202 | MAT2B | 5 | 162940662 | A | T | A2403,A3201,B3801,B4101,C1203,C1701 | C1203 | 275 | 4365 | Fakeaaavg | Lakeaaavg |
| HE3202 | OR5V1 | 6 | 29323257 | G | A | A2403,A3201,B3801,B4101,C1203,C1701 | A2403 | 419 | 689 | afFtcashl | afStcashl |
| HE3202 | OR5V1 | 6 | 29323257 | G | A | A2403,A3201,B3801,B4101,C1203,C1701 | C1203 | 91 | 3391 | Ftcashlai | Stcashlai |
| HE3202 | SRPK1 | 6 | 35836878 | G | A | A2403,A3201,B3801,B4101,C1203,C1701 | A3201 | 238 | 3990 | ksMagnflv | ksTagnflv |
| HE3202 | NFKBIE | 6 | 44233281 | C | T | A2403,A3201,B3801,B4101,C1203,C1701 | A3201 | 92 | 169 | rlptvtTgw | rlptvtAgw |
| HE3202 | BAI3 | 6 | 70049281 | C | T | A2403,A3201,B3801,B4101,C1203,C1701 | A2403 | 191 | 18969 | pllaltwmF | pllaltwmS |
| HE3202 | BAI3 | 6 | 70049281 | C | T | A2403,A3201,B3801,B4101,C1203,C1701 | A3201 | 247 | 22286 | pllaltwmF | pllaltwmS |
| HE3202 | BAI3 | 6 | 70049281 | C | T | A2403,A3201,B3801,B4101,C1203,C1701 | C1203 | 67 | 19 | laltwmFav | laltwmSav |
| HE3202 | KHDC3L | 6 | 74072827 | G | T | A2403,A3201,B3801,B4101,C1203,C1701 | C1203 | 291 | 818 | rgVeriphv | rgGeriphv |
| HE3202 | MYO6 | 6 | 76550358 | A | T | A2403,A3201,B3801,B4101,C1203,C1701 | C1203 | 97 | 125 | nsCrfgkfv | nsSrfgkfv |
| HE3202 | MRAP2 | 6 | 84772677 | A | G | A2403,A3201,B3801,B4101,C1203,C1701 | A2403 | 107 | 41 | ifmffvlAl | ifmffvlTl |
| HE3202 | MRAP2 | 6 | 84772677 | A | G | A2403,A3201,B3801,B4101,C1203,C1701 | C1203 | 37 | 36 | fmffvlAll | fmffvlTll |
| HE3202 | MYCT1 | 6 | 153042915 | G | T | A2403,A3201,B3801,B4101,C1203,C1701 | A2403 | 62 | 17415 | iWlvlggfi | iGlvlggfi |
| HE3202 | MYCT1 | 6 | 153042915 | G | T | A2403,A3201,B3801,B4101,C1203,C1701 | C1203 | 362 | 318 | vsmaiWlvl | vsmaiGlvl |
| HE3202 | FRMD1 | 6 | 168457910 | G | T | A2403,A3201,B3801,B4101,C1203,C1701 | C1203 | 386 | 1675 | lshNfhral | lshTfhral |
| HE3202 | SDK1 | 7 | 4091415 | G | T | A2403,A3201,B3801,B4101,C1203,C1701 | A3201 | 109 | 2588 | svlcfttpV | svlcfttpG |

Figure 21 (Cont.)

| | | | | | | | | | | | |
|---|---|---|---|---|---|---|---|---|---|---|---|
| HE3202 | SDK1 | 7 | 4091415 | G | T | A2403,A3201,B3801,B4101,C1203,C1701 | C1203 | 117 | 20055 | svlcfttpV | svlcfttpG |
| HE3202 | FBXL18 | 7 | 5545069 | T | A | A2403,A3201,B3801,B4101,C1203,C1701 | A3201 | 88 | 62 | kslihSvll | kslihTvll |
| HE3202 | THSD7A | 7 | 11676273 | G | A | A2403,A3201,B3801,B4101,C1203,C1701 | C1203 | 282 | 10268 | iqkdkdipV | iqkdkdipA |
| HE3202 | DNAH11 | 7 | 21603848 | A | T | A2403,A3201,B3801,B4101,C1203,C1701 | C1203 | 17 | 19 | ylrplWrhi | ylrplRrhi |
| HE3202 | DNAH11 | 7 | 21657374 | C | A | A2403,A3201,B3801,B4101,C1203,C1701 | A2403 | 39 | 39 | hwQqlmkai | hwHqlmkai |
| HE3202 | DNAH11 | 7 | 21657375 | C | G | A2403,A3201,B3801,B4101,C1203,C1701 | A2403 | 95 | 39 | hwhElmkai | hwhQlmkai |
| HE3202 | OSBPL3 | 7 | 24874137 | C | A | A2403,A3201,B3801,B4101,C1203,C1701 | A3201 | 89 | 777 | kSaqipspl | kAaqipspl |
| HE3202 | OSBPL3 | 7 | 24874138 | C | A | A2403,A3201,B3801,B4101,C1203,C1701 | C1203 | 311 | 676 | elldNaaqi | elldKaaqi |
| HE3202 | OSBPL3 | 7 | 24874138 | C | A | A2403,A3201,B3801,B4101,C1203,C1701 | C1203 | 64 | 76 | Naaqipspl | Kaaqipspl |
| HE3202 | LSM5 | 7 | 32527311 | T | A | A2403,A3201,B3801,B4101,C1203,C1701 | A3201 | 174 | 1465 | qillngYni | qillngNni |
| HE3202 | LSM5 | 7 | 32527311 | T | A | A2403,A3201,B3801,B4101,C1203,C1701 | C1203 | 122 | 2148 | ngYnitmlv | ngNnitmlv |
| HE3202 | HECW1 | 7 | 43400557 | C | G | A2403,A3201,B3801,B4101,C1203,C1701 | A3201 | 40 | 1861 | Rvknsaapi | Tvknsaapi |
| HE3202 | HECW1 | 7 | 43400557 | C | G | A2403,A3201,B3801,B4101,C1203,C1701 | C1203 | 88 | 16 | rattpsvRv | rattpsvTv |
| HE3202 | HECW1 | 7 | 43400557 | C | G | A2403,A3201,B3801,B4101,C1203,C1701 | C1203 | 127 | 295 | Rvknsaapi | Tvknsaapi |
| HE3202 | IGFBP1 | 7 | 45928465 | G | A | A2403,A3201,B3801,B4101,C1203,C1701 | C1203 | 341 | 1629 | lplgaacSv | lplgaacGv |
| HE3202 | VSTM2A | 7 | 54617773 | A | T | A2403,A3201,B3801,B4101,C1203,C1701 | C1203 | 431 | 272 | vsaaipCsi | vsaaipSsi |
| HE3202 | CCL24 | 7 | 75441156 | C | A | A2403,A3201,B3801,B4101,C1203,C1701 | C1203 | 121 | 151 | ravavNgpv | ravavKgpv |
| HE3202 | MDH2 | 7 | 75677504 | C | T | A2403,A3201,B3801,B4101,C1203,C1701 | A3201 | 489 | 219 | Vsaalrrsf | Asaalrrsf |
| HE3202 | MDH2 | 7 | 75677504 | C | T | A2403,A3201,B3801,B4101,C1203,C1701 | C1203 | 42 | 35 | larpVsaal | larpAsaal |
| HE3202 | SEMA3D | 7 | 84636246 | C | T | A2403,A3201,B3801,B4101,C1203,C1701 | A3201 | 337 | 12424 | Ktadekvif | Etadekvif |
| HE3202 | SLC25A40 | 7 | 87477254 | C | A | A2403,A3201,B3801,B4101,C1203,C1701 | A2403 | 6 | 6 | iyftFydql | iyftCydql |
| HE3202 | SLC25A40 | 7 | 87477254 | C | A | A2403,A3201,B3801,B4101,C1203,C1701 | A2403 | 304 | 16920 | tFydqlsal | tCydqlsal |
| HE3202 | SLC25A40 | 7 | 87477254 | C | A | A2403,A3201,B3801,B4101,C1203,C1701 | A2403 | 21 | 15 | Fydqlsall | Cydqlsall |

Figure 21 (Cont.)

| | | | | | | | | | | | |
|---|---|---|---|---|---|---|---|---|---|---|---|
| HE3202 | SLC25A40 | 7 | 87477254 | C | A | A2403,A3201,B3801,B4101,C1203,C1701 | C1203 | 338 | 195 | tFydqlsal | tCydqlsal |
| HE3202 | TECPR1 | 7 | 97872785 | C | A | A2403,A3201,B3801,B4101,C1203,C1701 | C1203 | 133 | 182 | wavslHgkv | wavslQgkv |
| HE3202 | NPTX2 | 7 | 98254267 | A | G | A2403,A3201,B3801,B4101,C1203,C1701 | C1203 | 410 | 250 | fkspdafRv | fkspdafKv |
| HE3202 | NPTX2 | 7 | 98254267 | A | G | A2403,A3201,B3801,B4101,C1203,C1701 | C1203 | 36 | 44 | dafRvslpl | dafKvslpl |
| HE3202 | TRRAP | 7 | 98528379 | C | G | A2403,A3201,B3801,B4101,C1203,C1701 | A3201 | 149 | 446 | lmerlpVtw | lmerlpLtw |
| HE3202 | TRRAP | 7 | 98528379 | C | G | A2403,A3201,B3801,B4101,C1203,C1701 | B3801 | 482 | 439 | erlpVtwvl | erlpLtwvl |
| HE3202 | TRRAP | 7 | 98528379 | C | G | A2403,A3201,B3801,B4101,C1203,C1701 | C1203 | 252 | 581 | flmerlpVt | flmerlpLt |
| HE3202 | PLOD3 | 7 | 100856465 | C | G | A2403,A3201,B3801,B4101,C1203,C1701 | A2403 | 184 | 2238 | kfHmrvri | kfDmrvri |
| HE3202 | LRRN3 | 7 | 110763362 | G | A | A2403,A3201,B3801,B4101,C1203,C1701 | A3201 | 246 | 134 | rlqlinskw | rlqMinskw |
| HE3202 | LRRN3 | 7 | 110763362 | G | A | A2403,A3201,B3801,B4101,C1203,C1701 | C1203 | 381 | 366 | lnsnrlqli | lnsnrlqMi |
| HE3202 | SMO | 7 | 128845131 | G | T | A2403,A3201,B3801,B4101,C1203,C1701 | C1203 | 127 | 692 | npkswyeYv | npkswyeDv |
| HE3202 | SMO | 7 | 128845131 | G | T | A2403,A3201,B3801,B4101,C1203,C1701 | C1203 | 85 | 1389 | yeYvegcgi | yeDvegcgi |
| HE3202 | LONRF1 | 8 | 12586418 | C | G | A2403,A3201,B3801,B4101,C1203,C1701 | C1203 | 338 | 413 | ieyleHvkv | ieyleDvkv |
| HE3202 | SCARA5 | 8 | 27779276 | G | A | A2403,A3201,B3801,B4101,C1203,C1701 | A2403 | 245 | 6665 | sydvalhrM | sydvalhrT |
| HE3202 | DUSP4 | 8 | 29195901 | G | T | A2403,A3201,B3801,B4101,C1203,C1701 | C1203 | 55 | 62 | vssdcTnhf | vssdcPnhf |
| HE3202 | PXDNL | 8 | 52321060 | C | T | A2403,A3201,B3801,B4101,C1203,C1701 | C1203 | 108 | 145 | npnvnTgii | npnvnAgii |
| HE3202 | CHD7 | 8 | 61712990 | A | T | A2403,A3201,B3801,B4101,C1203,C1701 | C1203 | 291 | 20014 | qvkrkrytV | qvkrkrytE |
| HE3202 | CHD7 | 8 | 61712990 | A | T | A2403,A3201,B3801,B4101,C1203,C1701 | C1203 | 57 | 80 | ytVdlefki | ytEdlefki |
| HE3202 | PPP1R42 | 8 | 67922950 | C | A | A2403,A3201,B3801,B4101,C1203,C1701 | B3801 | 418 | 357 | lhvNdlefl | lhvKdlefl |
| HE3202 | ZFHX4 | 8 | 77775792 | C | A | A2403,A3201,B3801,B4101,C1203,C1701 | C1203 | 106 | 25 | ftpqlpgKv | ftpqlpgTv |
| HE3202 | FABP4 | 8 | 82395348 | C | A | A2403,A3201,B3801,B4101,C1203,C1701 | C1203 | 216 | 2349 | vssenfdYy | vssenfdDy |
| HE3202 | RALYL | 8 | 85774568 | C | G | A2403,A3201,B3801,B4101,C1203,C1701 | C1203 | 157 | 92 | rvppppGav | rvppppRav |

Figure 21 (Cont.)

| | | | | | | | | | | | |
|---|---|---|---|---|---|---|---|---|---|---|---|
| HE3202 | RALYL | 8 | 85774568 | C | G | A2403,A3201,B3801,B4101,C1203,C1701 | C1203 | 40 | 46 | vppppGavi | vppppRavi |
| HE3202 | MMP16 | 8 | 89209450 | A | C | A2403,A3201,B3801,B4101,C1203,C1701 | A2403 | 401 | 46 | saRaamqqf | saLaamqqf |
| HE3202 | MATN2 | 8 | 99045870 | G | A | A2403,A3201,B3801,B4101,C1203,C1701 | C1203 | 13 | 14 | laneevKkl | laneevRkl |
| HE3202 | C8orf47 | 8 | 99101951 | T | C | A2403,A3201,B3801,B4101,C1203,C1701 | C1203 | 205 | 215 | eilegsqLv | eilegsqFv |
| HE3202 | CSMD3 | 8 | 113249419 | C | A | A2403,A3201,B3801,B4101,C1203,C1701 | A3201 | 483 | 23386 | snmelllsW | snmelllsG |
| HE3202 | TRPS1 | 8 | 116426736 | C | A | A2403,A3201,B3801,B4101,C1203,C1701 | A2403 | 12 | 3245 | fwskyklsF | fwskyklsV |
| HE3202 | TRPS1 | 8 | 116426736 | C | A | A2403,A3201,B3801,B4101,C1203,C1701 | A2403 | 8 | 235 | sFpgnphyl | sVpgnphyl |
| HE3202 | TRPS1 | 8 | 116426736 | C | A | A2403,A3201,B3801,B4101,C1203,C1701 | C1203 | 26 | 257 | lsFpgnphy | lsVpgnphy |
| HE3202 | SAMD12 | 8 | 119452186 | C | A | A2403,A3201,B3801,B4101,C1203,C1701 | C1203 | 379 | 173 | taksatvNl | taksatvKl |
| HE3202 | MTBP | 8 | 121500555 | C | T | A2403,A3201,B3801,B4101,C1203,C1701 | A3201 | 193 | 95 | kleeaklsf | kTeeaklsf |
| HE3202 | FAM135B | 8 | 139189631 | C | T | A2403,A3201,B3801,B4101,C1203,C1701 | A2403 | 5 | 20 | rfseaffyl | rfseaffyM |
| HE3202 | FAM135B | 8 | 139189631 | C | T | A2403,A3201,B3801,B4101,C1203,C1701 | A2403 | 126 | 97 | ffylehqkl | ffyMehqkl |
| HE3202 | FAM135B | 8 | 139189631 | C | T | A2403,A3201,B3801,B4101,C1203,C1701 | C1203 | 296 | 153 | ffylehqkl | ffyMehqkl |
| HE3202 | FAM135B | 8 | 139189631 | C | T | A2403,A3201,B3801,B4101,C1203,C1701 | C1203 | 226 | 111 | ylehqklav | yMehqklav |
| HE3202 | DENND3 | 8 | 142185347 | G | T | A2403,A3201,B3801,B4101,C1203,C1701 | A2403 | 44 | 505 | tfkdfynFw | tfkdfynCw |
| HE3202 | DENND3 | 8 | 142185347 | G | T | A2403,A3201,B3801,B4101,C1203,C1701 | A3201 | 142 | 17850 | etfkdfynF | etfkdfynC |
| HE3202 | GLI4 | 8 | 144356879 | C | G | A2403,A3201,B3801,B4101,C1203,C1701 | C1203 | 405 | 2322 | sAgsspkvl | sPgsspkvl |
| HE3202 | FAM83H | 8 | 144812314 | C | A | A2403,A3201,B3801,B4101,C1203,C1701 | A3201 | 226 | 137 | rsSqqvvav | rsAqqvvav |
| HE3202 | FAM83H | 8 | 144812314 | C | A | A2403,A3201,B3801,B4101,C1203,C1701 | C1203 | 494 | 351 | rmirsSqqv | rmirsAqqv |
| HE3202 | FAM83H | 8 | 144812314 | C | A | A2403,A3201,B3801,B4101,C1203,C1701 | C1203 | 444 | 339 | rsSqqvvav | rsAqqvvav |
| HE3202 | EPPK1 | 8 | 144940693 | C | T | A2403,A3201,B3801,B4101,C1203,C1701 | A3201 | 491 | 224 | klsiyqamw | kMsiyqamw |
| HE3202 | PLEC | 8 | 144993046 | G | A | A2403,A3201,B3801,B4101,C1203,C1701 | C1203 | 79 | 1060 | ydyvrrlM | ydyvrrlT |
| HE3202 | CDKN2A | 9 | 21971111 | G | A | A2403,A3201,B3801,B4101,C1203,C1701 | A2403 | 36 | 11042 | vYdaaregf | vHdaaregf |

Figure 21 (Cont.)

| | | | | | | | | | | | |
|---|---|---|---|---|---|---|---|---|---|---|---|
| HE3202 | PLAA | 9 | 26906015 | C | T | A2403,A3201,B3801,B4101,C1203,C1701 | A2403 | 229 | 136 | khpsvnKnf | khpsvnEnf |
| HE3202 | NFX1 | 9 | 33344171 | G | C | A2403,A3201,B3801,B4101,C1203,C1701 | C1203 | 322 | 77 | rvhQcdhpv | rvhEcdhpv |
| HE3202 | CCL27 | 9 | 34662576 | G | T | A2403,A3201,B3801,B4101,C1203,C1701 | C1203 | 304 | 384 | lsTdptaaf | lsPdptaaf |
| HE3202 | TLN1 | 9 | 35700005 | T | C | A2403,A3201,B3801,B4101,C1203,C1701 | C1203 | 496 | 319 | ygrecaSgy | ygrecaNgy |
| HE3202 | SPATA31D3 | 9 | 84562337 | G | C | A2403,A3201,B3801,B4101,C1203,C1701 | C1203 | 219 | 514 | Dsihgplni | Esihgplni |
| HE3202 | C9orf170 | 9 | 89763770 | G | A | A2403,A3201,B3801,B4101,C1203,C1701 | C1203 | 181 | 261 | larpgrEgl | larpgrGgl |
| HE3202 | SPATA31C1 | 9 | 90535307 | C | A | A2403,A3201,B3801,B4101,C1203,C1701 | C1203 | 48 | 19 | daapivYpl | daapivSpl |
| HE3202 | SPATA31C1 | 9 | 90537077 | G | T | A2403,A3201,B3801,B4101,C1203,C1701 | A2403 | 216 | 543 | qfqrapLgi | qfqrapRgi |
| HE3202 | WNK2 | 9 | 96021292 | C | T | A2403,A3201,B3801,B4101,C1203,C1701 | C1203 | 222 | 76 | lpdlLtatv | lpdlPtatv |
| HE3202 | WNK2 | 9 | 96062359 | G | C | A2403,A3201,B3801,B4101,C1203,C1701 | A2403 | 59 | 153 | vyhptsQrv | vyhptsErv |
| HE3202 | C9orf3 | 9 | 97823061 | G | T | A2403,A3201,B3801,B4101,C1203,C1701 | A3201 | 78 | 273 | qslqMtyhl | qslqRtyhl |
| HE3202 | TMEM246 | 9 | 104238619 | C | A | A2403,A3201,B3801,B4101,C1203,C1701 | C1203 | 46 | 44 | yhperlHhy | yhperlQhy |
| HE3202 | TMEM246 | 9 | 104238619 | C | A | A2403,A3201,B3801,B4101,C1203,C1701 | C1203 | 384 | 571 | Hhyinpepm | Qhyinpepm |
| HE3202 | OR1J2 | 9 | 125273802 | G | A | A2403,A3201,B3801,B4101,C1203,C1701 | A2403 | 80 | 19114 | tYgshlsvv | tCgshlsvv |
| HE3202 | OR1J2 | 9 | 125273802 | G | A | A2403,A3201,B3801,B4101,C1203,C1701 | A3201 | 276 | 1552 | stYgshlsv | stCgshlsv |
| HE3202 | OR1J2 | 9 | 125273802 | G | A | A2403,A3201,B3801,B4101,C1203,C1701 | C1203 | 245 | 3159 | stYgshlsv | stCgshlsv |
| HE3202 | CRB2 | 9 | 126139312 | A | G | A2403,A3201,B3801,B4101,C1203,C1701 | C1203 | 136 | 97 | lemdsvlEv | lemdsvlKv |
| HE3202 | SPTAN1 | 9 | 131340462 | G | T | A2403,A3201,B3801,B4101,C1203,C1701 | C1203 | 377 | 257 | kalinaYel | kalinaDel |
| HE3202 | SPTAN1 | 9 | 131340462 | G | T | A2403,A3201,B3801,B4101,C1203,C1701 | C1203 | 11 | 94 | naYelasdv | naDelasdv |
| HE3202 | USP20 | 9 | 132637920 | G | T | A2403,A3201,B3801,B4101,C1203,C1701 | A2403 | 9 | 11 | vwehlynlf | vwehlynRf |
| HE3202 | USP20 | 9 | 132637920 | G | T | A2403,A3201,B3801,B4101,C1203,C1701 | A3201 | 82 | 12666 | nvwehlynl | nvwehlynR |
| HE3202 | USP20 | 9 | 132637920 | G | T | A2403,A3201,B3801,B4101,C1203,C1701 | C1203 | 123 | 16344 | nvwehlynl | nvwehlynR |

Figure 21 (Cont.)

| | | | | | | | | | | | |
|---|---|---|---|---|---|---|---|---|---|---|---|
| HE3202 | USP20 | 9 | 132637920 | G | T | A2403,A3201,B3801,B4101,C1203,C1701 | C1203 | 95 | 489 | nlfgggpav | nRfgggpav |
| HE3202 | SURF4 | 9 | 136230530 | C | T | A2403,A3201,B3801,B4101,C1203,C1701 | A2403 | 335 | 175 | wlfainlyf | wlfainVyf |
| HE3202 | SURF4 | 9 | 136230530 | C | T | A2403,A3201,B3801,B4101,C1203,C1701 | A2403 | 3 | 3 | lyfnafwti | Vyfnafwti |
| HE3202 | SURF4 | 9 | 136230530 | C | T | A2403,A3201,B3801,B4101,C1203,C1701 | A3201 | 123 | 1548 | vvwlfainl | vvwlfainV |
| HE3202 | SURF4 | 9 | 136230530 | C | T | A2403,A3201,B3801,B4101,C1203,C1701 | A3201 | 247 | 92 | wlfainlyf | wlfainVyf |
| HE3202 | SURF4 | 9 | 136230530 | C | T | A2403,A3201,B3801,B4101,C1203,C1701 | A3201 | 90 | 65 | ainlyfnaf | ainVyfnaf |
| HE3202 | SURF4 | 9 | 136230530 | C | T | A2403,A3201,B3801,B4101,C1203,C1701 | A3201 | 57 | 84 | lyfnafwti | Vyfnafwti |
| HE3202 | SURF4 | 9 | 136230530 | C | T | A2403,A3201,B3801,B4101,C1203,C1701 | C1203 | 102 | 185 | lyfnafwti | Vyfnafwti |
| HE3202 | CACNA1B | 9 | 141016027 | C | A | A2403,A3201,B3801,B4101,C1203,C1701 | C1203 | 334 | 568 | tpltprHsi | tpltprPsi |
| HE3202 | CACNA1B | 9 | 141016027 | C | A | A2403,A3201,B3801,B4101,C1203,C1701 | C1203 | 268 | 312 | ltprHsity | ltprPsity |
| HE3202 | P2RY8 | X | 1585160 | C | A | A2403,A3201,B3801,B4101,C1203,C1701 | A2403 | 449 | 9261 | vfgvllcnL | vfgvllcnV |
| HE3202 | P2RY8 | X | 1585160 | C | A | A2403,A3201,B3801,B4101,C1203,C1701 | A3201 | 191 | 202 | lcnLvtvaf | lcnVvtvaf |
| HE3202 | P2RY8 | X | 1585160 | C | A | A2403,A3201,B3801,B4101,C1203,C1701 | C1203 | 82 | 47 | vllcnLvtv | vllcnVvtv |
| HE3202 | PPEF1 | X | 18748380 | C | A | A2403,A3201,B3801,B4101,C1203,C1701 | A2403 | 69 | 385 | rqhyalNif | rqhyalTif |
| HE3202 | PPEF1 | X | 18748380 | C | A | A2403,A3201,B3801,B4101,C1203,C1701 | A2403 | 67 | 233 | yalNifqsi | yalTifqsi |
| HE3202 | PPEF1 | X | 18748380 | C | A | A2403,A3201,B3801,B4101,C1203,C1701 | A3201 | 48 | 28 | rqhyalNif | rqhyalTif |
| HE3202 | PPEF1 | X | 18748380 | C | A | A2403,A3201,B3801,B4101,C1203,C1701 | C1203 | 3 | 5 | yalNifqsi | yalTifqsi |
| HE3202 | POLA1 | X | 24757502 | G | T | A2403,A3201,B3801,B4101,C1203,C1701 | C1203 | 183 | 17105 | mpklggrsV | mpklggrsG |
| HE3202 | IL1RAPL1 | X | 29417405 | C | T | A2403,A3201,B3801,B4101,C1203,C1701 | C1203 | 32 | 40 | fvvrrltel | fvvrrTtel |
| HE3202 | DMD | X | 32430284 | G | T | A2403,A3201,B3801,B4101,C1203,C1701 | A3201 | 138 | 547 | liffpayfl | liffpayfL |
| HE3202 | DMD | X | 32430284 | G | T | A2403,A3201,B3801,B4101,C1203,C1701 | C1203 | 147 | 640 | liffpayfl | liffpayfL |
| HE3202 | DMD | X | 32430284 | G | T | A2403,A3201,B3801,B4101,C1203,C1701 | C1203 | 18 | 26 | fpayflnav | fpayfLnav |
| HE3202 | SRPX | X | 38016207 | A | G | A2403,A3201,B3801,B4101,C1203,C1701 | C1203 | 16 | 37 | yekrrllTv | yekrrlllv |

Figure 21 (Cont.)

| | | | | | | | | | | | |
|---|---|---|---|---|---|---|---|---|---|---|---|
| HE3202 | PPP1R3F | X | 49142743 | G | T | A2403,A3201,B3801,B4101,C1203,C1701 | A2403 | 9 | 17108 | tYrdlilkw | tDrdlilkw |
| HE3202 | DGKK | X | 50127751 | G | C | A2403,A3201,B3801,B4101,C1203,C1701 | C1203 | 151 | 126 | fleddAedi | fleddPedi |
| HE3202 | USP51 | X | 55514268 | C | A | A2403,A3201,B3801,B4101,C1203,C1701 | A3201 | 378 | 2200 | linlWntcf | linlGntcf |
| HE3202 | EDA2R | X | 65824963 | C | A | A2403,A3201,B3801,B4101,C1203,C1701 | C1203 | 196 | 180 | itcSvinrv | itcAvinrv |
| HE3202 | EDA2R | X | 65824963 | C | A | A2403,A3201,B3801,B4101,C1203,C1701 | C1203 | 89 | 222 | Svinrvqkv | Avinrvqkv |
| HE3202 | OTUD6A | X | 69282423 | C | A | A2403,A3201,B3801,B4101,C1203,C1701 | B3801 | 489 | 963 | rhqSerqel | rhqRerqel |
| HE3202 | RAB41 | X | 69503166 | C | A | A2403,A3201,B3801,B4101,C1203,C1701 | A2403 | 405 | 287 | rfhslipsy | rfhsLipsy |
| HE3202 | RAB41 | X | 69503166 | C | A | A2403,A3201,B3801,B4101,C1203,C1701 | C1203 | 360 | 281 | fhslipsyi | fhsLipsyi |
| HE3202 | ATRX | X | 76814270 | T | C | A2403,A3201,B3801,B4101,C1203,C1701 | C1203 | 230 | 1699 | iSlvaanrv | iNlvaanrv |
| HE3202 | ATP7A | X | 77298204 | C | T | A2403,A3201,B3801,B4101,C1203,C1701 | A3201 | 497 | 217 | Vlamanvgi | Alamanvgi |
| HE3202 | PABPC5 | X | 90690727 | C | T | A2403,A3201,B3801,B4101,C1203,C1701 | C1203 | 139 | 92 | ftricCdpv | ftricRdpv |
| HE3202 | PCDH11X | X | 91090714 | G | A | A2403,A3201,B3801,B4101,C1203,C1701 | A2403 | 89 | 187 | vyktgNvpl | vyktgDvpl |
| HE3202 | PCDH11X | X | 91090714 | G | A | A2403,A3201,B3801,B4101,C1203,C1701 | C1203 | 134 | 452 | yktgNvpli | yktgDvpli |
| HE3202 | NXF5 | X | 101096032 | A | T | A2403,A3201,B3801,B4101,C1203,C1701 | B3801 | 464 | 642 | rrnSmaatl | rrnCmaatl |
| HE3202 | NXF5 | X | 101096032 | A | T | A2403,A3201,B3801,B4101,C1203,C1701 | C1203 | 148 | 401 | iilnrrnSm | iilnrrnCm |
| HE3202 | NXF5 | X | 101096032 | A | T | A2403,A3201,B3801,B4101,C1203,C1701 | C1203 | 95 | 477 | nSmaatlki | nCmaatlki |
| HE3202 | NXF5 | X | 101096065 | G | A | A2403,A3201,B3801,B4101,C1203,C1701 | C1203 | 423 | 355 | lmgCdidii | lmgRdidii |
| HE3202 | COL4A6 | X | 107403760 | G | T | A2403,A3201,B3801,B4101,C1203,C1701 | A3201 | 23 | 151 | Rqlwvgysl | Sqlwvgysl |
| HE3202 | COL4A6 | X | 107403760 | G | T | A2403,A3201,B3801,B4101,C1203,C1701 | B3801 | 247 | 235 | Rqlwvgysl | Sqlwvgysl |
| HE3202 | ALG13 | X | 110931130 | G | T | A2403,A3201,B3801,B4101,C1203,C1701 | A2403 | 45 | 10319 | ylqhaswaF | ylqhaswaV |
| HE3202 | ALG13 | X | 110931130 | G | T | A2403,A3201,B3801,B4101,C1203,C1701 | A2403 | 256 | 361 | swaFtvngl | swaVtvngl |
| HE3202 | ALG13 | X | 110931130 | G | T | A2403,A3201,B3801,B4101,C1203,C1701 | A3201 | 108 | 2326 | ylqhaswaF | ylqhaswaV |

Figure 21 (Cont.)

| | | | | | | | | | | | |
|---|---|---|---|---|---|---|---|---|---|---|---|
| HE3202 | ALG13 | X | 110931130 | G | T | A2403,A3201,B3801,B4101,C1203,C1701 | B3801 | 268 | 591 | qhaswaFtv | qhaswaVtv |
| HE3202 | ALG13 | X | 110931130 | G | T | A2403,A3201,B3801,B4101,C1203,C1701 | C1203 | 22 | 176 | waFtvngli | waVtvngli |
| HE3202 | KIAA1210 | X | 118219423 | C | A | A2403,A3201,B3801,B4101,C1203,C1701 | A3201 | 159 | 84 | ksfkShisv | ksfkAhisv |
| HE3202 | KIAA1210 | X | 118219423 | C | A | A2403,A3201,B3801,B4101,C1203,C1701 | C1203 | 209 | 224 | kqksfkShi | kqksfkAhi |
| HE3202 | KIAA1210 | X | 118219423 | C | A | A2403,A3201,B3801,B4101,C1203,C1701 | C1203 | 214 | 179 | ksfkShisv | ksfkAhisv |
| HE3202 | CT47B1 | X | 120009053 | C | G | A2403,A3201,B3801,B4101,C1203,C1701 | C1203 | 325 | 406 | lmvgphaPv | lmvgphaAv |
| HE3202 | DCAF12L1 | X | 125686435 | G | T | A2403,A3201,B3801,B4101,C1203,C1701 | A2403 | 7 | 7 | tyrsmaNyl | tyrsmaHyl |
| HE3202 | DCAF12L1 | X | 125686435 | G | T | A2403,A3201,B3801,B4101,C1203,C1701 | C1203 | 111 | 96 | rsmaNylkv | rsmaHylkv |
| HE3202 | OCRL | X | 128695159 | C | A | A2403,A3201,B3801,B4101,C1203,C1701 | A2403 | 23 | 12 | iycigLqel | iycigFqel |
| HE3202 | ZNF449 | X | 134494173 | G | T | A2403,A3201,B3801,B4101,C1203,C1701 | A3201 | 36 | 15 | kkmDtmypf | kkmEtmypf |
| HE3202 | CDR1 | X | 139865968 | C | A | A2403,A3201,B3801,B4101,C1203,C1701 | A2403 | 439 | 142 | ifwktCifw | ifwktWifw |
| HE3202 | CDR1 | X | 139865968 | C | A | A2403,A3201,B3801,B4101,C1203,C1701 | A2403 | 123 | 110 | Cifwktwif | Wifwktwif |
| HE3202 | CDR1 | X | 139865968 | C | A | A2403,A3201,B3801,B4101,C1203,C1701 | A3201 | 338 | 79 | wifwktCif | wifwktWif |
| HE3202 | CDR1 | X | 139865968 | C | A | A2403,A3201,B3801,B4101,C1203,C1701 | A3201 | 53 | 8 | ktCifwktw | ktWifwktw |
| HE3202 | CDR1 | X | 139865968 | C | A | A2403,A3201,B3801,B4101,C1203,C1701 | A3201 | 98 | 79 | Cifwktwif | Wifwktwif |
| HE3202 | SLITRK4 | X | 142718819 | C | T | A2403,A3201,B3801,B4101,C1203,C1701 | C1203 | 144 | 29 | vsvKnvlyv | vsvEnvlyv |
| HE3202 | MAGEA6 | X | 151869339 | G | A | A2403,A3201,B3801,B4101,C1203,C1701 | B3801 | 175 | 411 | qhYkpeegl | qhCkpeegl |
| JB112852 | ZBTB8B | 1 | 32946599 | C | T | A1101,A0201,B3512,B4402,C0401,C0704 | A1101 | 473 | 5645 | rshtgeWpy | rshtgeRpy |
| JB112852 | SH3D21 | 1 | 36786529 | G | A | A1101,A0201,B3512,B4402,C0401,C0704 | A0201 | 65 | 15 | kltNiweel | kltDiweel |
| JB112852 | SH3D21 | 1 | 36786529 | G | A | A1101,A0201,B3512,B4402,C0401,C0704 | A1101 | 56 | 180 | ltNiweelk | ltDiweelk |
| JB112852 | SH3D21 | 1 | 36786529 | G | A | A1101,A0201,B3512,B4402,C0401,C0704 | B4402 | 244 | 402 | lerkltNiw | lerkltDiw |
| JB112852 | CHRNB2 | 1 | 154544452 | G | A | A1101,A0201,B3512,B4402,C0401,C0704 | A1101 | 395 | 3514 | Nsctcfvnr | Dsctcfvnr |
| JB112852 | SLC30A1 | 1 | 211749485 | A | C | A1101,A0201,B3512,B4402,C0401,C0704 | A0201 | 74 | 267 | flhvlgdaV | flhvlgdaL |

Figure 21 (Cont.)

| | | | | | | | | | | | |
|---|---|---|---|---|---|---|---|---|---|---|---|
| JB112852 | SLC30A1 | 1 | 211749485 | A | C | A1101,A0201,B3512,B4402,C0401,C0704 | A0201 | 33 | 27 | vlgdaVgsv | vlgdaLgsv |
| JB112852 | SLC30A1 | 1 | 211749485 | A | C | A1101,A0201,B3512,B4402,C0401,C0704 | A0201 | 354 | 32 | aVgsvivvv | aLgsvivvv |
| JB112852 | OR2T1 | 1 | 248569328 | C | A | A1101,A0201,B3512,B4402,C0401,C0704 | A0201 | 23 | 38 | yflnvLfpl | yflnvFfpl |
| JB112852 | OR2T1 | 1 | 248569328 | C | A | A1101,A0201,B3512,B4402,C0401,C0704 | A0201 | 10 | 7 | flnvLfpll | flnvFfpll |
| JB112852 | TAF3 | 10 | 7860791 | G | A | A1101,A0201,B3512,B4402,C0401,C0704 | A0201 | 42 | 92 | vlqHylqql | vlqRylqql |
| JB112852 | ERCC6 | 10 | 50678912 | G | A | A1101,A0201,B3512,B4402,C0401,C0704 | A1101 | 447 | 178 | tgsdvqtSk | tgsdvqtPk |
| JB112852 | ERCC6 | 10 | 50678912 | G | A | A1101,A0201,B3512,B4402,C0401,C0704 | A1101 | 101 | 84 | vqtSkchlk | vqtPkchlk |
| JB112852 | ERCC6 | 10 | 50678912 | G | A | A1101,A0201,B3512,B4402,C0401,C0704 | A1101 | 310 | 2978 | qtSkchlkr | qtPkchlkr |
| JB112852 | ODF3 | 11 | 199391 | G | A | A1101,A0201,B3512,B4402,C0401,C0704 | A1101 | 274 | 77 | Hqtdvrvtk | Rqtdvrvtk |
| JB112852 | NLRP6 | 11 | 280085 | G | C | A1101,A0201,B3512,B4402,C0401,C0704 | A1101 | 18 | 19 | tllsvsDyk | tllsvsEyk |
| JB112852 | TRPM5 | 11 | 2436427 | C | A | A1101,A0201,B3512,B4402,C0401,C0704 | A0201 | 142 | 507 | fslhevsLv | fslhevsRv |
| JB112852 | TRPM5 | 11 | 2436427 | C | A | A1101,A0201,B3512,B4402,C0401,C0704 | A0201 | 39 | 290 | slhevsLvl | slhevsRvl |
| JB112852 | SLC35C1 | 11 | 45827396 | C | T | A1101,A0201,B3512,B4402,C0401,C0704 | A0201 | 294 | 339 | ilhmVltga | ilhmAltga |
| JB112852 | TRIM64C | 11 | 49080565 | A | C | A1101,A0201,B3512,B4402,C0401,C0704 | A0201 | 56 | 13884 | vttdcvhsV | vttdcvhsF |
| JB112852 | RAB3IL1 | 11 | 61672238 | G | C | A1101,A0201,B3512,B4402,C0401,C0704 | A0201 | 436 | 180 | cldLtmqel | cldFtmqel |
| JB112852 | NRXN2 | 11 | 64480912 | A | G | A1101,A0201,B3512,B4402,C0401,C0704 | A0201 | 108 | 153 | llvdgrPrl | llvdgrLrl |
| JB112852 | ARHGEF17 | 11 | 73074256 | G | A | A1101,A0201,B3512,B4402,C0401,C0704 | A1101 | 30 | 16484 | isssfgneK | isssfgneE |
| JB112852 | MYO7A | 11 | 76901072 | G | A | A1101,A0201,B3512,B4402,C0401,C0704 | A0201 | 412 | 4509 | ylQnfihgg | ylRnfihgg |
| JB112852 | BCL9L | 11 | 118773963 | G | A | A1101,A0201,B3512,B4402,C0401,C0704 | A0201 | 32 | 38 | fvyvflthl | fvyvfTthl |
| JB112852 | GRAMD1B | 11 | 123485512 | G | A | A1101,A0201,B3512,B4402,C0401,C0704 | A0201 | 83 | 1759 | sMsklllvi | sVsklllvi |
| JB112852 | ATP5G2 | 12 | 54066400 | T | C | A1101,A0201,B3512,B4402,C0401,C0704 | A0201 | 12 | 7 | Rmfacskfv | Kmfacskfv |
| JB112852 | NDUFA4L2 | 12 | 57630395 | G | A | A1101,A0201,B3512,B4402,C0401,C0704 | A0201 | 221 | 1428 | yllrlaFrs | yllrlaLrs |

Figure 21 (Cont.)

| | | | | | | | | | | | |
|---|---|---|---|---|---|---|---|---|---|---|---|
| JB112852 | NDUFA4L2 | 12 | 57630395 | G | A | A1101,A0201,B3512,B4402,C0401,C0704 | A0201 | 131 | 331 | rlaFrspdv | rlaLrspdv |
| JB112852 | TRPV4 | 12 | 110230174 | C | T | A1101,A0201,B3512,B4402,C0401,C0704 | A0201 | 51 | 13 | yllfmigyT | yllfmigyA |
| JB112852 | TRPV4 | 12 | 110230174 | C | T | A1101,A0201,B3512,B4402,C0401,C0704 | A0201 | 3 | 4 | fmigyTsal | fmigyAsal |
| JB112852 | TRPV4 | 12 | 110230174 | C | T | A1101,A0201,B3512,B4402,C0401,C0704 | A0201 | 65 | 49 | migyTsalv | migyAsalv |
| JB112852 | TRPV4 | 12 | 110230174 | C | T | A1101,A0201,B3512,B4402,C0401,C0704 | A0201 | 93 | 335 | yTsalvsll | yAsalvsll |
| JB112852 | TBX3 | 12 | 115110013 | G | A | A1101,A0201,B3512,B4402,C0401,C0704 | A0201 | 54 | 14128 | sLvhrhpfl | sSvhrhpfl |
| JB112852 | NOS1 | 12 | 117725904 | C | A | A1101,A0201,B3512,B4402,C0401,C0704 | A0201 | 22 | 44 | fiYqyyssi | fiDqyyssi |
| JB112852 | NOS1 | 12 | 117725904 | C | A | A1101,A0201,B3512,B4402,C0401,C0704 | A1101 | 204 | 6430 | Yqyyssikr | Dqyyssikr |
| JB112852 | HHIPL1 | 14 | 100111738 | G | A | A1101,A0201,B3512,B4402,C0401,C0704 | A0201 | 290 | 216 | alaNrvdaa | alaSrvdaa |
| JB112852 | CHST14 | 15 | 40763553 | T | A | A1101,A0201,B3512,B4402,C0401,C0704 | A0201 | 13 | 1446 | lllpsmlmL | lllpsmlmF |
| JB112852 | CHST14 | 15 | 40763553 | T | A | A1101,A0201,B3512,B4402,C0401,C0704 | A0201 | 62 | 26 | llpsmlmLa | llpsmlmFa |
| JB112852 | CHST14 | 15 | 40763553 | T | A | A1101,A0201,B3512,B4402,C0401,C0704 | A0201 | 35 | 21 | smlmLaviv | smlmFaviv |
| JB112852 | CHST14 | 15 | 40763553 | T | A | A1101,A0201,B3512,B4402,C0401,C0704 | A0201 | 29 | 14 | mlmLaviva | mlmFaviva |
| JB112852 | CHST14 | 15 | 40763553 | T | A | A1101,A0201,B3512,B4402,C0401,C0704 | A0201 | 458 | 293 | lmLavivas | lmFavivas |
| JB112852 | AP3B2 | 15 | 83346857 | C | G | A1101,A0201,B3512,B4402,C0401,C0704 | A0201 | 164 | 80 | vlrefHtyi | vlrefQtyi |
| JB112852 | AP3B2 | 15 | 83346857 | C | G | A1101,A0201,B3512,B4402,C0401,C0704 | A1101 | 88 | 1023 | tvlrefHty | tvlrefQty |
| JB112852 | AP3B2 | 15 | 83346857 | C | G | A1101,A0201,B3512,B4402,C0401,C0704 | A1101 | 22 | 30 | Htyirsmdk | Qtyirsmdk |
| JB112852 | SOCS1 | 16 | 11349236 | C | A | A1101,A0201,B3512,B4402,C0401,C0704 | A1101 | 85 | 164 | ssspSapar | ssspAapar |
| JB112852 | UMOD | 16 | 20360253 | C | T | A1101,A0201,B3512,B4402,C0401,C0704 | A0201 | 59 | 21 | alTtcvnvv | alAtcvnvv |
| JB112852 | SLC12A3 | 16 | 56912993 | G | A | A1101,A0201,B3512,B4402,C0401,C0704 | A1101 | 42 | 105 | atigscMvr | atigscVvr |
| JB112852 | OR1G1 | 17 | 3030733 | G | A | A1101,A0201,B3512,B4402,C0401,C0704 | A0201 | 3 | 3 | flfmylvMv | flfmylvTv |
| JB112852 | OR1G1 | 17 | 3030733 | G | A | A1101,A0201,B3512,B4402,C0401,C0704 | A0201 | 271 | 192 | ylvMvagnl | ylvTvagnl |
| JB112852 | OR1G1 | 17 | 3030733 | G | A | A1101,A0201,B3512,B4402,C0401,C0704 | A0201 | 55 | 2732 | vMvagnlli | vTvagnlli |

Figure 21 (Cont.)

| | | | | | | | | | | | |
|---|---|---|---|---|---|---|---|---|---|---|---|
| JB112852 | OR1G1 | 17 | 3030733 | G | A | A1101,A0201,B3512,B4402,C0401,C0704 | A0201 | 446 | 3439 | Mvagnliii | Tvagnliii |
| JB112852 | TRPV3 | 17 | 3421931 | G | A | A1101,A0201,B3512,B4402,C0401,C0704 | A0201 | 94 | 966 | vlllnmliV | vlllnmliA |
| JB112852 | TRPV3 | 17 | 3421931 | G | A | A1101,A0201,B3512,B4402,C0401,C0704 | A0201 | 20 | 11 | lllnmliVl | lllnmliAl |
| JB112852 | TRPV3 | 17 | 3421931 | G | A | A1101,A0201,B3512,B4402,C0401,C0704 | A0201 | 350 | 252 | llnmliVlm | llnmliAlm |
| JB112852 | TRPV2 | 17 | 16326159 | G | T | A1101,A0201,B3512,B4402,C0401,C0704 | A1101 | 11 | 15 | raFgrffqk | raCgrffqk |
| JB112852 | C17orf47 | 17 | 56621460 | C | T | A1101,A0201,B3512,B4402,C0401,C0704 | A1101 | 217 | 19075 | ttntspqqR | ttntspqqG |
| JB112852 | UNC13D | 17 | 73826499 | T | C | A1101,A0201,B3512,B4402,C0401,C0704 | A1101 | 22 | 20 | asyraseRk | asyraseQk |
| JB112852 | ZNF407 | 18 | 72776371 | G | T | A1101,A0201,B3512,B4402,C0401,C0704 | A1101 | 401 | 741 | Saaaiqsqr | Aaaaiqsqr |
| JB112852 | MED16 | 19 | 884942 | G | A | A1101,A0201,B3512,B4402,C0401,C0704 | A0201 | 144 | 750 | slrkegFpv | slrkegLpv |
| JB112852 | ABCA7 | 19 | 1064163 | G | T | A1101,A0201,B3512,B4402,C0401,C0704 | A0201 | 235 | 1399 | svmltshsl | svmltshsM |
| JB112852 | ADAT3 | 19 | 1912212 | G | A | A1101,A0201,B3512,B4402,C0401,C0704 | A0201 | 181 | 132 | kqsgdMelv | kqsgdVelv |
| JB112852 | ADAT3 | 19 | 1912212 | G | A | A1101,A0201,B3512,B4402,C0401,C0704 | B4402 | 89 | 1039 | gdMelvlay | gdVelvlay |
| JB112852 | ADAT3 | 19 | 1912212 | G | A | A1101,A0201,B3512,B4402,C0401,C0704 | B4402 | 224 | 1591 | Melvlayaa | Velvlayaa |
| JB112852 | HDGFRP2 | 19 | 4497995 | T | C | A1101,A0201,B3512,B4402,C0401,C0704 | A1101 | 33 | 44 | Lsmdrkvek | Fsmdrkvek |
| JB112852 | PTPRS | 19 | 5246012 | C | T | A1101,A0201,B3512,B4402,C0401,C0704 | A0201 | 202 | 44 | silpmshKi | silpmshEi |
| JB112852 | PTPRS | 19 | 5246012 | C | T | A1101,A0201,B3512,B4402,C0401,C0704 | A1101 | 63 | 19292 | fsilpmshK | fsilpmshE |
| JB112852 | RDH8 | 19 | 10127735 | G | A | A1101,A0201,B3512,B4402,C0401,C0704 | A1101 | 486 | 712 | Matmrdlgk | Vatmrdlgk |
| JB112852 | AP1M1 | 19 | 16344308 | G | A | A1101,A0201,B3512,B4402,C0401,C0704 | A1101 | 197 | 77 | siksfpgDk | siksfpgGk |
| JB112852 | LSM4 | 19 | 18418311 | G | A | A1101,A0201,B3512,B4402,C0401,C0704 | A1101 | 44 | 101 | gtgrgqLek | gtgrgqPek |
| JB112852 | CRLF1 | 19 | 18710626 | G | A | A1101,A0201,B3512,B4402,C0401,C0704 | A0201 | 39 | 221 | Mlligssll | Tlligssll |
| JB112852 | UPK1A | 19 | 36168911 | C | A | A1101,A0201,B3512,B4402,C0401,C0704 | A0201 | 180 | 156 | liamyfyNm | liamyfyTm |
| JB112852 | DLL3 | 19 | 39993479 | G | A | A1101,A0201,B3512,B4402,C0401,C0704 | A1101 | 468 | 626 | sllaHvagr | sllaRvagr |

Figure 21 (Cont.)

| | | | | | | | | | | | |
|---|---|---|---|---|---|---|---|---|---|---|---|
| JB112852 | CIC | 19 | 42794935 | T | A | A1101,A0201,B3512,B4402,C0401,C0704 | A1101 | 29 | 49 | atmDtnvvr | atmVtnvvr |
| JB112852 | NKPD1 | 19 | 45656184 | C | T | A1101,A0201,B3512,B4402,C0401,C0704 | A0201 | 47 | 30 | ilaacleNa | ilaacleSa |
| JB112852 | LIN7B | 19 | 49618551 | C | T | A1101,A0201,B3512,B4402,C0401,C0704 | A0201 | 65 | 1023 | qlydtldil | qlydtldiT |
| JB112852 | PRR12 | 19 | 50123709 | G | A | A1101,A0201,B3512,B4402,C0401,C0704 | A0201 | 72 | 146 | aldpdliqa | aldpdMiqa |
| JB112852 | COL4A4 | 2 | 227872061 | C | A | A1101,A0201,B3512,B4402,C0401,C0704 | A0201 | 66 | 454 | kisrcqFcv | kisrcqVcv |
| JB112852 | COL20A1 | 20 | 61926535 | G | A | A1101,A0201,B3512,B4402,C0401,C0704 | A0201 | 367 | 482 | lqasgllrl | Vqasgllrl |
| JB112852 | COL20A1 | 20 | 61926535 | G | A | A1101,A0201,B3512,B4402,C0401,C0704 | A1101 | 197 | 125 | qlqasgllr | qVqasgllr |
| JB112852 | COL20A1 | 20 | 61942781 | G | A | A1101,A0201,B3512,B4402,C0401,C0704 | A1101 | 137 | 174 | ltlaTvtpr | ltlaAvtpr |
| JB112852 | PRPF6 | 20 | 62626344 | C | T | A1101,A0201,B3512,B4402,C0401,C0704 | A1101 | 34 | 387 | rqWnpryek | rqRnpryek |
| JB112852 | SIM2 | 21 | 38114161 | C | T | A1101,A0201,B3512,B4402,C0401,C0704 | A1101 | 16 | 24 | yvFteieyk | yvLteieyk |
| JB112852 | AIFM3 | 22 | 21327616 | G | A | A1101,A0201,B3512,B4402,C0401,C0704 | A1101 | 245 | 170 | kievMlpek | kievVlpek |
| JB112852 | CLASP2 | 3 | 33618756 | G | A | A1101,A0201,B3512,B4402,C0401,C0704 | A1101 | 66 | 87 | rsfqplVsr | rsfqplAsr |
| JB112852 | SCN10A | 3 | 38770388 | C | T | A1101,A0201,B3512,B4402,C0401,C0704 | A1101 | 145 | 2257 | llHvfklak | llRvfklak |
| JB112852 | GORASP1 | 3 | 39148996 | C | T | A1101,A0201,B3512,B4402,C0401,C0704 | A1101 | 494 | 11831 | gSaegfhlh | gGaegfhlh |
| JB112852 | PRSS42 | 3 | 46875157 | C | T | A1101,A0201,B3512,B4402,C0401,C0704 | A0201 | 11 | 50 | sllcgQtpl | sllcgRtpl |
| JB112852 | ESYT3 | 3 | 138153891 | C | T | A1101,A0201,B3512,B4402,C0401,C0704 | A0201 | 55 | 26 | rlVaafefl | rlAaafefl |
| JB112852 | C4orf21 | 4 | 113469530 | C | T | A1101,A0201,B3512,B4402,C0401,C0704 | A0201 | 396 | 392 | tllkqvrlv | tllkqvrVv |
| JB112852 | ANK2 | 4 | 114186090 | G | A | A1101,A0201,B3512,B4402,C0401,C0704 | A0201 | 288 | 1482 | hmaaraEqv | hmaaraGqv |
| JB112852 | ANK2 | 4 | 114279562 | G | T | A1101,A0201,B3512,B4402,C0401,C0704 | A1101 | 96 | 8401 | ltMsvysdr | ltRsvysdr |
| JB112852 | SLC9A3 | 5 | 491998 | G | A | A1101,A0201,B3512,B4402,C0401,C0704 | A0201 | 56 | 189 | fmpnClffg | fmpnRlffg |
| JB112852 | APC | 5 | 112179224 | T | A | A1101,A0201,B3512,B4402,C0401,C0704 | A0201 | 42 | 66 | tliNqmapa | tliYqmapa |
| JB112852 | APC | 5 | 112179224 | T | A | A1101,A0201,B3512,B4402,C0401,C0704 | A0201 | 445 | 40 | liNqmapav | liYqmapav |
| JB112852 | APC | 5 | 112179224 | T | A | A1101,A0201,B3512,B4402,C0401,C0704 | A1101 | 67 | 29 | Nqmapavsk | Yqmapavsk |

Figure 21 (Cont.)

| | | | | | | | | | | | |
|---|---|---|---|---|---|---|---|---|---|---|---|
| JB112852 | GLRA1 | 5 | 151202285 | G | C | A1101,A0201,B3512,B4402,C0401,C0704 | A0201 | 11 | 16 | lifnmLywi | lifnmFywi |
| JB112852 | GLRA1 | 5 | 151202285 | G | C | A1101,A0201,B3512,B4402,C0401,C0704 | A0201 | 6 | 293 | mLywiiyki | mFywiiyki |
| JB112852 | GLRA1 | 5 | 151202285 | G | C | A1101,A0201,B3512,B4402,C0401,C0704 | A1101 | 18 | 13 | nmLywiiyk | nmFywiiyk |
| JB112852 | MAP7 | 6 | 136686965 | T | C | A1101,A0201,B3512,B4402,C0401,C0704 | A1101 | 24 | 21 | kvaSepslk | kvaNepslk |
| JB112852 | ZDHHC14 | 6 | 158093963 | G | A | A1101,A0201,B3512,B4402,C0401,C0704 | A1101 | 21 | 24 | atladMmpr | atladVmpr |
| JB112852 | ZDHHC14 | 6 | 158093963 | G | A | A1101,A0201,B3512,B4402,C0401,C0704 | A1101 | 29 | 24 | tladMmprk | tladVmprk |
| JB112852 | ZDHHC14 | 6 | 158093963 | G | A | A1101,A0201,B3512,B4402,C0401,C0704 | B4402 | 70 | 317 | aeatladMm | aeatladVm |
| JB112852 | ZNF316 | 7 | 6683477 | G | A | A1101,A0201,B3512,B4402,C0401,C0704 | A1101 | 366 | 274 | vtfedvTvy | vtfedvAvy |
| JB112852 | ZNF316 | 7 | 6683477 | G | A | A1101,A0201,B3512,B4402,C0401,C0704 | C0401 | 268 | 122 | tfedvTvyf | tfedvAvyf |
| JB112852 | CLIP2 | 7 | 73752970 | C | T | A1101,A0201,B3512,B4402,C0401,C0704 | A0201 | 6 | 1034 | ylgetqfaL | ylgetqfaP |
| JB112852 | CLIP2 | 7 | 73752970 | C | T | A1101,A0201,B3512,B4402,C0401,C0704 | A0201 | 60 | 525 | faLgqwagv | faPgqwagv |
| JB112852 | DLGAP2 | 8 | 1497796 | C | T | A1101,A0201,B3512,B4402,C0401,C0704 | A1101 | 65 | 12870 | kSllhqdak | kPllhqdak |
| JB112852 | TRIM35 | 8 | 27168703 | T | C | A1101,A0201,B3512,B4402,C0401,C0704 | B4402 | 28 | 34 | Gellcavcy | Eellcavcy |
| JB112852 | DDHD2 | 8 | 38091984 | G | A | A1101,A0201,B3512,B4402,C0401,C0704 | A0201 | 194 | 1046 | hlgermQya | hlgermRya |
| JB112852 | DDHD2 | 8 | 38091984 | G | A | A1101,A0201,B3512,B4402,C0401,C0704 | B4402 | 389 | 681 | germQyavy | germRyavy |
| JB112852 | PLEC | 8 | 145007245 | G | A | A1101,A0201,B3512,B4402,C0401,C0704 | A1101 | 131 | 3329 | aiCteynlr | aiRteynlr |
| JB112852 | PLEC | 8 | 145007272 | G | A | A1101,A0201,B3512,B4402,C0401,C0704 | A0201 | 58 | 56 | qmyrrvyCl | qmyrrvyRl |
| JB112852 | PLEC | 8 | 145007272 | G | A | A1101,A0201,B3512,B4402,C0401,C0704 | A0201 | 94 | 38 | Clherlvai | Rlherlvai |
| JB112852 | FREM1 | 9 | 14801746 | C | T | A1101,A0201,B3512,B4402,C0401,C0704 | A1101 | 25 | 30 | llidrRfsk | llidrGfsk |
| JB112852 | GTF3C4 | 9 | 135546167 | A | C | A1101,A0201,B3512,B4402,C0401,C0704 | A0201 | 100 | 59 | klPyavsgl | klQyavsgl |
| JB112852 | COL5A1 | 9 | 137703384 | G | A | A1101,A0201,B3512,B4402,C0401,C0704 | A1101 | 76 | 100 | gqqglfEqk | gqqglfGqk |
| JB112852 | PLCXD1 | X | 207339 | G | T | A1101,A0201,B3512,B4402,C0401,C0704 | A0201 | 65 | 222 | qlYagvryl | qlDagvryl |

Figure 21 (Cont.)

| | | | | | | | | | | | |
|---|---|---|---|---|---|---|---|---|---|---|---|
| KA3947 | NPHP4 | 1 | 5927930 | C | A | A2301,A2402,B4101,B4901,C0701,C1701 | C0701 | 401 | 495 | frasggNpi | frasggKpi |
| KA3947 | DLGAP3 | 1 | 35333205 | C | A | A2301,A2402,B4101,B4901,C0701,C1701 | C0701 | 399 | 428 | saLgstqll | saVgstqll |
| KA3947 | CYP4A11 | 1 | 47406916 | G | T | A2301,A2402,B4101,B4901,C0701,C1701 | C0701 | 221 | 69 | wlfghiKel | wlfghiQel |
| KA3947 | WLS | 1 | 68614279 | G | C | A2301,A2402,B4101,B4901,C0701,C1701 | A2301 | 246 | 528 | iavgCfclf | iavgSfclf |
| KA3947 | WLS | 1 | 68614279 | G | C | A2301,A2402,B4101,B4901,C0701,C1701 | A2301 | 203 | 282 | vgCfclfif | vgSfclfif |
| KA3947 | WDR63 | 1 | 85587453 | C | A | A2301,A2402,B4101,B4901,C0701,C1701 | A2301 | 239 | 176 | iyKdwkmek | iyTdwkmek |
| KA3947 | COL11A1 | 1 | 103343609 | C | A | A2301,A2402,B4101,B4901,C0701,C1701 | A2301 | 209 | 1208 | Vfevgpvcf | Gfevgpvcf |
| KA3947 | OR6K2 | 1 | 158670417 | A | G | A2301,A2402,B4101,B4901,C0701,C1701 | C0701 | 289 | 589 | nrttTqefi | nrttIqefi |
| KA3947 | FMO3 | 1 | 171073017 | C | A | A2301,A2402,B4101,B4901,C0701,C1701 | A2301 | 179 | 345 | pfHddfpnf | pfPddfpnf |
| KA3947 | FMO3 | 1 | 171073017 | C | A | A2301,A2402,B4101,B4901,C0701,C1701 | C0701 | 12 | 2504 | fHddfpnfm | fPddfpnfm |
| KA3947 | KCNT2 | 1 | 196436886 | C | A | A2301,A2402,B4101,B4901,C0701,C1701 | A2402 | 332 | 3658 | fFpvflncw | fVpvflncw |
| KA3947 | TMEM81 | 1 | 205053222 | G | A | A2301,A2402,B4101,B4901,C0701,C1701 | C0701 | 88 | 159 | rrkcqIrrl | rrkcqTrrl |
| KA3947 | ASCC1 | 10 | 73892845 | T | A | A2301,A2402,B4101,B4901,C0701,C1701 | C0701 | 203 | 286 | lhatvLntl | lhatvMntl |
| KA3947 | ASCC1 | 10 | 73912678 | C | A | A2301,A2402,B4101,B4901,C0701,C1701 | C0701 | 228 | 613 | ymnddpVmv | ymnddpGmv |
| KA3947 | OR52B2 | 11 | 6191319 | C | G | A2301,A2402,B4101,B4901,C0701,C1701 | A2402 | 253 | 280 | tLpkalaif | tVpkalaif |
| KA3947 | HIPK3 | 11 | 33370213 | A | T | A2301,A2402,B4101,B4901,C0701,C1701 | C0701 | 400 | 468 | arncceSsi | arncceTsi |
| KA3947 | OR4C16 | 11 | 55340399 | G | C | A2301,A2402,B4101,B4901,C0701,C1701 | C0701 | 302 | 735 | tvfpmHkmi | tvfpmDkmi |
| KA3947 | OR4P4 | 11 | 55406135 | C | G | A2301,A2402,B4101,B4901,C0701,C1701 | A2301 | 45 | 34 | iqlfSthff | iqlfTthff |
| KA3947 | OR4P4 | 11 | 55406135 | C | G | A2301,A2402,B4101,B4901,C0701,C1701 | A2402 | 199 | 163 | iqlfSthff | iqlfTthff |
| KA3947 | OR5F1 | 11 | 55761334 | G | C | A2301,A2402,B4101,B4901,C0701,C1701 | A2301 | 198 | 114 | fyatcMyty | fyatclyty |
| KA3947 | OR5F1 | 11 | 55761334 | G | C | A2301,A2402,B4101,B4901,C0701,C1701 | A2402 | 186 | 134 | fyatcMyty | fyatclyty |
| KA3947 | OR5AS1 | 11 | 55798309 | A | G | A2301,A2402,B4101,B4901,C0701,C1701 | C0701 | 354 | 128 | srGvcvcfi | srRvcvcfi |
| KA3947 | CCDC81 | 11 | 86133744 | G | A | A2301,A2402,B4101,B4901,C0701,C1701 | A2301 | 285 | 1113 | kflpgsQll | kflpgsRll |

Figure 21 (Cont.)

| | | | | | | | | | | | |
|---|---|---|---|---|---|---|---|---|---|---|---|
| KA3947 | CCDC81 | 11 | 86133744 | G | A | A2301,A2402,B4101,B4901,C0701,C1701 | A2402 | 329 | 1104 | kflpgsQll | kflpgsRll |
| KA3947 | PANX1 | 11 | 93886698 | C | T | A2301,A2402,B4101,B4901,C0701,C1701 | A2402 | 234 | 257 | sfswCqaaf | sfswRqaaf |
| KA3947 | CASP4 | 11 | 104821791 | C | A | A2301,A2402,B4101,B4901,C0701,C1701 | C0701 | 178 | 83 | ernnrtLla | ernnrtRla |
| KA3947 | LRTM2 | 12 | 1943775 | T | A | A2301,A2402,B4101,B4901,C0701,C1701 | A2301 | 230 | 194 | aygcNyasl | aygciyasl |
| KA3947 | LRTM2 | 12 | 1943775 | T | A | A2301,A2402,B4101,B4901,C0701,C1701 | A2402 | 149 | 81 | aygcNyasl | aygciyasl |
| KA3947 | CNTN1 | 12 | 41323633 | C | T | A2301,A2402,B4101,B4901,C0701,C1701 | A2301 | 79 | 95 | wllnefSvf | wllnefPvf |
| KA3947 | OR6C2 | 12 | 55846379 | C | A | A2301,A2402,B4101,B4901,C0701,C1701 | A2301 | 39 | 61 | ryvaickpl | ryvaickpL |
| KA3947 | OR6C2 | 12 | 55846379 | C | A | A2301,A2402,B4101,B4901,C0701,C1701 | A2402 | 44 | 150 | ryvaickpl | ryvaickpL |
| KA3947 | POC1B | 12 | 89860694 | T | G | A2301,A2402,B4101,B4901,C0701,C1701 | A2301 | 380 | 360 | qvFlwrtnf | qvLlwrtnf |
| KA3947 | SUPT20H | 13 | 37602382 | G | C | A2301,A2402,B4101,B4901,C0701,C1701 | A2301 | 82 | 52 | qyqktkVti | qyqktkLti |
| KA3947 | SUPT20H | 13 | 37602382 | G | C | A2301,A2402,B4101,B4901,C0701,C1701 | A2402 | 156 | 77 | qyqktkVti | qyqktkLti |
| KA3947 | NALCN | 13 | 101944624 | G | T | A2301,A2402,B4101,B4901,C0701,C1701 | A2301 | 30 | 99 | sfprwrYyf | sfprwrSyf |
| KA3947 | NALCN | 13 | 101944624 | G | T | A2301,A2402,B4101,B4901,C0701,C1701 | A2301 | 445 | 369 | prwrYyfyf | prwrSyfyf |
| KA3947 | NALCN | 13 | 101944624 | G | T | A2301,A2402,B4101,B4901,C0701,C1701 | A2301 | 49 | 36 | rwrYyfyfi | rwrSyfyfi |
| KA3947 | NALCN | 13 | 101944624 | G | T | A2301,A2402,B4101,B4901,C0701,C1701 | A2301 | 21 | 1245 | rYyfyfitl | rSyfyfitl |
| KA3947 | NALCN | 13 | 101944624 | G | T | A2301,A2402,B4101,B4901,C0701,C1701 | A2301 | 24 | 72 | Yyfyfitli | Syfyfitli |
| KA3947 | NALCN | 13 | 101944624 | G | T | A2301,A2402,B4101,B4901,C0701,C1701 | A2402 | 32 | 90 | sfprwrYyf | sfprwrSyf |
| KA3947 | NALCN | 13 | 101944624 | G | T | A2301,A2402,B4101,B4901,C0701,C1701 | A2402 | 34 | 17 | rwrYyfyfi | rwrSyfyfi |
| KA3947 | NALCN | 13 | 101944624 | G | T | A2301,A2402,B4101,B4901,C0701,C1701 | A2402 | 13 | 1720 | rYyfyfitl | rSyfyfitl |
| KA3947 | NALCN | 13 | 101944624 | G | T | A2301,A2402,B4101,B4901,C0701,C1701 | A2402 | 34 | 60 | Yyfyfitli | Syfyfitli |
| KA3947 | NALCN | 13 | 101944624 | G | T | A2301,A2402,B4101,B4901,C0701,C1701 | C0701 | 146 | 339 | Yyfyfitli | Syfyfitli |
| KA3947 | FAM181A | 14 | 94394767 | A | G | A2301,A2402,B4101,B4901,C0701,C1701 | A2301 | 409 | 669 | ylqkqlErf | ylqkqlKrf |

Figure 21 (Cont.)

| | | | | | | | | | | | |
|---|---|---|---|---|---|---|---|---|---|---|---|
| KA3947 | ZNF500 | 16 | 4802504 | C | T | A2301,A2402,B4101,B4901,C0701,C1701 | A2301 | 399 | 15586 | tYpacgrgf | tCpacgrgf |
| KA3947 | ZNF500 | 16 | 4802504 | C | T | A2301,A2402,B4101,B4901,C0701,C1701 | A2402 | 79 | 12749 | tYpacgrgf | tCpacgrgf |
| KA3947 | MINK1 | 17 | 4788900 | G | T | A2301,A2402,B4101,B4901,C0701,C1701 | A2301 | 65 | 1665 | tyYyrsdiw | tyDyrsdiw |
| KA3947 | MINK1 | 17 | 4788900 | G | T | A2301,A2402,B4101,B4901,C0701,C1701 | A2301 | 34 | 780 | Yyrsdiwsl | Dyrsdiwsl |
| KA3947 | MINK1 | 17 | 4788900 | G | T | A2301,A2402,B4101,B4901,C0701,C1701 | A2402 | 145 | 1190 | tyYyrsdiw | tyDyrsdiw |
| KA3947 | MINK1 | 17 | 4788900 | G | T | A2301,A2402,B4101,B4901,C0701,C1701 | A2402 | 83 | 1250 | Yyrsdiwsl | Dyrsdiwsl |
| KA3947 | MINK1 | 17 | 4788900 | G | T | A2301,A2402,B4101,B4901,C0701,C1701 | C0701 | 237 | 2322 | Yyrsdiwsl | Dyrsdiwsl |
| KA3947 | MYH1 | 17 | 10411211 | G | A | A2301,A2402,B4101,B4901,C0701,C1701 | A2301 | 252 | 167 | sfqtvsaFf | sfqtvsaLf |
| KA3947 | MYH1 | 17 | 10411211 | G | A | A2301,A2402,B4101,B4901,C0701,C1701 | A2402 | 68 | 44 | sfqtvsaFf | sfqtvsaLf |
| KA3947 | MYH1 | 17 | 10411211 | G | A | A2301,A2402,B4101,B4901,C0701,C1701 | C0701 | 344 | 2052 | Ffrenlnkl | Lfrenlnkl |
| KA3947 | COPZ2 | 17 | 46111290 | G | T | A2301,A2402,B4101,B4901,C0701,C1701 | C0701 | 230 | 801 | yyddtHpsm | yyddtFpsm |
| KA3947 | COPZ2 | 17 | 46111290 | G | T | A2301,A2402,B4101,B4901,C0701,C1701 | C0701 | 34 | 4362 | tHpsmkeqm | tFpsmkeqm |
| KA3947 | AKAP1 | 17 | 55184131 | G | A | A2301,A2402,B4101,B4901,C0701,C1701 | A2301 | 22 | 27 | tyMsclksl | tyVsclksl |
| KA3947 | AKAP1 | 17 | 55184131 | G | A | A2301,A2402,B4101,B4901,C0701,C1701 | A2402 | 62 | 332 | tyMsclksl | tyVsclksl |
| KA3947 | AKAP1 | 17 | 55184131 | G | A | A2301,A2402,B4101,B4901,C0701,C1701 | C0701 | 109 | 789 | tyMsclksl | tyVsclksl |
| KA3947 | INTS2 | 17 | 59947130 | C | G | A2301,A2402,B4101,B4901,C0701,C1701 | C0701 | 173 | 15601 | aHpniaklv | aDpniaklv |
| KA3947 | CD300C | 17 | 72541910 | C | A | A2301,A2402,B4101,B4901,C0701,C1701 | A2402 | 399 | 285 | mtaSawasw | mtaRawasw |
| KA3947 | SETBP1 | 18 | 42532291 | G | T | A2301,A2402,B4101,B4901,C0701,C1701 | C0701 | 302 | 126 | dhyypLpyi | dhyypVpyi |
| KA3947 | SERPINB7 | 18 | 61449677 | G | T | A2301,A2402,B4101,B4901,C0701,C1701 | C0701 | 343 | 17199 | fremddnqV | fremddnqG |
| KA3947 | APBA3 | 19 | 3751222 | G | A | A2301,A2402,B4101,B4901,C0701,C1701 | C0701 | 396 | 156 | phaCiiell | phaRiiell |
| KA3947 | CACNG7 | 19 | 54445445 | C | A | A2301,A2402,B4101,B4901,C0701,C1701 | C0701 | 407 | 2117 | rrgrRpsdi | rrgrSpsdi |
| KA3947 | DYSF | 2 | 71838722 | C | A | A2301,A2402,B4101,B4901,C0701,C1701 | C0701 | 200 | 2410 | lrknHnfdi | lrknPnfdi |
| KA3947 | DYSF | 2 | 71838722 | C | A | A2301,A2402,B4101,B4901,C0701,C1701 | C0701 | 222 | 17099 | nHnfdictl | nPnfdictl |

Figure 21 (Cont.)

| | | | | | | | | | | | |
|---|---|---|---|---|---|---|---|---|---|---|---|
| KA3947 | GTDC1 | 2 | 144764942 | G | A | A2301,A2402,B4101,B4901,C0701,C1701 | C0701 | 453 | 2933 | Fdtarqeyl | Ldtarqeyl |
| KA3947 | KIF1A | 2 | 241702476 | T | C | A2301,A2402,B4101,B4901,C0701,C1701 | C0701 | 343 | 164 | yrrGreeat | yrrEreeat |
| KA3947 | KIF1A | 2 | 241702476 | T | C | A2301,A2402,B4101,B4901,C0701,C1701 | C0701 | 53 | 34 | Greeatyll | Ereeatyll |
| KA3947 | PLCB4 | 20 | 9343590 | C | A | A2301,A2402,B4101,B4901,C0701,C1701 | C0701 | 139 | 103 | ihnfraKnv | ihnfraNnv |
| KA3947 | PLCB4 | 20 | 9343590 | C | A | A2301,A2402,B4101,B4901,C0701,C1701 | C0701 | 51 | 26 | fraKnvspm | fraNnvspm |
| KA3947 | SEC23B | 20 | 18526643 | T | C | A2301,A2402,B4101,B4901,C0701,C1701 | C0701 | 162 | 76 | Srlsdsfsl | Frlsdsfsl |
| KA3947 | MMP24 | 20 | 33851618 | T | G | A2301,A2402,B4101,B4901,C0701,C1701 | A2301 | 269 | 179 | lflvaGhel | lflvaVhel |
| KA3947 | KIAA1755 | 20 | 36869946 | G | A | A2301,A2402,B4101,B4901,C0701,C1701 | C0701 | 453 | 1904 | drpqvvnVl | drpqvvnAl |
| KA3947 | DOCK3 | 3 | 51264792 | C | T | A2301,A2402,B4101,B4901,C0701,C1701 | A2301 | 200 | 84 | lyhsnspCw | lyhsnspRw |
| KA3947 | DOCK3 | 3 | 51264792 | C | T | A2301,A2402,B4101,B4901,C0701,C1701 | A2402 | 85 | 80 | lyhsnspCw | lyhsnspRw |
| KA3947 | IQCB1 | 3 | 121515965 | C | A | A2301,A2402,B4101,B4901,C0701,C1701 | A2301 | 472 | 1106 | vyqeveeHk | vyqeveeQk |
| KA3947 | PLXNA1 | 3 | 126746836 | G | T | A2301,A2402,B4101,B4901,C0701,C1701 | A2301 | 184 | 1967 | lycaikqql | lycaikqqM |
| KA3947 | PLXNA1 | 3 | 126746836 | G | T | A2301,A2402,B4101,B4901,C0701,C1701 | A2402 | 155 | 1800 | lycaikqql | lycaikqqM |
| KA3947 | ZNF721 | 4 | 436550 | G | A | A2301,A2402,B4101,B4901,C0701,C1701 | C0701 | 41 | 8 | frqFanlyv | frqSanlyv |
| KA3947 | OTOP1 | 4 | 4228425 | T | C | A2301,A2402,B4101,B4901,C0701,C1701 | C0701 | 42 | 43 | vrasvpqRl | vrasvpqKl |
| KA3947 | UGT2B10 | 4 | 69683800 | C | G | A2301,A2402,B4101,B4901,C0701,C1701 | A2301 | 72 | 48 | wlmGnswnf | wlmRnswnf |
| KA3947 | UGT2B10 | 4 | 69683800 | C | G | A2301,A2402,B4101,B4901,C0701,C1701 | A2301 | 102 | 87 | mGnswnfkf | mRnswnfkf |
| KA3947 | UGT2B10 | 4 | 69683800 | C | G | A2301,A2402,B4101,B4901,C0701,C1701 | A2402 | 95 | 49 | wlmGnswnf | wlmRnswnf |
| KA3947 | ANK2 | 4 | 114280254 | C | A | A2301,A2402,B4101,B4901,C0701,C1701 | C0701 | 70 | 77 | tKsereqei | tQsereqei |
| KA3947 | CDH6 | 5 | 31294096 | G | C | A2301,A2402,B4101,B4901,C0701,C1701 | C0701 | 223 | 1599 | drgdRslky | drgdGslky |
| KA3947 | SHROOM1 | 5 | 132159924 | C | T | A2301,A2402,B4101,B4901,C0701,C1701 | C0701 | 197 | 86 | tanNnipti | tanDnipti |
| KA3947 | DND1 | 5 | 140052407 | G | A | A2301,A2402,B4101,B4901,C0701,C1701 | C0701 | 299 | 21314 | dvyehqliL | dvyehqliP |

Figure 21 (Cont.)

| | | | | | | | | | | | |
|---|---|---|---|---|---|---|---|---|---|---|---|
| KA3947 | PCDHGA1 | 5 | 140711185 | T | C | A2301,A2402,B4101,B4901,C0701,C1701 | C0701 | 55 | 1993 | eHkmysmev | eYkmysmev |
| KA3947 | GPR151 | 5 | 145895564 | A | G | A2301,A2402,B4101,B4901,C0701,C1701 | C0701 | 365 | 1812 | wrtTipall | wrtIipall |
| KA3947 | SLIT3 | 5 | 168201261 | G | T | A2301,A2402,B4101,B4901,C0701,C1701 | C0701 | 21 | 5687 | aHlqsiqtl | aPlqsiqtl |
| KA3947 | F13A1 | 6 | 6251139 | C | T | A2301,A2402,B4101,B4901,C0701,C1701 | C0701 | 438 | 523 | nKkereeyv | nEkereeyv |
| KA3947 | TNXB | 6 | 32065869 | G | A | A2301,A2402,B4101,B4901,C0701,C1701 | C0701 | 467 | 8755 | srsnvtlpV | srsnvtlpA |
| KA3947 | DST | 6 | 56484355 | C | A | A2301,A2402,B4101,B4901,C0701,C1701 | C0701 | 135 | 177 | dritrShav | dritrAhav |
| KA3947 | MMS22L | 6 | 97720747 | C | A | A2301,A2402,B4101,B4901,C0701,C1701 | A2301 | 68 | 300 | vfifrylkL | vfifrylkV |
| KA3947 | MMS22L | 6 | 97720747 | C | A | A2301,A2402,B4101,B4901,C0701,C1701 | A2402 | 267 | 1046 | vfifrylkL | vfifrylkV |
| KA3947 | GRIK2 | 6 | 102247637 | G | A | A2301,A2402,B4101,B4901,C0701,C1701 | C0701 | 71 | 11912 | fRtrfmsli | fGtrfmsli |
| KA3947 | ADCYAP1R1 | 7 | 31144501 | T | A | A2301,A2402,B4101,B4901,C0701,C1701 | A2301 | 107 | 73 | fvvavHycf | fvvavLycf |
| KA3947 | PCLO | 7 | 82764062 | C | A | A2301,A2402,B4101,B4901,C0701,C1701 | A2301 | 135 | 269 | lfgfVasif | lfgfGasif |
| KA3947 | PCLO | 7 | 82764062 | C | A | A2301,A2402,B4101,B4901,C0701,C1701 | A2402 | 382 | 569 | lfgfVasif | lfgfGasif |
| KA3947 | PTPRZ1 | 7 | 121652320 | A | T | A2301,A2402,B4101,B4901,C0701,C1701 | C0701 | 121 | 94 | nLydnvnkl | nMydnvnkl |
| KA3947 | GRM8 | 7 | 126746744 | G | T | A2301,A2402,B4101,B4901,C0701,C1701 | A2402 | 463 | 308 | syaYtapel | syaStapel |
| KA3947 | DPP6 | 7 | 154561281 | G | T | A2301,A2402,B4101,B4901,C0701,C1701 | C0701 | 436 | 776 | yhypNagse | yhypKagse |
| KA3947 | VPS13B | 8 | 100147871 | C | G | A2301,A2402,B4101,B4901,C0701,C1701 | A2301 | 472 | 290 | Ltyltnsif | Ftyltnsif |
| KA3947 | DCSTAMP | 8 | 105367202 | C | T | A2301,A2402,B4101,B4901,C0701,C1701 | A2301 | 406 | 504 | Iwvplsvil | Twvplsvil |
| KA3947 | EQTN | 9 | 27284936 | G | A | A2301,A2402,B4101,B4901,C0701,C1701 | C0701 | 305 | 454 | sqysvnSel | sqysvnPel |
| KA3947 | TGFBR1 | 9 | 101908834 | G | C | A2301,A2402,B4101,B4901,C0701,C1701 | A2301 | 298 | 3013 | Hiyamglvf | Diyamglvf |
| KA3947 | TGFBR1 | 9 | 101908834 | G | C | A2301,A2402,B4101,B4901,C0701,C1701 | C0701 | 407 | 2364 | fkraHiyam | fkraDiyam |
| KA3947 | SCAI | 9 | 127733725 | C | G | A2301,A2402,B4101,B4901,C0701,C1701 | A2301 | 130 | 211 | ffAdeflrl | ffGdeflrl |
| KA3947 | SCAI | 9 | 127733725 | C | G | A2301,A2402,B4101,B4901,C0701,C1701 | C0701 | 230 | 1396 | fAdeflrll | fGdeflrll |
| KA3947 | ZCCHC5 | X | 77912546 | A | T | A2301,A2402,B4101,B4901,C0701,C1701 | C0701 | 393 | 1291 | ghfardSpv | ghfardCpv |

Figure 21 (Cont.)

| | | | | | | | | | | | |
|---|---|---|---|---|---|---|---|---|---|---|---|
| KA3947 | F8 | X | 154221251 | C | G | A2301,A2402,B4101,B4901,C0701,C1701 | C0701 | 439 | 57 | shvdlvkdF | shvdlvkdL |
| LO3793 | EPHA2 | 1 | 16482387 | C | A | A0321,A0201,A0301,B2705,B4901,C0102,C0701 | A0201 | 200 | 45 | allLgcala | allWgcala |
| LO3793 | EPHA2 | 1 | 16482387 | C | A | A0321,A0201,A0301,B2705,B4901,C0102,C0701 | A0201 | 47 | 25 | llLgcalaa | llWgcalaa |
| LO3793 | EPHA2 | 1 | 16482387 | C | A | A0321,A0201,A0301,B2705,B4901,C0102,C0701 | A0201 | 134 | 13417 | lLgcalaaa | lWgcalaaa |
| LO3793 | EPHA2 | 1 | 16482387 | C | A | A0321,A0201,A0301,B2705,B4901,C0102,C0701 | B2705 | 32 | 458 | aracfallL | aracfallW |
| LO3793 | EPHA2 | 1 | 16482387 | C | A | A0321,A0201,A0301,B2705,B4901,C0102,C0701 | C0701 | 413 | 13555 | aracfallL | aracfallW |
| LO3793 | RNPEP | 1 | 201952182 | T | A | A0321,A0201,A0301,B2705,B4901,C0102,C0701 | C0701 | 94 | 462 | Sraaerlqv | Craaerlqv |
| LO3793 | TRIM17 | 1 | 228596323 | G | A | A0321,A0201,A0301,B2705,B4901,C0102,C0701 | A0201 | 264 | 22183 | yLcavgqta | yPcavgqta |
| LO3793 | ZSWIM8 | 10 | 75560799 | G | A | A0321,A0201,A0301,B2705,B4901,C0102,C0701 | A0301 | 57 | 70 | hqfYvgaak | hqfCvgaak |
| LO3793 | ZSWIM8 | 10 | 75560799 | G | A | A0321,A0201,A0301,B2705,B4901,C0102,C0701 | B2705 | 324 | 485 | hqfYvgaak | hqfCvgaak |
| LO3793 | CPEB3 | 10 | 93851668 | C | T | A0321,A0201,A0301,B2705,B4901,C0102,C0701 | A0201 | 202 | 487 | nlsdsNfvm | nlsdsDfvm |
| LO3793 | PTPMT1 | 11 | 47587286 | T | A | A0321,A0201,A0301,B2705,B4901,C0102,C0701 | C0701 | 9 | 17 | ahrdwNhri | ahrdwYhri |
| LO3793 | PTPMT1 | 11 | 47587286 | T | A | A0321,A0201,A0301,B2705,B4901,C0102,C0701 | C0701 | 122 | 35 | Nhridptvl | Yhridptvl |
| LO3793 | LRFN4 | 11 | 66626173 | C | T | A0321,A0201,A0301,B2705,B4901,C0102,C0701 | A0201 | 238 | 8199 | wvgpddWlv | wvgpddRlv |
| LO3793 | PITPNM1 | 11 | 67265144 | C | G | A0321,A0201,A0301,B2705,B4901,C0102,C0701 | B2705 | 176 | 240 | rrgsmnnQl | rrgsmnnEl |
| LO3793 | PITPNM1 | 11 | 67265144 | C | G | A0321,A0201,A0301,B2705,B4901,C0102,C0701 | C0701 | 125 | 68 | rrgsmnnQl | rrgsmnnEl |
| LO3793 | TMEM126A | 11 | 85365201 | A | C | A0321,A0201,A0301,B2705,B4901,C0102,C0701 | B2705 | 84 | 126 | frrilnvPk | frrilnvTk |
| LO3793 | TMEM126A | 11 | 85365201 | A | C | A0321,A0201,A0301,B2705,B4901,C0102,C0701 | B2705 | 75 | 68 | rrilnvPka | rrilnvTka |
| LO3793 | OTOGL | 12 | 80730229 | C | T | A0321,A0201,A0301,B2705,B4901,C0102,C0701 | A0201 | 11 | 99 | mlselsiil | mlselsiiT |
| LO3793 | OTOGL | 12 | 80730229 | C | T | A0321,A0201,A0301,B2705,B4901,C0102,C0701 | A0201 | 293 | 1586 | ilfdgnnaa | iTfdgnnaa |
| LO3793 | TBX3 | 12 | 115112106 | G | A | A0321,A0201,A0301,B2705,B4901,C0102,C0701 | A0201 | 24 | 22 | gmgpllaMv | gmgpllaTv |
| LO3793 | TBX3 | 12 | 115112106 | G | A | A0321,A0201,A0301,B2705,B4901,C0102,C0701 | A0201 | 153 | 1622 | Mvsgastgv | Tvsgastgv |

Figure 21 (Cont.)

| | | | | | | | | | | | |
|---|---|---|---|---|---|---|---|---|---|---|---|
| LO3793 | FRY | 13 | 32802623 | C | T | A0321,A0201,A0301,B2705,B4901,C0102,C0701 | C0701 | 236 | 155 | lredqLspv | lredqSspv |
| LO3793 | DNAAF2 | 14 | 50101660 | C | T | A0321,A0201,A0301,B2705,B4901,C0102,C0701 | A0201 | 57 | 1284 | fMhpepghv | fVhpepghv |
| LO3793 | DNAAF2 | 14 | 50101660 | C | T | A0321,A0201,A0301,B2705,B4901,C0102,C0701 | C0701 | 19 | 32 | Mhpepghvl | Vhpepghvl |
| LO3793 | GALC | 14 | 88450794 | C | A | A0321,A0201,A0301,B2705,B4901,C0102,C0701 | A0201 | 199 | 28 | lqltayyvL | lqltayyvV |
| LO3793 | GALC | 14 | 88450794 | C | A | A0321,A0201,A0301,B2705,B4901,C0102,C0701 | A0201 | 15 | 51 | yvLtwivga | yvVtwivga |
| LO3793 | GALC | 14 | 88450794 | C | A | A0321,A0201,A0301,B2705,B4901,C0102,C0701 | A0301 | 46 | 156 | vLtwivgak | vVtwivgak |
| LO3793 | FURIN | 15 | 91419010 | A | G | A0321,A0201,A0301,B2705,B4901,C0102,C0701 | A0201 | 28 | 101 | wllwvvaaA | wllwvvaaT |
| LO3793 | TSC2 | 16 | 2108843 | C | T | A0321,A0201,A0301,B2705,B4901,C0102,C0701 | A0201 | 161 | 295 | slrnLptsv | slrnSptsv |
| LO3793 | TSC2 | 16 | 2108843 | C | T | A0321,A0201,A0301,B2705,B4901,C0102,C0701 | B2705 | 112 | 2827 | hrlyslrnL | hrlyslrnS |
| LO3793 | TSC2 | 16 | 2108843 | C | T | A0321,A0201,A0301,B2705,B4901,C0102,C0701 | C0701 | 375 | 70 | lrnLptsvl | lrnSptsvl |
| LO3793 | TBC1D10B | 16 | 30371148 | T | C | A0321,A0201,A0301,B2705,B4901,C0102,C0701 | B2705 | 285 | 46 | Crilkayti | Yrilkayti |
| LO3793 | ARMC5 | 16 | 31477459 | C | T | A0321,A0201,A0301,B2705,B4901,C0102,C0701 | A0201 | 433 | 166 | llValtrpa | llAaltrpa |
| LO3793 | ARMC5 | 16 | 31477459 | C | T | A0321,A0201,A0301,B2705,B4901,C0102,C0701 | A0301 | 87 | 203 | rlllValtr | rlllAaltr |
| LO3793 | SLC9A5 | 16 | 67283051 | A | G | A0321,A0201,A0301,B2705,B4901,C0102,C0701 | B2705 | 447 | 630 | frwqwhevG | frwqwhevE |
| LO3793 | SLC9A5 | 16 | 67283051 | A | G | A0321,A0201,A0301,B2705,B4901,C0102,C0701 | C0701 | 216 | 249 | whevGapyl | whevEapyl |
| LO3793 | RLTPR | 16 | 67682112 | C | T | A0321,A0201,A0301,B2705,B4901,C0102,C0701 | B2705 | 466 | 883 | grgglgppV | grgglgppA |
| LO3793 | NF1 | 17 | 29533379 | G | A | A0321,A0201,A0301,B2705,B4901,C0102,C0701 | A0301 | 34 | 21 | Qmapsltfk | Rmapsltfk |
| LO3793 | MPP3 | 17 | 41903192 | C | G | A0321,A0201,A0301,B2705,B4901,C0102,C0701 | A0201 | 163 | 1050 | glvhvgHel | glvhvgDel |
| LO3793 | NFIC | 19 | 3456589 | G | T | A0321,A0201,A0301,B2705,B4901,C0102,C0701 | A0301 | 327 | 365 | rsfLglgpr | rsfVglgpr |
| LO3793 | KCNJ14 | 19 | 48965488 | G | T | A0321,A0201,A0301,B2705,B4901,C0102,C0701 | A0201 | 487 | 406 | vlHciagcv | vlQciagcv |
| LO3793 | RFPL4AL1 | 19 | 56284090 | G | A | A0321,A0201,A0301,B2705,B4901,C0102,C0701 | C0701 | 18 | 22 | erfdtTlcv | erfdtAlcv |
| LO3793 | AUP1 | 2 | 74755971 | C | A | A0321,A0201,A0301,B2705,B4901,C0102,C0701 | A0201 | 119 | 17577 | klfcastrl | kRfcastrl |
| LO3793 | MRPL19 | 2 | 75873993 | A | T | A0321,A0201,A0301,B2705,B4901,C0102,C0701 | C0701 | 488 | 15358 | fHaartllp | fQaartllp |

Figure 21 (Cont.)

| | | | | | | | | | | | |
|---|---|---|---|---|---|---|---|---|---|---|---|
| LO3793 | CHD6 | 20 | 40033762 | G | A | A0321,A0201,A0301,B2705,B4901,C0102,C0701 | A0201 | 230 | 917 | gllsLpmat | gllsPpmat |
| LO3793 | THOC5 | 22 | 29916996 | T | G | A0321,A0201,A0301,B2705,B4901,C0102,C0701 | A0201 | 257 | 83 | yqfAkvgil | yqfDkvgil |
| LO3793 | THOC5 | 22 | 29916996 | T | G | A0321,A0201,A0301,B2705,B4901,C0102,C0701 | C0701 | 362 | 78 | yqfAkvgil | yqfDkvgil |
| LO3793 | TIMP3 | 22 | 33198006 | C | T | A0321,A0201,A0301,B2705,B4901,C0102,C0701 | A0201 | 285 | 1346 | mtpwlgFiv | mtpwlgLiv |
| LO3793 | OXNAD1 | 3 | 16343351 | A | C | A0321,A0201,A0301,B2705,B4901,C0102,C0701 | C0701 | 87 | 216 | ysaNntsel | ysaKntsel |
| LO3793 | OXNAD1 | 3 | 16343351 | A | C | A0321,A0201,A0301,B2705,B4901,C0102,C0701 | C0701 | 274 | 652 | saNntsell | saKntsell |
| LO3793 | CEP70 | 3 | 138256148 | T | A | A0321,A0201,A0301,B2705,B4901,C0102,C0701 | C0701 | 112 | 77 | krteqDeti | krteqEeti |
| LO3793 | TBL1XR1 | 3 | 176744214 | C | A | A0321,A0201,A0301,B2705,B4901,C0102,C0701 | A0201 | 14 | 20 | gifeFcwna | gifeVcwna |
| LO3793 | PIK3CA | 3 | 178916876 | G | A | A0321,A0201,A0301,B2705,B4901,C0102,C0701 | B2705 | 254 | 24 | rQlcdlrlf | rRlcdlrlf |
| LO3793 | PIK3CA | 3 | 178916876 | G | A | A0321,A0201,A0301,B2705,B4901,C0102,C0701 | C0701 | 396 | 436 | effdetrQl | effdetrRl |
| LO3793 | PIK3CA | 3 | 178916876 | G | A | A0321,A0201,A0301,B2705,B4901,C0102,C0701 | C0701 | 178 | 136 | trQlcdlrl | trRlcdlrl |
| LO3793 | CKMT2 | 5 | 80546986 | G | A | A0321,A0201,A0301,B2705,B4901,C0102,C0701 | A0201 | 95 | 227 | lltgHnasl | lltgRnasl |
| LO3793 | PCDHB6 | 5 | 140532003 | G | A | A0321,A0201,A0301,B2705,B4901,C0102,C0701 | B2705 | 187 | 286 | sraasvgHy | sraasvgRy |
| LO3793 | HIST1H3I | 6 | 27840080 | T | A | A0321,A0201,A0301,B2705,B4901,C0102,C0701 | B2705 | 428 | 439 | artMqtark | artKqtark |
| LO3793 | SCUBE3 | 6 | 35182254 | C | T | A0321,A0201,A0301,B2705,B4901,C0102,C0701 | A0201 | 451 | 4659 | lvllvharV | lvllvharA |
| LO3793 | FANCE | 6 | 35426164 | G | A | A0321,A0201,A0301,B2705,B4901,C0102,C0701 | A0201 | 8 | 28 | wllalspNl | wllalspDl |
| LO3793 | FANCE | 6 | 35426164 | G | A | A0321,A0201,A0301,B2705,B4901,C0102,C0701 | A0201 | 144 | 5165 | Nlslsnatv | Dlslsnatv |
| LO3793 | ETV7 | 6 | 36339119 | C | A | A0321,A0201,A0301,B2705,B4901,C0102,C0701 | C0701 | 225 | 373 | Criadcrll | Griadcrll |
| LO3793 | MAP3K4 | 6 | 161505534 | G | C | A0321,A0201,A0301,B2705,B4901,C0102,C0701 | A0201 | 19 | 26 | klfcHiagm | klfcDiagm |
| LO3793 | FAM120B | 6 | 170639565 | G | T | A0321,A0201,A0301,B2705,B4901,C0102,C0701 | A0201 | 22 | 23 | clavNewfv | clavKewfv |
| LO3793 | GPER1 | 7 | 1131828 | G | A | A0321,A0201,A0301,B2705,B4901,C0102,C0701 | A0201 | 356 | 818 | msfdHyial | msfdRyial |
| LO3793 | GPER1 | 7 | 1131828 | G | A | A0321,A0201,A0301,B2705,B4901,C0102,C0701 | C0701 | 246 | 251 | msfdHyial | msfdRyial |

Figure 21 (Cont.)

| | | | | | | | | | | | |
|---|---|---|---|---|---|---|---|---|---|---|---|
| LO3793 | GHRHR | 7 | 31010781 | C | A | A0321,A0201,A0301,B2705,B4901,C0102,C0701 | A0201 | 302 | 151 | Risivalfv | Sisivalfv |
| LO3793 | GHRHR | 7 | 31010781 | C | A | A0321,A0201,A0301,B2705,B4901,C0102,C0701 | B2705 | 34 | 10052 | hRisivalf | hSisivalf |
| LO3793 | SHB | 9 | 38068108 | T | C | A0321,A0201,A0301,B2705,B4901,C0102,C0701 | A0301 | 192 | 147 | Vspkhrlik | Ispkhrlik |
| LO3793 | SHB | 9 | 38068108 | T | C | A0321,A0201,A0301,B2705,B4901,C0102,C0701 | B2705 | 357 | 581 | vryVspkhr | vryIspkhr |
| LO3793 | SHB | 9 | 38068108 | T | C | A0321,A0201,A0301,B2705,B4901,C0102,C0701 | C0701 | 69 | 127 | yVspkhrli | yIspkhrli |
| LO3793 | CLCN4 | X | 10162963 | G | T | A0321,A0201,A0301,B2705,B4901,C0102,C0701 | A0201 | 10 | 4509 | gllagtlaV | gllagtlaG |
| LO3793 | CLCN4 | X | 10162963 | G | T | A0321,A0201,A0301,B2705,B4901,C0102,C0701 | A0201 | 24 | 14 | llagtlaVv | llagtlaGv |
| LO3793 | TMEM255A | X | 119445152 | G | T | A0321,A0201,A0301,B2705,B4901,C0102,C0701 | C0701 | 456 | 861 | mhqsMtqqr | mhqsLtqqr |
| LO5004 | TMEM53 | 1 | 45125913 | A | G | A0201,A2601,B3801,B5501,C0303,C1203 | B3801 | 212 | 483 | trqpvvTll | trqpvvill |
| LO5004 | TMEM53 | 1 | 45125913 | A | G | A0201,A2601,B3801,B5501,C0303,C1203 | C1203 | 174 | 639 | etrqpvvTl | etrqpvvil |
| LO5004 | PDE4DIP | 1 | 144852477 | G | A | A0201,A2601,B3801,B5501,C0303,C1203 | C0303 | 14 | 6 | ralLctpal | ralPctpal |
| LO5004 | PDE4DIP | 1 | 144852477 | G | A | A0201,A2601,B3801,B5501,C0303,C1203 | C1203 | 223 | 20 | ralLctpal | ralPctpal |
| LO5004 | KDM5B | 1 | 202718159 | C | G | A0201,A2601,B3801,B5501,C0303,C1203 | C1203 | 147 | 176 | kadvlHvvv | kadvlDvvv |
| LO5004 | OBSCN | 1 | 228404201 | G | T | A0201,A2601,B3801,B5501,C0303,C1203 | A0201 | 58 | 207 | rlheeaHll | rlheeaQll |
| LO5004 | FAM89A | 1 | 231175815 | C | T | A0201,A2601,B3801,B5501,C0303,C1203 | C0303 | 13 | 12 | gasggwQhl | gasggwRhl |
| LO5004 | FAM89A | 1 | 231175815 | C | T | A0201,A2601,B3801,B5501,C0303,C1203 | C1203 | 286 | 343 | gasggwQhl | gasggwRhl |
| LO5004 | FBXO18 | 10 | 5948524 | C | T | A0201,A2601,B3801,B5501,C0303,C1203 | C0303 | 2 | 2 | faflSvedl | faflPvedl |
| LO5004 | FBXO18 | 10 | 5948524 | C | T | A0201,A2601,B3801,B5501,C0303,C1203 | C1203 | 27 | 25 | faflSvedl | faflPvedl |
| LO5004 | CACNB2 | 10 | 18429712 | C | T | A0201,A2601,B3801,B5501,C0303,C1203 | C0303 | 67 | 31 | aaaVvaqei | aaaAvaqei |
| LO5004 | CACNB2 | 10 | 18429712 | C | T | A0201,A2601,B3801,B5501,C0303,C1203 | C0303 | 384 | 12 | aVvaqeiqm | aAvaqeiqm |
| LO5004 | CACNB2 | 10 | 18429712 | C | T | A0201,A2601,B3801,B5501,C0303,C1203 | C1203 | 381 | 14710 | kspptaaaV | kspptaaaA |
| LO5004 | TOLLIP | 11 | 1307307 | T | C | A0201,A2601,B3801,B5501,C0303,C1203 | A0201 | 385 | 296 | allpaaVvm | allpaaMvm |
| LO5004 | TOLLIP | 11 | 1307307 | T | C | A0201,A2601,B3801,B5501,C0303,C1203 | A0201 | 260 | 57 | Vvmppqpvv | Mvmppqpvv |

Figure 21 (Cont.)

| | | | | | | | | | | | |
|---|---|---|---|---|---|---|---|---|---|---|---|
| LO5004 | TOLLIP | 11 | 1307307 | T | C | A0201,A2601,B3801,B5501,C0303,C1203 | C0303 | 4 | 5 | yallpaaVv | yallpaaMv |
| LO5004 | TOLLIP | 11 | 1307307 | T | C | A0201,A2601,B3801,B5501,C0303,C1203 | C0303 | 78 | 78 | allpaaVvm | allpaaMvm |
| LO5004 | TOLLIP | 11 | 1307307 | T | C | A0201,A2601,B3801,B5501,C0303,C1203 | C0303 | 291 | 1257 | aVvmppqpv | aMvmppqpv |
| LO5004 | TOLLIP | 11 | 1307307 | T | C | A0201,A2601,B3801,B5501,C0303,C1203 | C0303 | 99 | 108 | Vvmppqpvv | Mvmppqpvv |
| LO5004 | TOLLIP | 11 | 1307307 | T | C | A0201,A2601,B3801,B5501,C0303,C1203 | C1203 | 4 | 5 | yallpaaVv | yallpaaMv |
| LO5004 | TOLLIP | 11 | 1307307 | T | C | A0201,A2601,B3801,B5501,C0303,C1203 | C1203 | 71 | 30 | Vvmppqpvv | Mvmppqpvv |
| LO5004 | OR51F2 | 11 | 4843274 | C | A | A0201,A2601,B3801,B5501,C0303,C1203 | A0201 | 209 | 204 | glfallsNt | glfallsTt |
| LO5004 | OR51F2 | 11 | 4843274 | C | A | A0201,A2601,B3801,B5501,C0303,C1203 | C0303 | 4 | 4 | fallsNtgf | fallsTtgf |
| LO5004 | OR51F2 | 11 | 4843274 | C | A | A0201,A2601,B3801,B5501,C0303,C1203 | C1203 | 420 | 179 | fallsNtgf | fallsTtgf |
| LO5004 | USH1C | 11 | 17546009 | C | A | A0201,A2601,B3801,B5501,C0303,C1203 | C0303 | 412 | 334 | gslsaeLgl | gslsaeVgl |
| LO5004 | USH1C | 11 | 17546009 | C | A | A0201,A2601,B3801,B5501,C0303,C1203 | C1203 | 117 | 102 | lsaeLglei | lsaeVglei |
| LO5004 | KRAS | 12 | 25398285 | C | A | A0201,A2601,B3801,B5501,C0303,C1203 | C0303 | 399 | 1328 | lvvvgaCgv | lvvvgaGgv |
| LO5004 | RACGAP1 | 12 | 50388220 | T | C | A0201,A2601,B3801,B5501,C0303,C1203 | A0201 | 99 | 764 | ivvhcvneV | ivvhcvneI |
| LO5004 | RACGAP1 | 12 | 50388220 | T | C | A0201,A2601,B3801,B5501,C0303,C1203 | C1203 | 41 | 40 | ivvhcvneV | ivvhcvneI |
| LO5004 | ITGB7 | 12 | 53591674 | G | T | A0201,A2601,B3801,B5501,C0303,C1203 | C0303 | 23 | 92 | ellDrgcpl | ellArgcpl |
| LO5004 | MYO5A | 15 | 52638577 | C | T | A0201,A2601,B3801,B5501,C0303,C1203 | A2601 | 303 | 232 | eiaqayiSl | eiaqayiGl |
| LO5004 | MYO5A | 15 | 52638577 | C | T | A0201,A2601,B3801,B5501,C0303,C1203 | C0303 | 478 | 1287 | eiaqayiSl | eiaqayiGl |
| LO5004 | MYO5A | 15 | 52638577 | C | T | A0201,A2601,B3801,B5501,C0303,C1203 | C0303 | 106 | 638 | iSlketnrl | iGlketnrl |
| LO5004 | MYO5A | 15 | 52638577 | C | T | A0201,A2601,B3801,B5501,C0303,C1203 | C1203 | 476 | 3359 | iSlketnrl | iGlketnrl |
| LO5004 | CCDC33 | 15 | 74588221 | G | T | A0201,A2601,B3801,B5501,C0303,C1203 | A2601 | 345 | 2316 | dtvsstmYl | dtvsstmDl |
| LO5004 | UNKL | 16 | 1417098 | C | T | A0201,A2601,B3801,B5501,C0303,C1203 | A0201 | 156 | 73 | avNgvifql | avDgvifql |
| LO5004 | EARS2 | 16 | 23568654 | A | G | A0201,A2601,B3801,B5501,C0303,C1203 | C0303 | 5 | 14 | maaPlrrll | maaLlrrll |

Figure 21 (Cont.)

| | | | | | | | | | | | |
|---|---|---|---|---|---|---|---|---|---|---|---|
| LO5004 | EARS2 | 16 | 23568654 | A | G | A0201,A2601,B3801,B5501,C0303,C1203 | C1203 | 19 | 229 | maaPlrrll | maaLlrrll |
| LO5004 | HIC1 | 17 | 1961887 | C | A | A0201,A2601,B3801,B5501,C0303,C1203 | A0201 | 95 | 185 | Sltaeqlsl | Rltaeqlsl |
| LO5004 | HIC1 | 17 | 1961887 | C | A | A0201,A2601,B3801,B5501,C0303,C1203 | C0303 | 484 | 1095 | egvfavaSl | egvfavaRl |
| LO5004 | HIC1 | 17 | 1961887 | C | A | A0201,A2601,B3801,B5501,C0303,C1203 | C0303 | 27 | 43 | favaSltae | favaRltae |
| LO5004 | HIC1 | 17 | 1961887 | C | A | A0201,A2601,B3801,B5501,C0303,C1203 | C0303 | 10 | 110 | vaSltaeql | vaRltaeql |
| LO5004 | ERN1 | 17 | 62207346 | G | A | A0201,A2601,B3801,B5501,C0303,C1203 | A0201 | 99 | 7774 | lllltlllL | lllltlllP |
| LO5004 | ERN1 | 17 | 62207346 | G | A | A0201,A2601,B3801,B5501,C0303,C1203 | A0201 | 147 | 45 | lltlllLgl | lltlllPgl |
| LO5004 | TBC1D16 | 17 | 77918856 | G | A | A0201,A2601,B3801,B5501,C0303,C1203 | A0201 | 159 | 4467 | Yvrfyqhlv | Hvrfyqhlv |
| LO5004 | TBC1D16 | 17 | 77918856 | G | A | A0201,A2601,B3801,B5501,C0303,C1203 | C1203 | 173 | 3226 | Yvrfyqhlv | Hvrfyqhlv |
| LO5004 | FCER2 | 19 | 7761759 | G | T | A0201,A2601,B3801,B5501,C0303,C1203 | C1203 | 40 | 182 | easdllerl | easdllerL |
| LO5004 | FBN3 | 19 | 8150297 | G | A | A0201,A2601,B3801,B5501,C0303,C1203 | C1203 | 115 | 286 | cplpgtsVy | cplpgtsAy |
| LO5004 | LILRA6 | 19 | 54745646 | A | T | A0201,A2601,B3801,B5501,C0303,C1203 | C0303 | 287 | 270 | kgyhQfvlm | kgyhHfvlm |
| LO5004 | MZT2A | 2 | 132249862 | T | C | A0201,A2601,B3801,B5501,C0303,C1203 | C0303 | 6 | 5 | lalrrEkvl | lalrrKkvl |
| LO5004 | MZT2A | 2 | 132249862 | T | C | A0201,A2601,B3801,B5501,C0303,C1203 | C1203 | 36 | 32 | lalrrEkvl | lalrrKkvl |
| LO5004 | SPEG | 2 | 220300049 | C | A | A0201,A2601,B3801,B5501,C0303,C1203 | B3801 | 320 | 1323 | grDsceavl | grAsceavl |
| LO5004 | SPEG | 2 | 220300049 | C | A | A0201,A2601,B3801,B5501,C0303,C1203 | C1203 | 16 | 106 | Dsceavltv | Asceavltv |
| LO5004 | BLCAP | 20 | 36147433 | C | A | A0201,A2601,B3801,B5501,C0303,C1203 | A0201 | 211 | 384 | ticaFvfla | ticaLvfla |
| LO5004 | BLCAP | 20 | 36147433 | C | A | A0201,A2601,B3801,B5501,C0303,C1203 | A0201 | 66 | 476 | Fvflaalfl | Lvflaalfl |
| LO5004 | BLCAP | 20 | 36147433 | C | A | A0201,A2601,B3801,B5501,C0303,C1203 | C0303 | 149 | 645 | cticaFvfl | cticaLvfl |
| LO5004 | BLCAP | 20 | 36147433 | C | A | A0201,A2601,B3801,B5501,C0303,C1203 | C0303 | 89 | 55 | caFvflaal | caLvflaal |
| LO5004 | BLCAP | 20 | 36147433 | C | A | A0201,A2601,B3801,B5501,C0303,C1203 | C0303 | 7 | 56 | Fvflaalfl | Lvflaalfl |
| LO5004 | BLCAP | 20 | 36147433 | C | A | A0201,A2601,B3801,B5501,C0303,C1203 | C1203 | 67 | 262 | caFvflaal | caLvflaal |
| LO5004 | BLCAP | 20 | 36147433 | C | A | A0201,A2601,B3801,B5501,C0303,C1203 | C1203 | 52 | 667 | Fvflaalfl | Lvflaalfl |

Figure 21 (Cont.)

| | | | | | | | | | | | |
|---|---|---|---|---|---|---|---|---|---|---|---|
| LO5004 | ABHD16B | 20 | 62493887 | C | T | A0201,A2601,B3801,B5501,C0303,C1203 | C0303 | 154 | 248 | stsgrlCpl | stsgrlRpl |
| LO5004 | DERL3 | 22 | 24180796 | A | G | A0201,A2601,B3801,B5501,C0303,C1203 | C0303 | 284 | 1081 | tnflSfgpl | tnflFfgpl |
| LO5004 | SGSM1 | 22 | 25282618 | C | A | A0201,A2601,B3801,B5501,C0303,C1203 | C1203 | 170 | 222 | iqTeirkav | iqPeirkav |
| LO5004 | USP19 | 3 | 49146542 | C | A | A0201,A2601,B3801,B5501,C0303,C1203 | C1203 | 131 | 639 | Vpqdwvgpl | Gpqdwvgpl |
| LO5004 | DGKQ | 4 | 960816 | C | A | A0201,A2601,B3801,B5501,C0303,C1203 | A0201 | 115 | 258 | gvayvsvLv | gvayvsvRv |
| LO5004 | DGKQ | 4 | 960816 | C | A | A0201,A2601,B3801,B5501,C0303,C1203 | C0303 | 45 | 22817 | vgvayvsvL | vgvayvsvR |
| LO5004 | DGKQ | 4 | 960816 | C | A | A0201,A2601,B3801,B5501,C0303,C1203 | C0303 | 195 | 74 | vayvsvLvt | vayvsvRvt |
| LO5004 | DGKQ | 4 | 960816 | C | A | A0201,A2601,B3801,B5501,C0303,C1203 | C1203 | 112 | 84 | vayvsvLvt | vayvsvRvt |
| LO5004 | LRPAP1 | 4 | 3517916 | T | C | A0201,A2601,B3801,B5501,C0303,C1203 | C0303 | 142 | 130 | feGprvidl | feEprvidl |
| LO5004 | LRPAP1 | 4 | 3517916 | T | C | A0201,A2601,B3801,B5501,C0303,C1203 | C1203 | 56 | 125 | aefeGprvi | aefeEprvi |
| LO5004 | WDFY3 | 4 | 85654578 | T | C | A0201,A2601,B3801,B5501,C0303,C1203 | A0201 | 222 | 81 | mfynRypyv | mfynHypyv |
| LO5004 | WDFY3 | 4 | 85654578 | T | C | A0201,A2601,B3801,B5501,C0303,C1203 | C1203 | 251 | 502 | dmfynRypy | dmfynHypy |
| LO5004 | WDFY3 | 4 | 85654578 | T | C | A0201,A2601,B3801,B5501,C0303,C1203 | C1203 | 61 | 47 | mfynRypyv | mfynHypyv |
| LO5004 | WWC2 | 4 | 184161411 | C | A | A0201,A2601,B3801,B5501,C0303,C1203 | C1203 | 466 | 437 | qgfetlKqi | qgfetlQqi |
| LO5004 | KIAA0947 | 5 | 5443315 | A | G | A0201,A2601,B3801,B5501,C0303,C1203 | A2601 | 299 | 414 | dthqGyarv | dthqEyarv |
| LO5004 | KIAA0947 | 5 | 5443315 | A | G | A0201,A2601,B3801,B5501,C0303,C1203 | C1203 | 371 | 863 | dthqGyarv | dthqEyarv |
| LO5004 | FBXL7 | 5 | 15928056 | C | T | A0201,A2601,B3801,B5501,C0303,C1203 | C0303 | 491 | 344 | palicpLnl | palicpPnl |
| LO5004 | DOCK2 | 5 | 169446111 | A | G | A0201,A2601,B3801,B5501,C0303,C1203 | C1203 | 390 | 312 | kRfeneill | kKfeneill |
| LO5004 | KIAA1244 | 6 | 138642316 | G | A | A0201,A2601,B3801,B5501,C0303,C1203 | C1203 | 312 | 176 | cvTkpteti | cvAkpteti |
| LO5004 | CAMK2B | 7 | 44269098 | G | T | A0201,A2601,B3801,B5501,C0303,C1203 | C1203 | 204 | 258 | kaTrvpdil | kaPrvpdil |
| LO5004 | PTPRN2 | 7 | 157903551 | T | C | A0201,A2601,B3801,B5501,C0303,C1203 | A0201 | 300 | 205 | rllRvpssa | rllQvpssa |
| LO5004 | KBTBD11 | 8 | 1950710 | A | G | A0201,A2601,B3801,B5501,C0303,C1203 | C0303 | 5 | 18 | favahGatt | favahEatt |

Figure 21 (Cont.)

| | | | | | | | | | | | |
|---|---|---|---|---|---|---|---|---|---|---|---|
| LO5004 | KBTBD11 | 8 | 1950710 | A | G | A0201,A2601,B3801,B5501,C0303,C1203 | C1203 | 19 | 38 | favahGatt | favahEatt |
| LO5004 | GPSM1 | 9 | 139235352 | C | T | A0201,A2601,B3801,B5501,C0303,C1203 | C0303 | 35 | 60 | Marmnvaql | Tarmnvaql |
| LO5004 | GPSM1 | 9 | 139235352 | C | T | A0201,A2601,B3801,B5501,C0303,C1203 | C1203 | 41 | 213 | Marmnvaql | Tarmnvaql |
| LO5004 | SEC16A | 9 | 139354519 | G | T | A0201,A2601,B3801,B5501,C0303,C1203 | A0201 | 248 | 131 | qlmYgrmpa | qlmSgrmpa |
| LO5004 | SEC16A | 9 | 139354519 | G | T | A0201,A2601,B3801,B5501,C0303,C1203 | A0201 | 19 | 113 | lmYgrmpaa | lmSgrmpaa |
| M4945 | DRAXIN | 1 | 11766544 | G | T | A0201,A3001,B1302,B4403,C0602,C1602 | A0201 | 377 | 2584 | sqaqYgavv | sqaqDgavv |
| M4945 | DRAXIN | 1 | 11766544 | G | T | A0201,A3001,B1302,B4403,C0602,C1602 | A0201 | 479 | 2139 | aqYgavvta | aqDgavvta |
| M4945 | SYTL1 | 1 | 27679820 | G | T | A0201,A3001,B1302,B4403,C0602,C1602 | A3001 | 6 | 31 | asrqrtrFv | asrqrtrVv |
| M4945 | SYTL1 | 1 | 27679820 | G | T | A0201,A3001,B1302,B4403,C0602,C1602 | A3001 | 58 | 131 | rqrtrFvrr | rqrtrVvrr |
| M4945 | SYTL1 | 1 | 27679820 | G | T | A0201,A3001,B1302,B4403,C0602,C1602 | A3001 | 3 | 3 | rtrFvrrsl | rtrVvrrsl |
| M4945 | SYTL1 | 1 | 27679820 | G | T | A0201,A3001,B1302,B4403,C0602,C1602 | A3001 | 221 | 22 | Fvrrslspv | Vvrrslspv |
| M4945 | SYTL1 | 1 | 27679820 | G | T | A0201,A3001,B1302,B4403,C0602,C1602 | C0602 | 260 | 251 | asrqrtrFv | asrqrtrVv |
| M4945 | SYTL1 | 1 | 27679820 | G | T | A0201,A3001,B1302,B4403,C0602,C1602 | C0602 | 338 | 4725 | trFvrrsls | trVvrrsls |
| M4945 | PPP1R8 | 1 | 28157381 | C | T | A0201,A3001,B1302,B4403,C0602,C1602 | A0201 | 8 | 466 | Llfdcptwa | Plfdcptwa |
| M4945 | LCK | 1 | 32741252 | C | G | A0201,A3001,B1302,B4403,C0602,C1602 | A0201 | 139 | 450 | fliGesest | fliResest |
| M4945 | KIAA0319L | 1 | 35919190 | C | A | A0201,A3001,B1302,B4403,C0602,C1602 | A3001 | 209 | 560 | gskssddHk | gskssddQk |
| M4945 | HECTD3 | 1 | 45476222 | G | A | A0201,A3001,B1302,B4403,C0602,C1602 | C0602 | 8 | 36 | Frweqvvdl | Lrweqvvdl |
| M4945 | FAAH | 1 | 46860037 | T | C | A0201,A3001,B1302,B4403,C0602,C1602 | A0201 | 251 | 61 | vqyePwaal | vqyeLwaal |
| M4945 | ACOT11 | 1 | 55050466 | A | T | A0201,A3001,B1302,B4403,C0602,C1602 | C0602 | 136 | 184 | chSnqrgel | chTnqrgel |
| M4945 | DOCK7 | 1 | 63005260 | C | A | A0201,A3001,B1302,B4403,C0602,C1602 | A3001 | 10 | 2247 | mYrgfvfsl | mDrgfvfsl |
| M4945 | DOCK7 | 1 | 63005263 | T | A | A0201,A3001,B1302,B4403,C0602,C1602 | A0201 | 6 | 14 | flndllsvL | flndllsvM |
| M4945 | ACADM | 1 | 76211503 | G | T | A0201,A3001,B1302,B4403,C0602,C1602 | A3001 | 18 | 57 | kanwyflFa | kanwyflLa |
| M4945 | FAM69A | 1 | 93312753 | T | A | A0201,A3001,B1302,B4403,C0602,C1602 | A3001 | 32 | 40 | kfkemvFsl | kfkemvYsl |

Figure 21 (Cont.)

| | | | | | | | | | | | |
|---|---|---|---|---|---|---|---|---|---|---|---|
| M4945 | FAM69A | 1 | 93312753 | T | A | A0201,A3001,B1302,B4403,C0602,C1602 | A3001 | 89 | 197 | kemvFslfk | kemvYslfk |
| M4945 | FAM69A | 1 | 93312753 | T | A | A0201,A3001,B1302,B4403,C0602,C1602 | A3001 | 72 | 112 | mvFslfkak | mvYslfkak |
| M4945 | HSD3B2 | 1 | 119958098 | T | C | A0201,A3001,B1302,B4403,C0602,C1602 | A0201 | 204 | 183 | llgqriArl | llgqriVrl |
| M4945 | HSD3B2 | 1 | 119958098 | T | C | A0201,A3001,B1302,B4403,C0602,C1602 | A3001 | 28 | 71 | gqriArllv | gqriVrllv |
| M4945 | CGN | 1 | 151503189 | G | T | A0201,A3001,B1302,B4403,C0602,C1602 | A0201 | 41 | 325 | Fldrtvdrl | Lldrtvdrl |
| M4945 | CGN | 1 | 151503189 | G | T | A0201,A3001,B1302,B4403,C0602,C1602 | B4403 | 42 | 251 | aeleeqkrF | aeleeqkrL |
| M4945 | ATP8B2 | 1 | 154318891 | C | T | A0201,A3001,B1302,B4403,C0602,C1602 | A0201 | 68 | 40 | qlVdyqsfa | qlAdyqsfa |
| M4945 | ATP8B2 | 1 | 154318891 | C | T | A0201,A3001,B1302,B4403,C0602,C1602 | A0201 | 44 | 349 | lVdyqsfav | lAdyqsfav |
| M4945 | ATP8B2 | 1 | 154318891 | C | T | A0201,A3001,B1302,B4403,C0602,C1602 | C0602 | 15 | 431 | trddgtqlV | trddgtqlA |
| M4945 | SCYL3 | 1 | 169847812 | T | C | A0201,A3001,B1302,B4403,C0602,C1602 | A0201 | 145 | 19 | giCdillal | giYdillal |
| M4945 | PPFIA4 | 1 | 203020989 | G | A | A0201,A3001,B1302,B4403,C0602,C1602 | A3001 | 114 | 4892 | vhrrysalK | vhrrysalR |
| M4945 | ZP4 | 1 | 238050159 | C | G | A0201,A3001,B1302,B4403,C0602,C1602 | A3001 | 381 | 2049 | ttrqitgHr | ttrqitgDr |
| M4945 | ZP4 | 1 | 238050159 | C | G | A0201,A3001,B1302,B4403,C0602,C1602 | C0602 | 328 | 1385 | Hravyenel | Dravyenel |
| M4945 | PLD5 | 1 | 242287930 | C | A | A0201,A3001,B1302,B4403,C0602,C1602 | A0201 | 185 | 1150 | vifyncsFl | vifyncsCl |
| M4945 | PLD5 | 1 | 242287930 | C | A | A0201,A3001,B1302,B4403,C0602,C1602 | A0201 | 216 | 1672 | ifyncsFlv | ifyncsClv |
| M4945 | PLD5 | 1 | 242287930 | C | A | A0201,A3001,B1302,B4403,C0602,C1602 | A0201 | 60 | 2064 | Flvldlqri | Clvldlqri |
| M4945 | VN1R5 | 1 | 247419636 | C | A | A0201,A3001,B1302,B4403,C0602,C1602 | A0201 | 5 | 23 | miishlYli | miishlSli |
| M4945 | VN1R5 | 1 | 247419636 | C | A | A0201,A3001,B1302,B4403,C0602,C1602 | A0201 | 119 | 374 | hlYlihill | hlSlihill |
| M4945 | VN1R5 | 1 | 247419636 | C | A | A0201,A3001,B1302,B4403,C0602,C1602 | A0201 | 124 | 902 | Ylihillf | Slihillf |
| M4945 | VN1R5 | 1 | 247419636 | C | A | A0201,A3001,B1302,B4403,C0602,C1602 | A3001 | 190 | 164 | ishlYlihi | ishlSlihi |
| M4945 | VN1R5 | 1 | 247419636 | C | A | A0201,A3001,B1302,B4403,C0602,C1602 | C0602 | 348 | 139 | shlYlihil | shlSlihil |
| M4945 | OR6F1 | 1 | 247875186 | G | A | A0201,A3001,B1302,B4403,C0602,C1602 | A0201 | 6 | 5 | vlnpfiyMl | vlnpfiyTl |

Figure 21 (Cont.)

| | | | | | | | | | | | |
|---|---|---|---|---|---|---|---|---|---|---|---|
| M4945 | TRIM58 | 1 | 248039510 | G | T | A0201,A3001,B1302,B4403,C0602,C1602 | A0201 | 3 | 4 | ymFlaspsv | ymVlaspsv |
| M4945 | TRIM58 | 1 | 248039510 | G | T | A0201,A3001,B1302,B4403,C0602,C1602 | A0201 | 6 | 25 | Flaspsvpl | Vlaspsvpl |
| M4945 | CAMK1D | 10 | 12856257 | G | T | A0201,A3001,B1302,B4403,C0602,C1602 | A0201 | 7 | 9 | klfeqilNa | klfeqilKa |
| M4945 | CAMK1D | 10 | 12856257 | G | T | A0201,A3001,B1302,B4403,C0602,C1602 | A3001 | 181 | 543 | klfeqilNa | klfeqilKa |
| M4945 | CAMK1D | 10 | 12856257 | G | T | A0201,A3001,B1302,B4403,C0602,C1602 | B4403 | 124 | 200 | feqilNaey | feqilKaey |
| M4945 | CUBN | 10 | 16882480 | G | A | A0201,A3001,B1302,B4403,C0602,C1602 | A0201 | 220 | 24206 | sLnssdpdv | sPnssdpdv |
| M4945 | GPR158 | 10 | 25888174 | G | A | A0201,A3001,B1302,B4403,C0602,C1602 | B4403 | 329 | 151 | Keiwdsfkv | Eeiwdsfkv |
| M4945 | NCOA4 | 10 | 51579257 | A | T | A0201,A3001,B1302,B4403,C0602,C1602 | A3001 | 84 | 92 | vlraeLqik | vlraeQqik |
| M4945 | NCOA4 | 10 | 51579257 | A | T | A0201,A3001,B1302,B4403,C0602,C1602 | B4403 | 247 | 817 | aeLqikdnl | aeQqikdnl |
| M4945 | UNC5B | 10 | 72972770 | G | A | A0201,A3001,B1302,B4403,C0602,C1602 | A3001 | 34 | 18 | gargTllla | gargAllla |
| M4945 | UNC5B | 10 | 72972770 | G | A | A0201,A3001,B1302,B4403,C0602,C1602 | C0602 | 183 | 618 | arsgargTl | arsgargAl |
| M4945 | KCNMA1 | 10 | 78647061 | C | A | A0201,A3001,B1302,B4403,C0602,C1602 | A3001 | 432 | 151 | ksresLdkq | ksresRdkq |
| M4945 | KCNMA1 | 10 | 78647061 | C | A | A0201,A3001,B1302,B4403,C0602,C1602 | C0602 | 354 | 17666 | nrpksresL | nrpksresR |
| M4945 | BLNK | 10 | 97990569 | T | C | A0201,A3001,B1302,B4403,C0602,C1602 | B4403 | 142 | 246 | eeGqwsddf | eeEqwsddf |
| M4945 | PNLIPRP2 | 10 | 118385573 | C | T | A0201,A3001,B1302,B4403,C0602,C1602 | A0201 | 7 | 1266 | lmckkmfev | Dmckkmfev |
| M4945 | PNLIPRP2 | 10 | 118385573 | C | T | A0201,A3001,B1302,B4403,C0602,C1602 | A3001 | 486 | 5143 | kaedswpsl | kaedswpsD |
| M4945 | FAM24A | 10 | 124671166 | G | A | A0201,A3001,B1302,B4403,C0602,C1602 | A0201 | 147 | 31 | kmfNlrtki | kmfDlrtki |
| M4945 | FAM24A | 10 | 124671166 | G | A | A0201,A3001,B1302,B4403,C0602,C1602 | A3001 | 436 | 2835 | makmfNlrt | makmfDlrt |
| M4945 | CHST15 | 10 | 125804291 | C | T | A0201,A3001,B1302,B4403,C0602,C1602 | A3001 | 46 | 55 | rfrstfdTl | rfrstfdAl |
| M4945 | CHST15 | 10 | 125804291 | C | T | A0201,A3001,B1302,B4403,C0602,C1602 | A3001 | 115 | 282 | rstfdTlrk | rstfdAlrk |
| M4945 | TCERG1L | 10 | 132915093 | G | T | A0201,A3001,B1302,B4403,C0602,C1602 | A3001 | 267 | 1178 | rvNhfrdml | rvThfrdml |
| M4945 | TCERG1L | 10 | 132915093 | G | T | A0201,A3001,B1302,B4403,C0602,C1602 | C0602 | 227 | 618 | ervNhfrdm | ervThfrdm |
| M4945 | TUBGCP2 | 10 | 135107198 | C | A | A0201,A3001,B1302,B4403,C0602,C1602 | A0201 | 119 | 25936 | gMyvsaqpl | gRyvsaqpl |

Figure 21 (Cont.)

| | | | | | | | | | | | |
|---|---|---|---|---|---|---|---|---|---|---|---|
| M4945 | TUBGCP2 | 10 | 135107198 | C | A | A0201,A3001,B1302,B4403,C0602,C1602 | A3001 | 242 | 43 | Myvsaqpla | Ryvsaqpla |
| M4945 | CTSD | 11 | 1782696 | A | G | A0201,A3001,B1302,B4403,C0602,C1602 | A3001 | 312 | 371 | alvrTplhk | alvrlplhk |
| M4945 | PRKCDBP | 11 | 6341559 | G | T | A0201,A3001,B1302,B4403,C0602,C1602 | A3001 | 238 | 89 | larrKggla | larrQggla |
| M4945 | DCHS1 | 11 | 6645605 | T | C | A0201,A3001,B1302,B4403,C0602,C1602 | A0201 | 44 | 38 | tlftMvgtv | tlftlvgtv |
| M4945 | DCHS1 | 11 | 6645605 | T | C | A0201,A3001,B1302,B4403,C0602,C1602 | A0201 | 30 | 139 | ftMvgtval | ftlvgtval |
| M4945 | OR10A2 | 11 | 6891025 | C | A | A0201,A3001,B1302,B4403,C0602,C1602 | A0201 | 58 | 54 | sllfltflt | slLfltflt |
| M4945 | OR10A2 | 11 | 6891025 | C | A | A0201,A3001,B1302,B4403,C0602,C1602 | B4403 | 125 | 62 | teiqsllfl | teiqslLfl |
| M4945 | RBMXL2 | 11 | 7110583 | G | A | A0201,A3001,B1302,B4403,C0602,C1602 | A0201 | 17 | 39 | sldgkTlkv | sldgkAlkv |
| M4945 | RBMXL2 | 11 | 7110583 | G | A | A0201,A3001,B1302,B4403,C0602,C1602 | A3001 | 162 | 65 | ksldgkTlk | ksldgkAlk |
| M4945 | RBMXL2 | 11 | 7110583 | G | A | A0201,A3001,B1302,B4403,C0602,C1602 | A3001 | 39 | 9 | Tlkvaqatk | Alkvaqatk |
| M4945 | OR10A3 | 11 | 7960556 | G | T | A0201,A3001,B1302,B4403,C0602,C1602 | C0602 | 179 | 17361 | gHneinhlf | gPneinhlf |
| M4945 | PARVA | 11 | 12495317 | G | A | A0201,A3001,B1302,B4403,C0602,C1602 | A0201 | 276 | 22 | glnainlpl | gMnainlpl |
| M4945 | TPH1 | 11 | 18042599 | T | A | A0201,A3001,B1302,B4403,C0602,C1602 | A0201 | 28 | 145 | amnelLhdl | amnelQhdl |
| M4945 | F2 | 11 | 46741289 | G | T | A0201,A3001,B1302,B4403,C0602,C1602 | A3001 | 425 | 620 | rsllHrvrr | rsllQrvrr |
| M4945 | MYBPC3 | 11 | 47357495 | C | A | A0201,A3001,B1302,B4403,C0602,C1602 | A3001 | 411 | 1598 | slkCrpper | slkWrpper |
| M4945 | OR1S2 | 11 | 57970897 | T | C | A0201,A3001,B1302,B4403,C0602,C1602 | A3001 | 95 | 221 | kwkafsAcg | kwkafsTcg |
| M4945 | MTL5 | 11 | 68517702 | A | G | A0201,A3001,B1302,B4403,C0602,C1602 | A0201 | 327 | 144 | avlplgaRv | avlplgaWv |
| M4945 | MRGPRF | 11 | 68772877 | G | A | A0201,A3001,B1302,B4403,C0602,C1602 | A0201 | 17 | 26 | Wlweplrvv | Rlweplrvv |
| M4945 | SLC36A4 | 11 | 92895942 | T | A | A0201,A3001,B1302,B4403,C0602,C1602 | A0201 | 119 | 205 | tlyvtlaSl | tlyvtlaTl |
| M4945 | MFRP | 11 | 119215467 | C | T | A0201,A3001,B1302,B4403,C0602,C1602 | B4403 | 328 | 40741 | rEscahdef | rGscahdef |
| M4945 | CHD4 | 12 | 6711546 | T | A | A0201,A3001,B1302,B4403,C0602,C1602 | A3001 | 14 | 112 | kskrqkMer | kskrqkKer |
| M4945 | CHD4 | 12 | 6711546 | T | A | A0201,A3001,B1302,B4403,C0602,C1602 | A3001 | 20 | 27 | rqkMermll | rqkKermll |

Figure 21 (Cont.)

| | | | | | | | | | | | |
|---|---|---|---|---|---|---|---|---|---|---|---|
| M4945 | CHD4 | 12 | 6711546 | T | A | A0201,A3001,B1302,B4403,C0602,C1602 | C0602 | 306 | 206 | krqkMerml | krqkKerml |
| M4945 | FAM222A | 12 | 110206690 | G | T | A0201,A3001,B1302,B4403,C0602,C1602 | B4403 | 187 | 282 | peacggLay | peacggRay |
| M4945 | MPHOSPH9 | 12 | 123661241 | C | T | A0201,A3001,B1302,B4403,C0602,C1602 | A3001 | 21 | 66 | rihvrpsHa | rihvrpsRa |
| M4945 | MPHOSPH9 | 12 | 123661241 | C | T | A0201,A3001,B1302,B4403,C0602,C1602 | A3001 | 19 | 17 | hvrpsHant | hvrpsRant |
| M4945 | MPHOSPH9 | 12 | 123661241 | C | T | A0201,A3001,B1302,B4403,C0602,C1602 | C0602 | 20 | 45 | vrpsHantl | vrpsRantl |
| M4945 | ZNF268 | 12 | 133779594 | A | G | A0201,A3001,B1302,B4403,C0602,C1602 | A3001 | 7 | 6 | hqrthtgGk | hqrthtgEk |
| M4945 | ZNF268 | 12 | 133779594 | A | G | A0201,A3001,B1302,B4403,C0602,C1602 | A3001 | 22 | 104 | rthtgGkpy | rthtgEkpy |
| M4945 | ZNF268 | 12 | 133779594 | A | G | A0201,A3001,B1302,B4403,C0602,C1602 | C0602 | 234 | 209 | thtgGkpyv | thtgEkpyv |
| M4945 | PSPC1 | 13 | 20277431 | C | T | A0201,A3001,B1302,B4403,C0602,C1602 | A3001 | 204 | 332 | rtgsKtpqa | rtgsEtpqa |
| M4945 | PSPC1 | 13 | 20277431 | C | T | A0201,A3001,B1302,B4403,C0602,C1602 | A3001 | 243 | 10951 | gsKtpqapm | gsEtpqapm |
| M4945 | PCCA | 13 | 100807336 | G | T | A0201,A3001,B1302,B4403,C0602,C1602 | A3001 | 152 | 61 | aikktMaqa | aikktRaqa |
| M4945 | MYO16 | 13 | 109859068 | C | A | A0201,A3001,B1302,B4403,C0602,C1602 | A0201 | 63 | 67 | ilhNaeprv | ilhHaeprv |
| M4945 | ACOT1 | 14 | 74004385 | A | G | A0201,A3001,B1302,B4403,C0602,C1602 | A0201 | 338 | 668 | alepGkplv | alepEkplv |
| M4945 | LDHAL6B | 15 | 59499231 | G | C | A0201,A3001,B1302,B4403,C0602,C1602 | A0201 | 187 | 2937 | gmalcpPqa | gmalcpRqa |
| M4945 | SCAPER | 15 | 77021077 | T | G | A0201,A3001,B1302,B4403,C0602,C1602 | A3001 | 154 | 8449 | qArkralea | qErkralea |
| M4945 | SLC28A1 | 15 | 85461805 | C | A | A0201,A3001,B1302,B4403,C0602,C1602 | A0201 | 27 | 21 | cvisvlyQv | cvisvlyHv |
| M4945 | SLC28A1 | 15 | 85461805 | C | A | A0201,A3001,B1302,B4403,C0602,C1602 | A0201 | 12 | 6057 | yQvglmqwv | yHvglmqwv |
| M4945 | GFER | 16 | 2034898 | T | C | A0201,A3001,B1302,B4403,C0602,C1602 | A0201 | 270 | 247 | hlfPkfypc | hlfSkfypc |
| M4945 | GFER | 16 | 2034898 | T | C | A0201,A3001,B1302,B4403,C0602,C1602 | A3001 | 46 | 97 | aqfihlfPk | aqfihlfSk |
| M4945 | SMG1 | 16 | 18875348 | C | A | A0201,A3001,B1302,B4403,C0602,C1602 | A3001 | 7 | 13 | agrnsSspk | agrnsAspk |
| M4945 | EARS2 | 16 | 23568528 | G | A | A0201,A3001,B1302,B4403,C0602,C1602 | A3001 | 3 | 10 | rvrfapspl | rvrfapspT |
| M4945 | CBLN1 | 16 | 49315370 | C | A | A0201,A3001,B1302,B4403,C0602,C1602 | A0201 | 174 | 138 | mlCvlelll | mlGvlelll |
| M4945 | TAT | 16 | 71607468 | A | G | A0201,A3001,B1302,B4403,C0602,C1602 | A3001 | 22 | 127 | asyyhRpea | asyyhCpea |

Figure 21 (Cont.)

| | | | | | | | | | | | |
|---|---|---|---|---|---|---|---|---|---|---|---|
| M4945 | TAT | 16 | 71607468 | A | G | A0201,A3001,B1302,B4403,C0602,C1602 | B4403 | 453 | 719 | eeiasyyhR | eeiasyyhC |
| M4945 | GSG2 | 17 | 3627461 | C | T | A0201,A3001,B1302,B4403,C0602,C1602 | A3001 | 25 | 84 | rWrrrpgg | rRrrrpgg |
| M4945 | DLG4 | 17 | 7099591 | C | T | A0201,A3001,B1302,B4403,C0602,C1602 | A0201 | 26 | 48 | slSsgtasl | slGsgtasl |
| M4945 | KRBA2 | 17 | 8273015 | C | A | A0201,A3001,B1302,B4403,C0602,C1602 | A0201 | 10 | 53 | kqahevFsv | kqahevVsv |
| M4945 | TRIM16 | 17 | 15539387 | C | G | A0201,A3001,B1302,B4403,C0602,C1602 | A0201 | 18 | 17 | Tmaaisntv | Rmaaisntv |
| M4945 | C17orf75 | 17 | 30661839 | A | G | A0201,A3001,B1302,B4403,C0602,C1602 | A0201 | 28 | 22 | alsytpAev | alsytpVev |
| M4945 | PLEKHM1 | 17 | 43553058 | C | T | A0201,A3001,B1302,B4403,C0602,C1602 | B4403 | 205 | 435 | selehltfI | selehltfV |
| M4945 | BTBD17 | 17 | 72353182 | C | T | A0201,A3001,B1302,B4403,C0602,C1602 | A3001 | 9 | 129 | aSrrvtwnv | aGrrvtwnv |
| M4945 | FASN | 17 | 80042541 | C | G | A0201,A3001,B1302,B4403,C0602,C1602 | A3001 | 162 | 384 | ltrAdlssi | ltrGdlssi |
| M4945 | FASN | 17 | 80043708 | C | A | A0201,A3001,B1302,B4403,C0602,C1602 | A0201 | 16 | 10 | hlysripCl | hlysripGl |
| M4945 | FASN | 17 | 80043708 | C | A | A0201,A3001,B1302,B4403,C0602,C1602 | A0201 | 146 | 65 | Cllsphpll | Gllsphpll |
| M4945 | PIGN | 18 | 59751795 | G | T | A0201,A3001,B1302,B4403,C0602,C1602 | A0201 | 25 | 17 | fltvfsHfm | fltvfsPfm |
| M4945 | PIGN | 18 | 59751795 | G | T | A0201,A3001,B1302,B4403,C0602,C1602 | C0602 | 113 | 12596 | sHfmmgalm | sPfmmgalm |
| M4945 | SALL3 | 18 | 76754149 | G | T | A0201,A3001,B1302,B4403,C0602,C1602 | A3001 | 426 | 1315 | rafttkCnl | rafttkGnl |
| M4945 | TPGS1 | 19 | 507657 | G | A | A0201,A3001,B1302,B4403,C0602,C1602 | A0201 | 88 | 75 | mlraTllkv | mlraAllkv |
| M4945 | TPGS1 | 19 | 507657 | G | A | A0201,A3001,B1302,B4403,C0602,C1602 | A3001 | 62 | 29 | mlraTllkv | mlraAllkv |
| M4945 | HMHA1 | 19 | 1081824 | G | A | A0201,A3001,B1302,B4403,C0602,C1602 | A3001 | 109 | 98 | rtkDiyrvn | rtkGiyrvn |
| M4945 | SBNO2 | 19 | 1122195 | C | A | A0201,A3001,B1302,B4403,C0602,C1602 | C0602 | 84 | 88 | Hhrtrlrqi | Qhrtrlrqi |
| M4945 | APC2 | 19 | 1456130 | G | A | A0201,A3001,B1302,B4403,C0602,C1602 | A0201 | 444 | 465 | elleaqdQv | elleaqdRv |
| M4945 | PTPRS | 19 | 5240281 | A | T | A0201,A3001,B1302,B4403,C0602,C1602 | A3001 | 302 | 1204 | itlsRsppr | itlsWsppr |
| M4945 | PTPRS | 19 | 5240281 | A | T | A0201,A3001,B1302,B4403,C0602,C1602 | B4403 | 470 | 5 | setsitlsR | setsitlsW |
| M4945 | MLLT1 | 19 | 6222269 | A | T | A0201,A3001,B1302,B4403,C0602,C1602 | A3001 | 353 | 207 | rtsssssfT | rtsssssfS |

Figure 21 (Cont.)

| | | | | | | | | | | | |
|---|---|---|---|---|---|---|---|---|---|---|---|
| M4945 | DENND1C | 19 | 6471495 | G | A | A0201,A3001,B1302,B4403,C0602,C1602 | A0201 | 192 | 1606 | fieaWlekl | fieaRlekl |
| M4945 | SMARCA4 | 19 | 11144072 | C | G | A0201,A3001,B1302,B4403,C0602,C1602 | A0201 | 51 | 51 | ilaaGkykl | ilaaAkykl |
| M4945 | SMARCA4 | 19 | 11144072 | C | G | A0201,A3001,B1302,B4403,C0602,C1602 | A3001 | 12 | 13 | kilaaGkyk | kilaaAkyk |
| M4945 | BRD4 | 19 | 15355236 | G | A | A0201,A3001,B1302,B4403,C0602,C1602 | A3001 | 165 | 341 | ksLpppfia | ksSpppfia |
| M4945 | MAST3 | 19 | 18246636 | G | T | A0201,A3001,B1302,B4403,C0602,C1602 | A3001 | 109 | 1635 | rllrqsplY | rllrqsplD |
| M4945 | GRAMD1A | 19 | 35504236 | A | T | A0201,A3001,B1302,B4403,C0602,C1602 | A0201 | 99 | 1021 | ltsedVdyv | ltsedEdyv |
| M4945 | LGI4 | 19 | 35624949 | G | A | A0201,A3001,B1302,B4403,C0602,C1602 | A0201 | 417 | 532 | flripFlhl | flripSlhl |
| M4945 | LGI4 | 19 | 35624949 | G | A | A0201,A3001,B1302,B4403,C0602,C1602 | A0201 | 458 | 2336 | Flhlllfts | Slhlllfts |
| M4945 | LGI4 | 19 | 35624949 | G | A | A0201,A3001,B1302,B4403,C0602,C1602 | A3001 | 115 | 470 | gsflripFl | gsflripSl |
| M4945 | LGI4 | 19 | 35624949 | G | A | A0201,A3001,B1302,B4403,C0602,C1602 | C0602 | 37 | 32 | lripFlhll | lripSlhll |
| M4945 | NUMBL | 19 | 41183182 | C | T | A0201,A3001,B1302,B4403,C0602,C1602 | A3001 | 454 | 1324 | sfrlsRggr | sfrlsGggr |
| M4945 | NUMBL | 19 | 41183182 | C | T | A0201,A3001,B1302,B4403,C0602,C1602 | A3001 | 480 | 1218 | rlsRggrpa | rlsGggrpa |
| M4945 | ZC3H4 | 19 | 47575370 | C | A | A0201,A3001,B1302,B4403,C0602,C1602 | A3001 | 79 | 108 | gvrfpVpgg | gvrfpGpgg |
| M4945 | PPFIA3 | 19 | 49637375 | C | T | A0201,A3001,B1302,B4403,C0602,C1602 | A0201 | 82 | 78 | llsesneCl | llsesneRl |
| M4945 | PPFIA3 | 19 | 49637375 | C | T | A0201,A3001,B1302,B4403,C0602,C1602 | B4403 | 494 | 825 | sesneClql | sesneRlql |
| M4945 | POLD1 | 19 | 50919042 | A | G | A0201,A3001,B1302,B4403,C0602,C1602 | A3001 | 482 | 215 | rvpyviVsa | rvpyvilsa |
| M4945 | VN1R2 | 19 | 53762460 | C | T | A0201,A3001,B1302,B4403,C0602,C1602 | A0201 | 19 | 25 | lmFwasssi | lmLwasssi |
| M4945 | ZNF813 | 19 | 53994247 | G | A | A0201,A3001,B1302,B4403,C0602,C1602 | A3001 | 148 | 122 | kvfnQkml | kvfnRkml |
| M4945 | NLRP12 | 19 | 54310777 | G | A | A0201,A3001,B1302,B4403,C0602,C1602 | A3001 | 384 | 504 | glrYpnckl | glrHpnckl |
| M4945 | TMEM86B | 19 | 55739559 | C | A | A0201,A3001,B1302,B4403,C0602,C1602 | A0201 | 322 | 392 | fvpCmaafa | fvpGmaafa |
| M4945 | CCDC106 | 19 | 56162828 | T | G | A0201,A3001,B1302,B4403,C0602,C1602 | A3001 | 242 | 266 | gasrrrVgk | gasrrrFgk |
| M4945 | CCDC106 | 19 | 56162828 | T | G | A0201,A3001,B1302,B4403,C0602,C1602 | A3001 | 85 | 33 | srrrVgkpk | srrrFgkpk |
| M4945 | CCDC106 | 19 | 56162828 | T | G | A0201,A3001,B1302,B4403,C0602,C1602 | A3001 | 191 | 190 | rrrVgkpka | rrrFgkpka |

Figure 21 (Cont.)

| | | | | | | | | | | | |
|---|---|---|---|---|---|---|---|---|---|---|---|
| M4945 | TPO | 2 | 1500454 | G | T | A0201,A3001,B1302,B4403,C0602,C1602 | A0201 | 496 | 4647 | ysFrhgyel | ysCrhgyel |
| M4945 | TPO | 2 | 1500454 | G | T | A0201,A3001,B1302,B4403,C0602,C1602 | C0602 | 64 | 387 | ysFrhgyel | ysCrhgyel |
| M4945 | MYCN | 2 | 16082407 | C | G | A0201,A3001,B1302,B4403,C0602,C1602 | C0602 | 35 | 10653 | eRpswvtem | ePpswvtem |
| M4945 | MPV17 | 2 | 27534810 | C | G | A0201,A3001,B1302,B4403,C0602,C1602 | A0201 | 11 | 6 | ylwpPvqla | ylwpAvqla |
| M4945 | REG3A | 2 | 79385817 | T | C | A0201,A3001,B1302,B4403,C0602,C1602 | A3001 | 47 | 13 | kaygshcCa | kaygshcYa |
| M4945 | REG3A | 2 | 79385817 | T | C | A0201,A3001,B1302,B4403,C0602,C1602 | A3001 | 86 | 25 | gshcCalfl | gshcYalfl |
| M4945 | SFT2D3 | 2 | 128459121 | C | A | A0201,A3001,B1302,B4403,C0602,C1602 | C0602 | 351 | 225 | lhrKlqeyl | lhrQlqeyl |
| M4945 | LRP1B | 2 | 141751663 | C | T | A0201,A3001,B1302,B4403,C0602,C1602 | A3001 | 82 | 11321 | Kfrcknrhc | Efrcknrhc |
| M4945 | EVX2 | 2 | 176945475 | A | G | A0201,A3001,B1302,B4403,C0602,C1602 | A0201 | 85 | 122 | ytyTmthaa | ytyMmthaa |
| M4945 | FAM171B | 2 | 187605158 | C | G | A0201,A3001,B1302,B4403,C0602,C1602 | A3001 | 226 | 712 | yvltAlpwk | yvltPlpwk |
| M4945 | PRR21 | 2 | 240982003 | C | A | A0201,A3001,B1302,B4403,C0602,C1602 | C0602 | 137 | 232 | vhassptSl | vhassptAl |
| M4945 | TGM3 | 20 | 2320540 | A | G | A0201,A3001,B1302,B4403,C0602,C1602 | A3001 | 17 | 41 | rvrkpvnvR | rvrkpvnvQ |
| M4945 | TGM3 | 20 | 2320540 | A | G | A0201,A3001,B1302,B4403,C0602,C1602 | C0602 | 241 | 181 | vrkpvnvRm | vrkpvnvQm |
| M4945 | INSM1 | 20 | 20348928 | T | A | A0201,A3001,B1302,B4403,C0602,C1602 | A3001 | 249 | 133 | rgfQvkrsk | rgfLvkrsk |
| M4945 | LAMA5 | 20 | 60905664 | C | T | A0201,A3001,B1302,B4403,C0602,C1602 | A0201 | 45 | 735 | atMvftthv | atVvftthv |
| M4945 | LAMA5 | 20 | 60905664 | C | T | A0201,A3001,B1302,B4403,C0602,C1602 | A3001 | 117 | 582 | atMvftthv | atVvftthv |
| M4945 | LAMA5 | 20 | 60905664 | C | T | A0201,A3001,B1302,B4403,C0602,C1602 | C0602 | 91 | 110 | lrepqatMv | lrepqatVv |
| M4945 | RBBP8NL | 20 | 60991911 | C | T | A0201,A3001,B1302,B4403,C0602,C1602 | A0201 | 394 | 3816 | glYdrcmvt | glCdrcmvt |
| M4945 | RBBP8NL | 20 | 60991911 | C | T | A0201,A3001,B1302,B4403,C0602,C1602 | A3001 | 312 | 147 | rlraglYdr | rlraglCdr |
| M4945 | NPBWR2 | 20 | 62737553 | G | A | A0201,A3001,B1302,B4403,C0602,C1602 | A0201 | 426 | 2000 | qvwfkVsrv | qvwfkAsrv |
| M4945 | NPBWR2 | 20 | 62737553 | G | A | A0201,A3001,B1302,B4403,C0602,C1602 | A0201 | 315 | 2318 | kVsrvytlv | kAsrvytlv |
| M4945 | NPBWR2 | 20 | 62737553 | G | A | A0201,A3001,B1302,B4403,C0602,C1602 | A3001 | 107 | 443 | kVsrvytlv | kAsrvytlv |

Figure 21 (Cont.)

| | | | | | | | | | | | |
|---|---|---|---|---|---|---|---|---|---|---|---|
| M4945 | NPBWR2 | 20 | 62737553 | G | A | A0201,A3001,B1302,B4403,C0602,C1602 | A3001 | 55 | 11 | Vsrvytlvl | Asrvytlvl |
| M4945 | NPBWR2 | 20 | 62737553 | G | A | A0201,A3001,B1302,B4403,C0602,C1602 | C0602 | 274 | 215 | fkVsrvytl | fkAsrvytl |
| M4945 | XKR3 | 22 | 17288812 | C | G | A0201,A3001,B1302,B4403,C0602,C1602 | B4403 | 28 | 34 | gevafAlym | gevafGlym |
| M4945 | SMTN | 22 | 31487823 | G | T | A0201,A3001,B1302,B4403,C0602,C1602 | A3001 | 5 | 13 | ssrggFsik | ssrggCsik |
| M4945 | SH3BP1 | 22 | 38044382 | C | T | A0201,A3001,B1302,B4403,C0602,C1602 | A0201 | 14 | 69 | kmIpsniai | kmTpsniai |
| M4945 | SH3BP1 | 22 | 38044382 | C | T | A0201,A3001,B1302,B4403,C0602,C1602 | A0201 | 86 | 403 | mIpsniaiv | mTpsniaiv |
| M4945 | SH3BP1 | 22 | 38044382 | C | T | A0201,A3001,B1302,B4403,C0602,C1602 | A3001 | 269 | 399 | kmIpsniai | kmTpsniai |
| M4945 | FANCD2 | 3 | 10122824 | A | G | A0201,A3001,B1302,B4403,C0602,C1602 | C0602 | 175 | 8806 | qRrsaqeiv | qQrsaqeiv |
| M4945 | XPC | 3 | 14199948 | C | G | A0201,A3001,B1302,B4403,C0602,C1602 | A3001 | 4 | 4 | rtkaRsksa | rtkaGsksa |
| M4945 | XPC | 3 | 14199948 | C | G | A0201,A3001,B1302,B4403,C0602,C1602 | A3001 | 19 | 5121 | kaRsksasr | kaGsksasr |
| M4945 | XPC | 3 | 14199948 | C | G | A0201,A3001,B1302,B4403,C0602,C1602 | A3001 | 66 | 1305 | Rsksasrth | Gsksasrth |
| M4945 | DNAH1 | 3 | 52415830 | C | A | A0201,A3001,B1302,B4403,C0602,C1602 | A3001 | 11 | 14 | ltrlashma | Ltrlashma |
| M4945 | APPL1 | 3 | 57294666 | C | G | A0201,A3001,B1302,B4403,C0602,C1602 | A3001 | 14 | 172 | vtrltfplR | vtrltfplP |
| M4945 | APPL1 | 3 | 57294666 | C | G | A0201,A3001,B1302,B4403,C0602,C1602 | A3001 | 141 | 12559 | plRcvvlya | plPcvvlya |
| M4945 | C3orf58 | 3 | 143691263 | T | C | A0201,A3001,B1302,B4403,C0602,C1602 | A0201 | 16 | 35 | lmvPhspsl | lmvLhspsl |
| M4945 | CCDC39 | 3 | 180370000 | T | A | A0201,A3001,B1302,B4403,C0602,C1602 | A0201 | 55 | 5605 | alWkniski | alRkniski |
| M4945 | TMEM129 | 4 | 1719912 | C | T | A0201,A3001,B1302,B4403,C0602,C1602 | A0201 | 201 | 135 | rvaNtnpav | rvaStnpav |
| M4945 | TMEM129 | 4 | 1719912 | C | T | A0201,A3001,B1302,B4403,C0602,C1602 | A3001 | 87 | 101 | rvaNtnpav | rvaStnpav |
| M4945 | ACOX3 | 4 | 8417530 | T | C | A0201,A3001,B1302,B4403,C0602,C1602 | A0201 | 65 | 23 | gmyGsslaa | gmyDsslaa |
| M4945 | EPHA5 | 4 | 66535423 | C | A | A0201,A3001,B1302,B4403,C0602,C1602 | A3001 | 298 | 138 | agrrLppsg | agrrRppsg |
| M4945 | WDFY3 | 4 | 85707132 | C | A | A0201,A3001,B1302,B4403,C0602,C1602 | A3001 | 488 | 987 | kaiakHlgi | kaiakQlgi |
| M4945 | SLC9B2 | 4 | 103970081 | C | A | A0201,A3001,B1302,B4403,C0602,C1602 | A0201 | 14 | 9 | llahyllCl | llahyllGl |
| M4945 | TACR3 | 4 | 104511020 | A | T | A0201,A3001,B1302,B4403,C0602,C1602 | A3001 | 226 | 4838 | ssmytvtrK | ssmytvtrM |

Figure 21 (Cont.)

| | | | | | | | | | | | |
|---|---|---|---|---|---|---|---|---|---|---|---|
| M4945 | TACR3 | 4 | 104511020 | A | T | A0201,A3001,B1302,B4403,C0602,C1602 | A3001 | 26 | 19 | vtrKesmtv | vtrMesmtv |
| M4945 | TACR3 | 4 | 104511020 | A | T | A0201,A3001,B1302,B4403,C0602,C1602 | C0602 | 38 | 12 | trKesmtvv | trMesmtvv |
| M4945 | GALNT7 | 4 | 174242777 | G | T | A0201,A3001,B1302,B4403,C0602,C1602 | A0201 | 251 | 24606 | dLsevlhqv | dRsevlhqv |
| M4945 | KIAA0947 | 5 | 5464173 | G | T | A0201,A3001,B1302,B4403,C0602,C1602 | A3001 | 402 | 2312 | ktsassrFe | ktsassrVe |
| M4945 | KIAA0947 | 5 | 5464173 | G | T | A0201,A3001,B1302,B4403,C0602,C1602 | A3001 | 353 | 400 | ssrFethqs | ssrVethqs |
| M4945 | SEMA5A | 5 | 9224935 | T | A | A0201,A3001,B1302,B4403,C0602,C1602 | A3001 | 9 | 33 | marcpyspL | marcpyspQ |
| M4945 | TRIO | 5 | 14461158 | G | A | A0201,A3001,B1302,B4403,C0602,C1602 | A3001 | 20 | 18 | ssndaNppa | ssndaSppa |
| M4945 | CDH9 | 5 | 26881369 | G | A | A0201,A3001,B1302,B4403,C0602,C1602 | A0201 | 40 | 76 | siadLlssl | siadSlssl |
| M4945 | SLC45A2 | 5 | 33954600 | C | A | A0201,A3001,B1302,B4403,C0602,C1602 | A3001 | 6 | 4 | qtrrSmtlk | qtrrAmtlk |
| M4945 | FCHO2 | 5 | 72351896 | G | T | A0201,A3001,B1302,B4403,C0602,C1602 | C0602 | 477 | 133 | nmlsnDel | nmlsnEel |
| M4945 | RASA1 | 5 | 86672224 | C | A | A0201,A3001,B1302,B4403,C0602,C1602 | A0201 | 160 | 159 | fmrcKlsrl | fmrcQlsrl |
| M4945 | RASA1 | 5 | 86672224 | C | A | A0201,A3001,B1302,B4403,C0602,C1602 | A3001 | 8 | 195 | rcKlsrlqk | rcQlsrlqk |
| M4945 | APC | 5 | 112162827 | A | T | A0201,A3001,B1302,B4403,C0602,C1602 | A0201 | 271 | 202 | glqaiaDll | glqaiaEll |
| M4945 | MCC | 5 | 112363016 | T | A | A0201,A3001,B1302,B4403,C0602,C1602 | B4403 | 50 | 6685 | eensrphtY | eensrphtN |
| M4945 | HSPA9 | 5 | 137910934 | C | T | A0201,A3001,B1302,B4403,C0602,C1602 | A3001 | 469 | 57 | asrgptaaH | asrgptaaR |
| M4945 | ADRA1B | 5 | 159399008 | G | C | A0201,A3001,B1302,B4403,C0602,C1602 | C0602 | 121 | 262 | fkrPfvril | fkrAfvril |
| M4945 | CCNG1 | 5 | 162868280 | C | T | A0201,A3001,B1302,B4403,C0602,C1602 | A3001 | 7 | 7 | kvkattVfq | kvkattAfq |
| M4945 | CCNG1 | 5 | 162868280 | C | T | A0201,A3001,B1302,B4403,C0602,C1602 | A3001 | 315 | 105 | kattVfqfl | kattAfqfl |
| M4945 | PRSS16 | 6 | 27215551 | T | A | A0201,A3001,B1302,B4403,C0602,C1602 | A0201 | 435 | 181 | aqwlgpQll | aqwlgpLll |
| M4945 | PRSS16 | 6 | 27215551 | T | A | A0201,A3001,B1302,B4403,C0602,C1602 | A0201 | 20 | 7 | Qllvslwgl | Lllvslwgl |
| M4945 | SCAND3 | 6 | 28543358 | C | T | A0201,A3001,B1302,B4403,C0602,C1602 | A3001 | 62 | 49 | ssrYqvdli | ssrCqvdli |
| M4945 | TNXB | 6 | 32029492 | C | T | A0201,A3001,B1302,B4403,C0602,C1602 | A3001 | 491 | 15123 | saigvtaaK | saigvtaaE |

Figure 21 (Cont.)

| | | | | | | | | | | | |
|---|---|---|---|---|---|---|---|---|---|---|---|
| M4945 | PBX2 | 6 | 32157652 | C | G | A0201,A3001,B1302,B4403,C0602,C1602 | A3001 | 349 | 1731 | gArgglglv | gGrgglglv |
| M4945 | SLC29A1 | 6 | 44198335 | G | A | A0201,A3001,B1302,B4403,C0602,C1602 | A0201 | 172 | 577 | safDyfita | safGyfita |
| M4945 | SLC29A1 | 6 | 44198335 | G | A | A0201,A3001,B1302,B4403,C0602,C1602 | A3001 | 323 | 278 | safDyfita | safGyfita |
| M4945 | SLC29A1 | 6 | 44198335 | G | A | A0201,A3001,B1302,B4403,C0602,C1602 | B4403 | 94 | 34 | sesafDyfi | sesafGyfi |
| M4945 | DST | 6 | 56481250 | T | A | A0201,A3001,B1302,B4403,C0602,C1602 | A3001 | 83 | 235 | kthrFsvvd | kthrIsvvd |
| M4945 | REV3L | 6 | 111695347 | C | T | A0201,A3001,B1302,B4403,C0602,C1602 | A0201 | 19 | 46 | klseyHnsl | klseyRnsl |
| M4945 | REV3L | 6 | 111695347 | C | T | A0201,A3001,B1302,B4403,C0602,C1602 | C0602 | 80 | 42 | yHnsleskl | yRnsleskl |
| M4945 | VGLL2 | 6 | 117591812 | C | A | A0201,A3001,B1302,B4403,C0602,C1602 | A0201 | 252 | 16079 | aQselpfaa | aHselpfaa |
| M4945 | CEP85L | 6 | 118886705 | T | A | A0201,A3001,B1302,B4403,C0602,C1602 | C0602 | 82 | 446 | frqgsVtpm | frqgsEtpm |
| M4945 | GINM1 | 6 | 149887573 | C | T | A0201,A3001,B1302,B4403,C0602,C1602 | A0201 | 84 | 10224 | gLlalrlll | gSlalrlll |
| M4945 | SYNE1 | 6 | 152716775 | A | G | A0201,A3001,B1302,B4403,C0602,C1602 | A0201 | 220 | 29 | klnlRihem | klnlWihem |
| M4945 | MAS1 | 6 | 160328063 | G | A | A0201,A3001,B1302,B4403,C0602,C1602 | A3001 | 12 | 4564 | svRnahrqi | svGnahrqi |
| M4945 | MAS1 | 6 | 160328063 | G | A | A0201,A3001,B1302,B4403,C0602,C1602 | C0602 | 498 | 27741 | vRnahrqip | vGnahrqip |
| M4945 | CARD11 | 7 | 2984070 | C | A | A0201,A3001,B1302,B4403,C0602,C1602 | C0602 | 134 | 416 | qrcellSrl | qrcellArl |
| M4945 | CDK13 | 7 | 39991265 | G | T | A0201,A3001,B1302,B4403,C0602,C1602 | A3001 | 183 | 1104 | slrsrkspl | slrsrkspS |
| M4945 | CDK13 | 7 | 39991265 | G | T | A0201,A3001,B1302,B4403,C0602,C1602 | A3001 | 2 | 3 | rsrksplpa | rsrkspSpa |
| M4945 | NPC1L1 | 7 | 44556456 | G | A | A0201,A3001,B1302,B4403,C0602,C1602 | A0201 | 7 | 1854 | fmlslclvL | fmlslclvP |
| M4945 | NPC1L1 | 7 | 44556456 | G | A | A0201,A3001,B1302,B4403,C0602,C1602 | A0201 | 266 | 89 | mlslclvLt | mlslclvPt |
| M4945 | NPC1L1 | 7 | 44556456 | G | A | A0201,A3001,B1302,B4403,C0602,C1602 | A0201 | 260 | 455 | slclvLtfa | slclvPtfa |
| M4945 | NPC1L1 | 7 | 44556456 | G | A | A0201,A3001,B1302,B4403,C0602,C1602 | A0201 | 270 | 23832 | vLtfavscl | vPtfavscl |
| M4945 | NPC1L1 | 7 | 44556456 | G | A | A0201,A3001,B1302,B4403,C0602,C1602 | A0201 | 250 | 7624 | Ltfavscll | Ptfavscll |
| M4945 | NPC1L1 | 7 | 44556456 | G | A | A0201,A3001,B1302,B4403,C0602,C1602 | A3001 | 451 | 1958 | Ltfavscll | Ptfavscll |
| M4945 | LIMK1 | 7 | 73500134 | C | T | A0201,A3001,B1302,B4403,C0602,C1602 | C0602 | 239 | 47 | qriydgqyF | qriydgqyL |

Figure 21 (Cont.)

| | | | | | | | | | | | |
|---|---|---|---|---|---|---|---|---|---|---|---|
| M4945 | POR | 7 | 75615330 | A | T | A0201,A3001,B1302,B4403,C0602,C1602 | B4403 | 142 | 13978 | reelaqfhW | reelaqfhR |
| M4945 | POR | 7 | 75615330 | A | T | A0201,A3001,B1302,B4403,C0602,C1602 | B4403 | 402 | 1091 | eelaqfhWd | eelaqfhRd |
| M4945 | POR | 7 | 75615330 | A | T | A0201,A3001,B1302,B4403,C0602,C1602 | C0602 | 482 | 429 | fhWdgaltq | fhRdgaltq |
| M4945 | SEMA3A | 7 | 83590897 | C | A | A0201,A3001,B1302,B4403,C0602,C1602 | A3001 | 111 | 1159 | Cyrdfmqli | Wyrdfmqli |
| M4945 | DOCK4 | 7 | 111398729 | T | C | A0201,A3001,B1302,B4403,C0602,C1602 | A3001 | 11 | 14 | kfrCdrpfh | kfrYdrpfh |
| M4945 | ATP6V0A4 | 7 | 138424302 | G | T | A0201,A3001,B1302,B4403,C0602,C1602 | C0602 | 303 | 4780 | vyfgnpyTf | vyfgnpyPf |
| M4945 | NOBOX | 7 | 144101773 | C | A | A0201,A3001,B1302,B4403,C0602,C1602 | A3001 | 230 | 271 | kaqeVppla | kaqeGppla |
| M4945 | GIMAP8 | 7 | 150174233 | G | A | A0201,A3001,B1302,B4403,C0602,C1602 | A3001 | 42 | 6939 | atRnsilgs | atGnsilgs |
| M4945 | GIMAP8 | 7 | 150174233 | G | A | A0201,A3001,B1302,B4403,C0602,C1602 | C0602 | 154 | 20522 | tRnsilgsl | tGnsilgsl |
| M4945 | AGAP3 | 7 | 150839305 | G | A | A0201,A3001,B1302,B4403,C0602,C1602 | A3001 | 130 | 108 | avrtvHgns | avrtvRgns |
| M4945 | AGAP3 | 7 | 150839305 | G | A | A0201,A3001,B1302,B4403,C0602,C1602 | C0602 | 134 | 327 | vrtvHgnsf | vrtvRgnsf |
| M4945 | CSMD1 | 8 | 3015437 | G | A | A0201,A3001,B1302,B4403,C0602,C1602 | A3001 | 479 | 248 | tvrrwnySs | tvrrwnyPs |
| M4945 | CSMD1 | 8 | 3015437 | G | A | A0201,A3001,B1302,B4403,C0602,C1602 | C0602 | 119 | 134 | rrwnySspl | rrwnyPspl |
| M4945 | PCM1 | 8 | 17872255 | C | A | A0201,A3001,B1302,B4403,C0602,C1602 | A3001 | 494 | 7444 | lvHrvkevk | lvPrvkevk |
| M4945 | UBR5 | 8 | 103341409 | G | A | A0201,A3001,B1302,B4403,C0602,C1602 | A3001 | 17 | 5678 | hLratflgl | hPratflgl |
| M4945 | UBR5 | 8 | 103341409 | G | A | A0201,A3001,B1302,B4403,C0602,C1602 | C0602 | 161 | 40 | lhhLratfl | lhhPratfl |
| M4945 | PHF20L1 | 8 | 133806763 | G | C | A0201,A3001,B1302,B4403,C0602,C1602 | A0201 | 210 | 498 | wiywdsnTl | wiywdsnRl |
| M4945 | KCNK9 | 8 | 140630643 | T | A | A0201,A3001,B1302,B4403,C0602,C1602 | A0201 | 257 | 409 | klaphyfLs | klaphyfHs |
| M4945 | KCNK9 | 8 | 140630643 | T | A | A0201,A3001,B1302,B4403,C0602,C1602 | A0201 | 290 | 3413 | yfLsisyki | yfHsisyki |
| M4945 | KCNK9 | 8 | 140630643 | T | A | A0201,A3001,B1302,B4403,C0602,C1602 | A3001 | 16 | 12 | hyfLsisyk | hyfHsisyk |
| M4945 | ZC3H3 | 8 | 144523122 | C | A | A0201,A3001,B1302,B4403,C0602,C1602 | A3001 | 8 | 14 | rsrvsSshg | rsrvsAshg |
| M4945 | ZC3H3 | 8 | 144523122 | C | A | A0201,A3001,B1302,B4403,C0602,C1602 | A3001 | 381 | 194 | rvsSshgpr | rvsAshgpr |

Figure 21 (Cont.)

| | | | | | | | | | | | |
|---|---|---|---|---|---|---|---|---|---|---|---|
| M4945 | ZC3H3 | 8 | 144523122 | C | A | A0201,A3001,B1302,B4403,C0602,C1602 | A3001 | 424 | 671 | vsSshgprk | vsAshgprk |
| M4945 | ZNF707 | 8 | 144773874 | C | G | A0201,A3001,B1302,B4403,C0602,C1602 | A3001 | 29 | 82 | vqrgArpga | vqrgPrpga |
| M4945 | PLEC | 8 | 145000009 | G | C | A0201,A3001,B1302,B4403,C0602,C1602 | A0201 | 82 | 26 | rlGeveaal | rlAeveaal |
| M4945 | FOCAD | 9 | 20885197 | T | C | A0201,A3001,B1302,B4403,C0602,C1602 | A3001 | 101 | 28 | masrgrsLk | masrgrsFk |
| M4945 | FOCAD | 9 | 20885197 | T | C | A0201,A3001,B1302,B4403,C0602,C1602 | A3001 | 125 | 222 | asrgrsLkq | asrgrsFkq |
| M4945 | FOCAD | 9 | 20885197 | T | C | A0201,A3001,B1302,B4403,C0602,C1602 | A3001 | 54 | 25 | rsLkqtsla | rsFkqtsla |
| M4945 | FOXB2 | 9 | 79634574 | C | T | A0201,A3001,B1302,B4403,C0602,C1602 | A3001 | 49 | 9436 | mSrpgkssy | mPrpgkssy |
| M4945 | KIF27 | 9 | 86530349 | T | A | A0201,A3001,B1302,B4403,C0602,C1602 | A0201 | 3 | 856 | ftfdfvfgl | ftfdfvfgK |
| M4945 | KIF27 | 9 | 86530349 | T | A | A0201,A3001,B1302,B4403,C0602,C1602 | C0602 | 471 | 15124 | ftfdfvfgl | ftfdfvfgK |
| M4945 | GAS1 | 9 | 89561177 | C | T | A0201,A3001,B1302,B4403,C0602,C1602 | C0602 | 163 | 843 | rrYdrdsrc | rrCdrdsrc |
| M4945 | GOLGA1 | 9 | 127644196 | T | G | A0201,A3001,B1302,B4403,C0602,C1602 | A3001 | 335 | 10368 | rAkpgpema | rEkpgpema |
| M4945 | GOLGA1 | 9 | 127644196 | T | G | A0201,A3001,B1302,B4403,C0602,C1602 | C0602 | 381 | 450 | vrAkpgpem | vrEkpgpem |
| M4945 | C9orf50 | 9 | 132377837 | C | T | A0201,A3001,B1302,B4403,C0602,C1602 | A3001 | 165 | 1821 | gsrpcrqrY | gsrpcrqrC |
| M4945 | C9orf50 | 9 | 132377837 | C | T | A0201,A3001,B1302,B4403,C0602,C1602 | A3001 | 39 | 31 | rqrYpfrvr | rqrCpfrvr |
| M4945 | C9orf50 | 9 | 132377837 | C | T | A0201,A3001,B1302,B4403,C0602,C1602 | A3001 | 125 | 1042 | rYpfrvrfa | rCpfrvrfa |
| M4945 | C9orf50 | 9 | 132377837 | C | T | A0201,A3001,B1302,B4403,C0602,C1602 | C0602 | 117 | 657 | qrYpfrvrf | qrCpfrvrf |
| M4945 | USP20 | 9 | 132625509 | G | A | A0201,A3001,B1302,B4403,C0602,C1602 | C0602 | 138 | 72 | vHtdkkpal | vRtdkkpal |
| M4945 | MOSPD2 | X | 14910994 | G | A | A0201,A3001,B1302,B4403,C0602,C1602 | A0201 | 98 | 16 | fqwrkeisl | fqwrkeisV |
| M4945 | CTPS2 | X | 16627721 | A | G | A0201,A3001,B1302,B4403,C0602,C1602 | A0201 | 382 | 234 | ylgllPaat | ylgllLaat |
| M4945 | CTPS2 | X | 16711499 | G | C | A0201,A3001,B1302,B4403,C0602,C1602 | C0602 | 451 | 394 | ihvslvAql | ihvslvPql |
| M4945 | CCDC120 | X | 48923328 | T | C | A0201,A3001,B1302,B4403,C0602,C1602 | A3001 | 92 | 94 | rsApatpvl | rsVpatpvl |
| M4945 | AR | X | 66766214 | G | A | A0201,A3001,B1302,B4403,C0602,C1602 | C0602 | 63 | 215 | cryEdlasl | cryGdlasl |
| M4945 | MED12 | X | 70345918 | C | T | A0201,A3001,B1302,B4403,C0602,C1602 | A3001 | 9 | 11 | krrmWpea | krrmRpea |

Figure 21 (Cont.)

| | | | | | | | | | | | |
|---|---|---|---|---|---|---|---|---|---|---|---|
| M4945 | MED12 | X | 70345918 | C | T | A0201,A3001,B1302,B4403,C0602,C1602 | C0602 | 78 | 89 | rrmWpeaf | rrmRpeaf |
| M4945 | PABPC5 | X | 90690940 | C | A | A0201,A3001,B1302,B4403,C0602,C1602 | A0201 | 39 | 140 | raMfylfsa | raLfylfsa |
| M4945 | PABPC5 | X | 90690940 | C | A | A0201,A3001,B1302,B4403,C0602,C1602 | A3001 | 83 | 139 | raMfylfsa | raLfylfsa |
| M4945 | BHLHB9 | X | 102004593 | C | A | A0201,A3001,B1302,B4403,C0602,C1602 | A0201 | 111 | 43 | tiwpnaTav | tiwpnaPav |
| M4945 | MORC4 | X | 106242929 | G | C | A0201,A3001,B1302,B4403,C0602,C1602 | A3001 | 30 | 50 | sshtrpLsa | sshtrpFsa |
| M4945 | MORC4 | X | 106242929 | G | C | A0201,A3001,B1302,B4403,C0602,C1602 | A3001 | 4 | 3 | htrpLsaia | htrpFsaia |
| M4945 | ATG4A | X | 107381409 | A | T | A0201,A3001,B1302,B4403,C0602,C1602 | A0201 | 98 | 974 | fLgflgdel | flgflgdel |
| M4945 | DCX | X | 110574261 | C | G | A0201,A3001,B1302,B4403,C0602,C1602 | A0201 | 88 | 32 | sldenecrL | sldenecrV |
| M4945 | DCX | X | 110574261 | C | G | A0201,A3001,B1302,B4403,C0602,C1602 | A0201 | 22 | 814 | rLmkgnpsa | rVmkgnpsa |
| M4945 | DCX | X | 110574261 | C | G | A0201,A3001,B1302,B4403,C0602,C1602 | A3001 | 55 | 10 | rLmkgnpsa | rVmkgnpsa |
| M4945 | TRPC5 | X | 111155699 | C | A | A0201,A3001,B1302,B4403,C0602,C1602 | B4403 | 45 | 36 | venefkaDy | venefkaEy |
| M4945 | ZCCHC12 | X | 117959993 | T | A | A0201,A3001,B1302,B4403,C0602,C1602 | A0201 | 275 | 2494 | Kvieiddtl | Nvieiddtl |
| MA7027 | CROCC | 1 | 17264920 | C | T | A2402,A,B0702,B5108,C0702,C1602 | C0702 | 288 | 410 | lrlqeqVal | lrlqeqAal |
| MA7027 | IFI6 | 1 | 27992956 | T | C | A2402,A,B0702,B5108,C0702,C1602 | B0702 | 490 | 415 | vvigSigal | vvigNigal |
| MA7027 | MPC2 | 1 | 167904989 | A | T | A2402,A,B0702,B5108,C0702,C1602 | B0702 | 125 | 1635 | rpMynhpag | rpLynhpag |
| MA7027 | RFWD2 | 1 | 176054916 | G | C | A2402,A,B0702,B5108,C0702,C1602 | C0702 | 96 | 361 | yfstrmsrM | yfstrmsrI |
| MA7027 | TRIM58 | 1 | 248039577 | A | T | A2402,A,B0702,B5108,C0702,C1602 | C0702 | 389 | 3233 | Vyeageisf | Dyeageisf |
| MA7027 | ZNF239 | 10 | 44052488 | T | A | A2402,A,B0702,B5108,C0702,C1602 | B0702 | 228 | 9320 | rvhtgerpF | rvhtgerpY |
| MA7027 | EXOC6 | 10 | 94693927 | A | T | A2402,A,B0702,B5108,C0702,C1602 | A2402 | 404 | 334 | gyrSyftqi | gyrRyftqi |
| MA7027 | EXOC6 | 10 | 94693927 | A | T | A2402,A,B0702,B5108,C0702,C1602 | A2402 | 453 | 202 | Syftqivgf | Ryftqivgf |
| MA7027 | EXOC6 | 10 | 94693927 | A | T | A2402,A,B0702,B5108,C0702,C1602 | C0702 | 68 | 82 | Syftqivgf | Ryftqivgf |
| MA7027 | PKD2L1 | 10 | 102052826 | C | A | A2402,A,B0702,B5108,C0702,C1602 | A2402 | 139 | 940 | Cynktllrl | Gynktllrl |

Figure 21 (Cont.)

| | | | | | | | | | | | |
|---|---|---|---|---|---|---|---|---|---|---|---|
| MA7027 | IFITM5 | 11 | 299453 | G | T | A2402,A,B0702,B5108,C0702,C1602 | B0702 | 15 | 89 | ypredtraH | ypredtraP |
| MA7027 | AP2A2 | 11 | 986856 | G | A | A2402,A,B0702,B5108,C0702,C1602 | C0702 | 227 | 160 | hretnlHyl | hretnlRyl |
| MA7027 | OR9G4 | 11 | 56511070 | G | T | A2402,A,B0702,B5108,C0702,C1602 | A2402 | 355 | 157 | lhtHmyffi | lhtPmyffi |
| MA7027 | OR9G4 | 11 | 56511070 | G | T | A2402,A,B0702,B5108,C0702,C1602 | C0702 | 169 | 146 | hlhtHmyff | hlhtPmyff |
| MA7027 | CDC42BPG | 11 | 64594247 | C | T | A2402,A,B0702,B5108,C0702,C1602 | B0702 | 231 | 95 | apeekgQva | apeekgRva |
| MA7027 | MAP3K11 | 11 | 65380582 | C | G | A2402,A,B0702,B5108,C0702,C1602 | C0702 | 48 | 334 | rrvpphvlL | rrvpphvlV |
| MA7027 | AP5B1 | 11 | 65545931 | G | A | A2402,A,B0702,B5108,C0702,C1602 | B0702 | 31 | 87 | rvkgplLvl | rvkgplPvl |
| MA7027 | OR10S1 | 11 | 123847606 | A | G | A2402,A,B0702,B5108,C0702,C1602 | C0702 | 23 | 22 | Hyvppvciy | Yyvppvciy |
| MA7027 | DDX25 | 11 | 125792721 | G | T | A2402,A,B0702,B5108,C0702,C1602 | C0702 | 130 | 108 | hfnslikql | hfnsSikql |
| MA7027 | TENC1 | 12 | 53453182 | C | A | A2402,A,B0702,B5108,C0702,C1602 | C0702 | 287 | 340 | vypghrHgl | vypghrPgl |
| MA7027 | GDF11 | 12 | 56142390 | G | A | A2402,A,B0702,B5108,C0702,C1602 | B0702 | 33 | 118 | avqtNgspl | avqtDgspl |
| MA7027 | MDM1 | 12 | 68708905 | C | A | A2402,A,B0702,B5108,C0702,C1602 | B0702 | 32 | 18258 | aptipvrrL | aptipvrrR |
| MA7027 | MDM1 | 12 | 68708905 | C | A | A2402,A,B0702,B5108,C0702,C1602 | B0702 | 40 | 12 | ipvrrLlaw | ipvrrRlaw |
| MA7027 | NAV3 | 12 | 78583958 | G | T | A2402,A,B0702,B5108,C0702,C1602 | A2402 | 478 | 33186 | eYaiatfnv | eDaiatfnv |
| MA7027 | NR1H4 | 12 | 100957170 | G | T | A2402,A,B0702,B5108,C0702,C1602 | C0702 | 423 | 316 | grltelLtf | grltelRtf |
| MA7027 | OR11H2 | 14 | 20181379 | A | G | A2402,A,B0702,B5108,C0702,C1602 | A2402 | 456 | 356 | lfiigsHtl | lfiigsYtl |
| MA7027 | PPP1R36 | 14 | 65054980 | A | T | A2402,A,B0702,B5108,C0702,C1602 | C0702 | 451 | 14121 | rfpaemqkL | rfpaemqkH |
| MA7027 | KIF26A | 14 | 104639772 | G | A | A2402,A,B0702,B5108,C0702,C1602 | B0702 | 210 | 8464 | Narrsshml | Darrsshml |
| MA7027 | TPSG1 | 16 | 1275245 | A | G | A2402,A,B0702,B5108,C0702,C1602 | B0702 | 22 | 6311 | aPgacglll | aLgacglll |
| MA7027 | MAPK8IP3 | 16 | 1756465 | G | T | A2402,A,B0702,B5108,C0702,C1602 | A2402 | 153 | 330 | iyrefeLli | iyrefeRli |
| MA7027 | SPIRE2 | 16 | 89927187 | C | T | A2402,A,B0702,B5108,C0702,C1602 | C0702 | 209 | 405 | smtpdVkhl | smtpdAkhl |
| MA7027 | MYH8 | 17 | 10315724 | A | T | A2402,A,B0702,B5108,C0702,C1602 | A2402 | 299 | 233 | qyfNgvldi | qyfigvldi |
| MA7027 | MYH8 | 17 | 10315724 | A | T | A2402,A,B0702,B5108,C0702,C1602 | B0702 | 70 | 99 | qprqyfNgv | qprqyfigv |

Figure 21 (Cont.)

| | | | | | | | | | | | |
|---|---|---|---|---|---|---|---|---|---|---|---|
| MA7027 | KRT32 | 17 | 39623495 | C | A | A2402,A,B0702,B5108,C0702,C1602 | B0702 | 12 | 1204 | rpasvcssV | rpasvcssG |
| MA7027 | KIF2B | 17 | 51901192 | C | A | A2402,A,B0702,B5108,C0702,C1602 | C0702 | 403 | 262 | ylqnqtfcL | ylqnqtfcF |
| MA7027 | AATK | 17 | 79104922 | G | T | A2402,A,B0702,B5108,C0702,C1602 | B0702 | 49 | 60 | gpEvyvlpl | gpDvyvlpl |
| MA7027 | ENTHD2 | 17 | 79207488 | G | A | A2402,A,B0702,B5108,C0702,C1602 | C0702 | 171 | 222 | lfsdIvlpl | lfsdTvlpl |
| MA7027 | ZNF491 | 19 | 11917051 | A | T | A2402,A,B0702,B5108,C0702,C1602 | B0702 | 29 | 11 | Wphtrekpf | Rphtrekpf |
| MA7027 | SSBP4 | 19 | 18542194 | A | G | A2402,A,B0702,B5108,C0702,C1602 | B0702 | 7 | 8 | sphSpnapm | sphNpnapm |
| MA7027 | ATP13A1 | 19 | 19770777 | G | A | A2402,A,B0702,B5108,C0702,C1602 | C0702 | 226 | 328 | eydpskVtf | eydpskAtf |
| MA7027 | ALKBH6 | 19 | 36500443 | G | T | A2402,A,B0702,B5108,C0702,C1602 | B0702 | 10 | 19 | qprppTrpt | qprppPrpt |
| MA7027 | ALKBH6 | 19 | 36500443 | G | T | A2402,A,B0702,B5108,C0702,C1602 | B0702 | 36 | 91 | ppTrpttsl | ppPrpttsl |
| MA7027 | CD177 | 19 | 43866447 | G | T | A2402,A,B0702,B5108,C0702,C1602 | B0702 | 20 | 14 | apalwLgvv | apalwWgvv |
| MA7027 | ZNF468 | 19 | 53345307 | A | G | A2402,A,B0702,B5108,C0702,C1602 | C0702 | 232 | 972 | sksPhwril | sksShwril |
| MA7027 | LILRA2 | 19 | 55087309 | C | A | A2402,A,B0702,B5108,C0702,C1602 | B0702 | 30 | 15 | rpslsvqTv | rpslsvqPv |
| MA7027 | NAT14 | 19 | 55997928 | G | C | A2402,A,B0702,B5108,C0702,C1602 | B0702 | 115 | 12988 | aPvklglra | aAvklglra |
| MA7027 | ZNF530 | 19 | 58117933 | G | T | A2402,A,B0702,B5108,C0702,C1602 | C0702 | 347 | 7966 | yrhrsahtI | yrhrsahtS |
| MA7027 | RTN4 | 2 | 55276934 | G | A | A2402,A,B0702,B5108,C0702,C1602 | B0702 | 344 | 1352 | tppapapaV | tppapapaA |
| MA7027 | IL18R1 | 2 | 102984437 | A | T | A2402,A,B0702,B5108,C0702,C1602 | B0702 | 158 | 21 | npWsssria | npRsssria |
| MA7027 | NEB | 2 | 152487791 | C | A | A2402,A,B0702,B5108,C0702,C1602 | B0702 | 98 | 114 | vpigsmdvF | vpigsmdvV |
| MA7027 | CASP10 | 2 | 202093792 | A | G | A2402,A,B0702,B5108,C0702,C1602 | B0702 | 23 | 23 | ppmrrwGsv | ppmrrwSsv |
| MA7027 | MARCH4 | 2 | 217234671 | G | T | A2402,A,B0702,B5108,C0702,C1602 | B0702 | 212 | 84 | ppvTppppl | ppvPppppl |
| MA7027 | TGM6 | 20 | 2397917 | A | T | A2402,A,B0702,B5108,C0702,C1602 | A2402 | 108 | 40 | vyskavIrl | vyskavNrl |
| MA7027 | TGM6 | 20 | 2397917 | A | T | A2402,A,B0702,B5108,C0702,C1602 | C0702 | 367 | 677 | vyskavIrl | vyskavNrl |
| MA7027 | GRAMD4 | 22 | 47059938 | C | T | A2402,A,B0702,B5108,C0702,C1602 | C0702 | 310 | 28772 | rrlkrgakL | rrlkrgakP |

Figure 21 (Cont.)

| | | | | | | | | | | | |
|---|---|---|---|---|---|---|---|---|---|---|---|
| MA7027 | SRGAP3 | 3 | 9027306 | T | A | A2402,A,B0702,B5108,C0702,C1602 | B0702 | 15 | 495 | rpvrpvvqL | rpvrpvvqH |
| MA7027 | LEPREL1 | 3 | 189690812 | G | T | A2402,A,B0702,B5108,C0702,C1602 | C0702 | 463 | 1283 | Ygyegrvpl | Sgyegrvpl |
| MA7027 | PCDH10 | 4 | 134072946 | C | A | A2402,A,B0702,B5108,C0702,C1602 | B0702 | 389 | 3107 | rdagsTqal | rdagsPqal |
| MA7027 | ADAM29 | 4 | 175896824 | G | T | A2402,A,B0702,B5108,C0702,C1602 | A2402 | 39 | 162 | Cwlsyilpf | Gwlsyilpf |
| MA7027 | ADAM29 | 4 | 175896824 | G | T | A2402,A,B0702,B5108,C0702,C1602 | C0702 | 199 | 252 | Cwlsyilpf | Gwlsyilpf |
| MA7027 | ATG10 | 5 | 81460299 | G | T | A2402,A,B0702,B5108,C0702,C1602 | C0702 | 438 | 1340 | yhFlyscsy | yhVlyscsy |
| MA7027 | PCDHGA2 | 5 | 140720048 | T | A | A2402,A,B0702,B5108,C0702,C1602 | B0702 | 28 | 46 | apissNisi | apissYisi |
| MA7027 | TINAG | 6 | 54214537 | C | A | A2402,A,B0702,B5108,C0702,C1602 | A2402 | 83 | 154 | vshacyQlf | vshacyPlf |
| MA7027 | COL10A1 | 6 | 116441979 | C | T | A2402,A,B0702,B5108,C0702,C1602 | B0702 | 274 | 10174 | mpRhngeag | mpGhngeag |
| MA7027 | DNAH11 | 7 | 21737798 | G | T | A2402,A,B0702,B5108,C0702,C1602 | A2402 | 381 | 4643 | alarkfitF | alarkfitL |
| MA7027 | DNAH11 | 7 | 21737798 | G | T | A2402,A,B0702,B5108,C0702,C1602 | A2402 | 478 | 303 | Fytlckell | Lytlckell |
| MA7027 | DNAH11 | 7 | 21737798 | G | T | A2402,A,B0702,B5108,C0702,C1602 | C0702 | 60 | 529 | Fytlckell | Lytlckell |
| MA7027 | DNAH11 | 7 | 21737803 | C | T | A2402,A,B0702,B5108,C0702,C1602 | A2402 | 54 | 303 | lyMlckell | lyTlckell |
| MA7027 | DNAH11 | 7 | 21737803 | C | T | A2402,A,B0702,B5108,C0702,C1602 | C0702 | 164 | 529 | lyMlckell | lyTlckell |
| MA7027 | CYP3A43 | 7 | 99434081 | G | A | A2402,A,B0702,B5108,C0702,C1602 | A2402 | 381 | 99 | iyEthshkl | iyGthshkl |
| MA7027 | CYP3A43 | 7 | 99434081 | G | A | A2402,A,B0702,B5108,C0702,C1602 | C0702 | 455 | 575 | iyEthshkl | iyGthshkl |
| MA7027 | MUC17 | 7 | 100682318 | G | A | A2402,A,B0702,B5108,C0702,C1602 | B0702 | 36 | 72 | tpvNsnspv | tpvDsnspv |
| MA7027 | OR6B1 | 7 | 143701160 | G | T | A2402,A,B0702,B5108,C0702,C1602 | A2402 | 109 | 990 | smLaamfli | smRaamfli |
| MA7027 | OR6B1 | 7 | 143701160 | G | T | A2402,A,B0702,B5108,C0702,C1602 | A2402 | 230 | 851 | mLaamflif | mRaamflif |
| MA7027 | NOBOX | 7 | 144098336 | G | T | A2402,A,B0702,B5108,C0702,C1602 | B0702 | 83 | 418 | kpnamglaQ | kpnamglaP |
| MA7027 | RBM33 | 7 | 155538207 | A | C | A2402,A,B0702,B5108,C0702,C1602 | B0702 | 175 | 137 | kpgvQrtvt | kpgvKrtvt |
| MA7027 | SLC7A13 | 8 | 87229865 | G | A | A2402,A,B0702,B5108,C0702,C1602 | B0702 | 191 | 168 | spfIavlll | spfTavlll |
| MA7027 | SLC7A13 | 8 | 87229865 | G | A | A2402,A,B0702,B5108,C0702,C1602 | C0702 | 282 | 413 | hsspfIavl | hsspfTavl |

Figure 21 (Cont.)

| | | | | | | | | | | | |
|---|---|---|---|---|---|---|---|---|---|---|---|
| MA7027 | CSMD3 | 8 | 113421190 | G | C | A2402,A,B0702,B5108,C0702,C1602 | B0702 | 352 | 91 | gptEqssll | gptQqssll |
| MA7027 | FAM135B | 8 | 139209861 | G | A | A2402,A,B0702,B5108,C0702,C1602 | C0702 | 349 | 548 | hahkwYrdl | hahkwHrdl |
| MA7027 | FAM135B | 8 | 139209861 | G | A | A2402,A,B0702,B5108,C0702,C1602 | C0702 | 59 | 571 | wYrdlclll | wHrdlclll |
| MA7027 | PUF60 | 8 | 144898886 | C | A | A2402,A,B0702,B5108,C0702,C1602 | A2402 | 440 | 1460 | kfgavnLvi | kfgavnRvi |
| MA7027 | EXOSC4 | 8 | 145133696 | T | C | A2402,A,B0702,B5108,C0702,C1602 | B0702 | 95 | 15499 | ePrkiqarm | eLrkiqarm |
| MA7027 | SLC39A4 | 8 | 145641370 | C | T | A2402,A,B0702,B5108,C0702,C1602 | C0702 | 486 | 513 | arlsaaTvl | arlsaaAvl |
| MA7027 | C9orf66 | 9 | 215047 | G | A | A2402,A,B0702,B5108,C0702,C1602 | B0702 | 138 | 42 | nlrVaggvl | nlrAaggvl |
| MA7027 | C9orf66 | 9 | 215047 | G | A | A2402,A,B0702,B5108,C0702,C1602 | B0702 | 30 | 53 | rVaggvlpv | rAaggvlpv |
| MA7027 | OR13C9 | 9 | 107380101 | G | C | A2402,A,B0702,B5108,C0702,C1602 | A2402 | 73 | 38 | ryvaicnAl | ryvaicnPl |
| MA7027 | POLA1 | X | 24906190 | G | C | A2402,A,B0702,B5108,C0702,C1602 | B0702 | 72 | 21232 | sPtgplcpa | sRtgplcpa |
| MA7027 | PCDH11X | X | 91134013 | C | A | A2402,A,B0702,B5108,C0702,C1602 | A2402 | 123 | 76 | nwvttHttf | nwvttPttf |
| MA7027 | ESX1 | X | 103498983 | C | G | A2402,A,B0702,B5108,C0702,C1602 | B0702 | 221 | 7208 | Rpqpaegpq | Gpqpaegpq |
| NI9507 | ZMYND11 | 10 | 267187 | G | C | A0201,A1101,B0702,C0702 | A0201 | 428 | 10330 | ycfechlpA | ycfechlpG |
| NI9507 | EXOSC1 | 10 | 99200940 | C | T | A0201,A1101,B0702,C0702 | A1101 | 41 | 24 | nsfQgtirk | nsfRgtirk |
| NI9507 | SERPINA4 | 14 | 95035828 | C | T | A0201,A1101,B0702,C0702 | A1101 | 202 | 309 | aqtnChilr | aqtnRhilr |
| NI9507 | HIC1 | 17 | 1960255 | G | A | A0201,A1101,B0702,C0702 | A0201 | 50 | 177 | rladgTeaa | rladgAeaa |
| NI9507 | CPD | 17 | 28776601 | T | G | A0201,A1101,B0702,C0702 | C0702 | 163 | 196 | yrhMwslei | yrhIwslei |
| NI9507 | VEZF1 | 17 | 56052103 | C | T | A0201,A1101,B0702,C0702 | B0702 | 47 | 15 | spvnvssTv | spvnvssAv |
| NI9507 | ADAMTS10 | 19 | 8670187 | G | T | A0201,A1101,B0702,C0702 | B0702 | 444 | 505 | rvdNngall | rvdHngall |
| NI9507 | ADAMTS10 | 19 | 8670187 | G | T | A0201,A1101,B0702,C0702 | C0702 | 195 | 161 | trvdNngal | trvdHngal |
| NI9507 | OPRL1 | 20 | 62729760 | C | T | A0201,A1101,B0702,C0702 | A0201 | 16 | 116 | lmirWlrgv | lmirRlrgv |
| NI9507 | OPRL1 | 20 | 62729760 | C | T | A0201,A1101,B0702,C0702 | A1101 | 83 | 1141 | yslmirWlr | yslmirRlr |

Figure 21 (Cont.)

| | | | | | | | | | | | |
|---|---|---|---|---|---|---|---|---|---|---|---|
| NI9507 | OPRL1 | 20 | 62729760 | C | T | A0201,A1101,B0702,C0702 | C0702 | 105 | 193 | irWlrgvrl | irRlrgvrl |
| NI9507 | MAATS1 | 3 | 119459516 | C | T | A0201,A1101,B0702,C0702 | A1101 | 66 | 866 | vtlalqWqr | vtlalqRqr |
| NI9507 | BTNL9 | 5 | 180474968 | G | A | A0201,A1101,B0702,C0702 | A0201 | 68 | 77 | ilallgeev | ilalVgeev |
| NI9507 | CCM2 | 7 | 45113873 | G | A | A0201,A1101,B0702,C0702 | A0201 | 12 | 29 | ymltlHtkl | ymltlRtkl |
| NI9507 | EGFR | 7 | 55241672 | T | G | A0201,A1101,B0702,C0702 | A1101 | 28 | 26 | riWketefk | riLketefk |
| NI9507 | EGFR | 7 | 55241708 | G | C | A0201,A1101,B0702,C0702 | A0201 | 175 | 900 | vlAsgafgt | vlGsgafgt |
| NI9507 | MAGED2 | X | 54841736 | C | T | A0201,A1101,B0702,C0702 | A0201 | 296 | 4763 | aqyreameV | aqyreameA |
| NI9507 | MAGED2 | X | 54841736 | C | T | A0201,A1101,B0702,C0702 | C0702 | 277 | 429 | yreameVdl | yreameAdl |
| R7495_2 | AJAP1 | 1 | 4834512 | A | G | A1101,,B3801,B35132,C1203,C0401 | C1203 | 256 | 387 | ssdrhlVpv | ssdrhllpv |
| R7495_2 | DIRAS3 | 1 | 68512803 | C | T | A1101,,B3801,B35132,C1203,C0401 | A1101 | 48 | 145 | asSnfrhey | asGnfrhey |
| R7495_2 | IFI16 | 1 | 159021555 | C | A | A1101,,B3801,B35132,C1203,C0401 | C1203 | 462 | 195 | mvlKatesf | mvlNatesf |
| R7495_2 | MPZ | 1 | 161279663 | G | T | A1101,,B3801,B35132,C1203,C0401 | C1203 | 388 | 477 | spRpilavl | spSpilavl |
| R7495_2 | ZP4 | 1 | 238048479 | C | A | A1101,,B3801,B35132,C1203,C0401 | C1203 | 125 | 15 | qSlrgpvhl | qAlrgpvhl |
| R7495_2 | ZP4 | 1 | 238048480 | C | A | A1101,,B3801,B35132,C1203,C0401 | C1203 | 13 | 15 | Halrgpvhl | Qalrgpvhl |
| R7495_2 | OR2C3 | 1 | 247695077 | A | T | A1101,,B3801,B35132,C1203,C0401 | C1203 | 217 | 1863 | sshEavvsl | sshVavvsl |
| R7495_2 | SLIT1 | 10 | 98806812 | T | A | A1101,,B3801,B35132,C1203,C0401 | A1101 | 36 | 6110 | staelrlnY | staelrlnN |
| R7495_2 | SLIT1 | 10 | 98806812 | T | A | A1101,,B3801,B35132,C1203,C0401 | C1203 | 115 | 1341 | lnYneisil | lnNneisil |
| R7495_2 | GPR123 | 10 | 134942233 | T | C | A1101,,B3801,B35132,C1203,C0401 | A1101 | 94 | 138 | Lvlihhcak | Fvlihhcak |
| R7495_2 | GPR123 | 10 | 134942233 | T | C | A1101,,B3801,B35132,C1203,C0401 | C1203 | 411 | 412 | fcvtlglLv | fcvtlglFv |
| R7495_2 | GPR123 | 10 | 134942233 | T | C | A1101,,B3801,B35132,C1203,C0401 | C1203 | 435 | 442 | vtlglLvli | vtlglFvli |
| R7495_2 | FRG2B | 10 | 135440224 | G | T | A1101,,B3801,B35132,C1203,C0401 | B3801 | 132 | 8009 | dHdlhcssi | dPdlhcssi |
| R7495_2 | ANO5 | 11 | 22279281 | G | A | A1101,,B3801,B35132,C1203,C0401 | C1203 | 194 | 67 | wyflsEatv | wyflsGatv |
| R7495_2 | ANO5 | 11 | 22279281 | G | A | A1101,,B3801,B35132,C1203,C0401 | C1203 | 16 | 50 | flsEatvtl | flsGatvtl |

Figure 21 (Cont.)

| | | | | | | | | | | | |
|---|---|---|---|---|---|---|---|---|---|---|---|
| R7495_2 | INTS5 | 11 | 62416374 | T | A | A1101,,B3801,B35132,C1203,C0401 | C1203 | 359 | 189 | nmlnlavLl | nmlnlavHl |
| R7495_2 | LRFN4 | 11 | 66625925 | A | G | A1101,,B3801,B35132,C1203,C0401 | A1101 | 129 | 1742 | lsfsgnplR | lsfsgnplH |
| R7495_2 | WNK1 | 12 | 977098 | A | G | A1101,,B3801,B35132,C1203,C0401 | C1203 | 79 | 145 | fpAiherpv | fpTiherpv |
| R7495_2 | NAV3 | 12 | 78513337 | G | T | A1101,,B3801,B35132,C1203,C0401 | B3801 | 209 | 271 | sqnqYdvvl | sqnqDdvvl |
| R7495_2 | NAV3 | 12 | 78513337 | G | T | A1101,,B3801,B35132,C1203,C0401 | C1203 | 10 | 45 | nqYdvvlhv | nqDdvvlhv |
| R7495_2 | TRPV4 | 12 | 110231799 | T | C | A1101,,B3801,B35132,C1203,C0401 | C1203 | 30 | 30 | ypyrttvGy | ypyrttvDy |
| R7495_2 | CDK2AP1 | 12 | 123751805 | G | C | A1101,,B3801,B35132,C1203,C0401 | A1101 | 27 | 39 | Ssmatssqy | Tsmatssqy |
| R7495_2 | CMA1 | 14 | 24975288 | G | T | A1101,,B3801,B35132,C1203,C0401 | C1203 | 395 | 1192 | fEhnlqlcv | fDhnlqlcv |
| R7495_2 | AKAP6 | 14 | 33015129 | A | G | A1101,,B3801,B35132,C1203,C0401 | C1203 | 229 | 217 | msrGtpslv | msrStpslv |
| R7495_2 | HERC2 | 15 | 28518046 | G | A | A1101,,B3801,B35132,C1203,C0401 | C1203 | 441 | 2433 | Mlsqmlsai | Tlsqmlsai |
| R7495_2 | SPTBN5 | 15 | 42158373 | G | A | A1101,,B3801,B35132,C1203,C0401 | A1101 | 333 | 1024 | vsqWlqglr | vsqRlqglr |
| R7495_2 | SPTBN5 | 15 | 42158373 | G | A | A1101,,B3801,B35132,C1203,C0401 | A1101 | 54 | 957 | sqWlqglrk | sqRlqglrk |
| R7495_2 | SLC24A1 | 15 | 65937992 | C | T | A1101,,B3801,B35132,C1203,C0401 | C1203 | 315 | 9155 | lpavtvtpV | lpavtvtpA |
| R7495_2 | DOC2A | 16 | 30020555 | C | A | A1101,,B3801,B35132,C1203,C0401 | C1203 | 210 | 194 | dpyFklhll | dpyVklhll |
| R7495_2 | CES1 | 16 | 55862883 | C | A | A1101,,B3801,B35132,C1203,C0401 | C1203 | 93 | 873 | wVhpssppv | wGhpssppv |
| R7495_2 | TMEM95 | 17 | 7258938 | C | T | A1101,,B3801,B35132,C1203,C0401 | C1203 | 262 | 332 | kvteklhrv | kvtekThrv |
| R7495_2 | CDR2L | 17 | 72999783 | C | A | A1101,,B3801,B35132,C1203,C0401 | C1203 | 356 | 1297 | pasrhagnl | pasrhagnL |
| R7495_2 | TRIM65 | 17 | 73886888 | A | G | A1101,,B3801,B35132,C1203,C0401 | C1203 | 87 | 51 | fpPgpqeev | fpLgpqeev |
| R7495_2 | L3MBTL4 | 18 | 6138263 | C | A | A1101,,B3801,B35132,C1203,C0401 | A1101 | 294 | 548 | Svcptpgcr | Avcptpgcr |
| R7495_2 | LDLR | 19 | 11213371 | C | G | A1101,,B3801,B35132,C1203,C0401 | A1101 | 135 | 14645 | vtcksgdfR | vtcksgdfS |
| R7495_2 | RGL3 | 19 | 11508168 | G | A | A1101,,B3801,B35132,C1203,C0401 | C1203 | 188 | 117 | earviCvsi | earviRvsi |
| R7495_2 | RASAL3 | 19 | 15568258 | C | T | A1101,,B3801,B35132,C1203,C0401 | A1101 | 33 | 22 | rMlpseryk | rVlpseryk |

Figure 21 (Cont.)

| | | | | | | | | | | | |
|---|---|---|---|---|---|---|---|---|---|---|---|
| R7495_2 | UNC13A | 19 | 17750278 | G | T | A1101,,B3801,B35132,C1203,C0401 | C1203 | 401 | 350 | stvEltsi | stvDltsi |
| R7495_2 | ZNF540 | 19 | 38091932 | A | T | A1101,,B3801,B35132,C1203,C0401 | C1203 | 126 | 21929 | lgysgskpV | lgysgskpD |
| R7495_2 | ZNF540 | 19 | 38091932 | A | T | A1101,,B3801,B35132,C1203,C0401 | C1203 | 18 | 33 | ysgskpVvi | ysgskpDvi |
| R7495_2 | SCAF1 | 19 | 50154782 | T | C | A1101,,B3801,B35132,C1203,C0401 | C1203 | 331 | 2576 | gaaPpppll | gaaLpppll |
| R7495_2 | OTOF | 2 | 26700700 | G | A | A1101,,B3801,B35132,C1203,C0401 | A1101 | 41 | 45 | rsltLlinr | rsltPlinr |
| R7495_2 | OTOF | 2 | 26700700 | G | A | A1101,,B3801,B35132,C1203,C0401 | C1203 | 299 | 471 | imrsltLli | imrsltPli |
| R7495_2 | TCF23 | 2 | 27372174 | C | T | A1101,,B3801,B35132,C1203,C0401 | C1203 | 105 | 6562 | wsnqrwsrV | wsnqrwsrA |
| R7495_2 | TET3 | 2 | 74329273 | G | T | A1101,,B3801,B35132,C1203,C0401 | C1203 | 200 | 607 | yaytNvtgp | yaytKvtgp |
| R7495_2 | POTEF | 2 | 130832430 | G | T | A1101,,B3801,B35132,C1203,C0401 | B3801 | 381 | 4781 | Hhatlrldi | Phatlrldi |
| R7495_2 | KCNH7 | 2 | 163228425 | G | C | A1101,,B3801,B35132,C1203,C0401 | C1203 | 415 | 1902 | hAslpdssl | hPslpdssl |
| R7495_2 | MIS18A | 21 | 33651054 | G | A | A1101,,B3801,B35132,C1203,C0401 | C1203 | 401 | 17782 | flcsgcrrL | flcsgcrrP |
| R7495_2 | MB | 22 | 36013259 | C | G | A1101,,B3801,B35132,C1203,C0401 | C1203 | 110 | 175 | lvlnvwRkv | lvlnvwGkv |
| R7495_2 | CCDC54 | 3 | 107096960 | C | G | A1101,,B3801,B35132,C1203,C0401 | A1101 | 67 | 51 | kliqAatlk | kliqPatlk |
| R7495_2 | CCDC54 | 3 | 107096960 | C | G | A1101,,B3801,B35132,C1203,C0401 | C1203 | 371 | 350 | ykliqAatl | ykliqPatl |
| R7495_2 | CCDC54 | 3 | 107096960 | C | G | A1101,,B3801,B35132,C1203,C0401 | C1203 | 102 | 880 | qAatlkntl | qPatlkntl |
| R7495_2 | ZXDC | 3 | 126194384 | C | T | A1101,,B3801,B35132,C1203,C0401 | A1101 | 32 | 16171 | rvnlasrpK | rvnlasrpE |
| R7495_2 | TMEM44 | 3 | 194337848 | G | A | A1101,,B3801,B35132,C1203,C0401 | C1203 | 319 | 62 | Caaldlaii | Raaldlaii |
| R7495_2 | PDE6B | 4 | 655992 | G | A | A1101,,B3801,B35132,C1203,C0401 | C0401 | 251 | 734 | Sfnvaqtmf | Gfnvaqtmf |
| R7495_2 | PDE6B | 4 | 655992 | G | A | A1101,,B3801,B35132,C1203,C0401 | C1203 | 18 | 100 | hSfnvaqtm | hGfnvaqtm |
| R7495_2 | JAKMIP1 | 4 | 6107618 | A | C | A1101,,B3801,B35132,C1203,C0401 | A1101 | 26 | 26 | htaySselk | htaylselk |
| R7495_2 | JAKMIP1 | 4 | 6107618 | A | C | A1101,,B3801,B35132,C1203,C0401 | B3801 | 212 | 217 | rhtaySsel | rhtaylsel |
| R7495_2 | JAKMIP1 | 4 | 6107618 | A | C | A1101,,B3801,B35132,C1203,C0401 | C1203 | 40 | 91 | ySselkakl | ylselkakl |
| R7495_2 | PPP3CA | 4 | 102004389 | T | A | A1101,,B3801,B35132,C1203,C0401 | A1101 | 455 | 15345 | avceflqhY | avceflqhN |

Figure 21 (Cont.)

| | | | | | | | | | | | |
|---|---|---|---|---|---|---|---|---|---|---|---|
| R7495_2 | PPP3CA | 4 | 102004389 | T | A | A1101,,B3801,B35132,C1203,C0401 | B3801 | 49 | 85 | qhYnllsil | qhNnllsil |
| R7495_2 | PPP3CA | 4 | 102004389 | T | A | A1101,,B3801,B35132,C1203,C0401 | C1203 | 304 | 14714 | avceflqhY | avceflqhN |
| R7495_2 | PPP3CA | 4 | 102004389 | T | A | A1101,,B3801,B35132,C1203,C0401 | C1203 | 357 | 72 | lqhYnllsi | lqhNnllsi |
| R7495_2 | PPP3CA | 4 | 102004389 | T | A | A1101,,B3801,B35132,C1203,C0401 | C1203 | 250 | 3691 | qhYnllsil | qhNnllsil |
| R7495_2 | ADCY2 | 5 | 7804771 | G | T | A1101,,B3801,B35132,C1203,C0401 | C1203 | 186 | 2625 | stymaatVl | stymaatGl |
| R7495_2 | ADCY2 | 5 | 7804771 | G | T | A1101,,B3801,B35132,C1203,C0401 | C1203 | 40 | 26 | maatVlsav | maatGlsav |
| R7495_2 | MAST4 | 5 | 66461564 | A | T | A1101,,B3801,B35132,C1203,C0401 | A1101 | 59 | 8564 | aLsessshk | aHsessshk |
| R7495_2 | GPR98 | 5 | 90136692 | C | A | A1101,,B3801,B35132,C1203,C0401 | C1203 | 82 | 79 | ladqlhKpv | ladqlhQpv |
| R7495_2 | TRIM15 | 6 | 30136302 | C | G | A1101,,B3801,B35132,C1203,C0401 | C1203 | 333 | 609 | paselVqdv | paselLqdv |
| R7495_2 | KIF6 | 6 | 39311508 | C | G | A1101,,B3801,B35132,C1203,C0401 | A1101 | 53 | 265 | kaTqsilqk | kaRqsilqk |
| R7495_2 | KIF6 | 6 | 39311508 | C | G | A1101,,B3801,B35132,C1203,C0401 | C1203 | 467 | 152 | fikaTqsil | fikaRqsil |
| R7495_2 | LRP11 | 6 | 150185029 | G | A | A1101,,B3801,B35132,C1203,C0401 | C1203 | 38 | 43 | aalppaVpl | aalppaApl |
| R7495_2 | CHN2 | 7 | 29440161 | T | C | A1101,,B3801,B35132,C1203,C0401 | A1101 | 352 | 8969 | rSgnqtlny | rFgnqtlny |
| R7495_2 | ZNF716 | 7 | 57528983 | A | T | A1101,,B3801,B35132,C1203,C0401 | C1203 | 17 | 16 | ytcDergkv | ytcEergkv |
| R7495_2 | FLNC | 7 | 128496864 | G | A | A1101,,B3801,B35132,C1203,C0401 | C1203 | 190 | 122 | dvkfnSahi | dvkfnGahi |
| R7495_2 | FLNC | 7 | 128496864 | G | A | A1101,,B3801,B35132,C1203,C0401 | C1203 | 459 | 1573 | Sahipgspf | Gahipgspf |
| R7495_2 | PTPRN2 | 7 | 157959917 | G | A | A1101,,B3801,B35132,C1203,C0401 | C1203 | 173 | 282 | ypSgsrtql | ypPgsrtql |
| R7495_2 | CNBD1 | 8 | 88365945 | C | A | A1101,,B3801,B35132,C1203,C0401 | C1203 | 80 | 18 | lqvTftcti | lqvPftcti |
| R7495_2 | CSMD3 | 8 | 113678527 | G | T | A1101,,B3801,B35132,C1203,C0401 | C1203 | 59 | 65 | ieaepghYi | ieaepghSi |
| R7495_2 | GBGT1 | 9 | 136037742 | G | A | A1101,,B3801,B35132,C1203,C0401 | A1101 | 32 | 112 | tsFsvlwvy | tsLsvlwvy |
| R7495_2 | GBGT1 | 9 | 136037742 | G | A | A1101,,B3801,B35132,C1203,C0401 | C1203 | 344 | 323 | lagtsFsvl | lagtsLsvl |
| R7495_2 | CHIC1 | X | 72899493 | C | T | A1101,,B3801,B35132,C1203,C0401 | A1101 | 52 | 293 | lVlhwkltk | lAlhwkltk |

Figure 21 (Cont.)

| | | | | | | | | | | | |
|---|---|---|---|---|---|---|---|---|---|---|---|
| R7495_2 | PABPC5 | X | 90690988 | G | A | A1101,,B3801,B35132,C1203,C0401 | A1101 | 140 | 76 | vlcddngsk | vVcddngsk |
| RH090935 | MMEL1 | 1 | 2543638 | G | T | A3201,A2601,B3501,B3801,B3540,C0401,C1203 | C1203 | 6 | 9 | yadrrgkKl | yadrrgkQl |
| RH090935 | SLC2A7 | 1 | 9074861 | C | T | A3201,A2601,B3501,B3801,B3540,C0401,C1203 | C1203 | 418 | 262 | Qaeraeghl | Raeraeghl |
| RH090935 | SPEN | 1 | 16174642 | A | G | A3201,A2601,B3501,B3801,B3540,C0401,C1203 | A2601 | 413 | 824 | kiiehfRry | kiiehfKry |
| RH090935 | SPEN | 1 | 16174642 | A | G | A3201,A2601,B3501,B3801,B3540,C0401,C1203 | C1203 | 327 | 316 | kiiehfRry | kiiehfKry |
| RH090935 | SPEN | 1 | 16174642 | A | G | A3201,A2601,B3501,B3801,B3540,C0401,C1203 | C1203 | 60 | 80 | Rrygrvesv | Krygrvesv |
| RH090935 | MTF1 | 1 | 38323315 | G | C | A3201,A2601,B3501,B3801,B3540,C0401,C1203 | A2601 | 269 | 1327 | hsAdnniiy | hsPdnniiy |
| RH090935 | MTF1 | 1 | 38323315 | G | C | A3201,A2601,B3501,B3801,B3540,C0401,C1203 | B3501 | 9 | 112 | hsAdnniiy | hsPdnniiy |
| RH090935 | MTF1 | 1 | 38323315 | G | C | A3201,A2601,B3501,B3801,B3540,C0401,C1203 | B3501 | 220 | 79 | sAdnniiyf | sPdnniiyf |
| RH090935 | MTF1 | 1 | 38323315 | G | C | A3201,A2601,B3501,B3801,B3540,C0401,C1203 | B3801 | 70 | 32 | ehsAdnnii | ehsPdnnii |
| RH090935 | MTF1 | 1 | 38323315 | G | C | A3201,A2601,B3501,B3801,B3540,C0401,C1203 | C1203 | 114 | 229 | hsAdnniiy | hsPdnniiy |
| RH090935 | MTF1 | 1 | 38323315 | G | C | A3201,A2601,B3501,B3801,B3540,C0401,C1203 | C1203 | 65 | 624 | sAdnniiyf | sPdnniiyf |
| RH090935 | INPP5B | 1 | 38328030 | T | G | A3201,A2601,B3501,B3801,B3540,C0401,C1203 | B3501 | 242 | 1818 | Taqefihqf | Kaqefihqf |
| RH090935 | INPP5B | 1 | 38328030 | T | G | A3201,A2601,B3501,B3801,B3540,C0401,C1203 | C1203 | 95 | 57 | Taqefihqf | Kaqefihqf |
| RH090935 | INPP5B | 1 | 38328031 | T | C | A3201,A2601,B3501,B3801,B3540,C0401,C1203 | A2601 | 99 | 20490 | Eaqefihqf | Kaqefihqf |
| RH090935 | INPP5B | 1 | 38328031 | T | C | A3201,A2601,B3501,B3801,B3540,C0401,C1203 | B3501 | 217 | 1818 | Eaqefihqf | Kaqefihqf |
| RH090935 | INPP5B | 1 | 38328031 | T | C | A3201,A2601,B3501,B3801,B3540,C0401,C1203 | C1203 | 115 | 57 | Eaqefihqf | Kaqefihqf |
| RH090935 | SZT2 | 1 | 43892460 | G | A | A3201,A2601,B3501,B3801,B3540,C0401,C1203 | B3501 | 207 | 90 | tqatgNsaf | tqatgDsaf |
| RH090935 | FAF1 | 1 | 51050450 | C | A | A3201,A2601,B3501,B3801,B3540,C0401,C1203 | A2601 | 110 | 20417 | dvhmvsdsY | dvhmvsdsD |
| RH090935 | FAF1 | 1 | 51050450 | C | A | A3201,A2601,B3501,B3801,B3540,C0401,C1203 | B3501 | 29 | 23273 | dvhmvsdsY | dvhmvsdsD |
| RH090935 | ARHGAP29 | 1 | 94668279 | C | G | A3201,A2601,B3501,B3801,B3540,C0401,C1203 | A3201 | 32 | 49 | kmleaQnal | kmleaEnal |
| RH090935 | ARHGAP29 | 1 | 94668279 | C | G | A3201,A2601,B3501,B3801,B3540,C0401,C1203 | C1203 | 344 | 358 | kmleaQnal | kmleaEnal |
| RH090935 | MPC2 | 1 | 167905002 | C | G | A3201,A2601,B3501,B3801,B3540,C0401,C1203 | B3501 | 23 | 30 | lpDklrply | lpEklrply |

Figure 21 (Cont.)

| | | | | | | | | | | | |
|---|---|---|---|---|---|---|---|---|---|---|---|
| RH090935 | MPC2 | 1 | 167905002 | C | G | A3201,A2601,B3501,B3801,B3540,C0401,C1203 | C1203 | 478 | 527 | mlpDklrpl | mlpEklrpl |
| RH090935 | NMNAT2 | 1 | 183253868 | G | A | A3201,A2601,B3501,B3801,B3540,C0401,C1203 | B3501 | 123 | 1152 | rpLverftf | rpPverftf |
| RH090935 | C1orf65 | 1 | 223567517 | G | C | A3201,A2601,B3501,B3801,B3540,C0401,C1203 | B3501 | 80 | 33 | qplasskQm | qplasskEm |
| RH090935 | ZEB1 | 10 | 31810808 | G | T | A3201,A2601,B3501,B3801,B3540,C0401,C1203 | A3201 | 141 | 3681 | vaytysttF | vaytysttV |
| RH090935 | ZEB1 | 10 | 31810808 | G | T | A3201,A2601,B3501,B3801,B3540,C0401,C1203 | B3501 | 19 | 2630 | vaytysttF | vaytysttV |
| RH090935 | ZEB1 | 10 | 31810808 | G | T | A3201,A2601,B3501,B3801,B3540,C0401,C1203 | C1203 | 19 | 6 | vaytysttF | vaytysttV |
| RH090935 | ZEB1 | 10 | 31810808 | G | T | A3201,A2601,B3501,B3801,B3540,C0401,C1203 | C1203 | 90 | 332 | ysttFspav | ysttVspav |
| RH090935 | IPMK | 10 | 59955902 | C | G | A3201,A2601,B3501,B3801,B3540,C0401,C1203 | A2601 | 261 | 47 | ntiHegyvy | ntiDegyvy |
| RH090935 | IPMK | 10 | 59955902 | C | G | A3201,A2601,B3501,B3801,B3540,C0401,C1203 | B3501 | 148 | 6592 | hvfpsntiH | hvfpsntiD |
| RH090935 | IPMK | 10 | 59955902 | C | G | A3201,A2601,B3501,B3801,B3540,C0401,C1203 | B3501 | 238 | 303 | fpsntiHeg | fpsntiDeg |
| RH090935 | IPMK | 10 | 59955902 | C | G | A3201,A2601,B3501,B3801,B3540,C0401,C1203 | B3501 | 233 | 119 | ntiHegyvy | ntiDegyvy |
| RH090935 | MPEG1 | 11 | 58979562 | C | G | A3201,A2601,B3501,B3801,B3540,C0401,C1203 | C1203 | 331 | 530 | ytsHnvltk | ytsQnvltk |
| RH090935 | ANO1 | 11 | 70034082 | G | A | A3201,A2601,B3501,B3801,B3540,C0401,C1203 | B3801 | 499 | 616 | Nhayhggvl | Shayhggvl |
| RH090935 | PDE2A | 11 | 72292476 | T | C | A3201,A2601,B3501,B3801,B3540,C0401,C1203 | B3801 | 464 | 1843 | yrdppyhSw | yrdppyhNw |
| RH090935 | ROBO3 | 11 | 124743283 | G | A | A3201,A2601,B3501,B3801,B3540,C0401,C1203 | A3201 | 254 | 3239 | atwsgwlki | atwsgwlkM |
| RH090935 | DIP2B | 12 | 51122402 | G | C | A3201,A2601,B3501,B3801,B3540,C0401,C1203 | B3501 | 35 | 157 | Hiaicldpy | Qiaicldpy |
| RH090935 | DIP2B | 12 | 51122402 | G | C | A3201,A2601,B3501,B3801,B3540,C0401,C1203 | C1203 | 278 | 1444 | yssrHiaic | yssrQiaic |
| RH090935 | ACVR1B | 12 | 52370231 | A | G | A3201,A2601,B3501,B3801,B3540,C0401,C1203 | C1203 | 162 | 476 | lvinChqrv | lvinYhqrv |
| RH090935 | HNRNPA1 | 12 | 54676417 | A | G | A3201,A2601,B3501,B3801,B3540,C0401,C1203 | C1203 | 475 | 2525 | dSfgrggnf | dNfgrggnf |
| RH090935 | NR2C1 | 12 | 95456330 | T | C | A3201,A2601,B3501,B3801,B3540,C0401,C1203 | A2601 | 127 | 251 | daagvSqlf | daagvNqlf |
| RH090935 | NR2C1 | 12 | 95456330 | T | C | A3201,A2601,B3501,B3801,B3540,C0401,C1203 | B3501 | 46 | 119 | daagvSqlf | daagvNqlf |
| RH090935 | NR2C1 | 12 | 95456330 | T | C | A3201,A2601,B3501,B3801,B3540,C0401,C1203 | C1203 | 493 | 694 | daagvSqlf | daagvNqlf |

Figure 21 (Cont.)

| | | | | | | | | | | | |
|---|---|---|---|---|---|---|---|---|---|---|---|
| RH090935 | MYO1H | 12 | 109826635 | G | A | A3201,A2601,B3501,B3801,B3540,C0401,C1203 | B3501 | 308 | 58 | fsKnliyty | fsEnliyty |
| RH090935 | MYO1H | 12 | 109826635 | G | A | A3201,A2601,B3501,B3801,B3540,C0401,C1203 | C1203 | 16 | 21 | fsKnliyty | fsEnliyty |
| RH090935 | CABP1 | 12 | 121079138 | G | A | A3201,A2601,B3501,B3801,B3540,C0401,C1203 | C1203 | 31 | 138 | safDqdrsl | safGqdrsl |
| RH090935 | PITPNM2 | 12 | 123473363 | C | T | A3201,A2601,B3501,B3801,B3540,C0401,C1203 | B3501 | 29 | 14 | yalycpdTl | yalycpdAl |
| RH090935 | PITPNM2 | 12 | 123473363 | C | T | A3201,A2601,B3501,B3801,B3540,C0401,C1203 | B3501 | 464 | 247 | ycpdTltaf | ycpdAltaf |
| RH090935 | PITPNM2 | 12 | 123473363 | C | T | A3201,A2601,B3501,B3801,B3540,C0401,C1203 | C1203 | 5 | 14 | yalycpdTl | yalycpdAl |
| RH090935 | PITPNM2 | 12 | 123473363 | C | T | A3201,A2601,B3501,B3801,B3540,C0401,C1203 | C1203 | 439 | 245 | ycpdTltaf | ycpdAltaf |
| RH090935 | PITPNM2 | 12 | 123473363 | C | T | A3201,A2601,B3501,B3801,B3540,C0401,C1203 | C1203 | 286 | 25 | dTltafptv | dAltafptv |
| RH090935 | MZT1 | 13 | 73301694 | G | T | A3201,A2601,B3501,B3801,B3540,C0401,C1203 | C1203 | 15 | 65 | aaaEnlnav | aaaAnlnav |
| RH090935 | OR4K17 | 14 | 20586233 | T | A | A3201,A2601,B3501,B3801,B3540,C0401,C1203 | C1203 | 364 | 112 | dKyfvqvvi | dIyfvqvvi |
| RH090935 | OR4K17 | 14 | 20586233 | T | A | A3201,A2601,B3501,B3801,B3540,C0401,C1203 | C1203 | 247 | 142 | Kyfvqvviv | Iyfvqvviv |
| RH090935 | METTL3 | 14 | 21971952 | G | A | A3201,A2601,B3501,B3801,B3540,C0401,C1203 | B3501 | 17 | 867 | spvptaptF | spvptaptS |
| RH090935 | INSM2 | 14 | 36003885 | G | A | A3201,A2601,B3501,B3801,B3540,C0401,C1203 | B3501 | 32 | 56 | fpggaTava | fpggaAava |
| RH090935 | INSM2 | 14 | 36003885 | G | A | A3201,A2601,B3501,B3801,B3540,C0401,C1203 | C1203 | 234 | 1083 | esfpggaTa | esfpggaAa |
| RH090935 | FANCM | 14 | 45669080 | C | G | A3201,A2601,B3501,B3801,B3540,C0401,C1203 | A2601 | 375 | 1217 | sslEeismy | sslQeismy |
| RH090935 | FANCM | 14 | 45669080 | C | G | A3201,A2601,B3501,B3801,B3540,C0401,C1203 | C1203 | 23 | 16 | manssIEei | manssIQei |
| RH090935 | FANCM | 14 | 45669080 | C | G | A3201,A2601,B3501,B3801,B3540,C0401,C1203 | C1203 | 141 | 759 | sslEeismy | sslQeismy |
| RH090935 | PCNXL4 | 14 | 60591845 | G | C | A3201,A2601,B3501,B3801,B3540,C0401,C1203 | C1203 | 69 | 96 | fslfgiHnm | fslfgiDnm |
| RH090935 | HERC2 | 15 | 28362220 | C | T | A3201,A2601,B3501,B3801,B3540,C0401,C1203 | A3201 | 304 | 414 | qmcaklssf | qmcakMssf |
| RH090935 | SECISBP2L | 15 | 49288602 | A | G | A3201,A2601,B3501,B3801,B3540,C0401,C1203 | C1203 | 360 | 195 | fcsvTsepi | fcsvIsepi |
| RH090935 | SECISBP2L | 15 | 49288602 | A | G | A3201,A2601,B3501,B3801,B3540,C0401,C1203 | C1203 | 57 | 85 | vTsepisev | vIsepisev |
| RH090935 | LINS | 15 | 101109571 | A | T | A3201,A2601,B3501,B3801,B3540,C0401,C1203 | C1203 | 78 | 676 | ifyrivkcl | ifyrivkcF |
| RH090935 | HAGHL | 16 | 778317 | T | A | A3201,A2601,B3501,B3801,B3540,C0401,C1203 | B3501 | 17 | 54 | lahgeelrY | lahgeelrF |

Figure 21 (Cont.)

| | | | | | | | | | | | |
|---|---|---|---|---|---|---|---|---|---|---|---|
| RH090935 | TRAP1 | 16 | 3713560 | G | C | A3201,A2601,B3501,B3801,B3540,C0401,C1203 | A2601 | 317 | 5868 | evVfcfeqf | evLfcfeqf |
| RH090935 | BCAR1 | 16 | 75269391 | C | T | A3201,A2601,B3501,B3801,B3540,C0401,C1203 | C1203 | 47 | 275 | lqqDvsatv | lqqGvsatv |
| RH090935 | RAI1 | 17 | 17699425 | A | G | A3201,A2601,B3501,B3801,B3540,C0401,C1203 | B3501 | 160 | 88 | lprVctrsl | lprMctrsl |
| RH090935 | RAI1 | 17 | 17699425 | A | G | A3201,A2601,B3501,B3801,B3540,C0401,C1203 | C1203 | 199 | 567 | gaseglprV | gaseglprM |
| RH090935 | PSMD3 | 17 | 38151457 | C | A | A3201,A2601,B3501,B3801,B3540,C0401,C1203 | A3201 | 192 | 6825 | kLnqvldqf | kFnqvldqf |
| RH090935 | SIGLEC15 | 18 | 43417810 | G | C | A3201,A2601,B3501,B3801,B3540,C0401,C1203 | B3501 | 15 | 9 | fagHvhdry | fagDvhdry |
| RH090935 | SIGLEC15 | 18 | 43417810 | G | C | A3201,A2601,B3501,B3801,B3540,C0401,C1203 | C1203 | 77 | 23 | fagHvhdry | fagDvhdry |
| RH090935 | DOK6 | 18 | 67068518 | A | G | A3201,A2601,B3501,B3801,B3540,C0401,C1203 | C1203 | 208 | 146 | ivkqgCvki | ivkqgYvki |
| RH090935 | ADAT3 | 19 | 1912755 | C | A | A3201,A2601,B3501,B3801,B3540,C0401,C1203 | C1203 | 112 | 99 | npllhavmv | npLlhavmv |
| RH090935 | MAP2K2 | 19 | 4101275 | G | A | A3201,A2601,B3501,B3801,B3540,C0401,C1203 | B3501 | 17 | 25 | iavFrglay | iavLrglay |
| RH090935 | MAP2K2 | 19 | 4101275 | G | A | A3201,A2601,B3501,B3801,B3540,C0401,C1203 | C1203 | 91 | 131 | iavFrglay | iavLrglay |
| RH090935 | MAP2K2 | 19 | 4101275 | G | A | A3201,A2601,B3501,B3801,B3540,C0401,C1203 | C1203 | 379 | 1963 | avFrglayl | avLrglayl |
| RH090935 | ANGPTL4 | 19 | 8429480 | C | T | A3201,A2601,B3501,B3801,B3540,C0401,C1203 | C1203 | 441 | 287 | lplVpesrv | lplApesrv |
| RH090935 | ATG4D | 19 | 10659651 | C | A | A3201,A2601,B3501,B3801,B3540,C0401,C1203 | A3201 | 159 | 110 | ksvviMvpv | ksvviLvpv |
| RH090935 | CACNA1A | 19 | 13566011 | C | T | A3201,A2601,B3501,B3801,B3540,C0401,C1203 | B3501 | 222 | 624 | wppfeylil | wppfeyMil |
| RH090935 | CACNA1A | 19 | 13566011 | C | T | A3201,A2601,B3501,B3801,B3540,C0401,C1203 | C1203 | 291 | 914 | tewppfeyl | tewppfeyM |
| RH090935 | CACNA1A | 19 | 13566011 | C | T | A3201,A2601,B3501,B3801,B3540,C0401,C1203 | C1203 | 10 | 7 | feyilati | feyMilati |
| RH090935 | ZNF599 | 19 | 35250052 | G | C | A3201,A2601,B3501,B3801,B3540,C0401,C1203 | C1203 | 449 | 330 | dnfaltEhm | dnfaltQhm |
| RH090935 | ZNF382 | 19 | 37117436 | G | C | A3201,A2601,B3501,B3801,B3540,C0401,C1203 | B3801 | 136 | 447 | Hhneceksf | Dhneceksf |
| RH090935 | TRPM4 | 19 | 49669407 | A | T | A3201,A2601,B3501,B3801,B3540,C0401,C1203 | B3501 | 314 | 612 | tSekptday | tTekptday |
| RH090935 | PRR21 | 2 | 240982356 | A | G | A3201,A2601,B3501,B3801,B3540,C0401,C1203 | B3501 | 31 | 80 | hprpfThgf | hprpflhgf |
| RH090935 | PRR21 | 2 | 240982356 | A | G | A3201,A2601,B3501,B3801,B3540,C0401,C1203 | B3501 | 22 | 23 | rpfThgfsf | rpflhgfsf |

Figure 21 (Cont.)

| | | | | | | | | | | | |
|---|---|---|---|---|---|---|---|---|---|---|---|
| RH090935 | CRNKL1 | 20 | 20024270 | C | G | A3201,A2601,B3501,B3801,B3540,C0401,C1203 | C1203 | 34 | 14 | yalHriskq | yalDriskq |
| RH090935 | E2F1 | 20 | 32264690 | G | A | A3201,A2601,B3501,B3801,B3540,C0401,C1203 | B3501 | 359 | 4791 | hvWedfsgl | hvRedfsgl |
| RH090935 | RBM12 | 20 | 34242679 | G | C | A3201,A2601,B3501,B3801,B3540,C0401,C1203 | C1203 | 99 | 98 | vpppRippi | vpppPippi |
| RH090935 | GMEB2 | 20 | 62221980 | A | T | A3201,A2601,B3501,B3801,B3540,C0401,C1203 | B3501 | 315 | 137 | tpvsQpppv | tpvsLpppv |
| RH090935 | C2CD2 | 21 | 43373688 | C | T | A3201,A2601,B3501,B3801,B3540,C0401,C1203 | B3501 | 40 | 289 | Talatvgly | Aalatvgly |
| RH090935 | C2CD2 | 21 | 43373688 | C | T | A3201,A2601,B3501,B3801,B3540,C0401,C1203 | C1203 | 208 | 890 | Talatvgly | Aalatvgly |
| RH090935 | CARD10 | 22 | 37900275 | G | A | A3201,A2601,B3501,B3801,B3540,C0401,C1203 | C1203 | 481 | 681 | keinWlsil | keinRlsil |
| RH090935 | SGSM3 | 22 | 40803052 | C | A | A3201,A2601,B3501,B3801,B3540,C0401,C1203 | A3201 | 23 | 287 | rtqrrkYti | rtqrrkSti |
| RH090935 | SGSM3 | 22 | 40803052 | C | A | A3201,A2601,B3501,B3801,B3540,C0401,C1203 | C1203 | 228 | 91 | rtqrrkYti | rtqrrkSti |
| RH090935 | PLXNB2 | 22 | 50719808 | C | A | A3201,A2601,B3501,B3801,B3540,C0401,C1203 | B3501 | 14 | 120 | vpmvvviaL | vpmvvviaV |
| RH090935 | PLXNB2 | 22 | 50719808 | C | A | A3201,A2601,B3501,B3801,B3540,C0401,C1203 | B3501 | 152 | 93 | vvviaLsvy | vvviaVsvy |
| RH090935 | PLXNB2 | 22 | 50719808 | C | A | A3201,A2601,B3501,B3801,B3540,C0401,C1203 | C1203 | 494 | 267 | mvvviaLsv | mvvviaVsv |
| RH090935 | BOC | 3 | 112987184 | G | C | A3201,A2601,B3501,B3801,B3540,C0401,C1203 | C1203 | 127 | 248 | Qvdegntav | Evdegntav |
| RH090935 | GSX2 | 4 | 54967035 | C | A | A3201,A2601,B3501,B3801,B3540,C0401,C1203 | B3501 | 8 | 9 | apvctDtty | apvctAtty |
| RH090935 | PCDH10 | 4 | 134072416 | G | A | A3201,A2601,B3501,B3801,B3540,C0401,C1203 | C1203 | 261 | 1747 | aapDtvval | aapGtvval |
| RH090935 | FAM198B | 4 | 159091863 | C | T | A3201,A2601,B3501,B3801,B3540,C0401,C1203 | C1203 | 180 | 213 | lskddiQrm | lskddiRrm |
| RH090935 | NIPBL | 5 | 37064915 | C | T | A3201,A2601,B3501,B3801,B3540,C0401,C1203 | C1203 | 89 | 1527 | iiykkialM | iiykkialT |
| RH090935 | NIPBL | 5 | 37064915 | C | T | A3201,A2601,B3501,B3801,B3540,C0401,C1203 | C1203 | 41 | 46 | ialMsankl | ialTsankl |
| RH090935 | CSF1R | 5 | 149460527 | G | A | A3201,A2601,B3501,B3801,B3540,C0401,C1203 | C1203 | 87 | 38 | lvvkpgaMv | lvvkpgaTv |
| RH090935 | MDC1 | 6 | 30681071 | C | G | A3201,A2601,B3501,B3801,B3540,C0401,C1203 | C1203 | 51 | 141 | fafnFnsdt | fafnLnsdt |
| RH090935 | MDC1 | 6 | 30681071 | C | G | A3201,A2601,B3501,B3801,B3540,C0401,C1203 | C1203 | 224 | 866 | fnFnsdtdv | fnLnsdtdv |
| RH090935 | EHMT2 | 6 | 31864751 | C | T | A3201,A2601,B3501,B3801,B3540,C0401,C1203 | A2601 | 136 | 156 | eapaKmgal | eapaEmgal |
| RH090935 | KCNK17 | 6 | 39281916 | C | T | A3201,A2601,B3501,B3801,B3540,C0401,C1203 | A3201 | 140 | 9808 | Kllqnftcl | Ellqnftcl |

Figure 21 (Cont.)

| | | | | | | | | | | | |
|---|---|---|---|---|---|---|---|---|---|---|---|
| RH090935 | KCNK17 | 6 | 39281916 | C | T | A3201,A2601,B3501,B3801,B3540,C0401,C1203 | C1203 | 27 | 30 | fqrdkwKll | fqrdkwEll |
| RH090935 | PPP1R35 | 7 | 100033677 | C | T | A3201,A2601,B3501,B3801,B3540,C0401,C1203 | C1203 | 44 | 55 | fHltppspv | fRltppspv |
| RH090935 | STRIP2 | 7 | 129095091 | C | G | A3201,A2601,B3501,B3801,B3540,C0401,C1203 | B3501 | 85 | 22 | fCmhneepf | fSmhneepf |
| RH090935 | STRIP2 | 7 | 129095091 | C | G | A3201,A2601,B3501,B3801,B3540,C0401,C1203 | C1203 | 162 | 46 | fCmhneepf | fSmhneepf |
| RH090935 | CRH | 8 | 67089585 | G | T | A3201,A2601,B3501,B3801,B3540,C0401,C1203 | C1203 | 44 | 71 | qapqhpqHl | qapqhpqPl |
| RH090935 | C8orf34 | 8 | 69445363 | G | T | A3201,A2601,B3501,B3801,B3540,C0401,C1203 | C1203 | 57 | 945 | neYdamell | neDdamell |
| RH090935 | CA2 | 8 | 86377620 | G | A | A3201,A2601,B3501,B3801,B3540,C0401,C1203 | A3201 | 198 | 922 | vsyNqatsl | vsyDqatsl |
| RH090935 | CA2 | 8 | 86377620 | G | A | A3201,A2601,B3501,B3801,B3540,C0401,C1203 | C1203 | 68 | 39 | vsyNqatsl | vsyDqatsl |
| RH090935 | PKHD1L1 | 8 | 110465084 | G | C | A3201,A2601,B3501,B3801,B3540,C0401,C1203 | C1203 | 450 | 505 | qstpiFkml | qstpiLkml |
| RH090935 | ADCY8 | 8 | 132052326 | C | A | A3201,A2601,B3501,B3801,B3540,C0401,C1203 | B3501 | 227 | 2699 | sVdsalply | sGdsalply |
| RH090935 | ADCY8 | 8 | 132052326 | C | A | A3201,A2601,B3501,B3801,B3540,C0401,C1203 | C1203 | 338 | 949 | lsVdsalpl | lsGdsalpl |
| RH090935 | ADCK5 | 8 | 145618222 | C | A | A3201,A2601,B3501,B3801,B3540,C0401,C1203 | C1203 | 154 | 135 | tallDralv | tallAralv |
| RH090935 | SLC25A25 | 9 | 130868041 | G | A | A3201,A2601,B3501,B3801,B3540,C0401,C1203 | C1203 | 184 | 92 | iIggftqmi | iVggftqmi |
| RH090935 | NACC2 | 9 | 138903739 | C | T | A3201,A2601,B3501,B3801,B3540,C0401,C1203 | A2601 | 135 | 819 | mlpegMemy | mlpegVemy |
| RH090935 | NACC2 | 9 | 138903739 | C | T | A3201,A2601,B3501,B3801,B3540,C0401,C1203 | C1203 | 172 | 116 | mlpegMemy | mlpegVemy |
| RH090935 | NACC2 | 9 | 138903739 | C | T | A3201,A2601,B3501,B3801,B3540,C0401,C1203 | C1203 | 313 | 999 | egMemyrtv | egVemyrtv |
| RH090935 | KLHL34 | X | 21674301 | C | T | A3201,A2601,B3501,B3801,B3540,C0401,C1203 | B3501 | 295 | 53 | Kpfseiery | Epfseiery |
| RH090935 | KLHL34 | X | 21674301 | C | T | A3201,A2601,B3501,B3801,B3540,C0401,C1203 | C1203 | 180 | 419 | Kpfseiery | Epfseiery |
| RH090935 | TEX11 | X | 69773212 | C | G | A3201,A2601,B3501,B3801,B3540,C0401,C1203 | B3501 | 6 | 19 | ypliaIkaF | ypliaIkaL |
| RH090935 | TEX11 | X | 69773212 | C | G | A3201,A2601,B3501,B3801,B3540,C0401,C1203 | C1203 | 355 | 204 | ypliaIkaF | ypliaIkaL |
| RH090935 | TEX11 | X | 69773212 | C | G | A3201,A2601,B3501,B3801,B3540,C0401,C1203 | C1203 | 27 | 132 | kaFkkalll | kaLkkalll |
| RH090935 | PLXNB3 | X | 153031003 | G | A | A3201,A2601,B3501,B3801,B3540,C0401,C1203 | B3501 | 256 | 108 | haTqetpll | haAqetpll |

Figure 21 (Cont.)

| | | | | | | | | | | | |
|---|---|---|---|---|---|---|---|---|---|---|---|
| RH090935 | PLXNB3 | X | 153031003 | G | A | A3201,A2601,B3501,B3801,B3540,C0401,C1203 | C1203 | 461 | 246 | haTqetpll | haAqetpll |
| RI1933 | SCNN1D | 1 | 1222288 | T | A | A2601,A3101,B1302,B5701,C0602 | C0602 | 44 | 54 | fhQdreirl | fhLdreirl |
| RI1933 | CHD5 | 1 | 6189065 | C | A | A2601,A3101,B1302,B5701,C0602 | A3101 | 124 | 58 | vtLasveer | vtRasveer |
| RI1933 | CHD5 | 1 | 6189065 | C | A | A2601,A3101,B1302,B5701,C0602 | C0602 | 45 | 27 | yrfvtLasv | yrfvtRasv |
| RI1933 | KIAA2013 | 1 | 11985999 | G | A | A2601,A3101,B1302,B5701,C0602 | A3101 | 132 | 211 | lVldvaanr | lAldvaanr |
| RI1933 | HNRNPCL1 | 1 | 12907356 | C | G | A2601,A3101,B1302,B5701,C0602 | C0602 | 48 | 10984 | qRddqleli | qGddqleli |
| RI1933 | ALDH4A1 | 1 | 19215936 | G | T | A2601,A3101,B1302,B5701,C0602 | A3101 | 375 | 467 | kalkdMkgr | kalkdLkgr |
| RI1933 | RAP1GAP | 1 | 21930377 | C | T | A2601,A3101,B1302,B5701,C0602 | A3101 | 425 | 283 | gksaNrfgr | gksaSrfgr |
| RI1933 | RAP1GAP | 1 | 21930377 | C | T | A2601,A3101,B1302,B5701,C0602 | A3101 | 9 | 11 | ksaNrfgrr | ksaSrfgrr |
| RI1933 | RUNX3 | 1 | 25228662 | G | T | A2601,A3101,B1302,B5701,C0602 | C0602 | 126 | 87 | shsnsptDl | shsnsptAl |
| RI1933 | USP24 | 1 | 55563271 | C | A | A2601,A3101,B1302,B5701,C0602 | B5701 | 27 | 13573 | iSfpwmlnm | iRfpwmlnm |
| RI1933 | L1TD1 | 1 | 62676908 | C | A | A2601,A3101,B1302,B5701,C0602 | A3101 | 332 | 240 | llekgfnHr | llekgfnPr |
| RI1933 | EPHX4 | 1 | 92515892 | C | A | A2601,A3101,B1302,B5701,C0602 | C0602 | 331 | 2809 | ilrhHaqll | ilrhPaqll |
| RI1933 | ETV3L | 1 | 157068937 | G | T | A2601,A3101,B1302,B5701,C0602 | A3101 | 108 | 149 | lsralryyy | lsraLryyy |
| RI1933 | ETV3L | 1 | 157068937 | G | T | A2601,A3101,B1302,B5701,C0602 | A3101 | 8 | 7 | ralryyynk | raLryyynk |
| RI1933 | ETV3L | 1 | 157068937 | G | T | A2601,A3101,B1302,B5701,C0602 | A3101 | 14 | 13 | alryyynkr | aLryyynkr |
| RI1933 | ETV3L | 1 | 157068937 | G | T | A2601,A3101,B1302,B5701,C0602 | B5701 | 36 | 41 | lsralryyy | lsraLryyy |
| RI1933 | ETV3L | 1 | 157068937 | G | T | A2601,A3101,B1302,B5701,C0602 | C0602 | 46 | 65 | lryyynkri | Lryyynkri |
| RI1933 | FAM71A | 1 | 212799394 | G | T | A2601,A3101,B1302,B5701,C0602 | A3101 | 145 | 206 | aaVppvstr | aaGppvstr |
| RI1933 | OBSCN | 1 | 228493067 | C | T | A2601,A3101,B1302,B5701,C0602 | A3101 | 65 | 134 | ktLatltvk | ktSatltvk |
| RI1933 | ACTN2 | 1 | 236908039 | C | T | A2601,A3101,B1302,B5701,C0602 | C0602 | 63 | 54 | ahqdCveqi | ahqdRveqi |
| RI1933 | GREM2 | 1 | 240656453 | C | A | A2601,A3101,B1302,B5701,C0602 | A3101 | 120 | 54 | sfyipLhvk | sfyipRhvk |
| RI1933 | GREM2 | 1 | 240656453 | C | A | A2601,A3101,B1302,B5701,C0602 | A3101 | 317 | 157 | fyipLhvkk | fyipRhvkk |

Figure 21 (Cont.)

| | | | | | | | | | | | |
|---|---|---|---|---|---|---|---|---|---|---|---|
| RI1933 | C1orf101 | 1 | 244715632 | G | T | A2601,A3101,B1302,B5701,C0602 | C0602 | 105 | 51 | mrrgtwLiv | mrrgtwRiv |
| RI1933 | C1orf101 | 1 | 244715632 | G | T | A2601,A3101,B1302,B5701,C0602 | C0602 | 261 | 123 | rrgtwLivv | rrgtwRivv |
| RI1933 | OR2C3 | 1 | 247695009 | G | T | A2601,A3101,B1302,B5701,C0602 | C0602 | 447 | 333 | tsNeqgkfi | tsHeqgkfi |
| RI1933 | USP6NL | 10 | 11505670 | C | A | A2601,A3101,B1302,B5701,C0602 | A3101 | 129 | 495 | Hsrtgtper | Qsrtgtper |
| RI1933 | GPR158 | 10 | 25701401 | A | T | A2601,A3101,B1302,B5701,C0602 | A3101 | 40 | 35 | hfrkaMsir | hfrkaKsir |
| RI1933 | GPR158 | 10 | 25701401 | A | T | A2601,A3101,B1302,B5701,C0602 | C0602 | 22 | 43 | yhfrkaMsi | yhfrkaKsi |
| RI1933 | PTCHD3 | 10 | 27702594 | G | T | A2601,A3101,B1302,B5701,C0602 | A2601 | 491 | 954 | fttndsySf | fttndsyRf |
| RI1933 | PTCHD3 | 10 | 27702594 | G | T | A2601,A3101,B1302,B5701,C0602 | A3101 | 301 | 262 | dsySfsasr | dsyRfsasr |
| RI1933 | PTCHD3 | 10 | 27702594 | G | T | A2601,A3101,B1302,B5701,C0602 | A3101 | 167 | 40 | sySfsasrr | syRfsasrr |
| RI1933 | ALOX5 | 10 | 45920459 | T | A | A2601,A3101,B1302,B5701,C0602 | C0602 | 123 | 247 | fQngcnpvl | fLngcnpvl |
| RI1933 | DNMBP | 10 | 101640056 | C | T | A2601,A3101,B1302,B5701,C0602 | C0602 | 448 | 2006 | rrshsNasv | rrshsDasv |
| RI1933 | OR52A1 | 11 | 5173466 | G | T | A2601,A3101,B1302,B5701,C0602 | A2601 | 15 | 10850 | yliamignY | yliamignS |
| RI1933 | MRGPRX3 | 11 | 18159579 | C | A | A2601,A3101,B1302,B5701,C0602 | A3101 | 3 | 5 | iyffvgYfr | iyffvgSfr |
| RI1933 | MRGPRX3 | 11 | 18159579 | C | A | A2601,A3101,B1302,B5701,C0602 | A3101 | 96 | 254 | ffvgYfrqr | ffvgSfrqr |
| RI1933 | MRGPRX3 | 11 | 18159579 | C | A | A2601,A3101,B1302,B5701,C0602 | A3101 | 13 | 19 | gYfrqrqnr | gSfrqrqnr |
| RI1933 | SLC6A5 | 11 | 20628657 | G | T | A2601,A3101,B1302,B5701,C0602 | B5701 | 51 | 70 | asqgpvsLw | asqgpvsVw |
| RI1933 | NELL1 | 11 | 21556012 | G | A | A2601,A3101,B1302,B5701,C0602 | C0602 | 14 | 25 | yhcecrsSf | yhcecrsGf |
| RI1933 | OR5F1 | 11 | 55762097 | G | T | A2601,A3101,B1302,B5701,C0602 | C0602 | 368 | 139 | Nrknytslt | Trknytslt |
| RI1933 | OR8K1 | 11 | 56113719 | C | T | A2601,A3101,B1302,B5701,C0602 | A3101 | 4 | 6 | htpmyffFr | htpmyffLr |
| RI1933 | OR8K1 | 11 | 56113719 | C | T | A2601,A3101,B1302,B5701,C0602 | A3101 | 407 | 739 | myffFrhls | myffLrhls |
| RI1933 | OR8K1 | 11 | 56113719 | C | T | A2601,A3101,B1302,B5701,C0602 | C0602 | 38 | 407 | Frhlsitdl | Lrhlsitdl |
| RI1933 | RTN4RL2 | 11 | 57243728 | G | A | A2601,A3101,B1302,B5701,C0602 | A2601 | 465 | 243 | hvfrglSsl | hvfrglGsl |

Figure 21 (Cont.)

| | | | | | | | | | | | |
|---|---|---|---|---|---|---|---|---|---|---|---|
| RI1933 | OR4D6 | 11 | 59224629 | A | G | A2601,A3101,B1302,B5701,C0602 | C0602 | 30 | 143 | lrnEsvldi | lrnKsvldi |
| RI1933 | SLC22A12 | 11 | 64367294 | G | A | A2601,A3101,B1302,B5701,C0602 | C0602 | 98 | 45 | shlgrHptl | shlgrRptl |
| RI1933 | VPS51 | 11 | 64875275 | G | T | A2601,A3101,B1302,B5701,C0602 | A3101 | 446 | 628 | laVvhallr | laGvhallr |
| RI1933 | GAL3ST3 | 11 | 65810970 | C | T | A2601,A3101,B1302,B5701,C0602 | A3101 | 141 | 263 | cKhqfcypr | cEhqfcypr |
| RI1933 | SSH3 | 11 | 67075168 | G | T | A2601,A3101,B1302,B5701,C0602 | A3101 | 24 | 56 | amaYleslr | amaDleslr |
| RI1933 | UNC93B1 | 11 | 67759287 | C | A | A2601,A3101,B1302,B5701,C0602 | A3101 | 44 | 25 | vaaLvsylr | vaaAvsylr |
| RI1933 | FGF3 | 11 | 69631153 | C | A | A2601,A3101,B1302,B5701,C0602 | A3101 | 20 | 17 | Slrglfsgr | Airglfsgr |
| RI1933 | MYO7A | 11 | 76909587 | G | C | A2601,A3101,B1302,B5701,C0602 | A3101 | 40 | 17853 | vivavnwtR | vivavnwtG |
| RI1933 | DRD2 | 11 | 113283517 | G | T | A2601,A3101,B1302,B5701,C0602 | A3101 | 234 | 5753 | rtryspipH | rtryspipP |
| RI1933 | DRD2 | 11 | 113283517 | G | T | A2601,A3101,B1302,B5701,C0602 | C0602 | 128 | 18148 | pHshhqltl | pPshhqltl |
| RI1933 | DRD2 | 11 | 113287702 | G | A | A2601,A3101,B1302,B5701,C0602 | A2601 | 95 | 395 | ytavamSml | ytavamPml |
| RI1933 | DRD2 | 11 | 113287702 | G | A | A2601,A3101,B1302,B5701,C0602 | A2601 | 421 | 5141 | tavamSmly | tavamPmly |
| RI1933 | DRD2 | 11 | 113287702 | G | A | A2601,A3101,B1302,B5701,C0602 | A3101 | 16 | 54 | amSmlyntr | amPmlyntr |
| RI1933 | DRD2 | 11 | 113287702 | G | A | A2601,A3101,B1302,B5701,C0602 | B5701 | 425 | 426 | tavamSmly | tavamPmly |
| RI1933 | DRD2 | 11 | 113287702 | G | A | A2601,A3101,B1302,B5701,C0602 | B5701 | 159 | 16382 | mSmlyntry | mPmlyntry |
| RI1933 | KIRREL3 | 11 | 126318918 | G | T | A2601,A3101,B1302,B5701,C0602 | A3101 | 20 | 105 | Kvdvyfgpr | Tvdvyfgpr |
| RI1933 | KIRREL3 | 11 | 126318918 | G | T | A2601,A3101,B1302,B5701,C0602 | B5701 | 58 | 66 | lsrKvdvyf | lsrTvdvyf |
| RI1933 | ADCY6 | 12 | 49177133 | G | A | A2601,A3101,B1302,B5701,C0602 | A3101 | 77 | 97 | rngqkrsWr | rngqkrsRr |
| RI1933 | ADCY6 | 12 | 49177133 | G | A | A2601,A3101,B1302,B5701,C0602 | A3101 | 423 | 639 | krsWrrgtr | krsRrrgtr |
| RI1933 | OR6C74 | 12 | 55641850 | C | T | A2601,A3101,B1302,B5701,C0602 | A3101 | 96 | 170 | fmyvkLsak | fmyvkPsak |
| RI1933 | MMP19 | 12 | 56234663 | C | G | A2601,A3101,B1302,B5701,C0602 | A3101 | 30 | 34 | kylllgPwr | kylllgRwr |
| RI1933 | DGKA | 12 | 56334115 | G | T | A2601,A3101,B1302,B5701,C0602 | A3101 | 37 | 18 | gvqshvCvr | gvqshvWvr |
| RI1933 | PLXNC1 | 12 | 94580227 | G | T | A2601,A3101,B1302,B5701,C0602 | B5701 | 280 | 87 | tatdphcCw | tatdphcGw |

Figure 21 (Cont.)

| | | | | | | | | | | | |
|---|---|---|---|---|---|---|---|---|---|---|---|
| RI1933 | CUX2 | 12 | 111758431 | C | A | A2601,A3101,B1302,B5701,C0602 | A3101 | 46 | 20 | pyypayvQr | pyypayvPr |
| RI1933 | RPH3A | 12 | 113314486 | G | A | A2601,A3101,B1302,B5701,C0602 | A3101 | 371 | 116 | ttappQeer | ttappReer |
| RI1933 | SDS | 12 | 113835058 | G | T | A2601,A3101,B1302,B5701,C0602 | B5701 | 110 | 14578 | vTviametf | vPviametf |
| RI1933 | CCNA1 | 13 | 37016330 | C | A | A2601,A3101,B1302,B5701,C0602 | A2601 | 21 | 10 | etlaafKgy | etlaafTgy |
| RI1933 | PCDH8 | 13 | 53418849 | T | C | A2601,A3101,B1302,B5701,C0602 | A3101 | 395 | 5027 | vglqsvyeR | vglqsvyeK |
| RI1933 | PCDH8 | 13 | 53418849 | T | C | A2601,A3101,B1302,B5701,C0602 | A3101 | 14 | 19 | svyeRvlhr | svyeKvlhr |
| RI1933 | PCDH8 | 13 | 53418849 | T | C | A2601,A3101,B1302,B5701,C0602 | A3101 | 10 | 15 | Rvlhrdydr | Kvlhrdydr |
| RI1933 | PCDH9 | 13 | 67799709 | G | A | A2601,A3101,B1302,B5701,C0602 | C0602 | 185 | 3074 | fhlkpdtLv | fhlkpdtPv |
| RI1933 | SLITRK1 | 13 | 84453964 | G | A | A2601,A3101,B1302,B5701,C0602 | A3101 | 52 | 186 | ceMpvnffr | ceTpvnffr |
| RI1933 | GPR180 | 13 | 95275450 | G | T | A2601,A3101,B1302,B5701,C0602 | A3101 | 74 | 250 | agilliFlr | agilliVlr |
| RI1933 | GPR18 | 13 | 99907202 | T | G | A2601,A3101,B1302,B5701,C0602 | A3101 | 18 | 9282 | mlyrnylrR | mlyrnylrS |
| RI1933 | GPR18 | 13 | 99907202 | T | G | A2601,A3101,B1302,B5701,C0602 | A3101 | 7 | 17 | rnylrRmrr | rnylrSmrr |
| RI1933 | GPR18 | 13 | 99907202 | T | G | A2601,A3101,B1302,B5701,C0602 | A3101 | 18 | 3 | rRmrrksfr | rSmrrksfr |
| RI1933 | GPR18 | 13 | 99907202 | T | G | A2601,A3101,B1302,B5701,C0602 | A3101 | 280 | 2533 | Rmrrksfrs | Smrrksfrs |
| RI1933 | GPR18 | 13 | 99907202 | T | G | A2601,A3101,B1302,B5701,C0602 | C0602 | 252 | 194 | lyrnylrRm | lyrnylrSm |
| RI1933 | GPR18 | 13 | 99907202 | T | G | A2601,A3101,B1302,B5701,C0602 | C0602 | 291 | 275 | lrRmrrksf | lrSmrrksf |
| RI1933 | F7 | 13 | 113773164 | A | C | A2601,A3101,B1302,B5701,C0602 | B5701 | 92 | 34 | hathyrgPw | hathyrgTw |
| RI1933 | F7 | 13 | 113773164 | A | C | A2601,A3101,B1302,B5701,C0602 | C0602 | 51 | 46 | thyrgPwyl | thyrgTwyl |
| RI1933 | METTL17 | 14 | 21464875 | G | T | A2601,A3101,B1302,B5701,C0602 | B5701 | 17 | 12920 | tarrhgryW | tarrhgryG |
| RI1933 | FOXG1 | 14 | 29237140 | C | A | A2601,A3101,B1302,B5701,C0602 | A3101 | 138 | 2 | imknfpyyS | imknfpyyR |
| RI1933 | SYNE3 | 14 | 95899689 | C | A | A2601,A3101,B1302,B5701,C0602 | A3101 | 117 | 478 | nllrlWpar | nllrlGpar |
| RI1933 | RYR3 | 15 | 33795898 | C | A | A2601,A3101,B1302,B5701,C0602 | A3101 | 209 | 3995 | qslsvralK | qslsvralQ |

Figure 21 (Cont.)

| | | | | | | | | | | | |
|---|---|---|---|---|---|---|---|---|---|---|---|
| RI1933 | RYR3 | 15 | 33795898 | C | A | A2601,A3101,B1302,B5701,C0602 | B5701 | 289 | 307 | lsvralKem | lsvralQem |
| RI1933 | PGBD4 | 15 | 34396483 | A | G | A2601,A3101,B1302,B5701,C0602 | A2601 | 288 | 817 | eiyhtkkSy | eiyhtkkNy |
| RI1933 | AGBL1 | 15 | 87089341 | A | C | A2601,A3101,B1302,B5701,C0602 | A3101 | 152 | 161 | tLleevnyr | tlleevnyr |
| RI1933 | C16orf11 | 16 | 613440 | A | T | A2601,A3101,B1302,B5701,C0602 | A3101 | 95 | 45 | Mshlynhmk | Kshlynhmk |
| RI1933 | HYDIN | 16 | 71103193 | G | A | A2601,A3101,B1302,B5701,C0602 | A3101 | 15 | 480 | rSqgfaair | rPqgfaair |
| RI1933 | CLEC3A | 16 | 78064682 | G | T | A2601,A3101,B1302,B5701,C0602 | A3101 | 473 | 2280 | gkwsYeacr | gkwsDeacr |
| RI1933 | CLEC3A | 16 | 78064682 | G | T | A2601,A3101,B1302,B5701,C0602 | A3101 | 450 | 12377 | sYeacrssk | sDeacrssk |
| RI1933 | ITGAE | 17 | 3664377 | C | A | A2601,A3101,B1302,B5701,C0602 | A3101 | 415 | 1458 | dvntarHrr | dvntarQrr |
| RI1933 | POLR2A | 17 | 7400270 | A | G | A2601,A3101,B1302,B5701,C0602 | A3101 | 140 | 38 | lgmeprCar | lgmeprYar |
| RI1933 | TP53 | 17 | 7577535 | C | A | A2601,A3101,B1302,B5701,C0602 | C0602 | 85 | 207 | nrMpiltii | nrRpiltii |
| RI1933 | ALDH3A1 | 17 | 19642342 | T | A | A2601,A3101,B1302,B5701,C0602 | A2601 | 290 | 132 | dvivhFtlh | dvivhitlh |
| RI1933 | SEZ6 | 17 | 27283247 | C | G | A2601,A3101,B1302,B5701,C0602 | A3101 | 100 | 154 | sslqlpPpr | sslqlpRpr |
| RI1933 | SEZ6 | 17 | 27283247 | C | G | A2601,A3101,B1302,B5701,C0602 | A3101 | 152 | 51 | lqlpPprpr | lqlpRprpr |
| RI1933 | BCAS3 | 17 | 59118200 | C | A | A2601,A3101,B1302,B5701,C0602 | C0602 | 154 | 61 | fnanhHlll | fnanhPlll |
| RI1933 | MGAT5B | 17 | 74934124 | G | A | A2601,A3101,B1302,B5701,C0602 | A3101 | 18 | 60 | gtMyyesqr | gtVyyesqr |
| RI1933 | SLC35G4 | 18 | 11610580 | T | G | A2601,A3101,B1302,B5701,C0602 | A3101 | 70 | 31 | tamlScer | tamllcer |
| RI1933 | CBLN2 | 18 | 70205428 | A | T | A2601,A3101,B1302,B5701,C0602 | A2601 | 180 | 414 | stfsgfMvf | stfsgfLvf |
| RI1933 | CBLN2 | 18 | 70205428 | A | T | A2601,A3101,B1302,B5701,C0602 | B5701 | 300 | 551 | stfsgfMvf | stfsgfLvf |
| RI1933 | SNAPC2 | 19 | 7987377 | C | T | A2601,A3101,B1302,B5701,C0602 | B5701 | 124 | 365 | mslpeelSl | mslpeelPl |
| RI1933 | MUC16 | 19 | 9057715 | T | A | A2601,A3101,B1302,B5701,C0602 | A3101 | 323 | 71 | Lteimssnr | Mteimssnr |
| RI1933 | RAB3D | 19 | 11447880 | G | A | A2601,A3101,B1302,B5701,C0602 | A3101 | 17 | 15 | ktvyChdkr | ktvyRhdkr |
| RI1933 | USE1 | 19 | 17327087 | G | T | A2601,A3101,B1302,B5701,C0602 | A3101 | 494 | 599 | tvhlqsLar | tvhlqsRar |
| RI1933 | USE1 | 19 | 17327087 | G | T | A2601,A3101,B1302,B5701,C0602 | A3101 | 160 | 17 | Larytsemr | Rarytsemr |

Figure 21 (Cont.)

| | | | | | | | | | | | |
|---|---|---|---|---|---|---|---|---|---|---|---|
| RI1933 | PSMD8 | 19 | 38867075 | T | C | A2601,A3101,B1302,B5701,C0602 | B5701 | 246 | 842 | maqlkRyyf | maqlkCyyf |
| RI1933 | CRX | 19 | 48337791 | C | T | A2601,A3101,B1302,B5701,C0602 | A3101 | 33 | 129 | avSypsapr | avPypsapr |
| RI1933 | PTPRH | 19 | 55707979 | G | A | A2601,A3101,B1302,B5701,C0602 | A3101 | 159 | 122 | svlglgLar | svlglgPar |
| RI1933 | ZNF304 | 19 | 57868887 | G | C | A2601,A3101,B1302,B5701,C0602 | A3101 | 71 | 116 | nssllhHr | nssllhQr |
| RI1933 | ZNF304 | 19 | 57868887 | G | C | A2601,A3101,B1302,B5701,C0602 | A3101 | 485 | 23 | hHrvhtgar | hQrvhtgar |
| RI1933 | GALNT14 | 2 | 31135136 | C | A | A2601,A3101,B1302,B5701,C0602 | C0602 | 440 | 2758 | tlfpCapvv | tlfpGapvv |
| RI1933 | FSHR | 2 | 49210069 | G | T | A2601,A3101,B1302,B5701,C0602 | C0602 | 41 | 184 | fhgDsgpvi | fhgAsgpvi |
| RI1933 | MOGS | 2 | 74692191 | C | T | A2601,A3101,B1302,B5701,C0602 | A3101 | 212 | 223 | grwMlawyr | grwVlawyr |
| RI1933 | MOGS | 2 | 74692191 | C | T | A2601,A3101,B1302,B5701,C0602 | A3101 | 24 | 66 | wMlawyrar | wVlawyrar |
| RI1933 | MOGS | 2 | 74692191 | C | T | A2601,A3101,B1302,B5701,C0602 | A3101 | 8 | 14 | Mlawyrarr | Vlawyrarr |
| RI1933 | MOGS | 2 | 74692191 | C | T | A2601,A3101,B1302,B5701,C0602 | B5701 | 11 | 17 | msgrwMlaw | msgrwVlaw |
| RI1933 | CTNNA2 | 2 | 80874842 | G | T | A2601,A3101,B1302,B5701,C0602 | B5701 | 468 | 369 | avnspFvsw | avnspVvsw |
| RI1933 | COX5B | 2 | 98262590 | C | T | A2601,A3101,B1302,B5701,C0602 | A3101 | 22 | 43 | gtlaVqalr | gtlaAqalr |
| RI1933 | CNTNAP5 | 2 | 124783246 | C | A | A2601,A3101,B1302,B5701,C0602 | A3101 | 401 | 1378 | rMtsvltll | rLtsvltll |
| RI1933 | CNTNAP5 | 2 | 124783246 | C | A | A2601,A3101,B1302,B5701,C0602 | B5701 | 91 | 212 | Mtsvltllf | Ltsvltllf |
| RI1933 | CNTNAP5 | 2 | 124783246 | C | A | A2601,A3101,B1302,B5701,C0602 | C0602 | 53 | 290 | prMtsvltl | prLtsvltl |
| RI1933 | DCAF17 | 2 | 172337503 | A | T | A2601,A3101,B1302,B5701,C0602 | A3101 | 30 | 41 | yshevFfdr | yshevYfdr |
| RI1933 | DCAF17 | 2 | 172337503 | A | T | A2601,A3101,B1302,B5701,C0602 | B5701 | 211 | 137 | vtyshevFf | vtyshevYf |
| RI1933 | DCAF17 | 2 | 172337503 | A | T | A2601,A3101,B1302,B5701,C0602 | C0602 | 323 | 79 | vFfdrdlvl | vYfdrdlvl |
| RI1933 | CHRNA1 | 2 | 175618409 | C | A | A2601,A3101,B1302,B5701,C0602 | B5701 | 293 | 202 | wvikDsrgw | wvikEsrgw |
| RI1933 | HOXD3 | 2 | 177034310 | C | G | A2601,A3101,B1302,B5701,C0602 | B5701 | 245 | 378 | tMskqifpw | tlskqifpw |
| RI1933 | SNAP25 | 20 | 10277686 | G | A | A2601,A3101,B1302,B5701,C0602 | A3101 | 38 | 34 | maisgDfir | maisgGfir |

Figure 21 (Cont.)

| | | | | | | | | | | | |
|---|---|---|---|---|---|---|---|---|---|---|---|
| RI1933 | SNAP25 | 20 | 10277686 | G | A | A2601,A3101,B1302,B5701,C0602 | A3101 | 319 | 136 | aisgDfirr | aisgGfirr |
| RI1933 | FAM209A | 20 | 55100033 | G | A | A2601,A3101,B1302,B5701,C0602 | B5701 | 80 | 1285 | Rskwlwllf | Gskwlwllf |
| RI1933 | FAM209A | 20 | 55100033 | G | A | A2601,A3101,B1302,B5701,C0602 | C0602 | 31 | 7184 | lRskwlwll | lGskwlwll |
| RI1933 | DIDO1 | 20 | 61510920 | C | A | A2601,A3101,B1302,B5701,C0602 | A3101 | 20 | 717 | wsrerdwYr | wsrerdwDr |
| RI1933 | DIDO1 | 20 | 61510920 | C | A | A2601,A3101,B1302,B5701,C0602 | A3101 | 32 | 166 | rerdwYrpr | rerdwDrpr |
| RI1933 | DIDO1 | 20 | 61510920 | C | A | A2601,A3101,B1302,B5701,C0602 | A3101 | 269 | 7580 | wYrprewdr | wDrprewdr |
| RI1933 | SMIM11 | 21 | 35757791 | C | A | A2601,A3101,B1302,B5701,C0602 | C0602 | 235 | 368 | kvlehvTll | kvlehvPll |
| RI1933 | SSTR3 | 22 | 37602905 | T | C | A2601,A3101,B1302,B5701,C0602 | A3101 | 8 | 5 | ilCgflsyr | ilYgflsyr |
| RI1933 | PANX2 | 22 | 50616499 | A | T | A2601,A3101,B1302,B5701,C0602 | A3101 | 90 | 243 | rvVnskaek | rvEnskaek |
| RI1933 | TMPPE | 3 | 33135150 | C | T | A2601,A3101,B1302,B5701,C0602 | A3101 | 29 | 18832 | vtavlsvaR | vtavlsvaG |
| RI1933 | ZIC1 | 3 | 147128205 | C | A | A2601,A3101,B1302,B5701,C0602 | A3101 | 474 | 158 | nstrdflLr | nstrdflFr |
| RI1933 | MED12L | 3 | 151112519 | G | T | A2601,A3101,B1302,B5701,C0602 | A3101 | 75 | 123 | alsnmlqLr | alsnmlqRr |
| RI1933 | GMPS | 3 | 155621704 | A | G | A2601,A3101,B1302,B5701,C0602 | B5701 | 127 | 163 | ksvreGgvf | ksvreDgvf |
| RI1933 | WDR49 | 3 | 167272480 | C | G | A2601,A3101,B1302,B5701,C0602 | A3101 | 34 | 23 | kilvtAwer | kilvtGwer |
| RI1933 | TNIK | 3 | 170784514 | T | A | A2601,A3101,B1302,B5701,C0602 | C0602 | 397 | 17193 | yipshiqgI | yipshiqgN |
| RI1933 | HAUS3 | 4 | 2242001 | C | A | A2601,A3101,B1302,B5701,C0602 | C0602 | 233 | 1629 | qffqCihev | qffqGihev |
| RI1933 | FRAS1 | 4 | 79394606 | G | T | A2601,A3101,B1302,B5701,C0602 | A2601 | 194 | 456 | dvnlWliry | dvnlGliry |
| RI1933 | FRAS1 | 4 | 79394606 | G | T | A2601,A3101,B1302,B5701,C0602 | B5701 | 124 | 24305 | ftqedvnlW | ftqedvnlG |
| RI1933 | BBS7 | 4 | 122774188 | G | A | A2601,A3101,B1302,B5701,C0602 | A3101 | 10 | 23 | gvkdlFvgr | gvkdlLvgr |
| RI1933 | FBXL7 | 5 | 15928322 | C | T | A2601,A3101,B1302,B5701,C0602 | A3101 | 81 | 83 | lawdSrlwr | lawdPrlwr |
| RI1933 | FBXL7 | 5 | 15928322 | C | T | A2601,A3101,B1302,B5701,C0602 | A3101 | 292 | 4529 | dSrlwrtir | dPrlwrtir |
| RI1933 | FBXL7 | 5 | 15928322 | C | T | A2601,A3101,B1302,B5701,C0602 | C0602 | 124 | 1058 | Srlwrtirl | Prlwrtirl |
| RI1933 | SPZ1 | 5 | 79617071 | A | G | A2601,A3101,B1302,B5701,C0602 | C0602 | 90 | 258 | lhhqkRgtl | lhhqkQgtl |

Figure 21 (Cont.)

| | | | | | | | | | | | |
|---|---|---|---|---|---|---|---|---|---|---|---|
| RI1933 | CHSY3 | 5 | 129521153 | G | C | A2601,A3101,B1302,B5701,C0602 | A3101 | 29 | 22 | fskktAfwr | fskktGfwr |
| RI1933 | SOWAHA | 5 | 132150418 | G | A | A2601,A3101,B1302,B5701,C0602 | A3101 | 160 | 122 | alqlvevTr | alqlvevAr |
| RI1933 | SOWAHA | 5 | 132150418 | G | A | A2601,A3101,B1302,B5701,C0602 | A3101 | 264 | 232 | lqlvevTrr | lqlvevArr |
| RI1933 | PCDHA7 | 5 | 140216091 | C | A | A2601,A3101,B1302,B5701,C0602 | A2601 | 291 | 15787 | liiaicavY | liiaicavS |
| RI1933 | SLIT3 | 5 | 168135054 | G | C | A2601,A3101,B1302,B5701,C0602 | A3101 | 29 | 16027 | kcnaclssR | kcnaclssP |
| RI1933 | DOCK2 | 5 | 169101425 | C | A | A2601,A3101,B1302,B5701,C0602 | A3101 | 350 | 2654 | Kskidygnk | Tskidygnk |
| RI1933 | PFN3 | 5 | 176827552 | C | A | A2601,A3101,B1302,B5701,C0602 | A3101 | 7 | 10 | kvyilavlr | kvyiSavlr |
| RI1933 | PFN3 | 5 | 176827552 | C | A | A2601,A3101,B1302,B5701,C0602 | A3101 | 105 | 59 | ilavlrdqr | iSavlrdqr |
| RI1933 | RUFY1 | 5 | 178996370 | G | A | A2601,A3101,B1302,B5701,C0602 | A3101 | 106 | 18458 | mvivgllvR | mvivgllvG |
| RI1933 | BTNL8 | 5 | 180374525 | G | T | A2601,A3101,B1302,B5701,C0602 | B5701 | 94 | 82 | dtffDpisw | dtffEpisw |
| RI1933 | TRIM7 | 5 | 180622539 | G | A | A2601,A3101,B1302,B5701,C0602 | A3101 | 62 | 42 | Vscgfssgr | Ascgfssgr |
| RI1933 | SLC17A4 | 6 | 25779352 | A | G | A2601,A3101,B1302,B5701,C0602 | A3101 | 10 | 8 | lvfClifgr | lvfYlifgr |
| RI1933 | ITPR3 | 6 | 33632923 | G | A | A2601,A3101,B1302,B5701,C0602 | C0602 | 102 | 94 | fandTssml | fandAssml |
| RI1933 | TINAG | 6 | 54212199 | G | T | A2601,A3101,B1302,B5701,C0602 | A3101 | 84 | 211 | riaiqsNgr | riaiqsKgr |
| RI1933 | FAM83B | 6 | 54735436 | A | T | A2601,A3101,B1302,B5701,C0602 | C0602 | 10 | 9 | fhppraLll | fhppraHll |
| RI1933 | COL19A1 | 6 | 70852685 | G | A | A2601,A3101,B1302,B5701,C0602 | A3101 | 177 | 201 | gsagslgpr | gsagsMgpr |
| RI1933 | TBX18 | 6 | 85473758 | C | T | A2601,A3101,B1302,B5701,C0602 | A3101 | 273 | 24141 | klgaeeaaR | klgaeeaaG |
| RI1933 | EPHA7 | 6 | 93979378 | C | A | A2601,A3101,B1302,B5701,C0602 | A3101 | 109 | 3026 | ikyyekYqr | ikyyekDqr |
| RI1933 | PTPRK | 6 | 128303977 | T | A | A2601,A3101,B1302,B5701,C0602 | A3101 | 17 | 22 | Ltlnsvtpr | Qtlnsvtpr |
| RI1933 | SHPRH | 6 | 146271573 | C | A | A2601,A3101,B1302,B5701,C0602 | A2601 | 17 | 10509 | eVqdidely | eGqdidely |
| RI1933 | STXBP5 | 6 | 147631223 | G | T | A2601,A3101,B1302,B5701,C0602 | B5701 | 423 | 168 | kttrsgDpf | kttrsgEpf |
| RI1933 | STXBP5 | 6 | 147631223 | G | T | A2601,A3101,B1302,B5701,C0602 | C0602 | 179 | 240 | trsgDpfii | trsgEpfii |

Figure 21 (Cont.)

| | | | | | | | | | | | |
|---|---|---|---|---|---|---|---|---|---|---|---|
| RI1933 | IGF2R | 6 | 160511111 | G | T | A2601,A3101,B1302,B5701,C0602 | A3101 | 284 | 7421 | tsYktkyyl | tsDktkyyl |
| RI1933 | IGF2R | 6 | 160511111 | G | T | A2601,A3101,B1302,B5701,C0602 | A3101 | 307 | 13213 | sYktkyylq | sDktkyylq |
| RI1933 | PLG | 6 | 161132220 | C | A | A2601,A3101,B1302,B5701,C0602 | A3101 | 53 | 41 | sstsphrHr | sstsphrPr |
| RI1933 | ZNF736 | 7 | 63809296 | G | T | A2601,A3101,B1302,B5701,C0602 | A3101 | 451 | 25 | Lsstlfnhk | Rsstlfnhk |
| RI1933 | ZNF736 | 7 | 63809296 | G | T | A2601,A3101,B1302,B5701,C0602 | B5701 | 133 | 311 | kaftLsstl | kaftRsstl |
| RI1933 | COL1A2 | 7 | 94037510 | C | A | A2601,A3101,B1302,B5701,C0602 | A3101 | 457 | 542 | garglTger | garglPger |
| RI1933 | PAX4 | 7 | 127253515 | C | T | A2601,A3101,B1302,B5701,C0602 | A3101 | 236 | 547 | tslpeNtvr | tslpeDtvr |
| RI1933 | FLNC | 7 | 128470788 | C | A | A2601,A3101,B1302,B5701,C0602 | B5701 | 107 | 375 | kdlaedaTw | kdlaedaPw |
| RI1933 | FLNC | 7 | 128470789 | C | A | A2601,A3101,B1302,B5701,C0602 | B5701 | 105 | 375 | kdlaedaQw | kdlaedaPw |
| RI1933 | FLNC | 7 | 128486103 | G | A | A2601,A3101,B1302,B5701,C0602 | A3101 | 30 | 247 | tSgnhvtar | tGgnhvtar |
| RI1933 | FAM131B | 7 | 143057161 | C | T | A2601,A3101,B1302,B5701,C0602 | A3101 | 266 | 269 | slhEsslhr | slhGsslhr |
| RI1933 | PDIA4 | 7 | 148718060 | A | G | A2601,A3101,B1302,B5701,C0602 | A3101 | 11 | 9252 | vllefyapR | vllefyapW |
| RI1933 | DOCK5 | 8 | 25222165 | A | G | A2601,A3101,B1302,B5701,C0602 | A3101 | 7 | 1745 | rvflrainR | rvflrainQ |
| RI1933 | STMN4 | 8 | 27097511 | T | C | A2601,A3101,B1302,B5701,C0602 | C0602 | 456 | 431 | nreahlaaV | nreahlaaM |
| RI1933 | PENK | 8 | 57354091 | C | A | A2601,A3101,B1302,B5701,C0602 | A2601 | 46 | 5 | eLskryggf | eVskryggf |
| RI1933 | ZFHX4 | 8 | 77764807 | G | T | A2601,A3101,B1302,B5701,C0602 | A3101 | 206 | 4220 | glkegkYtk | glkegkDtk |
| RI1933 | DEPTOR | 8 | 121013833 | G | T | A2601,A3101,B1302,B5701,C0602 | A3101 | 3 | 4 | rmnfrrrLr | rmnfrrrRr |
| RI1933 | DEPTOR | 8 | 121013833 | G | T | A2601,A3101,B1302,B5701,C0602 | C0602 | 5 | 125 | frmnfrrrL | frmnfrrrR |
| RI1933 | DEPTOR | 8 | 121013833 | G | T | A2601,A3101,B1302,B5701,C0602 | C0602 | 219 | 65 | mnfrrrLrl | mnfrrrRrl |
| RI1933 | DEPTOR | 8 | 121013833 | G | T | A2601,A3101,B1302,B5701,C0602 | C0602 | 62 | 30 | rrrLrlmel | rrrRrlmel |
| RI1933 | DEPTOR | 8 | 121013833 | G | T | A2601,A3101,B1302,B5701,C0602 | C0602 | 434 | 170 | rrLrlmell | rrRrlmell |
| RI1933 | MTBP | 8 | 121471560 | C | T | A2601,A3101,B1302,B5701,C0602 | A3101 | 381 | 790 | lakkiiSsk | lakkiiPsk |
| RI1933 | TG | 8 | 134128912 | G | T | A2601,A3101,B1302,B5701,C0602 | B5701 | 103 | 108 | raLgnvfmy | raRgnvfmy |

Figure 21 (Cont.)

| | | | | | | | | | | | |
|---|---|---|---|---|---|---|---|---|---|---|---|
| RI1933 | RFX3 | 9 | 3248156 | C | G | A2601,A3101,B1302,B5701,C0602 | B5701 | 25 | 28 | ltlPsaasf | ltlRsaasf |
| RI1933 | TAF1L | 9 | 32635291 | T | A | A2601,A3101,B1302,B5701,C0602 | A3101 | 148 | 293 | lvnVegwir | lvnDegwir |
| RI1933 | TAF1L | 9 | 32635291 | T | A | A2601,A3101,B1302,B5701,C0602 | B5701 | 40 | 35 | galvnVegw | galvnDegw |
| RI1933 | TAF1L | 9 | 32635292 | C | A | A2601,A3101,B1302,B5701,C0602 | A3101 | 114 | 293 | lvnYegwir | lvnDegwir |
| RI1933 | TAF1L | 9 | 32635292 | C | A | A2601,A3101,B1302,B5701,C0602 | B5701 | 42 | 35 | galvnYegw | galvnDegw |
| RI1933 | NTRK2 | 9 | 87342772 | C | T | A2601,A3101,B1302,B5701,C0602 | C0602 | 380 | 1319 | lqldnptYm | lqldnptHm |
| RI1933 | GLRA2 | X | 14708956 | G | A | A2601,A3101,B1302,B5701,C0602 | A3101 | 236 | 307 | keflrlQrr | keflrlRrr |
| RI1933 | DUSP21 | X | 44703682 | A | T | A2601,A3101,B1302,B5701,C0602 | C0602 | 326 | 286 | mrqgrSllh | mrqgrTllh |
| RI1933 | GAGE2A | X | 49208335 | A | G | A2601,A3101,B1302,B5701,C0602 | A2601 | 41 | 102 | eppeVigpm | eppeMigpm |
| RI1933 | GAGE2A | X | 49208335 | A | G | A2601,A3101,B1302,B5701,C0602 | A2601 | 449 | 9165 | eVigpmrpe | eMigpmrpe |
| RI1933 | GAGE2A | X | 49208335 | A | G | A2601,A3101,B1302,B5701,C0602 | C0602 | 117 | 113 | rryveppeV | rryveppeM |
| RI1933 | GDPD2 | X | 69652182 | G | T | A2601,A3101,B1302,B5701,C0602 | A3101 | 178 | 98 | sLnlfvvnk | sVnlfvvnk |
| RI1933 | TAF1 | X | 70612785 | C | T | A2601,A3101,B1302,B5701,C0602 | A3101 | 439 | 2634 | rClslknak | rRlslknak |
| RI1933 | ABCB7 | X | 74288958 | C | A | A2601,A3101,B1302,B5701,C0602 | A3101 | 293 | 525 | gsgkstiLr | gsgkstiVr |
| RI1933 | ABCB7 | X | 74288958 | C | A | A2601,A3101,B1302,B5701,C0602 | A3101 | 14 | 10 | stiLrllfr | stiVrllfr |
| RI1933 | ABCB7 | X | 74288958 | C | A | A2601,A3101,B1302,B5701,C0602 | B5701 | 85 | 66 | kstiLrllf | kstiVrllf |
| RI1933 | MAGEE1 | X | 75649053 | C | A | A2601,A3101,B1302,B5701,C0602 | A3101 | 142 | 267 | lstpvpptr | Lstpvpptr |
| RI1933 | RHOXF1 | X | 119246821 | C | A | A2601,A3101,B1302,B5701,C0602 | C0602 | 60 | 68 | trSelaenl | trRelaenl |
| RI1933 | MAGEC3 | X | 140983290 | G | T | A2601,A3101,B1302,B5701,C0602 | C0602 | 173 | 6004 | rHedgrrgl | rQedgrrgl |
| RI1933 | AFF2 | X | 148048551 | C | G | A2601,A3101,B1302,B5701,C0602 | B5701 | 180 | 497 | tswaalAll | tswaalPll |
| RI1933 | MAGEA8 | X | 149013326 | G | T | A2601,A3101,B1302,B5701,C0602 | B5701 | 93 | 23814 | gsssneeeW | gsssneeeG |
| RI1933 | GABRA3 | X | 151376506 | C | A | A2601,A3101,B1302,B5701,C0602 | A3101 | 363 | 556 | hFvgteiir | hVvgteiir |

Figure 21 (Cont.)

| | | | | | | | | | | | |
|---|---|---|---|---|---|---|---|---|---|---|---|
| RI1933 | DUSP9 | X | 152915557 | G | T | A2601,A3101,B1302,B5701,C0602 | A3101 | 347 | 7025 | ayYlvkrkk | ayDlvkrkk |
| RI1933 | MPP1 | X | 154014673 | C | G | A2601,A3101,B1302,B5701,C0602 | C0602 | 180 | 102 | srlpalqlf | srlpalqMf |
| RI1933 | FUNDC2 | X | 154255247 | G | T | A2601,A3101,B1302,B5701,C0602 | A3101 | 74 | 156 | sqLvattar | sqVvattar |
| RI1933 | IL9R | X | 155234971 | G | T | A2601,A3101,B1302,B5701,C0602 | C0602 | 10 | 21 | qhrdhivVv | qhrdhivGv |
| RO3338 | VAMP3 | 1 | 7839691 | G | T | A0201,A3002,B0801,B3801,C0701,C1203 | A0201 | 8 | 26 | iiiiivwFv | iiiiivwVv |
| RO3338 | TMEM54 | 1 | 33366829 | C | A | A0201,A3002,B0801,B3801,C0701,C1203 | A0201 | 137 | 4050 | clLlggisv | clRlggisv |
| RO3338 | ZSCAN20 | 1 | 33961034 | C | G | A0201,A3002,B0801,B3801,C0701,C1203 | C1203 | 302 | 594 | kdfnnsshL | kdfnnsshF |
| RO3338 | DLGAP3 | 1 | 35370840 | C | T | A0201,A3002,B0801,B3801,C0701,C1203 | C1203 | 240 | 619 | Tpraglghi | Apraglghi |
| RO3338 | HRNR | 1 | 152186028 | C | T | A0201,A3002,B0801,B3801,C0701,C1203 | C0701 | 58 | 41 | srlghsslf | srlghssVf |
| RO3338 | IQGAP3 | 1 | 156510675 | C | T | A0201,A3002,B0801,B3801,C0701,C1203 | B0801 | 195 | 44 | svvHrfahl | svvRrfahl |
| RO3338 | IQGAP3 | 1 | 156510675 | C | T | A0201,A3002,B0801,B3801,C0701,C1203 | C1203 | 382 | 625 | vvHrfahll | vvRrfahll |
| RO3338 | SLC19A2 | 1 | 169435129 | C | G | A0201,A3002,B0801,B3801,C0701,C1203 | B0801 | 72 | 70 | svmkkcrNl | svmkkcrKl |
| RO3338 | COMTD1 | 10 | 76995082 | C | T | A0201,A3002,B0801,B3801,C0701,C1203 | A0201 | 127 | 87 | mmtceqTql | mmtceqAql |
| RO3338 | COMTD1 | 10 | 76995082 | C | T | A0201,A3002,B0801,B3801,C0701,C1203 | C0701 | 50 | 67 | mtceqTqll | mtceqAqll |
| RO3338 | COMTD1 | 10 | 76995082 | C | T | A0201,A3002,B0801,B3801,C0701,C1203 | C1203 | 151 | 201 | mtceqTqll | mtceqAqll |
| RO3338 | SLC1A2 | 11 | 35333930 | A | G | A0201,A3002,B0801,B3801,C0701,C1203 | A0201 | 110 | 668 | amvyymPtt | amvyymStt |
| RO3338 | SLC1A2 | 11 | 35333930 | A | G | A0201,A3002,B0801,B3801,C0701,C1203 | A0201 | 192 | 161 | mvyymPtti | mvyymStti |
| RO3338 | SLC1A2 | 11 | 35333930 | A | G | A0201,A3002,B0801,B3801,C0701,C1203 | A0201 | 15 | 9 | ymPttiiaa | ymSttiiaa |
| RO3338 | SLC1A2 | 11 | 35333930 | A | G | A0201,A3002,B0801,B3801,C0701,C1203 | C1203 | 16 | 19 | mvyymPtti | mvyymStti |
| RO3338 | SLC1A2 | 11 | 35333930 | A | G | A0201,A3002,B0801,B3801,C0701,C1203 | C1203 | 52 | 123 | vyymPttii | vyymSttii |
| RO3338 | SLC1A2 | 11 | 35333930 | A | G | A0201,A3002,B0801,B3801,C0701,C1203 | C1203 | 315 | 491 | mPttiiaav | mSttiiaav |
| RO3338 | ARAP1 | 11 | 72425235 | T | A | A0201,A3002,B0801,B3801,C0701,C1203 | C1203 | 177 | 386 | spppcppVi | spppcppEi |
| RO3338 | ACSM4 | 12 | 7459274 | G | A | A0201,A3002,B0801,B3801,C0701,C1203 | A0201 | 77 | 52 | Hlavilpri | Rlavilpri |

Figure 21 (Cont.)

| | | | | | | | | | | | |
|---|---|---|---|---|---|---|---|---|---|---|---|
| RO3338 | ACSM4 | 12 | 7459274 | G | A | A0201,A3002,B0801,B3801,C0701,C1203 | C0701 | 37 | 39 | qrgdHlavi | qrgdRlavi |
| RO3338 | ACSM4 | 12 | 7459274 | G | A | A0201,A3002,B0801,B3801,C0701,C1203 | C1203 | 479 | 671 | qrgdHlavi | qrgdRlavi |
| RO3338 | LRRK2 | 12 | 40668439 | G | A | A0201,A3002,B0801,B3801,C0701,C1203 | A0201 | 440 | 1294 | silhfpdal | siVhfpdal |
| RO3338 | LRRK2 | 12 | 40668439 | G | A | A0201,A3002,B0801,B3801,C0701,C1203 | C0701 | 9 | 10 | lhfpdalem | Vhfpdalem |
| RO3338 | LRRK2 | 12 | 40668439 | G | A | A0201,A3002,B0801,B3801,C0701,C1203 | C1203 | 303 | 574 | lhfpdalem | Vhfpdalem |
| RO3338 | MFSD5 | 12 | 53647471 | C | G | A0201,A3002,B0801,B3801,C0701,C1203 | A0201 | 83 | 383 | giMfssfma | gilfssfma |
| RO3338 | MFSD5 | 12 | 53647471 | C | G | A0201,A3002,B0801,B3801,C0701,C1203 | A0201 | 12 | 132 | iMfssfmaa | ilfssfmaa |
| RO3338 | TMEM132C | 12 | 128899882 | A | G | A0201,A3002,B0801,B3801,C0701,C1203 | C1203 | 462 | 102 | tpvelyyAv | tpvelyyTv |
| RO3338 | TMEM132C | 12 | 128899882 | A | G | A0201,A3002,B0801,B3801,C0701,C1203 | C1203 | 123 | 1160 | yAvhpgner | yTvhpgner |
| RO3338 | SLC7A1 | 13 | 30110205 | C | A | A0201,A3002,B0801,B3801,C0701,C1203 | C1203 | 286 | 6373 | ntfdlvalW | ntfdlvalG |
| RO3338 | SLC7A1 | 13 | 30110205 | C | A | A0201,A3002,B0801,B3801,C0701,C1203 | C1203 | 43 | 23 | valWvgstl | valGvgstl |
| RO3338 | CHD8 | 14 | 21894391 | G | C | A0201,A3002,B0801,B3801,C0701,C1203 | A0201 | 21 | 9 | klntitAvv | klntitPvv |
| RO3338 | ESRRB | 14 | 76957991 | G | T | A0201,A3002,B0801,B3801,C0701,C1203 | A3002 | 247 | 350 | ailqlvrMy | ailqlvrRy |
| RO3338 | ESRRB | 14 | 76957991 | G | T | A0201,A3002,B0801,B3801,C0701,C1203 | C0701 | 65 | 166 | vrMykklkv | vrRykklkv |
| RO3338 | ESRRB | 14 | 76957991 | G | T | A0201,A3002,B0801,B3801,C0701,C1203 | C1203 | 397 | 12884 | railqlvrM | railqlvrR |
| RO3338 | HCN4 | 15 | 73615421 | A | G | A0201,A3002,B0801,B3801,C0701,C1203 | A0201 | 372 | 1202 | rqpeppPlv | rqpeppSlv |
| RO3338 | HCN4 | 15 | 73615421 | A | G | A0201,A3002,B0801,B3801,C0701,C1203 | C1203 | 342 | 114 | rqpeppPlv | rqpeppSlv |
| RO3338 | C15orf26 | 15 | 81426714 | G | C | A0201,A3002,B0801,B3801,C0701,C1203 | A3002 | 115 | 77 | ignSnedvy | ignWnedvy |
| RO3338 | PKD1 | 16 | 2161401 | G | A | A0201,A3002,B0801,B3801,C0701,C1203 | A0201 | 33 | 148 | vlsgLeatv | vlsgPeatv |
| RO3338 | PKD1 | 16 | 2161401 | G | A | A0201,A3002,B0801,B3801,C0701,C1203 | A0201 | 257 | 26933 | gLeatvehv | gPeatvehv |
| RO3338 | PKD1 | 16 | 2161401 | G | A | A0201,A3002,B0801,B3801,C0701,C1203 | A3002 | 127 | 662 | Leatvehvy | Peatvehvy |
| RO3338 | ABCA3 | 16 | 2338192 | A | T | A0201,A3002,B0801,B3801,C0701,C1203 | A0201 | 251 | 204 | allainyTs | allainySs |

Figure 21 (Cont.)

| | | | | | | | | | | | |
|---|---|---|---|---|---|---|---|---|---|---|---|
| RO3338 | ABCA3 | 16 | 2338192 | A | T | A0201,A3002,B0801,B3801,C0701,C1203 | C1203 | 34 | 64 | lainyTsel | lainySsel |
| RO3338 | SEC14L5 | 16 | 5046388 | G | C | A0201,A3002,B0801,B3801,C0701,C1203 | A0201 | 419 | 3036 | yierclAhl | yierclGhl |
| RO3338 | SEC14L5 | 16 | 5046388 | G | C | A0201,A3002,B0801,B3801,C0701,C1203 | C1203 | 41 | 67 | yierclAhl | yierclGhl |
| RO3338 | RMI2 | 16 | 11439537 | G | A | A0201,A3002,B0801,B3801,C0701,C1203 | C1203 | 145 | 79 | madrDearl | madrGearl |
| RO3338 | RRAD | 16 | 66958811 | A | C | A0201,A3002,B0801,B3801,C0701,C1203 | A3002 | 136 | 123 | gsdsdesGy | gsdsdesVy |
| RO3338 | RRAD | 16 | 66958811 | A | C | A0201,A3002,B0801,B3801,C0701,C1203 | C1203 | 256 | 183 | dsdesGykv | dsdesVykv |
| RO3338 | VAT1L | 16 | 77850892 | G | A | A0201,A3002,B0801,B3801,C0701,C1203 | C1203 | 311 | 708 | pEfecsgiv | pGfecsgiv |
| RO3338 | FBXO39 | 17 | 6684076 | C | T | A0201,A3002,B0801,B3801,C0701,C1203 | C0701 | 221 | 149 | mkyeClari | mkyeRlari |
| RO3338 | FBXO39 | 17 | 6684076 | C | T | A0201,A3002,B0801,B3801,C0701,C1203 | C1203 | 20 | 25 | mkyeClari | mkyeRlari |
| RO3338 | CTDP1 | 18 | 77475031 | C | A | A0201,A3002,B0801,B3801,C0701,C1203 | C1203 | 296 | 466 | haQdkepel | haPdkepel |
| RO3338 | PPP1R14A | 19 | 38746876 | G | T | A0201,A3002,B0801,B3801,C0701,C1203 | C0701 | 394 | 1630 | krhErvtvk | krhArvtvk |
| RO3338 | ZNF230 | 19 | 44515376 | G | T | A0201,A3002,B0801,B3801,C0701,C1203 | C1203 | 468 | 806 | ncNecgksf | ncKecgksf |
| RO3338 | FOSB | 19 | 45974528 | G | T | A0201,A3002,B0801,B3801,C0701,C1203 | C0701 | 229 | 169 | Lrreltdrl | Rrreltdrl |
| RO3338 | FOSB | 19 | 45974528 | G | T | A0201,A3002,B0801,B3801,C0701,C1203 | C1203 | 453 | 13633 | laaakcrnL | laaakcrnR |
| RO3338 | GAD1 | 2 | 171709240 | T | A | A0201,A3002,B0801,B3801,C0701,C1203 | C1203 | 423 | 370 | vtRnphkmm | vtWnphkmm |
| RO3338 | PNKD | 2 | 219135299 | G | T | A0201,A3002,B0801,B3801,C0701,C1203 | C1203 | 243 | 2456 | rVarnarvl | rGarnarvl |
| RO3338 | DLGAP4 | 20 | 35061009 | C | G | A0201,A3002,B0801,B3801,C0701,C1203 | A0201 | 57 | 50 | Vtlshahev | Ltlshahev |
| RO3338 | DLGAP4 | 20 | 35061009 | C | G | A0201,A3002,B0801,B3801,C0701,C1203 | C0701 | 327 | 526 | Vtlshahev | Ltlshahev |
| RO3338 | DLGAP4 | 20 | 35061009 | C | G | A0201,A3002,B0801,B3801,C0701,C1203 | C1203 | 167 | 129 | Vtlshahev | Ltlshahev |
| RO3338 | MORC3 | 21 | 37692567 | C | T | A0201,A3002,B0801,B3801,C0701,C1203 | C1203 | 426 | 56 | mVaqpprgi | mAaqpprgi |
| RO3338 | EBLN2 | 3 | 73111281 | T | A | A0201,A3002,B0801,B3801,C0701,C1203 | A0201 | 72 | 10 | yvnshsllv | yvnshslFv |
| RO3338 | EBLN2 | 3 | 73111281 | T | A | A0201,A3002,B0801,B3801,C0701,C1203 | A3002 | 44 | 150 | lvwvcdrsy | Fvwvcdrsy |
| RO3338 | EBLN2 | 3 | 73111281 | T | A | A0201,A3002,B0801,B3801,C0701,C1203 | C0701 | 109 | 128 | yvnshsllv | yvnshslFv |

Figure 21 (Cont.)

| | | | | | | | | | | | |
|---|---|---|---|---|---|---|---|---|---|---|---|
| RO3338 | EBLN2 | 3 | 73111281 | T | A | A0201,A3002,B0801,B3801,C0701,C1203 | C1203 | 17 | 22 | yvnshsliv | yvnshslFv |
| RO3338 | PAICS | 4 | 57316827 | A | G | A0201,A3002,B0801,B3801,C0701,C1203 | C1203 | 75 | 82 | vtpeglqVv | vtpeglqMv |
| RO3338 | TLR2 | 4 | 154624362 | T | G | A0201,A3002,B0801,B3801,C0701,C1203 | A3002 | 371 | 658 | Rlehldlsy | Slehldlsy |
| RO3338 | TLR2 | 4 | 154624362 | T | G | A0201,A3002,B0801,B3801,C0701,C1203 | C1203 | 486 | 320 | dsfsslgRl | dsfsslgSl |
| RO3338 | CDH10 | 5 | 24491715 | C | T | A0201,A3002,B0801,B3801,C0701,C1203 | A0201 | 37 | 31 | aliTillci | aliAillci |
| RO3338 | CDH10 | 5 | 24491715 | C | T | A0201,A3002,B0801,B3801,C0701,C1203 | C1203 | 170 | 945 | lstgaliTi | lstgaliAi |
| RO3338 | NUP155 | 5 | 37329301 | C | A | A0201,A3002,B0801,B3801,C0701,C1203 | C1203 | 206 | 1285 | spFyssspv | spVyssspv |
| RO3338 | KIF2A | 5 | 61673528 | C | T | A0201,A3002,B0801,B3801,C0701,C1203 | A0201 | 103 | 43 | qlftfheVv | qlftfheAv |
| RO3338 | KIF2A | 5 | 61673528 | C | T | A0201,A3002,B0801,B3801,C0701,C1203 | C0701 | 20 | 11 | fheVvsqmv | fheAvsqmv |
| RO3338 | KIF2A | 5 | 61673528 | C | T | A0201,A3002,B0801,B3801,C0701,C1203 | C1203 | 198 | 449 | qlftfheVv | qlftfheAv |
| RO3338 | KIF2A | 5 | 61673528 | C | T | A0201,A3002,B0801,B3801,C0701,C1203 | C1203 | 204 | 377 | ftfheVvsq | ftfheAvsq |
| RO3338 | KIF2A | 5 | 61673528 | C | T | A0201,A3002,B0801,B3801,C0701,C1203 | C1203 | 474 | 219 | fheVvsqmv | fheAvsqmv |
| RO3338 | ARHGEF28 | 5 | 73181743 | G | C | A0201,A3002,B0801,B3801,C0701,C1203 | A0201 | 92 | 86 | miatvHlkv | miatvDlkv |
| RO3338 | KDM3B | 5 | 137766038 | A | T | A0201,A3002,B0801,B3801,C0701,C1203 | A0201 | 93 | 26670 | tlrkrlyeV | tlrkrlyeE |
| RO3338 | KDM3B | 5 | 137766038 | A | T | A0201,A3002,B0801,B3801,C0701,C1203 | B0801 | 14 | 180 | tlrkrlyeV | tlrkrlyeE |
| RO3338 | TNXB | 6 | 32064500 | C | T | A0201,A3002,B0801,B3801,C0701,C1203 | A3002 | 337 | 19202 | strtcprdY | strtcprdC |
| RO3338 | TAPBP | 6 | 33271707 | G | C | A0201,A3002,B0801,B3801,C0701,C1203 | A0201 | 164 | 1095 | vqcstslyV | vqcstslyL |
| RO3338 | TAPBP | 6 | 33271707 | G | C | A0201,A3002,B0801,B3801,C0701,C1203 | A0201 | 185 | 156 | stslyVslv | stslyLslv |
| RO3338 | TAPBP | 6 | 33271707 | G | C | A0201,A3002,B0801,B3801,C0701,C1203 | A0201 | 63 | 66 | slyVslvtl | slyLslvtl |
| RO3338 | TAPBP | 6 | 33271707 | G | C | A0201,A3002,B0801,B3801,C0701,C1203 | C1203 | 203 | 291 | slyVslvtl | slyLslvtl |
| RO3338 | ANKS1A | 6 | 35047683 | C | A | A0201,A3002,B0801,B3801,C0701,C1203 | B0801 | 100 | 2019 | qkHprfsql | qkPprfsql |
| RO3338 | ZNF76 | 6 | 35259389 | C | T | A0201,A3002,B0801,B3801,C0701,C1203 | C0701 | 453 | 63 | fttFnirkv | fttSnirkv |

Figure 21 (Cont.)

| | | | | | | | | | | | |
|---|---|---|---|---|---|---|---|---|---|---|---|
| RO3338 | ZNF76 | 6 | 35259389 | C | T | A0201,A3002,B0801,B3801,C0701,C1203 | C1203 | 26 | 15 | fttFnirkv | fttSnirkv |
| RO3338 | ROS1 | 6 | 117700313 | G | C | A0201,A3002,B0801,B3801,C0701,C1203 | A0201 | 486 | 536 | kviaVtldl | kviaLtldl |
| RO3338 | ROS1 | 6 | 117700313 | G | C | A0201,A3002,B0801,B3801,C0701,C1203 | B0801 | 470 | 88 | fsgkkviaV | fsgkkviaL |
| RO3338 | ROS1 | 6 | 117700313 | G | C | A0201,A3002,B0801,B3801,C0701,C1203 | C1203 | 51 | 189 | fsgkkviaV | fsgkkviaL |
| RO3338 | TAAR1 | 6 | 132966823 | C | A | A0201,A3002,B0801,B3801,C0701,C1203 | A0201 | 34 | 3349 | llsasifhl | lSsasifhl |
| RO3338 | GRM1 | 6 | 146755487 | A | T | A0201,A3002,B0801,B3801,C0701,C1203 | A0201 | 472 | 999 | taipVfhav | taipDfhav |
| RO3338 | GRM1 | 6 | 146755487 | A | T | A0201,A3002,B0801,B3801,C0701,C1203 | C1203 | 20 | 18 | taipVfhav | taipDfhav |
| RO3338 | EGFR | 7 | 55224306 | A | G | A0201,A3002,B0801,B3801,C0701,C1203 | B3801 | 186 | 122 | khfkncAsi | khfkncTsi |
| RO3338 | EGFR | 7 | 55224306 | A | G | A0201,A3002,B0801,B3801,C0701,C1203 | C0701 | 316 | 122 | khfkncAsi | khfkncTsi |
| RO3338 | EGFR | 7 | 55224306 | A | G | A0201,A3002,B0801,B3801,C0701,C1203 | C1203 | 200 | 204 | khfkncAsi | khfkncTsi |
| RO3338 | LAMB1 | 7 | 107601063 | T | A | A0201,A3002,B0801,B3801,C0701,C1203 | A0201 | 102 | 27699 | lmpycksIV | lmpycksID |
| RO3338 | LAMB1 | 7 | 107601063 | T | A | A0201,A3002,B0801,B3801,C0701,C1203 | B0801 | 15 | 27 | mpycksIVi | mpycksIDi |
| RO3338 | LAMB1 | 7 | 107601063 | T | A | A0201,A3002,B0801,B3801,C0701,C1203 | C1203 | 18 | 120 | mpycksIVi | mpycksIDi |
| RO3338 | HTR5A | 7 | 154862649 | A | T | A0201,A3002,B0801,B3801,C0701,C1203 | C1203 | 34 | 46 | fslsSpspl | fslsTpspl |
| RO3338 | CSMD1 | 8 | 3047569 | A | T | A0201,A3002,B0801,B3801,C0701,C1203 | C0701 | 412 | 356 | Tefsagsiv | Sefsagsiv |
| RO3338 | CSMD1 | 8 | 3047569 | A | T | A0201,A3002,B0801,B3801,C0701,C1203 | C1203 | 163 | 237 | Tefsagsiv | Sefsagsiv |
| RO3338 | PPP2CB | 8 | 30643777 | G | A | A0201,A3002,B0801,B3801,C0701,C1203 | A3002 | 105 | 601 | hvtWrtpdy | hvtRrtpdy |
| RO3338 | LYPLA1 | 8 | 55014370 | T | A | A0201,A3002,B0801,B3801,C0701,C1203 | A0201 | 249 | 16812 | nlmstplpa | nNmstplpa |
| RO3338 | LYPLA1 | 8 | 55014370 | T | A | A0201,A3002,B0801,B3801,C0701,C1203 | A0201 | 51 | 234 | lmstplpai | Nmstplpai |
| RO3338 | VPS13B | 8 | 100831686 | C | T | A0201,A3002,B0801,B3801,C0701,C1203 | C1203 | 330 | 157 | cavpistsF | cavpistsL |
| RO3338 | VPS13B | 8 | 100831686 | C | T | A0201,A3002,B0801,B3801,C0701,C1203 | C1203 | 219 | 887 | istsFikqi | istsLikqi |
| RO3338 | VPS13B | 8 | 100831686 | C | T | A0201,A3002,B0801,B3801,C0701,C1203 | C1203 | 46 | 960 | Fikqiatkv | Likqiatkv |
| RO3338 | MAN1B1 | 9 | 140001724 | C | T | A0201,A3002,B0801,B3801,C0701,C1203 | A0201 | 353 | 1564 | flLgtlalg | flPgtlalg |

Figure 21 (Cont.)

| | | | | | | | | | | | |
|---|---|---|---|---|---|---|---|---|---|---|---|
| RO3338 | MAN1B1 | 9 | 140001724 | C | T | A0201,A3002,B0801,B3801,C0701,C1203 | A0201 | 55 | 20150 | lLgtlalgv | lPgtlalgv |
| RO3338 | MAN1B1 | 9 | 140001724 | C | T | A0201,A3002,B0801,B3801,C0701,C1203 | A3002 | 121 | 671 | Lgtlalgvy | Pgtlalgvy |
| RO3338 | ZBED1 | X | 2408229 | C | A | A0201,A3002,B0801,B3801,C0701,C1203 | A0201 | 32 | 1999 | aipekyWav | aipekyGav |
| SA9755 | PANK4 | 1 | 2450006 | C | T | A0101,A11126,B3501,B0801,C0701,C0401 | C0701 | 255 | 214 | rhKgylgai | rhEgylgai |
| SA9755 | PRDM16 | 1 | 3350252 | G | T | A0101,A11126,B3501,B0801,C0701,C0401 | B0801 | 277 | 193 | qaknqayal | qaknqayaM |
| SA9755 | TAS1R2 | 1 | 19181067 | G | C | A0101,A11126,B3501,B0801,C0701,C0401 | B0801 | 393 | 1601 | wMaseswai | wlaseswai |
| SA9755 | PTPRU | 1 | 29644366 | G | T | A0101,A11126,B3501,B0801,C0701,C0401 | B3501 | 10 | 42 | lppdLclpf | lppdRclpf |
| SA9755 | TINAGL1 | 1 | 32049168 | G | A | A0101,A11126,B3501,B0801,C0701,C0401 | B0801 | 24 | 1713 | mnmhKiytv | mnmhEiytv |
| SA9755 | TINAGL1 | 1 | 32049168 | G | A | A0101,A11126,B3501,B0801,C0701,C0401 | B0801 | 72 | 337 | nmhKiytvl | nmhEiytvl |
| SA9755 | TINAGL1 | 1 | 32049168 | G | A | A0101,A11126,B3501,B0801,C0701,C0401 | B3501 | 338 | 128 | svmnmhKiy | svmnmhEiy |
| SA9755 | TINAGL1 | 1 | 32049168 | G | A | A0101,A11126,B3501,B0801,C0701,C0401 | C0701 | 405 | 1109 | mnmhKiytv | mnmhEiytv |
| SA9755 | MAP7D1 | 1 | 36644124 | G | A | A0101,A11126,B3501,B0801,C0701,C0401 | B0801 | 74 | 491 | llaKkrrqa | llaEkrrqa |
| SA9755 | MAP7D1 | 1 | 36644124 | G | A | A0101,A11126,B3501,B0801,C0701,C0401 | B0801 | 171 | 3107 | laKkrrqar | laEkrrqar |
| SA9755 | DIO1 | 1 | 54371839 | C | A | A0101,A11126,B3501,B0801,C0701,C0401 | C0701 | 175 | 96 | drlqaaNll | drlqaaHll |
| SA9755 | TTC4 | 1 | 55183294 | A | G | A0101,A11126,B3501,B0801,C0701,C0401 | A0101 | 70 | 31 | Ctnraaaqy | Ytnraaaqy |
| SA9755 | EPHX4 | 1 | 92528691 | G | C | A0101,A11126,B3501,B0801,C0701,C0401 | B3501 | 222 | 179 | Qmaevtkiy | Emaevtkiy |
| SA9755 | CELSR2 | 1 | 109794383 | G | T | A0101,A11126,B3501,B0801,C0701,C0401 | C0701 | 231 | 8545 | ftinngtgL | ftinngtgW |
| SA9755 | AMPD1 | 1 | 115216313 | C | A | A0101,A11126,B3501,B0801,C0701,C0401 | B3501 | 15 | 18758 | qvfklstcY | qvfklstcD |
| SA9755 | CELF3 | 1 | 151681509 | C | A | A0101,A11126,B3501,B0801,C0701,C0401 | C0701 | 58 | 100 | thaeaqaSi | thaeaqaAi |
| SA9755 | RPTN | 1 | 152128100 | C | G | A0101,A11126,B3501,B0801,C0701,C0401 | A0101 | 235 | 371 | kidTqdqsy | kidRqdqsy |
| SA9755 | RPTN | 1 | 152128100 | C | G | A0101,A11126,B3501,B0801,C0701,C0401 | A0101 | 162 | 18489 | dTqdqsyhy | dRqdqsyhy |
| SA9755 | RPTN | 1 | 152128100 | C | G | A0101,A11126,B3501,B0801,C0701,C0401 | C0701 | 183 | 395 | shygkidTq | shygkidRq |

Figure 21 (Cont.)

| | | | | | | | | | | | |
|---|---|---|---|---|---|---|---|---|---|---|---|
| SA9755 | RPTN | 1 | 152128419 | C | G | A0101,A11126,B3501,B0801,C0701,C0401 | A0101 | 380 | 312 | dtqHqsshy | dtqDqsshy |
| SA9755 | RPTN | 1 | 152128648 | C | G | A0101,A11126,B3501,B0801,C0701,C0401 | C0701 | 103 | 237 | yhygHtdrq | yhygQtdrq |
| SA9755 | FLG2 | 1 | 152325014 | C | A | A0101,A11126,B3501,B0801,C0701,C0401 | C0701 | 311 | 300 | thsghthCq | thsghthGq |
| SA9755 | FLG2 | 1 | 152327611 | A | T | A0101,A11126,B3501,B0801,C0701,C0401 | A0101 | 330 | 15059 | sssgqysgY | sssgqysgF |
| SA9755 | LCE3A | 1 | 152595507 | G | C | A0101,A11126,B3501,B0801,C0701,C0401 | B3501 | 71 | 114 | spaqcVppa | spaqcLppa |
| SA9755 | ASH1L | 1 | 155451315 | C | A | A0101,A11126,B3501,B0801,C0701,C0401 | C0701 | 474 | 16516 | stninnqel | stninnqeS |
| SA9755 | ASH1L | 1 | 155451315 | C | A | A0101,A11126,B3501,B0801,C0701,C0401 | C0701 | 447 | 748 | innqelqel | innqeSqel |
| SA9755 | OR10Z1 | 1 | 158577042 | C | A | A0101,A11126,B3501,B0801,C0701,C0401 | C0701 | 327 | 92 | yslerdKli | yslerdQli |
| SA9755 | OR10J1 | 1 | 159410123 | G | T | A0101,A11126,B3501,B0801,C0701,C0401 | B0801 | 72 | 158 | Lpvmklsci | Rpvmklsci |
| SA9755 | PIGM | 1 | 160000517 | C | G | A0101,A11126,B3501,B0801,C0701,C0401 | A0101 | 7 | 7 | ctsqyflSy | ctsqyflWy |
| SA9755 | PIGM | 1 | 160000517 | C | G | A0101,A11126,B3501,B0801,C0701,C0401 | B3501 | 273 | 1819 | ctsqyflSy | ctsqyflWy |
| SA9755 | LRRC52 | 1 | 165513676 | C | A | A0101,A11126,B3501,B0801,C0701,C0401 | C0701 | 495 | 24800 | yHldiplnt | yPldiplnt |
| SA9755 | MROH9 | 1 | 170965653 | C | A | A0101,A11126,B3501,B0801,C0701,C0401 | C0701 | 243 | 114 | yDqdalrvl | yAqdalrvl |
| SA9755 | TNN | 1 | 175086341 | G | T | A0101,A11126,B3501,B0801,C0701,C0401 | A0101 | 375 | 21394 | kadtkaqtY | kadtkaqtD |
| SA9755 | TNN | 1 | 175086341 | G | T | A0101,A11126,B3501,B0801,C0701,C0401 | C0701 | 90 | 926 | tYidspqnl | tDidspqnl |
| SA9755 | RNF2 | 1 | 185062227 | G | C | A0101,A11126,B3501,B0801,C0701,C0401 | B0801 | 414 | 1916 | cptcrkklL | cptcrkklV |
| SA9755 | KDM5B | 1 | 202702699 | G | C | A0101,A11126,B3501,B0801,C0701,C0401 | A0101 | 62 | 10495 | lAegdalry | lPegdalry |
| SA9755 | KDM5B | 1 | 202702699 | G | C | A0101,A11126,B3501,B0801,C0701,C0401 | B3501 | 19 | 8 | lAegdalry | lPegdalry |
| SA9755 | ZNF678 | 1 | 227842802 | G | A | A0101,A11126,B3501,B0801,C0701,C0401 | C0701 | 52 | 18 | shltrhKri | shltrhRri |
| SA9755 | ZNF678 | 1 | 227842802 | G | A | A0101,A11126,B3501,B0801,C0701,C0401 | C0701 | 466 | 832 | trhKrihtg | trhRrihtg |
| SA9755 | AGT | 1 | 230838946 | G | C | A0101,A11126,B3501,B0801,C0701,C0401 | B3501 | 52 | 101 | favydEsat | favydQsat |
| SA9755 | GNPAT | 1 | 231401814 | A | T | A0101,A11126,B3501,B0801,C0701,C0401 | B3501 | 11 | 12 | Flvpisisy | Ylvpisisy |
| SA9755 | ZP4 | 1 | 238049077 | G | C | A0101,A11126,B3501,B0801,C0701,C0401 | B3501 | 236 | 183 | qpgpltVel | qpgpltLel |

Figure 21 (Cont.)

| | | | | | | | | | | | |
|---|---|---|---|---|---|---|---|---|---|---|---|
| SA9755 | ZNF695 | 1 | 247150954 | T | C | A0101,A11126,B3501,B0801,C0701,C0401 | B0801 | 348 | 494 | svltkhkRi | svltkhkKi |
| SA9755 | UPF2 | 10 | 12041973 | G | C | A0101,A11126,B3501,B0801,C0701,C0401 | B3501 | 420 | 3221 | hVklivdaf | hLklivdaf |
| SA9755 | UPF2 | 10 | 12041973 | G | C | A0101,A11126,B3501,B0801,C0701,C0401 | C0701 | 260 | 517 | stgshVkli | stgshLkli |
| SA9755 | CDC123 | 10 | 12238300 | G | T | A0101,A11126,B3501,B0801,C0701,C0401 | B3501 | 29 | 131 | ypffLgvti | ypffRgvti |
| SA9755 | FAM21B | 10 | 51892617 | G | T | A0101,A11126,B3501,B0801,C0701,C0401 | B0801 | 353 | 751 | ttkpksLsa | ttkpksRsa |
| SA9755 | PCDH15 | 10 | 55719555 | G | T | A0101,A11126,B3501,B0801,C0701,C0401 | C0701 | 369 | 1782 | sssDtvkil | sssAtvkil |
| SA9755 | TET1 | 10 | 70406055 | G | T | A0101,A11126,B3501,B0801,C0701,C0401 | B0801 | 311 | 120 | Liaskfqnf | Wiaskfqnf |
| SA9755 | HK1 | 10 | 71142485 | C | T | A0101,A11126,B3501,B0801,C0701,C0401 | C0701 | 11 | 14 | Mhnnavvkm | Thnnavvkm |
| SA9755 | ADAMTS14 | 10 | 72511269 | C | A | A0101,A11126,B3501,B0801,C0701,C0401 | C0701 | 47 | 2444 | sRlaykyvi | sSlaykyvi |
| SA9755 | ZSWIM8 | 10 | 75558113 | G | A | A0101,A11126,B3501,B0801,C0701,C0401 | B0801 | 264 | 1167 | snmMraaae | snmVraaae |
| SA9755 | ZSWIM8 | 10 | 75558113 | G | A | A0101,A11126,B3501,B0801,C0701,C0401 | B0801 | 416 | 8697 | nmMraaael | nmVraaael |
| SA9755 | ZSWIM8 | 10 | 75558113 | G | A | A0101,A11126,B3501,B0801,C0701,C0401 | C0701 | 109 | 141 | srardsnmM | srardsnmV |
| SA9755 | ZSWIM8 | 10 | 75558113 | G | A | A0101,A11126,B3501,B0801,C0701,C0401 | C0701 | 143 | 436 | Mraaaelal | Vraaaelal |
| SA9755 | TLL2 | 10 | 98170145 | A | C | A0101,A11126,B3501,B0801,C0701,C0401 | B3501 | 222 | 63 | ypsyshcvG | ypsyshcvW |
| SA9755 | TLL2 | 10 | 98170145 | A | C | A0101,A11126,B3501,B0801,C0701,C0401 | C0701 | 457 | 92 | shcvGrisv | shcvWrisv |
| SA9755 | TDRD1 | 10 | 115964491 | G | A | A0101,A11126,B3501,B0801,C0701,C0401 | B3501 | 85 | 34 | fppcaikYf | fppcaikCf |
| SA9755 | MMP21 | 10 | 127456116 | G | T | A0101,A11126,B3501,B0801,C0701,C0401 | B3501 | 73 | 54 | yLfkeslvf | yFfkeslvf |
| SA9755 | MMP21 | 10 | 127456116 | G | T | A0101,A11126,B3501,B0801,C0701,C0401 | C0701 | 109 | 902 | drrqkliyL | drrqkliyF |
| SA9755 | GPR123 | 10 | 134942851 | G | A | A0101,A11126,B3501,B0801,C0701,C0401 | C0701 | 34 | 7449 | lRpghleml | lGpghleml |
| SA9755 | KNDC1 | 10 | 135012177 | G | A | A0101,A11126,B3501,B0801,C0701,C0401 | B3501 | 176 | 97 | eahaEspsl | eahaGspsl |
| SA9755 | PHRF1 | 11 | 581561 | G | T | A0101,A11126,B3501,B0801,C0701,C0401 | A0101 | 477 | 21785 | lvarspgpY | lvarspgpD |
| SA9755 | PHRF1 | 11 | 581561 | G | T | A0101,A11126,B3501,B0801,C0701,C0401 | B3501 | 19 | 25045 | lvarspgpY | lvarspgpD |

Figure 21 (Cont.)

| | | | | | | | | | | | |
|---|---|---|---|---|---|---|---|---|---|---|---|
| SA9755 | TRPM5 | 11 | 2434193 | G | A | A0101,A11126,B3501,B0801,C0701,C0401 | C0701 | 229 | 154 | drgpCavfl | drgpRavfl |
| SA9755 | OR52N1 | 11 | 5809503 | C | A | A0101,A11126,B3501,B0801,C0701,C0401 | B3501 | 5 | 10690 | nviphtycY | nviphtycD |
| SA9755 | OR52N1 | 11 | 5809503 | C | A | A0101,A11126,B3501,B0801,C0701,C0401 | B3501 | 171 | 568 | iphtycYhm | iphtycDhm |
| SA9755 | EHF | 11 | 34678517 | A | T | A0101,A11126,B3501,B0801,C0701,C0401 | C0701 | 9 | 16 | khYprgthl | khNprgthl |
| SA9755 | LDLRAD3 | 11 | 36250922 | C | G | A0101,A11126,B3501,B0801,C0701,C0401 | C0701 | 100 | 13859 | eRsqgteev | ePsqgteev |
| SA9755 | OR5L2 | 11 | 55595185 | T | C | A0101,A11126,B3501,B0801,C0701,C0401 | A0101 | 371 | 265 | slaPrilfy | slaLrilfy |
| SA9755 | OR5L2 | 11 | 55595185 | T | C | A0101,A11126,B3501,B0801,C0701,C0401 | C0701 | 70 | 46 | ihsslaPri | ihsslaLri |
| SA9755 | OR5M9 | 11 | 56230620 | C | A | A0101,A11126,B3501,B0801,C0701,C0401 | A0101 | 7 | 13 | lsDtktisy | lsEtktisy |
| SA9755 | OR5M9 | 11 | 56230620 | C | A | A0101,A11126,B3501,B0801,C0701,C0401 | B3501 | 492 | 962 | lsDtktisy | lsEtktisy |
| SA9755 | MS4A2 | 11 | 59861449 | A | T | A0101,A11126,B3501,B0801,C0701,C0401 | B0801 | 441 | 304 | vLmlfltil | vMmlfltil |
| SA9755 | MS4A2 | 11 | 59861449 | A | T | A0101,A11126,B3501,B0801,C0701,C0401 | B3501 | 162 | 100 | fsteivvLm | fsteivvMm |
| SA9755 | MS4A2 | 11 | 59861449 | A | T | A0101,A11126,B3501,B0801,C0701,C0401 | C0701 | 405 | 643 | fsteivvLm | fsteivvMm |
| SA9755 | MS4A4A | 11 | 60070164 | T | A | A0101,A11126,B3501,B0801,C0701,C0401 | C0701 | 40 | 140 | Shgtmsilm | Chgtmsilm |
| SA9755 | BBS1 | 11 | 66291310 | G | A | A0101,A11126,B3501,B0801,C0701,C0401 | B3501 | 9 | 23 | langevHiy | langevRiy |
| SA9755 | BBS1 | 11 | 66291310 | G | A | A0101,A11126,B3501,B0801,C0701,C0401 | C0701 | 299 | 480 | vHiyrdkal | vRiyrdkal |
| SA9755 | TPCN2 | 11 | 68830458 | G | T | A0101,A11126,B3501,B0801,C0701,C0401 | B3501 | 343 | 58 | lpemaIvgl | lpemaSvgl |
| SA9755 | P2RY2 | 11 | 72945917 | G | C | A0101,A11126,B3501,B0801,C0701,C0401 | B0801 | 76 | 9 | lpTakrksv | lpRakrksv |
| SA9755 | UVRAG | 11 | 75852332 | A | T | A0101,A11126,B3501,B0801,C0701,C0401 | B3501 | 13 | 20 | ipvdCavav | ipvdSavav |
| SA9755 | UBTFL1 | 11 | 89819499 | C | A | A0101,A11126,B3501,B0801,C0701,C0401 | B0801 | 13 | 13 | ypgmrsKel | ypgmrsQel |
| SA9755 | UBTFL1 | 11 | 89819499 | C | A | A0101,A11126,B3501,B0801,C0701,C0401 | B3501 | 449 | 177 | ypgmrsKel | ypgmrsQel |
| SA9755 | UBTFL1 | 11 | 89819499 | C | A | A0101,A11126,B3501,B0801,C0701,C0401 | C0701 | 100 | 71 | mrsKeltki | mrsQeltki |
| SA9755 | SLC36A4 | 11 | 92918924 | C | T | A0101,A11126,B3501,B0801,C0701,C0401 | C0701 | 294 | 217 | sdKeheqel | sdEeheqel |
| SA9755 | EXPH5 | 11 | 108409826 | G | A | A0101,A11126,B3501,B0801,C0701,C0401 | B0801 | 303 | 295 | srmsfrLsf | srmsfrSsf |

Figure 21 (Cont.)

| | | | | | | | | | | | |
|---|---|---|---|---|---|---|---|---|---|---|---|
| SA9755 | EXPH5 | 11 | 108409826 | G | A | A0101,A11126,B3501,B0801,C0701,C0401 | B0801 | 67 | 91 | sfrLsfasl | sfrSsfasl |
| SA9755 | EXPH5 | 11 | 108409826 | G | A | A0101,A11126,B3501,B0801,C0701,C0401 | B3501 | 74 | 189 | Lsfaslfsf | Ssfaslfsf |
| SA9755 | EXPH5 | 11 | 108409826 | G | A | A0101,A11126,B3501,B0801,C0701,C0401 | C0701 | 70 | 75 | srmsfrLsf | srmsfrSsf |
| SA9755 | EXPH5 | 11 | 108409826 | G | A | A0101,A11126,B3501,B0801,C0701,C0401 | C0701 | 77 | 31 | frLsfaslf | frSsfaslf |
| SA9755 | CADM1 | 11 | 115375043 | G | A | A0101,A11126,B3501,B0801,C0701,C0401 | B3501 | 98 | 3290 | aaaaappgF | aaaaappgL |
| SA9755 | CADM1 | 11 | 115375043 | G | A | A0101,A11126,B3501,B0801,C0701,C0401 | C0701 | 57 | 357 | Frlrlllll | Lrlrlllll |
| SA9755 | APOA4 | 11 | 116693900 | A | C | A0101,A11126,B3501,B0801,C0701,C0401 | C0701 | 26 | 2593 | fRkavvltl | fLkavvltl |
| SA9755 | OR8B8 | 11 | 124310108 | G | T | A0101,A11126,B3501,B0801,C0701,C0401 | B0801 | 318 | 108 | mlnpliysM | mlnpliysL |
| SA9755 | OR8B8 | 11 | 124310108 | G | T | A0101,A11126,B3501,B0801,C0701,C0401 | B0801 | 131 | 162 | sMmkdvkv | sLmkdvkv |
| SA9755 | OR8B8 | 11 | 124310108 | G | T | A0101,A11126,B3501,B0801,C0701,C0401 | B3501 | 279 | 3806 | mlnpliysM | mlnpliysL |
| SA9755 | TAS2R30 | 12 | 11286472 | T | A | A0101,A11126,B3501,B0801,C0701,C0401 | B0801 | 236 | 499 | flrikrSvk | flrikrRvk |
| SA9755 | TAS2R30 | 12 | 11286472 | T | A | A0101,A11126,B3501,B0801,C0701,C0401 | B0801 | 247 | 11 | rikrSvksv | rikrRvksv |
| SA9755 | TAS2R30 | 12 | 11286472 | T | A | A0101,A11126,B3501,B0801,C0701,C0401 | C0701 | 147 | 188 | krSvksvvl | krRvksvvl |
| SA9755 | NCKAP5L | 12 | 50192144 | C | T | A0101,A11126,B3501,B0801,C0701,C0401 | C0701 | 34 | 190 | ghcaRqrev | ghcaGqrev |
| SA9755 | LIMA1 | 12 | 50599813 | C | G | A0101,A11126,B3501,B0801,C0701,C0401 | C0701 | 59 | 37 | srsasgrNi | srsasgrKi |
| SA9755 | PDE1B | 12 | 54962974 | C | G | A0101,A11126,B3501,B0801,C0701,C0401 | C0701 | 210 | 275 | vyidetrqM | vyidetrql |
| SA9755 | PDE1B | 12 | 54962974 | C | G | A0101,A11126,B3501,B0801,C0701,C0401 | C0701 | 195 | 273 | yidetrqMl | yidetrqll |
| SA9755 | PAN2 | 12 | 56713165 | C | T | A0101,A11126,B3501,B0801,C0701,C0401 | B0801 | 224 | 75 | ylklHflid | ylklRflid |
| SA9755 | AGAP2 | 12 | 58124697 | G | T | A0101,A11126,B3501,B0801,C0701,C0401 | C0701 | 261 | 203 | thgkemdlM | thgkemdlL |
| SA9755 | FAM19A2 | 12 | 62148692 | C | A | A0101,A11126,B3501,B0801,C0701,C0401 | B3501 | 141 | 154 | fpgqLagtt | fpgqVagtt |
| SA9755 | PTPRB | 12 | 71029513 | C | A | A0101,A11126,B3501,B0801,C0701,C0401 | B0801 | 31 | 4431 | karkylhsL | karkylhsW |
| SA9755 | PTPRB | 12 | 71029513 | C | A | A0101,A11126,B3501,B0801,C0701,C0401 | C0701 | 423 | 3744 | arkylhsLm | arkylhsWm |

Figure 21 (Cont.)

| | | | | | | | | | | | |
|---|---|---|---|---|---|---|---|---|---|---|---|
| SA9755 | ZFC3H1 | 12 | 72013143 | G | T | A0101,A11126,B3501,B0801,C0701,C0401 | B0801 | 98 | 17 | flrkfiaYf | flrkfiaSf |
| SA9755 | TPH2 | 12 | 72425425 | A | T | A0101,A11126,B3501,B0801,C0701,C0401 | A0101 | 162 | 20131 | vqdlrsdlY | vqdlrsdlN |
| SA9755 | KCNC2 | 12 | 75444401 | C | A | A0101,A11126,B3501,B0801,C0701,C0401 | B3501 | 13 | 10 | lagLltiam | lagVltiam |
| SA9755 | APAF1 | 12 | 99056328 | G | C | A0101,A11126,B3501,B0801,C0701,C0401 | B0801 | 35 | 122 | llttrdksL | llttrdksV |
| SA9755 | SLC17A8 | 12 | 100787200 | C | T | A0101,A11126,B3501,B0801,C0701,C0401 | B3501 | 12 | 17 | ipFaarvhy | ipSaarvhy |
| SA9755 | STAB2 | 12 | 104155096 | G | C | A0101,A11126,B3501,B0801,C0701,C0401 | B3501 | 137 | 7574 | qptetrfvH | qptetrfvD |
| SA9755 | STAB2 | 12 | 104155096 | G | C | A0101,A11126,B3501,B0801,C0701,C0401 | C0701 | 16 | 65 | trfvHgrai | trfvDgrai |
| SA9755 | WSCD2 | 12 | 108600131 | G | A | A0101,A11126,B3501,B0801,C0701,C0401 | B0801 | 452 | 3860 | ffNykkmti | ffDykkmti |
| SA9755 | PPP1CC | 12 | 111169662 | C | T | A0101,A11126,B3501,B0801,C0701,C0401 | B0801 | 41 | 1512 | enKirglcl | enEirglcl |
| SA9755 | PTPN11 | 12 | 112892407 | T | G | A0101,A11126,B3501,B0801,C0701,C0401 | C0701 | 37 | 39 | erfdAltdl | erfdSltdl |
| SA9755 | FBXO21 | 12 | 117603295 | C | G | A0101,A11126,B3501,B0801,C0701,C0401 | B3501 | 130 | 112 | wpQkvldil | wpEkvldil |
| SA9755 | CIT | 12 | 120263147 | G | A | A0101,A11126,B3501,B0801,C0701,C0401 | B3501 | 9 | 11 | lpiglpdym | lpigTpdym |
| SA9755 | NCOR2 | 12 | 124870336 | C | G | A0101,A11126,B3501,B0801,C0701,C0401 | C0701 | 81 | 159 | fnykNrqnl | fnykKrqnl |
| SA9755 | NCOR2 | 12 | 124870336 | C | G | A0101,A11126,B3501,B0801,C0701,C0401 | C0701 | 178 | 566 | Nrqnldeil | Krqnldeil |
| SA9755 | SLC15A4 | 12 | 129283810 | C | A | A0101,A11126,B3501,B0801,C0701,C0401 | B3501 | 52 | 23879 | igwmsshtY | igwmsshtD |
| SA9755 | GLT1D1 | 12 | 129431897 | G | A | A0101,A11126,B3501,B0801,C0701,C0401 | C0701 | 63 | 72 | kraagvQli | kraagvRli |
| SA9755 | TMEM132D | 12 | 129558525 | G | C | A0101,A11126,B3501,B0801,C0701,C0401 | B3501 | 5 | 3 | yptrnsMvm | yptrnsIvm |
| SA9755 | PIWIL1 | 12 | 130847333 | C | G | A0101,A11126,B3501,B0801,C0701,C0401 | C0701 | 93 | 94 | ifEdrgqel | ifQdrgqel |
| SA9755 | ZNF891 | 12 | 133697237 | T | A | A0101,A11126,B3501,B0801,C0701,C0401 | C0701 | 55 | 431 | Mrihtgekl | Krihtgekl |
| SA9755 | ZNF268 | 12 | 133779761 | A | G | A0101,A11126,B3501,B0801,C0701,C0401 | C0701 | 225 | 178 | vhqrshtgV | vhqrshtgM |
| SA9755 | ZNF268 | 12 | 133779761 | A | G | A0101,A11126,B3501,B0801,C0701,C0401 | C0701 | 33 | 17 | shtgVkpyv | shtgMkpyv |
| SA9755 | ZNF268 | 12 | 133780674 | C | T | A0101,A11126,B3501,B0801,C0701,C0401 | B0801 | 140 | 112 | iihmrlhsg | iihmrThsg |
| SA9755 | ZNF268 | 12 | 133780679 | T | A | A0101,A11126,B3501,B0801,C0701,C0401 | B0801 | 407 | 112 | iihmrthTg | iihmrthSg |

Figure 21 (Cont.)

| | | | | | | | | | | | |
|---|---|---|---|---|---|---|---|---|---|---|---|
| SA9755 | HSPH1 | 13 | 31722586 | C | G | A0101,A11126,B3501,B0801,C0701,C0401 | B3501 | 77 | 299 | spafkvTef | spafkvRef |
| SA9755 | UFM1 | 13 | 38924334 | G | T | A0101,A11126,B3501,B0801,C0701,C0401 | B3501 | 12 | 28 | laralpVaf | laralpGaf |
| SA9755 | UFM1 | 13 | 38924334 | G | T | A0101,A11126,B3501,B0801,C0701,C0401 | B3501 | 163 | 2371 | lpVafptga | lpGafptga |
| SA9755 | KCNRG | 13 | 50589816 | G | A | A0101,A11126,B3501,B0801,C0701,C0401 | B0801 | 146 | 1437 | lNflrthql | lDflrthql |
| SA9755 | GPC6 | 13 | 95055415 | C | A | A0101,A11126,B3501,B0801,C0701,C0401 | B0801 | 38 | 22 | saaqrghsM | saaqrghsL |
| SA9755 | GPC6 | 13 | 95055415 | C | A | A0101,A11126,B3501,B0801,C0701,C0401 | B3501 | 226 | 3824 | saaqrghsM | saaqrghsL |
| SA9755 | GPC6 | 13 | 95055415 | C | A | A0101,A11126,B3501,B0801,C0701,C0401 | C0701 | 445 | 378 | saaqrghsM | saaqrghsL |
| SA9755 | GPC6 | 13 | 95055415 | C | A | A0101,A11126,B3501,B0801,C0701,C0401 | C0701 | 431 | 727 | ghsMlswsl | ghsLlswsl |
| SA9755 | ABCC4 | 13 | 95696575 | G | C | A0101,A11126,B3501,B0801,C0701,C0401 | C0701 | 21 | 32 | Vrknqilli | Lrknqilli |
| SA9755 | AKAP6 | 14 | 33201735 | G | T | A0101,A11126,B3501,B0801,C0701,C0401 | B0801 | 294 | 780 | ealkkCgvl | ealkkGgvl |
| SA9755 | DACT1 | 14 | 59113323 | G | C | A0101,A11126,B3501,B0801,C0701,C0401 | C0701 | 495 | 803 | ahghAreav | ahghGreav |
| SA9755 | SIX6 | 14 | 60976393 | G | C | A0101,A11126,B3501,B0801,C0701,C0401 | B0801 | 185 | 472 | wlQahyqea | wlEahyqea |
| SA9755 | SIX6 | 14 | 60976393 | G | C | A0101,A11126,B3501,B0801,C0701,C0401 | B3501 | 111 | 69 | qalwlQahy | qalwlEahy |
| SA9755 | LTBP2 | 14 | 74995765 | C | T | A0101,A11126,B3501,B0801,C0701,C0401 | B0801 | 377 | 4732 | gpgtYtlpl | gpgtCtlpl |
| SA9755 | VASH1 | 14 | 77229439 | C | T | A0101,A11126,B3501,B0801,C0701,C0401 | C0701 | 91 | 1788 | ihpdgekvV | ihpdgekvA |
| SA9755 | GALC | 14 | 88434799 | G | C | A0101,A11126,B3501,B0801,C0701,C0401 | C0701 | 212 | 116 | thsakdGkl | thsakdAkl |
| SA9755 | ZC3H14 | 14 | 89039050 | A | G | A0101,A11126,B3501,B0801,C0701,C0401 | B3501 | 217 | 1079 | dlidedlSf | dlidedlNf |
| SA9755 | CYP46A1 | 14 | 100166393 | G | A | A0101,A11126,B3501,B0801,C0701,C0401 | B3501 | 488 | 9951 | lvsecnyeH | lvsecnyeR |
| SA9755 | CYP46A1 | 14 | 100166393 | G | A | A0101,A11126,B3501,B0801,C0701,C0401 | C0701 | 76 | 121 | eHwhkqrrv | eRwhkqrrv |
| SA9755 | KLC1 | 14 | 104123947 | A | T | A0101,A11126,B3501,B0801,C0701,C0401 | B0801 | 56 | 8791 | sekqklraL | sekqklraQ |
| SA9755 | CYFIP1 | 15 | 22940799 | A | T | A0101,A11126,B3501,B0801,C0701,C0401 | B0801 | 290 | 2145 | miqireVhm | miqireDhm |
| SA9755 | CYFIP1 | 15 | 22940799 | A | T | A0101,A11126,B3501,B0801,C0701,C0401 | B0801 | 285 | 2996 | eVhmrfise | eDhmrfise |

Figure 21 (Cont.)

| | | | | | | | | | | | |
|---|---|---|---|---|---|---|---|---|---|---|---|
| SA9755 | CYFIP1 | 15 | 22940799 | A | T | A0101,A11126,B3501,B0801,C0701,C0401 | C0701 | 72 | 11 | ireVhmrfi | ireDhmrfi |
| SA9755 | CYFIP1 | 15 | 22940799 | A | T | A0101,A11126,B3501,B0801,C0701,C0401 | C0701 | 15 | 45 | Vhmrfisel | Dhmrfisel |
| SA9755 | GABRB3 | 15 | 26812742 | G | T | A0101,A11126,B3501,B0801,C0701,C0401 | B3501 | 381 | 257 | dasaDrval | dasaArval |
| SA9755 | HERC2 | 15 | 28518098 | C | A | A0101,A11126,B3501,B0801,C0701,C0401 | B3501 | 255 | 30498 | gpgsiplqY | gpgsiplqD |
| SA9755 | C15orf56 | 15 | 40544592 | G | A | A0101,A11126,B3501,B0801,C0701,C0401 | B0801 | 386 | 453 | pLalrlral | pPalrlral |
| SA9755 | C15orf56 | 15 | 40544592 | G | A | A0101,A11126,B3501,B0801,C0701,C0401 | B3501 | 136 | 1422 | fpLalrlra | fpPalrlra |
| SA9755 | INO80 | 15 | 41313290 | C | A | A0101,A11126,B3501,B0801,C0701,C0401 | B3501 | 52 | 23333 | vpldsycnY | vpldsycnD |
| SA9755 | INO80 | 15 | 41313290 | C | A | A0101,A11126,B3501,B0801,C0701,C0401 | B3501 | 68 | 43 | ycnYrsaey | ycnDrsaey |
| SA9755 | DUOX2 | 15 | 45403686 | G | A | A0101,A11126,B3501,B0801,C0701,C0401 | B3501 | 19 | 6 | lVsgpdpaf | lAsgpdpaf |
| SA9755 | DUOX2 | 15 | 45403686 | G | A | A0101,A11126,B3501,B0801,C0701,C0401 | C0701 | 254 | 6483 | rsfsggqlV | rsfsggqlA |
| SA9755 | DUOXA1 | 15 | 45409786 | C | T | A0101,A11126,B3501,B0801,C0701,C0401 | C0701 | 33 | 50 | yrHdaraff | yrRdaraff |
| SA9755 | RASL12 | 15 | 65347240 | G | C | A0101,A11126,B3501,B0801,C0701,C0401 | B0801 | 282 | 1397 | tllkgfkiL | tllkgfkiF |
| SA9755 | CLN6 | 15 | 68506678 | C | T | A0101,A11126,B3501,B0801,C0701,C0401 | B3501 | 336 | 980 | vgNyfhmay | vgDyfhmay |
| SA9755 | PAQR5 | 15 | 69682011 | C | G | A0101,A11126,B3501,B0801,C0701,C0401 | A0101 | 253 | 706 | gsaiayCay | gsaiaySay |
| SA9755 | PAQR5 | 15 | 69682011 | C | G | A0101,A11126,B3501,B0801,C0701,C0401 | B3501 | 217 | 372 | Caytfpdal | Saytfpdal |
| SA9755 | ULK3 | 15 | 75134449 | C | G | A0101,A11126,B3501,B0801,C0701,C0401 | B3501 | 30 | 28 | lpQkvarvf | lpEkvarvf |
| SA9755 | ULK3 | 15 | 75134449 | C | G | A0101,A11126,B3501,B0801,C0701,C0401 | C0701 | 181 | 427 | trrilpQkv | trrilpEkv |
| SA9755 | SNUPN | 15 | 75901958 | C | A | A0101,A11126,B3501,B0801,C0701,C0401 | B0801 | 17 | 20 | yFvnrfssl | yCvnrfssl |
| SA9755 | C15orf40 | 15 | 83677244 | T | C | A0101,A11126,B3501,B0801,C0701,C0401 | C0701 | 246 | 7732 | pRlecsgvv | pKlecsgvv |
| SA9755 | SEC11A | 15 | 85213242 | C | G | A0101,A11126,B3501,B0801,C0701,C0401 | B0801 | 127 | 103 | fivskkpPl | fivskkpAl |
| SA9755 | MESP2 | 15 | 90320211 | C | T | A0101,A11126,B3501,B0801,C0701,C0401 | C0701 | 374 | 521 | rrLglvsav | rrPglvsav |
| SA9755 | LUC7L | 16 | 249072 | C | G | A0101,A11126,B3501,B0801,C0701,C0401 | B0801 | 58 | 1155 | qireklHql | qireklDql |
| SA9755 | CREBBP | 16 | 3788632 | C | A | A0101,A11126,B3501,B0801,C0701,C0401 | B0801 | 35 | 54 | Lprclrtav | Rprclrtav |

Figure 21 (Cont.)

| | | | | | | | | | | | |
|---|---|---|---|---|---|---|---|---|---|---|---|
| SA9755 | CREBBP | 16 | 3788632 | C | A | A0101,A11126,B3501,B0801,C0701,C0401 | B3501 | 337 | 7711 | Lprclrtav | Rprclrtav |
| SA9755 | CREBBP | 16 | 3788632 | C | A | A0101,A11126,B3501,B0801,C0701,C0401 | C0701 | 41 | 11 | ihffLprcl | ihffRprcl |
| SA9755 | PPL | 16 | 4945366 | C | G | A0101,A11126,B3501,B0801,C0701,C0401 | B0801 | 176 | 1070 | Rlqkrgqqv | Glqkrgqqv |
| SA9755 | RBFOX1 | 16 | 7637292 | G | C | A0101,A11126,B3501,B0801,C0701,C0401 | B3501 | 295 | 25722 | ePgskgfgf | eRgskgfgf |
| SA9755 | UBFD1 | 16 | 23569480 | G | C | A0101,A11126,B3501,B0801,C0701,C0401 | C0701 | 390 | 23542 | gRgagrelv | gGgagrelv |
| SA9755 | SLC5A11 | 16 | 24902283 | C | A | A0101,A11126,B3501,B0801,C0701,C0401 | C0701 | 130 | 17175 | lHredafhi | lPredafhi |
| SA9755 | SLC5A11 | 16 | 24902283 | C | A | A0101,A11126,B3501,B0801,C0701,C0401 | C0701 | 359 | 1638 | Hredafhif | Predafhif |
| SA9755 | ARMC5 | 16 | 31474130 | G | T | A0101,A11126,B3501,B0801,C0701,C0401 | B3501 | 227 | 12502 | vpllagqlF | vpllagqlC |
| SA9755 | ABCC12 | 16 | 48134867 | G | A | A0101,A11126,B3501,B0801,C0701,C0401 | B3501 | 64 | 467 | Lpwfthits | Spwfthits |
| SA9755 | ABCC12 | 16 | 48134867 | G | A | A0101,A11126,B3501,B0801,C0701,C0401 | C0701 | 83 | 35 | srLpwfthi | srSpwfthi |
| SA9755 | CAPNS2 | 16 | 55601312 | G | A | A0101,A11126,B3501,B0801,C0701,C0401 | B3501 | 336 | 4185 | Hldamfraf | Rldamfraf |
| SA9755 | GNAO1 | 16 | 56377754 | C | G | A0101,A11126,B3501,B0801,C0701,C0401 | B0801 | 192 | 766 | eMythvtca | elythvtca |
| SA9755 | GNAO1 | 16 | 56377754 | C | G | A0101,A11126,B3501,B0801,C0701,C0401 | C0701 | 106 | 330 | ahkeMythv | ahkelythv |
| SA9755 | AMFR | 16 | 56401433 | C | G | A0101,A11126,B3501,B0801,C0701,C0401 | B0801 | 14 | 110 | fptqrsHsi | fptqrsDsi |
| SA9755 | AMFR | 16 | 56401433 | C | G | A0101,A11126,B3501,B0801,C0701,C0401 | B3501 | 60 | 82 | fptqrsHsi | fptqrsDsi |
| SA9755 | SLC12A3 | 16 | 56938316 | C | A | A0101,A11126,B3501,B0801,C0701,C0401 | B0801 | 168 | 3026 | lrKvrlnei | lrQvrlnei |
| SA9755 | SLC12A3 | 16 | 56938316 | C | A | A0101,A11126,B3501,B0801,C0701,C0401 | C0701 | 295 | 255 | nrvkslrKv | nrvkslrQv |
| SA9755 | SLC12A3 | 16 | 56938316 | C | A | A0101,A11126,B3501,B0801,C0701,C0401 | C0701 | 93 | 70 | lrKvrlnei | lrQvrlnei |
| SA9755 | CCL17 | 16 | 57449702 | A | T | A0101,A11126,B3501,B0801,C0701,C0401 | B3501 | 92 | 7735 | fvtvqgraF | fvtvqgral |
| SA9755 | DHX38 | 16 | 72134377 | G | T | A0101,A11126,B3501,B0801,C0701,C0401 | C0701 | 237 | 326 | nrmltsgLv | nrmltsgVv |
| SA9755 | BCAR1 | 16 | 75270735 | C | A | A0101,A11126,B3501,B0801,C0701,C0401 | B0801 | 88 | 64 | rarlrlCgv | rarlrlWgv |
| SA9755 | IRF8 | 16 | 85954883 | G | A | A0101,A11126,B3501,B0801,C0701,C0401 | C0701 | 15 | 14 | frenqqitI | frenqqitV |

Figure 21 (Cont.)

| | | | | | | | | | | | |
|---|---|---|---|---|---|---|---|---|---|---|---|
| SA9755 | POLR2A | 17 | 7416703 | C | G | A0101,A11126,B3501,B0801,C0701,C0401 | B3501 | 109 | 328 | syWptspsy | sySptspsy |
| SA9755 | FXR2 | 17 | 7507196 | C | G | A0101,A11126,B3501,B0801,C0701,C0401 | B3501 | 258 | 10742 | yvieyaacH | yvieyaacD |
| SA9755 | FXR2 | 17 | 7507196 | C | G | A0101,A11126,B3501,B0801,C0701,C0401 | B3501 | 223 | 63 | eyaacHaty | eyaacDaty |
| SA9755 | FXR2 | 17 | 7507196 | C | G | A0101,A11126,B3501,B0801,C0701,C0401 | C0701 | 39 | 8039 | cHatyneiv | cDatyneiv |
| SA9755 | DNAH2 | 17 | 7636510 | C | A | A0101,A11126,B3501,B0801,C0701,C0401 | C0701 | 59 | 81 | vrgpyiTal | vrgpyiPal |
| SA9755 | AURKB | 17 | 8108330 | C | T | A0101,A11126,B3501,B0801,C0701,C0401 | B3501 | 33 | 87 | fpasvplga | fpasvpMga |
| SA9755 | MYH8 | 17 | 10310096 | G | T | A0101,A11126,B3501,B0801,C0701,C0401 | C0701 | 421 | 680 | ehelvlQql | ehelvlHql |
| SA9755 | ZNF207 | 17 | 30689954 | G | C | A0101,A11126,B3501,B0801,C0701,C0401 | B3501 | 139 | 143 | mpmgglmpp | mpmgglmpp |
| SA9755 | SLFN11 | 17 | 33690301 | C | T | A0101,A11126,B3501,B0801,C0701,C0401 | C0701 | 113 | 53 | ihkgvyqKl | ihkgvyqEl |
| SA9755 | GPR179 | 17 | 36486762 | G | A | A0101,A11126,B3501,B0801,C0701,C0401 | B0801 | 151 | 113 | lerprgVpl | lerprgApl |
| SA9755 | GPR179 | 17 | 36486762 | G | A | A0101,A11126,B3501,B0801,C0701,C0401 | C0701 | 15 | 337 | rrlerprgV | rrlerprgA |
| SA9755 | PCGF2 | 17 | 36892399 | G | A | A0101,A11126,B3501,B0801,C0701,C0401 | B0801 | 168 | 4451 | Slkeyytlm | Plkeyytlm |
| SA9755 | KRT13 | 17 | 39661780 | G | T | A0101,A11126,B3501,B0801,C0701,C0401 | B0801 | 28 | 41 | slrlqsYsa | slrlqsSsa |
| SA9755 | FZD2 | 17 | 42635078 | C | T | A0101,A11126,B3501,B0801,C0701,C0401 | C0701 | 75 | 71 | prsalSrll | prsalPrll |
| SA9755 | FZD2 | 17 | 42635078 | C | T | A0101,A11126,B3501,B0801,C0701,C0401 | C0701 | 119 | 1311 | Srlllplll | Prlllplll |
| SA9755 | PLCD3 | 17 | 43194034 | C | A | A0101,A11126,B3501,B0801,C0701,C0401 | C0701 | 104 | 861 | lYspnpeel | lDspnpeel |
| SA9755 | SCRN2 | 17 | 45915354 | C | A | A0101,A11126,B3501,B0801,C0701,C0401 | B0801 | 390 | 430 | Hlqqkqqdl | Qlqqkqqdl |
| SA9755 | SCRN2 | 17 | 45915354 | C | A | A0101,A11126,B3501,B0801,C0701,C0401 | C0701 | 368 | 387 | rdqdrgqHl | rdqdrgqQl |
| SA9755 | MED13 | 17 | 60140467 | C | A | A0101,A11126,B3501,B0801,C0701,C0401 | B3501 | 9 | 100 | Ypsfadlih | Dpsfadlih |
| SA9755 | MED13 | 17 | 60140467 | C | A | A0101,A11126,B3501,B0801,C0701,C0401 | C0401 | 407 | 1051 | fwwgeYpsf | fwwgeDpsf |
| SA9755 | MRC2 | 17 | 60743461 | A | T | A0101,A11126,B3501,B0801,C0701,C0401 | B3501 | 89 | 22 | calpyhevF | calpyhevY |
| SA9755 | MRC2 | 17 | 60743461 | A | T | A0101,A11126,B3501,B0801,C0701,C0401 | B3501 | 46 | 61 | lpyhevFti | lpyhevYti |
| SA9755 | BPTF | 17 | 65888068 | A | G | A0101,A11126,B3501,B0801,C0701,C0401 | B0801 | 76 | 1368 | npGsklsql | npDsklsql |

Figure 21 (Cont.)

| | | | | | | | | | | | |
|---|---|---|---|---|---|---|---|---|---|---|---|
| SA9755 | ABCA6 | 17 | 67102211 | C | T | A0101,A11126,B3501,B0801,C0701,C0401 | B0801 | 10 | 16 | famarlHfl | famarlRfl |
| SA9755 | ABCA6 | 17 | 67102211 | C | T | A0101,A11126,B3501,B0801,C0701,C0401 | B0801 | 7 | 6 | marlHflkl | marlRflkl |
| SA9755 | ABCA6 | 17 | 67102211 | C | T | A0101,A11126,B3501,B0801,C0701,C0401 | C0701 | 103 | 87 | famarlHfl | famarlRfl |
| SA9755 | LLGL2 | 17 | 73566559 | C | A | A0101,A11126,B3501,B0801,C0701,C0401 | B0801 | 43 | 91 | ssrkrhTag | ssrkrhPag |
| SA9755 | BIRC5 | 17 | 76212066 | T | C | A0101,A11126,B3501,B0801,C0701,C0401 | C0701 | 59 | 1984 | aHacntstl | aYacntstl |
| SA9755 | RNF213 | 17 | 78341912 | G | A | A0101,A11126,B3501,B0801,C0701,C0401 | B3501 | 66 | 37 | lpdKfspav | lpdEfspav |
| SA9755 | ANKRD12 | 18 | 9257045 | A | C | A0101,A11126,B3501,B0801,C0701,C0401 | B3501 | 493 | 1067 | spalhDrel | spalhErel |
| SA9755 | ROCK1 | 18 | 18534861 | C | A | A0101,A11126,B3501,B0801,C0701,C0401 | B3501 | 20 | 10 | fpancdacS | fpancdacA |
| SA9755 | CDH7 | 18 | 63481814 | C | T | A0101,A11126,B3501,B0801,C0701,C0401 | A0101 | 96 | 165 | ysilqgqLy | ysilqgqPy |
| SA9755 | CDH7 | 18 | 63481814 | C | T | A0101,A11126,B3501,B0801,C0701,C0401 | B3501 | 451 | 46 | ysilqgqLy | ysilqgqPy |
| SA9755 | NETO1 | 18 | 70451119 | T | C | A0101,A11126,B3501,B0801,C0701,C0401 | B0801 | 386 | 263 | ylrfldCem | ylrfldYem |
| SA9755 | MKNK2 | 19 | 2042511 | A | G | A0101,A11126,B3501,B0801,C0701,C0401 | B3501 | 52 | 163 | hpnqvspAk | hpnqvspVk |
| SA9755 | AP3D1 | 19 | 2129098 | A | G | A0101,A11126,B3501,B0801,C0701,C0401 | B3501 | 4 | 103 | nPihstsam | nLihstsam |
| SA9755 | NCLN | 19 | 3204745 | G | A | A0101,A11126,B3501,B0801,C0701,C0401 | C0701 | 240 | 617 | simdMrsrv | simdVrsrv |
| SA9755 | ANGPTL4 | 19 | 8435967 | G | A | A0101,A11126,B3501,B0801,C0701,C0401 | C0701 | 169 | 375 | rHhdgsvdf | rRhdgsvdf |
| SA9755 | OR7G2 | 19 | 9213880 | G | A | A0101,A11126,B3501,B0801,C0701,C0401 | B0801 | 143 | 242 | taiskflFl | taiskflLl |
| SA9755 | SMARCA4 | 19 | 11123685 | G | T | A0101,A11126,B3501,B0801,C0701,C0401 | C0701 | 496 | 6884 | Yemglgkti | Demglgkti |
| SA9755 | KANK2 | 19 | 11304671 | C | A | A0101,A11126,B3501,B0801,C0701,C0401 | B3501 | 46 | 22202 | pafpakdpY | pafpakdpD |
| SA9755 | KANK2 | 19 | 11304671 | C | A | A0101,A11126,B3501,B0801,C0701,C0401 | B3501 | 74 | 156 | fpakdpYpp | fpakdpDpp |
| SA9755 | ZNF844 | 19 | 12187589 | A | G | A0101,A11126,B3501,B0801,C0701,C0401 | B0801 | 125 | 24 | fkfmkGhtl | fkfmkRhtl |
| SA9755 | ZNF844 | 19 | 12187589 | A | G | A0101,A11126,B3501,B0801,C0701,C0401 | C0701 | 99 | 76 | fkfmkGhtl | fkfmkRhtl |
| SA9755 | ZNF844 | 19 | 12187618 | G | C | A0101,A11126,B3501,B0801,C0701,C0401 | B0801 | 58 | 114 | Snmekhsti | Rnmekhsti |

Figure 21 (Cont.)

| | | | | | | | | | | | |
|---|---|---|---|---|---|---|---|---|---|---|---|
| SA9755 | ZNF844 | 19 | 12187618 | G | C | A0101,A11126,B3501,B0801,C0701,C0401 | C0701 | 140 | 386 | Snmekhsti | Rnmekhsti |
| SA9755 | ZNF844 | 19 | 12187632 | A | C | A0101,A11126,B3501,B0801,C0701,C0401 | B3501 | 14 | 8120 | kPstislpf | kHstislpf |
| SA9755 | ZNF844 | 19 | 12187632 | A | C | A0101,A11126,B3501,B0801,C0701,C0401 | C0701 | 229 | 386 | rnmekPsti | rnmekHsti |
| SA9755 | MAN2B1 | 19 | 12775786 | G | T | A0101,A11126,B3501,B0801,C0701,C0401 | C0701 | 186 | 624 | vrqgrleLa | vrqgrleFa |
| SA9755 | RASAL3 | 19 | 15565012 | G | T | A0101,A11126,B3501,B0801,C0701,C0401 | B3501 | 4 | 4 | qpvlvsvpm | qpvLvsvpm |
| SA9755 | CHERP | 19 | 16640672 | C | T | A0101,A11126,B3501,B0801,C0701,C0401 | B3501 | 228 | 275 | vvqpMqlaf | vvqpVqlaf |
| SA9755 | CHERP | 19 | 16640672 | C | T | A0101,A11126,B3501,B0801,C0701,C0401 | B3501 | 391 | 334 | qpMqlafqq | qpVqlafqq |
| SA9755 | ZNF253 | 19 | 20002885 | G | A | A0101,A11126,B3501,B0801,C0701,C0401 | B3501 | 413 | 101 | iihtgekpy | iVhtgekpy |
| SA9755 | ZNF90 | 19 | 20229964 | C | A | A0101,A11126,B3501,B0801,C0701,C0401 | B3501 | 413 | 322 | iihtgEkpy | iihtgAkpy |
| SA9755 | ZNF737 | 19 | 20728254 | C | G | A0101,A11126,B3501,B0801,C0701,C0401 | B3501 | 413 | 237 | iihTgekpy | iihSgekpy |
| SA9755 | ZNF626 | 19 | 20807208 | T | C | A0101,A11126,B3501,B0801,C0701,C0401 | B0801 | 382 | 6160 | kafnRssil | kafnQssil |
| SA9755 | ZNF626 | 19 | 20807208 | T | C | A0101,A11126,B3501,B0801,C0701,C0401 | C0701 | 229 | 480 | kafnRssil | kafnQssil |
| SA9755 | ZNF430 | 19 | 21240085 | G | A | A0101,A11126,B3501,B0801,C0701,C0401 | B0801 | 469 | 121 | Kafnrsshl | Rafnrsshl |
| SA9755 | ZNF430 | 19 | 21240085 | G | A | A0101,A11126,B3501,B0801,C0701,C0401 | C0701 | 267 | 139 | Kafnrsshl | Rafnrsshl |
| SA9755 | ZNF430 | 19 | 21240216 | G | A | A0101,A11126,B3501,B0801,C0701,C0401 | B3501 | 413 | 165 | iihTgekpy | iihAgekpy |
| SA9755 | ZNF431 | 19 | 21366217 | T | C | A0101,A11126,B3501,B0801,C0701,C0401 | B3501 | 413 | 1528 | iihtgekPy | iihtgekSy |
| SA9755 | ZNF708 | 19 | 21476951 | C | T | A0101,A11126,B3501,B0801,C0701,C0401 | B0801 | 286 | 389 | snltkhkil | snltkhkiV |
| SA9755 | ZNF708 | 19 | 21476951 | C | T | A0101,A11126,B3501,B0801,C0701,C0401 | B3501 | 413 | 101 | iihtgekpy | iVhtgekpy |
| SA9755 | ZNF708 | 19 | 21477016 | A | G | A0101,A11126,B3501,B0801,C0701,C0401 | B3501 | 413 | 2480 | iihtgekPy | iihtgekLy |
| SA9755 | ZNF429 | 19 | 21719781 | A | G | A0101,A11126,B3501,B0801,C0701,C0401 | B3501 | 413 | 752 | iihtGekpy | iihtEekpy |
| SA9755 | ZNF208 | 19 | 22156983 | T | A | A0101,A11126,B3501,B0801,C0701,C0401 | B3501 | 413 | 26173 | iihtgekpY | iihtgekpN |
| SA9755 | ZNF257 | 19 | 22271475 | G | T | A0101,A11126,B3501,B0801,C0701,C0401 | B3501 | 413 | 1400 | iihtgekpy | Rihtgekpy |
| SA9755 | ZNF676 | 19 | 22363008 | C | G | A0101,A11126,B3501,B0801,C0701,C0401 | B3501 | 413 | 4155 | iihtgekPy | iihtgekRy |

Figure 21 (Cont.)

| | | | | | | | | | | | |
|---|---|---|---|---|---|---|---|---|---|---|---|
| SA9755 | ZNF729 | 19 | 22497504 | A | G | A0101,A11126,B3501,B0801,C0701,C0401 | B3501 | 413 | 1291 | iihtgEkpy | iihtgKkpy |
| SA9755 | ZNF729 | 19 | 22497756 | A | G | A0101,A11126,B3501,B0801,C0701,C0401 | B3501 | 413 | 1291 | iihtgEkpy | iihtgKkpy |
| SA9755 | ZNF99 | 19 | 22940265 | A | G | A0101,A11126,B3501,B0801,C0701,C0401 | B3501 | 413 | 1528 | iihtgekPy | iihtgekSy |
| SA9755 | ZNF99 | 19 | 22940859 | T | C | A0101,A11126,B3501,B0801,C0701,C0401 | B3501 | 413 | 1291 | iihtgEkpy | iihtgKkpy |
| SA9755 | ZNF536 | 19 | 31039633 | G | T | A0101,A11126,B3501,B0801,C0701,C0401 | C0701 | 32 | 61 | krkdntiVv | krkdntiGv |
| SA9755 | PEPD | 19 | 33878938 | C | T | A0101,A11126,B3501,B0801,C0701,C0401 | C0701 | 98 | 101 | Qhlqpgmvl | Rhlqpgmvl |
| SA9755 | PRODH2 | 19 | 36293922 | G | A | A0101,A11126,B3501,B0801,C0701,C0401 | B3501 | 233 | 6373 | varhgpmcY | varhgpmcH |
| SA9755 | PRODH2 | 19 | 36293922 | G | A | A0101,A11126,B3501,B0801,C0701,C0401 | C0701 | 349 | 923 | arhgpmcYl | arhgpmcHl |
| SA9755 | PRODH2 | 19 | 36293922 | G | A | A0101,A11126,B3501,B0801,C0701,C0401 | C0701 | 213 | 91 | rhgpmcYlm | rhgpmcHlm |
| SA9755 | ZNF850 | 19 | 37239591 | A | G | A0101,A11126,B3501,B0801,C0701,C0401 | B3501 | 420 | 2320 | qihtgekPy | qihtgekLy |
| SA9755 | PSG8 | 19 | 43258694 | C | T | A0101,A11126,B3501,B0801,C0701,C0401 | B3501 | 476 | 1704 | yyHsgevly | yyRsgevly |
| SA9755 | PSG8 | 19 | 43258694 | C | T | A0101,A11126,B3501,B0801,C0701,C0401 | C0701 | 220 | 219 | ftyyHsgev | ftyyRsgev |
| SA9755 | PSG8 | 19 | 43258694 | C | T | A0101,A11126,B3501,B0801,C0701,C0401 | C0701 | 184 | 248 | tyyHsgevl | tyyRsgevl |
| SA9755 | PSG8 | 19 | 43258694 | C | T | A0101,A11126,B3501,B0801,C0701,C0401 | C0701 | 6 | 8 | yHsgevlyl | yRsgevlyl |
| SA9755 | PSG11 | 19 | 43519510 | A | T | A0101,A11126,B3501,B0801,C0701,C0401 | C0701 | 305 | 356 | lhgpdHpri | lhgpdLpri |
| SA9755 | PSG11 | 19 | 43519511 | G | T | A0101,A11126,B3501,B0801,C0701,C0401 | C0701 | 159 | 356 | lhgpdlpri | lhgpdLpri |
| SA9755 | HSD17B14 | 19 | 49335955 | C | T | A0101,A11126,B3501,B0801,C0701,C0401 | B0801 | 257 | 324 | etirrfgHl | etirrfgRl |
| SA9755 | HSD17B14 | 19 | 49335955 | C | T | A0101,A11126,B3501,B0801,C0701,C0401 | C0701 | 24 | 24 | rrfgHldcv | rrfgRldcv |
| SA9755 | GYS1 | 19 | 49473867 | C | A | A0101,A11126,B3501,B0801,C0701,C0401 | C0701 | 275 | 837 | cqqsrrqLi | cqqsrrqRi |
| SA9755 | SNRNP70 | 19 | 49607965 | G | A | A0101,A11126,B3501,B0801,C0701,C0401 | C0701 | 481 | 1495 | Mkgwrprl | Vkgwrprl |
| SA9755 | NR1H2 | 19 | 50885827 | C | G | A0101,A11126,B3501,B0801,C0701,C0401 | B3501 | 125 | 2249 | lpVllseiw | lpPllseiw |
| SA9755 | KLK14 | 19 | 51584867 | C | T | A0101,A11126,B3501,B0801,C0701,C0401 | B0801 | 21 | 25 | Dprrrflcg | Gprrrflcg |

Figure 21 (Cont.)

| | | | | | | | | | | | |
|---|---|---|---|---|---|---|---|---|---|---|---|
| SA9755 | ZNF677 | 19 | 53747041 | C | G | A0101,A11126,B3501,B0801,C0701,C0401 | C0701 | 256 | 211 | mlenyTnll | mlenyRnll |
| SA9755 | OSCAR | 19 | 54599172 | G | A | A0101,A11126,B3501,B0801,C0701,C0401 | B0801 | 108 | 464 | vlLqrsevl | vlSqrsevl |
| SA9755 | TSEN34 | 19 | 54697065 | C | A | A0101,A11126,B3501,B0801,C0701,C0401 | C0701 | 224 | 196 | fhahyiaKc | fhahyiaQc |
| SA9755 | LILRB4 | 19 | 55175834 | G | T | A0101,A11126,B3501,B0801,C0701,C0401 | A0101 | 30 | 44 | Ltsvhggty | Vtsvhggty |
| SA9755 | LILRB4 | 19 | 55175834 | G | T | A0101,A11126,B3501,B0801,C0701,C0401 | B3501 | 129 | 90 | fpmspLtsv | fpmspVtsv |
| SA9755 | LILRB4 | 19 | 55175834 | G | T | A0101,A11126,B3501,B0801,C0701,C0401 | B3501 | 262 | 854 | Ltsvhggty | Vtsvhggty |
| SA9755 | ZNF805 | 19 | 57765995 | T | C | A0101,A11126,B3501,B0801,C0701,C0401 | B3501 | 8 | 446 | nPlqeeasy | nLlqeeasy |
| SA9755 | ZNF530 | 19 | 58118605 | G | T | A0101,A11126,B3501,B0801,C0701,C0401 | B3501 | 64 | 50 | tvhtVerpy | tvhtGerpy |
| SA9755 | PPP1CB | 2 | 29011673 | C | G | A0101,A11126,B3501,B0801,C0701,C0401 | B3501 | 23 | 25 | Evvedgyef | Qvvedgyef |
| SA9755 | SULT6B1 | 2 | 37410590 | G | C | A0101,A11126,B3501,B0801,C0701,C0401 | C0701 | 116 | 759 | lhydklpgC | lhydklpgS |
| SA9755 | ATL2 | 2 | 38604377 | C | T | A0101,A11126,B3501,B0801,C0701,C0401 | B3501 | 286 | 1087 | eaaQgqqph | eaaRgqqph |
| SA9755 | ADD2 | 2 | 70903875 | G | C | A0101,A11126,B3501,B0801,C0701,C0401 | B3501 | 39 | 65 | lpsgCsvpg | lpsgSsvpg |
| SA9755 | ADD2 | 2 | 70919548 | G | T | A0101,A11126,B3501,B0801,C0701,C0401 | B3501 | 5 | 45 | Qataavsam | Pataavsam |
| SA9755 | ADD2 | 2 | 70919548 | G | T | A0101,A11126,B3501,B0801,C0701,C0401 | C0701 | 455 | 266 | lhtQataav | lhtPataav |
| SA9755 | ADD2 | 2 | 70919549 | G | T | A0101,A11126,B3501,B0801,C0701,C0401 | B3501 | 4 | 45 | Tataavsam | Pataavsam |
| SA9755 | EMX1 | 2 | 73161007 | C | T | A0101,A11126,B3501,B0801,C0701,C0401 | C0701 | 19 | 38 | Fhhinrwri | Shhinrwri |
| SA9755 | LRRTM4 | 2 | 77746284 | T | G | A0101,A11126,B3501,B0801,C0701,C0401 | C0701 | 9 | 515 | lHwnrirsi | lQwnrirsi |
| SA9755 | RPIA | 2 | 88991274 | G | A | A0101,A11126,B3501,B0801,C0701,C0401 | B3501 | 483 | 639 | lpRraggaa | lpGraggaa |
| SA9755 | BCL2L11 | 2 | 111907692 | G | A | A0101,A11126,B3501,B0801,C0701,C0401 | C0701 | 410 | 20398 | iRdefnayy | iGdefnayy |
| SA9755 | AMER3 | 2 | 131519784 | C | A | A0101,A11126,B3501,B0801,C0701,C0401 | C0701 | 269 | 1965 | Thsekgpqa | Phsekgpqa |
| SA9755 | MAP3K19 | 2 | 135757571 | C | T | A0101,A11126,B3501,B0801,C0701,C0401 | B3501 | 94 | 149 | egveitItf | egveitVtf |
| SA9755 | NXPH2 | 2 | 139537784 | C | A | A0101,A11126,B3501,B0801,C0701,C0401 | B3501 | 171 | 159 | lplvLvpgl | lplvVvpgl |
| SA9755 | ZEB2 | 2 | 145155992 | C | T | A0101,A11126,B3501,B0801,C0701,C0401 | B3501 | 33 | 78 | tsipglQpy | tsipglRpy |

Figure 21 (Cont.)

| | | | | | | | | | | | |
|---|---|---|---|---|---|---|---|---|---|---|---|
| SA9755 | ZEB2 | 2 | 145155992 | C | T | A0101,A11126,B3501,B0801,C0701,C0401 | B3501 | 50 | 163 | Qpypgldqm | Rpypgldqm |
| SA9755 | TTN | 2 | 179466064 | G | C | A0101,A11126,B3501,B0801,C0701,C0401 | C0701 | 465 | 1527 | frvGaenrf | frvRaenrf |
| SA9755 | FSIP2 | 2 | 186678561 | C | G | A0101,A11126,B3501,B0801,C0701,C0401 | C0701 | 64 | 1702 | sRsslkkfl | sTsslkkfl |
| SA9755 | ADAM23 | 2 | 207459498 | G | T | A0101,A11126,B3501,B0801,C0701,C0401 | B3501 | 315 | 1308 | ldddtdvCy | ldddtdvGy |
| SA9755 | PIKFYVE | 2 | 209190443 | G | T | A0101,A11126,B3501,B0801,C0701,C0401 | B3501 | 11 | 5 | cpaglpcSf | cpaglpcAf |
| SA9755 | PIKFYVE | 2 | 209190443 | G | T | A0101,A11126,B3501,B0801,C0701,C0401 | B3501 | 368 | 237 | lpcSffapv | lpcAffapv |
| SA9755 | IRS1 | 2 | 227661886 | C | G | A0101,A11126,B3501,B0801,C0701,C0401 | B0801 | 31 | 17 | rfrNrthsa | rfrKrthsa |
| SA9755 | GIGYF2 | 2 | 233684667 | G | T | A0101,A11126,B3501,B0801,C0701,C0401 | C0701 | 137 | 9340 | rrreeeerL | rrreeeerR |
| SA9755 | GIGYF2 | 2 | 233684667 | G | T | A0101,A11126,B3501,B0801,C0701,C0401 | C0701 | 92 | 54 | erLkqeell | erRkqeell |
| SA9755 | RNPEPL1 | 2 | 241512671 | G | C | A0101,A11126,B3501,B0801,C0701,C0401 | B0801 | 76 | 299 | Rprsrvwae | Gprsrvwae |
| SA9755 | AQP12A | 2 | 241631740 | C | G | A0101,A11126,B3501,B0801,C0701,C0401 | B3501 | 26 | 29 | waweVsdlh | waweLsdlh |
| SA9755 | AQP12A | 2 | 241631740 | C | G | A0101,A11126,B3501,B0801,C0701,C0401 | C0701 | 83 | 60 | mrlcwaweV | mrlcwaweL |
| SA9755 | SIGLEC1 | 20 | 3672025 | C | A | A0101,A11126,B3501,B0801,C0701,C0401 | B3501 | 266 | 130 | lptVaaasa | lptGaaasa |
| SA9755 | SIGLEC1 | 20 | 3672025 | C | A | A0101,A11126,B3501,B0801,C0701,C0401 | B3501 | 12 | 138 | Vaaasapvm | Gaaasapvm |
| SA9755 | CHGB | 20 | 5904594 | G | T | A0101,A11126,B3501,B0801,C0701,C0401 | A0101 | 222 | 21348 | kldlkrqyY | kldlkrqyD |
| SA9755 | CHGB | 20 | 5904594 | G | T | A0101,A11126,B3501,B0801,C0701,C0401 | B0801 | 128 | 3161 | dlkrqyYrv | dlkrqyDrv |
| SA9755 | CHGB | 20 | 5904594 | G | T | A0101,A11126,B3501,B0801,C0701,C0401 | C0701 | 57 | 1235 | Yrvaqldql | Drvaqldql |
| SA9755 | LRRN4 | 20 | 6033289 | C | T | A0101,A11126,B3501,B0801,C0701,C0401 | B3501 | 5 | 3 | lpTadatal | lpAadatal |
| SA9755 | LRRN4 | 20 | 6033289 | C | T | A0101,A11126,B3501,B0801,C0701,C0401 | B3501 | 325 | 1993 | Tadataltl | Aadataltl |
| SA9755 | ISM1 | 20 | 13279927 | A | T | A0101,A11126,B3501,B0801,C0701,C0401 | B3501 | 17 | 12 | tpnlFstef | tpnlIstef |
| SA9755 | ISM1 | 20 | 13279927 | A | T | A0101,A11126,B3501,B0801,C0701,C0401 | B3501 | 236 | 2808 | Fstefsael | Istefsael |
| SA9755 | TRPC4AP | 20 | 33595408 | C | T | A0101,A11126,B3501,B0801,C0701,C0401 | B3501 | 154 | 549 | sflQgttsy | sflRgttsy |

Figure 21 (Cont.)

| | | | | | | | | | | | |
|---|---|---|---|---|---|---|---|---|---|---|---|
| SA9755 | CEP250 | 20 | 34091436 | G | C | A0101,A11126,B3501,B0801,C0701,C0401 | C0701 | 375 | 188 | cqqehihQl | cqqehihEl |
| SA9755 | CEP250 | 20 | 34091436 | G | C | A0101,A11126,B3501,B0801,C0701,C0401 | C0701 | 27 | 75 | ehihQlqel | ehihElqel |
| SA9755 | KIAA1755 | 20 | 36868064 | T | A | A0101,A11126,B3501,B0801,C0701,C0401 | B3501 | 67 | 12236 | apspleeM | apspleeK |
| SA9755 | RALGAPB | 20 | 37168527 | C | T | A0101,A11126,B3501,B0801,C0701,C0401 | B3501 | 329 | 6686 | aplhsrdlY | aplhsrdlH |
| SA9755 | RALGAPB | 20 | 37168527 | C | T | A0101,A11126,B3501,B0801,C0701,C0401 | C0701 | 434 | 146 | lhsrdlYsm | lhsrdlHsm |
| SA9755 | RALGAPB | 20 | 37168527 | C | T | A0101,A11126,B3501,B0801,C0701,C0401 | C0701 | 113 | 89 | srdlYsmiv | srdlHsmiv |
| SA9755 | EYA2 | 20 | 45725785 | C | A | A0101,A11126,B3501,B0801,C0701,C0401 | A0101 | 62 | 32 | ltgKfasry | ltgTfasry |
| SA9755 | PREX1 | 20 | 47262401 | C | T | A0101,A11126,B3501,B0801,C0701,C0401 | A0101 | 410 | 1354 | dtmsyHdsy | dtmsyRdsy |
| SA9755 | PREX1 | 20 | 47262401 | C | T | A0101,A11126,B3501,B0801,C0701,C0401 | B3501 | 198 | 710 | dtmsyHdsy | dtmsyRdsy |
| SA9755 | NPEPL1 | 20 | 57273798 | G | T | A0101,A11126,B3501,B0801,C0701,C0401 | B3501 | 131 | 20145 | aarivdtpF | aarivdtpC |
| SA9755 | CHRNA4 | 20 | 61991022 | C | G | A0101,A11126,B3501,B0801,C0701,C0401 | C0701 | 442 | 169 | trahPeerl | trahAeerl |
| SA9755 | KCNQ2 | 20 | 62038671 | C | A | A0101,A11126,B3501,B0801,C0701,C0401 | B0801 | 170 | 1035 | niymqrmCi | niymqrmGi |
| SA9755 | ABHD16B | 20 | 62494191 | G | A | A0101,A11126,B3501,B0801,C0701,C0401 | B0801 | 377 | 187 | lssQrrrl | lssRrrrl |
| SA9755 | ABHD16B | 20 | 62494191 | G | A | A0101,A11126,B3501,B0801,C0701,C0401 | B0801 | 9 | 8 | sQrrrlal | sRrrrlal |
| SA9755 | ABHD16B | 20 | 62494191 | G | A | A0101,A11126,B3501,B0801,C0701,C0401 | B0801 | 326 | 269 | Qrrrlalf | Rrrrlalf |
| SA9755 | ABHD16B | 20 | 62494191 | G | A | A0101,A11126,B3501,B0801,C0701,C0401 | C0701 | 481 | 1171 | lssQrrrl | lssRrrrl |
| SA9755 | ABHD16B | 20 | 62494191 | G | A | A0101,A11126,B3501,B0801,C0701,C0401 | C0701 | 451 | 397 | Qrrrlalf | Rrrrlalf |
| SA9755 | CLDN17 | 21 | 31538719 | G | A | A0101,A11126,B3501,B0801,C0701,C0401 | B3501 | 249 | 1270 | Fppaletar | Lppaletar |
| SA9755 | DOPEY2 | 21 | 37650378 | C | A | A0101,A11126,B3501,B0801,C0701,C0401 | B0801 | 15 | 12 | fpylrnNsa | fpylrnHsa |
| SA9755 | DOPEY2 | 21 | 37650378 | C | A | A0101,A11126,B3501,B0801,C0701,C0401 | B3501 | 121 | 32 | Nsaynapsf | Hsaynapsf |
| SA9755 | DYRK1A | 21 | 38884727 | G | T | A0101,A11126,B3501,B0801,C0701,C0401 | B3501 | 143 | 144 | santgpShy | santgpAhy |
| SA9755 | DYRK1A | 21 | 38884727 | G | T | A0101,A11126,B3501,B0801,C0701,C0401 | C0701 | 127 | 403 | Shymteghl | Ahymteghl |
| SA9755 | PLAC4 | 21 | 42551311 | A | G | A0101,A11126,B3501,B0801,C0701,C0401 | B3501 | 255 | 123 | hphspwTps | hphspwlps |

Figure 21 (Cont.)

| | | | | | | | | | | | |
|---|---|---|---|---|---|---|---|---|---|---|---|
| SA9755 | PLAC4 | 21 | 42551311 | A | G | A0101,A11126,B3501,B0801,C0701,C0401 | C0701 | 43 | 27 | phspwTpsl | phspwIpsl |
| SA9755 | TRAPPC10 | 21 | 45511859 | G | C | A0101,A11126,B3501,B0801,C0701,C0401 | B3501 | 142 | 126 | ldfqlsHsy | ldfqlsDsy |
| SA9755 | TRAPPC10 | 21 | 45511859 | G | C | A0101,A11126,B3501,B0801,C0701,C0401 | C0701 | 153 | 1151 | fqlsHsylv | fqlsDsylv |
| SA9755 | TRPM2 | 21 | 45845667 | C | A | A0101,A11126,B3501,B0801,C0701,C0401 | B0801 | 290 | 11259 | ypncHvtrf | ypncPvtrf |
| SA9755 | TRPM2 | 21 | 45845667 | C | A | A0101,A11126,B3501,B0801,C0701,C0401 | B3501 | 8 | 19 | ypncHvtrf | ypncPvtrf |
| SA9755 | KRTAP10-6 | 21 | 46011461 | G | C | A0101,A11126,B3501,B0801,C0701,C0401 | C0701 | 126 | 425 | crpsCsvsl | crpsSsvsl |
| SA9755 | PCNT | 21 | 47786839 | G | C | A0101,A11126,B3501,B0801,C0701,C0401 | C0701 | 8 | 8 | irQehrqal | irEehrqal |
| SA9755 | BCL2L13 | 22 | 18138583 | C | G | A0101,A11126,B3501,B0801,C0701,C0401 | C0701 | 56 | 45 | qhVsspqgv | qhLsspqgv |
| SA9755 | PRODH | 22 | 18900795 | G | T | A0101,A11126,B3501,B0801,C0701,C0401 | B0801 | 292 | 119 | lpylsrraM | lpylsrraL |
| SA9755 | PRODH | 22 | 18900795 | G | T | A0101,A11126,B3501,B0801,C0701,C0401 | B3501 | 10 | 62 | lpylsrraM | lpylsrraL |
| SA9755 | PRODH | 22 | 18900795 | G | T | A0101,A11126,B3501,B0801,C0701,C0401 | B3501 | 30 | 82 | raMenssIm | raLenssIm |
| SA9755 | PRODH | 22 | 18900795 | G | T | A0101,A11126,B3501,B0801,C0701,C0401 | C0701 | 463 | 780 | rraMenssl | rraLenssl |
| SA9755 | PRODH | 22 | 18900795 | G | T | A0101,A11126,B3501,B0801,C0701,C0401 | C0701 | 84 | 335 | raMenssIm | raLenssIm |
| SA9755 | CRYBB2 | 22 | 25620943 | G | A | A0101,A11126,B3501,B0801,C0701,C0401 | A0101 | 90 | 19631 | hshelngpY | hshelngpC |
| SA9755 | CRYBB2 | 22 | 25620943 | G | A | A0101,A11126,B3501,B0801,C0701,C0401 | B3501 | 12 | 11281 | hshelngpY | hshelngpC |
| SA9755 | OSBP2 | 22 | 31284273 | C | A | A0101,A11126,B3501,B0801,C0701,C0401 | B3501 | 114 | 4 | dDmedstsf | dAmedstsf |
| SA9755 | IL2RB | 22 | 37538546 | C | G | A0101,A11126,B3501,B0801,C0701,C0401 | C0701 | 63 | 62 | rrCnqtcel | rrWnqtcel |
| SA9755 | BAIAP2L2 | 22 | 38506519 | A | G | A0101,A11126,B3501,B0801,C0701,C0401 | B3501 | 11 | 11 | mapeTdqfy | mapeMdqfy |
| SA9755 | APOBEC3B | 22 | 39385577 | G | T | A0101,A11126,B3501,B0801,C0701,C0401 | B0801 | 489 | 5184 | Flmdqhmgf | Vlmdqhmgf |
| SA9755 | APOBEC3B | 22 | 39385577 | G | T | A0101,A11126,B3501,B0801,C0701,C0401 | C0701 | 471 | 105 | erldngtwF | erldngtwV |
| SA9755 | APOBEC3B | 22 | 39388075 | A | T | A0101,A11126,B3501,B0801,C0701,C0401 | B3501 | 45 | 58 | fvyrLgcpf | fvyrQgcpf |
| SA9755 | APOBEC3B | 22 | 39388075 | A | T | A0101,A11126,B3501,B0801,C0701,C0401 | C0401 | 299 | 3780 | cwdtfvyrL | cwdtfvyrQ |

Figure 21 (Cont.)

| | | | | | | | | | | | |
|---|---|---|---|---|---|---|---|---|---|---|---|
| SA9755 | MCHR1 | 22 | 41077742 | A | G | A0101,A11126,B3501,B0801,C0701,C0401 | A0101 | 254 | 352 | ptltfvCly | ptltfvYly |
| SA9755 | ACVR2B | 3 | 38518844 | G | T | A0101,A11126,B3501,B0801,C0701,C0401 | C0701 | 210 | 11161 | ynanweleL | ynanweleR |
| SA9755 | SCN10A | 3 | 38797385 | G | T | A0101,A11126,B3501,B0801,C0701,C0401 | C0701 | 31 | 683 | shngspltY | shngspltS |
| SA9755 | BSN | 3 | 49688111 | A | T | A0101,A11126,B3501,B0801,C0701,C0401 | B3501 | 434 | 549 | epSplpppt | epTplpppt |
| SA9755 | ADAMTS9 | 3 | 64599095 | C | G | A0101,A11126,B3501,B0801,C0701,C0401 | B0801 | 304 | 842 | dpQtkptsm | dpEtkptsm |
| SA9755 | NXPE3 | 3 | 101520615 | C | G | A0101,A11126,B3501,B0801,C0701,C0401 | B0801 | 160 | 2349 | yLkslfrsg | yFkslfrsg |
| SA9755 | DZIP3 | 3 | 108403129 | C | G | A0101,A11126,B3501,B0801,C0701,C0401 | B3501 | 69 | 206 | rpiltvpEm | rpiltvpQm |
| SA9755 | UMPS | 3 | 124461043 | T | G | A0101,A11126,B3501,B0801,C0701,C0401 | B3501 | 263 | 409 | fMsgsrvsm | fisgsrvsm |
| SA9755 | TF | 3 | 133467420 | G | T | A0101,A11126,B3501,B0801,C0701,C0401 | C0701 | 36 | 58 | syldcirSi | syldcirAi |
| SA9755 | PIK3CB | 3 | 138461514 | C | G | A0101,A11126,B3501,B0801,C0701,C0401 | A0101 | 52 | 19 | wldwlkqty | wMdwlkqty |
| SA9755 | PIK3CB | 3 | 138461514 | C | G | A0101,A11126,B3501,B0801,C0701,C0401 | B3501 | 71 | 48 | wldwlkqty | wMdwlkqty |
| SA9755 | IGSF10 | 3 | 151164737 | C | T | A0101,A11126,B3501,B0801,C0701,C0401 | C0701 | 7 | 9 | rrfErqrki | rrfGrqrki |
| SA9755 | MUC4 | 3 | 195507925 | C | T | A0101,A11126,B3501,B0801,C0701,C0401 | B3501 | 101 | 109 | lpvtDassa | lpvtGassa |
| SA9755 | MUC4 | 3 | 195509941 | A | C | A0101,A11126,B3501,B0801,C0701,C0401 | B3501 | 218 | 146 | lpvtSpssa | lpvtlpssa |
| SA9755 | MUC4 | 3 | 195509941 | A | C | A0101,A11126,B3501,B0801,C0701,C0401 | B3501 | 275 | 119 | Spssassgh | Ipssassgh |
| SA9755 | MUC4 | 3 | 195513515 | C | T | A0101,A11126,B3501,B0801,C0701,C0401 | B3501 | 485 | 885 | lstghTtpl | lstghAtpl |
| SA9755 | MUC4 | 3 | 195515401 | A | G | A0101,A11126,B3501,B0801,C0701,C0401 | B3501 | 218 | 217 | lpvtspssA | lpvtspssV |
| SA9755 | MUC4 | 3 | 195515401 | A | G | A0101,A11126,B3501,B0801,C0701,C0401 | B3501 | 209 | 359 | spssAstgh | spssVstgh |
| SA9755 | MFSD7 | 4 | 680440 | C | T | A0101,A11126,B3501,B0801,C0701,C0401 | B3501 | 490 | 198 | apvadviaK | apvadviaE |
| SA9755 | MFSD7 | 4 | 680440 | C | T | A0101,A11126,B3501,B0801,C0701,C0401 | B3501 | 386 | 94 | iaKdlvlsm | iaEdlvlsm |
| SA9755 | FGFRL1 | 4 | 1019076 | T | A | A0101,A11126,B3501,B0801,C0701,C0401 | C0701 | 84 | 46 | thThthshv | thShthshv |
| SA9755 | FGFRL1 | 4 | 1019088 | T | A | A0101,A11126,B3501,B0801,C0701,C0401 | C0701 | 51 | 46 | thshthThv | thshthShv |
| SA9755 | ADD1 | 4 | 2877795 | G | A | A0101,A11126,B3501,B0801,C0701,C0401 | B0801 | 375 | 647 | dlrqdfnim | dlrqdfnMm |

Figure 21 (Cont.)

| | | | | | | | | | | | |
|---|---|---|---|---|---|---|---|---|---|---|---|
| SA9755 | GPR78 | 4 | 8583368 | T | G | A0101,A11126,B3501,B0801,C0701,C0401 | B0801 | 114 | 7045 | lladRhpsv | lladLhpsv |
| SA9755 | SLC30A9 | 4 | 42068596 | C | T | A0101,A11126,B3501,B0801,C0701,C0401 | C0701 | 77 | 46 | Crnarakgm | Rrnarakgm |
| SA9755 | CABS1 | 4 | 71201902 | C | G | A0101,A11126,B3501,B0801,C0701,C0401 | A0101 | 117 | 313 | etdMfellk | etdlfellk |
| SA9755 | NPFFR2 | 4 | 73013298 | C | G | A0101,A11126,B3501,B0801,C0701,C0401 | C0701 | 224 | 225 | frrgLqeaf | frrgFqeaf |
| SA9755 | LRBA | 4 | 151727470 | C | T | A0101,A11126,B3501,B0801,C0701,C0401 | B3501 | 267 | 579 | fapflsQtl | fapflsRtl |
| SA9755 | GLRB | 4 | 158091806 | G | C | A0101,A11126,B3501,B0801,C0701,C0401 | B0801 | 226 | 7630 | riHlyaral | riDlyaral |
| SA9755 | GLRB | 4 | 158091806 | G | C | A0101,A11126,B3501,B0801,C0701,C0401 | B3501 | 258 | 261 | taakriHly | taakriDly |
| SA9755 | PLEKHG4B | 5 | 169497 | G | C | A0101,A11126,B3501,B0801,C0701,C0401 | B3501 | 52 | 188 | emiatDrey | emiatErey |
| SA9755 | PLEKHG4B | 5 | 169497 | G | C | A0101,A11126,B3501,B0801,C0701,C0401 | C0701 | 389 | 140 | tDreyircl | tEreyircl |
| SA9755 | ADAMTS16 | 5 | 5239838 | C | A | A0101,A11126,B3501,B0801,C0701,C0401 | C0701 | 383 | 70 | arsiSiyem | arsiRiyem |
| SA9755 | CDH9 | 5 | 26906860 | C | A | A0101,A11126,B3501,B0801,C0701,C0401 | A0101 | 218 | 165 | ysilqVqpy | ysilqGqpy |
| SA9755 | CDH9 | 5 | 26906860 | C | A | A0101,A11126,B3501,B0801,C0701,C0401 | B3501 | 33 | 46 | ysilqVqpy | ysilqGqpy |
| SA9755 | AGXT2 | 5 | 35037123 | G | T | A0101,A11126,B3501,B0801,C0701,C0401 | C0701 | 220 | 174 | grlwhKstv | grlwhTstv |
| SA9755 | EGFLAM | 5 | 38427339 | G | T | A0101,A11126,B3501,B0801,C0701,C0401 | C0701 | 15 | 24 | frfdcgsVt | frfdcgsGt |
| SA9755 | C7 | 5 | 40979857 | G | T | A0101,A11126,B3501,B0801,C0701,C0401 | B0801 | 217 | 67 | Drskrilpl | Erskrilpl |
| SA9755 | C7 | 5 | 40979857 | G | T | A0101,A11126,B3501,B0801,C0701,C0401 | C0701 | 297 | 133 | Drskrilpl | Erskrilpl |
| SA9755 | MSH3 | 5 | 79950745 | C | G | A0101,A11126,B3501,B0801,C0701,C0401 | B3501 | 28 | 111 | ppapAapaf | ppapPapaf |
| SA9755 | KCNN2 | 5 | 113698635 | G | A | A0101,A11126,B3501,B0801,C0701,C0401 | B3501 | 293 | 71 | spsaaaaTa | spsaaaaAa |
| SA9755 | KCNN2 | 5 | 113698635 | G | A | A0101,A11126,B3501,B0801,C0701,C0401 | B3501 | 78 | 174 | saaaaTaaa | saaaaAaaa |
| SA9755 | SEC24A | 5 | 134050782 | C | A | A0101,A11126,B3501,B0801,C0701,C0401 | B0801 | 50 | 88 | mcqvkKqpl | mcqvkNqpl |
| SA9755 | PCDHB1 | 5 | 140432961 | C | A | A0101,A11126,B3501,B0801,C0701,C0401 | B0801 | 25 | 386 | Tmmqkliil | Pmmqkliil |
| SA9755 | PCDHB1 | 5 | 140432961 | C | A | A0101,A11126,B3501,B0801,C0701,C0401 | C0701 | 243 | 101 | erdTmmqkl | erdPmmqkl |

Figure 21 (Cont.)

| | | | | | | | | | | | |
|---|---|---|---|---|---|---|---|---|---|---|---|
| SA9755 | PCYOX1L | 5 | 148748113 | G | T | A0101,A11126,B3501,B0801,C0701,C0401 | B0801 | 419 | 3870 | aLaaknval | aVaaknval |
| SA9755 | FOXI1 | 5 | 169533200 | A | G | A0101,A11126,B3501,B0801,C0701,C0401 | B3501 | 13 | 11 | lpgpSaspf | lpgpNaspf |
| SA9755 | LCP2 | 5 | 169679472 | G | T | A0101,A11126,B3501,B0801,C0701,C0401 | C0701 | 202 | 461 | trQeaeaal | trPeaeaal |
| SA9755 | RNF44 | 5 | 175956764 | C | A | A0101,A11126,B3501,B0801,C0701,C0401 | B3501 | 314 | 764 | dlYvddvem | dlDvddvem |
| SA9755 | OR2V2 | 5 | 180582392 | G | T | A0101,A11126,B3501,B0801,C0701,C0401 | B3501 | 229 | 115 | qitgssCaf | qitgssWaf |
| SA9755 | OR11A1 | 6 | 29394613 | T | C | A0101,A11126,B3501,B0801,C0701,C0401 | B0801 | 45 | 49 | Rllskvfsl | Qllskvfsl |
| SA9755 | OR11A1 | 6 | 29394613 | T | C | A0101,A11126,B3501,B0801,C0701,C0401 | C0701 | 234 | 87 | vhsRllskv | vhsQllskv |
| SA9755 | LRFN2 | 6 | 40399500 | C | G | A0101,A11126,B3501,B0801,C0701,C0401 | B0801 | 34 | 53 | aprvklyql | aprvkMyql |
| SA9755 | YIPF3 | 6 | 43481330 | G | A | A0101,A11126,B3501,B0801,C0701,C0401 | B3501 | 122 | 8886 | ipikmvnfL | ipikmvnfP |
| SA9755 | CAPN11 | 6 | 44148671 | C | G | A0101,A11126,B3501,B0801,C0701,C0401 | B0801 | 70 | 16 | rmaikLksf | rmaikFksf |
| SA9755 | TDRD6 | 6 | 46659771 | G | T | A0101,A11126,B3501,B0801,C0701,C0401 | B3501 | 144 | 384 | fpqktiIpg | fpqktiMpg |
| SA9755 | TDRD6 | 6 | 46659771 | G | T | A0101,A11126,B3501,B0801,C0701,C0401 | B3501 | 20 | 5 | Ipgfkttvy | Mpgfkttvy |
| SA9755 | DST | 6 | 56376177 | C | G | A0101,A11126,B3501,B0801,C0701,C0401 | C0701 | 21 | 25 | Qhkphidkm | Ehkphidkm |
| SA9755 | LGSN | 6 | 63989995 | C | T | A0101,A11126,B3501,B0801,C0701,C0401 | B0801 | 133 | 43 | fvaIkkyel | fvaMkkyel |
| SA9755 | LGSN | 6 | 63990075 | C | G | A0101,A11126,B3501,B0801,C0701,C0401 | B3501 | 21 | 22 | iplkleHal | iplkleDal |
| SA9755 | MMS22L | 6 | 97599709 | C | A | A0101,A11126,B3501,B0801,C0701,C0401 | C0701 | 262 | 218 | latenlqyI | latenlqyM |
| SA9755 | LAMA4 | 6 | 112462669 | C | T | A0101,A11126,B3501,B0801,C0701,C0401 | C0701 | 398 | 151 | iknNnlvyv | iknDnlvyv |
| SA9755 | ROS1 | 6 | 117662440 | G | A | A0101,A11126,B3501,B0801,C0701,C0401 | C0701 | 232 | 5757 | chseemwcI | chseemwcT |
| SA9755 | LAMA2 | 6 | 129486743 | C | A | A0101,A11126,B3501,B0801,C0701,C0401 | B3501 | 60 | 137 | yprQcqpch | yprPcqpch |
| SA9755 | SASH1 | 6 | 148865634 | G | C | A0101,A11126,B3501,B0801,C0701,C0401 | B3501 | 179 | 85 | vpmgpsgPl | vpmgpsgAl |
| SA9755 | FNDC1 | 6 | 159655244 | G | A | A0101,A11126,B3501,B0801,C0701,C0401 | B0801 | 135 | 1191 | alaprRgsl | alaprGgsl |
| SA9755 | RNASET2 | 6 | 167366000 | C | A | A0101,A11126,B3501,B0801,C0701,C0401 | B0801 | 87 | 971 | limvHhwpe | limvQhwpe |
| SA9755 | RNASET2 | 6 | 167366000 | C | A | A0101,A11126,B3501,B0801,C0701,C0401 | C0701 | 193 | 400 | mvHhwpetv | mvQhwpetv |

Figure 21 (Cont.)

| | | | | | | | | | | | |
|---|---|---|---|---|---|---|---|---|---|---|---|
| SA9755 | MLLT4 | 6 | 168319609 | G | C | A0101,A11126,B3501,B0801,C0701,C0401 | C0701 | 146 | 6973 | cHrgfcrli | cQrgfcrli |
| SA9755 | SDK1 | 7 | 4172043 | G | T | A0101,A11126,B3501,B0801,C0701,C0401 | B3501 | 11 | 8 | epnCiilgy | epnGiilgy |
| SA9755 | FOXK1 | 7 | 4801831 | G | T | A0101,A11126,B3501,B0801,C0701,C0401 | A0101 | 255 | 353 | ltspFqlla | ltspLqlla |
| SA9755 | FOXK1 | 7 | 4801831 | G | T | A0101,A11126,B3501,B0801,C0701,C0401 | B3501 | 4 | 29 | nayaltspF | nayaltspL |
| SA9755 | FOXK1 | 7 | 4801831 | G | T | A0101,A11126,B3501,B0801,C0701,C0401 | B3501 | 146 | 253 | yaltspFql | yaltspLql |
| SA9755 | TNRC18 | 7 | 5360030 | G | A | A0101,A11126,B3501,B0801,C0701,C0401 | B3501 | 51 | 172 | dvrpastCf | dvrpastRf |
| SA9755 | DAGLB | 7 | 6449833 | G | C | A0101,A11126,B3501,B0801,C0701,C0401 | A0101 | 308 | 1262 | Cspkypply | Sspkypply |
| SA9755 | DAGLB | 7 | 6449833 | G | C | A0101,A11126,B3501,B0801,C0701,C0401 | B3501 | 9 | 16 | spldCspky | spldSspky |
| SA9755 | PHF14 | 7 | 11014501 | C | T | A0101,A11126,B3501,B0801,C0701,C0401 | C0701 | 294 | 7702 | krrqvkplV | krrqvkplA |
| SA9755 | TWIST1 | 7 | 19156384 | G | C | A0101,A11126,B3501,B0801,C0701,C0401 | C0701 | 73 | 264 | erlsyaLsv | erlsyaFsv |
| SA9755 | TWIST1 | 7 | 19156583 | G | T | A0101,A11126,B3501,B0801,C0701,C0401 | B0801 | 37 | 23 | rerqrNqsl | rerqrTqsl |
| SA9755 | TWIST1 | 7 | 19156583 | G | T | A0101,A11126,B3501,B0801,C0701,C0401 | C0701 | 421 | 439 | rerqrNqsl | rerqrTqsl |
| SA9755 | MACC1 | 7 | 20199042 | C | A | A0101,A11126,B3501,B0801,C0701,C0401 | B3501 | 331 | 902 | hsFgkegpf | hsLgkegpf |
| SA9755 | DNAH11 | 7 | 21641137 | G | T | A0101,A11126,B3501,B0801,C0701,C0401 | C0701 | 42 | 90 | srHratdel | srQratdel |
| SA9755 | DNAH11 | 7 | 21641137 | G | T | A0101,A11126,B3501,B0801,C0701,C0401 | C0701 | 378 | 15373 | rHratdelf | rQratdelf |
| SA9755 | STK31 | 7 | 23808743 | A | T | A0101,A11126,B3501,B0801,C0701,C0401 | C0701 | 205 | 197 | vrseSdasl | vrseTdasl |
| SA9755 | CHN2 | 7 | 29519961 | C | T | A0101,A11126,B3501,B0801,C0701,C0401 | C0701 | 41 | 708 | nhfnyektY | nhfnyektH |
| SA9755 | PDE1C | 7 | 32209408 | C | G | A0101,A11126,B3501,B0801,C0701,C0401 | B0801 | 377 | 3032 | Ntsfrlrsl | Ktsfrlrsl |
| SA9755 | ANLN | 7 | 36447505 | G | A | A0101,A11126,B3501,B0801,C0701,C0401 | C0701 | 340 | 1069 | skRelsrei | skGelsrei |
| SA9755 | ABCA13 | 7 | 48315793 | G | T | A0101,A11126,B3501,B0801,C0701,C0401 | B3501 | 14 | 64 | lagnfdvaf | Ragnfdvaf |
| SA9755 | DDC | 7 | 50605670 | C | A | A0101,A11126,B3501,B0801,C0701,C0401 | B3501 | 385 | 1001 | Ipactelet | Spactelet |
| SA9755 | ZNF727 | 7 | 63538173 | A | T | A0101,A11126,B3501,B0801,C0701,C0401 | B0801 | 95 | 9859 | saltkhkrI | saltkhkrN |

Figure 21 (Cont.)

| | | | | | | | | | | | |
|---|---|---|---|---|---|---|---|---|---|---|---|
| SA9755 | ZNF727 | 7 | 63538173 | A | T | A0101,A11126,B3501,B0801,C0701,C0401 | B3501 | 251 | 2367 | rlhtgdrpy | rNhtgdrpy |
| SA9755 | ZNF727 | 7 | 63538872 | C | T | A0101,A11126,B3501,B0801,C0701,C0401 | C0701 | 388 | 8393 | htgdrptsV | htgdrptsA |
| SA9755 | ZNF679 | 7 | 63726633 | A | G | A0101,A11126,B3501,B0801,C0701,C0401 | B3501 | 332 | 1912 | iihtGensy | iihtRensy |
| SA9755 | ZNF92 | 7 | 64864618 | T | C | A0101,A11126,B3501,B0801,C0701,C0401 | A0101 | 113 | 27 | Htgekpyky | Ytgekpyky |
| SA9755 | ZNF92 | 7 | 64864618 | T | C | A0101,A11126,B3501,B0801,C0701,C0401 | B3501 | 413 | 361 | iiHtgekpy | iiYtgekpy |
| SA9755 | GTF2IRD1 | 7 | 73944178 | G | T | A0101,A11126,B3501,B0801,C0701,C0401 | B3501 | 5 | 16 | ipfkrpFty | ipfkrpCty |
| SA9755 | TRIM73 | 7 | 75028408 | G | T | A0101,A11126,B3501,B0801,C0701,C0401 | B3501 | 362 | 547 | qvvdgsIsl | qvvdgsSsl |
| SA9755 | DLX5 | 7 | 96651632 | C | G | A0101,A11126,B3501,B0801,C0701,C0401 | C0701 | 432 | 515 | mvngkpNkv | mvngkpKkv |
| SA9755 | PTCD1 | 7 | 99026792 | C | G | A0101,A11126,B3501,B0801,C0701,C0401 | B3501 | 24 | 48 | vvteDtfsf | vvteEtfsf |
| SA9755 | TRIM4 | 7 | 99490052 | C | A | A0101,A11126,B3501,B0801,C0701,C0401 | C0701 | 130 | 1195 | drskmspYv | drskmspDv |
| SA9755 | ZAN | 7 | 100334483 | C | T | A0101,A11126,B3501,B0801,C0701,C0401 | C0701 | 13 | 23 | fhrggvVrl | fhrggvArl |
| SA9755 | ZAN | 7 | 100334483 | C | T | A0101,A11126,B3501,B0801,C0701,C0401 | C0701 | 45 | 77 | hrggvVrll | hrggvArll |
| SA9755 | SPDYE6 | 7 | 101988845 | C | T | A0101,A11126,B3501,B0801,C0701,C0401 | C0701 | 79 | 58 | rrfqlyHsm | rrfqlyRsm |
| SA9755 | SPDYE6 | 7 | 101988849 | A | C | A0101,A11126,B3501,B0801,C0701,C0401 | C0701 | 63 | 58 | rrfqlDrsm | rrfqlYrsm |
| SA9755 | SPDYE6 | 7 | 101988861 | G | A | A0101,A11126,B3501,B0801,C0701,C0401 | B0801 | 12 | 9 | llrkrWfql | llrkrRfql |
| SA9755 | CTTNBP2 | 7 | 117451028 | C | T | A0101,A11126,B3501,B0801,C0701,C0401 | B0801 | 31 | 40 | alrarrkel | alrarrkeV |
| SA9755 | CTTNBP2 | 7 | 117451028 | C | T | A0101,A11126,B3501,B0801,C0701,C0401 | C0701 | 446 | 292 | lrarrkelf | lrarrkeVf |
| SA9755 | CPED1 | 7 | 120782148 | C | A | A0101,A11126,B3501,B0801,C0701,C0401 | C0701 | 145 | 122 | yredrTslp | yredrPslp |
| SA9755 | TRPV5 | 7 | 142626553 | G | T | A0101,A11126,B3501,B0801,C0701,C0401 | C0701 | 25 | 51 | Srsprnliy | Rrsprnliy |
| SA9755 | TRPV5 | 7 | 142626554 | G | T | A0101,A11126,B3501,B0801,C0701,C0401 | B0801 | 493 | 2064 | saratgtaL | saratgtaF |
| SA9755 | TRPV5 | 7 | 142626554 | G | T | A0101,A11126,B3501,B0801,C0701,C0401 | C0701 | 100 | 17 | Lrrsprnli | Frrsprnli |
| SA9755 | GIMAP1 | 7 | 150417568 | G | A | A0101,A11126,B3501,B0801,C0701,C0401 | A0101 | 262 | 5374 | laEgslhdy | laGgslhdy |
| SA9755 | GIMAP1 | 7 | 150417568 | G | A | A0101,A11126,B3501,B0801,C0701,C0401 | B3501 | 103 | 116 | laEgslhdy | laGgslhdy |

Figure 21 (Cont.)

| | | | | | | | | | | | |
|---|---|---|---|---|---|---|---|---|---|---|---|
| SA9755 | INSIG1 | 7 | 155093337 | G | T | A0101,A11126,B3501,B0801,C0701,C0401 | C0701 | 71 | 67 | fNrewasvm | fKrewasvm |
| SA9755 | CSMD1 | 8 | 3165926 | C | A | A0101,A11126,B3501,B0801,C0701,C0401 | B3501 | 40 | 377 | ysFnpgyam | ysCnpgyam |
| SA9755 | MSR1 | 8 | 15967707 | T | A | A0101,A11126,B3501,B0801,C0701,C0401 | B3501 | 134 | 265 | gpiwlYevf | gpiwlNevf |
| SA9755 | EBF2 | 8 | 25708241 | G | A | A0101,A11126,B3501,B0801,C0701,C0401 | B3501 | 170 | 348 | sslssilpf | ssTssilpf |
| SA9755 | TEX15 | 8 | 30701232 | C | T | A0101,A11126,B3501,B0801,C0701,C0401 | C0701 | 90 | 44 | tyhdqlvKl | tyhdqlvEl |
| SA9755 | TEX15 | 8 | 30701232 | C | T | A0101,A11126,B3501,B0801,C0701,C0401 | C0701 | 14 | 10 | yhdqlvKll | yhdqlvEll |
| SA9755 | DDHD2 | 8 | 38110321 | G | C | A0101,A11126,B3501,B0801,C0701,C0401 | B0801 | 36 | 394 | hkRrkrmhl | hkGrkrmhl |
| SA9755 | DDHD2 | 8 | 38110321 | G | C | A0101,A11126,B3501,B0801,C0701,C0401 | B0801 | 290 | 1652 | Rrkrmhlel | Grkrmhlel |
| SA9755 | DDHD2 | 8 | 38110321 | G | C | A0101,A11126,B3501,B0801,C0701,C0401 | C0701 | 54 | 319 | phhkRrkrm | phhkGrkrm |
| SA9755 | DDHD2 | 8 | 38110321 | G | C | A0101,A11126,B3501,B0801,C0701,C0401 | C0701 | 123 | 257 | Rrkrmhlel | Grkrmhlel |
| SA9755 | YWHAZ | 8 | 101936423 | G | C | A0101,A11126,B3501,B0801,C0701,C0401 | B3501 | 9 | 7 | lalnLsvfy | lalnFsvfy |
| SA9755 | YWHAZ | 8 | 101936423 | G | C | A0101,A11126,B3501,B0801,C0701,C0401 | C0701 | 383 | 1604 | irlglalnL | irlglalnF |
| SA9755 | KLF10 | 8 | 103663766 | C | A | A0101,A11126,B3501,B0801,C0701,C0401 | B3501 | 477 | 190 | vsaVgvppm | vsaGgvppm |
| SA9755 | CSMD3 | 8 | 113303843 | G | T | A0101,A11126,B3501,B0801,C0701,C0401 | A0101 | 35 | 45 | ftygNvvfy | ftygTvvfy |
| SA9755 | CSMD3 | 8 | 113303843 | G | T | A0101,A11126,B3501,B0801,C0701,C0401 | B3501 | 51 | 99 | ftygNvvfy | ftygTvvfy |
| SA9755 | CSMD3 | 8 | 113303843 | G | T | A0101,A11126,B3501,B0801,C0701,C0401 | C0701 | 332 | 1185 | ftygNvvfy | ftygTvvfy |
| SA9755 | CSMD3 | 8 | 113349779 | C | A | A0101,A11126,B3501,B0801,C0701,C0401 | B3501 | 28 | 116 | hplpSceal | hplpRceal |
| SA9755 | CSMD3 | 8 | 113349779 | C | A | A0101,A11126,B3501,B0801,C0701,C0401 | B3501 | 490 | 1701 | lpScealcg | lpRcealcg |
| SA9755 | FAM135B | 8 | 139149456 | G | C | A0101,A11126,B3501,B0801,C0701,C0401 | B3501 | 385 | 368 | lvaspqdGy | lvaspqdRy |
| SA9755 | FAM135B | 8 | 139149456 | G | C | A0101,A11126,B3501,B0801,C0701,C0401 | B3501 | 11 | 55 | spqdGyvpf | spqdRyvpf |
| SA9755 | FAM135B | 8 | 139278044 | C | A | A0101,A11126,B3501,B0801,C0701,C0401 | B0801 | 193 | 1905 | tLhsrvfqi | tVhsrvfqi |
| SA9755 | FAM135B | 8 | 139278044 | C | A | A0101,A11126,B3501,B0801,C0701,C0401 | C0701 | 306 | 184 | Lhsrvfqil | Vhsrvfqil |

Figure 21 (Cont.)

| | | | | | | | | | | | |
|---|---|---|---|---|---|---|---|---|---|---|---|
| SA9755 | SCRIB | 8 | 144887475 | G | A | A0101,A11126,B3501,B0801,C0701,C0401 | B3501 | 63 | 2508 | epenavtiM | epenavtiT |
| SA9755 | SCRIB | 8 | 144887475 | G | A | A0101,A11126,B3501,B0801,C0701,C0401 | B3501 | 17 | 267 | Mplrpeddy | Tplrpeddy |
| SA9755 | MLANA | 9 | 5892501 | C | G | A0101,A11126,B3501,B0801,C0701,C0401 | B3501 | 6 | 362 | mpredahfM | mpredahfl |
| SA9755 | TMEM261 | 9 | 7798625 | C | A | A0101,A11126,B3501,B0801,C0701,C0401 | B3501 | 247 | 24 | iatLgivvm | iatWgivvm |
| SA9755 | CDKN2A | 9 | 21970972 | T | C | A0101,A11126,B3501,B0801,C0701,C0401 | C0701 | 52 | 15 | ghrdvarCl | ghrdvarYl |
| SA9755 | TLN1 | 9 | 35714624 | C | A | A0101,A11126,B3501,B0801,C0701,C0401 | B3501 | 469 | 1376 | qpYspsaql | qpDspsaql |
| SA9755 | NMRK1 | 9 | 77683978 | C | T | A0101,A11126,B3501,B0801,C0701,C0401 | B3501 | 30 | 72 | yfNghvwpm | yfDghvwpm |
| SA9755 | SLC44A1 | 9 | 108097935 | G | C | A0101,A11126,B3501,B0801,C0701,C0401 | B0801 | 46 | 218 | cprqQlktl | cprqElktl |
| SA9755 | KIF12 | 9 | 116855540 | G | A | A0101,A11126,B3501,B0801,C0701,C0401 | B0801 | 282 | 184 | vplahwVcl | vplahwAcl |
| SA9755 | KIF12 | 9 | 116855540 | G | A | A0101,A11126,B3501,B0801,C0701,C0401 | B3501 | 48 | 58 | vplahwVcl | vplahwAcl |
| SA9755 | PAPPA | 9 | 119106856 | C | G | A0101,A11126,B3501,B0801,C0701,C0401 | A0101 | 334 | 1087 | ktdcAelav | ktdcPelav |
| SA9755 | ASTN2 | 9 | 119770442 | G | T | A0101,A11126,B3501,B0801,C0701,C0401 | B3501 | 309 | 20718 | lyyqinatY | lyyqinatS |
| SA9755 | ASTN2 | 9 | 119770442 | G | T | A0101,A11126,B3501,B0801,C0701,C0401 | B3501 | 169 | 3287 | Ypwvrdlcg | Spwvrdlcg |
| SA9755 | ASTN2 | 9 | 119770442 | G | T | A0101,A11126,B3501,B0801,C0701,C0401 | C0701 | 265 | 721 | atYpwvrdl | atSpwvrdl |
| SA9755 | TLR4 | 9 | 120475630 | C | A | A0101,A11126,B3501,B0801,C0701,C0401 | B0801 | 37 | 126 | slkyldlsL | slkyldlsF |
| SA9755 | TLR4 | 9 | 120475630 | C | A | A0101,A11126,B3501,B0801,C0701,C0401 | B3501 | 284 | 99 | lsLngvitm | lsFngvitm |
| SA9755 | TLR4 | 9 | 120476850 | T | C | A0101,A11126,B3501,B0801,C0701,C0401 | B0801 | 12 | 54 | wrrlrkaPl | wrrlrkaLl |
| SA9755 | GSN | 9 | 124081070 | G | C | A0101,A11126,B3501,B0801,C0701,C0401 | B3501 | 22 | 74 | ianvePvpf | ianveRvpf |
| SA9755 | GSN | 9 | 124081070 | G | C | A0101,A11126,B3501,B0801,C0701,C0401 | B3501 | 91 | 16927 | ePvpfdaat | eRvpfdaat |
| SA9755 | GSN | 9 | 124081070 | G | C | A0101,A11126,B3501,B0801,C0701,C0401 | C0701 | 108 | 16 | shianvePv | shianveRv |
| SA9755 | LHX2 | 9 | 126777622 | A | T | A0101,A11126,B3501,B0801,C0701,C0401 | B3501 | 312 | 261 | ypahflhad | ypahfNhad |
| SA9755 | SPTAN1 | 9 | 131337019 | C | G | A0101,A11126,B3501,B0801,C0701,C0401 | B0801 | 226 | 1153 | kmrekgMkl | kmrekglkl |
| SA9755 | SPTAN1 | 9 | 131337019 | C | G | A0101,A11126,B3501,B0801,C0701,C0401 | C0701 | 104 | 36 | mrekgMkll | mrekglkll |

Figure 21 (Cont.)

| | | | | | | | | | | | |
|---|---|---|---|---|---|---|---|---|---|---|---|
| SA9755 | PPP1R26 | 9 | 138379035 | G | C | A0101,A11126,B3501,B0801,C0701,C0401 | C0701 | 16 | 13 | trsHrargv | trsQrargv |
| SA9755 | PPP1R26 | 9 | 138379035 | G | C | A0101,A11126,B3501,B0801,C0701,C0401 | C0701 | 377 | 407 | Hrargvphl | Qrargvphl |
| SA9755 | UAP1L1 | 9 | 139975295 | G | T | A0101,A11126,B3501,B0801,C0701,C0401 | C0401 | 354 | 342 | fldShgawl | fldAhgawl |
| SA9755 | UAP1L1 | 9 | 139975295 | G | T | A0101,A11126,B3501,B0801,C0701,C0401 | C0701 | 25 | 59 | Shgawlpel | Ahgawlpel |
| SA9755 | SLC25A6 | X | 1508533 | C | A | A0101,A11126,B3501,B0801,C0701,C0401 | C0701 | 35 | 38 | vripkeqgL | vripkeqgV |
| SA9755 | ASMT | X | 1742131 | G | T | A0101,A11126,B3501,B0801,C0701,C0401 | C0701 | 332 | 657 | rasShgtel | rasAhgtel |
| SA9755 | GYG2 | X | 2778025 | G | T | A0101,A11126,B3501,B0801,C0701,C0401 | B3501 | 97 | 85 | flhlCwtvy | flhlWwtvy |
| SA9755 | MAGEB5 | X | 26236114 | C | A | A0101,A11126,B3501,B0801,C0701,C0401 | B3501 | 59 | 69 | apgaLssqy | apgaFssqy |
| SA9755 | DCAF8L2 | X | 27766585 | C | G | A0101,A11126,B3501,B0801,C0701,C0401 | B3501 | 258 | 358 | ephpyVpvl | ephpyLpvl |
| SA9755 | GK | X | 30709248 | G | T | A0101,A11126,B3501,B0801,C0701,C0401 | B0801 | 80 | 2328 | wlYlrtqst | wlDlrtqst |
| SA9755 | DMD | X | 31792151 | C | T | A0101,A11126,B3501,B0801,C0701,C0401 | A0101 | 198 | 505 | ltdwlslIN | ltdwlslID |
| SA9755 | DMD | X | 32536202 | C | T | A0101,A11126,B3501,B0801,C0701,C0401 | B3501 | 261 | 38 | Kavlqspef | Eavlqspef |
| SA9755 | FAM47C | X | 37028003 | T | C | A0101,A11126,B3501,B0801,C0701,C0401 | B0801 | 234 | 137 | ppktrAshl | ppktrVshl |
| SA9755 | XK | X | 37553712 | C | G | A0101,A11126,B3501,B0801,C0701,C0401 | B0801 | 155 | 345 | safsraWvi | safsraSvi |
| SA9755 | XK | X | 37553712 | C | G | A0101,A11126,B3501,B0801,C0701,C0401 | C0701 | 91 | 61 | safsraWvi | safsraSvi |
| SA9755 | ZNF674 | X | 46360114 | C | G | A0101,A11126,B3501,B0801,C0701,C0401 | C0701 | 408 | 112 | thtRekpfv | thtGekpfv |
| SA9755 | MAGED1 | X | 51644746 | C | A | A0101,A11126,B3501,B0801,C0701,C0401 | C0701 | 139 | 58 | Draeartrm | Araeartrm |
| SA9755 | HSD17B10 | X | 53461277 | G | A | A0101,A11126,B3501,B0801,C0701,C0401 | B3501 | 288 | 1565 | maaacWsvk | maaacRsvk |
| SA9755 | GNL3L | X | 54566614 | C | A | A0101,A11126,B3501,B0801,C0701,C0401 | B3501 | 164 | 173 | vpsEphfvh | vpsAphfvh |
| SA9755 | EDA | X | 69253278 | C | G | A0101,A11126,B3501,B0801,C0701,C0401 | C0701 | 322 | 106 | Critmnpkv | Sritmnpkv |
| SA9755 | MED12 | X | 70357445 | A | T | A0101,A11126,B3501,B0801,C0701,C0401 | B3501 | 104 | 139 | hLmtpsssy | hQmtpsssy |
| SA9755 | FLJ44635 | X | 71379966 | G | T | A0101,A11126,B3501,B0801,C0701,C0401 | B0801 | 124 | 1008 | Fikdymksi | Cikdymksi |

Figure 21 (Cont.)

| | | | | | | | | | | | |
|---|---|---|---|---|---|---|---|---|---|---|---|
| SA9755 | ARMCX1 | X | 100808814 | G | T | A0101,A11126,B3501,B0801,C0701,C0401 | B0801 | 41 | 1131 | tmvcrlYsa | tmvcrlDsa |
| SA9755 | RBM41 | X | 106332039 | G | A | A0101,A11126,B3501,B0801,C0701,C0401 | A0101 | 222 | 884 | Lmnnlesfy | Pmnnlesfy |
| SA9755 | GUCY2F | X | 108696796 | C | A | A0101,A11126,B3501,B0801,C0701,C0401 | B3501 | 362 | 4095 | fpVgrppra | fpGgrppra |
| SA9755 | CT47B1 | X | 120009200 | C | G | A0101,A11126,B3501,B0801,C0701,C0401 | B3501 | 394 | 285 | eaanfdlPv | eaanfdlAv |
| SA9755 | STAG2 | X | 123184090 | G | A | A0101,A11126,B3501,B0801,C0701,C0401 | B0801 | 32 | 15 | wlkmysdaf | wMkmysdaf |
| SA9755 | STAG2 | X | 123184090 | G | A | A0101,A11126,B3501,B0801,C0701,C0401 | B3501 | 228 | 163 | wlkmysdaf | wMkmysdaf |
| SA9755 | DCAF12L2 | X | 125299320 | C | G | A0101,A11126,B3501,B0801,C0701,C0401 | C0701 | 93 | 244 | drhghkdCi | drhghkdWi |
| SA9755 | DCAF12L2 | X | 125299320 | C | G | A0101,A11126,B3501,B0801,C0701,C0401 | C0701 | 57 | 49 | ghkdCifav | ghkdWifav |
| SA9755 | DCAF12L2 | X | 125299871 | C | G | A0101,A11126,B3501,B0801,C0701,C0401 | B0801 | 327 | 149 | gsrkrkPpa | gsrkrkApa |
| SA9755 | DCAF12L2 | X | 125299871 | C | G | A0101,A11126,B3501,B0801,C0701,C0401 | B0801 | 77 | 88 | srkrkPpav | srkrkApav |
| SA9755 | DCAF12L2 | X | 125299871 | C | G | A0101,A11126,B3501,B0801,C0701,C0401 | C0701 | 174 | 273 | srkrkPpav | srkrkApav |
| SA9755 | MAP7D3 | X | 135303038 | A | G | A0101,A11126,B3501,B0801,C0701,C0401 | B3501 | 87 | 15814 | fPedgtsqv | fLedgtsqv |
| SA9755 | GPR112 | X | 135427919 | C | G | A0101,A11126,B3501,B0801,C0701,C0401 | B3501 | 199 | 8 | sGfhentty | sAfhentty |
| SA9755 | ARHGEF6 | X | 135758840 | G | T | A0101,A11126,B3501,B0801,C0701,C0401 | B0801 | 373 | 112 | spktmkkfl | spktmkkfL |
| SA9755 | AFF2 | X | 148038030 | C | A | A0101,A11126,B3501,B0801,C0701,C0401 | C0701 | 146 | 116 | srvpghssl | srvpghssL |
| SA9755 | FLNA | X | 153582391 | C | A | A0101,A11126,B3501,B0801,C0701,C0401 | B3501 | 9 | 12 | splqfyLdy | splqfyVdy |
| SA9755 | F8 | X | 154159241 | C | A | A0101,A11126,B3501,B0801,C0701,C0401 | B0801 | 271 | 61 | lfCkksspl | lfGkksspl |
| SB010944 | CROCC | 1 | 17285085 | T | C | A0104,A0326,A0101,B0702,B0801,C0702,C0701 | B0801 | 33 | 66 | elrrqmkTl | elrrqmkMl |
| SB010944 | STIL | 1 | 47726073 | C | T | A0104,A0326,A0101,B0702,B0801,C0702,C0701 | B0801 | 120 | 4147 | rlMdkdcvl | rlVdkdcvl |
| SB010944 | DMRTA2 | 1 | 50884447 | C | T | A0104,A0326,A0101,B0702,B0801,C0702,C0701 | B0801 | 127 | 1524 | sNlmrdrsa | sDlmrdrsa |
| SB010944 | DMRTA2 | 1 | 50884447 | C | T | A0104,A0326,A0101,B0702,B0801,C0702,C0701 | B0801 | 43 | 225 | Nlmrdrsaa | Dlmrdrsaa |
| SB010944 | ZNF496 | 1 | 247464566 | G | A | A0104,A0326,A0101,B0702,B0801,C0702,C0701 | B0801 | 184 | 201 | nLrslensl | nPrslensl |
| SB010944 | HECTD4 | 12 | 112623279 | G | T | A0104,A0326,A0101,B0702,B0801,C0702,C0701 | B0801 | 52 | 2688 | flwtKdmaa | flwtTdmaa |

Figure 21 (Cont.)

| | | | | | | | | | | | |
|---|---|---|---|---|---|---|---|---|---|---|---|
| SB010944 | KCNH5 | 14 | 63447900 | C | T | A0104,A0326,A0101,B0702,B0801,C0702,C0701 | B0801 | 75 | 108 | hiilhyYaf | hiilhyCaf |
| SB010944 | KCNH5 | 14 | 63447900 | C | T | A0104,A0326,A0101,B0702,B0801,C0702,C0701 | C0702 | 154 | 359 | hiilhyYaf | hiilhyCaf |
| SB010944 | KCNH5 | 14 | 63447900 | C | T | A0104,A0326,A0101,B0702,B0801,C0702,C0701 | C0702 | 141 | 665 | hyYafkttw | hyCafkttw |
| SB010944 | VASH1 | 14 | 77229439 | C | T | A0104,A0326,A0101,B0702,B0801,C0702,C0701 | C0701 | 91 | 1788 | ihpdgekvV | ihpdgekvA |
| SB010944 | TRAF3 | 14 | 103371853 | G | A | A0104,A0326,A0101,B0702,B0801,C0702,C0701 | C0701 | 21 | 39 | mrEeydall | mrGeydall |
| SB010944 | SPTBN5 | 15 | 42163688 | G | T | A0104,A0326,A0101,B0702,B0801,C0702,C0701 | C0701 | 353 | 240 | akfqNqvem | akfqHqvem |
| SB010944 | HERC1 | 15 | 63972870 | A | G | A0104,A0326,A0101,B0702,B0801,C0702,C0701 | A0101 | 48 | 64 | tsdmwlHra | tsdmwlYra |
| SB010944 | HERC1 | 15 | 63972870 | A | G | A0104,A0326,A0101,B0702,B0801,C0702,C0701 | C0701 | 168 | 4242 | lHraysgnl | lYraysgnl |
| SB010944 | DAPK2 | 15 | 64200766 | C | T | A0104,A0326,A0101,B0702,B0801,C0702,C0701 | B0801 | 331 | 539 | ediTrrkal | ediArrkal |
| SB010944 | HIC1 | 17 | 1960934 | C | G | A0104,A0326,A0101,B0702,B0801,C0702,C0701 | C0702 | 427 | 915 | rwmkheRgl | rwmkhePgl |
| SB010944 | KIF1C | 17 | 4918106 | G | T | A0104,A0326,A0101,B0702,B0801,C0702,C0701 | C0701 | 96 | 7113 | ireqhclfL | ireqhclfR |
| SB010944 | ZNF624 | 17 | 16526275 | C | A | A0104,A0326,A0101,B0702,B0801,C0702,C0701 | C0702 | 111 | 3035 | kFydcgksf | kCydcgksf |
| SB010944 | TBC1D29 | 17 | 28890301 | G | A | A0104,A0326,A0101,B0702,B0801,C0702,C0701 | C0701 | 309 | 352 | sesNrgpsl | sesSrgpsl |
| SB010944 | CNN2 | 19 | 1037648 | C | T | A0104,A0326,A0101,B0702,B0801,C0702,C0701 | C0701 | 494 | 338 | Wrhiydtkl | Rrhiydtkl |
| SB010944 | CNN2 | 19 | 1037648 | C | T | A0104,A0326,A0101,B0702,B0801,C0702,C0701 | C0702 | 308 | 303 | Wrhiydtkl | Rrhiydtkl |
| SB010944 | AP3D1 | 19 | 2108687 | T | C | A0104,A0326,A0101,B0702,B0801,C0702,C0701 | C0701 | 108 | 4288 | kRgensvsv | kKgensvsv |
| SB010944 | GPR108 | 19 | 6734304 | T | C | A0104,A0326,A0101,B0702,B0801,C0702,C0701 | C0701 | 43 | 1631 | rRygeqktl | rKygeqktl |
| SB010944 | GPR108 | 19 | 6734304 | T | C | A0104,A0326,A0101,B0702,B0801,C0702,C0701 | C0702 | 118 | 1041 | rRygeqktl | rKygeqktl |
| SB010944 | GPR108 | 19 | 6734304 | T | C | A0104,A0326,A0101,B0702,B0801,C0702,C0701 | C0702 | 246 | 374 | Rygeqktlf | Kygeqktlf |
| SB010944 | CC2D1A | 19 | 14024105 | G | A | A0104,A0326,A0101,B0702,B0801,C0702,C0701 | B0801 | 202 | 734 | sakmrrydQ | sakmrrydR |
| SB010944 | CC2D1A | 19 | 14024105 | G | A | A0104,A0326,A0101,B0702,B0801,C0702,C0701 | B0801 | 219 | 429 | kmrrydQgl | kmrrydRgl |
| SB010944 | CC2D1A | 19 | 14024105 | G | A | A0104,A0326,A0101,B0702,B0801,C0702,C0701 | C0701 | 140 | 61 | rrydQglkt | rrydRglkt |

Figure 21 (Cont.)

| | | | | | | | | | | | |
|---|---|---|---|---|---|---|---|---|---|---|---|
| SB010944 | ZNF737 | 19 | 20727459 | C | G | A0104,A0326,A0101,B0702,B0801,C0702,C0701 | C0701 | 441 | 2765 | kAfkcpstl | kGfkcpstl |
| SB010944 | ZNF737 | 19 | 20727799 | C | T | A0104,A0326,A0101,B0702,B0801,C0702,C0701 | B0702 | 418 | 10181 | Kafkysssl | Eafkysssl |
| SB010944 | ZNF737 | 19 | 20727799 | C | T | A0104,A0326,A0101,B0702,B0801,C0702,C0701 | B0801 | 305 | 81 | Kafkysssl | Eafkysssl |
| SB010944 | ZNF626 | 19 | 20807199 | A | G | A0104,A0326,A0101,B0702,B0801,C0702,C0701 | C0701 | 319 | 480 | kafnqssTl | kafnqssll |
| SB010944 | ZNF714 | 19 | 21300550 | G | A | A0104,A0326,A0101,B0702,B0801,C0702,C0701 | C0701 | 121 | 115 | shltthImi | shltthKmi |
| SB010944 | ZNF429 | 19 | 21720201 | A | G | A0104,A0326,A0101,B0702,B0801,C0702,C0701 | C0701 | 466 | 297 | trhkrihtG | trhkrihtE |
| SB010944 | ZNF730 | 19 | 23328424 | A | G | A0104,A0326,A0101,B0702,B0801,C0702,C0701 | C0701 | 106 | 97 | shlaqhkRi | shlaqhkKi |
| SB010944 | NPHS1 | 19 | 36317454 | C | T | A0104,A0326,A0101,B0702,B0801,C0702,C0701 | C0702 | 316 | 291 | tlepNslpf | tlepDslpf |
| SB010944 | SIPA1L3 | 19 | 38684274 | C | T | A0104,A0326,A0101,B0702,B0801,C0702,C0701 | B0702 | 313 | 20846 | faspagleL | faspagleP |
| SB010944 | SIPA1L3 | 19 | 38684274 | C | T | A0104,A0326,A0101,B0702,B0801,C0702,C0701 | B0702 | 27 | 65 | spagleLgl | spaglePgl |
| SB010944 | SIPA1L3 | 19 | 38684274 | C | T | A0104,A0326,A0101,B0702,B0801,C0702,C0701 | C0701 | 255 | 16116 | faspagleL | faspagleP |
| SB010944 | RASIP1 | 19 | 49232822 | C | T | A0104,A0326,A0101,B0702,B0801,C0702,C0701 | C0701 | 165 | 97 | yvmtQeqhv | yvmtReqhv |
| SB010944 | ZNF534 | 19 | 52942533 | A | G | A0104,A0326,A0101,B0702,B0801,C0702,C0701 | C0701 | 177 | 6665 | yRcnecskv | yKcnecskv |
| SB010944 | NTSR2 | 2 | 11810051 | G | A | A0104,A0326,A0101,B0702,B0801,C0702,C0701 | B0801 | 294 | 11 | rlChhvlsl | rlRhhvlsl |
| SB010944 | NTSR2 | 2 | 11810051 | G | A | A0104,A0326,A0101,B0702,B0801,C0702,C0701 | C0701 | 274 | 130 | Chhvlslal | Rhhvlslal |
| SB010944 | APOB | 2 | 21224813 | T | A | A0104,A0326,A0101,B0702,B0801,C0702,C0701 | B0801 | 384 | 1109 | Lfryklqdf | Qfryklqdf |
| SB010944 | APOB | 2 | 21224813 | T | A | A0104,A0326,A0101,B0702,B0801,C0702,C0701 | C0701 | 424 | 1004 | iisdyhqLf | iisdyhqQf |
| SB010944 | APOB | 2 | 21224813 | T | A | A0104,A0326,A0101,B0702,B0801,C0702,C0701 | C0701 | 79 | 22 | yhqLfrykl | yhqQfrykl |
| SB010944 | APOB | 2 | 21224813 | T | A | A0104,A0326,A0101,B0702,B0801,C0702,C0701 | C0702 | 254 | 320 | yhqLfrykl | yhqQfrykl |
| SB010944 | C2orf73 | 2 | 54587647 | C | T | A0104,A0326,A0101,B0702,B0801,C0702,C0701 | B0801 | 13 | 16 | Vlftrhkpl | Alftrhkpl |
| SB010944 | C2orf73 | 2 | 54587647 | C | T | A0104,A0326,A0101,B0702,B0801,C0702,C0701 | C0702 | 480 | 1140 | Vlftrhkpl | Alftrhkpl |
| SB010944 | RTN4 | 2 | 55277007 | G | A | A0104,A0326,A0101,B0702,B0801,C0702,C0701 | B0702 | 223 | 2922 | rpSppppas | rpPppppas |
| SB010944 | SP3 | 2 | 174829141 | C | T | A0104,A0326,A0101,B0702,B0801,C0702,C0701 | B0702 | 403 | 55 | aaTaqpspl | aaAaqpspl |

Figure 21 (Cont.)

| | | | | | | | | | | | |
|---|---|---|---|---|---|---|---|---|---|---|---|
| SB010944 | REM1 | 20 | 30072156 | C | T | A0104,A0326,A0101,B0702,B0801,C0702,C0701 | B0702 | 142 | 43 | rarrflaCl | rarrflaRl |
| SB010944 | REM1 | 20 | 30072156 | C | T | A0104,A0326,A0101,B0702,B0801,C0702,C0701 | B0801 | 330 | 3810 | qrarrflaC | qrarrflaR |
| SB010944 | REM1 | 20 | 30072156 | C | T | A0104,A0326,A0101,B0702,B0801,C0702,C0701 | B0801 | 103 | 358 | rarrflaCl | rarrflaRl |
| SB010944 | PLAC4 | 21 | 42551149 | A | G | A0104,A0326,A0101,B0702,B0801,C0702,C0701 | B0702 | 216 | 31 | spwtpsllT | spwtpslll |
| SB010944 | PLAC4 | 21 | 42551245 | A | G | A0104,A0326,A0101,B0702,B0801,C0702,C0701 | B0702 | 9 | 11 | spwtPsltl | spwtLsltl |
| SB010944 | PLAC4 | 21 | 42551245 | A | G | A0104,A0326,A0101,B0702,B0801,C0702,C0701 | C0702 | 227 | 179 | hsspwtPsl | hsspwtLsl |
| SB010944 | PLAC4 | 21 | 42551270 | A | G | A0104,A0326,A0101,B0702,B0801,C0702,C0701 | B0702 | 25 | 21 | Hphsspwtl | Yphsspwtl |
| SB010944 | GCAT | 22 | 38203999 | G | A | A0104,A0326,A0101,B0702,B0801,C0702,C0701 | B0702 | 124 | 22 | wpgnawrTa | wpgnawrAa |
| SB010944 | KLHDC7B | 22 | 50987760 | C | T | A0104,A0326,A0101,B0702,B0801,C0702,C0701 | B0702 | 62 | 17 | Wpmqqaraq | Rpmqqaraq |
| SB010944 | KLHDC7B | 22 | 50987760 | C | T | A0104,A0326,A0101,B0702,B0801,C0702,C0701 | C0702 | 417 | 291 | niwsqvWpm | niwsqvRpm |
| SB010944 | CRTAP | 3 | 33155792 | C | T | A0104,A0326,A0101,B0702,B0801,C0702,C0701 | B0801 | 73 | 198 | eislrlhCl | eislrlhRl |
| SB010944 | SCAP | 3 | 47459858 | G | A | A0104,A0326,A0101,B0702,B0801,C0702,C0701 | B0702 | 99 | 5641 | Speteivpl | Ppeteivpl |
| SB010944 | EEFSEC | 3 | 127872582 | G | A | A0104,A0326,A0101,B0702,B0801,C0702,C0701 | B0702 | 246 | 8276 | Kpepgepll | Epepgepll |
| SB010944 | IRX4 | 5 | 1882023 | A | T | A0104,A0326,A0101,B0702,B0801,C0702,C0701 | A0101 | 87 | 243 | nTaaalgvy | nSaaalgvy |
| SB010944 | PCDHB12 | 5 | 140590124 | G | A | A0104,A0326,A0101,B0702,B0801,C0702,C0701 | B0801 | 84 | 49 | ealvrMlvl | ealvrVlvl |
| SB010944 | LRP11 | 6 | 150185018 | C | T | A0104,A0326,A0101,B0702,B0801,C0702,C0701 | B0702 | 130 | 60 | ppaaplsKl | ppaaplsEl |
| SB010944 | ZNF316 | 7 | 6692603 | G | A | A0104,A0326,A0101,B0702,B0801,C0702,C0701 | A0101 | 32 | 17642 | htgerpypY | htgerpypC |
| SB010944 | ZNF273 | 7 | 64388889 | G | A | A0104,A0326,A0101,B0702,B0801,C0702,C0701 | B0801 | 167 | 230 | stltrhkil | stltrhkiV |
| SB010944 | USP17L2 | 8 | 11995474 | T | A | A0104,A0326,A0101,B0702,B0801,C0702,C0701 | B0702 | 10 | 9 | apaskSltl | apaskTltl |
| SB010944 | USP17L2 | 8 | 11995474 | T | A | A0104,A0326,A0101,B0702,B0801,C0702,C0701 | B0801 | 284 | 313 | apaskSltl | apaskTltl |
| SB010944 | USP17L2 | 8 | 11995474 | T | A | A0104,A0326,A0101,B0702,B0801,C0702,C0701 | C0701 | 132 | 70 | qrapaskSl | qrapaskTl |
| SB010944 | TNFRSF10A | 8 | 23082340 | C | T | A0104,A0326,A0101,B0702,B0801,C0702,C0701 | B0702 | 319 | 214 | gprpTreas | gprpAreas |

Figure 21 (Cont.)

| | | | | | | | | | | | |
|---|---|---|---|---|---|---|---|---|---|---|---|
| SB010944 | E2F5 | 8 | 86115381 | C | T | A0104,A0326,A0101,B0702,B0801,C0702,C0701 | C0701 | 416 | 73 | evidriryF | evidriryL |
| SB010944 | E2F5 | 8 | 86115381 | C | T | A0104,A0326,A0101,B0702,B0801,C0702,C0701 | C0702 | 167 | 1159 | yFkaeiedl | yLkaeiedl |
| SB010944 | WNK2 | 9 | 96010074 | C | T | A0104,A0326,A0101,B0702,B0801,C0702,C0701 | C0702 | 325 | 2102 | hFlpptlpt | hLlpptlpt |
| SB010944 | SAPCD2 | 9 | 139964779 | C | T | A0104,A0326,A0101,B0702,B0801,C0702,C0701 | C0701 | 140 | 401 | rrrDcvhlr | rrrGcvhlr |
| SB010944 | SLC38A5 | X | 48320104 | C | T | A0104,A0326,A0101,B0702,B0801,C0702,C0701 | B0702 | 109 | 11 | Qpskrrmqa | Rpskrrmqa |
| SB010944 | SLC38A5 | X | 48320104 | C | T | A0104,A0326,A0101,B0702,B0801,C0702,C0701 | B0801 | 59 | 47 | Qpskrrmqa | Rpskrrmqa |
| SB010944 | DRP2 | X | 100513519 | G | A | A0104,A0326,A0101,B0702,B0801,C0702,C0701 | B0801 | 268 | 454 | sqlqrlKel | sqlqrlRel |
| SC0899 | PLCH2 | 1 | 2421200 | G | C | A2402,A2601,B3502,B3801,C0401,C1203 | C1203 | 94 | 8189 | kAkklpani | kGkklpani |
| SC0899 | FBXO44 | 1 | 11721272 | G | T | A2402,A2601,B3502,B3801,C0401,C1203 | A2601 | 22 | 5 | dthywaVwy | dthywaGwy |
| SC0899 | FBXO44 | 1 | 11721272 | G | T | A2402,A2601,B3502,B3801,C0401,C1203 | C1203 | 211 | 515 | waVwygprv | waGwygprv |
| SC0899 | OR10K1 | 1 | 158436004 | A | G | A2402,A2601,B3502,B3801,C0401,C1203 | C1203 | 167 | 330 | ilvsCirii | ilvsYirii |
| SC0899 | OR10Z1 | 1 | 158576424 | C | A | A2402,A2601,B3502,B3801,C0401,C1203 | C1203 | 171 | 600 | pmylflsfl | pmylflsfL |
| SC0899 | OR10Z1 | 1 | 158576424 | C | A | A2402,A2601,B3502,B3801,C0401,C1203 | C1203 | 137 | 150 | ylflsflsf | ylflsfLsf |
| SC0899 | RCSD1 | 1 | 167654704 | C | A | A2402,A2601,B3502,B3801,C0401,C1203 | C1203 | 357 | 2493 | Hlfppkvdl | Plfppkvdl |
| SC0899 | PAPPA2 | 1 | 176671853 | G | C | A2402,A2601,B3502,B3801,C0401,C1203 | C1203 | 442 | 285 | apycAdgkv | apycGdgkv |
| SC0899 | BRINP3 | 1 | 190067657 | G | A | A2402,A2601,B3502,B3801,C0401,C1203 | C0401 | 171 | 366 | fpdweWtkl | fpdweRtkl |
| SC0899 | BRINP3 | 1 | 190067657 | G | A | A2402,A2601,B3502,B3801,C0401,C1203 | C1203 | 228 | 255 | fpdweWtkl | fpdweRtkl |
| SC0899 | CFH | 1 | 196642186 | C | A | A2402,A2601,B3502,B3801,C0401,C1203 | A2402 | 247 | 145 | typegNqai | typegTqai |
| SC0899 | CFH | 1 | 196642186 | C | A | A2402,A2601,B3502,B3801,C0401,C1203 | C1203 | 71 | 273 | ypegNqaiy | ypegTqaiy |
| SC0899 | CRB1 | 1 | 197390517 | T | C | A2402,A2601,B3502,B3801,C0401,C1203 | A2402 | 34 | 36 | vqpTalllf | vqpMalllf |
| SC0899 | PTPRC | 1 | 198682177 | A | T | A2402,A2601,B3502,B3801,C0401,C1203 | B3801 | 46 | 42 | qrsfhnfSl | qrsfhnfTl |
| SC0899 | PTPRC | 1 | 198682177 | A | T | A2402,A2601,B3502,B3801,C0401,C1203 | C1203 | 334 | 493 | fhnfSlcyi | fhnfTlcyi |
| SC0899 | KIF21B | 1 | 200965377 | C | G | A2402,A2601,B3502,B3801,C0401,C1203 | A2402 | 311 | 1647 | ryQrelkkl | ryErelkkl |

Figure 21 (Cont.)

| | | | | | | | | | | | |
|---|---|---|---|---|---|---|---|---|---|---|---|
| SC0899 | HSD11B1 | 1 | 209880347 | G | A | A2402,A2601,B3502,B3801,C0401,C1203 | C1203 | 319 | 155 | lfhNdihhv | lfhDdihhv |
| SC0899 | RYR2 | 1 | 237972269 | C | G | A2402,A2601,B3502,B3801,C0401,C1203 | C1203 | 96 | 213 | ytvvafnfL | ytvvafnfF |
| SC0899 | RYR2 | 1 | 237972269 | C | G | A2402,A2601,B3502,B3801,C0401,C1203 | C1203 | 9 | 9 | vafnfLrkf | vafnfFrkf |
| SC0899 | NLRP3 | 1 | 247588679 | G | C | A2402,A2601,B3502,B3801,C0401,C1203 | A2601 | 485 | 597 | fvqTamdyf | fvqRamdyf |
| SC0899 | NLRP3 | 1 | 247588679 | G | C | A2402,A2601,B3502,B3801,C0401,C1203 | C1203 | 14 | 10 | Tamdyfpki | Ramdyfpki |
| SC0899 | OR1C1 | 1 | 247921182 | T | A | A2402,A2601,B3502,B3801,C0401,C1203 | A2402 | 484 | 1967 | casniihLf | casniihHf |
| SC0899 | OR1C1 | 1 | 247921182 | T | A | A2402,A2601,B3502,B3801,C0401,C1203 | C1203 | 66 | 2751 | fcasniihL | fcasniihH |
| SC0899 | OR2M2 | 1 | 248344134 | C | A | A2402,A2601,B3502,B3801,C0401,C1203 | C1203 | 311 | 800 | vfytiltTm | vfytiltPm |
| SC0899 | OR2T11 | 1 | 248789612 | G | C | A2402,A2601,B3502,B3801,C0401,C1203 | A2402 | 255 | 125 | kvvsGfyti | kvvsAfyti |
| SC0899 | OR2T11 | 1 | 248789612 | G | C | A2402,A2601,B3502,B3801,C0401,C1203 | C1203 | 156 | 296 | kvvsGfyti | kvvsAfyti |
| SC0899 | OR2T11 | 1 | 248789612 | G | C | A2402,A2601,B3502,B3801,C0401,C1203 | C1203 | 224 | 196 | vvsGfytiv | vvsAfytiv |
| SC0899 | RHOBTB1 | 10 | 62645901 | C | A | A2402,A2601,B3502,B3801,C0401,C1203 | A2601 | 260 | 1259 | maamfVgsf | maamfGgsf |
| SC0899 | RHOBTB1 | 10 | 62645901 | C | A | A2402,A2601,B3502,B3801,C0401,C1203 | C1203 | 53 | 76 | maamfVgsf | maamfGgsf |
| SC0899 | RHOBTB1 | 10 | 62645901 | C | A | A2402,A2601,B3502,B3801,C0401,C1203 | C1203 | 177 | 78 | aamfVgsfv | aamfGgsfv |
| SC0899 | ABCC2 | 10 | 101551997 | G | T | A2402,A2601,B3502,B3801,C0401,C1203 | A2402 | 83 | 576 | lylakqvfF | lylakqvfV |
| SC0899 | ABCC2 | 10 | 101551997 | G | T | A2402,A2601,B3502,B3801,C0401,C1203 | C1203 | 98 | 91 | qvfFgflli | qvfVgflli |
| SC0899 | FAM204A | 10 | 120070825 | G | A | A2402,A2601,B3502,B3801,C0401,C1203 | C1203 | 140 | 562 | atreFgvki | atreLgvki |
| SC0899 | FAM204A | 10 | 120070825 | G | A | A2402,A2601,B3502,B3801,C0401,C1203 | C1203 | 327 | 4187 | Fgvkiakav | Lgvkiakav |
| SC0899 | MOB2 | 11 | 1491503 | C | T | A2402,A2601,B3502,B3801,C0401,C1203 | C1203 | 72 | 82 | imddltKvl | imddltEvl |
| SC0899 | OR51B4 | 11 | 5322318 | T | A | A2402,A2601,B3502,B3801,C0401,C1203 | A2402 | 36 | 152 | lfppfvnpF | lfppfvnpl |
| SC0899 | OR51B4 | 11 | 5322318 | T | A | A2402,A2601,B3502,B3801,C0401,C1203 | C1203 | 341 | 212 | fppfvnpFi | fppfvnpli |
| SC0899 | OR51B4 | 11 | 5322318 | T | A | A2402,A2601,B3502,B3801,C0401,C1203 | C1203 | 6 | 10 | fvnpFiysi | fvnpliysi |

Figure 21 (Cont.)

| | | | | | | | | | | | |
|---|---|---|---|---|---|---|---|---|---|---|---|
| SC0899 | FBXO3 | 11 | 33772161 | C | A | A2402,A2601,B3502,B3801,C0401,C1203 | C1203 | 251 | 65 | vattgditL | vattgditV |
| SC0899 | FBXO3 | 11 | 33772161 | C | A | A2402,A2601,B3502,B3801,C0401,C1203 | C1203 | 490 | 287 | ttgditLsv | ttgditVsv |
| SC0899 | EXT2 | 11 | 44129393 | A | T | A2402,A2601,B3502,B3801,C0401,C1203 | A2402 | 366 | 911 | liatgmfLf | liatgmfQf |
| SC0899 | EXT2 | 11 | 44129393 | A | T | A2402,A2601,B3502,B3801,C0401,C1203 | A2402 | 34 | 31 | mfLfwphsi | mfQfwphsi |
| SC0899 | EXT2 | 11 | 44129393 | A | T | A2402,A2601,B3502,B3801,C0401,C1203 | C1203 | 236 | 883 | mfLfwphsi | mfQfwphsi |
| SC0899 | TRIM51 | 11 | 55659052 | C | G | A2402,A2601,B3502,B3801,C0401,C1203 | A2402 | 135 | 206 | iytiAncsf | iytiPncsf |
| SC0899 | OR4D9 | 11 | 59282793 | G | T | A2402,A2601,B3502,B3801,C0401,C1203 | C1203 | 80 | 246 | kplhymtil | kplhymtiM |
| SC0899 | MOGAT2 | 11 | 75438547 | T | A | A2402,A2601,B3502,B3801,C0401,C1203 | C1203 | 61 | 97 | fhphgvQav | fhphgvLav |
| SC0899 | MOGAT2 | 11 | 75438547 | T | A | A2402,A2601,B3502,B3801,C0401,C1203 | C1203 | 499 | 331 | Qavgafanl | Lavgafanl |
| SC0899 | FAM118B | 11 | 126126688 | C | T | A2402,A2601,B3502,B3801,C0401,C1203 | A2402 | 281 | 118 | dyVdlpeyf | dyAdlpeyf |
| SC0899 | DYRK4 | 12 | 4702206 | G | A | A2402,A2601,B3502,B3801,C0401,C1203 | C1203 | 246 | 52 | spyKqseil | spyEqseil |
| SC0899 | KRT6B | 12 | 52844205 | T | A | A2402,A2601,B3502,B3801,C0401,C1203 | C1203 | 451 | 646 | lvVdlknky | lvEdlknky |
| SC0899 | BEST3 | 12 | 70087531 | G | T | A2402,A2601,B3502,B3801,C0401,C1203 | A2402 | 166 | 109 | ryvnlNsll | ryvnlTsll |
| SC0899 | BEST3 | 12 | 70087531 | G | T | A2402,A2601,B3502,B3801,C0401,C1203 | C1203 | 109 | 174 | mryvnlNsl | mryvnlTsl |
| SC0899 | BEST3 | 12 | 70087531 | G | T | A2402,A2601,B3502,B3801,C0401,C1203 | C1203 | 47 | 137 | yvnlNslli | yvnlTslli |
| SC0899 | E2F7 | 12 | 77423855 | A | T | A2402,A2601,B3502,B3801,C0401,C1203 | A2402 | 219 | 39 | Eyvpsaslf | Vyvpsaslf |
| SC0899 | E2F7 | 12 | 77423855 | A | T | A2402,A2601,B3502,B3801,C0401,C1203 | C1203 | 48 | 35 | lagqplEyv | lagqplVyv |
| SC0899 | E2F7 | 12 | 77423855 | A | T | A2402,A2601,B3502,B3801,C0401,C1203 | C1203 | 211 | 75 | lEyvpsasl | lVyvpsasl |
| SC0899 | APAF1 | 12 | 99042235 | G | T | A2402,A2601,B3502,B3801,C0401,C1203 | B3801 | 110 | 196 | dhmisdVfl | dhmisdGfl |
| SC0899 | APAF1 | 12 | 99042235 | G | T | A2402,A2601,B3502,B3801,C0401,C1203 | C1203 | 32 | 17 | misdVflti | misdGflti |
| SC0899 | RXFP2 | 13 | 32360742 | C | A | A2402,A2601,B3502,B3801,C0401,C1203 | C1203 | 152 | 105 | Kqfeslkql | Nqfeslkql |
| SC0899 | LCP1 | 13 | 46701733 | C | A | A2402,A2601,B3502,B3801,C0401,C1203 | C1203 | 202 | 576 | lmgkgmkMv | lmgkgmkRv |
| SC0899 | MDGA2 | 14 | 47389309 | T | A | A2402,A2601,B3502,B3801,C0401,C1203 | A2402 | 432 | 924 | tynpvwqlr | tynpvwqNr |

Figure 21 (Cont.)

| | | | | | | | | | | | |
|---|---|---|---|---|---|---|---|---|---|---|---|
| SC0899 | MDGA2 | 14 | 47389309 | T | A | A2402,A2601,B3502,B3801,C0401,C1203 | C1203 | 68 | 8182 | dtynpvwql | dtynpvwqN |
| SC0899 | RHOJ | 14 | 63749899 | C | A | A2402,A2601,B3502,B3801,C0401,C1203 | C1203 | 172 | 551 | llymkekpl | llymkekpL |
| SC0899 | RHOJ | 14 | 63749899 | C | A | A2402,A2601,B3502,B3801,C0401,C1203 | C1203 | 11 | 11 | ymkekplty | ymkekpLty |
| SC0899 | RHOJ | 14 | 63749899 | C | A | A2402,A2601,B3502,B3801,C0401,C1203 | C1203 | 16 | 19 | ltyehgvkl | Ltyehgvkl |
| SC0899 | KCNK10 | 14 | 88729890 | C | A | A2402,A2601,B3502,B3801,C0401,C1203 | C1203 | 5 | 11 | vaFpaaapv | vaVpaaapv |
| SC0899 | BCL11B | 14 | 99641992 | G | A | A2402,A2601,B3502,B3801,C0401,C1203 | C1203 | 334 | 13418 | npmhrllnL | npmhrllnP |
| SC0899 | AHNAK2 | 14 | 105408025 | T | A | A2402,A2601,B3502,B3801,C0401,C1203 | C1203 | 225 | 606 | evmapdvVv | evmapdvEv |
| SC0899 | AHNAK2 | 14 | 105408025 | T | A | A2402,A2601,B3502,B3801,C0401,C1203 | C1203 | 14 | 47 | mapdvVvsl | mapdvEvsl |
| SC0899 | AHNAK2 | 14 | 105408026 | C | G | A2402,A2601,B3502,B3801,C0401,C1203 | C1203 | 48 | 47 | mapdvQvsl | mapdvEvsl |
| SC0899 | ACTC1 | 15 | 35084412 | C | A | A2402,A2601,B3502,B3801,C0401,C1203 | C1203 | 6 | 12 | valdfenel | valdfeneM |
| SC0899 | SLC12A1 | 15 | 48595038 | C | A | A2402,A2601,B3502,B3801,C0401,C1203 | C1203 | 115 | 168 | knlppvllv | knlppvlLv |
| SC0899 | CLN3 | 16 | 28499034 | G | A | A2402,A2601,B3502,B3801,C0401,C1203 | C1203 | 480 | 13855 | vlladilpl | vlladilpT |
| SC0899 | CLN3 | 16 | 28499034 | G | A | A2402,A2601,B3502,B3801,C0401,C1203 | C1203 | 213 | 164 | ladilpllv | ladilpTlv |
| SC0899 | ACD | 16 | 67694101 | A | G | A2402,A2601,B3502,B3801,C0401,C1203 | C1203 | 151 | 74 | magsgrlAl | magsgrlVl |
| SC0899 | FOXF1 | 16 | 86544412 | G | T | A2402,A2601,B3502,B3801,C0401,C1203 | A2402 | 10 | 17 | iyqflHsrf | iyqflQsrf |
| SC0899 | FOXF1 | 16 | 86544412 | G | T | A2402,A2601,B3502,B3801,C0401,C1203 | C1203 | 475 | 1035 | flHsrfpff | flQsrfpff |
| SC0899 | OR1A1 | 17 | 3119711 | G | C | A2402,A2601,B3502,B3801,C0401,C1203 | C1203 | 81 | 119 | Tlkdavitv | Slkdavitv |
| SC0899 | SLC13A2 | 17 | 26817813 | G | A | A2402,A2601,B3502,B3801,C0401,C1203 | C1203 | 40 | 41 | mmvpiahal | mmvpiahaV |
| SC0899 | SLC13A2 | 17 | 26817813 | G | A | A2402,A2601,B3502,B3801,C0401,C1203 | C1203 | 226 | 261 | iahalldql | iahaVldql |
| SC0899 | NF1 | 17 | 29667577 | G | C | A2402,A2601,B3502,B3801,C0401,C1203 | C1203 | 341 | 633 | vavlqlHev | vavlqlDev |
| SC0899 | NF1 | 17 | 29667577 | G | C | A2402,A2601,B3502,B3801,C0401,C1203 | C1203 | 310 | 105 | lqlHevnly | lqlDevnly |
| SC0899 | UNC45B | 17 | 33481660 | G | A | A2402,A2601,B3502,B3801,C0401,C1203 | C1203 | 38 | 17 | fqnnEvall | fqnnGvall |

Figure 21 (Cont.)

| | | | | | | | | | | | |
|---|---|---|---|---|---|---|---|---|---|---|---|
| SC0899 | ACACA | 17 | 35601543 | C | T | A2402,A2601,B3502,B3801,C0401,C1203 | A2601 | 119 | 46 | nlvnvlngy | nlvnvMngy |
| SC0899 | ACACA | 17 | 35601543 | C | T | A2402,A2601,B3502,B3801,C0401,C1203 | C1203 | 136 | 482 | vldnlvnvl | vldnlvnvM |
| SC0899 | KRT16 | 17 | 39768468 | G | T | A2402,A2601,B3502,B3801,C0401,C1203 | C1203 | 30 | 16 | yqrqrHsei | yqrqrPsei |
| SC0899 | KRT16 | 17 | 39768469 | G | T | A2402,A2601,B3502,B3801,C0401,C1203 | C1203 | 13 | 16 | yqrqrTsei | yqrqrPsei |
| SC0899 | C17orf104 | 17 | 42745474 | C | A | A2402,A2601,B3502,B3801,C0401,C1203 | A2402 | 158 | 134 | sfYglmptf | sfSglmptf |
| SC0899 | C17orf104 | 17 | 42745474 | C | A | A2402,A2601,B3502,B3801,C0401,C1203 | C1203 | 97 | 4777 | mmygdnsfY | mmygdnsfS |
| SC0899 | C17orf67 | 17 | 54892240 | T | C | A2402,A2601,B3502,B3801,C0401,C1203 | C1203 | 47 | 17 | fpdGpmrey | fpdEpmrey |
| SC0899 | ACE | 17 | 61562422 | G | T | A2402,A2601,B3502,B3801,C0401,C1203 | C1203 | 159 | 19159 | tahqtsaql | tahqtsaqS |
| SC0899 | ACE | 17 | 61562422 | G | T | A2402,A2601,B3502,B3801,C0401,C1203 | C1203 | 484 | 518 | tsaqlpnlv | tsaqSpnlv |
| SC0899 | CACNA1A | 19 | 13341018 | C | G | A2402,A2601,B3502,B3801,C0401,C1203 | A2402 | 443 | 281 | iflcsflQl | iflcsflMl |
| SC0899 | CACNA1A | 19 | 13341018 | C | G | A2402,A2601,B3502,B3801,C0401,C1203 | C1203 | 158 | 104 | lQlnlfvav | lMlnlfvav |
| SC0899 | CACNA1A | 19 | 13341018 | C | G | A2402,A2601,B3502,B3801,C0401,C1203 | C1203 | 345 | 82 | Qlnlfvavi | Mlnlfvavi |
| SC0899 | ZNF257 | 19 | 22271111 | C | A | A2402,A2601,B3502,B3801,C0401,C1203 | C1203 | 218 | 573 | ksfcmlsKl | ksfcmlsQl |
| SC0899 | ZNF726 | 19 | 24116390 | G | T | A2402,A2601,B3502,B3801,C0401,C1203 | C1203 | 23 | 10 | kaflqsstl | kafSqsstl |
| SC0899 | PSG6 | 19 | 43415001 | G | A | A2402,A2601,B3502,B3801,C0401,C1203 | C1203 | 344 | 104 | ysetLkpsi | ysetPkpsi |
| SC0899 | SHANK1 | 19 | 51207757 | C | A | A2402,A2601,B3502,B3801,C0401,C1203 | A2601 | 17 | 13 | etcaSilly | etcaRilly |
| SC0899 | SHANK1 | 19 | 51207757 | C | A | A2402,A2601,B3502,B3801,C0401,C1203 | C1203 | 54 | 120 | ynketcaSi | ynketcaRi |
| SC0899 | SUV420H2 | 19 | 55855182 | G | T | A2402,A2601,B3502,B3801,C0401,C1203 | C1203 | 248 | 1188 | lLlgpaafi | lWlgpaafi |
| SC0899 | ZNF418 | 19 | 58437573 | C | T | A2402,A2601,B3502,B3801,C0401,C1203 | C1203 | 71 | 61 | ksfhrNssl | ksfhrSssl |
| SC0899 | GALNT14 | 2 | 31215720 | C | T | A2402,A2601,B3502,B3801,C0401,C1203 | C1203 | 7 | 11 | raipNtrhl | raipDtrhl |
| SC0899 | GALNT14 | 2 | 31215720 | C | T | A2402,A2601,B3502,B3801,C0401,C1203 | C1203 | 422 | 537 | Ntrhlrctl | Dtrhlrctl |
| SC0899 | CIAO1 | 2 | 96933172 | A | G | A2402,A2601,B3502,B3801,C0401,C1203 | C1203 | 96 | 100 | asfdatAci | asfdatTci |
| SC0899 | RANBP2 | 2 | 109384632 | G | T | A2402,A2601,B3502,B3801,C0401,C1203 | C1203 | 11 | 50 | fVfsfnapl | fGfsfnapl |

Figure 21 (Cont.)

| | | | | | | | | | | | |
|---|---|---|---|---|---|---|---|---|---|---|---|
| SC0899 | POTEE | 2 | 132021517 | C | T | A2402,A2601,B3502,B3801,C0401,C1203 | A2601 | 2 | 8 | etfntLamy | etfntPamy |
| SC0899 | POTEE | 2 | 132021517 | C | T | A2402,A2601,B3502,B3801,C0401,C1203 | C1203 | 11 | 864 | imfetfntL | imfetfntP |
| SC0899 | POTEE | 2 | 132021517 | C | T | A2402,A2601,B3502,B3801,C0401,C1203 | C1203 | 176 | 143 | etfntLamy | etfntPamy |
| SC0899 | POTEE | 2 | 132021517 | C | T | A2402,A2601,B3502,B3801,C0401,C1203 | C1203 | 234 | 1241 | ntLamyvai | ntPamyvai |
| SC0899 | LCT | 2 | 136566905 | G | C | A2402,A2601,B3502,B3801,C0401,C1203 | A2402 | 342 | 284 | yynrlMngl | yynrlIngl |
| SC0899 | DAPL1 | 2 | 159672269 | C | A | A2402,A2601,B3502,B3801,C0401,C1203 | C1203 | 279 | 602 | mahqkptHa | mahqkptPa |
| SC0899 | DAPL1 | 2 | 159672269 | C | A | A2402,A2601,B3502,B3801,C0401,C1203 | C1203 | 11 | 41 | Halekvvpl | Palekvvpl |
| SC0899 | SCN1A | 2 | 166848638 | C | A | A2402,A2601,B3502,B3801,C0401,C1203 | A2601 | 8 | 2365 | etfgnsmiF | etfgnsmiC |
| SC0899 | SCN1A | 2 | 166848638 | C | A | A2402,A2601,B3502,B3801,C0401,C1203 | C1203 | 384 | 13162 | Flfqittsa | Clfqittsa |
| SC0899 | EVX2 | 2 | 176945532 | C | G | A2402,A2601,B3502,B3801,C0401,C1203 | C1203 | 430 | 573 | rmkdkPqrl | rmkdkRqrl |
| SC0899 | SF3B1 | 2 | 198267359 | C | G | A2402,A2601,B3502,B3801,C0401,C1203 | C1203 | 94 | 42 | qarhtgiNi | qarhtgiKi |
| SC0899 | SIRPA | 20 | 1902125 | G | C | A2402,A2601,B3502,B3801,C0401,C1203 | C1203 | 159 | 9871 | hAfsprdit | hGfsprdit |
| SC0899 | ATRN | 20 | 3515928 | G | A | A2402,A2601,B3502,B3801,C0401,C1203 | C1203 | 128 | 54 | fvtNgpgny | fvtDgpgny |
| SC0899 | PLCB1 | 20 | 8698454 | G | T | A2402,A2601,B3502,B3801,C0401,C1203 | A2402 | 101 | 170 | tyldsssmf | tySdsssmf |
| SC0899 | PLCB1 | 20 | 8698454 | G | T | A2402,A2601,B3502,B3801,C0401,C1203 | C1203 | 272 | 81 | ntyldsssm | ntySdsssm |
| SC0899 | BFSP1 | 20 | 17474787 | C | A | A2402,A2601,B3502,B3801,C0401,C1203 | A2601 | 55 | 45 | etaLivetm | etaVivetm |
| SC0899 | BFSP1 | 20 | 17474787 | C | A | A2402,A2601,B3502,B3801,C0401,C1203 | C1203 | 17 | 11 | qtyeetaLi | qtyeetaVi |
| SC0899 | BFSP1 | 20 | 17474787 | C | A | A2402,A2601,B3502,B3801,C0401,C1203 | C1203 | 229 | 609 | taLivetmi | taVivetmi |
| SC0899 | PREX1 | 20 | 47307566 | A | T | A2402,A2601,B3502,B3801,C0401,C1203 | C1203 | 488 | 2603 | ntaknkRfv | ntaknkWfv |
| SC0899 | BCAS1 | 20 | 52674630 | C | G | A2402,A2601,B3502,B3801,C0401,C1203 | A2601 | 133 | 334 | htvqhlQev | htvqhlEev |
| SC0899 | BCAS1 | 20 | 52674630 | C | G | A2402,A2601,B3502,B3801,C0401,C1203 | C1203 | 214 | 303 | htvqhlQev | htvqhlEev |
| SC0899 | DIP2A | 21 | 47910627 | G | A | A2402,A2601,B3502,B3801,C0401,C1203 | C1203 | 446 | 302 | Qsdvhteav | Rsdvhteav |

Figure 21 (Cont.)

| | | | | | | | | | | | |
|---|---|---|---|---|---|---|---|---|---|---|---|
| SC0899 | SLC6A1 | 3 | 11070466 | T | G | A2402,A2601,B3502,B3801,C0401,C1203 | C1203 | 426 | 1576 | vtqRpispl | vtqLpispl |
| SC0899 | KCNH8 | 3 | 19436692 | C | A | A2402,A2601,B3502,B3801,C0401,C1203 | B3801 | 98 | 114 | qhstivMtl | qhstivLtl |
| SC0899 | KCNH8 | 3 | 19436692 | C | A | A2402,A2601,B3502,B3801,C0401,C1203 | C1203 | 28 | 32 | ysqhstivM | ysqhstivL |
| SC0899 | KCNH8 | 3 | 19575272 | A | C | A2402,A2601,B3502,B3801,C0401,C1203 | C1203 | 180 | 601 | yqvvPeghl | yqvvQeghl |
| SC0899 | ADAMTS9 | 3 | 64527039 | C | A | A2402,A2601,B3502,B3801,C0401,C1203 | C1203 | 178 | 55 | hpkeyvtlL | hpkeyvtlV |
| SC0899 | CD96 | 3 | 111261127 | A | G | A2402,A2601,B3502,B3801,C0401,C1203 | A2402 | 19 | 9 | kycavCyii | kycavYyii |
| SC0899 | CD96 | 3 | 111261127 | A | G | A2402,A2601,B3502,B3801,C0401,C1203 | A2402 | 215 | 86 | Cyiiqihfv | Yyiiqihfv |
| SC0899 | CD96 | 3 | 111261127 | A | G | A2402,A2601,B3502,B3801,C0401,C1203 | C1203 | 92 | 94 | wkycavCyi | wkycavYyi |
| SC0899 | CD96 | 3 | 111261127 | A | G | A2402,A2601,B3502,B3801,C0401,C1203 | C1203 | 377 | 824 | cavCyiiqi | cavYyiiqi |
| SC0899 | INPP4B | 4 | 143226677 | C | A | A2402,A2601,B3502,B3801,C0401,C1203 | A2402 | 210 | 500 | rsflVyasf | rsflGyasf |
| SC0899 | DDX60L | 4 | 169393038 | C | A | A2402,A2601,B3502,B3801,C0401,C1203 | A2601 | 173 | 48 | fviYgdsll | fviDgdsll |
| SC0899 | DDX60L | 4 | 169393038 | C | A | A2402,A2601,B3502,B3801,C0401,C1203 | C1203 | 191 | 26 | fviYgdsll | fviDgdsll |
| SC0899 | DDX60L | 4 | 169393038 | C | A | A2402,A2601,B3502,B3801,C0401,C1203 | C1203 | 203 | 3070 | viYgdsllv | viDgdsllv |
| SC0899 | EXOC3 | 5 | 465834 | G | T | A2402,A2601,B3502,B3801,C0401,C1203 | C1203 | 12 | 4723 | flfrklasV | flfrklasG |
| SC0899 | EXOC3 | 5 | 465834 | G | T | A2402,A2601,B3502,B3801,C0401,C1203 | C1203 | 218 | 141 | lasVfgedv | lasGfgedv |
| SC0899 | CDH18 | 5 | 19483509 | C | G | A2402,A2601,B3502,B3801,C0401,C1203 | C1203 | 82 | 140 | cacerdRrv | cacerdGrv |
| SC0899 | ARL15 | 5 | 53182509 | C | T | A2402,A2601,B3502,B3801,C0401,C1203 | C1203 | 481 | 754 | laHgkrwil | laRgkrwil |
| SC0899 | SV2C | 5 | 75490923 | G | T | A2402,A2601,B3502,B3801,C0401,C1203 | C1203 | 473 | 3821 | Wiggaiptv | Giggaiptv |
| SC0899 | PCDHA1 | 5 | 140167728 | C | A | A2402,A2601,B3502,B3801,C0401,C1203 | C1203 | 285 | 246 | qpaaggEri | qpaaggAri |
| SC0899 | PCDHA6 | 5 | 140208447 | C | G | A2402,A2601,B3502,B3801,C0401,C1203 | C1203 | 273 | 120 | enadKgttv | enadNgttv |
| SC0899 | PCDHA6 | 5 | 140208447 | C | G | A2402,A2601,B3502,B3801,C0401,C1203 | C1203 | 10 | 6 | nadKgttvi | nadNgttvi |
| SC0899 | PCDHA13 | 5 | 140263558 | G | T | A2402,A2601,B3502,B3801,C0401,C1203 | C1203 | 22 | 294 | Wagsaggtv | Gagsaggtv |
| SC0899 | PCDHGA10 | 5 | 140794720 | G | T | A2402,A2601,B3502,B3801,C0401,C1203 | C1203 | 258 | 200 | lsStvtltv | lsAtvtltv |

Figure 21 (Cont.)

| | | | | | | | | | | | |
|---|---|---|---|---|---|---|---|---|---|---|---|
| SC0899 | JAKMIP2 | 5 | 147011044 | G | C | A2402,A2601,B3502,B3801,C0401,C1203 | C1203 | 210 | 386 | rsppfnVqi | rsppfnLqi |
| SC0899 | SOX30 | 5 | 157078764 | C | A | A2402,A2601,B3502,B3801,C0401,C1203 | C1203 | 323 | 439 | lqfrpdlLl | lqfrpdlRl |
| SC0899 | EBF1 | 5 | 158250240 | C | A | A2402,A2601,B3502,B3801,C0401,C1203 | C1203 | 8 | 2019 | fvhnnskhV | fvhnnskhG |
| SC0899 | F13A1 | 6 | 6182342 | C | A | A2402,A2601,B3502,B3801,C0401,C1203 | C1203 | 21 | 28 | taNkdgthv | taKkdgthv |
| SC0899 | TNXB | 6 | 32029942 | C | A | A2402,A2601,B3502,B3801,C0401,C1203 | C1203 | 272 | 22777 | rvgpvsaiV | rvgpvsaiG |
| SC0899 | TFAP2D | 6 | 50712883 | C | A | A2402,A2601,B3502,B3801,C0401,C1203 | C1203 | 114 | 471 | pakEvgehl | pakAvgehl |
| SC0899 | BAI3 | 6 | 70034812 | T | A | A2402,A2601,B3502,B3801,C0401,C1203 | A2402 | 432 | 306 | ffflaTfcw | ffflaSfcw |
| SC0899 | BAI3 | 6 | 70034812 | T | A | A2402,A2601,B3502,B3801,C0401,C1203 | C1203 | 222 | 1060 | lhffflaTf | lhffflaSf |
| SC0899 | GPR31 | 6 | 167571255 | C | A | A2402,A2601,B3502,B3801,C0401,C1203 | C1203 | 280 | 3661 | tavgvllVl | tavgvllGl |
| SC0899 | NFE2L3 | 7 | 26225102 | G | A | A2402,A2601,B3502,B3801,C0401,C1203 | C1203 | 118 | 6319 | Yrkrkldii | Crkrkldii |
| SC0899 | ABCA13 | 7 | 48619855 | G | T | A2402,A2601,B3502,B3801,C0401,C1203 | C1203 | 88 | 1930 | lssagtaVv | lssagtaGv |
| SC0899 | ABCA13 | 7 | 48619855 | G | T | A2402,A2601,B3502,B3801,C0401,C1203 | C1203 | 246 | 351 | sagtaVvli | sagtaGvli |
| SC0899 | KIAA1147 | 7 | 141385414 | A | T | A2402,A2601,B3502,B3801,C0401,C1203 | A2402 | 41 | 38 | iyfrkgpfl | iyfrkgpfF |
| SC0899 | KIAA1147 | 7 | 141385414 | A | T | A2402,A2601,B3502,B3801,C0401,C1203 | C1203 | 204 | 1424 | iyfrkgpfl | iyfrkgpfF |
| SC0899 | PXDNL | 8 | 52321067 | G | C | A2402,A2601,B3502,B3801,C0401,C1203 | C1203 | 215 | 145 | npKvnagii | npNvnagii |
| SC0899 | ZFHX4 | 8 | 77768099 | G | T | A2402,A2601,B3502,B3801,C0401,C1203 | C0401 | 473 | 696 | wfqnaMake | wfqnaRake |
| SC0899 | ZFHX4 | 8 | 77768099 | G | T | A2402,A2601,B3502,B3801,C0401,C1203 | C1203 | 147 | 519 | naMakekkf | naRakekkf |
| SC0899 | ZFHX4 | 8 | 77768099 | G | T | A2402,A2601,B3502,B3801,C0401,C1203 | C1203 | 29 | 56 | Makekkfki | Rakekkfki |
| SC0899 | MMP16 | 8 | 89179940 | C | A | A2402,A2601,B3502,B3801,C0401,C1203 | A2402 | 34 | 12532 | fYsdepwtl | fDsdepwtl |
| SC0899 | MMP16 | 8 | 89179940 | C | A | A2402,A2601,B3502,B3801,C0401,C1203 | B3801 | 452 | 227 | thfYsdepw | thfDsdepw |
| SC0899 | MMP16 | 8 | 89179940 | C | A | A2402,A2601,B3502,B3801,C0401,C1203 | C1203 | 170 | 620 | fYsdepwtl | fDsdepwtl |
| SC0899 | FER1L6 | 8 | 125072911 | C | A | A2402,A2601,B3502,B3801,C0401,C1203 | C1203 | 180 | 101 | ykKnpnfsi | ykNnpnfsi |

Figure 21 (Cont.)

| | | | | | | | | | | | |
|---|---|---|---|---|---|---|---|---|---|---|---|
| SC0899 | SPATA31A6 | 9 | 43627729 | G | T | A2402,A2601,B3502,B3801,C0401,C1203 | C1203 | 27 | 36 | lssdgqnvv | Lssdgqnvv |
| SC0899 | IKBKAP | 9 | 111642394 | C | T | A2402,A2601,B3502,B3801,C0401,C1203 | C1203 | 98 | 121 | fsHhkkrll | fsRhkkrll |
| SC0899 | C5 | 9 | 123768218 | G | C | A2402,A2601,B3502,B3801,C0401,C1203 | A2402 | 204 | 499 | Kyrtsgmqf | Nyrtsgmqf |
| SC0899 | REXO4 | 9 | 136277597 | T | A | A2402,A2601,B3502,B3801,C0401,C1203 | C1203 | 94 | 490 | raFaldcem | raLaldcem |
| SC0899 | REXO4 | 9 | 136277597 | T | A | A2402,A2601,B3502,B3801,C0401,C1203 | C1203 | 343 | 3516 | Faldcemvg | Laldcemvg |
| SC0899 | MAGED1 | X | 51640346 | A | G | A2402,A2601,B3502,B3801,C0401,C1203 | C1203 | 377 | 297 | lmlkdytEv | lmlkdytKv |
| SC0899 | SPIN4 | X | 62570670 | C | A | A2402,A2601,B3502,B3801,C0401,C1203 | A2601 | 3 | 1315 | mVvdgvsay | mGvdgvsay |
| SC0899 | SPIN4 | X | 62570670 | C | A | A2402,A2601,B3502,B3801,C0401,C1203 | C1203 | 36 | 343 | mVvdgvsay | mGvdgvsay |
| SC0899 | SPIN4 | X | 62570671 | C | A | A2402,A2601,B3502,B3801,C0401,C1203 | C0401 | 136 | 1043 | Wvdgvsayl | Gvdgvsayl |
| SC0899 | DLG3 | X | 69712022 | A | G | A2402,A2601,B3502,B3801,C0401,C1203 | C1203 | 63 | 160 | lsfsCgdil | lsfsYgdil |
| SC0899 | DLG3 | X | 69712022 | A | G | A2402,A2601,B3502,B3801,C0401,C1203 | C1203 | 13 | 5 | fsCgdilhv | fsYgdilhv |
| SC0899 | NLGN3 | X | 70389502 | C | A | A2402,A2601,B3502,B3801,C0401,C1203 | B3801 | 239 | 13919 | nHrdystel | nPrdystel |
| SC0899 | GPR174 | X | 78426833 | T | C | A2402,A2601,B3502,B3801,C0401,C1203 | A2402 | 79 | 13 | myasiyflA | myasiyflV |
| SC0899 | GPR174 | X | 78426833 | T | C | A2402,A2601,B3502,B3801,C0401,C1203 | A2402 | 314 | 313 | iyflAcisv | iyflVcisv |
| SC0899 | CHM | X | 85211182 | C | G | A2402,A2601,B3502,B3801,C0401,C1203 | C1203 | 272 | 433 | fplygqAel | fplygqGel |
| SC0899 | DCAF12L2 | X | 125299165 | C | G | A2402,A2601,B3502,B3801,C0401,C1203 | C1203 | 17 | 19 | yahirpTdv | yahirpRdv |
| SC0899 | MCF2 | X | 138701864 | A | T | A2402,A2601,B3502,B3801,C0401,C1203 | C1203 | 16 | 41 | feqdfqqHv | feqdfqqLv |
| SC0899 | MAGEA4 | X | 151092550 | G | T | A2402,A2601,B3502,B3801,C0401,C1203 | C1203 | 243 | 230 | kaemlDrvi | kaemlErvi |
| SC6470 | NBPF9 | 1 | 144816504 | C | G | A3002,A3101,B1801,B3502,C0401,C0501 | A3101 | 371 | 22533 | mqkaeekeR | mqkaeekeV |
| SC6470 | FLG | 1 | 152285803 | G | T | A3002,A3101,B1801,B3502,C0401,C0501 | A3101 | 208 | 2949 | hQgssrggr | hPgssrggr |
| SC6470 | SPTA1 | 1 | 158644392 | C | A | A3002,A3101,B1801,B3502,C0401,C0501 | A3101 | 373 | 7371 | ktaainaYe | ktaainaDe |
| SC6470 | PIGR | 1 | 207110547 | G | C | A3002,A3101,B1801,B3502,C0401,C0501 | A3101 | 106 | 349 | fsvviRglr | fsvviTglr |
| SC6470 | PLXNA2 | 1 | 208217896 | C | G | A3002,A3101,B1801,B3502,C0401,C0501 | C0501 | 168 | 187 | Hmdnlesrv | Qmdnlesrv |

Figure 21 (Cont.)

| | | | | | | | | | | | |
|---|---|---|---|---|---|---|---|---|---|---|---|
| SC6470 | HHIPL2 | 1 | 222717161 | C | A | A3002,A3101,B1801,B3502,C0401,C0501 | C0501 | 356 | 898 | agdgthLff | agdgthRff |
| SC6470 | WNT9A | 1 | 228111890 | G | C | A3002,A3101,B1801,B3502,C0401,C0501 | A3101 | 32 | 120 | rsRkdlrar | rsSkdlrar |
| SC6470 | ZNF248 | 10 | 38121275 | C | A | A3002,A3101,B1801,B3502,C0401,C0501 | B1801 | 73 | 316 | weNsallkh | weKsallkh |
| SC6470 | CTNNA3 | 10 | 68940230 | G | T | A3002,A3101,B1801,B3502,C0401,C0501 | B1801 | 103 | 51 | teeeirTsl | teeeirPsl |
| SC6470 | SLC17A6 | 11 | 22396404 | C | A | A3002,A3101,B1801,B3502,C0401,C0501 | A3101 | 29 | 4899 | rskqilstK | rskqilstT |
| SC6470 | SLC17A6 | 11 | 22396404 | C | A | A3002,A3101,B1801,B3502,C0401,C0501 | A3101 | 121 | 245 | qilstKtvr | qilstTtvr |
| SC6470 | ATM | 11 | 108205736 | A | T | A3002,A3101,B1801,B3502,C0401,C0501 | A3101 | 98 | 73 | iLsfkaefr | iQsfkaefr |
| SC6470 | NALCN | 13 | 101910811 | C | G | A3002,A3101,B1801,B3502,C0401,C0501 | A3101 | 359 | 971 | rqydQfyla | rqydEfyla |
| SC6470 | CLEC14A | 14 | 38724241 | C | A | A3002,A3101,B1801,B3502,C0401,C0501 | B1801 | 84 | 111 | deklgDtpl | deklgEtpl |
| SC6470 | DDHD1 | 14 | 53513592 | G | A | A3002,A3101,B1801,B3502,C0401,C0501 | A3101 | 94 | 168 | rywsavtLh | rywsavtSh |
| SC6470 | RTN1 | 14 | 60212641 | A | T | A3002,A3101,B1801,B3502,C0401,C0501 | C0501 | 139 | 278 | yiddHseeq | yiddLseeq |
| SC6470 | KIAA0247 | 14 | 70175433 | G | T | A3002,A3101,B1801,B3502,C0401,C0501 | C0501 | 21 | 8 | Ivdgvqval | Mvdgvqval |
| SC6470 | YLPM1 | 14 | 75295987 | G | T | A3002,A3101,B1801,B3502,C0401,C0501 | A3002 | 38 | 129 | aiasrmeYy | aiasrmeDy |
| SC6470 | YLPM1 | 14 | 75295987 | G | T | A3002,A3101,B1801,B3502,C0401,C0501 | B1801 | 54 | 2048 | meYylqlpd | meDylqlpd |
| SC6470 | EIF2AK4 | 15 | 40259896 | G | T | A3002,A3101,B1801,B3502,C0401,C0501 | A3002 | 204 | 19420 | rladickeY | rladickeD |
| SC6470 | EIF2AK4 | 15 | 40259896 | G | T | A3002,A3101,B1801,B3502,C0401,C0501 | A3101 | 383 | 5343 | keYvfeqtr | keDvfeqtr |
| SC6470 | EIF2AK4 | 15 | 40259896 | G | T | A3002,A3101,B1801,B3502,C0401,C0501 | A3101 | 446 | 4799 | Yvfeqtrvr | Dvfeqtrvr |
| SC6470 | EIF2AK4 | 15 | 40259896 | G | T | A3002,A3101,B1801,B3502,C0401,C0501 | C0501 | 7 | 122 | ladickeYv | ladickeDv |
| SC6470 | TGM7 | 15 | 43585770 | G | T | A3002,A3101,B1801,B3502,C0401,C0501 | A3101 | 285 | 50 | Ntqemgvkr | Htqemgvkr |
| SC6470 | FBN1 | 15 | 48712954 | G | T | A3002,A3101,B1801,B3502,C0401,C0501 | A3002 | 239 | 107 | gcqKiiggy | gcqNiiggy |
| SC6470 | FBN1 | 15 | 48712954 | G | T | A3002,A3101,B1801,B3502,C0401,C0501 | A3101 | 19 | 22 | cqKiiggyr | cqNiiggyr |
| SC6470 | PEMT | 17 | 17409560 | C | T | A3002,A3101,B1801,B3502,C0401,C0501 | A3002 | 84 | 60 | ltyiMally | ltyiVally |

Figure 21 (Cont.)

| | | | | | | | | | | | |
|---|---|---|---|---|---|---|---|---|---|---|---|
| SC6470 | GRAP | 17 | 18925411 | T | A | A3002,A3101,B1801,B3502,C0401,C0501 | C0501 | 10 | 363 | aLdpsqlsf | aQdpsqlsf |
| SC6470 | TBC1D3C | 17 | 36339597 | G | T | A3002,A3101,B1801,B3502,C0401,C0501 | A3101 | 434 | 11547 | smkkltrkK | smkkltrkQ |
| SC6470 | RALBP1 | 18 | 9535817 | C | T | A3002,A3101,B1801,B3502,C0401,C0501 | A3101 | 92 | 80 | rggVvqppr | rggAvqppr |
| SC6470 | WDR7 | 18 | 54363499 | G | T | A3002,A3101,B1801,B3502,C0401,C0501 | A3101 | 22 | 70 | rtlrChmk | rtlrGhmk |
| SC6470 | MFSD12 | 19 | 3550983 | T | A | A3002,A3101,B1801,B3502,C0401,C0501 | B1801 | 168 | 2450 | veltalWya | veltalRya |
| SC6470 | ZNF536 | 19 | 30934536 | G | A | A3002,A3101,B1801,B3502,C0401,C0501 | A3002 | 99 | 436 | sSpvlngqy | sGpvlngqy |
| SC6470 | LRP3 | 19 | 33698018 | C | T | A3002,A3101,B1801,B3502,C0401,C0501 | A3101 | 9 | 10 | lfhrprVpr | lfhrprApr |
| SC6470 | ATP4A | 19 | 36044635 | G | T | A3002,A3101,B1801,B3502,C0401,C0501 | A3002 | 46 | 65 | lvnepMaay | lvnepLaay |
| SC6470 | ATP4A | 19 | 36044635 | G | T | A3002,A3101,B1801,B3502,C0401,C0501 | B1801 | 6 | 6 | nepMaaysy | nepLaaysy |
| SC6470 | ZNF569 | 19 | 37904959 | G | T | A3002,A3101,B1801,B3502,C0401,C0501 | A3101 | 97 | 145 | tldlirhlr | tldLirhlr |
| SC6470 | PSG6 | 19 | 43411094 | G | T | A3002,A3101,B1801,B3502,C0401,C0501 | A3002 | 93 | 12838 | atgkeiskY | atgkeiskS |
| SC6470 | ZNF230 | 19 | 44515389 | A | T | A3002,A3101,B1801,B3502,C0401,C0501 | A3101 | 179 | 223 | kecgkCfsr | kecgkSfsr |
| SC6470 | SPACA4 | 19 | 49110490 | C | A | A3002,A3101,B1801,B3502,C0401,C0501 | A3101 | 6 | 5141 | vsyrgvtyR | vsyrgvtyS |
| SC6470 | ZNF154 | 19 | 58213656 | C | T | A3002,A3101,B1801,B3502,C0401,C0501 | C0501 | 217 | 56 | ecdKcgklf | ecdEcgklf |
| SC6470 | RRM2 | 2 | 10262920 | T | G | A3002,A3101,B1801,B3502,C0401,C0501 | A3101 | 139 | 158 | caAtmlslr | caStmlslr |
| SC6470 | FAM161A | 2 | 62069257 | C | A | A3002,A3101,B1801,B3502,C0401,C0501 | A3002 | 59 | 40 | lsvseknsy | Rsvseknsy |
| SC6470 | FAM161A | 2 | 62069257 | C | A | A3002,A3101,B1801,B3502,C0401,C0501 | C0501 | 369 | 489 | lsdssisvs | lsdssRsvs |
| SC6470 | IL1R2 | 2 | 102644772 | G | T | A3002,A3101,B1801,B3502,C0401,C0501 | A3101 | 350 | 344 | giwmhrLck | giwmhrRck |
| SC6470 | IL1R2 | 2 | 102644772 | G | T | A3002,A3101,B1801,B3502,C0401,C0501 | A3101 | 109 | 64 | wmhrLckhr | wmhrRckhr |
| SC6470 | IL1R2 | 2 | 102644772 | G | T | A3002,A3101,B1801,B3502,C0401,C0501 | A3101 | 28 | 1700 | rLckhrtgk | rRckhrtgk |
| SC6470 | RANBP2 | 2 | 109368093 | A | T | A3002,A3101,B1801,B3502,C0401,C0501 | A3101 | 399 | 704 | vckLlcter | vckQlcter |
| SC6470 | DYTN | 2 | 207530641 | G | T | A3002,A3101,B1801,B3502,C0401,C0501 | A3101 | 43 | 2161 | rihklktnK | rihklktnQ |
| SC6470 | D2HGDH | 2 | 242695312 | G | T | A3002,A3101,B1801,B3502,C0401,C0501 | A3002 | 17 | 28 | alsrdCyvy | alsrdGyvy |

Figure 21 (Cont.)

| | | | | | | | | | | | |
|---|---|---|---|---|---|---|---|---|---|---|---|
| SC6470 | D2HGDH | 2 | 242695312 | G | T | A3002,A3101,B1801,B3502,C0401,C0501 | A3101 | 19 | 57 | lsrdCyvyk | lsrdGyvyk |
| SC6470 | D2HGDH | 2 | 242695312 | G | T | A3002,A3101,B1801,B3502,C0401,C0501 | B1801 | 334 | 401 | tealsrdCy | tealsrdGy |
| SC6470 | CHGB | 20 | 5903391 | G | A | A3002,A3101,B1801,B3502,C0401,C0501 | A3101 | 19 | 19 | tqnaflnKr | tqnaflnEr |
| SC6470 | EMILIN3 | 20 | 39991683 | G | T | A3002,A3101,B1801,B3502,C0401,C0501 | A3101 | 238 | 1109 | kgTglfger | kgPglfger |
| SC6470 | CDH22 | 20 | 44869868 | C | T | A3002,A3101,B1801,B3502,C0401,C0501 | B1801 | 17 | 8 | degdEaiky | degdGaiky |
| SC6470 | CDH22 | 20 | 44869868 | C | T | A3002,A3101,B1801,B3502,C0401,C0501 | C0501 | 19 | 11 | dsdegdEai | dsdegdGai |
| SC6470 | MYT1 | 20 | 62839656 | G | A | A3002,A3101,B1801,B3502,C0401,C0501 | B1801 | 55 | 47 | deselqdmm | deseMqdmm |
| SC6470 | MYT1 | 20 | 62839656 | G | A | A3002,A3101,B1801,B3502,C0401,C0501 | C0501 | 442 | 379 | vtdeselqd | vtdeseMqd |
| SC6470 | SCN10A | 3 | 38739105 | C | T | A3002,A3101,B1801,B3502,C0401,C0501 | A3101 | 123 | 759 | rsyvlhHsm | rsyvlhRsm |
| SC6470 | PROS1 | 3 | 93593123 | C | A | A3002,A3101,B1801,B3502,C0401,C0501 | A3101 | 78 | 279 | hsFpsvwkk | hsCpsvwkk |
| SC6470 | EPHA6 | 3 | 96963032 | G | A | A3002,A3101,B1801,B3502,C0401,C0501 | C0501 | 288 | 161 | fvshMnytf | fvshVnytf |
| SC6470 | LPHN3 | 4 | 62849284 | G | T | A3002,A3101,B1801,B3502,C0401,C0501 | A3002 | 469 | 300 | vavsSavdy | vavsAavdy |
| SC6470 | LPHN3 | 4 | 62849284 | G | T | A3002,A3101,B1801,B3502,C0401,C0501 | A3002 | 36 | 101 | sSavdyrsy | sAavdyrsy |
| SC6470 | LPHN3 | 4 | 62849284 | G | T | A3002,A3101,B1801,B3502,C0401,C0501 | A3101 | 66 | 58 | avsSavdyr | avsAavdyr |
| SC6470 | CDH9 | 5 | 26915972 | C | G | A3002,A3101,B1801,B3502,C0401,C0501 | C0501 | 98 | 225 | tgdgPgslf | tgdgAgslf |
| SC6470 | ITGA1 | 5 | 52235469 | C | A | A3002,A3101,B1801,B3502,C0401,C0501 | B1801 | 49 | 8630 | fedpfsinY | fedpfsinS |
| SC6470 | ITGA1 | 5 | 52235469 | C | A | A3002,A3101,B1801,B3502,C0401,C0501 | C0501 | 403 | 13055 | fedpfsinY | fedpfsinS |
| SC6470 | PCDHB13 | 5 | 140594221 | A | T | A3002,A3101,B1801,B3502,C0401,C0501 | A3002 | 362 | 19599 | ienyiispY | ienyiispN |
| SC6470 | PCDHB13 | 5 | 140594221 | A | T | A3002,A3101,B1801,B3502,C0401,C0501 | A3002 | 159 | 408 | nyiispYsy | nyiispNsy |
| SC6470 | PCDHB13 | 5 | 140594221 | A | T | A3002,A3101,B1801,B3502,C0401,C0501 | A3101 | 8 | 17 | iispYsyfr | iispNsyfr |
| SC6470 | PCDHB13 | 5 | 140594221 | A | T | A3002,A3101,B1801,B3502,C0401,C0501 | A3101 | 29 | 49 | Ysyfrvltr | Nsyfrvltr |
| SC6470 | PCDHB13 | 5 | 140594221 | A | T | A3002,A3101,B1801,B3502,C0401,C0501 | B1801 | 5 | 1049 | ienyiispY | ienyiispN |

Figure 21 (Cont.)

| | | | | | | | | | | | |
|---|---|---|---|---|---|---|---|---|---|---|---|
| SC6470 | PCDHB13 | 5 | 140594221 | A | T | A3002,A3101,B1801,B3502,C0401,C0501 | C0501 | 362 | 94 | yiispYsyf | yiispNsyf |
| SC6470 | PCDHGB3 | 5 | 140750682 | G | C | A3002,A3101,B1801,B3502,C0401,C0501 | A3101 | 176 | 133 | pLftqdmyr | pVftqdmyr |
| SC6470 | PCDHGB6 | 5 | 140789355 | C | A | A3002,A3101,B1801,B3502,C0401,C0501 | A3101 | 395 | 129 | afEltlqar | afAltlqar |
| SC6470 | FAM71B | 5 | 156592647 | G | C | A3002,A3101,B1801,B3502,C0401,C0501 | A3101 | 21 | 14177 | klvyllrpR | klvyllrpP |
| SC6470 | MDGA1 | 6 | 37612360 | C | A | A3002,A3101,B1801,B3502,C0401,C0501 | A3101 | 25 | 126 | ltdnfYwtr | ltdnfDwtr |
| SC6470 | PTCHD4 | 6 | 47847267 | G | A | A3002,A3101,B1801,B3502,C0401,C0501 | A3002 | 297 | 577 | tshheMnpy | tshheTnpy |
| SC6470 | FRMD1 | 6 | 168461569 | G | T | A3002,A3101,B1801,B3502,C0401,C0501 | A3002 | 83 | 10059 | ytsgikanY | ytsgikanS |
| SC6470 | FRMD1 | 6 | 168461569 | G | T | A3002,A3101,B1801,B3502,C0401,C0501 | A3101 | 11 | 25 | gikanYwlr | gikanSwlr |
| SC6470 | FRMD1 | 6 | 168461569 | G | T | A3002,A3101,B1801,B3502,C0401,C0501 | A3101 | 45 | 205 | anYwlresr | anSwlresr |
| SC6470 | SDK1 | 7 | 4285348 | G | T | A3002,A3101,B1801,B3502,C0401,C0501 | A3002 | 204 | 1987 | sYedicnky | sDedicnky |
| SC6470 | SDK1 | 7 | 4285348 | G | T | A3002,A3101,B1801,B3502,C0401,C0501 | B1801 | 233 | 17763 | spgglhysY | spgglhysD |
| SC6470 | RSPH10B2 | 7 | 5966067 | G | T | A3002,A3101,B1801,B3502,C0401,C0501 | C0501 | 424 | 82 | ildTpkedv | ildPpkedv |
| SC6470 | HIP1 | 7 | 75228508 | C | T | A3002,A3101,B1801,B3502,C0401,C0501 | A3101 | 426 | 296 | vavkekhTr | vavkekhAr |
| SC6470 | SEMA3D | 7 | 84636171 | G | T | A3002,A3101,B1801,B3502,C0401,C0501 | A3002 | 422 | 264 | sqKatikwy | sqQatikwy |
| SC6470 | MBLAC1 | 7 | 99725088 | C | G | A3002,A3101,B1801,B3502,C0401,C0501 | A3002 | 158 | 373 | svvvVlqgy | svvvLlqgy |
| SC6470 | PPP1R3A | 7 | 113518704 | C | G | A3002,A3101,B1801,B3502,C0401,C0501 | B1801 | 163 | 23 | Hemekeetm | Demekeetm |
| SC6470 | NUP205 | 7 | 135269607 | A | T | A3002,A3101,B1801,B3502,C0401,C0501 | C0501 | 292 | 11 | eadVamael | eadEamael |
| SC6470 | CSMD1 | 8 | 2807790 | C | T | A3002,A3101,B1801,B3502,C0401,C0501 | A3101 | 243 | 366 | gqadifvNk | gqadifvSk |
| SC6470 | CSMD1 | 8 | 2807790 | C | T | A3002,A3101,B1801,B3502,C0401,C0501 | C0501 | 52 | 13 | qadifvNkf | qadifvSkf |
| SC6470 | PRUNE2 | 9 | 79323154 | C | T | A3002,A3101,B1801,B3502,C0401,C0501 | B1801 | 338 | 262 | deeeviTsg | deeeviAsg |
| SC6470 | PRUNE2 | 9 | 79323154 | C | T | A3002,A3101,B1801,B3502,C0401,C0501 | C0501 | 316 | 530 | hldeeeviT | hldeeeviA |
| SC6470 | COL27A1 | 9 | 116931019 | C | T | A3002,A3101,B1801,B3502,C0401,C0501 | A3101 | 21 | 38 | ktapsLftk | ktapsSftk |
| SC6470 | TLR4 | 9 | 120475888 | G | T | A3002,A3101,B1801,B3502,C0401,C0501 | C0501 | 2 | 17 | ftDlmltf | ftElmltf |

Figure 21 (Cont.)

| | | | | | | | | | | | |
|---|---|---|---|---|---|---|---|---|---|---|---|
| SC6470 | P2RY8 | X | 1585019 | C | A | A3002,A3101,B1801,B3502,C0401,C0501 | C0501 | 319 | 417 | vaacSgtwl | vaacAgtwl |
| SC6470 | ARHGAP6 | X | 11157289 | A | C | A3002,A3101,B1801,B3502,C0401,C0501 | A3101 | 139 | 52 | cqrphgRgr | cqrphgSgr |
| SC6470 | MAGEB3 | X | 30254946 | C | A | A3002,A3101,B1801,B3502,C0401,C0501 | B1801 | 278 | 20784 | sEfqfwyee | sAfqfwyee |
| SC6470 | TRO | X | 54956263 | A | T | A3002,A3101,B1801,B3502,C0401,C0501 | A3002 | 150 | 13027 | gyggavstY | gyggavstN |
| SC6470 | TRO | X | 54956263 | A | T | A3002,A3101,B1801,B3502,C0401,C0501 | C0501 | 4 | 212 | Ytdfggtls | Ntdfggtls |
| SI9946_2 | KAZN | 1 | 15430679 | C | T | A2601,A0206,B3502,B4801,C0401,C0803 | A0206 | 145 | 46 | emsavfhLa | emsavfhPa |
| SI9946_2 | CEP85 | 1 | 26601486 | G | C | A2601,A0206,B3502,B4801,C0401,C0803 | A0206 | 198 | 177 | aqeeAtsqa | aqeeGtsqa |
| SI9946_2 | CLDN19 | 1 | 43201701 | C | A | A2601,A0206,B3502,B4801,C0401,C0803 | A0206 | 133 | 2608 | aSyefgpal | aRyefgpal |
| SI9946_2 | IPO9 | 1 | 201798378 | C | T | A2601,A0206,B3502,B4801,C0401,C0803 | A0206 | 82 | 2471 | aasglLgpv | aasglPgpv |
| SI9946_2 | IPO9 | 1 | 201798378 | C | T | A2601,A0206,B3502,B4801,C0401,C0803 | A0206 | 201 | 17853 | lLgpvaqgl | lPgpvaqgl |
| SI9946_2 | OBSCN | 1 | 228528221 | G | T | A2601,A0206,B3502,B4801,C0401,C0803 | B4801 | 405 | 261 | kkyaeDall | kkyaeEall |
| SI9946_2 | ANKRD2 | 10 | 99332530 | G | T | A2601,A0206,B3502,B4801,C0401,C0803 | A0206 | 32 | 8 | kapealCpa | kapealWpa |
| SI9946_2 | KNDC1 | 10 | 135012675 | C | T | A2601,A0206,B3502,B4801,C0401,C0803 | A0206 | 212 | 1910 | Macpslqea | Tacpslqea |
| SI9946_2 | CDC42BPG | 11 | 64611888 | T | C | A2601,A0206,B3502,B4801,C0401,C0803 | A0206 | 288 | 126 | svaqflGwa | svaqflSwa |
| SI9946_2 | CDC42BPG | 11 | 64611888 | T | C | A2601,A0206,B3502,B4801,C0401,C0803 | A0206 | 421 | 944 | aqflGwasp | aqflSwasp |
| SI9946_2 | CDC42BPG | 11 | 64611888 | T | C | A2601,A0206,B3502,B4801,C0401,C0803 | A0206 | 4 | 2 | flGwaspfv | flSwaspfv |
| SI9946_2 | VPS51 | 11 | 64877237 | C | T | A2601,A0206,B3502,B4801,C0401,C0803 | A0206 | 14 | 20 | Wllthyvkv | Rllthyvkv |
| SI9946_2 | VPS51 | 11 | 64877237 | C | T | A2601,A0206,B3502,B4801,C0401,C0803 | A2601 | 192 | 405 | etarWllth | etarRllth |
| SI9946_2 | CARS2 | 13 | 111358235 | T | C | A2601,A0206,B3502,B4801,C0401,C0803 | A0206 | 156 | 46 | livaRaeaa | livaHaeaa |
| SI9946_2 | PRKD1 | 14 | 30396595 | C | T | A2601,A0206,B3502,B4801,C0401,C0803 | A0206 | 2 | 2 | flaplaapv | flapVaapv |
| SI9946_2 | GGT6 | 17 | 4461972 | G | T | A2601,A0206,B3502,B4801,C0401,C0803 | A0206 | 442 | 192 | lagdailsl | lagdaLlsl |
| SI9946_2 | NME1 | 17 | 49238564 | T | C | A2601,A0206,B3502,B4801,C0401,C0803 | A0206 | 126 | 26 | vmPgetnpa | vmLgetnpa |

Figure 21 (Cont.)

| | | | | | | | | | | | |
|---|---|---|---|---|---|---|---|---|---|---|---|
| SI9946_2 | NPLOC4 | 17 | 79575820 | A | G | A2601,A0206,B3502,B4801,C0401,C0803 | A0206 | 22 | 10 | yinhPeppv | yinhLeppv |
| SI9946_2 | TMEM259 | 19 | 1020868 | C | A | A2601,A0206,B3502,B4801,C0401,C0803 | A0206 | 97 | 186 | nvrdLlfha | nvrdRlfha |
| SI9946_2 | RFX2 | 19 | 6044235 | G | T | A2601,A0206,B3502,B4801,C0401,C0803 | A0206 | 5 | 11 | mqpiYlprv | mqpiSlprv |
| SI9946_2 | FBN3 | 19 | 8212358 | G | T | A2601,A0206,B3502,B4801,C0401,C0803 | A0206 | 3 | 3 | mtMeglyla | mtLeglyla |
| SI9946_2 | CCDC155 | 19 | 49899040 | A | T | A2601,A0206,B3502,B4801,C0401,C0803 | A0206 | 30 | 8149 | qlhggleIV | qlhggleIE |
| SI9946_2 | POLD1 | 19 | 50919027 | G | A | A2601,A0206,B3502,B4801,C0401,C0803 | A0206 | 8 | 12 | slgdrlpyv | slgdrVpyv |
| SI9946_2 | POLD1 | 19 | 50919027 | G | A | A2601,A0206,B3502,B4801,C0401,C0803 | A0206 | 424 | 328 | rlpyviisa | rVpyviisa |
| SI9946_2 | CNOT3 | 19 | 54651935 | C | T | A2601,A0206,B3502,B4801,C0401,C0803 | A0206 | 8 | 32 | nqhpqFpav | nqhpqSpav |
| SI9946_2 | SPATS2L | 2 | 201281127 | A | T | A2601,A0206,B3502,B4801,C0401,C0803 | A0206 | 249 | 498 | iqvlkDwnm | iqvlkEwnm |
| SI9946_2 | AIFM3 | 22 | 21333577 | A | T | A2601,A0206,B3502,B4801,C0401,C0803 | A0206 | 265 | 667 | rvaaqYmla | rvaaqNmla |
| SI9946_2 | AIFM3 | 22 | 21333577 | A | T | A2601,A0206,B3502,B4801,C0401,C0803 | A0206 | 25 | 161 | aqYmlaqea | aqNmlaqea |
| SI9946_2 | AIFM3 | 22 | 21333577 | A | T | A2601,A0206,B3502,B4801,C0401,C0803 | A0206 | 46 | 1288 | Ymlaqeaem | Nmlaqeaem |
| SI9946_2 | UCN2 | 3 | 48600338 | G | T | A2601,A0206,B3502,B4801,C0401,C0803 | A0206 | 35 | 40 | ivlsldvpi | ivLsldvpi |
| SI9946_2 | NELFA | 4 | 2010566 | T | C | A2601,A0206,B3502,B4801,C0401,C0803 | A0206 | 33 | 177 | ltaavidnV | ltaavidnl |
| SI9946_2 | NELFA | 4 | 2010566 | T | C | A2601,A0206,B3502,B4801,C0401,C0803 | A0206 | 494 | 568 | nVrlcfhgl | nlrlcfhgl |
| SI9946_2 | STOX2 | 4 | 184938423 | G | C | A2601,A0206,B3502,B4801,C0401,C0803 | A0206 | 42 | 159 | clqasLtsv | clqasVtsv |
| SI9946_2 | MSH3 | 5 | 79950715 | G | C | A2601,A0206,B3502,B4801,C0401,C0803 | A0206 | 300 | 320 | aaaaaaPaa | aaaaaaAaa |
| SI9946_2 | MSH3 | 5 | 79950715 | G | C | A2601,A0206,B3502,B4801,C0401,C0803 | A0206 | 247 | 320 | aaaPaaaaa | aaaAaaaaa |
| SI9946_2 | CYFIP2 | 5 | 156712400 | C | T | A2601,A0206,B3502,B4801,C0401,C0803 | A0206 | 52 | 50 | tledVlsnv | tledAlsnv |
| SI9946_2 | GLP1R | 6 | 39016678 | C | T | A2601,A0206,B3502,B4801,C0401,C0803 | A0206 | 59 | 709 | lllgmvgrV | lllgmvgrA |
| SI9946_2 | DGKI | 7 | 137531323 | C | T | A2601,A0206,B3502,B4801,C0401,C0803 | A0206 | 75 | 206 | aTaagaaal | aAaagaaal |
| SI9946_2 | SOX17 | 8 | 55372181 | A | G | A2601,A0206,B3502,B4801,C0401,C0803 | A0206 | 80 | 139 | lappGalhv | lappSalhv |
| SI9946_2 | SOX17 | 8 | 55372181 | A | G | A2601,A0206,B3502,B4801,C0401,C0803 | A0206 | 320 | 119 | Galhvyyga | Salhvyyga |

Figure 21 (Cont.)

| | | | | | | | | | | | |
|---|---|---|---|---|---|---|---|---|---|---|---|
| SR070761 | CSMD2 | 1 | 34498210 | G | A | A0101,A6801,B5601,B3502,C0401,C0102 | A6801 | 124 | 1120 | yavsaqgfY | yavsaqgfH |
| SR070761 | KIAA0754 | 1 | 39878645 | C | A | A0101,A6801,B5601,B3502,C0401,C0102 | A6801 | 125 | 117 | aaavsDper | aaavsAper |
| SR070761 | VANGL1 | 1 | 116206358 | G | A | A0101,A6801,B5601,B3502,C0401,C0102 | A6801 | 493 | 130 | sisqediaK | sisqediaR |
| SR070761 | BRINP2 | 1 | 177249613 | G | C | A0101,A6801,B5601,B3502,C0401,C0102 | A6801 | 95 | 153 | stfpAtfle | stfpGtfle |
| SR070761 | ZNF648 | 1 | 182025950 | C | T | A0101,A6801,B5601,B3502,C0401,C0102 | A6801 | 478 | 1847 | dQefavasr | dRefavasr |
| SR070761 | C1orf106 | 1 | 200870215 | C | G | A0101,A6801,B5601,B3502,C0401,C0102 | A6801 | 33 | 251 | eVqrclver | eLqrclver |
| SR070761 | ANKRD30A | 10 | 37451585 | G | A | A0101,A6801,B5601,B3502,C0401,C0102 | A6801 | 11 | 11655 | qtfkaeppR | qtfkaeppG |
| SR070761 | ADAM12 | 10 | 128076654 | C | T | A0101,A6801,B5601,B3502,C0401,C0102 | A6801 | 238 | 2949 | Tllapcear | Allapcear |
| SR070761 | IFITM5 | 11 | 299472 | G | A | A0101,A6801,B5601,B3502,C0401,C0102 | A6801 | 16 | 21 | taypCedtr | taypRedtr |
| SR070761 | RFC5 | 12 | 118462784 | C | T | A0101,A6801,B5601,B3502,C0401,C0102 | A6801 | 167 | 165 | ltpelmvSr | ltpelmvPr |
| SR070761 | MSI1 | 12 | 120796840 | A | G | A0101,A6801,B5601,B3502,C0401,C0102 | C0401 | 306 | 2243 | kvddamPmf | kvddamLmf |
| SR070761 | ULK1 | 12 | 132392061 | G | A | A0101,A6801,B5601,B3502,C0401,C0102 | A6801 | 29 | 74 | lTdylhamr | lAdylhamr |
| SR070761 | DTD2 | 14 | 31926584 | G | A | A0101,A6801,B5601,B3502,C0401,C0102 | A6801 | 204 | 975 | egsWipqar | egsRipqar |
| SR070761 | SAMD4A | 14 | 55215538 | C | G | A0101,A6801,B5601,B3502,C0401,C0102 | A6801 | 24 | 35 | stnvAawlk | stnvPawlk |
| SR070761 | SAMD4A | 14 | 55215538 | C | G | A0101,A6801,B5601,B3502,C0401,C0102 | A6801 | 19 | 312 | vAawlkslr | vPawlkslr |
| SR070761 | MAGEL2 | 15 | 23890294 | C | T | A0101,A6801,B5601,B3502,C0401,C0102 | A6801 | 19 | 61 | tTttqeask | tAttqeask |
| SR070761 | PDILT | 16 | 20370715 | C | G | A0101,A6801,B5601,B3502,C0401,C0102 | A6801 | 241 | 619 | Lvvvvakpk | Vvvvvakpk |
| SR070761 | TP53 | 17 | 7579369 | G | C | A0101,A6801,B5601,B3502,C0401,C0102 | A6801 | 325 | 137 | tyqgRygfr | tyqgSygfr |
| SR070761 | KRT23 | 17 | 39081650 | C | A | A0101,A6801,B5601,B3502,C0401,C0102 | A6801 | 206 | 434 | leNeittyr | leKeittyr |
| SR070761 | KRT23 | 17 | 39081650 | C | A | A0101,A6801,B5601,B3502,C0401,C0102 | A6801 | 180 | 1368 | eNeittyrr | eKeittyrr |
| SR070761 | TTC25 | 17 | 40113476 | G | A | A0101,A6801,B5601,B3502,C0401,C0102 | A6801 | 167 | 1535 | Naqaqvklr | Vaqaqvklr |
| SR070761 | CACNA1G | 17 | 48647132 | T | C | A0101,A6801,B5601,B3502,C0401,C0102 | A6801 | 442 | 196 | avrtvrvPr | avrtvrvLr |

Figure 21 (Cont.)

| | | | | | | | | | | | |
|---|---|---|---|---|---|---|---|---|---|---|---|
| SR070761 | CACNA1G | 17 | 48647132 | T | C | A0101,A6801,B5601,B3502,C0401,C0102 | A6801 | 103 | 90 | tvrvPrplr | tvrvLrplr |
| SR070761 | BTBD17 | 17 | 72353704 | C | T | A0101,A6801,B5601,B3502,C0401,C0102 | A6801 | 208 | 4496 | Mgtgdealr | Vgtgdealr |
| SR070761 | SPHK1 | 17 | 74381694 | C | T | A0101,A6801,B5601,B3502,C0401,C0102 | A6801 | 56 | 154 | tapglpwqr | tapgTpwqr |
| SR070761 | ZNF626 | 19 | 20807265 | T | C | A0101,A6801,B5601,B3502,C0401,C0102 | A6801 | 52 | 147 | ssnltthkR | ssnltthkK |
| SR070761 | RHPN2 | 19 | 33487079 | G | A | A0101,A6801,B5601,B3502,C0401,C0102 | A6801 | 481 | 929 | svWeaslck | svReaslck |
| SR070761 | ZNF850 | 19 | 37239363 | T | C | A0101,A6801,B5601,B3502,C0401,C0102 | A6801 | 110 | 68 | rstliehRr | rstliehQr |
| SR070761 | KLC3 | 19 | 45849880 | G | A | A0101,A6801,B5601,B3502,C0401,C0102 | A6801 | 30 | 67 | lTqenvwlr | lAqenvwlr |
| SR070761 | SYT3 | 19 | 51128526 | C | T | A0101,A6801,B5601,B3502,C0401,C0102 | A6801 | 373 | 600 | hnevigMcr | hnevigVcr |
| SR070761 | SYT3 | 19 | 51128535 | C | T | A0101,A6801,B5601,B3502,C0401,C0102 | A6801 | 356 | 600 | hneMigvcr | hneVigvcr |
| SR070761 | ZNF841 | 19 | 52569098 | G | T | A0101,A6801,B5601,B3502,C0401,C0102 | A6801 | 438 | 23620 | hlvihtgeK | hlvihtgeN |
| SR070761 | TTC31 | 2 | 74717152 | G | A | A0101,A6801,B5601,B3502,C0401,C0102 | A6801 | 36 | 217 | eeNivdflr | eeDivdflr |
| SR070761 | TTC31 | 2 | 74717152 | G | A | A0101,A6801,B5601,B3502,C0401,C0102 | A6801 | 170 | 811 | eNivdflrr | eDivdflrr |
| SR070761 | TACR1 | 2 | 75425690 | G | A | A0101,A6801,B5601,B3502,C0401,C0102 | A0101 | 397 | 23 | mMavafdry | mTavafdry |
| SR070761 | TACR1 | 2 | 75425690 | G | A | A0101,A6801,B5601,B3502,C0401,C0102 | A6801 | 31 | 60 | smMavafdr | smTavafdr |
| SR070761 | HELZ2 | 20 | 62194256 | C | A | A0101,A6801,B5601,B3502,C0401,C0102 | A6801 | 52 | 52 | lsvsCeasr | lsvsWeasr |
| SR070761 | POTEH | 22 | 16269934 | A | G | A0101,A6801,B5601,B3502,C0401,C0102 | A6801 | 456 | 225 | nsnpeqdSk | nsnpeqdLk |
| SR070761 | MLC1 | 22 | 50508988 | G | A | A0101,A6801,B5601,B3502,C0401,C0102 | A6801 | 20 | 28 | Yvaaecpsk | Hvaaecpsk |
| SR070761 | ZNF860 | 3 | 32031859 | A | G | A0101,A6801,B5601,B3502,C0401,C0102 | A6801 | 285 | 213 | cnEcgkffr | cnKcgkffr |
| SR070761 | GATA2 | 3 | 128205724 | G | A | A0101,A6801,B5601,B3502,C0401,C0102 | A0101 | 8 | 14 | Yldsqgnpy | Hldsqgnpy |
| SR070761 | CC2D2A | 4 | 15529275 | A | G | A0101,A6801,B5601,B3502,C0401,C0102 | A6801 | 74 | 106 | ltGklqalr | ltDklqalr |
| SR070761 | CDHR2 | 5 | 176004484 | G | A | A0101,A6801,B5601,B3502,C0401,C0102 | A6801 | 58 | 166 | sTsvqvlvr | sAsvqvlvr |
| SR070761 | MYO1G | 7 | 45005395 | C | T | A0101,A6801,B5601,B3502,C0401,C0102 | A6801 | 45 | 48 | iytimHwfr | iytimRwfr |
| SR070761 | MYO1G | 7 | 45005395 | C | T | A0101,A6801,B5601,B3502,C0401,C0102 | A6801 | 5 | 7 | ytimHwfrr | ytimRwfrr |

Figure 21 (Cont.)

| | | | | | | | | | | | |
|---|---|---|---|---|---|---|---|---|---|---|---|
| SR070761 | ZNF716 | 7 | 57528987 | C | T | A0101,A6801,B5601,B3502,C0401,C0102 | A6801 | 495 | 1929 | eeCgkvfsr | eeRgkvfsr |
| SR070761 | ARHGEF5 | 7 | 144076992 | G | C | A0101,A6801,B5601,B3502,C0401,C0102 | A0101 | 369 | 547 | ssdAwlegv | ssdGwlegv |
| SR070761 | FRMPD1 | 9 | 37745978 | G | C | A0101,A6801,B5601,B3502,C0401,C0102 | A6801 | 330 | 31615 | slrvatslR | slrvatslG |
| SR070761 | TNFSF8 | 9 | 117692426 | G | A | A0101,A6801,B5601,B3502,C0401,C0102 | A6801 | 487 | 1322 | Mvatimvlv | Tvatimvlv |
| SR070761 | FATE1 | X | 150884659 | G | A | A0101,A6801,B5601,B3502,C0401,C0102 | A6801 | 103 | 128 | laeelnhEr | laeelnhGr |
| TU0428 | PLEKHN1 | 1 | 908929 | C | T | A0101,A0301,B0702,B3501,C0401,C0702 | B0702 | 31 | 13507 | spdapdhtL | spdapdhtS |
| TU0428 | PLEKHN1 | 1 | 908929 | C | T | A0101,A0301,B0702,B3501,C0401,C0702 | B3501 | 311 | 989 | Letshsply | Setshsply |
| TU0428 | TMCO4 | 1 | 20072082 | C | T | A0101,A0301,B0702,B3501,C0401,C0702 | B0702 | 195 | 80 | lplteSrql | lplteGrql |
| TU0428 | TMCO4 | 1 | 20072082 | C | T | A0101,A0301,B0702,B3501,C0401,C0702 | B3501 | 249 | 728 | lplteSrql | lplteGrql |
| TU0428 | E2F2 | 1 | 23836589 | A | T | A0101,A0301,B0702,B3501,C0401,C0702 | B3501 | 73 | 36 | Dpleatdsl | Vpleatdsl |
| TU0428 | MYOM3 | 1 | 24419457 | C | T | A0101,A0301,B0702,B3501,C0401,C0702 | B0702 | 124 | 84 | gpreqNtyv | gpreqStyv |
| TU0428 | MAN1C1 | 1 | 26107502 | A | G | A0101,A0301,B0702,B3501,C0401,C0702 | A0101 | 59 | 74 | atqlseGyy | atqlseSyy |
| TU0428 | MAN1C1 | 1 | 26107502 | A | G | A0101,A0301,B0702,B3501,C0401,C0702 | B3501 | 93 | 23 | vatqlseGy | vatqlseSy |
| TU0428 | EPB41 | 1 | 29320013 | G | A | A0101,A0301,B0702,B3501,C0401,C0702 | B3501 | 102 | 189 | Isllddtvy | Vsllddtvy |
| TU0428 | KLF17 | 1 | 44595047 | T | A | A0101,A0301,B0702,B3501,C0401,C0702 | B0702 | 448 | 652 | apNlnmsss | apllnmsss |
| TU0428 | CYP4B1 | 1 | 47264905 | C | T | A0101,A0301,B0702,B3501,C0401,C0702 | B0702 | 38 | 13 | fpgpplhwl | fpgppThwl |
| TU0428 | INADL | 1 | 62614029 | C | T | A0101,A0301,B0702,B3501,C0401,C0702 | B3501 | 471 | 3371 | Lptaehhpe | Sptaehhpe |
| TU0428 | GBP5 | 1 | 89735081 | T | A | A0101,A0301,B0702,B3501,C0401,C0702 | A0301 | 394 | 427 | tgksFlmnk | tgksYlmnk |
| TU0428 | GBP5 | 1 | 89735081 | T | A | A0101,A0301,B0702,B3501,C0401,C0702 | A0301 | 48 | 38 | Flmnklagk | Ylmnklagk |
| TU0428 | GBP5 | 1 | 89735081 | T | A | A0101,A0301,B0702,B3501,C0401,C0702 | C0702 | 201 | 228 | yrtgksFlm | yrtgksYlm |
| TU0428 | ECM1 | 1 | 150483355 | C | T | A0101,A0301,B0702,B3501,C0401,C0702 | B3501 | 77 | 4640 | hpneqkegM | hpneqkegT |
| TU0428 | ECM1 | 1 | 150483355 | C | T | A0101,A0301,B0702,B3501,C0401,C0702 | B3501 | 369 | 4011 | Mpapfgdqs | Tpapfgdqs |

Figure 21 (Cont.)

| | | | | | | | | | | | |
|---|---|---|---|---|---|---|---|---|---|---|---|
| TU0428 | FLG2 | 1 | 152329852 | C | T | A0101,A0301,B0702,B3501,C0401,C0702 | A0101 | 9 | 15 | wseEeehgy | wseGeehgy |
| TU0428 | FLG2 | 1 | 152329852 | C | T | A0101,A0301,B0702,B3501,C0401,C0702 | B3501 | 471 | 1165 | wseEeehgy | wseGeehgy |
| TU0428 | FCRL3 | 1 | 157648543 | T | C | A0101,A0301,B0702,B3501,C0401,C0702 | C0702 | 145 | 282 | Syenvprvl | Nyenvprvl |
| TU0428 | LY9 | 1 | 160784526 | G | T | A0101,A0301,B0702,B3501,C0401,C0702 | A0101 | 126 | 40 | lthvtlliy | Mthvtlliy |
| TU0428 | SLC9C2 | 1 | 173499050 | T | C | A0101,A0301,B0702,B3501,C0401,C0702 | A0301 | 316 | 334 | avcesMyqk | avceslyqk |
| TU0428 | SLC9C2 | 1 | 173499050 | T | C | A0101,A0301,B0702,B3501,C0401,C0702 | B3501 | 342 | 310 | qiavcesMy | qiavcesly |
| TU0428 | SLC9C2 | 1 | 173499050 | T | C | A0101,A0301,B0702,B3501,C0401,C0702 | C0702 | 403 | 393 | Myqklceil | lyqklceil |
| TU0428 | SWT1 | 1 | 185240471 | A | C | A0101,A0301,B0702,B3501,C0401,C0702 | A0301 | 272 | 69 | rilapnRny | rilapnSny |
| TU0428 | SWT1 | 1 | 185240471 | A | C | A0101,A0301,B0702,B3501,C0401,C0702 | B0702 | 188 | 267 | apnRnyqdv | apnSnyqdv |
| TU0428 | PTPRC | 1 | 198671653 | A | G | A0101,A0301,B0702,B3501,C0401,C0702 | A0101 | 59 | 33 | itanAsday | itanTsday |
| TU0428 | PTPRC | 1 | 198671653 | A | G | A0101,A0301,B0702,B3501,C0401,C0702 | B3501 | 11 | 19 | itanAsday | itanTsday |
| TU0428 | PTPRC | 1 | 198671653 | A | G | A0101,A0301,B0702,B3501,C0401,C0702 | B3501 | 403 | 959 | tanAsdayl | tanTsdayl |
| TU0428 | NFASC | 1 | 204937982 | C | T | A0101,A0301,B0702,B3501,C0401,C0702 | A0301 | 88 | 288 | kVkfenfnk | kAkfenfnk |
| TU0428 | NFASC | 1 | 204944441 | G | A | A0101,A0301,B0702,B3501,C0401,C0702 | A0301 | 414 | 6177 | rmpedqvaK | rmpedqvaR |
| TU0428 | NFASC | 1 | 204944536 | A | G | A0101,A0301,B0702,B3501,C0401,C0702 | A0301 | 428 | 449 | plyVgnrmk | plylgnrmk |
| TU0428 | NFASC | 1 | 204944536 | A | G | A0101,A0301,B0702,B3501,C0401,C0702 | B3501 | 103 | 88 | eplyVgnrm | eplylgnrm |
| TU0428 | SERTAD4 | 1 | 210411315 | G | T | A0101,A0301,B0702,B3501,C0401,C0702 | A0301 | 93 | 240 | mtlFlsmnr | mtlVlsmnr |
| TU0428 | ITPKB | 1 | 226923938 | A | C | A0101,A0301,B0702,B3501,C0401,C0702 | A0301 | 123 | 131 | Alswsrlpr | Slswsrlpr |
| TU0428 | ITPKB | 1 | 226923938 | A | C | A0101,A0301,B0702,B3501,C0401,C0702 | B3501 | 312 | 1721 | qsaessdAl | qsaessdSl |
| TU0428 | OBSCN | 1 | 228506912 | T | C | A0101,A0301,B0702,B3501,C0401,C0702 | A0301 | 396 | 844 | vtyPkkagr | vtyLkkagr |
| TU0428 | OBSCN | 1 | 228506912 | T | C | A0101,A0301,B0702,B3501,C0401,C0702 | B0702 | 496 | 18764 | yPkkagrpg | yLkkagrpg |
| TU0428 | RYR2 | 1 | 237791148 | G | T | A0101,A0301,B0702,B3501,C0401,C0702 | B0702 | 490 | 424 | mvrwSqesv | mvrwAqesv |
| TU0428 | RYR2 | 1 | 237791148 | G | T | A0101,A0301,B0702,B3501,C0401,C0702 | C0702 | 303 | 662 | vrwSqesvi | vrwAqesvi |

Figure 21 (Cont.)

| | | | | | | | | | | | |
|---|---|---|---|---|---|---|---|---|---|---|---|
| TU0428 | OR2T33 | 1 | 248436738 | G | T | A0101,A0301,B0702,B3501,C0401,C0702 | B3501 | 35 | 103 | aavchTlry | aavchPlry |
| TU0428 | OR2T6 | 1 | 248551672 | G | T | A0101,A0301,B0702,B3501,C0401,C0702 | A0301 | 57 | 85 | tlfygaSly | tlfygaAly |
| TU0428 | OR2T6 | 1 | 248551672 | G | T | A0101,A0301,B0702,B3501,C0401,C0702 | B3501 | 333 | 410 | tlfygaSly | tlfygaAly |
| TU0428 | OR2T6 | 1 | 248551672 | G | T | A0101,A0301,B0702,B3501,C0401,C0702 | B3501 | 303 | 211 | fygaSlyty | fygaAlyty |
| TU0428 | OR2T6 | 1 | 248551672 | G | T | A0101,A0301,B0702,B3501,C0401,C0702 | C0702 | 165 | 225 | fygaSlyty | fygaAlyty |
| TU0428 | OR2G6 | 1 | 248685363 | G | T | A0101,A0301,B0702,B3501,C0401,C0702 | B0702 | 36 | 19 | hpMfcasla | hpRfcasla |
| TU0428 | OR2G6 | 1 | 248685363 | G | T | A0101,A0301,B0702,B3501,C0401,C0702 | B3501 | 197 | 379 | yiaimhpMf | yiaimhpRf |
| TU0428 | OR2G6 | 1 | 248685363 | G | T | A0101,A0301,B0702,B3501,C0401,C0702 | B3501 | 102 | 852 | hpMfcasla | hpRfcasla |
| TU0428 | OR2G6 | 1 | 248685363 | G | T | A0101,A0301,B0702,B3501,C0401,C0702 | C0702 | 241 | 10977 | ryiaimhpM | ryiaimhpR |
| TU0428 | MCM10 | 10 | 13239651 | A | G | A0101,A0301,B0702,B3501,C0401,C0702 | A0301 | 113 | 217 | raRgqvltk | raKgqvltk |
| TU0428 | MCM10 | 10 | 13239651 | A | G | A0101,A0301,B0702,B3501,C0401,C0702 | B0702 | 16 | 27 | klraRgqvl | klraKgqvl |
| TU0428 | SEPHS1 | 10 | 13364902 | C | A | A0101,A0301,B0702,B3501,C0401,C0702 | B0702 | 128 | 44 | lpvlakiaa | lpvlakMaa |
| TU0428 | SEPHS1 | 10 | 13364902 | C | A | A0101,A0301,B0702,B3501,C0401,C0702 | B3501 | 31 | 78 | lpvlakiaa | lpvlakMaa |
| TU0428 | BAMBI | 10 | 28966893 | C | T | A0101,A0301,B0702,B3501,C0401,C0702 | A0301 | 68 | 54 | camavlFtk | camavlLtk |
| TU0428 | ZNF485 | 10 | 44112428 | C | T | A0101,A0301,B0702,B3501,C0401,C0702 | B3501 | 431 | 8033 | kafrksstF | kafrksstL |
| TU0428 | ARHGAP22 | 10 | 49658943 | G | T | A0101,A0301,B0702,B3501,C0401,C0702 | A0301 | 50 | 19525 | avlsrtapK | avlsrtapT |
| TU0428 | ARHGAP22 | 10 | 49658943 | G | T | A0101,A0301,B0702,B3501,C0401,C0702 | B0702 | 333 | 275 | apKgpgsrc | apTgpgsrc |
| TU0428 | PCDH15 | 10 | 55780070 | C | G | A0101,A0301,B0702,B3501,C0401,C0702 | A0101 | 240 | 450 | lsllTsldy | lsllRsldy |
| TU0428 | POLR3A | 10 | 79769647 | C | A | A0101,A0301,B0702,B3501,C0401,C0702 | A0301 | 49 | 45 | Llppptilk | Rlppptilk |
| TU0428 | POLR3A | 10 | 79769647 | C | A | A0101,A0301,B0702,B3501,C0401,C0702 | C0702 | 172 | 33 | vLlppptil | vRlppptil |
| TU0428 | LRIT1 | 10 | 85992115 | C | A | A0101,A0301,B0702,B3501,C0401,C0702 | B0702 | 366 | 142 | qpgNtrvti | qpgKtrvti |
| TU0428 | ACTA2 | 10 | 90701577 | G | A | A0101,A0301,B0702,B3501,C0401,C0702 | C0702 | 366 | 578 | myvaiqVvl | myvaiqAvl |

Figure 21 (Cont.)

| | | | | | | | | | | | |
|---|---|---|---|---|---|---|---|---|---|---|---|
| TU0428 | SORCS3 | 10 | 106974303 | G | T | A0101,A0301,B0702,B3501,C0401,C0702 | B0702 | 66 | 18 | aprglhvLt | aprglhvVt |
| TU0428 | DOCK1 | 10 | 129172340 | G | T | A0101,A0301,B0702,B3501,C0401,C0702 | A0301 | 121 | 117 | killehcSk | killehcRk |
| TU0428 | DOCK1 | 10 | 129172340 | G | T | A0101,A0301,B0702,B3501,C0401,C0702 | A0301 | 176 | 16920 | cSkhkylak | cRkhkylak |
| TU0428 | IFITM2 | 11 | 308314 | T | C | A0101,A0301,B0702,B3501,C0401,C0702 | B0702 | 54 | 12 | vphnpappT | vphnpappM |
| TU0428 | IFITM2 | 11 | 308314 | T | C | A0101,A0301,B0702,B3501,C0401,C0702 | B0702 | 11 | 14 | npappTstv | npappMstv |
| TU0428 | MUC5B | 11 | 1260222 | G | T | A0101,A0301,B0702,B3501,C0401,C0702 | B3501 | 184 | 466 | yaqachdaV | yaqachdaG |
| TU0428 | ASCL2 | 11 | 2291369 | A | C | A0101,A0301,B0702,B3501,C0401,C0702 | B0702 | 27 | 196 | Rvnlgfqal | Lvnlgfqal |
| TU0428 | KCNQ1 | 11 | 2869102 | G | T | A0101,A0301,B0702,B3501,C0401,C0702 | B0702 | 135 | 108 | ppreCgahi | ppreGgahi |
| TU0428 | OR52A5 | 11 | 5153082 | G | T | A0101,A0301,B0702,B3501,C0401,C0702 | A0301 | 16 | 10294 | llaffsffK | llaffsffT |
| TU0428 | OR52A5 | 11 | 5153082 | G | T | A0101,A0301,B0702,B3501,C0401,C0702 | C0702 | 240 | 291 | ffsffKhrf | ffsffThrf |
| TU0428 | OR52E8 | 11 | 5878836 | T | A | A0101,A0301,B0702,B3501,C0401,C0702 | B3501 | 318 | 422 | hiwFgvpff | hiwlgvpff |
| TU0428 | OR52E8 | 11 | 5878836 | T | A | A0101,A0301,B0702,B3501,C0401,C0702 | B3501 | 19 | 174 | Fgvpfffvy | lgvpfffvy |
| TU0428 | PRKCDBP | 11 | 6341514 | C | T | A0101,A0301,B0702,B3501,C0401,C0702 | B0702 | 94 | 107 | riqsglSal | riqsglGal |
| TU0428 | AMPD3 | 11 | 10503736 | C | T | A0101,A0301,B0702,B3501,C0401,C0702 | B3501 | 48 | 439 | hpWadtapp | hpRadtapp |
| TU0428 | LDLRAD3 | 11 | 36103230 | C | T | A0101,A0301,B0702,B3501,C0401,C0702 | C0702 | 323 | 356 | Iffpcasgi | Tffpcasgi |
| TU0428 | RAG1 | 11 | 36597879 | C | T | A0101,A0301,B0702,B3501,C0401,C0702 | A0101 | 159 | 16585 | ylqkfmnaY | ylqkfmnaH |
| TU0428 | RAG1 | 11 | 36597879 | C | T | A0101,A0301,B0702,B3501,C0401,C0702 | A0301 | 37 | 28 | fmnaYnalk | fmnaHnalk |
| TU0428 | RAG1 | 11 | 36597879 | C | T | A0101,A0301,B0702,B3501,C0401,C0702 | B3501 | 134 | 7202 | ylqkfmnaY | ylqkfmnaH |
| TU0428 | RAG1 | 11 | 36597879 | C | T | A0101,A0301,B0702,B3501,C0401,C0702 | C0702 | 435 | 632 | kfmnaYnal | kfmnaHnal |
| TU0428 | OR4C6 | 11 | 55433061 | G | T | A0101,A0301,B0702,B3501,C0401,C0702 | B0702 | 16 | 22 | sprvcFlmv | sprvcClmv |
| TU0428 | OR4C6 | 11 | 55433061 | G | T | A0101,A0301,B0702,B3501,C0401,C0702 | C0702 | 306 | 20936 | iimsprvcF | iimsprvcC |
| TU0428 | OR4C6 | 11 | 55433061 | G | T | A0101,A0301,B0702,B3501,C0401,C0702 | C0702 | 371 | 202 | imsprvcFl | imsprvcCl |
| TU0428 | OR8J1 | 11 | 56128081 | A | G | A0101,A0301,B0702,B3501,C0401,C0702 | B3501 | 17 | 15 | lalmaCdry | lalmaYdry |

Figure 21 (Cont.)

| | | | | | | | | | | | |
|---|---|---|---|---|---|---|---|---|---|---|---|
| TU0428 | OR5M11 | 11 | 56310730 | A | C | A0101,A0301,B0702,B3501,C0401,C0702 | B0702 | 435 | 6767 | mAntngsai | mSntngsai |
| TU0428 | OR5M11 | 11 | 56310730 | A | C | A0101,A0301,B0702,B3501,C0401,C0702 | B3501 | 54 | 1268 | mAntngsai | mSntngsai |
| TU0428 | OR5B3 | 11 | 58170780 | T | A | A0101,A0301,B0702,B3501,C0401,C0702 | B3501 | 5 | 6 | fpfiyiFtl | fpfiyiltl |
| TU0428 | OR5B3 | 11 | 58170780 | T | A | A0101,A0301,B0702,B3501,C0401,C0702 | C0702 | 180 | 1530 | itfpfiyiF | itfpfiyil |
| TU0428 | OR5B3 | 11 | 58170780 | T | A | A0101,A0301,B0702,B3501,C0401,C0702 | C0702 | 420 | 628 | fpfiyiFtl | fpfiyiltl |
| TU0428 | OR4D6 | 11 | 59225191 | C | A | A0101,A0301,B0702,B3501,C0401,C0702 | B3501 | 153 | 79 | hfvHcvyiy | hfvPcvyiy |
| TU0428 | OR4D6 | 11 | 59225191 | C | A | A0101,A0301,B0702,B3501,C0401,C0702 | C0702 | 77 | 22 | hfvHcvyiy | hfvPcvyiy |
| TU0428 | MS4A7 | 11 | 60152690 | C | G | A0101,A0301,B0702,B3501,C0401,C0702 | B3501 | 3 | 3 | ypflgaVcf | ypflgaLcf |
| TU0428 | MACROD1 | 11 | 63767022 | C | A | A0101,A0301,B0702,B3501,C0401,C0702 | B0702 | 216 | 5703 | rlrsvafpF | rlrsvafpC |
| TU0428 | MACROD1 | 11 | 63767022 | C | A | A0101,A0301,B0702,B3501,C0401,C0702 | B0702 | 37 | 115 | fpFistgvf | fpCistgvf |
| TU0428 | MACROD1 | 11 | 63767022 | C | A | A0101,A0301,B0702,B3501,C0401,C0702 | B3501 | 4 | 15 | fpFistgvf | fpCistgvf |
| TU0428 | MACROD1 | 11 | 63767022 | C | A | A0101,A0301,B0702,B3501,C0401,C0702 | B3501 | 69 | 722 | Fistgvfgy | Cistgvfgy |
| TU0428 | MACROD1 | 11 | 63767022 | C | A | A0101,A0301,B0702,B3501,C0401,C0702 | C0702 | 186 | 20259 | rlrsvafpF | rlrsvafpC |
| TU0428 | CCDC87 | 11 | 66360129 | C | T | A0101,A0301,B0702,B3501,C0401,C0702 | B3501 | 225 | 2564 | Mllsseqlf | Vllsseqlf |
| TU0428 | CCDC87 | 11 | 66360129 | C | T | A0101,A0301,B0702,B3501,C0401,C0702 | C0702 | 333 | 323 | krleayMll | krleayVll |
| TU0428 | SSH3 | 11 | 67076926 | A | G | A0101,A0301,B0702,B3501,C0401,C0702 | B3501 | 104 | 132 | nfyperfAy | nfyperfTy |
| TU0428 | SSH3 | 11 | 67076926 | A | G | A0101,A0301,B0702,B3501,C0401,C0702 | C0702 | 37 | 35 | nfyperfAy | nfyperfTy |
| TU0428 | ALDH3B1 | 11 | 67789138 | C | T | A0101,A0301,B0702,B3501,C0401,C0702 | B3501 | 293 | 2278 | dMvlcspem | dYvlcspem |
| TU0428 | TYR | 11 | 88911696 | C | A | A0101,A0301,B0702,B3501,C0401,C0702 | A0101 | 21 | 15542 | smdallggY | smdallggS |
| TU0428 | ALKBH8 | 11 | 107422570 | C | A | A0101,A0301,B0702,B3501,C0401,C0702 | C0702 | 402 | 683 | khkpYqmti | khkpDqmti |
| TU0428 | FDXACB1 | 11 | 111745756 | T | C | A0101,A0301,B0702,B3501,C0401,C0702 | A0101 | 430 | 1065 | vslcyGlty | vslcyRlty |
| TU0428 | MCAM | 11 | 119182355 | G | T | A0101,A0301,B0702,B3501,C0401,C0702 | C0702 | 51 | 49 | ifgpHwmaf | ifgpPwmaf |

Figure 21 (Cont.)

| | | | | | | | | | | | |
|---|---|---|---|---|---|---|---|---|---|---|---|
| TU0428 | OR10G4 | 11 | 123887164 | A | C | A0101,A0301,B0702,B3501,C0401,C0702 | A0301 | 132 | 118 | tlmkevQk | tlmkevKk |
| TU0428 | OR8G2 | 11 | 124095986 | C | T | A0101,A0301,B0702,B3501,C0401,C0702 | B3501 | 375 | 4176 | hyfcdlfpF | hyfcdlfpL |
| TU0428 | OR8G2 | 11 | 124095986 | C | T | A0101,A0301,B0702,B3501,C0401,C0702 | B3501 | 201 | 387 | fpFlglscs | fpLlglscs |
| TU0428 | OR8G2 | 11 | 124095986 | C | T | A0101,A0301,B0702,B3501,C0401,C0702 | C0702 | 14 | 14 | hyfcdlfpF | hyfcdlfpL |
| TU0428 | OR8G2 | 11 | 124095986 | C | T | A0101,A0301,B0702,B3501,C0401,C0702 | C0702 | 142 | 105 | yfcdlfpFl | yfcdlfpLl |
| TU0428 | CACNA2D4 | 12 | 1992116 | C | T | A0101,A0301,B0702,B3501,C0401,C0702 | A0101 | 143 | 62 | dtqenvmKy | dtqenvmEy |
| TU0428 | CACNA2D4 | 12 | 1992116 | C | T | A0101,A0301,B0702,B3501,C0401,C0702 | B0702 | 311 | 1618 | nvmKylhvl | nvmEylhvl |
| TU0428 | CACNA2D4 | 12 | 2027566 | A | G | A0101,A0301,B0702,B3501,C0401,C0702 | B0702 | 16 | 145 | mpatpnfPa | mpatpnfLa |
| TU0428 | CACNA2D4 | 12 | 2027566 | A | G | A0101,A0301,B0702,B3501,C0401,C0702 | B0702 | 125 | 15899 | fPanpssss | fLanpssss |
| TU0428 | CACNA2D4 | 12 | 2027566 | A | G | A0101,A0301,B0702,B3501,C0401,C0702 | B3501 | 36 | 191 | mpatpnfPa | mpatpnfLa |
| TU0428 | CACNA2D4 | 12 | 2027566 | A | G | A0101,A0301,B0702,B3501,C0401,C0702 | B3501 | 143 | 15603 | fPanpssss | fLanpssss |
| TU0428 | ANO2 | 12 | 5941684 | A | G | A0101,A0301,B0702,B3501,C0401,C0702 | B0702 | 164 | 549 | Apehsnnkm | Vpehsnnkm |
| TU0428 | PLCZ1 | 12 | 18841115 | G | A | A0101,A0301,B0702,B3501,C0401,C0702 | A0301 | 240 | 200 | plthsLsnk | plthsSsnk |
| TU0428 | PLCZ1 | 12 | 18841115 | G | A | A0101,A0301,B0702,B3501,C0401,C0702 | B3501 | 318 | 560 | lplthsLsn | lplthsSsn |
| TU0428 | ADAMTS20 | 12 | 43833836 | C | T | A0101,A0301,B0702,B3501,C0401,C0702 | C0702 | 384 | 560 | flfnEnfll | flfnGnfll |
| TU0428 | KMT2D | 12 | 49433652 | T | A | A0101,A0301,B0702,B3501,C0401,C0702 | A0301 | 448 | 1046 | ylshgasLr | ylshgasQr |
| TU0428 | DIP2B | 12 | 51117078 | C | T | A0101,A0301,B0702,B3501,C0401,C0702 | B3501 | 406 | 1099 | taMlptvrm | taTlptvrm |
| TU0428 | TRHDE | 12 | 72666748 | C | T | A0101,A0301,B0702,B3501,C0401,C0702 | B3501 | 16 | 40 | lavllslCf | lavllslRf |
| TU0428 | MYF6 | 12 | 81101887 | A | T | A0101,A0301,B0702,B3501,C0401,C0702 | B0702 | 437 | 1130 | npnqrlpMv | npnqrlpKv |
| TU0428 | MYF6 | 12 | 81101887 | A | T | A0101,A0301,B0702,B3501,C0401,C0702 | C0702 | 37 | 50 | qrlpMveil | qrlpKveil |
| TU0428 | HSP90B1 | 12 | 104335468 | A | G | A0101,A0301,B0702,B3501,C0401,C0702 | B3501 | 334 | 1751 | dmmpkylSf | dmmpkylNf |
| TU0428 | HSP90B1 | 12 | 104335468 | A | G | A0101,A0301,B0702,B3501,C0401,C0702 | B3501 | 281 | 946 | mpkylSfvk | mpkylNfvk |
| TU0428 | ACACB | 12 | 109692053 | C | T | A0101,A0301,B0702,B3501,C0401,C0702 | B0702 | 31 | 327 | spvpiitpl | spvpiitpT |

Figure 21 (Cont.)

| | | | | | | | | | | | |
|---|---|---|---|---|---|---|---|---|---|---|---|
| TU0428 | ACACB | 12 | 109692053 | C | T | A0101,A0301,B0702,B3501,C0401,C0702 | B3501 | 244 | 245 | spvpiitpl | spvpiitpT |
| TU0428 | DDX54 | 12 | 113596866 | G | A | A0101,A0301,B0702,B3501,C0401,C0702 | A0301 | 448 | 381 | rvrLelktk | rvrPelktk |
| TU0428 | C12orf43 | 12 | 121454148 | C | T | A0101,A0301,B0702,B3501,C0401,C0702 | B0702 | 424 | 719 | rphvaRkpr | rphvaGkpr |
| TU0428 | C12orf43 | 12 | 121454148 | C | T | A0101,A0301,B0702,B3501,C0401,C0702 | B0702 | 412 | 12006 | vaRkpraga | vaGkpraga |
| TU0428 | LRRC43 | 12 | 122684753 | C | A | A0101,A0301,B0702,B3501,C0401,C0702 | A0301 | 85 | 52 | tvlfsNahk | tvlfsTahk |
| TU0428 | MIPEP | 13 | 24415590 | A | T | A0101,A0301,B0702,B3501,C0401,C0702 | C0702 | 244 | 490 | slycpffTl | slycpffSl |
| TU0428 | PARP4 | 13 | 25000617 | C | G | A0101,A0301,B0702,B3501,C0401,C0702 | A0301 | 395 | 1223 | kmddPsisr | kmddAsisr |
| TU0428 | PABPC3 | 13 | 25671786 | G | A | A0101,A0301,B0702,B3501,C0401,C0702 | B3501 | 31 | 5542 | vantstqtM | vantstqtV |
| TU0428 | GSX1 | 13 | 28367805 | T | A | A0101,A0301,B0702,B3501,C0401,C0702 | A0301 | 137 | 98 | nmyQsrlrr | nmyLsrlrr |
| TU0428 | GSX1 | 13 | 28367805 | T | A | A0101,A0301,B0702,B3501,C0401,C0702 | C0702 | 319 | 348 | myQsrlrri | myLsrlrri |
| TU0428 | MYO16 | 13 | 109779779 | T | A | A0101,A0301,B0702,B3501,C0401,C0702 | A0301 | 71 | 110 | sssHpsprk | sssLpsprk |
| TU0428 | MYO16 | 13 | 109779779 | T | A | A0101,A0301,B0702,B3501,C0401,C0702 | B3501 | 101 | 62 | fsmddsssH | fsmddsssL |
| TU0428 | OR4K15 | 14 | 20444012 | A | T | A0101,A0301,B0702,B3501,C0401,C0702 | B3501 | 292 | 1556 | lvVrktisf | lvErktisf |
| TU0428 | OR4K17 | 14 | 20586152 | A | T | A0101,A0301,B0702,B3501,C0401,C0702 | B0702 | 131 | 48 | ipfavllpf | ipfavNlpf |
| TU0428 | OR4K17 | 14 | 20586152 | A | T | A0101,A0301,B0702,B3501,C0401,C0702 | B3501 | 3 | 4 | ipfavllpf | ipfavNlpf |
| TU0428 | OR4K17 | 14 | 20586152 | A | T | A0101,A0301,B0702,B3501,C0401,C0702 | C0702 | 159 | 360 | fqipfavll | fqipfavNl |
| TU0428 | REM2 | 14 | 23352566 | C | A | A0101,A0301,B0702,B3501,C0401,C0702 | B3501 | 263 | 1683 | cpsgsSras | cpsgsRras |
| TU0428 | NYNRIN | 14 | 24885139 | G | T | A0101,A0301,B0702,B3501,C0401,C0702 | B0702 | 59 | 51 | lplwraLgf | lplwraRgf |
| TU0428 | NYNRIN | 14 | 24885139 | G | T | A0101,A0301,B0702,B3501,C0401,C0702 | B3501 | 16 | 91 | lplwraLgf | lplwraRgf |
| TU0428 | NID2 | 14 | 52485947 | G | T | A0101,A0301,B0702,B3501,C0401,C0702 | A0301 | 148 | 243 | aqyayTgar | aqyayPgar |
| TU0428 | SYNE2 | 14 | 64444631 | G | A | A0101,A0301,B0702,B3501,C0401,C0702 | A0301 | 117 | 57 | tlfksIldr | tlfksIMdr |
| TU0428 | SYNE2 | 14 | 64444631 | G | A | A0101,A0301,B0702,B3501,C0401,C0702 | C0702 | 465 | 460 | lfksIldrf | lfksIMdrf |

Figure 21 (Cont.)

| | | | | | | | | | | | |
|---|---|---|---|---|---|---|---|---|---|---|---|
| TU0428 | DCAF4 | 14 | 73421186 | C | T | A0101,A0301,B0702,B3501,C0401,C0702 | B3501 | 47 | 1146 | dvlaqqfaF | dvlaqqfaL |
| TU0428 | DCAF4 | 14 | 73421186 | C | T | A0101,A0301,B0702,B3501,C0401,C0702 | B3501 | 6 | 13 | faFmapllf | faLmapllf |
| TU0428 | DCAF4 | 14 | 73421186 | C | T | A0101,A0301,B0702,B3501,C0401,C0702 | C0401 | 437 | 732 | qfaFmapll | qfaLmapll |
| TU0428 | NEK9 | 14 | 75570664 | G | T | A0101,A0301,B0702,B3501,C0401,C0702 | A0301 | 192 | 22392 | kaliivavK | kaliivavQ |
| TU0428 | SAMD15 | 14 | 77845121 | A | G | A0101,A0301,B0702,B3501,C0401,C0702 | A0101 | 27 | 62 | lsdEfrkey | lsdKfrkey |
| TU0428 | SAMD15 | 14 | 77845121 | A | G | A0101,A0301,B0702,B3501,C0401,C0702 | C0702 | 246 | 100 | Efrkeyyal | Kfrkeyyal |
| TU0428 | FLRT2 | 14 | 86087875 | C | T | A0101,A0301,B0702,B3501,C0401,C0702 | C0702 | 396 | 456 | Ikwpshgaf | Tkwpshgaf |
| TU0428 | BCL11B | 14 | 99641754 | G | T | A0101,A0301,B0702,B3501,C0401,C0702 | A0301 | 35 | 1079 | rQmkthmhk | rHmkthmhk |
| TU0428 | AHNAK2 | 14 | 105405599 | G | C | A0101,A0301,B0702,B3501,C0401,C0702 | B0702 | 240 | 934 | vprfsfAap | vprfsfPap |
| TU0428 | AHNAK2 | 14 | 105411781 | G | A | A0101,A0301,B0702,B3501,C0401,C0702 | A0301 | 330 | 731 | asvdvsaLk | asvdvsaPk |
| TU0428 | AHNAK2 | 14 | 105411781 | G | A | A0101,A0301,B0702,B3501,C0401,C0702 | B3501 | 298 | 12078 | qasvdvsaL | qasvdvsaP |
| TU0428 | GABRA5 | 15 | 27188418 | C | A | A0101,A0301,B0702,B3501,C0401,C0702 | A0301 | 53 | 54 | isamslTk | isamslPk |
| TU0428 | LCMT2 | 15 | 43622072 | C | T | A0101,A0301,B0702,B3501,C0401,C0702 | A0301 | 287 | 441 | aliawTaqr | aliawAaqr |
| TU0428 | LCMT2 | 15 | 43622072 | C | T | A0101,A0301,B0702,B3501,C0401,C0702 | B3501 | 253 | 163 | liawTaqrf | liawAaqrf |
| TU0428 | CLPX | 15 | 65471352 | G | A | A0101,A0301,B0702,B3501,C0401,C0702 | A0301 | 87 | 142 | ksgFgnsgk | ksgSgnsgk |
| TU0428 | NOX5 | 15 | 69339813 | G | T | A0101,A0301,B0702,B3501,C0401,C0702 | B3501 | 142 | 171 | fasehaLli | fasehaVli |
| TU0428 | SCAPER | 15 | 77067396 | T | C | A0101,A0301,B0702,B3501,C0401,C0702 | B0702 | 8 | 10 | rpirsrsAa | rpirsrsTa |
| TU0428 | SCAPER | 15 | 77067396 | T | C | A0101,A0301,B0702,B3501,C0401,C0702 | B0702 | 190 | 2144 | Aavmpkvsl | Tavmpkvsl |
| TU0428 | BTBD1 | 15 | 83686964 | T | A | A0101,A0301,B0702,B3501,C0401,C0702 | A0301 | 18 | 2832 | sLygtkglk | sHygtkglk |
| TU0428 | ACAN | 15 | 89415247 | C | G | A0101,A0301,B0702,B3501,C0401,C0702 | A0101 | 207 | 300 | fvnnnaqEy | fvnnnaqDy |
| TU0428 | ACAN | 15 | 89415247 | C | G | A0101,A0301,B0702,B3501,C0401,C0702 | B3501 | 4 | 16 | fvnnnaqEy | fvnnnaqDy |
| TU0428 | WFIKKN1 | 16 | 683682 | C | A | A0101,A0301,B0702,B3501,C0401,C0702 | C0702 | 383 | 1060 | crlrRklal | crlrSklal |
| TU0428 | PKD1 | 16 | 2161704 | C | A | A0101,A0301,B0702,B3501,C0401,C0702 | B0702 | 12 | 2755 | yphplpspV | yphplpspG |

Figure 21 (Cont.)

| | | | | | | | | | | | |
|---|---|---|---|---|---|---|---|---|---|---|---|
| TU0428 | PKD1 | 16 | 2161704 | C | A | A0101,A0301,B0702,B3501,C0401,C0702 | B0702 | 352 | 119 | hplpspVgv | hplpspGgv |
| TU0428 | PKD1 | 16 | 2161704 | C | A | A0101,A0301,B0702,B3501,C0401,C0702 | B3501 | 30 | 74 | yphplpspV | yphplpspG |
| TU0428 | PKD1 | 16 | 2161704 | C | A | A0101,A0301,B0702,B3501,C0401,C0702 | B3501 | 7 | 6 | lpspVgvly | lpspGgvly |
| TU0428 | PKD1 | 16 | 2161704 | C | A | A0101,A0301,B0702,B3501,C0401,C0702 | B3501 | 224 | 2227 | spVgvlytw | spGgvlytw |
| TU0428 | FLYWCH1 | 16 | 2979797 | G | T | A0101,A0301,B0702,B3501,C0401,C0702 | B0702 | 86 | 705 | ipaaprkpS | ipaaprkpR |
| TU0428 | RRN3 | 16 | 15166842 | G | C | A0101,A0301,B0702,B3501,C0401,C0702 | B3501 | 75 | 37 | haschvEff | haschvQff |
| TU0428 | DNAH3 | 16 | 20975329 | C | A | A0101,A0301,B0702,B3501,C0401,C0702 | A0101 | 52 | 50 | qidetrmCy | qidetrmGy |
| TU0428 | SLC5A11 | 16 | 24919354 | C | A | A0101,A0301,B0702,B3501,C0401,C0702 | A0301 | 168 | 22580 | vvqasqggK | vvqasqggQ |
| TU0428 | SLC5A11 | 16 | 24919354 | C | A | A0101,A0301,B0702,B3501,C0401,C0702 | B3501 | 431 | 93 | qasqggKlf | qasqggQlf |
| TU0428 | SPN | 16 | 29675855 | T | C | A0101,A0301,B0702,B3501,C0401,C0702 | B3501 | 133 | 242 | laviAlval | laviVlval |
| TU0428 | LPCAT2 | 16 | 55562452 | G | T | A0101,A0301,B0702,B3501,C0401,C0702 | B3501 | 81 | 73 | cvvaWlpsm | cvvaGlpsm |
| TU0428 | CSNK2A2 | 16 | 58231621 | C | A | A0101,A0301,B0702,B3501,C0401,C0702 | B3501 | 363 | 1736 | mpgpaaVsr | mpgpaaGsr |
| TU0428 | CSNK2A2 | 16 | 58231621 | C | A | A0101,A0301,B0702,B3501,C0401,C0702 | B3501 | 363 | 2576 | aaVsrarvy | aaGsrarvy |
| TU0428 | FUK | 16 | 70501344 | G | T | A0101,A0301,B0702,B3501,C0401,C0702 | B0702 | 329 | 1027 | yaHnhgvyl | yaQnhgvyl |
| TU0428 | FUK | 16 | 70501344 | G | T | A0101,A0301,B0702,B3501,C0401,C0702 | B3501 | 64 | 587 | lpgspayaH | lpgspayaQ |
| TU0428 | FUK | 16 | 70501344 | G | T | A0101,A0301,B0702,B3501,C0401,C0702 | B3501 | 145 | 639 | yaHnhgvyl | yaQnhgvyl |
| TU0428 | CHST5 | 16 | 75563447 | G | T | A0101,A0301,B0702,B3501,C0401,C0702 | A0301 | 304 | 22916 | hvriaeaaK | hvriaeaaT |
| TU0428 | CHST5 | 16 | 75563447 | G | T | A0101,A0301,B0702,B3501,C0401,C0702 | A0301 | 103 | 53 | riaeaaKlk | riaeaaTlk |
| TU0428 | CHST5 | 16 | 75563447 | G | T | A0101,A0301,B0702,B3501,C0401,C0702 | A0301 | 104 | 331 | Klkpppflr | Tlkpppflr |
| TU0428 | WWOX | 16 | 78198149 | G | A | A0101,A0301,B0702,B3501,C0401,C0702 | A0301 | 19 | 167 | ilacrnmaK | ilacrnmaR |
| TU0428 | CDH13 | 16 | 83636135 | C | A | A0101,A0301,B0702,B3501,C0401,C0702 | A0301 | 455 | 23090 | gldvgltgK | gldvgltgT |
| TU0428 | KLHDC4 | 16 | 87782322 | G | C | A0101,A0301,B0702,B3501,C0401,C0702 | C0702 | 78 | 135 | yhykdVwvl | yhykdLwvl |

Figure 21 (Cont.)

| | | | | | | | | | | | |
|---|---|---|---|---|---|---|---|---|---|---|---|
| TU0428 | FANCA | 16 | 89866043 | T | C | A0101,A0301,B0702,B3501,C0401,C0702 | B0702 | 41 | 53 | mpqvAvdvl | mpqvTvdvl |
| TU0428 | FANCA | 16 | 89866043 | T | C | A0101,A0301,B0702,B3501,C0401,C0702 | B3501 | 35 | 51 | mpqvAvdvl | mpqvTvdvl |
| TU0428 | FANCA | 16 | 89866043 | T | C | A0101,A0301,B0702,B3501,C0401,C0702 | B3501 | 404 | 9052 | vAvdvlqrm | vTvdvlqrm |
| TU0428 | MYH13 | 17 | 10265727 | G | T | A0101,A0301,B0702,B3501,C0401,C0702 | A0301 | 170 | 94 | hlheTavly | hlhePavly |
| TU0428 | MYH13 | 17 | 10265727 | G | T | A0101,A0301,B0702,B3501,C0401,C0702 | B3501 | 150 | 436 | hlheTavly | hlhePavly |
| TU0428 | CCR10 | 17 | 40832380 | T | A | A0101,A0301,B0702,B3501,C0401,C0702 | B3501 | 157 | 230 | lllalSlpf | lllalTlpf |
| TU0428 | CCR10 | 17 | 40832380 | T | A | A0101,A0301,B0702,B3501,C0401,C0702 | B3501 | 268 | 614 | lalSlpfaa | lalTlpfaa |
| TU0428 | MARCH10 | 17 | 60813682 | A | G | A0101,A0301,B0702,B3501,C0401,C0702 | B0702 | 10 | 9 | spTrnrtpf | splrnrtpf |
| TU0428 | MARCH10 | 17 | 60813682 | A | G | A0101,A0301,B0702,B3501,C0401,C0702 | B3501 | 98 | 34 | spTrnrtpf | splrnrtpf |
| TU0428 | APOH | 17 | 64216725 | T | A | A0101,A0301,B0702,B3501,C0401,C0702 | B3501 | 486 | 616 | hamfgnVti | hamfgnDti |
| TU0428 | GRIN2C | 17 | 72848279 | C | A | A0101,A0301,B0702,B3501,C0401,C0702 | B0702 | 25 | 58 | kvrYgvail | kvrDgvail |
| TU0428 | QRICH2 | 17 | 74287594 | G | A | A0101,A0301,B0702,B3501,C0401,C0702 | B3501 | 80 | 4672 | lstglgstY | lstglgstH |
| TU0428 | QRICH2 | 17 | 74287594 | G | A | A0101,A0301,B0702,B3501,C0401,C0702 | B3501 | 48 | 105 | Ypdqqhvas | Hpdqqhvas |
| TU0428 | BAHCC1 | 17 | 79423369 | C | A | A0101,A0301,B0702,B3501,C0401,C0702 | B0702 | 20 | 40 | kvkaHrtsl | kvkaVrtsl |
| TU0428 | EPG5 | 18 | 43462397 | C | A | A0101,A0301,B0702,B3501,C0401,C0702 | A0101 | 326 | 1738 | lsdrtMlle | lsdrtRlle |
| TU0428 | EPG5 | 18 | 43462397 | C | A | A0101,A0301,B0702,B3501,C0401,C0702 | B0702 | 133 | 22760 | kpplsdrtM | kpplsdrtR |
| TU0428 | EPG5 | 18 | 43462397 | C | A | A0101,A0301,B0702,B3501,C0401,C0702 | B0702 | 391 | 493 | pplsdrtMl | pplsdrtRl |
| TU0428 | SERPINB11 | 18 | 61387277 | C | T | A0101,A0301,B0702,B3501,C0401,C0702 | B3501 | 412 | 740 | slidpssvm | sTidpssvm |
| TU0428 | CDH19 | 18 | 64235895 | C | A | A0101,A0301,B0702,B3501,C0401,C0702 | B0702 | 327 | 11769 | lVagagstf | lGagagstf |
| TU0428 | CDH19 | 18 | 64235895 | C | A | A0101,A0301,B0702,B3501,C0401,C0702 | B3501 | 18 | 207 | lVagagstf | lGagagstf |
| TU0428 | MED16 | 19 | 868115 | C | T | A0101,A0301,B0702,B3501,C0401,C0702 | A0301 | 126 | 18836 | rsldhlhpK | rsldhlhpE |
| TU0428 | ZBTB7A | 19 | 4054614 | A | T | A0101,A0301,B0702,B3501,C0401,C0702 | B0702 | 383 | 118 | avaaaEaav | avaaaVaav |
| TU0428 | ZBTB7A | 19 | 4054614 | A | T | A0101,A0301,B0702,B3501,C0401,C0702 | B3501 | 417 | 108 | eavaaaEaa | eavaaaVaa |

Figure 21 (Cont.)

| | | | | | | | | | | | |
|---|---|---|---|---|---|---|---|---|---|---|---|
| TU0428 | CAMSAP3 | 19 | 7677541 | C | T | A0101,A0301,B0702,B3501,C0401,C0702 | C0702 | 334 | 826 | rlMdqqrl | rlTdqqrl |
| TU0428 | MUC16 | 19 | 9061111 | T | C | A0101,A0301,B0702,B3501,C0401,C0702 | B0702 | 92 | 140 | tpltAtgsa | tpltTtgsa |
| TU0428 | MUC16 | 19 | 9061111 | T | C | A0101,A0301,B0702,B3501,C0401,C0702 | B3501 | 206 | 543 | ltAtgsaem | ltTtgsaem |
| TU0428 | MUC16 | 19 | 9068670 | A | T | A0101,A0301,B0702,B3501,C0401,C0702 | A0301 | 254 | 77 | svptptQak | svptptLak |
| TU0428 | MUC16 | 19 | 9084401 | C | T | A0101,A0301,B0702,B3501,C0401,C0702 | B0702 | 9 | 9 | rplrtfstm | rpVrtfstm |
| TU0428 | MUC16 | 19 | 9084401 | C | T | A0101,A0301,B0702,B3501,C0401,C0702 | B3501 | 37 | 33 | rplrtfstm | rpVrtfstm |
| TU0428 | MUC16 | 19 | 9090784 | C | T | A0101,A0301,B0702,B3501,C0401,C0702 | B0702 | 69 | 9 | rvKstissl | rvRstissl |
| TU0428 | OR7G1 | 19 | 9225973 | G | A | A0101,A0301,B0702,B3501,C0401,C0702 | C0702 | 242 | 279 | mfmstmdVl | mfmstmdAl |
| TU0428 | JUNB | 19 | 12903437 | G | T | A0101,A0301,B0702,B3501,C0401,C0702 | A0301 | 34 | 35 | rlaatNcrk | rlaatKcrk |
| TU0428 | IL27RA | 19 | 14153272 | C | T | A0101,A0301,B0702,B3501,C0401,C0702 | B3501 | 176 | 9232 | eaawtlleL | eaawtlleP |
| TU0428 | PKN1 | 19 | 14578707 | G | A | A0101,A0301,B0702,B3501,C0401,C0702 | B3501 | 170 | 1052 | Qpsgelfai | Rpsgelfai |
| TU0428 | PKN1 | 19 | 14578707 | G | A | A0101,A0301,B0702,B3501,C0401,C0702 | C0702 | 379 | 218 | efQpsgelf | efRpsgelf |
| TU0428 | F2RL3 | 19 | 17001127 | A | G | A0101,A0301,B0702,B3501,C0401,C0702 | B0702 | 142 | 176 | alrlAavvl | alrlTavvl |
| TU0428 | USHBP1 | 19 | 17361108 | C | T | A0101,A0301,B0702,B3501,C0401,C0702 | A0301 | 88 | 4465 | Kataralgk | Eataralgk |
| TU0428 | KIRREL2 | 19 | 36349629 | C | G | A0101,A0301,B0702,B3501,C0401,C0702 | B0702 | 287 | 3504 | vVggpsvsl | vLggpsvsl |
| TU0428 | SUPT5H | 19 | 39949671 | A | C | A0101,A0301,B0702,B3501,C0401,C0702 | A0301 | 172 | 374 | elgAyymkk | elgEyymkk |
| TU0428 | PSG8 | 19 | 43258649 | G | T | A0101,A0301,B0702,B3501,C0401,C0702 | B3501 | 215 | 2404 | Qpaqyswti | Ppaqyswti |
| TU0428 | PSG8 | 19 | 43258650 | G | T | A0101,A0301,B0702,B3501,C0401,C0702 | B0702 | 239 | 1866 | Tpaqyswti | Ppaqyswti |
| TU0428 | PSG8 | 19 | 43258650 | G | T | A0101,A0301,B0702,B3501,C0401,C0702 | B3501 | 157 | 2404 | Tpaqyswti | Ppaqyswti |
| TU0428 | NKPD1 | 19 | 45656425 | G | T | A0101,A0301,B0702,B3501,C0401,C0702 | A0301 | 320 | 1480 | Mgfmcevkk | Lgfmcevkk |
| TU0428 | CCDC8 | 19 | 46915091 | T | C | A0101,A0301,B0702,B3501,C0401,C0702 | B0702 | 25 | 44 | apaGqgaea | apaDqgaea |
| TU0428 | SPIB | 19 | 50926126 | C | T | A0101,A0301,B0702,B3501,C0401,C0702 | A0301 | 27 | 32 | hlsqppLmk | hlsqppPmk |

Figure 21 (Cont.)

| | | | | | | | | | | | |
|---|---|---|---|---|---|---|---|---|---|---|---|
| TU0428 | SPIB | 19 | 50926126 | C | T | A0101,A0301,B0702,B3501,C0401,C0702 | B0702 | 12 | 9414 | wphlsqppL | wphlsqppP |
| TU0428 | SPIB | 19 | 50926126 | C | T | A0101,A0301,B0702,B3501,C0401,C0702 | B3501 | 20 | 1708 | wphlsqppL | wphlsqppP |
| TU0428 | SIGLEC12 | 19 | 52000672 | G | A | A0101,A0301,B0702,B3501,C0401,C0702 | B0702 | 101 | 4973 | kmrpisgvM | kmrpisgvT |
| TU0428 | SIGLEC12 | 19 | 52000672 | G | A | A0101,A0301,B0702,B3501,C0401,C0702 | C0702 | 496 | 15186 | kmrpisgvM | kmrpisgvT |
| TU0428 | SIGLEC12 | 19 | 52004743 | G | A | A0101,A0301,B0702,B3501,C0401,C0702 | B0702 | 27 | 84 | ipvatnnpV | ipvatnnpA |
| TU0428 | SIGLEC12 | 19 | 52004743 | G | A | A0101,A0301,B0702,B3501,C0401,C0702 | B3501 | 135 | 137 | ipvatnnpV | ipvatnnpA |
| TU0428 | ZSCAN5A | 19 | 56733425 | C | A | A0101,A0301,B0702,B3501,C0401,C0702 | B3501 | 307 | 2853 | spVpaspvs | spGpaspvs |
| TU0428 | SNTG2 | 2 | 1204796 | C | T | A0101,A0301,B0702,B3501,C0401,C0702 | B0702 | 10 | 9 | apLspsspi | apSspsspi |
| TU0428 | NTSR2 | 2 | 11809819 | A | G | A0101,A0301,B0702,B3501,C0401,C0702 | B0702 | 9 | 25 | qplrarsPl | qplrarsLl |
| TU0428 | NTSR2 | 2 | 11809819 | A | G | A0101,A0301,B0702,B3501,C0401,C0702 | B3501 | 224 | 2397 | qplrarsPl | qplrarsLl |
| TU0428 | SNX17 | 2 | 27596143 | G | A | A0101,A0301,B0702,B3501,C0401,C0702 | A0301 | 31 | 632 | Ktfnsflrr | Etfnsflrr |
| TU0428 | PLB1 | 2 | 28814033 | A | G | A0101,A0301,B0702,B3501,C0401,C0702 | B0702 | 188 | 2955 | sVqghgtwl | sMqghgtwl |
| TU0428 | USP34 | 2 | 61528586 | C | A | A0101,A0301,B0702,B3501,C0401,C0702 | B0702 | 30 | 18 | fpgVlmgpv | fpgGlmgpv |
| TU0428 | USP34 | 2 | 61528586 | C | A | A0101,A0301,B0702,B3501,C0401,C0702 | B3501 | 392 | 219 | fpgVlmgpv | fpgGlmgpv |
| TU0428 | FBXO48 | 2 | 68692035 | C | A | A0101,A0301,B0702,B3501,C0401,C0702 | B0702 | 134 | 63 | kphcltvra | kphcMtvra |
| TU0428 | FABP1 | 2 | 88425806 | C | A | A0101,A0301,B0702,B3501,C0401,C0702 | A0301 | 60 | 154 | ivHngkhfk | ivQngkhfk |
| TU0428 | PTPN4 | 2 | 120643390 | G | T | A0101,A0301,B0702,B3501,C0401,C0702 | B3501 | 10 | 8 | spaeSefny | spaeAefny |
| TU0428 | CLASP1 | 2 | 122125239 | C | G | A0101,A0301,B0702,B3501,C0401,C0702 | B0702 | 17 | 50 | npypysHai | npypysDai |
| TU0428 | CLASP1 | 2 | 122125239 | C | G | A0101,A0301,B0702,B3501,C0401,C0702 | B3501 | 118 | 136 | npypysHai | npypysDai |
| TU0428 | CLASP1 | 2 | 122125239 | C | G | A0101,A0301,B0702,B3501,C0401,C0702 | B3501 | 50 | 57 | ypysHaint | ypysDaint |
| TU0428 | MAP3K19 | 2 | 135743719 | A | C | A0101,A0301,B0702,B3501,C0401,C0702 | A0301 | 119 | 62 | ltnfsCqak | ltnfsFqak |
| TU0428 | SCN9A | 2 | 167141109 | G | T | A0101,A0301,B0702,B3501,C0401,C0702 | C0702 | 337 | 115 | srspTmlpv | srspPmlpv |
| TU0428 | DFNB59 | 2 | 179325735 | C | G | A0101,A0301,B0702,B3501,C0401,C0702 | B3501 | 35 | 179 | dvisGsqly | dvisRsqly |

Figure 21 (Cont.)

| | | | | | | | | | | | |
|---|---|---|---|---|---|---|---|---|---|---|---|
| TU0428 | TTN | 2 | 179429959 | A | G | A0101,A0301,B0702,B3501,C0401,C0702 | A0301 | 122 | 309 | nlsAivlek | nlsVivlek |
| TU0428 | ITGA4 | 2 | 182322476 | G | T | A0101,A0301,B0702,B3501,C0401,C0702 | B3501 | 41 | 162 | lgvptgLpy | lgvptgRpy |
| TU0428 | ITGA4 | 2 | 182322476 | G | T | A0101,A0301,B0702,B3501,C0401,C0702 | B3501 | 165 | 2657 | Lpynvdtes | Rpynvdtes |
| TU0428 | GLS | 2 | 191745844 | G | T | A0101,A0301,B0702,B3501,C0401,C0702 | A0301 | 90 | 558 | gmlrYlllr | gmlrDlllr |
| TU0428 | HJURP | 2 | 234758409 | C | T | A0101,A0301,B0702,B3501,C0401,C0702 | A0301 | 203 | 1092 | rtvlgaNsk | rtvlgaDsk |
| TU0428 | HDAC4 | 2 | 240033338 | C | A | A0101,A0301,B0702,B3501,C0401,C0702 | B3501 | 43 | 18 | eaaVipvsf | eaaGipvsf |
| TU0428 | CST9L | 20 | 23546639 | T | G | A0101,A0301,B0702,B3501,C0401,C0702 | B3501 | 15 | 12688 | cPfqestel | cHfqestel |
| TU0428 | CST9 | 20 | 23584316 | C | T | A0101,A0301,B0702,B3501,C0401,C0702 | A0301 | 194 | 174 | qlrqtvcKk | qlrqtvcRk |
| TU0428 | MYH7B | 20 | 33567193 | G | T | A0101,A0301,B0702,B3501,C0401,C0702 | A0301 | 457 | 467 | htipwdVkk | htipwdGkk |
| TU0428 | DLGAP4 | 20 | 35060850 | C | T | A0101,A0301,B0702,B3501,C0401,C0702 | B3501 | 6 | 9 | qpryfmYay | qpryfmHay |
| TU0428 | FAM83D | 20 | 37555479 | G | A | A0101,A0301,B0702,B3501,C0401,C0702 | A0301 | 381 | 2504 | rvKthfqpr | rvEthfqpr |
| TU0428 | SGK2 | 20 | 42194989 | T | A | A0101,A0301,B0702,B3501,C0401,C0702 | B0702 | 349 | 215 | kpTggrct | kpSggrct |
| TU0428 | SLC2A10 | 20 | 45353683 | A | G | A0101,A0301,B0702,B3501,C0401,C0702 | C0702 | 51 | 214 | gRsppvlpl | gHsppvlpl |
| TU0428 | CTCFL | 20 | 56099114 | C | G | A0101,A0301,B0702,B3501,C0401,C0702 | B3501 | 61 | 66 | eaQrtsgaf | eaErtsgaf |
| TU0428 | CDH4 | 20 | 60348116 | C | A | A0101,A0301,B0702,B3501,C0401,C0702 | B0702 | 269 | 594 | spppkdtMl | spppkdtLl |
| TU0428 | GATA5 | 20 | 61050516 | G | T | A0101,A0301,B0702,B3501,C0401,C0702 | B3501 | 7 | 4082 | qaayadsgY | qaayadsgS |
| TU0428 | GATA5 | 20 | 61050516 | G | T | A0101,A0301,B0702,B3501,C0401,C0702 | B3501 | 141 | 53 | aayadsgYf | aayadsgSf |
| TU0428 | GATA5 | 20 | 61050516 | G | T | A0101,A0301,B0702,B3501,C0401,C0702 | B3501 | 94 | 32 | yadsgYflh | yadsgSflh |
| TU0428 | ZNF512B | 20 | 62594747 | T | A | A0101,A0301,B0702,B3501,C0401,C0702 | A0301 | 50 | 4931 | rVrlrkvlk | rErlrkvlk |
| TU0428 | ZNF512B | 20 | 62595547 | C | T | A0101,A0301,B0702,B3501,C0401,C0702 | A0301 | 27 | 51 | kTrvhrskk | kArvhrskk |
| TU0428 | SON | 21 | 34925750 | A | G | A0101,A0301,B0702,B3501,C0401,C0702 | B0702 | 15 | 12 | Vpvpvvsal | lpvpvvsal |
| TU0428 | SON | 21 | 34925750 | A | G | A0101,A0301,B0702,B3501,C0401,C0702 | B3501 | 128 | 85 | epdyvtVpv | epdyvtlpv |

Figure 21 (Cont.)

| | | | | | | | | | | | |
|---|---|---|---|---|---|---|---|---|---|---|---|
| TU0428 | SON | 21 | 34925750 | A | G | A0101,A0301,B0702,B3501,C0401,C0702 | B3501 | 15 | 8 | Vpvpvvsal | lpvpvvsal |
| TU0428 | DIP2A | 21 | 47949092 | A | T | A0101,A0301,B0702,B3501,C0401,C0702 | B0702 | 340 | 475 | kpgVrvalv | kpgDrvalv |
| TU0428 | OR11H1 | 22 | 16449012 | G | T | A0101,A0301,B0702,B3501,C0401,C0702 | A0301 | 86 | 112 | hlavvsMcy | hlavvsLcy |
| TU0428 | OR11H1 | 22 | 16449012 | G | T | A0101,A0301,B0702,B3501,C0401,C0702 | B0702 | 500 | 803 | vvsMcyssl | vvsLcyssl |
| TU0428 | OR11H1 | 22 | 16449012 | G | T | A0101,A0301,B0702,B3501,C0401,C0702 | B3501 | 211 | 93 | hlavvsMcy | hlavvsLcy |
| TU0428 | OR11H1 | 22 | 16449012 | G | T | A0101,A0301,B0702,B3501,C0401,C0702 | B3501 | 391 | 1916 | Mcysslmvm | Lcysslmvm |
| TU0428 | SEZ6L | 22 | 26747090 | G | C | A0101,A0301,B0702,B3501,C0401,C0702 | A0101 | 246 | 7700 | isdpvllvA | isdpvllvG |
| TU0428 | SEZ6L | 22 | 26747090 | G | C | A0101,A0301,B0702,B3501,C0401,C0702 | B3501 | 104 | 188 | llvAttiqy | llvGttiqy |
| TU0428 | TRIOBP | 22 | 38121793 | C | G | A0101,A0301,B0702,B3501,C0401,C0702 | C0702 | 214 | 1512 | Rrhtqfdpf | Prhtqfdpf |
| TU0428 | PNPLA3 | 22 | 44324727 | C | G | A0101,A0301,B0702,B3501,C0401,C0702 | B3501 | 296 | 9280 | dalvcscfM | dalvcscfl |
| TU0428 | PNPLA3 | 22 | 44324727 | C | G | A0101,A0301,B0702,B3501,C0401,C0702 | B3501 | 135 | 41 | lvcscfMpf | lvcscflpf |
| TU0428 | PNPLA3 | 22 | 44324727 | C | G | A0101,A0301,B0702,B3501,C0401,C0702 | B3501 | 311 | 3693 | Mpfysglip | lpfysglip |
| TU0428 | PNPLA3 | 22 | 44324727 | C | G | A0101,A0301,B0702,B3501,C0401,C0702 | C0702 | 85 | 198 | cfMpfysgl | cflpfysgl |
| TU0428 | C22orf26 | 22 | 46449697 | G | A | A0101,A0301,B0702,B3501,C0401,C0702 | B0702 | 36 | 16 | aararWraw | aararRraw |
| TU0428 | KLHDC7B | 22 | 50988105 | G | A | A0101,A0301,B0702,B3501,C0401,C0702 | A0301 | 197 | 881 | gMgaavmry | gVgaavmry |
| TU0428 | KLHDC7B | 22 | 50988105 | G | A | A0101,A0301,B0702,B3501,C0401,C0702 | B0702 | 90 | 156 | llrgMgaav | llrgVgaav |
| TU0428 | KLHDC7B | 22 | 50988105 | G | A | A0101,A0301,B0702,B3501,C0401,C0702 | C0702 | 31 | 138 | yrfdllrgM | yrfdllrgV |
| TU0428 | CHL1 | 3 | 361508 | C | T | A0101,A0301,B0702,B3501,C0401,C0702 | A0301 | 435 | 887 | vylmfFllk | vylmfLllk |
| TU0428 | CHL1 | 3 | 361508 | C | T | A0101,A0301,B0702,B3501,C0401,C0702 | A0301 | 219 | 1617 | mfFllkfsk | mfLllkfsk |
| TU0428 | CHL1 | 3 | 361508 | C | T | A0101,A0301,B0702,B3501,C0401,C0702 | C0702 | 485 | 504 | ylmfFllkf | ylmfLllkf |
| TU0428 | SYN2 | 3 | 12046078 | T | C | A0101,A0301,B0702,B3501,C0401,C0702 | B0702 | 271 | 28 | Ppngymtdl | Lpngymtdl |
| TU0428 | SYN2 | 3 | 12046078 | T | C | A0101,A0301,B0702,B3501,C0401,C0702 | B3501 | 423 | 157 | fianPpngy | fianLpngy |
| TU0428 | FBLN2 | 3 | 13611896 | T | A | A0101,A0301,B0702,B3501,C0401,C0702 | B0702 | 452 | 720 | laQglalal | laLglalal |

Figure 21 (Cont.)

| | | | | | | | | | | | |
|---|---|---|---|---|---|---|---|---|---|---|---|
| TU0428 | FBLN2 | 3 | 13611896 | T | A | A0101,A0301,B0702,B3501,C0401,C0702 | B3501 | 42 | 8 | epagawlaQ | epagawlaL |
| TU0428 | FBLN2 | 3 | 13611896 | T | A | A0101,A0301,B0702,B3501,C0401,C0702 | B3501 | 168 | 66 | laQglalal | laLglalal |
| TU0428 | OSBPL10 | 3 | 31710315 | C | T | A0101,A0301,B0702,B3501,C0401,C0702 | C0702 | 470 | 623 | fyggkvhrl | fyggkvhrV |
| TU0428 | ITGA9 | 3 | 37818949 | C | A | A0101,A0301,B0702,B3501,C0401,C0702 | B3501 | 326 | 108 | ipqeKenif | ipqeQenif |
| TU0428 | SCN10A | 3 | 38798272 | C | T | A0101,A0301,B0702,B3501,C0401,C0702 | A0101 | 430 | 379 | ilaIvtmay | ilaVvtmay |
| TU0428 | SCN10A | 3 | 38798272 | C | T | A0101,A0301,B0702,B3501,C0401,C0702 | A0301 | 82 | 71 | ilaIvtmay | ilaVvtmay |
| TU0428 | SCN10A | 3 | 38798272 | C | T | A0101,A0301,B0702,B3501,C0401,C0702 | B3501 | 358 | 276 | ilaIvtmay | ilaVvtmay |
| TU0428 | MST1R | 3 | 49924840 | G | A | A0101,A0301,B0702,B3501,C0401,C0702 | C0702 | 415 | 22551 | ymnlgpstL | ymnlgpstS |
| TU0428 | IFRD2 | 3 | 50326091 | T | C | A0101,A0301,B0702,B3501,C0401,C0702 | A0301 | 352 | 222 | vlyVdswar | vlyMdswar |
| TU0428 | B4GALT4 | 3 | 118945796 | G | C | A0101,A0301,B0702,B3501,C0401,C0702 | C0702 | 114 | 190 | yrpEeckal | yrpQeckal |
| TU0428 | HEG1 | 3 | 124729380 | G | T | A0101,A0301,B0702,B3501,C0401,C0702 | A0301 | 485 | 22486 | asvnscavK | asvnscavN |
| TU0428 | SNX4 | 3 | 125199163 | C | A | A0101,A0301,B0702,B3501,C0401,C0702 | B0702 | 93 | 47 | npdNrftdl | npdKrftdl |
| TU0428 | SI | 3 | 164709226 | T | A | A0101,A0301,B0702,B3501,C0401,C0702 | B3501 | 65 | 866 | Yasydtinl | Nasydtinl |
| TU0428 | ZBBX | 3 | 167023493 | C | T | A0101,A0301,B0702,B3501,C0401,C0702 | A0301 | 30 | 89 | slKlsnlyk | slElsnlyk |
| TU0428 | ZBBX | 3 | 167023493 | C | T | A0101,A0301,B0702,B3501,C0401,C0702 | B3501 | 464 | 123 | eslKlsnly | eslElsnly |
| TU0428 | ATP13A4 | 3 | 193220394 | A | T | A0101,A0301,B0702,B3501,C0401,C0702 | A0301 | 64 | 18231 | qiyswkkvK | qiyswkkvl |
| TU0428 | GP5 | 3 | 194117882 | G | A | A0101,A0301,B0702,B3501,C0401,C0702 | A0301 | 57 | 256 | rVlpralfr | rAlpralfr |
| TU0428 | GP5 | 3 | 194117882 | G | A | A0101,A0301,B0702,B3501,C0401,C0702 | B0702 | 33 | 17 | rlrVlpral | rlrAlpral |
| TU0428 | GP5 | 3 | 194117882 | G | A | A0101,A0301,B0702,B3501,C0401,C0702 | C0702 | 123 | 118 | lrmrlrVl | lrmrlrAl |
| TU0428 | GP5 | 3 | 194117882 | G | A | A0101,A0301,B0702,B3501,C0401,C0702 | C0702 | 484 | 809 | lrVlpralf | lrAlpralf |
| TU0428 | HTT | 4 | 3215835 | T | C | A0101,A0301,B0702,B3501,C0401,C0702 | B3501 | 161 | 144 | vthacsHiy | vthacsLiy |
| TU0428 | HTT | 4 | 3215835 | T | C | A0101,A0301,B0702,B3501,C0401,C0702 | C0702 | 198 | 1804 | Hiycvhfil | Liycvhfil |

Figure 21 (Cont.)

| | | | | | | | | | | | |
|---|---|---|---|---|---|---|---|---|---|---|---|
| TU0428 | HTT | 4 | 3234980 | G | A | A0101,A0301,B0702,B3501,C0401,C0702 | B0702 | 123 | 5509 | lpsrvgalI | lpsrvgalH |
| TU0428 | HTT | 4 | 3234980 | G | A | A0101,A0301,B0702,B3501,C0401,C0702 | B0702 | 335 | 101 | rvgalIgvl | rvgalHgvl |
| TU0428 | EVC2 | 4 | 5630442 | A | G | A0101,A0301,B0702,B3501,C0401,C0702 | A0301 | 396 | 69 | lTdffqask | lMdffqask |
| TU0428 | EVC2 | 4 | 5630442 | A | G | A0101,A0301,B0702,B3501,C0401,C0702 | B3501 | 271 | 824 | nveelTdff | nveelMdff |
| TU0428 | EVC | 4 | 5733236 | C | G | A0101,A0301,B0702,B3501,C0401,C0702 | B0702 | 347 | 9 | sAssslgsl | sPssslgsl |
| TU0428 | EVC | 4 | 5733236 | C | G | A0101,A0301,B0702,B3501,C0401,C0702 | B3501 | 169 | 180 | qpveasAss | qpveasPss |
| TU0428 | EVC | 4 | 5747005 | G | T | A0101,A0301,B0702,B3501,C0401,C0702 | A0101 | 468 | 320 | msgagdsDy | msgagdsEy |
| TU0428 | EVC | 4 | 5747005 | G | T | A0101,A0301,B0702,B3501,C0401,C0702 | B3501 | 40 | 10 | msgagdsDy | msgagdsEy |
| TU0428 | GPR78 | 4 | 8588954 | C | G | A0101,A0301,B0702,B3501,C0401,C0702 | A0301 | 55 | 9995 | rllkrtprR | rllkrtprP |
| TU0428 | GPR78 | 4 | 8588954 | C | G | A0101,A0301,B0702,B3501,C0401,C0702 | B0702 | 102 | 10135 | Rasthdssl | Pasthdssl |
| TU0428 | ARAP2 | 4 | 36162098 | T | G | A0101,A0301,B0702,B3501,C0401,C0702 | A0301 | 484 | 187 | sltQeelnk | sltKeelnk |
| TU0428 | GABRB1 | 4 | 47427856 | C | A | A0101,A0301,B0702,B3501,C0401,C0702 | C0702 | 237 | 154 | sreaygSal | sreaygRal |
| TU0428 | KDR | 4 | 55955136 | G | T | A0101,A0301,B0702,B3501,C0401,C0702 | B0702 | 217 | 748 | tpemyKtml | tpemyQtml |
| TU0428 | UBA6 | 4 | 68494811 | T | A | A0101,A0301,B0702,B3501,C0401,C0702 | A0301 | 63 | 1086 | iLefkpsnk | iQefkpsnk |
| TU0428 | UGT2B10 | 4 | 69870751 | T | A | A0101,A0301,B0702,B3501,C0401,C0702 | B3501 | 273 | 89 | aMfwiefvm | aVfwiefvm |
| TU0428 | UGT2A1 | 4 | 70505162 | G | A | A0101,A0301,B0702,B3501,C0401,C0702 | B3501 | 487 | 468 | tvlassVtl | tvlassAtl |
| TU0428 | CSN3 | 4 | 71114956 | G | T | A0101,A0301,B0702,B3501,C0401,C0702 | B0702 | 204 | 20 | Lpnlhpsfi | Rpnlhpsfi |
| TU0428 | CSN3 | 4 | 71114956 | G | T | A0101,A0301,B0702,B3501,C0401,C0702 | C0702 | 276 | 17020 | shpptvvrL | shpptvvrR |
| TU0428 | GC | 4 | 72618334 | A | C | A0101,A0301,B0702,B3501,C0401,C0702 | B0702 | 102 | 112 | lpEatptel | lpDatptel |
| TU0428 | GC | 4 | 72618334 | A | C | A0101,A0301,B0702,B3501,C0401,C0702 | B3501 | 59 | 41 | lpEatptel | lpDatptel |
| TU0428 | PPEF2 | 4 | 76817445 | C | A | A0101,A0301,B0702,B3501,C0401,C0702 | B3501 | 224 | 42 | tstqhhfSf | tstqhhfAf |
| TU0428 | PPEF2 | 4 | 76817445 | C | A | A0101,A0301,B0702,B3501,C0401,C0702 | C0702 | 169 | 515 | Sfqnaeraf | Afqnaeraf |
| TU0428 | ART3 | 4 | 77025119 | C | A | A0101,A0301,B0702,B3501,C0401,C0702 | B3501 | 209 | 538 | eptqiTapg | eptqiPapg |

Figure 21 (Cont.)

| | | | | | | | | | | | |
|---|---|---|---|---|---|---|---|---|---|---|---|
| TU0428 | COQ2 | 4 | 84185440 | A | G | A0101,A0301,B0702,B3501,C0401,C0702 | C0702 | 334 | 327 | nrtlgliAf | nrtlgliVf |
| TU0428 | PPM1K | 4 | 89198298 | C | A | A0101,A0301,B0702,B3501,C0401,C0702 | A0301 | 380 | 20488 | ssharlsaY | ssharlsaD |
| TU0428 | PPM1K | 4 | 89198298 | C | A | A0101,A0301,B0702,B3501,C0401,C0702 | B3501 | 221 | 31615 | ssharlsaY | ssharlsaD |
| TU0428 | PPM1K | 4 | 89198298 | C | A | A0101,A0301,B0702,B3501,C0401,C0702 | C0702 | 295 | 836 | arlsaYatl | arlsaDatl |
| TU0428 | DCHS2 | 4 | 155219549 | T | G | A0101,A0301,B0702,B3501,C0401,C0702 | B0702 | 39 | 12467 | lPdeasgaf | lTdeasgaf |
| TU0428 | DCHS2 | 4 | 155219549 | T | G | A0101,A0301,B0702,B3501,C0401,C0702 | B3501 | 5 | 62 | lPdeasgaf | lTdeasgaf |
| TU0428 | DCHS2 | 4 | 155241735 | C | T | A0101,A0301,B0702,B3501,C0401,C0702 | B0702 | 278 | 255 | rlrsltTqi | rlrsltAqi |
| TU0428 | NPY1R | 4 | 164246890 | C | A | A0101,A0301,B0702,B3501,C0401,C0702 | A0301 | 81 | 79 | kiyirlkSr | kiyirlkRr |
| TU0428 | NPY1R | 4 | 164246890 | C | A | A0101,A0301,B0702,B3501,C0401,C0702 | A0301 | 51 | 9832 | kSmnmmdk | kRmnmmdk |
| TU0428 | NPY1R | 4 | 164246891 | C | A | A0101,A0301,B0702,B3501,C0401,C0702 | A0301 | 87 | 79 | kiyirlkMr | kiyirlkRr |
| TU0428 | NPY1R | 4 | 164246891 | C | A | A0101,A0301,B0702,B3501,C0401,C0702 | A0301 | 24 | 9832 | kMmnmmdk | kRmnmmdk |
| TU0428 | TLR3 | 4 | 187004074 | C | T | A0101,A0301,B0702,B3501,C0401,C0702 | A0301 | 28 | 70 | hiFnltknk | hiLnltknk |
| TU0428 | TLR3 | 4 | 187004074 | C | T | A0101,A0301,B0702,B3501,C0401,C0702 | B3501 | 73 | 3079 | lahsplhiF | lahsplhiL |
| TU0428 | ADAMTS12 | 5 | 33588907 | C | A | A0101,A0301,B0702,B3501,C0401,C0702 | B0702 | 84 | 123 | pprwwSgew | pprwwAgew |
| TU0428 | IL7R | 5 | 35876274 | A | G | A0101,A0301,B0702,B3501,C0401,C0702 | B3501 | 114 | 209 | cpsedvvVt | cpsedvvIt |
| TU0428 | PLCXD3 | 5 | 41382119 | C | A | A0101,A0301,B0702,B3501,C0401,C0702 | B0702 | 335 | 544 | vpflCpgqm | vpflWpgqm |
| TU0428 | PLCXD3 | 5 | 41382119 | C | A | A0101,A0301,B0702,B3501,C0401,C0702 | B3501 | 97 | 224 | vpflCpgqm | vpflWpgqm |
| TU0428 | DHX29 | 5 | 54563535 | G | A | A0101,A0301,B0702,B3501,C0401,C0702 | B3501 | 372 | 10644 | amadsdhlM | amadsdhlT |
| TU0428 | VCAN | 5 | 82843868 | G | T | A0101,A0301,B0702,B3501,C0401,C0702 | C0702 | 471 | 429 | frclFlpsy | frclClpsy |
| TU0428 | VCAN | 5 | 82843868 | G | T | A0101,A0301,B0702,B3501,C0401,C0702 | C0702 | 142 | 1882 | Flpsyvgal | Clpsyvgal |
| TU0428 | TTC37 | 5 | 94860202 | T | A | A0101,A0301,B0702,B3501,C0401,C0702 | C0702 | 274 | 225 | trNdktkal | trKdktkal |
| TU0428 | FNIP1 | 5 | 131039874 | C | A | A0101,A0301,B0702,B3501,C0401,C0702 | A0301 | 375 | 1433 | igLifslsk | igVifslsk |

Figure 21 (Cont.)

| | | | | | | | | | | | |
|---|---|---|---|---|---|---|---|---|---|---|---|
| TU0428 | AFF4 | 5 | 132270203 | T | A | A0101,A0301,B0702,B3501,C0401,C0702 | B0702 | 200 | 17729 | rssspgkpL | rssspgkpQ |
| TU0428 | PCDHB10 | 5 | 140574284 | G | A | A0101,A0301,B0702,B3501,C0401,C0702 | A0301 | 123 | 2473 | avrlcrrsK | avrlcrrsR |
| TU0428 | PCDHGA10 | 5 | 140795128 | T | C | A0101,A0301,B0702,B3501,C0401,C0702 | B3501 | 26 | 823 | lPllddskf | lSllddskf |
| TU0428 | ARSI | 5 | 149681864 | G | A | A0101,A0301,B0702,B3501,C0401,C0702 | C0401 | 234 | 148 | swdwakSsf | swdwakPsf |
| TU0428 | NSD1 | 5 | 176721151 | T | C | A0101,A0301,B0702,B3501,C0401,C0702 | B0702 | 310 | 711 | ppadtnqTl | ppadtnqMl |
| TU0428 | NSD1 | 5 | 176722005 | G | A | A0101,A0301,B0702,B3501,C0401,C0702 | B3501 | 82 | 183 | qppakTfly | qppakAfly |
| TU0428 | OR2H2 | 6 | 29556436 | T | A | A0101,A0301,B0702,B3501,C0401,C0702 | A0301 | 402 | 933 | kafgtSssh | kafgtCssh |
| TU0428 | POLH | 6 | 43582136 | T | G | A0101,A0301,B0702,B3501,C0401,C0702 | B3501 | 9 | 27 | falelqkAf | falelqkSf |
| TU0428 | RARS2 | 6 | 88240570 | C | T | A0101,A0301,B0702,B3501,C0401,C0702 | A0301 | 182 | 611 | Mqalslwqk | Vqalslwqk |
| TU0428 | RPS6KA2 | 6 | 166918041 | G | C | A0101,A0301,B0702,B3501,C0401,C0702 | B3501 | 130 | 187 | lalEhlhsl | lalDhlhsl |
| TU0428 | ERMARD | 6 | 170162535 | T | A | A0101,A0301,B0702,B3501,C0401,C0702 | B3501 | 232 | 741 | fadSailll | fadCailll |
| TU0428 | ERMARD | 6 | 170162535 | T | A | A0101,A0301,B0702,B3501,C0401,C0702 | C0702 | 58 | 56 | hrfadSail | hrfadCail |
| TU0428 | IQCE | 7 | 2645522 | C | T | A0101,A0301,B0702,B3501,C0401,C0702 | B3501 | 220 | 1396 | lpdqsspvS | lpdqsspvP |
| TU0428 | SDK1 | 7 | 4304940 | A | C | A0101,A0301,B0702,B3501,C0401,C0702 | B0702 | 61 | 43 | hpvittPsa | hpvittQsa |
| TU0428 | SDK1 | 7 | 4304940 | A | C | A0101,A0301,B0702,B3501,C0401,C0702 | B3501 | 65 | 128 | hpvittPsa | hpvittQsa |
| TU0428 | FBXL18 | 7 | 5521551 | T | A | A0101,A0301,B0702,B3501,C0401,C0702 | B0702 | 178 | 15474 | aVrpalnvv | aErpalnvv |
| TU0428 | FBXL18 | 7 | 5521551 | T | A | A0101,A0301,B0702,B3501,C0401,C0702 | C0702 | 364 | 237 | sfqaVrpal | sfqaErpal |
| TU0428 | TWIST1 | 7 | 19156386 | A | T | A0101,A0301,B0702,B3501,C0401,C0702 | A0301 | 333 | 202 | lsyalsvwr | lsyaFsvwr |
| TU0428 | TWIST1 | 7 | 19156386 | A | T | A0101,A0301,B0702,B3501,C0401,C0702 | C0702 | 429 | 623 | syalsvwrm | syaFsvwrm |
| TU0428 | GPNMB | 7 | 23300310 | C | A | A0101,A0301,B0702,B3501,C0401,C0702 | A0301 | 15 | 10502 | vlngtfslK | vlngtfslN |
| TU0428 | GPR141 | 7 | 37780182 | A | C | A0101,A0301,B0702,B3501,C0401,C0702 | B3501 | 182 | 54 | Rvflltvpf | Svflltvpf |
| TU0428 | ABCA13 | 7 | 48285485 | C | T | A0101,A0301,B0702,B3501,C0401,C0702 | A0301 | 20 | 8414 | cLngrfsek | cPngrfsek |
| TU0428 | ABCA13 | 7 | 48285485 | C | T | A0101,A0301,B0702,B3501,C0401,C0702 | B3501 | 421 | 1328 | navcLngrf | navcPngrf |

Figure 21 (Cont.)

| | | | | | | | | | | | |
|---|---|---|---|---|---|---|---|---|---|---|---|
| TU0428 | ABCA13 | 7 | 48431666 | C | T | A0101,A0301,B0702,B3501,C0401,C0702 | A0301 | 62 | 24 | Ylllfasik | Hlllfasik |
| TU0428 | PON1 | 7 | 94937446 | T | C | A0101,A0301,B0702,B3501,C0401,C0702 | B3501 | 71 | 27 | dpylRswem | dpylQswem |
| TU0428 | PON1 | 7 | 94937446 | T | C | A0101,A0301,B0702,B3501,C0401,C0702 | C0702 | 104 | 165 | ylRswemyl | ylQswemyl |
| TU0428 | TECPR1 | 7 | 97847319 | A | T | A0101,A0301,B0702,B3501,C0401,C0702 | B3501 | 323 | 42 | Npqgssweh | Ypqgssweh |
| TU0428 | ZAN | 7 | 100331837 | C | A | A0101,A0301,B0702,B3501,C0401,C0702 | A0301 | 113 | 151 | lvgaalfrk | lvgaaLfrk |
| TU0428 | EPHB4 | 7 | 100417473 | T | C | A0101,A0301,B0702,B3501,C0401,C0702 | B0702 | 392 | 76 | vsrlDgssl | vsrlNgssl |
| TU0428 | OR2A5 | 7 | 143748257 | G | A | A0101,A0301,B0702,B3501,C0401,C0702 | A0301 | 155 | 130 | Tivmymapk | Aivmymapk |
| TU0428 | OR2A5 | 7 | 143748257 | G | A | A0101,A0301,B0702,B3501,C0401,C0702 | B3501 | 159 | 307 | lffgsTivm | lffgsAivm |
| TU0428 | OR2A5 | 7 | 143748257 | G | A | A0101,A0301,B0702,B3501,C0401,C0702 | C0702 | 291 | 254 | ffgsTivmy | ffgsAivmy |
| TU0428 | ZBED6CL | 7 | 150028087 | G | T | A0101,A0301,B0702,B3501,C0401,C0702 | B3501 | 257 | 156 | wasiivkNy | wasiivkKy |
| TU0428 | GBX1 | 7 | 150864368 | C | T | A0101,A0301,B0702,B3501,C0401,C0702 | A0301 | 416 | 17681 | rltntfcaR | rltntfcaG |
| TU0428 | MYOM2 | 8 | 2021539 | G | T | A0101,A0301,B0702,B3501,C0401,C0702 | C0702 | 261 | 15055 | lytlrivsL | lytlrivsR |
| TU0428 | CSMD1 | 8 | 3000193 | G | C | A0101,A0301,B0702,B3501,C0401,C0702 | B0702 | 64 | 108 | lpigygGhi | lpigygAhi |
| TU0428 | CSMD1 | 8 | 3253725 | G | A | A0101,A0301,B0702,B3501,C0401,C0702 | A0101 | 40 | 13358 | rssigfliY | rssigfliH |
| TU0428 | CSMD1 | 8 | 3253725 | G | A | A0101,A0301,B0702,B3501,C0401,C0702 | A0301 | 444 | 1469 | rssigfliY | rssigfliH |
| TU0428 | SLC7A2 | 8 | 17412140 | G | C | A0101,A0301,B0702,B3501,C0401,C0702 | A0301 | 42 | 630 | kSlaqinsk | kClaqinsk |
| TU0428 | ZNF703 | 8 | 37554940 | C | T | A0101,A0301,B0702,B3501,C0401,C0702 | C0702 | 229 | 17505 | srkdsgssL | srkdsgssS |
| TU0428 | RP1 | 8 | 55539057 | G | A | A0101,A0301,B0702,B3501,C0401,C0702 | A0301 | 480 | 417 | tlksqkkHk | tlksqkkRk |
| TU0428 | CYP7B1 | 8 | 65528568 | G | A | A0101,A0301,B0702,B3501,C0401,C0702 | A0101 | 286 | 530 | tswdMaely | tswdTaely |
| TU0428 | CYP7B1 | 8 | 65528568 | G | A | A0101,A0301,B0702,B3501,C0401,C0702 | B3501 | 191 | 201 | tswdMaely | tswdTaely |
| TU0428 | CYP7B1 | 8 | 65528568 | G | A | A0101,A0301,B0702,B3501,C0401,C0702 | B3501 | 106 | 292 | wdMaelypf | wdTaelypf |
| TU0428 | INTS8 | 8 | 95869015 | A | T | A0101,A0301,B0702,B3501,C0401,C0702 | A0301 | 140 | 324 | tvkdfsLak | tvkdfsHak |

Figure 21 (Cont.)

| | | | | | | | | | | | |
|---|---|---|---|---|---|---|---|---|---|---|---|
| TU0428 | DGAT1 | 8 | 145541766 | G | T | A0101,A0301,B0702,B3501,C0401,C0702 | A0101 | 201 | 1025 | nlNyrdlyy | nlTyrdlyy |
| TU0428 | DGAT1 | 8 | 145541766 | G | T | A0101,A0301,B0702,B3501,C0401,C0702 | A0301 | 292 | 626 | vsypdnlNy | vsypdnlTy |
| TU0428 | DGAT1 | 8 | 145541766 | G | T | A0101,A0301,B0702,B3501,C0401,C0702 | B3501 | 348 | 24 | vsypdnlNy | vsypdnlTy |
| TU0428 | DGAT1 | 8 | 145541766 | G | T | A0101,A0301,B0702,B3501,C0401,C0702 | C0702 | 34 | 39 | Nyrdlyyfl | Tyrdlyyfl |
| TU0428 | CD72 | 9 | 35618053 | C | A | A0101,A0301,B0702,B3501,C0401,C0702 | B0702 | 478 | 407 | avlgLpssl | avlgVpssl |
| TU0428 | CD72 | 9 | 35618053 | C | A | A0101,A0301,B0702,B3501,C0401,C0702 | B0702 | 39 | 35 | Lpsslassv | Vpsslassv |
| TU0428 | CD72 | 9 | 35618053 | C | A | A0101,A0301,B0702,B3501,C0401,C0702 | B3501 | 476 | 529 | vpavlgLps | vpavlgVps |
| TU0428 | CD72 | 9 | 35618053 | C | A | A0101,A0301,B0702,B3501,C0401,C0702 | B3501 | 103 | 876 | Lpsslassv | Vpsslassv |
| TU0428 | WNK2 | 9 | 96021312 | G | A | A0101,A0301,B0702,B3501,C0401,C0702 | B0702 | 37 | 106 | lptatvppM | lptatvppV |
| TU0428 | WNK2 | 9 | 96021312 | G | A | A0101,A0301,B0702,B3501,C0401,C0702 | B3501 | 4 | 73 | lptatvppM | lptatvppV |
| TU0428 | C9orf156 | 9 | 100672338 | C | T | A0101,A0301,B0702,B3501,C0401,C0702 | B0702 | 464 | 2792 | radgaprsM | radgaprsV |
| TU0428 | C9orf156 | 9 | 100672338 | C | T | A0101,A0301,B0702,B3501,C0401,C0702 | B0702 | 15 | 21 | aprsMvpaw | aprsVvpaw |
| TU0428 | OR13D1 | 9 | 107456892 | C | G | A0101,A0301,B0702,B3501,C0401,C0702 | C0702 | 289 | 352 | flfllcVim | flfllcLim |
| TU0428 | MXRA5 | X | 3240568 | G | C | A0101,A0301,B0702,B3501,C0401,C0702 | A0301 | 99 | 113 | Sllikkgmk | Tllikkgmk |
| TU0428 | CXorf22 | X | 36007614 | T | G | A0101,A0301,B0702,B3501,C0401,C0702 | B3501 | 153 | 134 | eLvgytlvy | eFvgytlvy |
| TU0428 | CCNB3 | X | 50094370 | C | A | A0101,A0301,B0702,B3501,C0401,C0702 | C0702 | 70 | 91 | yykyshQvf | yykyshPvf |
| TU0428 | CCNB3 | X | 50094370 | C | A | A0101,A0301,B0702,B3501,C0401,C0702 | C0702 | 178 | 212 | ykyshQvff | ykyshPvff |
| TU0428 | DGKK | X | 50113438 | G | T | A0101,A0301,B0702,B3501,C0401,C0702 | C0702 | 137 | 3808 | sYqsfignl | sVqsfignl |
| TU0428 | PAK3 | X | 110463619 | A | G | A0101,A0301,B0702,B3501,C0401,C0702 | B0702 | 9 | 10 | kplsGltpl | kplsSltpl |
| TU0428 | PAK3 | X | 110463619 | A | G | A0101,A0301,B0702,B3501,C0401,C0702 | B3501 | 312 | 417 | kplsGltpl | kplsSltpl |
| TU0428 | MAGEC1 | X | 140994591 | C | G | A0101,A0301,B0702,B3501,C0401,C0702 | B0702 | 120 | 42 | spertQstf | spertHstf |
| TU0428 | MAGEC1 | X | 140994591 | C | G | A0101,A0301,B0702,B3501,C0401,C0702 | B3501 | 439 | 289 | spertQstf | spertHstf |
| TU0428 | MAGEA3 | X | 151935932 | G | T | A0101,A0301,B0702,B3501,C0401,C0702 | B0702 | 76 | 16 | lpttmnypl | lpttmnypL |

Figure 21 (Cont.)

| | | | | | | | | | | | |
|---|---|---|---|---|---|---|---|---|---|---|---|
| TU0428 | MAGEA3 | X | 151935932 | G | T | A0101,A0301,B0702,B3501,C0401,C0702 | B3501 | 70 | 14 | lpttmnypl | lpttmnypL |
| VA1330 | LPPR4 | 1 | 99764708 | A | T | A0301,A2601,B3502,B4403,C0401 | A0301 | 351 | 443 | ytsllvsck | ytslNvsck |
| VA1330 | NTRK1 | 1 | 156830779 | G | A | A0301,A2601,B3502,B4403,C0401 | B4403 | 29 | 25055 | aEpgsllaw | aGpgsllaw |
| VA1330 | GXYLT1 | 12 | 42512967 | A | T | A0301,A2601,B3502,B4403,C0401 | A0301 | 131 | 372 | Rlkiqpvek | Slkiqpvek |
| VA1330 | TTN | 2 | 179426788 | T | C | A0301,A2601,B3502,B4403,C0401 | A0301 | 91 | 168 | slslkGask | slslkEask |
| VA1330 | NIPBL | 5 | 37007486 | A | G | A0301,A2601,B3502,B4403,C0401 | A0301 | 151 | 208 | kqrvMvmly | kqrvlvmly |
| VA1330 | NIPBL | 5 | 37007486 | A | G | A0301,A2601,B3502,B4403,C0401 | A0301 | 42 | 89 | rvMvmlynk | rvlvmlynk |
| VA1330 | SKAP2 | 7 | 26765561 | C | G | A0301,A2601,B3502,B4403,C0401 | B4403 | 39 | 81 | eewvqHlkf | eewvqQlkf |
| VA1330 | SMU1 | 9 | 33056230 | C | T | A0301,A2601,B3502,B4403,C0401 | A0301 | 149 | 293 | qtirihSlk | qtirihGlk |
| VA1330 | SMU1 | 9 | 33056230 | C | T | A0301,A2601,B3502,B4403,C0401 | A0301 | 53 | 63 | rihSlksgk | rihGlksgk |
| VA1330 | SMU1 | 9 | 33056230 | C | T | A0301,A2601,B3502,B4403,C0401 | A0301 | 79 | 87 | Slksgktlk | Glksgktlk |
| VA1330 | SVEP1 | 9 | 113275377 | A | G | A0301,A2601,B3502,B4403,C0401 | A0301 | 348 | 326 | elvhRpalk | elvhCpalk |
| VA7859 | UPF3A | 13 | 115047496 | G | C | A2301,A2902,B4403,B4901,C0701,C1601 | C0701 | 388 | 591 | krtalskLv | krtalskVv |
| VA7859 | MEF2A | 15 | 100211794 | C | T | A2301,A2902,B4403,B4901,C0701,C1601 | A2902 | 302 | 14877 | dtsyvltpY | dtsyvltpH |
| VA7859 | IL11 | 19 | 55879672 | C | T | A2301,A2902,B4403,B4901,C0701,C1601 | C0701 | 120 | 305 | lHraggssl | lRraggssl |
| VA7859 | ZNF814 | 19 | 58385748 | G | A | A2301,A2902,B4403,B4901,C0701,C1601 | A2301 | 199 | 293 | ksfskyVsf | ksfskyAsf |
| VA7859 | ZNF814 | 19 | 58385748 | G | A | A2301,A2902,B4403,B4901,C0701,C1601 | C0701 | 112 | 192 | Vsfsnhqrv | Asfsnhqrv |
| VA7859 | SERHL2 | 22 | 42951058 | G | A | A2301,A2902,B4403,B4901,C0701,C1601 | A2301 | 335 | 331 | gwldnaNsf | gwldnaSsf |
| VA7859 | CCNC | 6 | 99999739 | C | G | A2301,A2902,B4403,B4901,C0701,C1601 | A2902 | 5 | 8 | yafpkQfpy | yafpkEfpy |
| VA7859 | PSIP1 | 9 | 15469280 | A | G | A2301,A2902,B4403,B4901,C0701,C1601 | B4403 | 41 | 17 | aeiknsPki | aeiknsLki |
| WA7899 | WARS2 | 1 | 119575619 | T | C | A0321,A2402,A0301,B3501,B3502,C0401, | A0301 | 48 | 46 | Rvlqigsak | Kvlqigsak |
| WA7899 | OR10Z1 | 1 | 158577070 | T | C | A0321,A2402,A0301,B3501,B3502,C0401, | A2402 | 131 | 106 | tytvAtpll | tytvVtpll |

Figure 21 (Cont.)

| | | | | | | | | | | | |
|---|---|---|---|---|---|---|---|---|---|---|---|
| WA7899 | OR13A1 | 10 | 45799438 | A | G | A0321,A2402,A0301,B3501,B3502,C0401, | A2402 | 61 | 12 | ryaaiRhpl | ryaaiChpl |
| WA7899 | OR13A1 | 10 | 45799438 | A | G | A0321,A2402,A0301,B3501,B3502,C0401, | B3501 | 391 | 257 | aaiRhplhy | aaiChplhy |
| WA7899 | OR51F2 | 11 | 4842722 | C | A | A0321,A2402,A0301,B3501,B3502,C0401, | B3501 | 180 | 207 | ipglkDtqy | ipglkAtqy |
| WA7899 | OR51I2 | 11 | 5474809 | C | T | A0321,A2402,A0301,B3501,B3502,C0401, | B3501 | 436 | 684 | lsgpFcvmy | lsgpLcvmy |
| WA7899 | NAV2 | 11 | 20066658 | C | A | A0321,A2402,A0301,B3501,B3502,C0401, | B3501 | 25 | 27 | tptDnansf | tptAnansf |
| WA7899 | OR4A5 | 11 | 51411591 | T | C | A0321,A2402,A0301,B3501,B3502,C0401, | A2402 | 5 | 5 | kfmAvfyti | kfmTvfyti |
| WA7899 | OR4A5 | 11 | 51411591 | T | C | A0321,A2402,A0301,B3501,B3502,C0401, | B3501 | 35 | 158 | fptdkfmAv | fptdkfmTv |
| WA7899 | OR4A5 | 11 | 51411591 | T | C | A0321,A2402,A0301,B3501,B3502,C0401, | B3501 | 262 | 9133 | mAvfytiit | mTvfytiit |
| WA7899 | GRIK4 | 11 | 120856811 | C | A | A0321,A2402,A0301,B3501,B3502,C0401, | B3501 | 184 | 1275 | epdqlaqrM | epdqlaqrL |
| WA7899 | GRIK4 | 11 | 120856811 | C | A | A0321,A2402,A0301,B3501,B3502,C0401, | B3501 | 136 | 1067 | Maqeaalva | Laqeaalva |
| WA7899 | TBX3 | 12 | 115112188 | G | A | A0321,A2402,A0301,B3501,B3502,C0401, | B3501 | 292 | 3135 | qqffnghpF | qqffnghpL |
| WA7899 | PARP4 | 13 | 25009318 | G | A | A0321,A2402,A0301,B3501,B3502,C0401, | A0301 | 235 | 296 | ilaSavgsy | ilaPavgsy |
| WA7899 | PARP4 | 13 | 25009318 | G | A | A0321,A2402,A0301,B3501,B3502,C0401, | B3501 | 31 | 68 | fpilaSavg | fpilaPavg |
| WA7899 | PARP4 | 13 | 25009318 | G | A | A0321,A2402,A0301,B3501,B3502,C0401, | B3501 | 330 | 251 | ilaSavgsy | ilaPavgsy |
| WA7899 | TEX26 | 13 | 31549022 | A | T | A0321,A2402,A0301,B3501,B3502,C0401, | A0301 | 72 | 284 | rthcVtnkk | rthcDtnkk |
| WA7899 | FITM1 | 14 | 24601871 | G | A | A0321,A2402,A0301,B3501,B3502,C0401, | A0301 | 242 | 330 | liyfhqyth | Viyfhqyth |
| WA7899 | FITM1 | 14 | 24601871 | G | A | A0321,A2402,A0301,B3501,B3502,C0401, | B3501 | 120 | 192 | flllctliy | flllctViy |
| WA7899 | EXD1 | 15 | 41476650 | T | C | A0321,A2402,A0301,B3501,B3502,C0401, | A0301 | 57 | 64 | klvAetagk | klvTetagk |
| WA7899 | WFIKKN1 | 16 | 683789 | A | G | A0321,A2402,A0301,B3501,B3502,C0401, | A0301 | 210 | 502 | rvalGdvlk | rvalEdvlk |
| WA7899 | DNASE1L2 | 16 | 2286897 | T | A | A0321,A2402,A0301,B3501,B3502,C0401, | B3501 | 69 | 333 | taalrigaY | taalrigaF |
| WA7899 | QPRT | 16 | 29706506 | G | A | A0321,A2402,A0301,B3501,B3502,C0401, | A0301 | 119 | 215 | vvaaSgvek | vvaaGgvek |
| WA7899 | FAM92B | 16 | 85135861 | A | G | A0321,A2402,A0301,B3501,B3502,C0401, | A0301 | 178 | 77 | ssaLqtlek | ssaFqtlek |
| WA7899 | FAM92B | 16 | 85135861 | A | G | A0321,A2402,A0301,B3501,B3502,C0401, | A2402 | 20 | 10 | vyssaLqtl | vyssaFqtl |

Figure 21 (Cont.)

| | | | | | | | | | | | |
|---|---|---|---|---|---|---|---|---|---|---|---|
| WA7899 | FAM92B | 16 | 85135861 | A | G | A0321,A2402,A0301,B3501,B3502,C0401, | B3501 | 264 | 99 | saLqtleky | saFqtleky |
| WA7899 | ANKRD11 | 16 | 89335057 | C | T | A0321,A2402,A0301,B3501,B3502,C0401, | A0301 | 109 | 78 | rmktcllIr | rmktcllMr |
| WA7899 | SMCHD1 | 18 | 2703734 | G | T | A0321,A2402,A0301,B3501,B3502,C0401, | B3501 | 74 | 272 | falwlNdch | falwlKdch |
| WA7899 | SMCHD1 | 18 | 2703734 | G | T | A0321,A2402,A0301,B3501,B3502,C0401, | B3501 | 447 | 4257 | wlNdcheky | wlKdcheky |
| WA7899 | ASXL3 | 18 | 31226317 | G | T | A0321,A2402,A0301,B3501,B3502,C0401, | B3501 | 197 | 15824 | nahgeengF | nahgeengV |
| WA7899 | CELF4 | 18 | 34846502 | C | T | A0321,A2402,A0301,B3501,B3502,C0401, | B3501 | 215 | 87 | qqyTgpaay | qqyAgpaay |
| WA7899 | DCC | 18 | 49867192 | A | G | A0321,A2402,A0301,B3501,B3502,C0401, | B3501 | 441 | 405 | cvwvpRlaf | cvwvpKlaf |
| WA7899 | DCC | 18 | 49867192 | A | G | A0321,A2402,A0301,B3501,B3502,C0401, | B3501 | 131 | 495 | vpRlafvlf | vpKlafvlf |
| WA7899 | ZNF414 | 19 | 8576800 | A | G | A0321,A2402,A0301,B3501,B3502,C0401, | A0301 | 305 | 221 | rthrslSkh | rthrslFkh |
| WA7899 | ZSWIM4 | 19 | 13928558 | G | T | A0321,A2402,A0301,B3501,B3502,C0401, | B3501 | 156 | 371 | gpekrNvay | gpekrKvay |
| WA7899 | HIPK4 | 19 | 40886552 | G | T | A0321,A2402,A0301,B3501,B3502,C0401, | B3501 | 384 | 510 | ctnEvsdmm | ctnAvsdmm |
| WA7899 | PNMAL1 | 19 | 46973386 | A | T | A0321,A2402,A0301,B3501,B3502,C0401, | A0301 | 83 | 223 | laMkkpmak | laLkkpmak |
| WA7899 | PNMAL1 | 19 | 46973386 | A | T | A0321,A2402,A0301,B3501,B3502,C0401, | B3501 | 72 | 1837 | cvnkeelaM | cvnkeelaL |
| WA7899 | NLRP5 | 19 | 56515393 | C | T | A0321,A2402,A0301,B3501,B3502,C0401, | A2402 | 132 | 138 | awaMsisif | awaTsisif |
| WA7899 | NLRP5 | 19 | 56515393 | C | T | A0321,A2402,A0301,B3501,B3502,C0401, | B3501 | 44 | 6581 | ygaslawaM | ygaslawaT |
| WA7899 | NLRP5 | 19 | 56515393 | C | T | A0321,A2402,A0301,B3501,B3502,C0401, | B3501 | 38 | 48 | lawaMsisi | lawaTsisi |
| WA7899 | PDCD1 | 2 | 242793341 | T | C | A0321,A2402,A0301,B3501,B3502,C0401, | B3501 | 178 | 344 | vpeqAeyat | vpeqTeyat |
| WA7899 | PDCD1 | 2 | 242793341 | T | C | A0321,A2402,A0301,B3501,B3502,C0401, | B3501 | 12 | 821 | qAeyativf | qTeyativf |
| WA7899 | THBD | 20 | 23029781 | T | A | A0321,A2402,A0301,B3501,B3502,C0401, | A2402 | 442 | 1929 | tsysWwarl | tsysRwarl |
| WA7899 | USP13 | 3 | 179439323 | G | C | A0321,A2402,A0301,B3501,B3502,C0401, | B3501 | 188 | 1071 | nsSylssvm | nsCylssvm |
| WA7899 | MUC4 | 3 | 195507241 | G | A | A0321,A2402,A0301,B3501,B3502,C0401, | B3501 | 359 | 209 | spssVstgh | spssAstgh |
| WA7899 | FBN2 | 5 | 127599309 | G | A | A0321,A2402,A0301,B3501,B3502,C0401, | B3501 | 295 | 92 | npnacgsVs | npnacgsAs |

Figure 21 (Cont.)

| | | | | | | | | | | | |
|---|---|---|---|---|---|---|---|---|---|---|---|
| WA7899 | FBN2 | 5 | 127599309 | G | A | A0321,A2402,A0301,B3501,B3502,C0401, | B3501 | 26 | 23 | nacgsVscy | nacgsAscy |
| WA7899 | OR5V1 | 6 | 29323186 | T | G | A0321,A2402,A0301,B3501,B3502,C0401, | A0301 | 108 | 288 | pLstyslkk | plstyslkk |
| WA7899 | EEF1A1 | 6 | 74229664 | T | C | A0321,A2402,A0301,B3501,B3502,C0401, | A0301 | 180 | 58 | ttghliCk | ttghliYk |
| WA7899 | FIG4 | 6 | 110012688 | T | C | A0321,A2402,A0301,B3501,B3502,C0401, | B3501 | 343 | 3526 | ssvqklvPy | ssvqklvLy |
| WA7899 | FIG4 | 6 | 110012688 | T | C | A0321,A2402,A0301,B3501,B3502,C0401, | B3501 | 25 | 2924 | vPyetrary | vLyetrary |
| WA7899 | OPRM1 | 6 | 154412236 | C | T | A0321,A2402,A0301,B3501,B3502,C0401, | A0301 | 208 | 86 | svCmlsgsk | svRmlsgsk |
| WA7899 | OPRM1 | 6 | 154412236 | C | T | A0321,A2402,A0301,B3501,B3502,C0401, | A0301 | 177 | 66 | Cmlsgskek | Rmlsgskek |
| WA7899 | PARK2 | 6 | 162864386 | C | A | A0321,A2402,A0301,B3501,B3502,C0401, | A0301 | 75 | 89 | qlrLifagk | qlrVifagk |
| WA7899 | THBS2 | 6 | 169633107 | A | T | A0321,A2402,A0301,B3501,B3502,C0401, | B3501 | 110 | 412 | cpvdgSlsn | cpvdgClsn |
| WA7899 | RP1 | 8 | 55540205 | A | G | A0321,A2402,A0301,B3501,B3502,C0401, | B3501 | 349 | 913 | evAcspcem | evTcspcem |
| WA7899 | PKHD1L1 | 8 | 110453580 | C | G | A0321,A2402,A0301,B3501,B3502,C0401, | A0301 | 167 | 9148 | iLritnngk | iFritnngk |
| Y2087 | AGRN | 1 | 976729 | G | A | A3101,A1101,B1302,B3501,C0401,C0602 | A3101 | 70 | 121 | qllrrTcar | qllrrAcar |
| Y2087 | GABRD | 1 | 1960694 | G | T | A3101,A1101,B1302,B3501,C0401,C0602 | B3501 | 201 | 20574 | isqaavpaM | isqaavpaR |
| Y2087 | PLCH2 | 1 | 2435676 | G | A | A3101,A1101,B1302,B3501,C0401,C0602 | A1101 | 465 | 8806 | tlghlpviK | tlghlpviR |
| Y2087 | ARHGEF16 | 1 | 3392580 | A | T | A3101,A1101,B1302,B3501,C0401,C0602 | C0602 | 13 | 11 | hrmermVqm | hrmermEqm |
| Y2087 | ARHGEF16 | 1 | 3392580 | A | T | A3101,A1101,B1302,B3501,C0401,C0602 | C0602 | 196 | 21 | ermVqmytl | ermEqmytl |
| Y2087 | ARHGEF16 | 1 | 3392583 | A | T | A3101,A1101,B1302,B3501,C0401,C0602 | C0602 | 236 | 10664 | ahrmermeL | ahrmermeQ |
| Y2087 | ARHGEF16 | 1 | 3392583 | A | T | A3101,A1101,B1302,B3501,C0401,C0602 | C0602 | 7 | 11 | hrmermeLm | hrmermeQm |
| Y2087 | ARHGEF16 | 1 | 3392583 | A | T | A3101,A1101,B1302,B3501,C0401,C0602 | C0602 | 55 | 21 | ermeLmytl | ermeQmytl |
| Y2087 | CASZ1 | 1 | 10699808 | C | T | A3101,A1101,B1302,B3501,C0401,C0602 | A1101 | 121 | 125 | vldNfkrfk | vldDfkrfk |
| Y2087 | CROCC | 1 | 17282543 | G | T | A3101,A1101,B1302,B3501,C0401,C0602 | A3101 | 371 | 160 | klalleDar | klalleEar |
| Y2087 | ECE1 | 1 | 21554530 | T | A | A3101,A1101,B1302,B3501,C0401,C0602 | B3501 | 142 | 133 | apnrdqwCm | apnrdqwSm |
| Y2087 | ECE1 | 1 | 21554530 | T | A | A3101,A1101,B1302,B3501,C0401,C0602 | B3501 | 208 | 71 | dqwCmtppm | dqwSmtppm |

Figure 21 (Cont.)

| | | | | | | | | | | | |
|---|---|---|---|---|---|---|---|---|---|---|---|
| Y2087 | EPHA8 | 1 | 22919857 | G | A | A3101,A1101,B1302,B3501,C0401,C0602 | A3101 | 497 | 27629 | vwirqeraR | vwirqeraG |
| Y2087 | EPHA8 | 1 | 22919857 | G | A | A3101,A1101,B1302,B3501,C0401,C0602 | C0602 | 206 | 1967 | irqeraRqt | irqeraGqt |
| Y2087 | EPHA8 | 1 | 22919857 | G | A | A3101,A1101,B1302,B3501,C0401,C0602 | C0602 | 60 | 13403 | aRqtsvsll | aGqtsvsll |
| Y2087 | ARID1A | 1 | 27023360 | C | T | A3101,A1101,B1302,B3501,C0401,C0602 | B3501 | 303 | 1394 | qpygWspsa | qpygRspsa |
| Y2087 | C1orf94 | 1 | 34684295 | C | T | A3101,A1101,B1302,B3501,C0401,C0602 | B3501 | 41 | 645 | fpqgygfgL | fpqgygfgS |
| Y2087 | CCDC17 | 1 | 46088325 | G | A | A3101,A1101,B1302,B3501,C0401,C0602 | A3101 | 15 | 33 | ralreVyir | ralreAyir |
| Y2087 | CCDC17 | 1 | 46088325 | G | A | A3101,A1101,B1302,B3501,C0401,C0602 | C0602 | 489 | 935 | iralreVyi | iralreAyi |
| Y2087 | PTGER3 | 1 | 71512801 | C | T | A3101,A1101,B1302,B3501,C0401,C0602 | A1101 | 97 | 20094 | fiasamavK | fiasamavE |
| Y2087 | PTGER3 | 1 | 71512801 | C | T | A3101,A1101,B1302,B3501,C0401,C0602 | A3101 | 225 | 257 | iasamavKr | iasamavEr |
| Y2087 | PTGER3 | 1 | 71512801 | C | T | A3101,A1101,B1302,B3501,C0401,C0602 | A3101 | 22 | 253 | avKralair | avEralair |
| Y2087 | PTGER3 | 1 | 71512801 | C | T | A3101,A1101,B1302,B3501,C0401,C0602 | B3501 | 253 | 63 | mavKralai | mavEralai |
| Y2087 | NTRK1 | 1 | 156838320 | G | A | A3101,A1101,B1302,B3501,C0401,C0602 | B3501 | 40 | 1115 | Mpnasvdvg | Vpnasvdvg |
| Y2087 | ARHGAP30 | 1 | 161023102 | C | T | A3101,A1101,B1302,B3501,C0401,C0602 | A1101 | 56 | 986 | ivMefilth | ivVefilth |
| Y2087 | PRRC2C | 1 | 171501728 | C | A | A3101,A1101,B1302,B3501,C0401,C0602 | A3101 | 290 | 1117 | kqTspeeir | kqPspeeir |
| Y2087 | KIF26B | 1 | 245530421 | C | T | A3101,A1101,B1302,B3501,C0401,C0602 | B3501 | 334 | 2931 | paScatsny | paPcatsny |
| Y2087 | C10orf71 | 10 | 50531278 | C | A | A3101,A1101,B1302,B3501,C0401,C0602 | B3501 | 10 | 10 | macNgsssf | macHgsssf |
| Y2087 | C10orf71 | 10 | 50531281 | G | A | A3101,A1101,B1302,B3501,C0401,C0602 | B3501 | 11 | 10 | machSsssf | machGsssf |
| Y2087 | CHST3 | 10 | 73768129 | C | T | A3101,A1101,B1302,B3501,C0401,C0602 | A1101 | 24 | 62 | pVmrlfgyk | pAmrlfgyk |
| Y2087 | CHST3 | 10 | 73768129 | C | T | A3101,A1101,B1302,B3501,C0401,C0602 | A3101 | 447 | 715 | pVmrlfgyk | pAmrlfgyk |
| Y2087 | CHST3 | 10 | 73768129 | C | T | A3101,A1101,B1302,B3501,C0401,C0602 | B3501 | 270 | 296 | gpVmrlfgy | gpAmrlfgy |
| Y2087 | LCOR | 10 | 98715674 | G | A | A3101,A1101,B1302,B3501,C0401,C0602 | A1101 | 446 | 21847 | qsanesknK | qsaneskn E |
| Y2087 | TLX1NB | 10 | 102849349 | C | T | A3101,A1101,B1302,B3501,C0401,C0602 | A3101 | 122 | 462 | leksriHlr | leksriRlr |

Figure 21 (Cont.)

| | | | | | | | | | | | |
|---|---|---|---|---|---|---|---|---|---|---|---|
| Y2087 | TLX1NB | 10 | 102849349 | C | T | A3101,A1101,B1302,B3501,C0401,C0602 | A3101 | 5 | 4 | riHlrrtlr | riRlrrtlr |
| Y2087 | TLX1NB | 10 | 102849349 | C | T | A3101,A1101,B1302,B3501,C0401,C0602 | C0602 | 29 | 37 | sriHlrrtl | sriRlrrtl |
| Y2087 | TCERG1L | 10 | 133058600 | A | G | A3101,A1101,B1302,B3501,C0401,C0602 | C0602 | 400 | 198 | lrgpPpssv | lrgpSpssv |
| Y2087 | PWWP2B | 10 | 134218728 | G | A | A3101,A1101,B1302,B3501,C0401,C0602 | A3101 | 28 | 84 | rTpaeqvpr | rApaeqvpr |
| Y2087 | ADAM8 | 10 | 135080864 | G | A | A3101,A1101,B1302,B3501,C0401,C0602 | A1101 | 258 | 109 | pvytrqaSk | pvytrqaPk |
| Y2087 | PTDSS2 | 11 | 489597 | G | A | A3101,A1101,B1302,B3501,C0401,C0602 | A1101 | 301 | 263 | Telntfylk | Aelntfylk |
| Y2087 | PTDSS2 | 11 | 489597 | G | A | A3101,A1101,B1302,B3501,C0401,C0602 | B3501 | 495 | 209 | llTelntfy | llAelntfy |
| Y2087 | MUC5B | 11 | 1265707 | A | G | A3101,A1101,B1302,B3501,C0401,C0602 | B3501 | 21 | 56 | tpAatsfta | tpTatsfta |
| Y2087 | MUC5B | 11 | 1265708 | C | G | A3101,A1101,B1302,B3501,C0401,C0602 | B3501 | 128 | 56 | tpRatsfta | tpTatsfta |
| Y2087 | MUC5B | 11 | 1265716 | A | G | A3101,A1101,B1302,B3501,C0401,C0602 | B3501 | 128 | 56 | tptatGfta | tptatSfta |
| Y2087 | MUC5B | 11 | 1265717 | G | T | A3101,A1101,B1302,B3501,C0401,C0602 | B3501 | 149 | 56 | tptatIfta | tptatSfta |
| Y2087 | MUC5B | 11 | 1265718 | C | G | A3101,A1101,B1302,B3501,C0401,C0602 | A3101 | 274 | 20106 | tattptatR | tattptatS |
| Y2087 | MUC5B | 11 | 1265718 | C | G | A3101,A1101,B1302,B3501,C0401,C0602 | B3501 | 403 | 56 | tptatRfta | tptatSfta |
| Y2087 | MUC5B | 11 | 1265720 | T | C | A3101,A1101,B1302,B3501,C0401,C0602 | B3501 | 290 | 56 | tptatsSta | tptatsFta |
| Y2087 | MUC5B | 11 | 1265722 | A | G | A3101,A1101,B1302,B3501,C0401,C0602 | B3501 | 16 | 56 | tptatsfAa | tptatsfTa |
| Y2087 | MUC5B | 11 | 1265722 | A | G | A3101,A1101,B1302,B3501,C0401,C0602 | B3501 | 57 | 5065 | fAaipsssl | fTaipsssl |
| Y2087 | MUC5B | 11 | 1269489 | C | G | A3101,A1101,B1302,B3501,C0401,C0602 | A3101 | 274 | 20106 | tattptatR | tattptatS |
| Y2087 | MUC5B | 11 | 1269489 | C | G | A3101,A1101,B1302,B3501,C0401,C0602 | B3501 | 403 | 56 | tptatRfta | tptatSfta |
| Y2087 | MUC5B | 11 | 1269491 | T | C | A3101,A1101,B1302,B3501,C0401,C0602 | B3501 | 290 | 56 | tptatsSta | tptatsFta |
| Y2087 | DCHS1 | 11 | 6644476 | G | A | A3101,A1101,B1302,B3501,C0401,C0602 | A1101 | 144 | 11618 | Svflapafh | Pvflapafh |
| Y2087 | DCHS1 | 11 | 6644476 | G | A | A3101,A1101,B1302,B3501,C0401,C0602 | B3501 | 226 | 8 | dSvflapaf | dPvflapaf |
| Y2087 | RBMXL2 | 11 | 7110649 | C | T | A3101,A1101,B1302,B3501,C0401,C0602 | C0602 | 491 | 247 | Csrgrprfl | Rsrgrprfl |
| Y2087 | SF1 | 11 | 64533340 | G | A | A3101,A1101,B1302,B3501,C0401,C0602 | B3501 | 27 | 26 | mgvagmSpf | mgvagmPpf |

Figure 21 (Cont.)

| | | | | | | | | | | | |
|---|---|---|---|---|---|---|---|---|---|---|---|
| Y2087 | BRMS1 | 11 | 66105162 | C | A | A3101,A1101,B1302,B3501,C0401,C0602 | B3501 | 342 | 350 | lpssrpSql | lpssrpAql |
| Y2087 | TCIRG1 | 11 | 67817247 | G | A | A3101,A1101,B1302,B3501,C0401,C0602 | A3101 | 6 | 14 | rlrrrpaNr | rlrrrpaDr |
| Y2087 | HEPHL1 | 11 | 93844072 | G | A | A3101,A1101,B1302,B3501,C0401,C0602 | A1101 | 37 | 156 | esflfkiNk | esflfkiDk |
| Y2087 | HEPHL1 | 11 | 93844072 | G | A | A3101,A1101,B1302,B3501,C0401,C0602 | A3101 | 7 | 13 | lfkiNksyr | lfkiDksyr |
| Y2087 | HEPHL1 | 11 | 93844072 | G | A | A3101,A1101,B1302,B3501,C0401,C0602 | B3501 | 276 | 102 | flfkiNksy | flfkiDksy |
| Y2087 | CNTN5 | 11 | 99942451 | G | A | A3101,A1101,B1302,B3501,C0401,C0602 | C0602 | 167 | 103 | srvelvngv | srveMvngv |
| Y2087 | NCAM1 | 11 | 113075013 | G | A | A3101,A1101,B1302,B3501,C0401,C0602 | A3101 | 6 | 5537 | kfflcqvaR | kfflcqvaG |
| Y2087 | PRDM10 | 11 | 129793146 | A | T | A3101,A1101,B1302,B3501,C0401,C0602 | A1101 | 101 | 47 | stcgkqLkr | stcgkqFkr |
| Y2087 | PRDM10 | 11 | 129793146 | A | T | A3101,A1101,B1302,B3501,C0401,C0602 | A3101 | 130 | 14 | stcgkqLkr | stcgkqFkr |
| Y2087 | PRDM10 | 11 | 129793146 | A | T | A3101,A1101,B1302,B3501,C0401,C0602 | A3101 | 202 | 100 | qLkrkdklr | qFkrkdklr |
| Y2087 | IGSF9B | 11 | 133795666 | C | T | A3101,A1101,B1302,B3501,C0401,C0602 | A1101 | 20 | 28 | gtKgeffak | gtEgeffak |
| Y2087 | IGSF9B | 11 | 133795666 | C | T | A3101,A1101,B1302,B3501,C0401,C0602 | A3101 | 38 | 669 | gtKgeffak | gtEgeffak |
| Y2087 | ANO2 | 12 | 5672593 | C | T | A3101,A1101,B1302,B3501,C0401,C0602 | A1101 | 136 | 131 | klmNepalr | klmDepalr |
| Y2087 | ANO2 | 12 | 5672593 | C | T | A3101,A1101,B1302,B3501,C0401,C0602 | A3101 | 23 | 55 | klmNepalr | klmDepalr |
| Y2087 | APOLD1 | 12 | 12940084 | G | A | A3101,A1101,B1302,B3501,C0401,C0602 | B3501 | 260 | 231 | spvtlEtsl | spvtlGtsl |
| Y2087 | WBP11 | 12 | 14942014 | G | A | A3101,A1101,B1302,B3501,C0401,C0602 | C0602 | 50 | 58 | lrgplSrll | lrgplPrll |
| Y2087 | KLHL42 | 12 | 27933900 | C | G | A3101,A1101,B1302,B3501,C0401,C0602 | B3501 | 46 | 44 | hpyEgepps | hpyQgepps |
| Y2087 | DHH | 12 | 49483680 | G | A | A3101,A1101,B1302,B3501,C0401,C0602 | A3101 | 12 | 12 | hwysWllyr | hwysRllyr |
| Y2087 | DHH | 12 | 49483680 | G | A | A3101,A1101,B1302,B3501,C0401,C0602 | B3501 | 218 | 1024 | mhwysWlly | mhwysRlly |
| Y2087 | ITGA5 | 12 | 54812942 | T | G | A3101,A1101,B1302,B3501,C0401,C0602 | A3101 | 96 | 19 | avPlrwgpr | avQlrwgpr |
| Y2087 | PA2G4 | 12 | 56501023 | G | A | A3101,A1101,B1302,B3501,C0401,C0602 | B3501 | 98 | 10249 | ianvahtfM | ianvahtfV |
| Y2087 | PA2G4 | 12 | 56501029 | G | C | A3101,A1101,B1302,B3501,C0401,C0602 | C0602 | 423 | 20851 | vHvaqgtqv | vDvaqgtqv |

Figure 21 (Cont.)

| | | | | | | | | | | | |
|---|---|---|---|---|---|---|---|---|---|---|---|
| Y2087 | MSRB3 | 12 | 65672606 | T | C | A3101,A1101,B1302,B3501,C0401,C0602 | A1101 | 231 | 20977 | slclslclR | slclslclC |
| Y2087 | MSRB3 | 12 | 65672606 | T | C | A3101,A1101,B1302,B3501,C0401,C0602 | A3101 | 73 | 18901 | slclslclR | slclslclC |
| Y2087 | NOS1 | 12 | 117703146 | C | T | A3101,A1101,B1302,B3501,C0401,C0602 | B3501 | 86 | 1145 | yQltpsfey | yRltpsfey |
| Y2087 | NOS1 | 12 | 117703146 | C | T | A3101,A1101,B1302,B3501,C0401,C0602 | C0602 | 408 | 816 | fhqemlnyQ | fhqemlnyR |
| Y2087 | DENR | 12 | 123247420 | A | C | A3101,A1101,B1302,B3501,C0401,C0602 | A1101 | 18 | 7875 | aTcrqwiek | aKcrqwiek |
| Y2087 | HIP1R | 12 | 123340527 | G | T | A3101,A1101,B1302,B3501,C0401,C0602 | A1101 | 410 | 723 | Sqryiaqlk | Aqryiaqlk |
| Y2087 | KL | 13 | 33590849 | G | A | A3101,A1101,B1302,B3501,C0401,C0602 | A1101 | 116 | 202 | asiwNtfth | asiwDtfth |
| Y2087 | KL | 13 | 33590849 | G | A | A3101,A1101,B1302,B3501,C0401,C0602 | A3101 | 400 | 813 | siwNtfthh | siwDtfthh |
| Y2087 | CDH24 | 14 | 23518427 | T | A | A3101,A1101,B1302,B3501,C0401,C0602 | B3501 | 439 | 620 | apFlvpiel | apYlvpiel |
| Y2087 | CDH24 | 14 | 23518482 | C | T | A3101,A1101,B1302,B3501,C0401,C0602 | C0602 | 97 | 117 | nrdSsasll | nrdGsasll |
| Y2087 | RABGGTA | 14 | 24738874 | C | A | A3101,A1101,B1302,B3501,C0401,C0602 | C0602 | 491 | 502 | hcwdyrrfL | hcwdyrrfV |
| Y2087 | GPR137C | 14 | 53067051 | G | A | A3101,A1101,B1302,B3501,C0401,C0602 | A1101 | 14 | 7091 | mssanvylK | mssanvylE |
| Y2087 | GPR137C | 14 | 53067051 | G | A | A3101,A1101,B1302,B3501,C0401,C0602 | A1101 | 65 | 33 | sanvylKsk | sanvylEsk |
| Y2087 | GPR137C | 14 | 53067051 | G | A | A3101,A1101,B1302,B3501,C0401,C0602 | A3101 | 99 | 5259 | mssanvylK | mssanvylE |
| Y2087 | PTPN21 | 14 | 88946027 | C | T | A3101,A1101,B1302,B3501,C0401,C0602 | B3501 | 106 | 230 | tpdlsHhly | tpdlsRhly |
| Y2087 | XRCC3 | 14 | 104165238 | C | T | A3101,A1101,B1302,B3501,C0401,C0602 | B3501 | 103 | 484 | cpaQtlrvl | cpaRtlrvl |
| Y2087 | C14orf80 | 14 | 105964990 | G | A | A3101,A1101,B1302,B3501,C0401,C0602 | A3101 | 230 | 169 | rgpewsaTr | rgpewsaAr |
| Y2087 | C14orf80 | 14 | 105964990 | G | A | A3101,A1101,B1302,B3501,C0401,C0602 | A3101 | 75 | 61 | wsaTrrasr | wsaArrasr |
| Y2087 | C14orf80 | 14 | 105964990 | G | A | A3101,A1101,B1302,B3501,C0401,C0602 | C0602 | 111 | 338 | Trrasreav | Arrasreav |
| Y2087 | ARHGAP11A | 15 | 32917814 | A | T | A3101,A1101,B1302,B3501,C0401,C0602 | C0602 | 173 | 123 | ykrMrrqsv | ykrKrrqsv |
| Y2087 | ARHGAP11A | 15 | 32917814 | A | T | A3101,A1101,B1302,B3501,C0401,C0602 | C0602 | 329 | 4433 | Mrrqsvgdf | Krrqsvgdf |
| Y2087 | SPTBN5 | 15 | 42144506 | C | A | A3101,A1101,B1302,B3501,C0401,C0602 | C0602 | 204 | 807 | temeHelll | temeQelll |
| Y2087 | MEGF11 | 15 | 66214799 | C | A | A3101,A1101,B1302,B3501,C0401,C0602 | A3101 | 274 | 1533 | ricppWfyg | ricppGfyg |

Figure 21 (Cont.)

| | | | | | | | | | | | |
|---|---|---|---|---|---|---|---|---|---|---|---|
| Y2087 | ITGA11 | 15 | 68619102 | G | A | A3101,A1101,B1302,B3501,C0401,C0602 | A3101 | 274 | 369 | mderWytpr | mderRytpr |
| Y2087 | ITGA11 | 15 | 68619102 | G | A | A3101,A1101,B1302,B3501,C0401,C0602 | B3501 | 352 | 268 | natmderWy | natmderRy |
| Y2087 | C15orf60 | 15 | 73735666 | C | A | A3101,A1101,B1302,B3501,C0401,C0602 | A1101 | 69 | 38 | gtDpcptwk | gtApcptwk |
| Y2087 | LMAN1L | 15 | 75111117 | C | A | A3101,A1101,B1302,B3501,C0401,C0602 | A1101 | 104 | 17485 | hTfrarity | hPfrarity |
| Y2087 | LMAN1L | 15 | 75111117 | C | A | A3101,A1101,B1302,B3501,C0401,C0602 | A3101 | 281 | 568 | frnrphTfr | frnrphPfr |
| Y2087 | LMAN1L | 15 | 75111117 | C | A | A3101,A1101,B1302,B3501,C0401,C0602 | B3501 | 66 | 4 | hTfrarity | hPfrarity |
| Y2087 | GOLGA6L4 | 15 | 84909434 | G | A | A3101,A1101,B1302,B3501,C0401,C0602 | A3101 | 83 | 33 | rlQelerlr | rlRelerlr |
| Y2087 | RGS11 | 16 | 320644 | C | T | A3101,A1101,B1302,B3501,C0401,C0602 | A3101 | 37 | 20210 | vyeqflapR | vyeqflapG |
| Y2087 | TRAF7 | 16 | 2226371 | G | T | A3101,A1101,B1302,B3501,C0401,C0602 | A1101 | 464 | 2933 | sgavYstvk | sgavDstvk |
| Y2087 | TBC1D24 | 16 | 2550467 | G | A | A3101,A1101,B1302,B3501,C0401,C0602 | A1101 | 71 | 17327 | ktesmfmaR | ktesmfmaG |
| Y2087 | TBC1D24 | 16 | 2550467 | G | A | A3101,A1101,B1302,B3501,C0401,C0602 | A3101 | 9 | 9881 | ktesmfmaR | ktesmfmaG |
| Y2087 | ZNF629 | 16 | 30793763 | G | A | A3101,A1101,B1302,B3501,C0401,C0602 | C0602 | 311 | 9703 | frgnsypgV | frgnsypgA |
| Y2087 | SLC5A2 | 16 | 31501684 | G | T | A3101,A1101,B1302,B3501,C0401,C0602 | A1101 | 399 | 1131 | llwfcVmsr | llwfcGmsr |
| Y2087 | SLC5A2 | 16 | 31501684 | G | T | A3101,A1101,B1302,B3501,C0401,C0602 | A3101 | 29 | 44 | llwfcVmsr | llwfcGmsr |
| Y2087 | C16orf78 | 16 | 49411715 | T | C | A3101,A1101,B1302,B3501,C0401,C0602 | A3101 | 41 | 23 | kgkglTtar | kgkglMtar |
| Y2087 | C16orf78 | 16 | 49411715 | T | C | A3101,A1101,B1302,B3501,C0401,C0602 | A3101 | 209 | 86 | lTtarggnr | lMtarggnr |
| Y2087 | C16orf78 | 16 | 49411715 | T | C | A3101,A1101,B1302,B3501,C0401,C0602 | A3101 | 376 | 75 | Ttarggnrr | Mtarggnrr |
| Y2087 | B3GNT9 | 16 | 67183523 | C | T | A3101,A1101,B1302,B3501,C0401,C0602 | B3501 | 209 | 496 | ypayagDgg | ypayagGgg |
| Y2087 | B3GNT9 | 16 | 67183523 | C | T | A3101,A1101,B1302,B3501,C0401,C0602 | B3501 | 77 | 118 | yagDggfvl | yagGggfvl |
| Y2087 | NOL3 | 16 | 67208344 | G | T | A3101,A1101,B1302,B3501,C0401,C0602 | B3501 | 451 | 1534 | tagapdpaL | tagapdpaW |
| Y2087 | ZDHHC1 | 16 | 67429104 | G | A | A3101,A1101,B1302,B3501,C0401,C0602 | A1101 | 133 | 1978 | asLdptpgr | asPdptpgr |
| Y2087 | ZDHHC1 | 16 | 67429104 | G | A | A3101,A1101,B1302,B3501,C0401,C0602 | A3101 | 302 | 2284 | asLdptpgr | asPdptpgr |

Figure 21 (Cont.)

| | | | | | | | | | | | |
|---|---|---|---|---|---|---|---|---|---|---|---|
| Y2087 | MTSS1L | 16 | 70699401 | G | T | A3101,A1101,B1302,B3501,C0401,C0602 | A1101 | 160 | 20646 | sseasetcK | sseasetcQ |
| Y2087 | BANP | 16 | 88105702 | G | A | A3101,A1101,B1302,B3501,C0401,C0602 | B3501 | 102 | 148 | iaMassdpa | iaVassdpa |
| Y2087 | BANP | 16 | 88105702 | G | A | A3101,A1101,B1302,B3501,C0401,C0602 | B3501 | 42 | 1436 | Massdpaaa | Vassdpaaa |
| Y2087 | GP1BA | 17 | 4837139 | A | G | A3101,A1101,B1302,B3501,C0401,C0602 | B3501 | 389 | 951 | epAsepaps | epTsepaps |
| Y2087 | GP1BA | 17 | 4837140 | C | T | A3101,A1101,B1302,B3501,C0401,C0602 | B3501 | 389 | 951 | epIsepaps | epTsepaps |
| Y2087 | POLR2A | 17 | 7416703 | C | G | A3101,A1101,B1302,B3501,C0401,C0602 | B3501 | 109 | 328 | syWptspsy | sySptspsy |
| Y2087 | SOX15 | 17 | 7492606 | C | A | A3101,A1101,B1302,B3501,C0401,C0602 | A1101 | 350 | 1065 | kssgaVpsr | kssgaGpsr |
| Y2087 | SOX15 | 17 | 7492606 | C | A | A3101,A1101,B1302,B3501,C0401,C0602 | A3101 | 158 | 284 | kssgaVpsr | kssgaGpsr |
| Y2087 | NTN1 | 17 | 8926469 | A | T | A3101,A1101,B1302,B3501,C0401,C0602 | B3501 | 189 | 2671 | dVneddsel | dEneddsel |
| Y2087 | DNAH9 | 17 | 11672629 | C | T | A3101,A1101,B1302,B3501,C0401,C0602 | B3501 | 316 | 91 | fnyytMsam | fnyytTsam |
| Y2087 | POLDIP2 | 17 | 26680758 | T | A | A3101,A1101,B1302,B3501,C0401,C0602 | A3101 | 175 | 130 | yFqvlidar | yYqvlidar |
| Y2087 | PPM1D | 17 | 58677983 | G | A | A3101,A1101,B1302,B3501,C0401,C0602 | B3501 | 218 | 13008 | evsgkgpaM | evsgkgpaV |
| Y2087 | RAB37 | 17 | 72739292 | C | T | A3101,A1101,B1302,B3501,C0401,C0602 | B3501 | 63 | 1145 | Wfrsvthay | Rfrsvthay |
| Y2087 | CASKIN2 | 17 | 73498293 | C | G | A3101,A1101,B1302,B3501,C0401,C0602 | B3501 | 177 | 293 | lpfaDegnl | lpfaEegnl |
| Y2087 | CASKIN2 | 17 | 73498293 | C | G | A3101,A1101,B1302,B3501,C0401,C0602 | B3501 | 121 | 241 | faDegnlti | faEegnlti |
| Y2087 | UNK | 17 | 73809850 | C | T | A3101,A1101,B1302,B3501,C0401,C0602 | A1101 | 66 | 38 | rssLcpnvk | rssPcpnvk |
| Y2087 | UNK | 17 | 73809850 | C | T | A3101,A1101,B1302,B3501,C0401,C0602 | C0602 | 274 | 262 | yrssLcpnv | yrssPcpnv |
| Y2087 | RPTOR | 17 | 78681726 | G | A | A3101,A1101,B1302,B3501,C0401,C0602 | C0602 | 170 | 242 | rrnakeeQv | rrnakeeRv |
| Y2087 | BAHCC1 | 17 | 79409139 | C | A | A3101,A1101,B1302,B3501,C0401,C0602 | A3101 | 108 | 683 | gscsrdHdr | gscsrdRdr |
| Y2087 | C17orf70 | 17 | 79514019 | G | A | A3101,A1101,B1302,B3501,C0401,C0602 | B3501 | 25 | 63 | gpaslWaey | gpaslRaey |
| Y2087 | FASN | 17 | 80041488 | G | A | A3101,A1101,B1302,B3501,C0401,C0602 | A1101 | 83 | 143 | vlnslVeek | vlnslAeek |
| Y2087 | B3GNTL1 | 17 | 80914629 | C | T | A3101,A1101,B1302,B3501,C0401,C0602 | A3101 | 45 | 1512 | pQipilhfr | pRipilhfr |
| Y2087 | ANKRD30B | 18 | 14851890 | A | G | A3101,A1101,B1302,B3501,C0401,C0602 | C0602 | 343 | 759 | vtsrRnqel | vtsrKnqel |

Figure 21 (Cont.)

| | | | | | | | | | | | |
|---|---|---|---|---|---|---|---|---|---|---|---|
| Y2087 | ANKRD30B | 18 | 14851890 | A | G | A3101,A1101,B1302,B3501,C0401,C0602 | C0602 | 231 | 528 | srRnqelaf | srKnqelaf |
| Y2087 | KLHL14 | 18 | 30321918 | C | T | A3101,A1101,B1302,B3501,C0401,C0602 | A1101 | 297 | 350 | lvqyyddKk | lvqyyddEk |
| Y2087 | EPG5 | 18 | 43460176 | T | C | A3101,A1101,B1302,B3501,C0401,C0602 | A1101 | 266 | 1705 | Rllspecwk | Qllspecwk |
| Y2087 | EPG5 | 18 | 43460176 | T | C | A3101,A1101,B1302,B3501,C0401,C0602 | A3101 | 342 | 19769 | llmqssaeR | llmqssaeQ |
| Y2087 | EPG5 | 18 | 43460176 | T | C | A3101,A1101,B1302,B3501,C0401,C0602 | A3101 | 396 | 4678 | Rllspecwk | Qllspecwk |
| Y2087 | EPG5 | 18 | 43460176 | T | C | A3101,A1101,B1302,B3501,C0401,C0602 | C0602 | 458 | 497 | mqssaeRll | mqssaeQll |
| Y2087 | RNF165 | 18 | 44013244 | C | A | A3101,A1101,B1302,B3501,C0401,C0602 | B3501 | 38 | 90 | qpqqlapEf | qpqqlapDf |
| Y2087 | RNF165 | 18 | 44013244 | C | A | A3101,A1101,B1302,B3501,C0401,C0602 | B3501 | 414 | 579 | lapEfplah | lapDfplah |
| Y2087 | MYO5B | 18 | 47462623 | G | A | A3101,A1101,B1302,B3501,C0401,C0602 | A1101 | 42 | 64 | klpfYfdpk | klpfHfdpk |
| Y2087 | MYO5B | 18 | 47462623 | G | A | A3101,A1101,B1302,B3501,C0401,C0602 | C0602 | 45 | 11 | fYfdpkrav | fHfdpkrav |
| Y2087 | MBD1 | 18 | 47799969 | C | T | A3101,A1101,B1302,B3501,C0401,C0602 | B3501 | 189 | 551 | spvqvpSpv | spvqvpGpv |
| Y2087 | MBD1 | 18 | 47799969 | C | T | A3101,A1101,B1302,B3501,C0401,C0602 | B3501 | 114 | 645 | Spvaastea | Gpvaastea |
| Y2087 | SALL3 | 18 | 76753019 | C | T | A3101,A1101,B1302,B3501,C0401,C0602 | B3501 | 45 | 3666 | Lpalapgsl | Ppalapgsl |
| Y2087 | GIPC3 | 19 | 3590153 | G | A | A3101,A1101,B1302,B3501,C0401,C0602 | A3101 | 478 | 477 | vwTaigear | vwAaigear |
| Y2087 | GIPC3 | 19 | 3590153 | G | A | A3101,A1101,B1302,B3501,C0401,C0602 | B3501 | 88 | 110 | fvvevwTai | fvvevwAai |
| Y2087 | TJP3 | 19 | 3728609 | G | A | A3101,A1101,B1302,B3501,C0401,C0602 | A3101 | 31 | 64 | atlskdpHr | atlskdpRr |
| Y2087 | PLIN4 | 19 | 4511651 | A | G | A3101,A1101,B1302,B3501,C0401,C0602 | A1101 | 42 | 52 | stgltgaAk | stgltgaVk |
| Y2087 | PLIN4 | 19 | 4511651 | A | G | A3101,A1101,B1302,B3501,C0401,C0602 | A1101 | 98 | 49 | ltgaAklak | ltgaVklak |
| Y2087 | PLIN4 | 19 | 4511664 | G | C | A3101,A1101,B1302,B3501,C0401,C0602 | A1101 | 49 | 52 | stgVtgavk | stgLtgavk |
| Y2087 | PLIN4 | 19 | 4511664 | G | C | A3101,A1101,B1302,B3501,C0401,C0602 | A1101 | 28 | 49 | Vtgavklak | Ltgavklak |
| Y2087 | PLIN4 | 19 | 4511669 | G | C | A3101,A1101,B1302,B3501,C0401,C0602 | A1101 | 95 | 52 | sSgltgavk | sTgltgavk |
| Y2087 | MUC16 | 19 | 8962372 | G | C | A3101,A1101,B1302,B3501,C0401,C0602 | C0602 | 475 | 1878 | yspnrneAl | yspnrnePl |

Figure 21 (Cont.)

| | | | | | | | | | | | |
|---|---|---|---|---|---|---|---|---|---|---|---|
| Y2087 | STX10 | 19 | 13255297 | C | T | A3101,A1101,B1302,B3501,C0401,C0602 | A3101 | 165 | 344 | vshmtsdHr | vshmtsdRr |
| Y2087 | STX10 | 19 | 13255297 | C | T | A3101,A1101,B1302,B3501,C0401,C0602 | C0602 | 410 | 875 | mtsdHrqwc | mtsdRrqwc |
| Y2087 | DCAF15 | 19 | 14071359 | G | A | A3101,A1101,B1302,B3501,C0401,C0602 | A3101 | 464 | 1001 | ryInrmtne | ryVnrmtne |
| Y2087 | IL27RA | 19 | 14162694 | G | C | A3101,A1101,B1302,B3501,C0401,C0602 | A1101 | 64 | 73 | tsgrSyhlr | tsgrCyhlr |
| Y2087 | IL27RA | 19 | 14162694 | G | C | A3101,A1101,B1302,B3501,C0401,C0602 | A3101 | 38 | 18 | tsgrSyhlr | tsgrCyhlr |
| Y2087 | IL27RA | 19 | 14162694 | G | C | A3101,A1101,B1302,B3501,C0401,C0602 | A3101 | 179 | 2713 | rSyhlrhkv | rCyhlrhkv |
| Y2087 | HSH2D | 19 | 16263983 | C | T | A3101,A1101,B1302,B3501,C0401,C0602 | A3101 | 144 | 41 | hqqkpieSr | hqqkpiePr |
| Y2087 | HSH2D | 19 | 16263983 | C | T | A3101,A1101,B1302,B3501,C0401,C0602 | A3101 | 78 | 161 | qqkpieSrr | qqkpiePrr |
| Y2087 | ZNF90 | 19 | 20229097 | C | T | A3101,A1101,B1302,B3501,C0401,C0602 | A1101 | 47 | 49 | ysstlIahk | ysstlTahk |
| Y2087 | ZNF90 | 19 | 20229097 | C | T | A3101,A1101,B1302,B3501,C0401,C0602 | A1101 | 284 | 489 | sstlIahkr | sstlTahkr |
| Y2087 | ZNF90 | 19 | 20229097 | C | T | A3101,A1101,B1302,B3501,C0401,C0602 | A3101 | 112 | 256 | sstlIahkr | sstlTahkr |
| Y2087 | ZNF737 | 19 | 20728254 | C | G | A3101,A1101,B1302,B3501,C0401,C0602 | B3501 | 413 | 237 | iihTgekpy | iihSgekpy |
| Y2087 | ZNF626 | 19 | 20807274 | G | T | A3101,A1101,B1302,B3501,C0401,C0602 | A1101 | 249 | 54 | cssnltKhk | cssnltThk |
| Y2087 | ZNF626 | 19 | 20807274 | G | T | A3101,A1101,B1302,B3501,C0401,C0602 | A1101 | 27 | 16 | ssnltKhkk | ssnltThkk |
| Y2087 | ZNF626 | 19 | 20807274 | G | T | A3101,A1101,B1302,B3501,C0401,C0602 | A3101 | 239 | 545 | ssnltKhkk | ssnltThkk |
| Y2087 | ZNF429 | 19 | 21720861 | A | T | A3101,A1101,B1302,B3501,C0401,C0602 | A3101 | 343 | 852 | itrsgVrdr | itrsgDrdr |
| Y2087 | ZNF257 | 19 | 22271717 | A | C | A3101,A1101,B1302,B3501,C0401,C0602 | A1101 | 66 | 142 | rsshltQhk | rsshltKhk |
| Y2087 | ZNF257 | 19 | 22271717 | A | C | A3101,A1101,B1302,B3501,C0401,C0602 | A1101 | 306 | 600 | sshltQhkr | sshltKhkr |
| Y2087 | ZNF257 | 19 | 22271717 | A | C | A3101,A1101,B1302,B3501,C0401,C0602 | A3101 | 178 | 340 | rsshltQhk | rsshltKhk |
| Y2087 | ZNF257 | 19 | 22271717 | A | C | A3101,A1101,B1302,B3501,C0401,C0602 | A3101 | 56 | 28 | sshltQhkr | sshltKhkr |
| Y2087 | ZNF257 | 19 | 22271717 | A | C | A3101,A1101,B1302,B3501,C0401,C0602 | A3101 | 17 | 275 | tQhkrihtr | tKhkrihtr |
| Y2087 | ZNF729 | 19 | 22497138 | T | C | A3101,A1101,B1302,B3501,C0401,C0602 | A1101 | 40 | 22 | gssnLnahk | gssnFnahk |
| Y2087 | ZNF729 | 19 | 22497138 | T | C | A3101,A1101,B1302,B3501,C0401,C0602 | A3101 | 425 | 191 | gssnLnahk | gssnFnahk |

Figure 21 (Cont.)

| | | | | | | | | | | | |
|---|---|---|---|---|---|---|---|---|---|---|---|
| Y2087 | ZNF729 | 19 | 22497142 | A | C | A3101,A1101,B1302,B3501,C0401,C0602 | A1101 | 18 | 22 | gssnfTahk | gssnfNahk |
| Y2087 | ZNF729 | 19 | 22497142 | A | C | A3101,A1101,B1302,B3501,C0401,C0602 | A3101 | 217 | 191 | gssnfTahk | gssnfNahk |
| Y2087 | ZNF729 | 19 | 22497145 | C | A | A3101,A1101,B1302,B3501,C0401,C0602 | A1101 | 33 | 22 | gssnfnEhk | gssnfnAhk |
| Y2087 | ZNF729 | 19 | 22497153 | G | A | A3101,A1101,B1302,B3501,C0401,C0602 | B3501 | 313 | 524 | lihtaekpy | Vihtaekpy |
| Y2087 | ZNF492 | 19 | 22847582 | A | G | A3101,A1101,B1302,B3501,C0401,C0602 | A3101 | 463 | 259 | evcGkafsr | evcSkafsr |
| Y2087 | ZNF850 | 19 | 37240749 | C | T | A3101,A1101,B1302,B3501,C0401,C0602 | A3101 | 100 | 2055 | eYgksftfr | eCgksftfr |
| Y2087 | RYR1 | 19 | 38955336 | C | G | A3101,A1101,B1302,B3501,C0401,C0602 | A1101 | 153 | 2302 | Klkktklpk | Nlkktklpk |
| Y2087 | RYR1 | 19 | 38955336 | C | G | A3101,A1101,B1302,B3501,C0401,C0602 | A3101 | 69 | 1742 | Klkktklpk | Nlkktklpk |
| Y2087 | ZNF780B | 19 | 40542468 | G | A | A3101,A1101,B1302,B3501,C0401,C0602 | A1101 | 88 | 47 | difeinlSk | difeinlPk |
| Y2087 | PPM1N | 19 | 46001986 | T | A | A3101,A1101,B1302,B3501,C0401,C0602 | A3101 | 16 | 12064 | rmedahctR | rmedahctW |
| Y2087 | PPM1N | 19 | 46001986 | T | A | A3101,A1101,B1302,B3501,C0401,C0602 | C0401 | 171 | 555 | medahctRl | medahctWl |
| Y2087 | NOVA2 | 19 | 46443666 | C | T | A3101,A1101,B1302,B3501,C0401,C0602 | B3501 | 63 | 10887 | aasgvlaaM | aasgvlaaV |
| Y2087 | NOVA2 | 19 | 46443666 | C | T | A3101,A1101,B1302,B3501,C0401,C0602 | B3501 | 15 | 457 | Maaganpaa | Vaaganpaa |
| Y2087 | SIGLEC14 | 19 | 52147240 | C | A | A3101,A1101,B1302,B3501,C0401,C0602 | B3501 | 123 | 242 | vpiqegHsl | vpiqegQsl |
| Y2087 | ZNF534 | 19 | 52942317 | C | T | A3101,A1101,B1302,B3501,C0401,C0602 | A3101 | 36 | 75 | mLhlvrhr | mShlvrhr |
| Y2087 | ZNF784 | 19 | 56133485 | C | T | A3101,A1101,B1302,B3501,C0401,C0602 | A3101 | 5 | 5 | rfcTkpfrr | rfcAkpfrr |
| Y2087 | GPR113 | 2 | 26536249 | G | A | A3101,A1101,B1302,B3501,C0401,C0602 | C0602 | 486 | 421 | alftrIkll | alftrTkll |
| Y2087 | TEKT4 | 2 | 95540529 | C | T | A3101,A1101,B1302,B3501,C0401,C0602 | A1101 | 43 | 181 | asIpetrak | asTpetrak |
| Y2087 | TMEM131 | 2 | 98412820 | C | T | A3101,A1101,B1302,B3501,C0401,C0602 | C0602 | 228 | 667 | fkIentgql | fkVentgql |
| Y2087 | NCKAP5 | 2 | 133618070 | G | A | A3101,A1101,B1302,B3501,C0401,C0602 | A1101 | 32 | 59 | ptsdllFqk | ptsdllLqk |
| Y2087 | NCKAP5 | 2 | 133618070 | G | A | A3101,A1101,B1302,B3501,C0401,C0602 | A3101 | 46 | 128 | llFqklhsr | llLqklhsr |
| Y2087 | NCKAP5 | 2 | 133618070 | G | A | A3101,A1101,B1302,B3501,C0401,C0602 | C0602 | 98 | 855 | Fqklhsrll | Lqklhsrll |

Figure 21 (Cont.)

| | | | | | | | | | | | |
|---|---|---|---|---|---|---|---|---|---|---|---|
| Y2087 | ZRANB3 | 2 | 136148377 | C | G | A3101,A1101,B1302,B3501,C0401,C0602 | A1101 | 112 | 203 | vaHemglgk | vaDemglgk |
| Y2087 | VPS16 | 20 | 2842540 | T | C | A3101,A1101,B1302,B3501,C0401,C0602 | B3501 | 135 | 43 | Apaaseeif | Vpaaseeif |
| Y2087 | SPEF1 | 20 | 3759180 | G | A | A3101,A1101,B1302,B3501,C0401,C0602 | B3501 | 4 | 53 | Lpaprppay | Ppaprppay |
| Y2087 | KIAA1755 | 20 | 36841850 | G | A | A3101,A1101,B1302,B3501,C0401,C0602 | A3101 | 34 | 91 | aahsVrper | aahsArper |
| Y2087 | MYBL2 | 20 | 42302453 | C | A | A3101,A1101,B1302,B3501,C0401,C0602 | C0602 | 222 | 187 | srrtrcedM | srrtrcedL |
| Y2087 | MYBL2 | 20 | 42302453 | C | A | A3101,A1101,B1302,B3501,C0401,C0602 | C0602 | 65 | 54 | trcedMdel | trcedLdel |
| Y2087 | EYA2 | 20 | 45618692 | G | A | A3101,A1101,B1302,B3501,C0401,C0602 | A1101 | 35 | 51 | tvnsNcldk | tvnsDcldk |
| Y2087 | TMEM189 | 20 | 48760075 | G | A | A3101,A1101,B1302,B3501,C0401,C0602 | B3501 | 73 | 56 | laCwedtpl | laRwedtpl |
| Y2087 | HRH3 | 20 | 60791162 | G | A | A3101,A1101,B1302,B3501,C0401,C0602 | A3101 | 370 | 223 | avnpvlyLl | avnpvlyPl |
| Y2087 | HRH3 | 20 | 60791162 | G | A | A3101,A1101,B1302,B3501,C0401,C0602 | A3101 | 10 | 141 | yLlchhsfr | yPlchhsfr |
| Y2087 | HRH3 | 20 | 60791162 | G | A | A3101,A1101,B1302,B3501,C0401,C0602 | A3101 | 17 | 175 | Llchhsfrr | Plchhsfrr |
| Y2087 | HRH3 | 20 | 60791162 | G | A | A3101,A1101,B1302,B3501,C0401,C0602 | B3501 | 314 | 246 | npvlyLlch | npvlyPlch |
| Y2087 | HRH3 | 20 | 60791383 | C | A | A3101,A1101,B1302,B3501,C0401,C0602 | A1101 | 247 | 126 | Ivsqsftqr | Mvsqsftqr |
| Y2087 | HRH3 | 20 | 60791383 | C | A | A3101,A1101,B1302,B3501,C0401,C0602 | A3101 | 58 | 24 | Ivsqsftqr | Mvsqsftqr |
| Y2087 | CHRNA4 | 20 | 61981376 | C | A | A3101,A1101,B1302,B3501,C0401,C0602 | C0602 | 57 | 134 | Srslsvqhm | Arslsvqhm |
| Y2087 | KCNQ2 | 20 | 62076073 | C | A | A3101,A1101,B1302,B3501,C0401,C0602 | A3101 | 69 | 30 | ilrmiLmdr | ilrmiRmdr |
| Y2087 | ZNF512B | 20 | 62594056 | G | A | A3101,A1101,B1302,B3501,C0401,C0602 | A3101 | 27 | 19 | rtpsgrvCr | rtpsgrvRr |
| Y2087 | ZNF512B | 20 | 62594061 | C | T | A3101,A1101,B1302,B3501,C0401,C0602 | A3101 | 16 | 19 | rtpsgHvrr | rtpsgRvrr |
| Y2087 | SLC19A1 | 21 | 46951704 | G | A | A3101,A1101,B1302,B3501,C0401,C0602 | A1101 | 18 | 28 | rvsfFtlny | rvsfStlny |
| Y2087 | UFD1L | 22 | 19444429 | C | T | A3101,A1101,B1302,B3501,C0401,C0602 | B3501 | 468 | 607 | mnvdfdTpl | mnvdfdApl |
| Y2087 | RIMBP3 | 22 | 20458276 | G | A | A3101,A1101,B1302,B3501,C0401,C0602 | A1101 | 234 | 126 | tsVnitwvy | tsAnitwvy |
| Y2087 | RIMBP3 | 22 | 20458276 | G | A | A3101,A1101,B1302,B3501,C0401,C0602 | B3501 | 111 | 80 | tsVnitwvy | tsAnitwvy |
| Y2087 | KLHL22 | 22 | 20800738 | C | T | A3101,A1101,B1302,B3501,C0401,C0602 | C0602 | 72 | 169 | yrrdMhqva | yrrdVhqva |

Figure 21 (Cont.)

| | | | | | | | | | | | |
|---|---|---|---|---|---|---|---|---|---|---|---|
| Y2087 | LZTR1 | 22 | 21346026 | G | A | A3101,A1101,B1302,B3501,C0401,C0602 | B3501 | 290 | 1722 | fgSaadntl | fgGaadntl |
| Y2087 | SDF2L1 | 22 | 21996690 | T | C | A3101,A1101,B1302,B3501,C0401,C0602 | A1101 | 158 | 1971 | Svpgggaak | Lvpgggaak |
| Y2087 | CBX6 | 22 | 39262527 | T | C | A3101,A1101,B1302,B3501,C0401,C0602 | C0602 | 485 | 376 | wrGpevldl | wrEpevldl |
| Y2087 | MCAT | 22 | 43529477 | G | T | A3101,A1101,B1302,B3501,C0401,C0602 | A1101 | 73 | 20129 | hqealrflK | hqealrflQ |
| Y2087 | MCAT | 22 | 43529477 | G | T | A3101,A1101,B1302,B3501,C0401,C0602 | A3101 | 101 | 3687 | hqealrflK | hqealrflQ |
| Y2087 | MCAT | 22 | 43529477 | G | T | A3101,A1101,B1302,B3501,C0401,C0602 | A3101 | 73 | 167 | rflKknssk | rflQknssk |
| Y2087 | DENND6B | 22 | 50753112 | C | T | A3101,A1101,B1302,B3501,C0401,C0602 | A1101 | 27 | 374 | ltsclqplK | ltsclqplR |
| Y2087 | DENND6B | 22 | 50753112 | C | T | A3101,A1101,B1302,B3501,C0401,C0602 | A3101 | 219 | 405 | plKfccdfr | plRfccdfr |
| Y2087 | DENND6B | 22 | 50753112 | C | T | A3101,A1101,B1302,B3501,C0401,C0602 | B3501 | 247 | 443 | qplKfccdf | qplRfccdf |
| Y2087 | BSN | 3 | 49679825 | C | T | A3101,A1101,B1302,B3501,C0401,C0602 | A1101 | 98 | 315 | lspahsLak | lspahsPak |
| Y2087 | BSN | 3 | 49679825 | C | T | A3101,A1101,B1302,B3501,C0401,C0602 | A1101 | 74 | 9481 | sLakqplgk | sPakqplgk |
| Y2087 | MST1R | 3 | 49934212 | C | A | A3101,A1101,B1302,B3501,C0401,C0602 | A3101 | 196 | 820 | pgswtfHyr | pgswtfQyr |
| Y2087 | MST1R | 3 | 49934212 | C | A | A3101,A1101,B1302,B3501,C0401,C0602 | B3501 | 24 | 10 | vpgswtfHy | vpgswtfQy |
| Y2087 | MST1R | 3 | 49934212 | C | A | A3101,A1101,B1302,B3501,C0401,C0602 | C0602 | 93 | 3239 | fHyredpvv | fQyredpvv |
| Y2087 | MST1R | 3 | 49934212 | C | A | A3101,A1101,B1302,B3501,C0401,C0602 | C0602 | 497 | 622 | Hyredpvvl | Qyredpvvl |
| Y2087 | DNAH1 | 3 | 52381845 | G | A | A3101,A1101,B1302,B3501,C0401,C0602 | C0602 | 39 | 93 | yrpQknplf | yrpRknplf |
| Y2087 | ITIH1 | 3 | 52820341 | G | A | A3101,A1101,B1302,B3501,C0401,C0602 | A1101 | 182 | 2977 | clMdeeemk | clVdeeemk |
| Y2087 | EBLN2 | 3 | 73111287 | T | C | A3101,A1101,B1302,B3501,C0401,C0602 | A1101 | 47 | 2082 | Rvcdrsykr | Wvcdrsykr |
| Y2087 | EBLN2 | 3 | 73111287 | T | C | A3101,A1101,B1302,B3501,C0401,C0602 | A3101 | 154 | 20194 | vnshslfvR | vnshslfvW |
| Y2087 | EBLN2 | 3 | 73111287 | T | C | A3101,A1101,B1302,B3501,C0401,C0602 | A3101 | 40 | 34 | slfvRvcdr | slfvWvcdr |
| Y2087 | EBLN2 | 3 | 73111287 | T | C | A3101,A1101,B1302,B3501,C0401,C0602 | A3101 | 8 | 103 | Rvcdrsykr | Wvcdrsykr |
| Y2087 | EBLN2 | 3 | 73111287 | T | C | A3101,A1101,B1302,B3501,C0401,C0602 | B3501 | 33 | 5 | fvRvcdrsy | fvWvcdrsy |

Figure 21 (Cont.)

| | | | | | | | | | | | |
|---|---|---|---|---|---|---|---|---|---|---|---|
| Y2087 | CPOX | 3 | 98312084 | C | T | A3101,A1101,B1302,B3501,C0401,C0602 | B3501 | 105 | 56 | lvglTtaaf | lvglAtaaf |
| Y2087 | COL6A5 | 3 | 130095440 | C | T | A3101,A1101,B1302,B3501,C0401,C0602 | B3501 | 224 | 3292 | ppilvvlaL | ppilvvlaS |
| Y2087 | A4GNT | 3 | 137849984 | G | A | A3101,A1101,B1302,B3501,C0401,C0602 | B3501 | 226 | 8979 | fclpsfksY | fclpsfksH |
| Y2087 | PRR23C | 3 | 138762721 | G | A | A3101,A1101,B1302,B3501,C0401,C0602 | A3101 | 129 | 254 | harpelSer | harpelPer |
| Y2087 | ABCC5 | 3 | 183696434 | G | A | A3101,A1101,B1302,B3501,C0401,C0602 | A3101 | 113 | 81 | vqkiCeeer | vqkiReeer |
| Y2087 | TMEM41A | 3 | 185214734 | C | A | A3101,A1101,B1302,B3501,C0401,C0602 | B3501 | 17 | 832 | fpsdlaelL | fpsdlaelR |
| Y2087 | MUC4 | 3 | 195511390 | T | A | A3101,A1101,B1302,B3501,C0401,C0602 | B3501 | 485 | 252 | tplLvtdas | tplHvtdas |
| Y2087 | MUC4 | 3 | 195511717 | C | T | A3101,A1101,B1302,B3501,C0401,C0602 | B3501 | 229 | 276 | lpvtNissa | lpvtSissa |
| Y2087 | MUC4 | 3 | 195512735 | G | A | A3101,A1101,B1302,B3501,C0401,C0602 | A1101 | 58 | 335 | stgdttplY | stgdttplH |
| Y2087 | MUC4 | 3 | 195512735 | G | A | A3101,A1101,B1302,B3501,C0401,C0602 | B3501 | 221 | 252 | tplYvtdas | tplHvtdas |
| Y2087 | MUC4 | 3 | 195513442 | G | A | A3101,A1101,B1302,B3501,C0401,C0602 | B3501 | 224 | 89 | lpvtsIssa | lpvtsTssa |
| Y2087 | MUC4 | 3 | 195515411 | G | C | A3101,A1101,B1302,B3501,C0401,C0602 | B3501 | 160 | 336 | tplpvtsAs | tplpvtsPs |
| Y2087 | MUC4 | 3 | 195515411 | G | C | A3101,A1101,B1302,B3501,C0401,C0602 | B3501 | 146 | 217 | lpvtsAssv | lpvtsPssv |
| Y2087 | ADRA2C | 4 | 3769028 | G | C | A3101,A1101,B1302,B3501,C0401,C0602 | A3101 | 60 | 19 | glvyaPiyr | glvyaRiyr |
| Y2087 | ADRA2C | 4 | 3769028 | G | C | A3101,A1101,B1302,B3501,C0401,C0602 | B3501 | 245 | 957 | mglvyaPiy | mglvyaRiy |
| Y2087 | USP17L10 | 4 | 9213194 | A | C | A3101,A1101,B1302,B3501,C0401,C0602 | A1101 | 144 | 298 | tltlhTsak | tltlhNsak |
| Y2087 | USP17L10 | 4 | 9213194 | A | C | A3101,A1101,B1302,B3501,C0401,C0602 | C0602 | 296 | 147 | lhTsakvli | lhNsakvli |
| Y2087 | NOA1 | 4 | 57843732 | G | A | A3101,A1101,B1302,B3501,C0401,C0602 | A3101 | 35 | 30 | mlparlLfr | mlparlPfr |
| Y2087 | NOA1 | 4 | 57843732 | G | A | A3101,A1101,B1302,B3501,C0401,C0602 | B3501 | 73 | 42 | lparlLfrl | lparlPfrl |
| Y2087 | UGT2B10 | 4 | 69885837 | A | T | A3101,A1101,B1302,B3501,C0401,C0602 | A1101 | 50 | 40 | evypQsltk | evypTsltk |
| Y2087 | ANTXR2 | 4 | 80898786 | C | T | A3101,A1101,B1302,B3501,C0401,C0602 | A1101 | 26 | 13747 | rvslmrpqK | rvslmrpqE |
| Y2087 | ANTXR2 | 4 | 80898786 | C | T | A3101,A1101,B1302,B3501,C0401,C0602 | A3101 | 135 | 6622 | rvslmrpqK | rvslmrpqE |
| Y2087 | MTTP | 4 | 100512886 | G | A | A3101,A1101,B1302,B3501,C0401,C0602 | A1101 | 282 | 20426 | sfviavlaK | sfviavlaE |

Figure 21 (Cont.)

| | | | | | | | | | | | |
|---|---|---|---|---|---|---|---|---|---|---|---|
| Y2087 | C5orf42 | 5 | 37198899 | G | A | A3101,A1101,B1302,B3501,C0401,C0602 | A1101 | 373 | 7579 | lqCvllifr | lqRvllifr |
| Y2087 | C5orf42 | 5 | 37198899 | G | A | A3101,A1101,B1302,B3501,C0401,C0602 | A3101 | 32 | 20 | lqCvllifr | lqRvllifr |
| Y2087 | N4BP3 | 5 | 177548222 | G | A | A3101,A1101,B1302,B3501,C0401,C0602 | A3101 | 115 | 90 | lfmTqqeqr | lfmAqqeqr |
| Y2087 | N4BP3 | 5 | 177548222 | G | A | A3101,A1101,B1302,B3501,C0401,C0602 | A3101 | 235 | 130 | Tqqeqrrlr | Aqqeqrrlr |
| Y2087 | F13A1 | 6 | 6266913 | G | A | A3101,A1101,B1302,B3501,C0401,C0602 | A1101 | 19 | 48 | rlsiqsFpk | rlsiqsSpk |
| Y2087 | F13A1 | 6 | 6266913 | G | A | A3101,A1101,B1302,B3501,C0401,C0602 | A3101 | 45 | 271 | rlsiqsFpk | rlsiqsSpk |
| Y2087 | F13A1 | 6 | 6266913 | G | A | A3101,A1101,B1302,B3501,C0401,C0602 | B3501 | 125 | 3832 | Fpkcivgkf | Spkcivgkf |
| Y2087 | MDFI | 6 | 41606524 | G | T | A3101,A1101,B1302,B3501,C0401,C0602 | B3501 | 5 | 5 | rpsgcYapy | rpsgcDapy |
| Y2087 | TDRD6 | 6 | 46656631 | A | G | A3101,A1101,B1302,B3501,C0401,C0602 | A1101 | 462 | 621 | Vtqvchphr | Itqvchphr |
| Y2087 | TDRD6 | 6 | 46656631 | A | G | A3101,A1101,B1302,B3501,C0401,C0602 | A3101 | 12 | 10 | Vtqvchphr | Itqvchphr |
| Y2087 | TPBG | 6 | 83074836 | C | A | A3101,A1101,B1302,B3501,C0401,C0602 | B3501 | 10 | 1520 | apflasavY | apflasavS |
| Y2087 | TPBG | 6 | 83074836 | C | A | A3101,A1101,B1302,B3501,C0401,C0602 | B3501 | 152 | 129 | savYaqppl | savSaqppl |
| Y2087 | TPBG | 6 | 83074838 | G | A | A3101,A1101,B1302,B3501,C0401,C0602 | B3501 | 257 | 129 | savsTqppl | savsAqppl |
| Y2087 | ZNF292 | 6 | 87965266 | T | C | A3101,A1101,B1302,B3501,C0401,C0602 | B3501 | 43 | 375 | rpikknsPy | rpikknsLy |
| Y2087 | ZNF292 | 6 | 87965266 | T | C | A3101,A1101,B1302,B3501,C0401,C0602 | B3501 | 356 | 9825 | sPystdfiv | sLystdfiv |
| Y2087 | CASP8AP2 | 6 | 90578686 | T | A | A3101,A1101,B1302,B3501,C0401,C0602 | A1101 | 26 | 22 | vtkdpsTlk | vtkdpsSlk |
| Y2087 | CASP8AP2 | 6 | 90578686 | T | A | A3101,A1101,B1302,B3501,C0401,C0602 | A3101 | 362 | 441 | vtkdpsTlk | vtkdpsSlk |
| Y2087 | PRDM13 | 6 | 100062207 | G | A | A3101,A1101,B1302,B3501,C0401,C0602 | A1101 | 314 | 252 | gsggsgTgk | gsggsgAgk |
| Y2087 | MOXD1 | 6 | 132722364 | C | A | A3101,A1101,B1302,B3501,C0401,C0602 | B3501 | 43 | 89 | fgfsptWam | fgfsptGam |
| Y2087 | MOXD1 | 6 | 132722364 | C | A | A3101,A1101,B1302,B3501,C0401,C0602 | B3501 | 312 | 15315 | Wamasadiv | Gamasadiv |
| Y2087 | ARID1B | 6 | 157099481 | T | A | A3101,A1101,B1302,B3501,C0401,C0602 | B3501 | 11 | 44 | hpisnnnsM | hpisnnnsL |
| Y2087 | GPR146 | 7 | 1097767 | G | A | A3101,A1101,B1302,B3501,C0401,C0602 | A3101 | 262 | 220 | lyTlvllsr | lyAlvllsr |

Figure 21 (Cont.)

| | | | | | | | | | | | |
|---|---|---|---|---|---|---|---|---|---|---|---|
| Y2087 | RADIL | 7 | 4917679 | G | T | A3101,A1101,B1302,B3501,C0401,C0602 | A1101 | 143 | 21724 | llssmlsrK | llssmlsrT |
| Y2087 | RADIL | 7 | 4917679 | G | T | A3101,A1101,B1302,B3501,C0401,C0602 | A1101 | 319 | 72 | smlsrKlsy | smlsrTlsy |
| Y2087 | RADIL | 7 | 4917679 | G | T | A3101,A1101,B1302,B3501,C0401,C0602 | A1101 | 27 | 21 | mlsrKlsyk | mlsrTlsyk |
| Y2087 | RADIL | 7 | 4917679 | G | T | A3101,A1101,B1302,B3501,C0401,C0602 | A3101 | 54 | 78 | mlsrKlsyk | mlsrTlsyk |
| Y2087 | RSPH10B2 | 7 | 6838144 | G | C | A3101,A1101,B1302,B3501,C0401,C0602 | A1101 | 14 | 28 | ssNtitskk | ssKtitskk |
| Y2087 | RSPH10B2 | 7 | 6838144 | G | C | A3101,A1101,B1302,B3501,C0401,C0602 | A3101 | 244 | 204 | ssNtitskk | ssKtitskk |
| Y2087 | RSPH10B2 | 7 | 6838144 | G | C | A3101,A1101,B1302,B3501,C0401,C0602 | B3501 | 196 | 1423 | spssNtits | spssKtits |
| Y2087 | HOXA4 | 7 | 27169173 | C | T | A3101,A1101,B1302,B3501,C0401,C0602 | A1101 | 129 | 18213 | savnpsynR | savnpsynG |
| Y2087 | HOXA4 | 7 | 27169173 | C | T | A3101,A1101,B1302,B3501,C0401,C0602 | A1101 | 296 | 376 | psynRgepk | psynGgepk |
| Y2087 | HOXA4 | 7 | 27169173 | C | T | A3101,A1101,B1302,B3501,C0401,C0602 | A3101 | 51 | 21788 | savnpsynR | savnpsynG |
| Y2087 | HOXA4 | 7 | 27169173 | C | T | A3101,A1101,B1302,B3501,C0401,C0602 | A3101 | 148 | 324 | synRgepkr | synGgepkr |
| Y2087 | HOXA10 | 7 | 27213712 | G | A | A3101,A1101,B1302,B3501,C0401,C0602 | B3501 | 4 | 3 | lppaadlSy | lppaadlPy |
| Y2087 | PKD1L1 | 7 | 47969079 | G | A | A3101,A1101,B1302,B3501,C0401,C0602 | B3501 | 248 | 3415 | Masqsgsei | Tasqsgsei |
| Y2087 | DLX6 | 7 | 96635665 | C | T | A3101,A1101,B1302,B3501,C0401,C0602 | B3501 | 15 | 6 | mshsqhsSy | mshsqhsPy |
| Y2087 | DLX6 | 7 | 96635665 | C | T | A3101,A1101,B1302,B3501,C0401,C0602 | C0602 | 7 | 9 | shsqhsSyl | shsqhsPyl |
| Y2087 | DLX6 | 7 | 96635665 | C | T | A3101,A1101,B1302,B3501,C0401,C0602 | C0602 | 235 | 193 | qhsSylqsy | qhsPylqsy |
| Y2087 | TECPR1 | 7 | 97862838 | C | T | A3101,A1101,B1302,B3501,C0401,C0602 | B3501 | 7 | 5 | lplglKepy | lplglEepy |
| Y2087 | MEPCE | 7 | 100028005 | A | T | A3101,A1101,B1302,B3501,C0401,C0602 | C0602 | 316 | 317 | rrggggSel | rrggggTel |
| Y2087 | WNT16 | 7 | 120969428 | C | A | A3101,A1101,B1302,B3501,C0401,C0602 | A1101 | 53 | 20061 | lvlfpygaK | lvlfpygaQ |
| Y2087 | WNT16 | 7 | 120969428 | C | A | A3101,A1101,B1302,B3501,C0401,C0602 | B3501 | 470 | 280 | fpygaKgnw | fpygaQgnw |
| Y2087 | EPHA1 | 7 | 143096972 | G | A | A3101,A1101,B1302,B3501,C0401,C0602 | C0602 | 433 | 161 | fyqCcpetl | fyqRcpetl |
| Y2087 | POU5F1B | 8 | 128429115 | C | T | A3101,A1101,B1302,B3501,C0401,C0602 | B3501 | 17 | 5 | talysLvpf | talysSvpf |
| Y2087 | AQP7 | 9 | 33386429 | C | T | A3101,A1101,B1302,B3501,C0401,C0602 | A1101 | 328 | 272 | Tatiyslfy | Aatiyslfy |

Figure 21 (Cont.)

| | | | | | | | | | | | |
|---|---|---|---|---|---|---|---|---|---|---|---|
| Y2087 | AQP7 | 9 | 33386429 | C | T | A3101,A1101,B1302,B3501,C0401,C0602 | B3501 | 390 | 200 | sflaTatiy | sflaAatiy |
| Y2087 | AQP7 | 9 | 33386429 | C | T | A3101,A1101,B1302,B3501,C0401,C0602 | B3501 | 259 | 105 | laTatiysl | laAatiysl |
| Y2087 | AQP7 | 9 | 33386429 | C | T | A3101,A1101,B1302,B3501,C0401,C0602 | B3501 | 33 | 204 | Tatiyslfy | Aatiyslfy |
| Y2087 | ZNF658 | 9 | 40772910 | C | G | A3101,A1101,B1302,B3501,C0401,C0602 | A1101 | 44 | 63 | ksylsghQr | ksylsghEr |
| Y2087 | ZNF658 | 9 | 40772910 | C | G | A3101,A1101,B1302,B3501,C0401,C0602 | A3101 | 9 | 11 | ksylsghQr | ksylsghEr |
| Y2087 | ZNF658 | 9 | 40772993 | C | T | A3101,A1101,B1302,B3501,C0401,C0602 | A3101 | 9 | 11 | ktrlsthQr | ktrlsthRr |
| Y2087 | ZNF658 | 9 | 40772993 | C | T | A3101,A1101,B1302,B3501,C0401,C0602 | C0602 | 146 | 120 | trlsthQri | trlsthRri |
| Y2087 | TJP2 | 9 | 71835984 | C | T | A3101,A1101,B1302,B3501,C0401,C0602 | A1101 | 367 | 1312 | rswedsLer | rswedsPer |
| Y2087 | TJP2 | 9 | 71835984 | C | T | A3101,A1101,B1302,B3501,C0401,C0602 | A3101 | 92 | 61 | rswedsLer | rswedsPer |
| Y2087 | PRUNE2 | 9 | 79239372 | C | T | A3101,A1101,B1302,B3501,C0401,C0602 | B3501 | 42 | 18 | eaTktscly | eaAktscly |
| Y2087 | LHX6 | 9 | 124989737 | C | T | A3101,A1101,B1302,B3501,C0401,C0602 | A1101 | 129 | 169 | maqpgsDck | maqpgsGck |
| Y2087 | CRB2 | 9 | 126139299 | G | T | A3101,A1101,B1302,B3501,C0401,C0602 | C0602 | 272 | 176 | arleIdsvl | arleMdsvl |
| Y2087 | FAM69B | 9 | 139617957 | G | A | A3101,A1101,B1302,B3501,C0401,C0602 | A3101 | 27 | 29 | hstdctyRr | hstdctyGr |
| Y2087 | FAM69B | 9 | 139617957 | G | A | A3101,A1101,B1302,B3501,C0401,C0602 | C0602 | 372 | 21648 | yRrdcrapc | yGrdcrapc |
| Y2087 | ABCA2 | 9 | 139905956 | G | A | A3101,A1101,B1302,B3501,C0401,C0602 | B3501 | 61 | 123 | wfevLssay | wfevPssay |
| Y2087 | ABCA2 | 9 | 139905956 | G | A | A3101,A1101,B1302,B3501,C0401,C0602 | B3501 | 54 | 333 | evLssayvf | evPssayvf |
| Y2087 | CACNA1B | 9 | 140919480 | C | T | A3101,A1101,B1302,B3501,C0401,C0602 | A1101 | 77 | 178 | tlpstcFqk | tlpstcLqk |
| Y2087 | CACNA1B | 9 | 141015238 | C | T | A3101,A1101,B1302,B3501,C0401,C0602 | A3101 | 100 | 83 | yscdCfggr | yscdRfggr |
| Y2087 | CLCN4 | X | 10176291 | C | G | A3101,A1101,B1302,B3501,C0401,C0602 | A1101 | 299 | 793 | glwgtlfMr | glwgtlflr |
| Y2087 | CLCN4 | X | 10176291 | C | G | A3101,A1101,B1302,B3501,C0401,C0602 | A3101 | 15 | 20 | glwgtlfMr | glwgtlflr |
| Y2087 | CXorf36 | X | 45011205 | T | C | A3101,A1101,B1302,B3501,C0401,C0602 | B3501 | 489 | 1649 | ragenEdif | ragenKdif |
| Y2087 | SLC38A5 | X | 48326159 | G | A | A3101,A1101,B1302,B3501,C0401,C0602 | C0602 | 30 | 25 | yrqeCegfl | yrqeRegfl |

Figure 21 (Cont.)

| | | | | | | | | | | | |
|---|---|---|---|---|---|---|---|---|---|---|---|
| Y2087 | KCND1 | X | 48826177 | G | T | A3101,A1101,B1302,B3501,C0401,C0602 | A1101 | 33 | 150 | ssMrqrlwr | ssLrqrlwr |
| Y2087 | KCND1 | X | 48826177 | G | T | A3101,A1101,B1302,B3501,C0401,C0602 | A3101 | 27 | 48 | ssMrqrlwr | ssLrqrlwr |
| Y2087 | KCND1 | X | 48826177 | G | T | A3101,A1101,B1302,B3501,C0401,C0602 | B3501 | 323 | 3409 | palpagssM | palpagssL |
| Y2087 | ARHGEF9 | X | 62898305 | C | A | A3101,A1101,B1302,B3501,C0401,C0602 | B3501 | 340 | 1416 | midiaidCf | midiaidGf |
| Y2087 | KIF4A | X | 69606486 | G | A | A3101,A1101,B1302,B3501,C0401,C0602 | A3101 | 82 | 1024 | qyKllkler | qyEllkler |
| Y2087 | NHSL2 | X | 71360262 | C | T | A3101,A1101,B1302,B3501,C0401,C0602 | B3501 | 281 | 18594 | lvftpfasF | lvftpfasS |
| Y2087 | NHSL2 | X | 71360262 | C | T | A3101,A1101,B1302,B3501,C0401,C0602 | B3501 | 7 | 4 | fasFsdaff | fasSsdaff |
| Y2087 | NRK | X | 105153269 | C | T | A3101,A1101,B1302,B3501,C0401,C0602 | C0602 | 303 | 534 | qrhnqvSeq | qrhnqvPeq |
| Y2087 | CTAG2 | X | 153881623 | G | A | A3101,A1101,B1302,B3501,C0401,C0602 | A3101 | 222 | 1971 | sgLrggapr | sgPrggapr |
| ZA6505 | NPHP4 | 1 | 6029314 | C | A | A2501,A2901,B1801,B0705,C1203,C1505 | B1801 | 146 | 184 | nepFyfhts | nepLyfhts |
| ZA6505 | NPHP4 | 1 | 6029314 | C | A | A2501,A2901,B1801,B0705,C1203,C1505 | C1203 | 392 | 178 | ivfnepFyf | ivfnepLyf |
| ZA6505 | NPHP4 | 1 | 6029314 | C | A | A2501,A2901,B1801,B0705,C1203,C1505 | C1203 | 412 | 1654 | epFyfhtsl | epLyfhtsl |
| ZA6505 | PRAMEF2 | 1 | 12919064 | T | G | A2501,A2901,B1801,B0705,C1203,C1505 | C1203 | 222 | 108 | ftclplGsl | ftclplVsl |
| ZA6505 | ARHGEF19 | 1 | 16534646 | C | G | A2501,A2901,B1801,B0705,C1203,C1505 | C1203 | 116 | 85 | vflepRqvv | vflepGqvv |
| ZA6505 | ZNF683 | 1 | 26691030 | T | C | A2501,A2901,B1801,B0705,C1203,C1505 | C1203 | 250 | 702 | ksfgqlsSl | ksfgqlsNl |
| ZA6505 | FAAH | 1 | 46860048 | C | A | A2501,A2901,B1801,B0705,C1203,C1505 | B1801 | 56 | 113 | yelwaaMpg | yelwaaLpg |
| ZA6505 | FAAH | 1 | 46860048 | C | A | A2501,A2901,B1801,B0705,C1203,C1505 | C1203 | 45 | 48 | vqyelwaaM | vqyelwaaL |
| ZA6505 | FAAH | 1 | 46860048 | C | A | A2501,A2901,B1801,B0705,C1203,C1505 | C1203 | 96 | 147 | aaMpgasgv | aaLpgasgv |
| ZA6505 | WDR63 | 1 | 85594466 | G | A | A2501,A2901,B1801,B0705,C1203,C1505 | B1801 | 398 | 1399 | leipwtlsH | leipwtlsR |
| ZA6505 | WDR63 | 1 | 85594466 | G | A | A2501,A2901,B1801,B0705,C1203,C1505 | C1203 | 79 | 125 | lsHpstnem | lsRpstnem |
| ZA6505 | EVI5 | 1 | 93142746 | G | A | A2501,A2901,B1801,B0705,C1203,C1505 | C1203 | 485 | 446 | yttikMkem | yttikTkem |
| ZA6505 | DPYD | 1 | 98165091 | T | C | A2501,A2901,B1801,B0705,C1203,C1505 | C1203 | 5 | 7 | fatevfkaV | fatevfkaM |
| ZA6505 | DENND2C | 1 | 115168440 | T | G | A2501,A2901,B1801,B0705,C1203,C1505 | C1203 | 425 | 107 | vrynchqeL | vrynchqel |

Figure 21 (Cont.)

| | | | | | | | | | | | |
|---|---|---|---|---|---|---|---|---|---|---|---|
| ZA6505 | CASQ2 | 1 | 116280896 | T | C | A2501,A2901,B1801,B0705,C1203,C1505 | C1203 | 15 | 16 | qaferVedy | qaferIedy |
| ZA6505 | CASQ2 | 1 | 116280896 | T | C | A2501,A2901,B1801,B0705,C1203,C1505 | C1203 | 114 | 222 | rVedyikli | rIedyikli |
| ZA6505 | ABL2 | 1 | 179112145 | C | G | A2501,A2901,B1801,B0705,C1203,C1505 | C1203 | 172 | 846 | tvllppnTy | tvllppnSy |
| ZA6505 | C1orf27 | 1 | 186375305 | A | G | A2501,A2901,B1801,B0705,C1203,C1505 | C1203 | 300 | 121 | fdGesaeei | fdDesaeei |
| ZA6505 | SLC41A1 | 1 | 205764054 | G | A | A2501,A2901,B1801,B0705,C1203,C1505 | C1203 | 298 | 3378 | Yttltlifi | Httltlifi |
| ZA6505 | RPS6KC1 | 1 | 213414543 | A | G | A2501,A2901,B1801,B0705,C1203,C1505 | B1801 | 174 | 1384 | helkffpSd | helkffpNd |
| ZA6505 | RPS6KC1 | 1 | 213414543 | A | G | A2501,A2901,B1801,B0705,C1203,C1505 | C1203 | 15 | 12 | fpSddpeav | fpNddpeav |
| ZA6505 | CAPN2 | 1 | 223900469 | G | A | A2501,A2901,B1801,B0705,C1203,C1505 | B1801 | 82 | 274 | necleaRtl | necleaGtl |
| ZA6505 | OR2T27 | 1 | 248813483 | C | G | A2501,A2901,B1801,B0705,C1203,C1505 | C1203 | 81 | 61 | eaegrRkav | eaegrGkav |
| ZA6505 | DCLRE1C | 10 | 14976727 | G | C | A2501,A2901,B1801,B0705,C1203,C1505 | C1203 | 188 | 63 | fcdRrfyqi | fcdPrfyqi |
| ZA6505 | TACR2 | 10 | 71176012 | A | G | A2501,A2901,B1801,B0705,C1203,C1505 | A2501 | 258 | 3097 | Ttafsmpsw | Itafsmpsw |
| ZA6505 | R3HCC1L | 10 | 99969498 | G | C | A2501,A2901,B1801,B0705,C1203,C1505 | B1801 | 45 | 38 | iefgLsfpd | iefgVsfpd |
| ZA6505 | CUZD1 | 10 | 124591832 | G | A | A2501,A2901,B1801,B0705,C1203,C1505 | C1203 | 172 | 286 | Wadykyqkl | Radykyqkl |
| ZA6505 | ADAM12 | 10 | 128019025 | C | G | A2501,A2901,B1801,B0705,C1203,C1505 | C1203 | 299 | 1869 | Rsgdlwipv | Gsgdlwipv |
| ZA6505 | MUC6 | 11 | 1013953 | C | T | A2501,A2901,B1801,B0705,C1203,C1505 | B1801 | 253 | 21783 | qeeitfkgY | qeeitfkgC |
| ZA6505 | MUC6 | 11 | 1013953 | C | T | A2501,A2901,B1801,B0705,C1203,C1505 | C1203 | 149 | 2399 | kgYmanvtv | kgCmanvtv |
| ZA6505 | MUC6 | 11 | 1013953 | C | T | A2501,A2901,B1801,B0705,C1203,C1505 | C1203 | 365 | 11081 | Ymanvtvtr | Cmanvtvtr |
| ZA6505 | CNGA4 | 11 | 6262909 | G | A | A2501,A2901,B1801,B0705,C1203,C1505 | C1203 | 412 | 259 | iiQegqlav | iiRegqlav |
| ZA6505 | NR1H3 | 11 | 47281345 | C | G | A2501,A2901,B1801,B0705,C1203,C1505 | C1203 | 156 | 316 | ippdCavel | ippdSavel |
| ZA6505 | MYBPC3 | 11 | 47372097 | G | T | A2501,A2901,B1801,B0705,C1203,C1505 | C1203 | 317 | 467 | eaQapaael | eaPapaael |
| ZA6505 | OR4D6 | 11 | 59224608 | A | G | A2501,A2901,B1801,B0705,C1203,C1505 | B1801 | 278 | 29 | cesrlhtpV | cesrlhtpM |
| ZA6505 | PGM2L1 | 11 | 74047743 | T | A | A2501,A2901,B1801,B0705,C1203,C1505 | C1203 | 287 | 23506 | klidalieI | klidalieN |

Figure 21 (Cont.)

| | | | | | | | | | | | |
|---|---|---|---|---|---|---|---|---|---|---|---|
| ZA6505 | ARRB1 | 11 | 74998418 | A | G | A2501,A2901,B1801,B0705,C1203,C1505 | C1203 | 243 | 339 | kaspngkPt | kaspngkLt |
| ZA6505 | MMP27 | 11 | 102576375 | G | A | A2501,A2901,B1801,B0705,C1203,C1505 | B1801 | 235 | 1024 | Meneenmql | Teneenmql |
| ZA6505 | MMP27 | 11 | 102576375 | G | A | A2501,A2901,B1801,B0705,C1203,C1505 | C1203 | 7 | 73 | safplvrmM | safplvrmT |
| ZA6505 | MMP27 | 11 | 102576375 | G | A | A2501,A2901,B1801,B0705,C1203,C1505 | C1203 | 305 | 1355 | rmMeneenm | rmTeneenm |
| ZA6505 | KLRC4-KLRK1 | 12 | 10532326 | T | C | A2501,A2901,B1801,B0705,C1203,C1505 | C1203 | 462 | 91 | irfiimvAi | irfiimvTi |
| ZA6505 | KLRC4-KLRK1 | 12 | 10532326 | T | C | A2501,A2901,B1801,B0705,C1203,C1505 | C1203 | 159 | 354 | imvAiwsav | imvTiwsav |
| ZA6505 | KLRC4-KLRK1 | 12 | 10532326 | T | C | A2501,A2901,B1801,B0705,C1203,C1505 | C1203 | 202 | 3304 | vAiwsavfl | vTiwsavfl |
| ZA6505 | KLRC4 | 12 | 10560957 | T | C | A2501,A2901,B1801,B0705,C1203,C1505 | C1203 | 445 | 2784 | nSfslnrrm | nNfslnrrm |
| ZA6505 | OVCH1 | 12 | 29596365 | T | C | A2501,A2901,B1801,B0705,C1203,C1505 | C1203 | 8 | 9 | fpmRpttfv | fpmKpttfv |
| ZA6505 | OVCH1 | 12 | 29598292 | G | A | A2501,A2901,B1801,B0705,C1203,C1505 | C1203 | 220 | 130 | mtfmsSgpl | mtfmsPgpl |
| ZA6505 | OVCH1 | 12 | 29598292 | G | A | A2501,A2901,B1801,B0705,C1203,C1505 | C1203 | 154 | 292 | msSgplvrv | msPgplvrv |
| ZA6505 | OVCH1 | 12 | 29617550 | G | A | A2501,A2901,B1801,B0705,C1203,C1505 | A2501 | 377 | 14672 | dialiqlsF | dialiqlsS |
| ZA6505 | OVCH1 | 12 | 29617550 | G | A | A2501,A2901,B1801,B0705,C1203,C1505 | C1203 | 400 | 1365 | iqlsFpley | iqlsSpley |
| ZA6505 | OVCH1 | 12 | 29617550 | G | A | A2501,A2901,B1801,B0705,C1203,C1505 | C1203 | 6 | 90 | Fpleynsvv | Spleynsvv |
| ZA6505 | OR10AD1 | 12 | 48596241 | A | G | A2501,A2901,B1801,B0705,C1203,C1505 | C1203 | 21 | 35 | kpfsllHti | kpfsllYti |
| ZA6505 | ZFC3H1 | 12 | 72008421 | T | C | A2501,A2901,B1801,B0705,C1203,C1505 | B1801 | 467 | 141 | qefRfftdl | qefKfftdl |
| ZA6505 | APAF1 | 12 | 99061365 | C | G | A2501,A2901,B1801,B0705,C1203,C1505 | B1801 | 24 | 65 | dqeEcmywy | dqeDcmywy |
| ZA6505 | APAF1 | 12 | 99061365 | C | G | A2501,A2901,B1801,B0705,C1203,C1505 | B1801 | 22 | 3768 | eEcmywynf | eDcmywynf |
| ZA6505 | UTP20 | 12 | 101685524 | C | T | A2501,A2901,B1801,B0705,C1203,C1505 | C1203 | 349 | 12763 | tffeclqeL | tffeclqeS |
| ZA6505 | UTP20 | 12 | 101685524 | C | T | A2501,A2901,B1801,B0705,C1203,C1505 | C1203 | 380 | 1208 | Llldlhtkv | Slldlhtkv |
| ZA6505 | MYBPC1 | 12 | 102043091 | G | A | A2501,A2901,B1801,B0705,C1203,C1505 | C1203 | 187 | 199 | iKvegkkhi | iRvegkkhi |
| ZA6505 | KIAA1033 | 12 | 105504953 | T | C | A2501,A2901,B1801,B0705,C1203,C1505 | C1203 | 56 | 140 | fleeHtsql | fleeYtsql |
| ZA6505 | TPTE2 | 13 | 20038639 | A | T | A2501,A2901,B1801,B0705,C1203,C1505 | B1801 | 8 | 11 | teriiamsY | teriiamsF |

Figure 21 (Cont.)

| | | | | | | | | | | | |
|---|---|---|---|---|---|---|---|---|---|---|---|
| ZA6505 | TPTE2 | 13 | 20038639 | A | T | A2501,A2901,B1801,B0705,C1203,C1505 | C1203 | 71 | 95 | Ypssgrqsf | Fpssgrqsf |
| ZA6505 | PROSER1 | 13 | 39586979 | G | T | A2501,A2901,B1801,B0705,C1203,C1505 | A2501 | 480 | 852 | svtpalTsf | svtpalPsf |
| ZA6505 | OR4L1 | 14 | 20528250 | G | T | A2501,A2901,B1801,B0705,C1203,C1505 | B1801 | 5 | 10 | tefillVff | tefillGff |
| ZA6505 | OR4L1 | 14 | 20528250 | G | T | A2501,A2901,B1801,B0705,C1203,C1505 | C1203 | 57 | 15367 | lvtefillV | lvtefillG |
| ZA6505 | PARP2 | 14 | 20823052 | G | A | A2501,A2901,B1801,B0705,C1203,C1505 | C1203 | 92 | 110 | ragqhgQal | ragqhgRal |
| ZA6505 | CMA1 | 14 | 24976574 | T | C | A2501,A2901,B1801,B0705,C1203,C1505 | C1203 | 151 | 92 | aaRcagrsi | aaHcagrsi |
| ZA6505 | CMA1 | 14 | 24976574 | T | C | A2501,A2901,B1801,B0705,C1203,C1505 | C1203 | 452 | 395 | Rcagrsitv | Hcagrsitv |
| ZA6505 | FSCB | 14 | 44976050 | C | G | A2501,A2901,B1801,B0705,C1203,C1505 | C1203 | 28 | 19 | ysakayDsi | ysakayEsi |
| ZA6505 | FSCB | 14 | 44976050 | C | G | A2501,A2901,B1801,B0705,C1203,C1505 | C1203 | 55 | 55 | kayDsirvs | kayEsirvs |
| ZA6505 | LGMN | 14 | 93176042 | G | A | A2501,A2901,B1801,B0705,C1203,C1505 | C1203 | 470 | 518 | lMeeiqrhl | lTeeiqrhl |
| ZA6505 | TECPR2 | 14 | 102900798 | T | G | A2501,A2901,B1801,B0705,C1203,C1505 | C1203 | 364 | 787 | ntdpetfKv | ntdpetfNv |
| ZA6505 | TECPR2 | 14 | 102900798 | T | G | A2501,A2901,B1801,B0705,C1203,C1505 | C1203 | 490 | 289 | Kvlevsgsm | Nvlevsgsm |
| ZA6505 | CEP170B | 14 | 105350882 | A | T | A2501,A2901,B1801,B0705,C1203,C1505 | C1203 | 156 | 367 | earkmiVqv | earkmiDqv |
| ZA6505 | CDCA4 | 14 | 105477699 | C | T | A2501,A2901,B1801,B0705,C1203,C1505 | C1203 | 19 | 52 | spyyNldtv | spyyDldtv |
| ZA6505 | OR4M2 | 15 | 22369426 | G | A | A2501,A2901,B1801,B0705,C1203,C1505 | C1203 | 29 | 20 | lifplHnpi | lifplRnpi |
| ZA6505 | OR4M2 | 15 | 22369426 | G | A | A2501,A2901,B1801,B0705,C1203,C1505 | C1203 | 16 | 15 | fplHnpiiy | fplRnpiiy |
| ZA6505 | OR4M2 | 15 | 22369426 | G | A | A2501,A2901,B1801,B0705,C1203,C1505 | C1203 | 393 | 496 | lHnpiiytl | lRnpiiytl |
| ZA6505 | PGBD4 | 15 | 34395256 | T | C | A2501,A2901,B1801,B0705,C1203,C1505 | C1203 | 421 | 1280 | vqkpeleTf | vqkpeleMf |
| ZA6505 | FSIP1 | 15 | 39910431 | A | G | A2501,A2901,B1801,B0705,C1203,C1505 | C1203 | 160 | 228 | nvlestsRl | nvlestsCl |
| ZA6505 | CASC5 | 15 | 40920815 | G | A | A2501,A2901,B1801,B0705,C1203,C1505 | C1203 | 326 | 399 | fstyHssqm | fstyRssqm |
| ZA6505 | PLA2G4E | 15 | 42278176 | T | A | A2501,A2901,B1801,B0705,C1203,C1505 | C1203 | 456 | 783 | Lltesanhl | Qltesanhl |
| ZA6505 | MYZAP | 15 | 57925836 | C | T | A2501,A2901,B1801,B0705,C1203,C1505 | C1203 | 154 | 374 | etnsflkVi | etnsflkAi |

Figure 21 (Cont.)

| | | | | | | | | | | | |
|---|---|---|---|---|---|---|---|---|---|---|---|
| ZA6505 | SLC28A1 | 15 | 85438206 | G | T | A2501,A2901,B1801,B0705,C1203,C1505 | C1203 | 496 | 1498 | lYfqralal | lDfqralal |
| ZA6505 | DNASE1L2 | 16 | 2287391 | C | T | A2501,A2901,B1801,B0705,C1203,C1505 | C1203 | 22 | 649 | fvyrkdavL | fvyrkdavS |
| ZA6505 | DNASE1L2 | 16 | 2287391 | C | T | A2501,A2901,B1801,B0705,C1203,C1505 | C1203 | 18 | 12 | yrkdavLvv | yrkdavSvv |
| ZA6505 | DNASE1L2 | 16 | 2287391 | C | T | A2501,A2901,B1801,B0705,C1203,C1505 | C1203 | 97 | 33 | davLvvdty | davSvvdty |
| ZA6505 | UQCRC2 | 16 | 21976762 | G | A | A2501,A2901,B1801,B0705,C1203,C1505 | C1203 | 219 | 78 | haaayQnal | haaayRnal |
| ZA6505 | UQCRC2 | 16 | 21976762 | G | A | A2501,A2901,B1801,B0705,C1203,C1505 | C1203 | 42 | 210 | yQnalanpl | yRnalanpl |
| ZA6505 | CENPN | 16 | 81060197 | C | T | A2501,A2901,B1801,B0705,C1203,C1505 | B1801 | 158 | 408 | qeIfgdypq | qeTfgdypq |
| ZA6505 | CENPN | 16 | 81060197 | C | T | A2501,A2901,B1801,B0705,C1203,C1505 | C1203 | 339 | 12341 | rvqritqeI | rvqritqeT |
| ZA6505 | CRISPLD2 | 16 | 84906098 | C | G | A2501,A2901,B1801,B0705,C1203,C1505 | C1203 | 425 | 480 | kakifgSlf | kakifgTlf |
| ZA6505 | RNF166 | 16 | 88765393 | C | T | A2501,A2901,B1801,B0705,C1203,C1505 | C1203 | 139 | 184 | Npnrvvcpi | Dpnrvvcpi |
| ZA6505 | ZZEF1 | 17 | 3953102 | A | G | A2501,A2901,B1801,B0705,C1203,C1505 | C1203 | 422 | 1707 | sPedqalpv | sLedqalpv |
| ZA6505 | ATAD5 | 17 | 29167653 | A | C | A2501,A2901,B1801,B0705,C1203,C1505 | C1203 | 17 | 78 | kasntskHi | kasntskNi |
| ZA6505 | COASY | 17 | 40714804 | C | A | A2501,A2901,B1801,B0705,C1203,C1505 | B1801 | 66 | 10992 | legpaqpqY | legpaqpqS |
| ZA6505 | COASY | 17 | 40714804 | C | A | A2501,A2901,B1801,B0705,C1203,C1505 | C1203 | 158 | 154 | paqpqYspv | paqpqSspv |
| ZA6505 | NAGS | 17 | 42083175 | C | A | A2501,A2901,B1801,B0705,C1203,C1505 | C1203 | 31 | 46 | lakRckvlv | lakSckvlv |
| ZA6505 | CA10 | 17 | 49713256 | C | A | A2501,A2901,B1801,B0705,C1203,C1505 | B1801 | 21 | 85 | yetasLiim | yetasWiim |
| ZA6505 | CA10 | 17 | 49713256 | C | A | A2501,A2901,B1801,B0705,C1203,C1505 | C1203 | 253 | 1604 | pcyetasLi | pcyetasWi |
| ZA6505 | CA10 | 17 | 49713256 | C | A | A2501,A2901,B1801,B0705,C1203,C1505 | C1203 | 445 | 343 | yetasLiim | yetasWiim |
| ZA6505 | RNF43 | 17 | 56492800 | T | C | A2501,A2901,B1801,B0705,C1203,C1505 | C1203 | 116 | 153 | rsaeqkaVi | rsaeqkali |
| ZA6505 | RNF43 | 17 | 56492800 | T | C | A2501,A2901,B1801,B0705,C1203,C1505 | C1203 | 146 | 74 | kaVirvipl | kalirvipl |
| ZA6505 | ACE | 17 | 61554619 | C | T | A2501,A2901,B1801,B0705,C1203,C1505 | C1203 | 67 | 841 | ynFsaeqvl | ynSsaeqvl |
| ZA6505 | SLC16A5 | 17 | 73089923 | C | G | A2501,A2901,B1801,B0705,C1203,C1505 | C1203 | 245 | 170 | Qmagplcsi | Hmagplcsi |
| ZA6505 | CIDEA | 18 | 12254405 | C | T | A2501,A2901,B1801,B0705,C1203,C1505 | C1203 | 203 | 376 | aardyVgal | aardyAgal |

Figure 21 (Cont.)

| | | | | | | | | | | | |
|---|---|---|---|---|---|---|---|---|---|---|---|
| ZA6505 | CIDEA | 18 | 12254405 | C | T | A2501,A2901,B1801,B0705,C1203,C1505 | C1203 | 107 | 18 | yVgalirpl | yAgalirpl |
| ZA6505 | TAF4B | 18 | 23866185 | G | C | A2501,A2901,B1801,B0705,C1203,C1505 | C1203 | 276 | 137 | tskplLtsv | tskplVtsv |
| ZA6505 | TAF4B | 18 | 23866185 | G | C | A2501,A2901,B1801,B0705,C1203,C1505 | C1203 | 275 | 99 | lLtsvantv | lVtsvantv |
| ZA6505 | SETBP1 | 18 | 42532606 | G | A | A2501,A2901,B1801,B0705,C1203,C1505 | C1203 | 344 | 403 | pqfhtnshl | pqfhtnshV |
| ZA6505 | CTDP1 | 18 | 77475447 | C | A | A2501,A2901,B1801,B0705,C1203,C1505 | B1801 | 317 | 978 | rehyhataM | rehyhataL |
| ZA6505 | CTDP1 | 18 | 77475447 | C | A | A2501,A2901,B1801,B0705,C1203,C1505 | C1203 | 49 | 48 | hataMgaki | hataLgaki |
| ZA6505 | SIRT6 | 19 | 4179173 | T | A | A2501,A2901,B1801,B0705,C1203,C1505 | C1203 | 31 | 39 | malvqlVrv | malvqlErv |
| ZA6505 | KHSRP | 19 | 6422423 | C | A | A2501,A2901,B1801,B0705,C1203,C1505 | C1203 | 326 | 320 | iggdSattv | iggdAattv |
| ZA6505 | PNPLA6 | 19 | 7621349 | C | T | A2501,A2901,B1801,B0705,C1203,C1505 | B1801 | 475 | 3813 | rewaksmtL | rewaksmtS |
| ZA6505 | PNPLA6 | 19 | 7621349 | C | T | A2501,A2901,B1801,B0705,C1203,C1505 | C1203 | 74 | 48 | waksmtLvl | waksmtSvl |
| ZA6505 | PNPLA6 | 19 | 7621349 | C | T | A2501,A2901,B1801,B0705,C1203,C1505 | C1203 | 368 | 1126 | Lvlepvldl | Svlepvldl |
| ZA6505 | MUC16 | 19 | 9048362 | A | G | A2501,A2901,B1801,B0705,C1203,C1505 | C1203 | 63 | 559 | tAspgvsgv | tVspgvsgv |
| ZA6505 | FARSA | 19 | 13035722 | T | C | A2501,A2901,B1801,B0705,C1203,C1505 | C1203 | 485 | 1581 | yrlaRkkpf | yrlaQkkpf |
| ZA6505 | NOTCH3 | 19 | 15291638 | G | A | A2501,A2901,B1801,B0705,C1203,C1505 | C1203 | 93 | 37 | ftgpqcqMl | ftgpqcqTl |
| ZA6505 | USHBP1 | 19 | 17367435 | T | C | A2501,A2901,B1801,B0705,C1203,C1505 | C1203 | 242 | 656 | rlqerrslV | rlqerrslM |
| ZA6505 | ZNF681 | 19 | 23927555 | G | A | A2501,A2901,B1801,B0705,C1203,C1505 | C1203 | 4 | 5 | kafnlLshi | kafnlSshi |
| ZA6505 | ZNF681 | 19 | 23927555 | G | A | A2501,A2901,B1801,B0705,C1203,C1505 | C1203 | 190 | 688 | Lshitthti | Sshitthti |
| ZA6505 | PPP1R13L | 19 | 45898900 | C | A | A2501,A2901,B1801,B0705,C1203,C1505 | B1801 | 29 | 8 | Lehgasram | Wehgasram |
| ZA6505 | DHDH | 19 | 49439409 | A | G | A2501,A2901,B1801,B0705,C1203,C1505 | C1203 | 13 | 11 | naaevrGmv | naaevrEmv |
| ZA6505 | FPR1 | 19 | 52249947 | C | G | A2501,A2901,B1801,B0705,C1203,C1505 | C1203 | 34 | 19 | flckfLfti | flckfVfti |
| ZA6505 | KIR3DL1 | 19 | 55331308 | C | A | A2501,A2901,B1801,B0705,C1203,C1505 | C1203 | 43 | 54 | iskdpsSlv | iskdpsRlv |
| ZA6505 | NLRP4 | 19 | 56373462 | G | A | A2501,A2901,B1801,B0705,C1203,C1505 | C1203 | 95 | 120 | lsHddirsl | lsRddirsl |

Figure 21 (Cont.)

| | | | | | | | | | | | |
|---|---|---|---|---|---|---|---|---|---|---|---|
| ZA6505 | LPIN1 | 2 | 11927238 | G | A | A2501,A2901,B1801,B0705,C1203,C1505 | C1203 | 101 | 224 | qfMdnpaii | qfVdnpaii |
| ZA6505 | APOB | 2 | 21263900 | G | A | A2501,A2901,B1801,B0705,C1203,C1505 | C1203 | 133 | 8209 | filktsqcl | filktsqcT |
| ZA6505 | KHK | 2 | 27315252 | G | A | A2501,A2901,B1801,B0705,C1203,C1505 | C1203 | 61 | 53 | nasnsctll | nasnsctVl |
| ZA6505 | DHX57 | 2 | 39088323 | G | A | A2501,A2901,B1801,B0705,C1203,C1505 | C1203 | 389 | 11025 | etsepvvyF | etsepvvyS |
| ZA6505 | DHX57 | 2 | 39088323 | G | A | A2501,A2901,B1801,B0705,C1203,C1505 | C1203 | 189 | 91 | vvyFlitll | vvySlitll |
| ZA6505 | PLEKHH2 | 2 | 43989525 | C | G | A2501,A2901,B1801,B0705,C1203,C1505 | C1203 | 26 | 40 | leynCmrli | leynSmrli |
| ZA6505 | ZNF638 | 2 | 71654175 | G | A | A2501,A2901,B1801,B0705,C1203,C1505 | C1203 | 178 | 191 | qMpedpstl | qVpedpstl |
| ZA6505 | ZNF638 | 2 | 71654175 | G | A | A2501,A2901,B1801,B0705,C1203,C1505 | C1203 | 47 | 105 | Mpedpstlv | Vpedpstlv |
| ZA6505 | REG1B | 2 | 79313990 | C | T | A2501,A2901,B1801,B0705,C1203,C1505 | C1203 | 11 | 11 | nayHsycyy | nayRsycyy |
| ZA6505 | RMND5A | 2 | 86947816 | G | A | A2501,A2901,B1801,B0705,C1203,C1505 | B1801 | 378 | 544 | veHelekvl | veRelekvl |
| ZA6505 | TMEM87B | 2 | 112854816 | T | C | A2501,A2901,B1801,B0705,C1203,C1505 | C1203 | 37 | 48 | favlasTvf | favlasIvf |
| ZA6505 | NBEAL1 | 2 | 204073414 | A | G | A2501,A2901,B1801,B0705,C1203,C1505 | C1203 | 30 | 24 | ilyghAnev | ilyghTnev |
| ZA6505 | STK36 | 2 | 219562675 | G | A | A2501,A2901,B1801,B0705,C1203,C1505 | C1203 | 406 | 406 | dadlliDvl | dadlliGvl |
| ZA6505 | GGT7 | 20 | 33447807 | A | T | A2501,A2901,B1801,B0705,C1203,C1505 | C1203 | 447 | 185 | Eaqdgfnvt | Vaqdgfnvt |
| ZA6505 | SETD4 | 21 | 37416085 | G | A | A2501,A2901,B1801,B0705,C1203,C1505 | C1203 | 206 | 6537 | nphacvyvL | nphacvyvS |
| ZA6505 | SETD4 | 21 | 37416085 | G | A | A2501,A2901,B1801,B0705,C1203,C1505 | C1203 | 28 | 35 | yvLrgwnql | yvSrgwnql |
| ZA6505 | PRAME | 22 | 22892449 | T | C | A2501,A2901,B1801,B0705,C1203,C1505 | C1203 | 46 | 20 | Vpmqdikmi | Mpmqdikmi |
| ZA6505 | RFPL3 | 22 | 32756703 | C | T | A2501,A2901,B1801,B0705,C1203,C1505 | C1203 | 154 | 115 | saeeplCpf | saeeplRpf |
| ZA6505 | SH3BP1 | 22 | 38051291 | C | A | A2501,A2901,B1801,B0705,C1203,C1505 | C1203 | 177 | 91 | rpEparptm | rpAparptm |
| ZA6505 | CAPN7 | 3 | 15259992 | G | A | A2501,A2901,B1801,B0705,C1203,C1505 | C1203 | 24 | 30 | tsyetTdkv | tsyetAdkv |
| ZA6505 | PDCD6IP | 3 | 33879770 | G | A | A2501,A2901,B1801,B0705,C1203,C1505 | C1203 | 235 | 295 | ynqrkadll | ynqrkadlV |
| ZA6505 | PDCD6IP | 3 | 33879770 | G | A | A2501,A2901,B1801,B0705,C1203,C1505 | C1203 | 178 | 217 | kadllnrsi | kadlVnrsi |
| ZA6505 | LZTFL1 | 3 | 45869972 | C | T | A2501,A2901,B1801,B0705,C1203,C1505 | C1203 | 277 | 910 | latakhNll | latakhDll |

Figure 21 (Cont.)

| | | | | | | | | | | | |
|---|---|---|---|---|---|---|---|---|---|---|---|
| ZA6505 | LZTFL1 | 3 | 45869972 | C | T | A2501,A2901,B1801,B0705,C1203,C1505 | C1203 | 43 | 139 | takhNllrv | takhDllrv |
| ZA6505 | NBEAL2 | 3 | 47040352 | A | G | A2501,A2901,B1801,B0705,C1203,C1505 | C1203 | 114 | 1678 | aAgddggav | aTgddggav |
| ZA6505 | SETD2 | 3 | 47162683 | G | A | A2501,A2901,B1801,B0705,C1203,C1505 | C1203 | 184 | 90 | ftqFsrkqi | ftqSsrkqi |
| ZA6505 | DALRD3 | 3 | 49055483 | T | C | A2501,A2901,B1801,B0705,C1203,C1505 | C1203 | 172 | 157 | vadRlaral | vadHlaral |
| ZA6505 | PXK | 3 | 58395863 | A | G | A2501,A2901,B1801,B0705,C1203,C1505 | C1203 | 329 | 193 | nseehsaRy | nseehsaKy |
| ZA6505 | FAM194A | 3 | 150377770 | A | C | A2501,A2901,B1801,B0705,C1203,C1505 | C1203 | 233 | 515 | ylssRslkl | ylssLslkl |
| ZA6505 | FAM194A | 3 | 150377770 | A | C | A2501,A2901,B1801,B0705,C1203,C1505 | C1203 | 362 | 1476 | lssRslkli | lssLslkli |
| ZA6505 | TACC3 | 4 | 1729953 | G | A | A2501,A2901,B1801,B0705,C1203,C1505 | C1203 | 467 | 201 | ealgYpagv | ealgCpagv |
| ZA6505 | TACC3 | 4 | 1729953 | G | A | A2501,A2901,B1801,B0705,C1203,C1505 | C1203 | 18 | 915 | Ypagvgtpv | Cpagvgtpv |
| ZA6505 | CC2D2A | 4 | 15517557 | C | T | A2501,A2901,B1801,B0705,C1203,C1505 | C1203 | 49 | 2016 | flledeglyl | fledeglyT |
| ZA6505 | AASDH | 4 | 57204777 | A | C | A2501,A2901,B1801,B0705,C1203,C1505 | C1203 | 358 | 161 | fafhnDngs | fafhnYngs |
| ZA6505 | ADH7 | 4 | 100349669 | C | G | A2501,A2901,B1801,B0705,C1203,C1505 | C1203 | 411 | 3348 | ivesigeAv | ivesigeGv |
| ZA6505 | ADH7 | 4 | 100349669 | C | G | A2501,A2901,B1801,B0705,C1203,C1505 | C1203 | 206 | 111 | sigeAvttv | sigeGvttv |
| ZA6505 | TET2 | 4 | 106158539 | G | A | A2501,A2901,B1801,B0705,C1203,C1505 | C1203 | 84 | 469 | Dvypelanl | Gvypelanl |
| ZA6505 | MAP9 | 4 | 156289917 | G | A | A2501,A2901,B1801,B0705,C1203,C1505 | C1203 | 79 | 82 | kpspWprsm | kpspRprsm |
| ZA6505 | SDHA | 5 | 256509 | G | A | A2501,A2901,B1801,B0705,C1203,C1505 | A2501 | 153 | 86 | tIppairsy | tVppairsy |
| ZA6505 | CDH10 | 5 | 24535931 | C | A | A2501,A2901,B1801,B0705,C1203,C1505 | C1203 | 485 | 24267 | svpemsvvV | svpemsvvG |
| ZA6505 | CDH10 | 5 | 24535931 | C | A | A2501,A2901,B1801,B0705,C1203,C1505 | C1203 | 146 | 64 | msvvVtsvv | msvvGtsvv |
| ZA6505 | AMACR | 5 | 34008100 | C | T | A2501,A2901,B1801,B0705,C1203,C1505 | C1203 | 8 | 5 | malggisvM | malggisvV |
| ZA6505 | RAI14 | 5 | 34823487 | G | A | A2501,A2901,B1801,B0705,C1203,C1505 | C1203 | 59 | 100 | Ksmdnyshf | Esmdnyshf |
| ZA6505 | IL7R | 5 | 35861068 | T | C | A2501,A2901,B1801,B0705,C1203,C1505 | C1203 | 132 | 459 | fedpdvnTt | fedpdvnlt |
| ZA6505 | IL7R | 5 | 35871190 | G | A | A2501,A2901,B1801,B0705,C1203,C1505 | C1203 | 213 | 273 | eapfdlsvl | eapfdlsvV |

Figure 21 (Cont.)

| | | | | | | | | | | | |
|---|---|---|---|---|---|---|---|---|---|---|---|
| ZA6505 | IL7R | 5 | 35871190 | G | A | A2501,A2901,B1801,B0705,C1203,C1505 | C1203 | 163 | 147 | apfdlsvly | apfdlsvVy |
| ZA6505 | PTGER4 | 5 | 40691893 | G | A | A2501,A2901,B1801,B0705,C1203,C1505 | C1203 | 223 | 245 | iplvvrvfl | iplvvrvfV |
| ZA6505 | FBXO4 | 5 | 41934413 | A | C | A2501,A2901,B1801,B0705,C1203,C1505 | C1203 | 274 | 106 | naeahksQy | naeahksKy |
| ZA6505 | LARS | 5 | 145499996 | C | T | A2501,A2901,B1801,B0705,C1203,C1505 | C1203 | 382 | 284 | Kqgdncdsi | Rqgdncdsi |
| ZA6505 | LARS | 5 | 145508636 | T | C | A2501,A2901,B1801,B0705,C1203,C1505 | B1801 | 14 | 29 | Devlihssq | Nevlihssq |
| ZA6505 | LARS | 5 | 145508636 | T | C | A2501,A2901,B1801,B0705,C1203,C1505 | C1203 | 205 | 107 | vagpvDevl | vagpvNevl |
| ZA6505 | BTN3A3 | 6 | 26448862 | C | T | A2501,A2901,B1801,B0705,C1203,C1505 | C1203 | 165 | 2358 | Fkwrkiqym | Lkwrkiqym |
| ZA6505 | HIST1H2BM | 6 | 27782940 | T | C | A2501,A2901,B1801,B0705,C1203,C1505 | B1801 | 30 | 13 | kesysAyvy | kesysVyvy |
| ZA6505 | HIST1H2BM | 6 | 27782940 | T | C | A2501,A2901,B1801,B0705,C1203,C1505 | C1203 | 75 | 93 | ysAyvykvl | ysVyvykvl |
| ZA6505 | NUDCD3 | 7 | 44530039 | G | T | A2501,A2901,B1801,B0705,C1203,C1505 | C1203 | 243 | 182 | fQpgaaqal | fPpgaaqal |
| ZA6505 | PLXNA4 | 7 | 131883311 | C | T | A2501,A2901,B1801,B0705,C1203,C1505 | B1801 | 407 | 315 | lefrdiTsh | lefrdiAsh |
| ZA6505 | PLXNA4 | 7 | 131883311 | C | T | A2501,A2901,B1801,B0705,C1203,C1505 | C1203 | 465 | 623 | efrdiTshv | efrdiAshv |
| ZA6505 | OR2A2 | 7 | 143807304 | T | C | A2501,A2901,B1801,B0705,C1203,C1505 | C1203 | 79 | 58 | fvlvgpPsl | fvlvgpLsl |
| ZA6505 | OR2A2 | 7 | 143807304 | T | C | A2501,A2901,B1801,B0705,C1203,C1505 | C1203 | 417 | 624 | vlvgpPsli | vlvgpLsli |
| ZA6505 | OR2A2 | 7 | 143807304 | T | C | A2501,A2901,B1801,B0705,C1203,C1505 | C1203 | 413 | 1194 | lvgpPslil | lvgpLslil |
| ZA6505 | RP1L1 | 8 | 10464604 | T | C | A2501,A2901,B1801,B0705,C1203,C1505 | C1203 | 186 | 170 | Raerkatrm | Haerkatrm |
| ZA6505 | LONRF1 | 8 | 12600720 | T | A | A2501,A2901,B1801,B0705,C1203,C1505 | B1801 | 192 | 209 | Ledlnavlf | iedlnavlf |
| ZA6505 | LONRF1 | 8 | 12600720 | T | A | A2501,A2901,B1801,B0705,C1203,C1505 | C1203 | 22 | 24 | aaLedlnav | aaiedlnav |
| ZA6505 | MTUS1 | 8 | 17541943 | T | G | A2501,A2901,B1801,B0705,C1203,C1505 | A2501 | 380 | 18926 | tTcenqsgf | tKcenqsgf |
| ZA6505 | LRRCC1 | 8 | 86021994 | G | A | A2501,A2901,B1801,B0705,C1203,C1505 | C1203 | 146 | 8510 | Ytlnlscnl | Ctlnlscnl |
| ZA6505 | CA13 | 8 | 86180719 | A | G | A2501,A2901,B1801,B0705,C1203,C1505 | C1203 | 19 | 252 | fAnfdllsl | fTnfdllsl |
| ZA6505 | DMRT3 | 9 | 990653 | G | T | A2501,A2901,B1801,B0705,C1203,C1505 | C1203 | 115 | 20984 | nvvpsplaV | nvvpsplaG |
| ZA6505 | DMRT3 | 9 | 990653 | G | T | A2501,A2901,B1801,B0705,C1203,C1505 | C1203 | 363 | 699 | vpsplaVpl | vpsplaGpl |

Figure 21 (Cont.)

| | | | | | | | | | | | |
|---|---|---|---|---|---|---|---|---|---|---|---|
| ZA6505 | DMRT3 | 9 | 990653 | G | T | A2501,A2901,B1801,B0705,C1203,C1505 | C1203 | 448 | 1221 | laVplqppf | laGplqppf |
| ZA6505 | NOL6 | 9 | 33464897 | T | C | A2501,A2901,B1801,B0705,C1203,C1505 | C1203 | 45 | 384 | vSlnneltv | vNlnneltv |
| ZA6505 | UBAP2 | 9 | 33941759 | T | C | A2501,A2901,B1801,B0705,C1203,C1505 | C1203 | 496 | 194 | sslSsaspv | sslNsaspv |
| ZA6505 | WNK2 | 9 | 96055065 | T | C | A2501,A2901,B1801,B0705,C1203,C1505 | C1203 | 20 | 18 | ysappdAyl | ysappdVyl |
| ZA6505 | WDR34 | 9 | 131397004 | C | A | A2501,A2901,B1801,B0705,C1203,C1505 | C1203 | 330 | 653 | tfsphgVpi | tfsphgGpi |
| ZA6505 | WDR34 | 9 | 131397004 | C | A | A2501,A2901,B1801,B0705,C1203,C1505 | C1203 | 52 | 58 | fsphgVpiy | fsphgGpiy |
| ZA6505 | SETX | 9 | 135202829 | T | C | A2501,A2901,B1801,B0705,C1203,C1505 | C1203 | 188 | 257 | taqnsdVfv | taqnsdIfv |
| ZA6505 | CAMSAP1 | 9 | 138715080 | G | A | A2501,A2901,B1801,B0705,C1203,C1505 | C1203 | 327 | 7780 | pasqptpfV | pasqptpfA |
| ZA6505 | CAMSAP1 | 9 | 138715080 | G | A | A2501,A2901,B1801,B0705,C1203,C1505 | C1203 | 420 | 45 | fVlhhaasc | fAlhhaasc |
| ZA6505 | CXorf58 | X | 23928489 | C | T | A2501,A2901,B1801,B0705,C1203,C1505 | C1203 | 321 | 206 | rslqkvCrv | rslqkvRrv |
| ZA6505 | CENPI | X | 100387411 | C | T | A2501,A2901,B1801,B0705,C1203,C1505 | C1203 | 94 | 112 | llfdhlVql | llfdhlAql |
| ZA6505 | CENPI | X | 100387411 | C | T | A2501,A2901,B1801,B0705,C1203,C1505 | C1203 | 36 | 197 | Vqlfftsti | Aqlfftsti |
| ZA6505 | CNGA2 | X | 150909307 | G | T | A2501,A2901,B1801,B0705,C1203,C1505 | C1203 | 66 | 539 | fvldpagdL | fvldpagdW |
| ZA6505 | CNGA2 | X | 150909307 | G | T | A2501,A2901,B1801,B0705,C1203,C1505 | C1203 | 85 | 530 | dLyycwlfv | dWyycwlfv |
| ZA6505 | CNGA2 | X | 150909307 | G | T | A2501,A2901,B1801,B0705,C1203,C1505 | C1203 | 54 | 48 | Lyycwlfvi | Wyycwlfvi |
| ZA6965 | TNFRSF4 | 1 | 1149437 | C | A | A0201,A3201,A0289,B400102,B450101,C0602,C0304 | A0201 | 308 | 7101 | lllIglgll | lllIglglS |
| ZA6965 | TNFRSF4 | 1 | 1149437 | C | A | A0201,A3201,A0289,B400102,B450101,C0602,C0304 | A0201 | 33 | 51 | llglglltv | llglglStv |
| ZA6965 | TNFRSF4 | 1 | 1149437 | C | A | A0201,A3201,A0289,B400102,B450101,C0602,C0304 | A0201 | 241 | 228 | ltvtglhcv | Stvtglhcv |
| ZA6965 | FAM132A | 1 | 1178871 | G | A | A0201,A3201,A0289,B400102,B450101,C0602,C0304 | A0201 | 88 | 83 | slasgrfMa | slasgrfTa |
| ZA6965 | ATAD3C | 1 | 1398059 | A | G | A0201,A3201,A0289,B400102,B450101,C0602,C0304 | A3201 | 137 | 5 | Eiaqlavsw | Kiaqlavsw |
| ZA6965 | CSMD2 | 1 | 34099082 | C | A | A0201,A3201,A0289,B400102,B450101,C0602,C0304 | C0602 | 332 | 1496 | Fhdghsqhs | Vhdghsqhs |
| ZA6965 | CLDN19 | 1 | 43205676 | C | A | A0201,A3201,A0289,B400102,B450101,C0602,C0304 | A0201 | 6 | 4889 | flalggwvV | flalggwvG |

Figure 21 (Cont.)

| | | | | | | | | | | | |
|---|---|---|---|---|---|---|---|---|---|---|---|
| ZA6965 | CLDN19 | 1 | 43205676 | C | A | A0201,A3201,A0289,B400102,B450101,C0602,C0304 | A0201 | 72 | 581 | alggwvVii | alggwvGii |
| ZA6965 | CLDN19 | 1 | 43205676 | C | A | A0201,A3201,A0289,B400102,B450101,C0602,C0304 | A3201 | 134 | 2708 | alggwvVii | alggwvGii |
| ZA6965 | RUSC1 | 1 | 155295182 | G | A | A0201,A3201,A0289,B400102,B450101,C0602,C0304 | A0201 | 48 | 60 | tlcpalhTl | tlcpalhAl |
| ZA6965 | CD1C | 1 | 158261944 | G | T | A0201,A3201,A0289,B400102,B450101,C0602,C0304 | A0201 | 340 | 458 | kspegffHv | kspegffQv |
| ZA6965 | CCSAP | 1 | 229478067 | C | A | A0201,A3201,A0289,B400102,B450101,C0602,C0304 | A0201 | 34 | 12 | wlLddwgpa | wlWddwgpa |
| ZA6965 | OR2T33 | 1 | 248436275 | G | T | A0201,A3201,A0289,B400102,B450101,C0602,C0304 | C0602 | 236 | 555 | fytmftHll | fytmftPll |
| ZA6965 | SORCS1 | 10 | 108380233 | G | T | A0201,A3201,A0289,B400102,B450101,C0602,C0304 | A3201 | 10 | 79 | Kvgtltyvw | Qvgtltyvw |
| ZA6965 | B4GALNT4 | 11 | 379558 | C | A | A0201,A3201,A0289,B400102,B450101,C0602,C0304 | A0201 | 330 | 54 | yvflrlQga | yvflrlPga |
| ZA6965 | OR4C12 | 11 | 50003420 | T | A | A0201,A3201,A0289,B400102,B450101,C0602,C0304 | A0201 | 29 | 66 | ficFlnfli | ficLlnfli |
| ZA6965 | OR4C12 | 11 | 50003420 | T | A | A0201,A3201,A0289,B400102,B450101,C0602,C0304 | A0201 | 8 | 31 | Flnflilvv | Llnflilvv |
| ZA6965 | CDC42BPG | 11 | 64601934 | G | T | A0201,A3201,A0289,B400102,B450101,C0602,C0304 | A0201 | 169 | 29 | glqerlKqv | glqerlTqv |
| ZA6965 | OVOL1 | 11 | 65562807 | C | G | A0201,A3201,A0289,B400102,B450101,C0602,C0304 | A0201 | 7 | 14 | sllqgsphV | sllqgsphL |
| ZA6965 | ANKRD13D | 11 | 67069775 | T | C | A0201,A3201,A0289,B400102,B450101,C0602,C0304 | A3201 | 256 | 517 | rTlqlslte | rIlqlslte |
| ZA6965 | HOXC9 | 12 | 54394403 | G | A | A0201,A3201,A0289,B400102,B450101,C0602,C0304 | A0201 | 8 | 17 | ymyDspgel | ymyGspgel |
| ZA6965 | HOXC9 | 12 | 54394403 | G | A | A0201,A3201,A0289,B400102,B450101,C0602,C0304 | C0602 | 144 | 358 | ymyDspgel | ymyGspgel |
| ZA6965 | ZFC3H1 | 12 | 72008629 | T | C | A0201,A3201,A0289,B400102,B450101,C0602,C0304 | C0602 | 11 | 11 | mrcdivRki | mrcdivQki |
| ZA6965 | DRAM1 | 12 | 102271640 | A | T | A0201,A3201,A0289,B400102,B450101,C0602,C0304 | A0201 | 216 | 103 | saafiFsyv | saafilsyv |
| ZA6965 | DRAM1 | 12 | 102271640 | A | T | A0201,A3201,A0289,B400102,B450101,C0602,C0304 | A0201 | 233 | 421 | aafiFsyvv | aafilsyvv |
| ZA6965 | DRAM1 | 12 | 102271640 | A | T | A0201,A3201,A0289,B400102,B450101,C0602,C0304 | A0201 | 3 | 3 | fiFsyvvav | filsyvvav |
| ZA6965 | DRAM1 | 12 | 102271640 | A | T | A0201,A3201,A0289,B400102,B450101,C0602,C0304 | A3201 | 217 | 515 | ssaafiFsy | ssaafilsy |
| ZA6965 | DRAM1 | 12 | 102271640 | A | T | A0201,A3201,A0289,B400102,B450101,C0602,C0304 | C0602 | 148 | 554 | fiFsyvvav | filsyvvav |
| ZA6965 | TAOK3 | 12 | 118673393 | G | A | A0201,A3201,A0289,B400102,B450101,C0602,C0304 | A0201 | 462 | 24252 | sLansfvgt | sPansfvgt |
| ZA6965 | TAOK3 | 12 | 118673393 | G | A | A0201,A3201,A0289,B400102,B450101,C0602,C0304 | A3201 | 19 | 48 | smasLansf | smasPansf |

Figure 21 (Cont.)

| | | | | | | | | | | | |
|---|---|---|---|---|---|---|---|---|---|---|---|
| ZA6965 | VPS36 | 13 | 52990023 | C | A | A0201,A3201,A0289,B400102,B450101,C0602,C0304 | A0201 | 56 | 20524 | cLddsvegl | cRddsvegl |
| ZA6965 | RNASE3 | 14 | 21360056 | C | T | A0201,A3201,A0289,B400102,B450101,C0602,C0304 | C0602 | 32 | 347 | Frttfanvv | Lrttfanvv |
| ZA6965 | C14orf178 | 14 | 78235797 | C | T | A0201,A3201,A0289,B400102,B450101,C0602,C0304 | A0201 | 497 | 98 | llgssnSpa | llgssnPpa |
| ZA6965 | TECPR2 | 14 | 102916036 | C | T | A0201,A3201,A0289,B400102,B450101,C0602,C0304 | A0201 | 36 | 34 | tiihathLv | tiihathSv |
| ZA6965 | CHP1 | 15 | 41562800 | G | T | A0201,A3201,A0289,B400102,B450101,C0602,C0304 | A0201 | 21 | 19662 | sLdellqvl | sRdellqvl |
| ZA6965 | TLE3 | 15 | 70349933 | G | T | A0201,A3201,A0289,B400102,B450101,C0602,C0304 | C0602 | 136 | 613 | fammRhhem | fammShhem |
| ZA6965 | TLE3 | 15 | 70349933 | G | T | A0201,A3201,A0289,B400102,B450101,C0602,C0304 | C0602 | 85 | 45 | Rhhemngsl | Shhemngsl |
| ZA6965 | AGBL1 | 15 | 86822961 | G | A | A0201,A3201,A0289,B400102,B450101,C0602,C0304 | C0602 | 133 | 105 | vtfphsKdv | vtfphsEdv |
| ZA6965 | NTRK3 | 15 | 88726673 | G | T | A0201,A3201,A0289,B400102,B450101,C0602,C0304 | C0602 | 463 | 2317 | rafDknphl | rafAknphl |
| ZA6965 | NTRK3 | 15 | 88726673 | G | T | A0201,A3201,A0289,B400102,B450101,C0602,C0304 | C0602 | 291 | 78 | Dknphlryi | Aknphlryi |
| ZA6965 | IGF1R | 15 | 99442775 | G | T | A0201,A3201,A0289,B400102,B450101,C0602,C0304 | A0201 | 64 | 4801 | kiLhshalv | kiRhshalv |
| ZA6965 | FBXL16 | 16 | 745521 | G | A | A0201,A3201,A0289,B400102,B450101,C0602,C0304 | A0201 | 494 | 3555 | lvaenlCkl | lvaenlRkl |
| ZA6965 | KIF19 | 17 | 72348210 | C | G | A0201,A3201,A0289,B400102,B450101,C0602,C0304 | C0602 | 43 | 9 | hrheavGrl | hrheavRrl |
| ZA6965 | KIF19 | 17 | 72348210 | C | G | A0201,A3201,A0289,B400102,B450101,C0602,C0304 | C0602 | 81 | 27 | Grleqhrsl | Rrleqhrsl |
| ZA6965 | RNF213 | 17 | 78319855 | A | T | A0201,A3201,A0289,B400102,B450101,C0602,C0304 | A0201 | 11 | 14 | alppClipl | alppSlipl |
| ZA6965 | ENTHD2 | 17 | 79210780 | C | A | A0201,A3201,A0289,B400102,B450101,C0602,C0304 | A0201 | 292 | 2197 | klNvlkill | klKvlkill |
| ZA6965 | ENTHD2 | 17 | 79210780 | C | A | A0201,A3201,A0289,B400102,B450101,C0602,C0304 | A0201 | 148 | 34 | Nvlkillyl | Kvlkillyl |
| ZA6965 | ENTHD2 | 17 | 79210780 | C | A | A0201,A3201,A0289,B400102,B450101,C0602,C0304 | A3201 | 470 | 3142 | klNvlkill | klKvlkill |
| ZA6965 | APC2 | 19 | 1467049 | G | A | A0201,A3201,A0289,B400102,B450101,C0602,C0304 | C0602 | 89 | 479 | erYrlpsel | erCrlpsel |
| ZA6965 | SEMA6B | 19 | 4550159 | G | T | A0201,A3201,A0289,B400102,B450101,C0602,C0304 | A0201 | 114 | 56 | slghaHwil | slghaPwil |
| ZA6965 | MUC16 | 19 | 9067187 | C | A | A0201,A3201,A0289,B400102,B450101,C0602,C0304 | A3201 | 9 | 45 | stsqgtftF | stsqgtftL |
| ZA6965 | PGLYRP2 | 19 | 15580579 | G | A | A0201,A3201,A0289,B400102,B450101,C0602,C0304 | A0201 | 116 | 981 | Mlpscavra | Tlpscavra |

Figure 21 (Cont.)

| | | | | | | | | | | | |
|---|---|---|---|---|---|---|---|---|---|---|---|
| ZA6965 | C19orf60 | 19 | 18700363 | C | G | A0201,A3201,A0289,B400102,B450101,C0602,C0304 | A3201 | 156 | 114 | tvhgvSqaf | tvhgvTqaf |
| ZA6965 | ZNF536 | 19 | 31025865 | G | T | A0201,A3201,A0289,B400102,B450101,C0602,C0304 | A0201 | 15 | 18251 | fLtshhlkv | fRtshhlkv |
| ZA6965 | ZNF536 | 19 | 31025865 | G | T | A0201,A3201,A0289,B400102,B450101,C0602,C0304 | A3201 | 28 | 28 | ktfLtshhl | ktfRtshhl |
| ZA6965 | CIC | 19 | 42791731 | C | T | A0201,A3201,A0289,B400102,B450101,C0602,C0304 | C0602 | 42 | 88 | irrpmnVfm | irrpmnAfm |
| ZA6965 | CIC | 19 | 42791731 | C | T | A0201,A3201,A0289,B400102,B450101,C0602,C0304 | C0602 | 308 | 956 | rrpmnVfmi | rrpmnAfmi |
| ZA6965 | SLC1A5 | 19 | 47290921 | C | A | A0201,A3201,A0289,B400102,B450101,C0602,C0304 | A0201 | 52 | 359 | lllrllLmi | lllrllRmi |
| ZA6965 | SLC1A5 | 19 | 47290921 | C | A | A0201,A3201,A0289,B400102,B450101,C0602,C0304 | A0201 | 11 | 149 | llLmiilpl | llRmiilpl |
| ZA6965 | SLC1A5 | 19 | 47290921 | C | A | A0201,A3201,A0289,B400102,B450101,C0602,C0304 | A0201 | 4 | 3491 | lLmiilplv | lRmiilplv |
| ZA6965 | SLC1A5 | 19 | 47290921 | C | A | A0201,A3201,A0289,B400102,B450101,C0602,C0304 | A0201 | 57 | 83 | Lmiilplvv | Rmiilplvv |
| ZA6965 | NLRP13 | 19 | 56424632 | A | T | A0201,A3201,A0289,B400102,B450101,C0602,C0304 | C0602 | 24 | 34 | yrenKkael | yrenMkael |
| ZA6965 | IFT172 | 2 | 27677239 | G | T | A0201,A3201,A0289,B400102,B450101,C0602,C0304 | C0602 | 202 | 22381 | kHkeavlmf | kPkeavlmf |
| ZA6965 | INHBB | 2 | 121104199 | C | A | A0201,A3201,A0289,B400102,B450101,C0602,C0304 | C0602 | 357 | 12465 | iRfaetdgl | iSfaetdgl |
| ZA6965 | TTN | 2 | 179485248 | A | T | A0201,A3201,A0289,B400102,B450101,C0602,C0304 | C0602 | 100 | 21520 | kRtkngeev | kWtkngeev |
| ZA6965 | PIKFYVE | 2 | 209200043 | C | T | A0201,A3201,A0289,B400102,B450101,C0602,C0304 | A0201 | 43 | 3775 | fsyspiWll | fsyspiRll |
| ZA6965 | PIKFYVE | 2 | 209200043 | C | T | A0201,A3201,A0289,B400102,B450101,C0602,C0304 | A0201 | 157 | 1491 | yspiWllev | yspiRllev |
| ZA6965 | PIKFYVE | 2 | 209200043 | C | T | A0201,A3201,A0289,B400102,B450101,C0602,C0304 | A0201 | 4 | 5 | Wllevcvpl | Rllevcvpl |
| ZA6965 | PIKFYVE | 2 | 209200043 | C | T | A0201,A3201,A0289,B400102,B450101,C0602,C0304 | A3201 | 180 | 21126 | asfsyspiW | asfsyspiR |
| ZA6965 | PIKFYVE | 2 | 209200043 | C | T | A0201,A3201,A0289,B400102,B450101,C0602,C0304 | C0602 | 162 | 39 | fsyspiWll | fsyspiRll |
| ZA6965 | DNPEP | 2 | 220251410 | G | A | A0201,A3201,A0289,B400102,B450101,C0602,C0304 | A0201 | 344 | 6584 | Ytdspclrv | Htdspclrv |
| ZA6965 | SRXN1 | 20 | 633648 | T | A | A0201,A3201,A0289,B400102,B450101,C0602,C0304 | A3201 | 112 | 25 | Mvqslvdti | Kvqslvdti |
| ZA6965 | GATA5 | 20 | 61050544 | G | T | A0201,A3201,A0289,B400102,B450101,C0602,C0304 | A0201 | 405 | 1833 | alaaspSqa | alaaspRqa |
| ZA6965 | TTLL12 | 22 | 43572360 | T | C | A0201,A3201,A0289,B400102,B450101,C0602,C0304 | A0201 | 22 | 16 | klpldiDpv | klpldiNpv |
| ZA6965 | SBF1 | 22 | 50903729 | C | A | A0201,A3201,A0289,B400102,B450101,C0602,C0304 | A0201 | 22 | 426 | flLlfaqll | flRlfaqll |

Figure 21 (Cont.)

| | | | | | | | | | | | |
|---|---|---|---|---|---|---|---|---|---|---|---|
| ZA6965 | SEMA3G | 3 | 52475856 | G | A | A0201,A3201,A0289,B400102,B450101,C0602,C0304 | C0602 | 452 | 1320 | srSfastfi | srPfastfi |
| ZA6965 | CHST13 | 3 | 126260690 | G | A | A0201,A3201,A0289,B400102,B450101,C0602,C0304 | A0201 | 9 | 26 | Mlvddahgl | Vlvddahgl |
| ZA6965 | SHROOM3 | 4 | 77662104 | C | A | A0201,A3201,A0289,B400102,B450101,C0602,C0304 | C0602 | 370 | 368 | fsrayrKsi | fsrayrNsi |
| ZA6965 | HERC6 | 4 | 89300251 | G | A | A0201,A3201,A0289,B400102,B450101,C0602,C0304 | C0602 | 332 | 356 | rrgTqrgel | rrgAqrgel |
| ZA6965 | PCDHGA6 | 5 | 140755875 | G | A | A0201,A3201,A0289,B400102,B450101,C0602,C0304 | C0602 | 129 | 236 | shfvDvegv | shfvGvegv |
| ZA6965 | LEMD2 | 6 | 33756262 | G | C | A0201,A3201,A0289,B400102,B450101,C0602,C0304 | A0201 | 274 | 127 | wlCrlllwa | wlSrlllwa |
| ZA6965 | LEMD2 | 6 | 33756262 | G | C | A0201,A3201,A0289,B400102,B450101,C0602,C0304 | C0602 | 63 | 184 | erwlCrlll | erwlSrlll |
| ZA6965 | PTCHD4 | 6 | 47976813 | C | A | A0201,A3201,A0289,B400102,B450101,C0602,C0304 | A0201 | 20 | 25 | hqlgVvvev | hqlgGvvev |
| ZA6965 | NPSR1 | 7 | 34884524 | C | A | A0201,A3201,A0289,B400102,B450101,C0602,C0304 | C0602 | 191 | 8048 | cRsynrgli | cSsynrgli |
| ZA6965 | GLI3 | 7 | 42005681 | G | A | A0201,A3201,A0289,B400102,B450101,C0602,C0304 | C0602 | 284 | 6774 | rrhlqphdV | rrhlqphdA |
| ZA6965 | VWC2 | 7 | 49815060 | G | C | A0201,A3201,A0289,B400102,B450101,C0602,C0304 | A0201 | 341 | 557 | Aalssslv | Galssslv |
| ZA6965 | VWC2 | 7 | 49815060 | G | C | A0201,A3201,A0289,B400102,B450101,C0602,C0304 | A3201 | 431 | 2468 | stamavAal | stamavGal |
| ZA6965 | VWC2 | 7 | 49815111 | G | T | A0201,A3201,A0289,B400102,B450101,C0602,C0304 | A0201 | 67 | 115 | mvalFspsi | mvalCspsi |
| ZA6965 | VWC2 | 7 | 49815111 | G | T | A0201,A3201,A0289,B400102,B450101,C0602,C0304 | A0201 | 11 | 75 | alFspsipl | alCspsipl |
| ZA6965 | VWC2 | 7 | 49815111 | G | T | A0201,A3201,A0289,B400102,B450101,C0602,C0304 | A3201 | 41 | 390 | mvalFspsi | mvalCspsi |
| ZA6965 | VWC2 | 7 | 49815111 | G | T | A0201,A3201,A0289,B400102,B450101,C0602,C0304 | A3201 | 32 | 367 | alFspsipl | alCspsipl |
| ZA6965 | ZNF716 | 7 | 57529089 | T | C | A0201,A3201,A0289,B400102,B450101,C0602,C0304 | C0602 | 306 | 345 | kafsrPstl | kafsrSstl |
| ZA6965 | ERV3-1 | 7 | 64452197 | T | A | A0201,A3201,A0289,B400102,B450101,C0602,C0304 | A0201 | 31 | 39 | slnhswFql | slnhswYql |
| ZA6965 | WBSCR17 | 7 | 71177066 | G | T | A0201,A3201,A0289,B400102,B450101,C0602,C0304 | A0201 | 113 | 97 | glaCidlll | glaGidlll |
| ZA6965 | GPC2 | 7 | 99769282 | C | A | A0201,A3201,A0289,B400102,B450101,C0602,C0304 | A0201 | 349 | 21107 | rlvwelreL | rlvwelreR |
| ZA6965 | GPC2 | 7 | 99769282 | C | A | A0201,A3201,A0289,B400102,B450101,C0602,C0304 | A0201 | 234 | 638 | lvwelreLl | lvwelreRl |
| ZA6965 | LRWD1 | 7 | 102113000 | C | T | A0201,A3201,A0289,B400102,B450101,C0602,C0304 | A0201 | 119 | 1532 | stvavvvlV | stvavvvlA |

Figure 21 (Cont.)

| | | | | | | | | | | | |
|---|---|---|---|---|---|---|---|---|---|---|---|
| ZA6965 | ZNF862 | 7 | 149545167 | G | T | A0201,A3201,A0289,B400102,B450101,C0602,C0304 | C0602 | 158 | 353 | yhaNskahm | yhaKskahm |
| ZA6965 | TMUB1 | 7 | 150778955 | C | T | A0201,A3201,A0289,B400102,B450101,C0602,C0304 | C0602 | 51 | 39 | greqqvQli | greqqvRli |
| ZA6965 | DMTN | 8 | 21938352 | A | T | A0201,A3201,A0289,B400102,B450101,C0602,C0304 | C0602 | 27 | 24 | grmdrgYsl | grmdrgNsl |
| ZA6965 | CSMD3 | 8 | 113353849 | C | A | A0201,A3201,A0289,B400102,B450101,C0602,C0304 | A0201 | 453 | 16505 | sVssetstv | sGssetstv |
| ZA6965 | CSMD3 | 8 | 113697930 | C | A | A0201,A3201,A0289,B400102,B450101,C0602,C0304 | A0201 | 29 | 127 | clsnftapl | clsnftapM |
| ZA6965 | CSMD3 | 8 | 113697930 | C | A | A0201,A3201,A0289,B400102,B450101,C0602,C0304 | A3201 | 71 | 1850 | clsnftapl | clsnftapM |
| ZA6965 | ZNF517 | 8 | 146033463 | C | T | A0201,A3201,A0289,B400102,B450101,C0602,C0304 | A0201 | 169 | 150 | sllllhlCl | sllllhlRl |
| ZA6965 | ZNF517 | 8 | 146033463 | C | T | A0201,A3201,A0289,B400102,B450101,C0602,C0304 | A0201 | 380 | 2597 | lllhlClht | lllhlRlht |
| ZA6965 | DPH7 | 9 | 140473202 | C | A | A0201,A3201,A0289,B400102,B450101,C0602,C0304 | A0201 | 147 | 142 | alqtLdtel | alqtVdtel |
| ZA6965 | FAM155B | X | 68749680 | T | A | A0201,A3201,A0289,B400102,B450101,C0602,C0304 | A0201 | 172 | 419 | rlSvlvlml | rlCvlvlml |
| ZA6965 | FAM155B | X | 68749680 | T | A | A0201,A3201,A0289,B400102,B450101,C0602,C0304 | A3201 | 314 | 516 | rlSvlvlml | rlCvlvlml |
| ZA6965 | FAM155B | X | 68749680 | T | A | A0201,A3201,A0289,B400102,B450101,C0602,C0304 | C0602 | 146 | 751 | srirlSvlv | srirlCvlv |
| ZA6965 | FAM155B | X | 68749680 | T | A | A0201,A3201,A0289,B400102,B450101,C0602,C0304 | C0602 | 279 | 2682 | irlSvlvlm | irlCvlvlm |
| ZA6965 | ZFP92 | X | 152686788 | G | A | A0201,A3201,A0289,B400102,B450101,C0602,C0304 | A3201 | 72 | 70 | rshsgeQpf | rshsgeRpf |

Figure 21 (Cont.)

DETERMINANTS OF CANCER RESPONSE TO IMMUNOTHERAPY BY PD-1 BLOCKADE

SEQUENCE LISTING

The instant application contains a Sequence Listing which has been submitted electronically in ASCII format and is hereby incorporated by reference in its entirety. Said ASCII copy, created on Dec. 30, 2015, is named 2003080-0984_SL.txt and is 1,630,136 bytes in size.

BACKGROUND

Cancer immunotherapy involves the attack of cancer cells by a patient's immune system. Regulation and activation of T lymphocytes depends on signaling by the T cell receptor and also cosignaling receptors that deliver positive or negative signals for activation. Immune responses by T cells are controlled by a balance of costimulatory and inhibitory signals, called immune checkpoints.

Immunotherapy with immune checkpoint inhibitors is revolutionizing cancer therapy. For example, in certain melanoma patients, anti-CTLA4 and anti-PD1 antibodies have offered a remarkable opportunity for long-term disease control in the metastatic setting.

SUMMARY

The present invention encompasses the discovery that the likelihood of a favorable response to cancer immunotherapy can be predicted. The present invention particularly comprises the discovery that, for certain cancers, mutation burden can correlate with responsiveness to particular therapy. Still further, the present invention provides the finding that certain cancer cells may harbor somatic mutations that result in neoepitopes that are recognizable by a patient's immune system as non-self, and that presence and/or identity of such neoepitopes may correlate with responsiveness to particular therapy. The identification of multiple mutations in a cancer sample as described herein is useful for determining which cancer patients are likely to respond favorably to immunotherapy, in particular, treatment with an immune checkpoint modulator.

The present disclosure defines certain characteristics of particular tumor cells that can be detected to predict responsiveness to immunotherapy, and particularly to therapy with immune checkpoint modulators. Among other things, the present disclosure provides tools and technologies that can be practically applied to define, characterize, and/or detect "signatures" of tumor responsiveness.

For example, the present disclosure provides tools and technologies that provide effective prediction or assessment of the likelihood that a particular tumor will respond to a particular therapy. Among other things, the present disclosure provides tools for defining or detecting particular features of cancer cells that may act as a proxy for underlying aspects of biology that support the natural correlation. The present disclosure demonstrates, for example, that particular, limited, signatures can be defined that are useful to define or detect such features, and provides detection formats that utilize these signatures. Moreover, the present disclosure demonstrates that provided formats are more effective and/or informative, in at least some contexts, than are other methodologies for applying the biological correlation.

In some embodiments, the invention provides methods for identifying a subject as likely to respond to treatment with an immune checkpoint modulator.

In some embodiments, the methods comprise steps of detecting a marker of high mutations in a cancer sample from a subject; and identifying the subject as a candidate for treatment with an immune checkpoint modulator. In some embodiments, the step of detecting comprises sequencing one or more exomes from the cancer sample.

In some embodiments, the number of mutations identifies the subject as a candidate for treatment with an immune checkpoint modulator. In some embodiments, a high number of mutations identifies the subject as a candidate for treatment with an immune checkpoint modulator. In some embodiments, a high number of nonsynonymous mutations identifies the subject as a candidate for treatment with an immune checkpoint modulator.

In some embodiments, the ratio of transition mutations to transversion mutations identifies the subject as a candidate for treatment with an immune checkpoint modulator. In some embodiments, the ratio comprises the molecular smoking signature.

In some embodiments, the somatic mutation comprises a neoepitope recognized by a T cell. In some embodiments, the number of neoepitopes identifies the subject as a candidate for treatment with an immune checkpoint modulator. In some embodiments, neoepitopes identify the subject as a candidate for treatment with an immune checkpoint modulator.

In some embodiments, the neoepitopes are associated with high mutation rate. In some embodiments, high mutations are present in genes encoding proteins involved in DNA repair. In some embodiments, high mutations are present in genes encoding proteins involved in cell signal transduction.

In some embodiments, the neoepitope has greater binding affinity to a major histocompatibility complex (MHC) molecule compared to a corresponding epitope that does not have a mutation.

In some embodiments, the somatic mutation comprises a neoepitope comprising a nonamer that is not expressed in the same cell type that does not have a somatic mutation.

In some embodiments, the neoepitope shares a consensus sequence with an infectious agent.

In some embodiments, the cancer is or comprises a cancer selected from the group comprising: carcinoma, sarcoma, myeloma, leukemia, or lymphoma. In some embodiments, the cancer is selected from a group comprising: lung carcinoma, melanoma, renal carcinoma, bladder carcinoma, small cell carcinoma, and head and neck cancer.

In some embodiments, the immune checkpoint modulator interacts with cytotoxic T-lymphocyte antigen 4 (CTLA4), programmed death 1 (PD-1) or its ligands, lymphocyte activation gene-3 (LAG3), B7 homolog 3 (B7-H3), B7 homolog 4 (B7-H4), indoleamine (2,3)-dioxygenase (IDO), adenosine A2a receptor, neuritin, B- and T-lymphocyte attenuator (BTLA), killer immunoglobulin-like receptors (KIR), T cell immunoglobulin and mucin domain-containing protein 3 (TIM-3), inducible T cell costimulator (ICOS), CD27, CD28, CD40, CD137, or combinations thereof.

In some embodiments, the immune checkpoint modulator is an antibody agent. In some embodiments, the antibody agent is or comprises a monoclonal antibody or antigen binding fragment thereof. In some embodiments, the antibody is pembrolizumab.

In some embodiments, the subject has not previously been treated with a cancer therapeutic. In some embodiments, the subject has not previously been treated with a cancer immunotherapeutic.

In some embodiments, the method of identifying a subject for treatment with an immune checkpoint modulator further comprises a step of administering pembrolizumab to the subject.

In some embodiments, the invention provides methods for detecting a low number of mutations in a cancer sample from a subject; and identifying the subject as a poor candidate for treatment with an immune checkpoint modulator.

In some embodiments, the invention provides methods for determining a subject has a cancer comprising a marker of high mutations, wherein the mutations comprises a neoepitope comprising a nonamer, and selecting for the subject a cancer treatment comprising an immune checkpoint modulator. In some embodiments, the cancer comprises lung carcinoma.

In some embodiments, the invention provides methods for improving efficacy of cancer therapy with an immune checkpoint modulator, the method comprising a step of: selecting for receipt of the therapy a subject identified as having a cancer with markers of high mutation comprising a neoepitope recognized by a T cell.

In some embodiments, the invention provides methods for treating cancer by administering immune checkpoint modulator therapy, the improvement that comprises: administering the therapy to a subject identified as having a cancer with one or more markers of high mutation comprising a neoepitope recognized by a T cell.

In some embodiments, the invention provides methods for treating a cancer selected from the group consisting of carcinoma, sarcoma, myeloma, leukemia, or lymphoma, the method comprising a step of: administering immune checkpoint modulator therapy to a subject identified as having a cancer with a marker of high mutations comprising a neoepitope recognized by a T cell. In some embodiments, the cancer is or comprises lung carcinoma.

In some embodiments, the invention provides methods for defining a mutation signature that correlates with responsiveness to therapy with an immune checkpoint modulator, the method comprising: determining one or more mutation characteristics in a plurality of samples of tumors sharing a response characteristic to immune checkpoint modulator therapy; comparing the determined one or more mutation characteristics with those in a plurality of samples of tumors that do not share the response characteristic; and identifying a set of mutation characteristics whose presence correlates with the response characteristic.

In some embodiments, the one or more mutation characteristics include a mutation characteristic selected from the group consisting of mutation burden, nonsynonymous mutation burden, neoantigen burden, transversion burden, transition burden, relative transversion vs transition burden, mutation burden in genes associated with DNA repair, presence of mutation in one or more particular genes associated with DNA repair, identity of mutation in one or more particular genes associated with DNA repair, and combinations thereof. In some embodiments, the determined burden is or comprises rate or number. In some embodiments, the genes associated with DNA repair are or include a genes selected from the group consisting of POLD1, PRKDC, DNA-PK, RAD17, POLE, and MSH2. In some embodiments, genes not associated with DNA repair that harbor mutation characteristics include genes selected from the group consisting of POLR2A, KEAP1, PAPPA2, PXDNL, RYR1, SCN8A, SLIT3 and KRAS.

In some embodiments, the response characteristic is or comprises a characteristic selected from the group consisting of partial or stable response lasting longer than 6 months ("durable clinical benefit"; "DCB"), a reduction in tumor size for more than 4 weeks ("objective response rate"; "ORR"); no disease progression for more than 9 weeks ("progression-free survival"; "PFS"), and combinations thereof.

In some embodiments, the invention provides methods for characterizing a tumor sample by determining presence of a set of mutation characteristics that correlates with a response characteristic to immune checkpoint modulator therapy.

In some embodiments, the step of determining comprises detecting at least one of the mutation characteristics by nucleic acid sequencing. In some embodiments, the nucleic acid sequencing is or comprises whole exome sequencing.

BRIEF DESCRIPTION OF THE DRAWING

The following figures are presented for the purpose of illustration only, and are not intended to be limiting.

In FIG. 1B, higher nonsynonymous mutation burden (above median of discovery cohort (n=8)) correlated with improved PFS compared to tumors with lower nonsynonymous mutation burden (n=8) (HR 0.19, 95% CI 0.05-0.70, p=0.01). IN FIG. 1C, in validation cohort, median nonsynonymous mutation burden is also greater in tumors from patients with DCB (n=7) compared to those with NDB (n=7) (median 244 vs 125, p=0.04). In FIG. 1D, higher nonsynonymous mutation burden (above median of validation cohort, n=9) again correlated with improved PFS compared to those with lower nonsynonymous mutation burden (n=9) (HR 0.15, 95% CI 0.04-0.59, p=0.006). In FIG. 1E the ROC curve for nonsynonymous mutation burden prediction of DCB in discovery cohort. AUC is 0.86 (95% CI 0.66-1.05, p=0.02). Cut-off of ≥178 nonsynonymous mutations is designated by triangle. According to FIG. 1F nonsynonymous mutation burden in those with DCB (n=14) compared to those with NCB (n=17) for the entire set of sequenced tumors (median 299 vs 127, p=0.0008). According to FIG. 1G PFS is improved in those with higher nonsynonymous mutation burden (n=17) compared to those with lower nonsynonymous mutation burden (n=17) in the entire set of sequenced tumors (HR 0.19, 95% CI 0.08-0.47, p=0.0004). In FIGS. 1A, 1C, and 1F, median and interquartile ranges of total nonsynonymous mutations are shown, with individual values for each tumor shown with dots.

FIG. 2A shows the molecular smoking signature significantly associates with improved PFS. Tumors characterized as TH as by molecular smoking signature classifier (n=16) have improved progression-free survival compared to those with TL signature (n=18) (HR 0.15, 95% 0.06-0.39, p=0.0001). FIG. 2B shows there is no significant difference in PFS between ever (n=28) and never smokers (n=6) (HR 0.52, 95% CI 0.15-1.8, p=0.29).

Figure 4A:
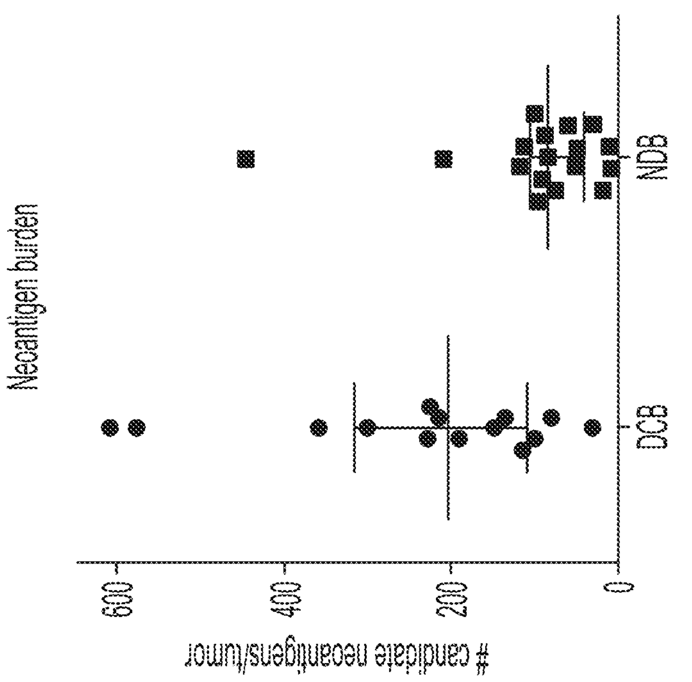
Figure 4B:
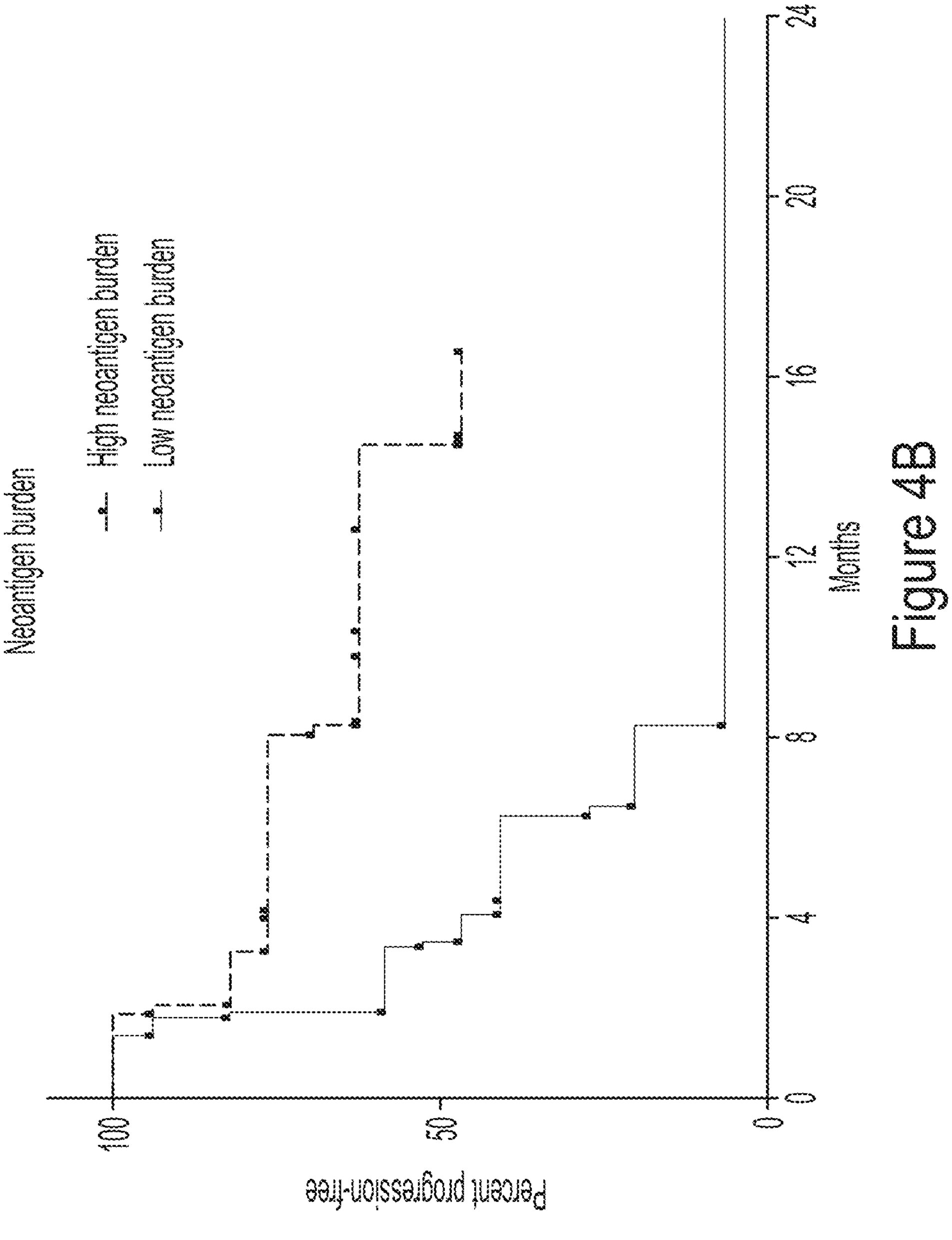
Figure 4C:
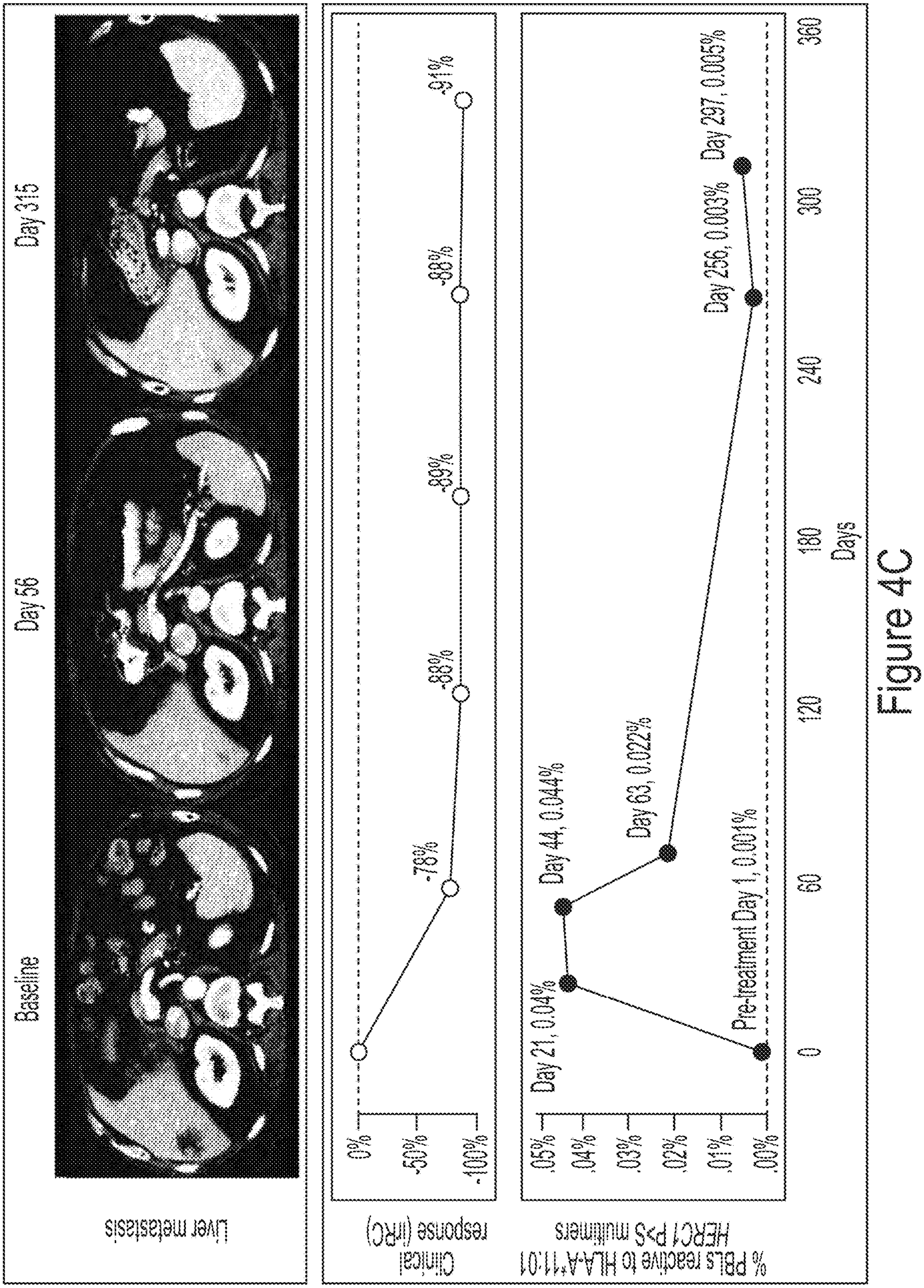
Figure 4D:
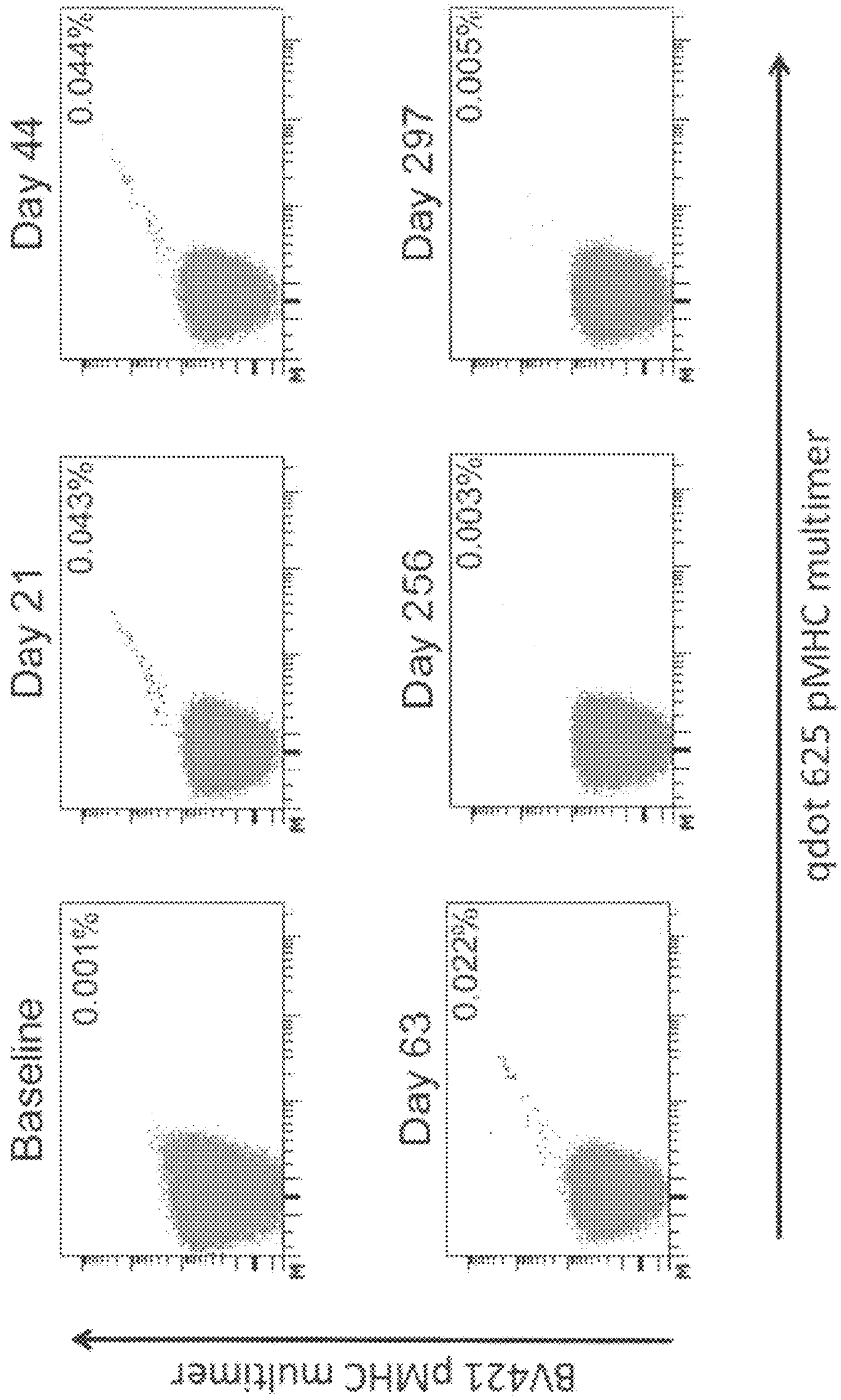
Figure 4E:
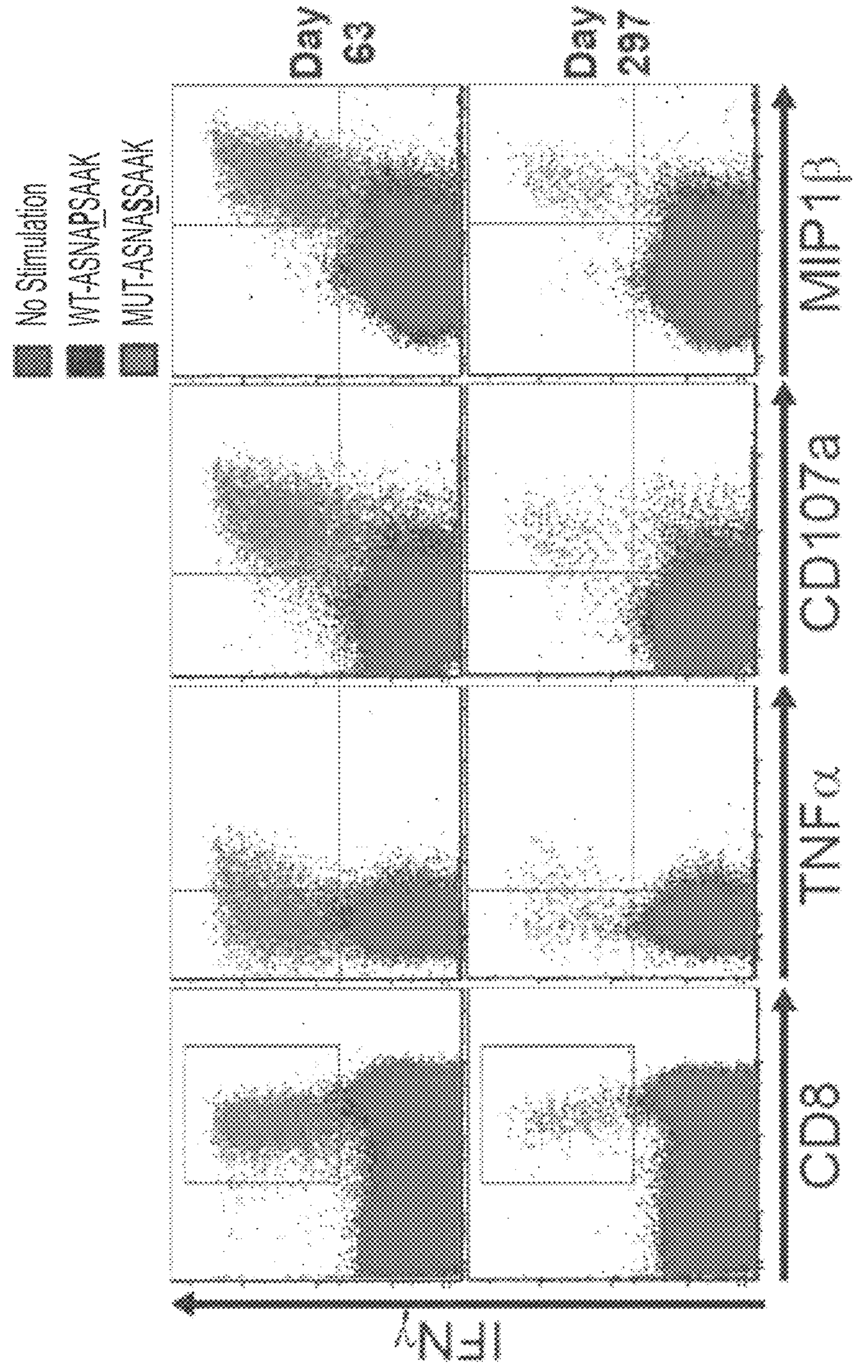

FIGS. 4A-4E show candidate neoantigens, neoantigen-specific T-cell response, and response to pembrolizumab. FIG. 4A illustrates that across the overall set of sequenced tumors, neoantigen burden is greater tumors from patients with DCB (n=14) compared to NDB (n=17) (median 203 vs 83, p=0.001). FIG. 4B shows higher neoantigen burden (above median of overall set, n=17)) correlates with improved PFS compared to tumors with lower neoantigen burden (n=17) (HR 0.23, 95% CI 0.09-0.58, p=0.002). In FIG. 4C the top panel shows representative computed tomography (CT) images of a liver metastasis prior to and at days after initiating treatment, as indicated. Middle panel of FIG. 4C shows decline of tumor burden. While the bottom panel of FIG. 4C shows the anti-HERC1 P>S CD8+ T-cell response measured in peripheral blood. FIG. 4D shows a CD8+ T-cell population in serially-collected autologous PBLs recognizing the HERC1 P>S neoantigen (ASNASSAAK (SEQ ID NO: 344)) was detected after beginning pembrolizumab, represented by the events in the double positive position indicated in black. Percentages indicate the number of CD8+ MHC multimer+ cells out of total CD8 cells. FIG. 4E shows autologous T-cell response to WT HERC1 peptide (SEQ ID NO: 5925) (black) vs. mutant HERC1 P>S neoantigen (SEQ ID NO: 344) (red) vs. no stimulation (blue), as detected by intracellular cytokine staining. T-cell co-stains for IFNγ and CD8, TNFα, CD107a, and MIP1β, respectively, are displayed for the Day 63 and Day 297 time points.

Figure 5:
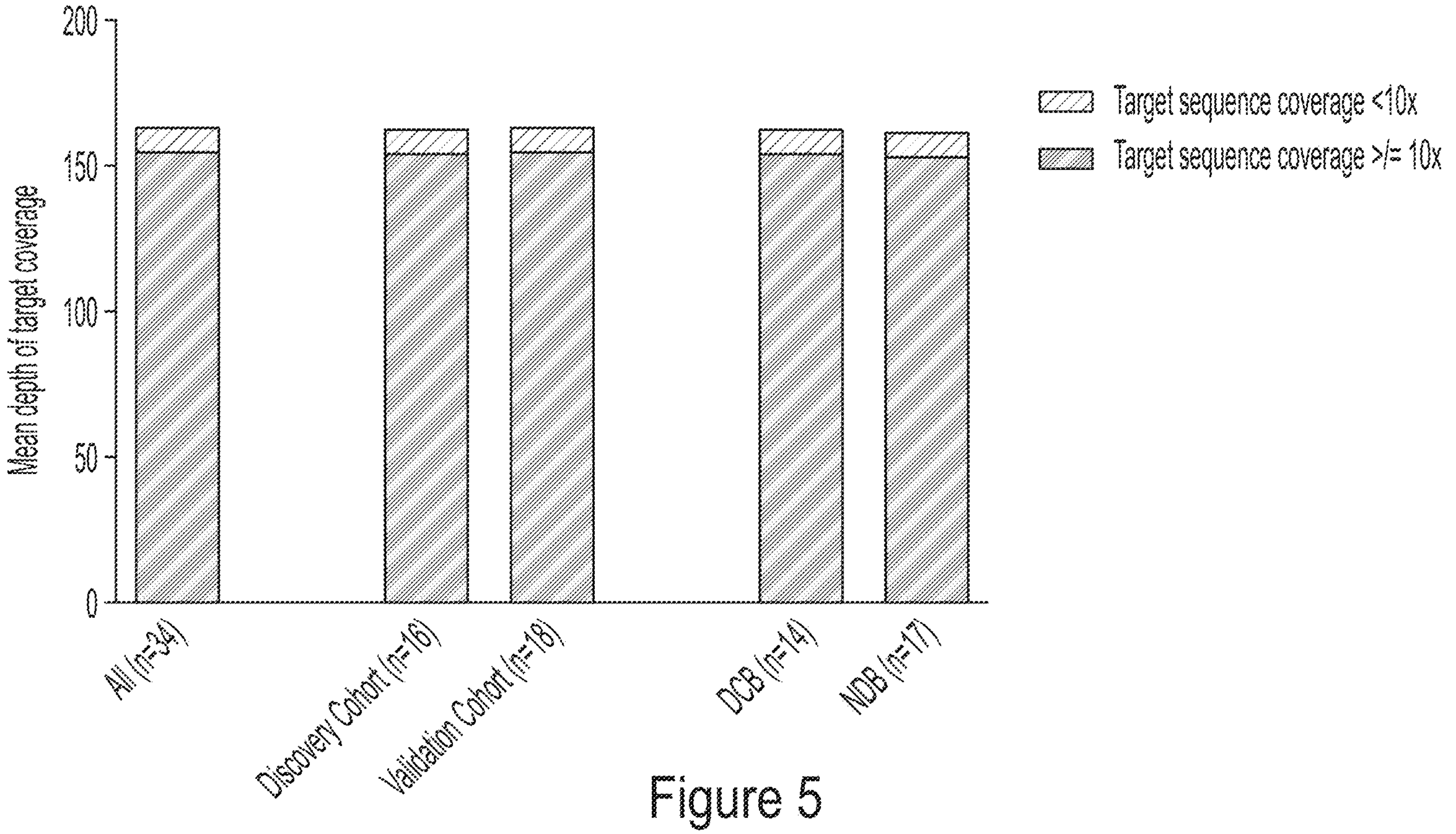

FIG. 5 coverage and depth of target exome sequence. Coverage and depth of sequenced exomes is similar in discovery compared to validation cohorts and is similar in those with durable clinical benefit (DCB) compared to those with no durable benefit (NDB).

Figure 6:
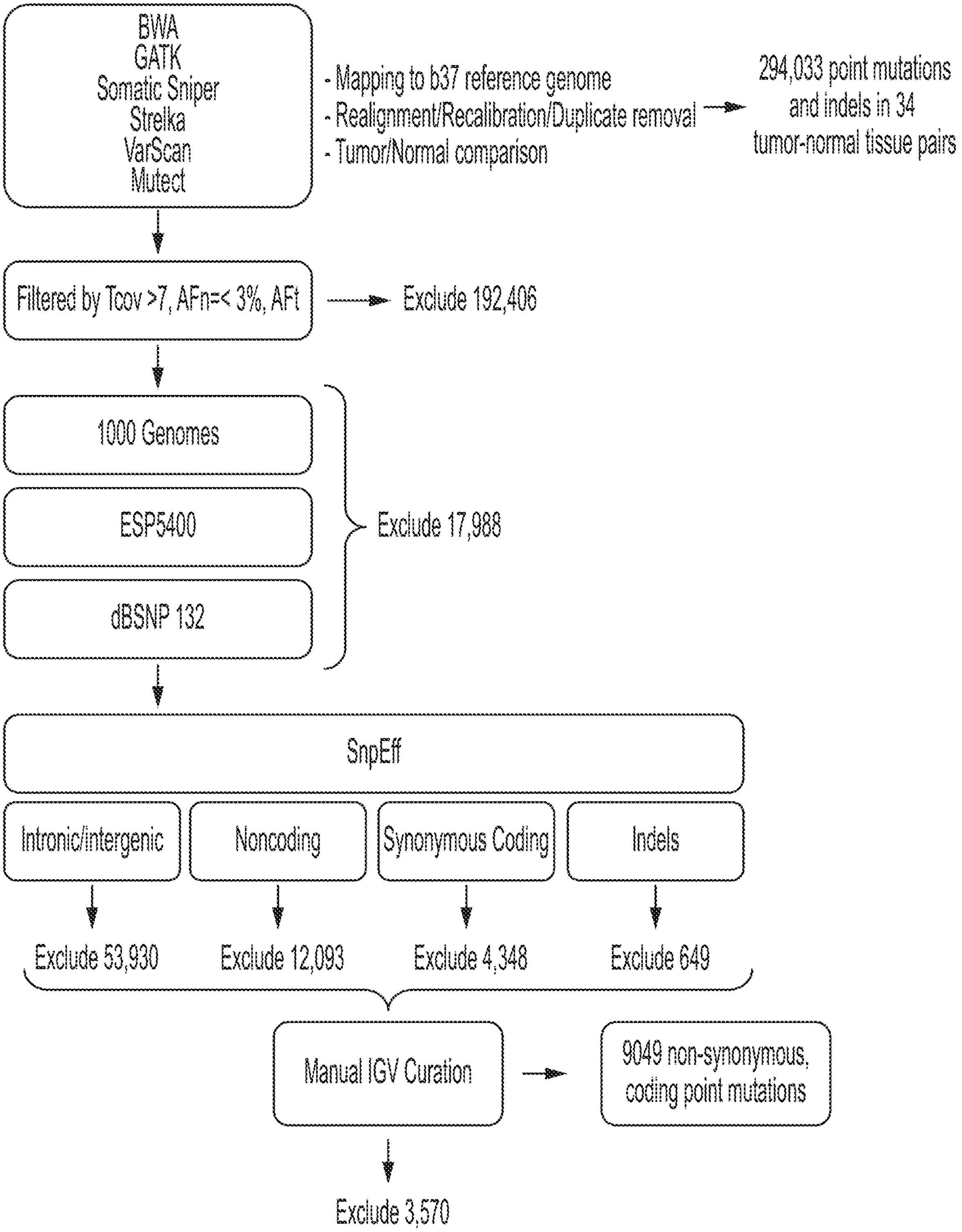

FIG. 6 shows an exome analysis pipeline.

Figure 7A:
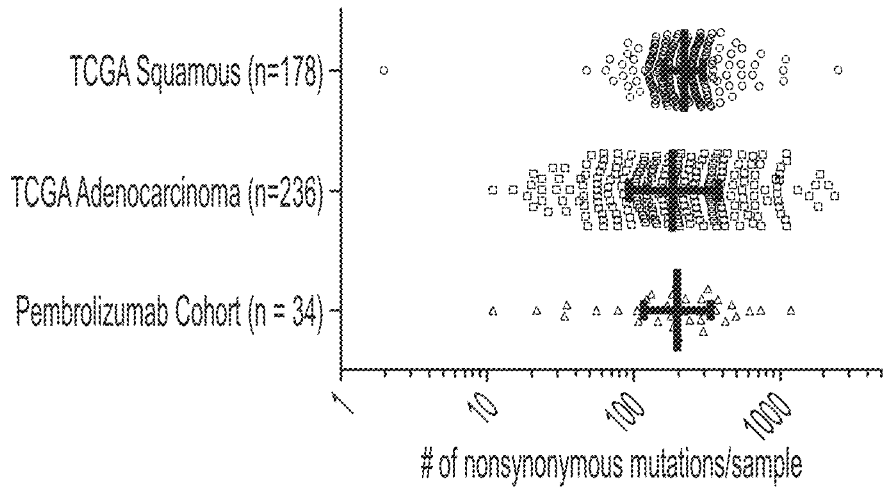
Figure 7B:
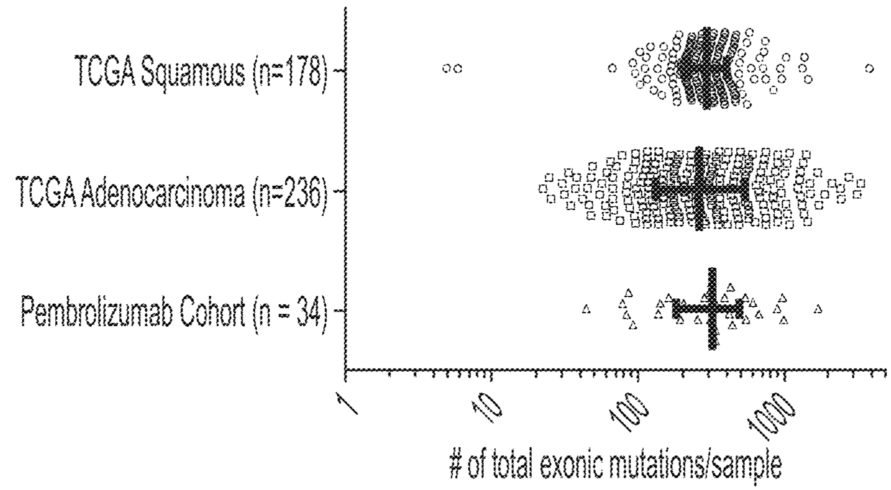

FIGS. 7A-7B show median and interquartile range of mutations in the current study and in published series of NSCLC (13, 14). FIG. 7A shows somatic nonsynonymous mutation burden. FIG. 7B shows total exonic mutations.

Figure 8:
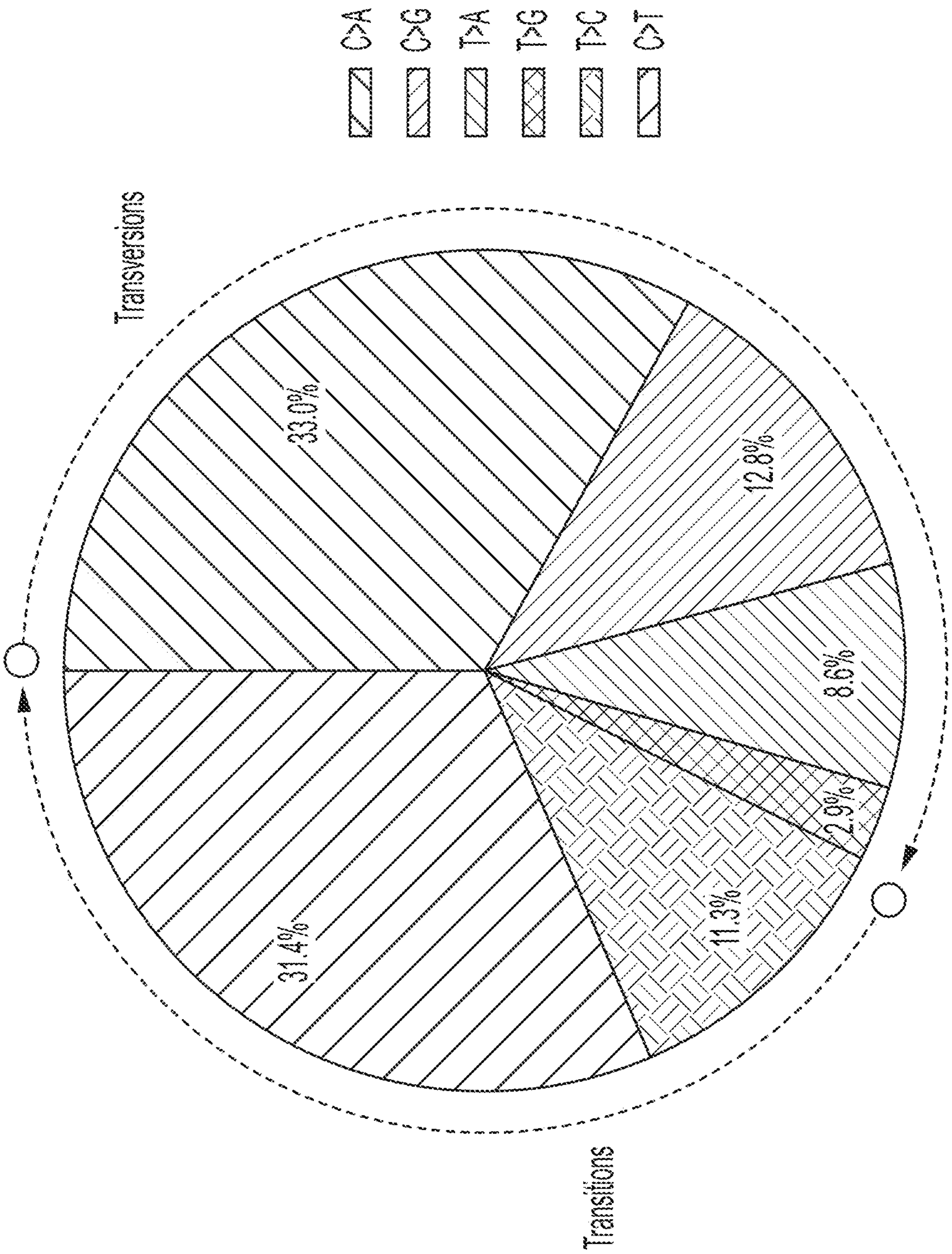

FIG. 8 shows a pattern of nucleotide changes in tumors sequenced. The spectrum and frequency of nucleotide changes in the pembrolizumab-treated NSCLCs is typical of non-small cell lung cancers.

Figure 9:
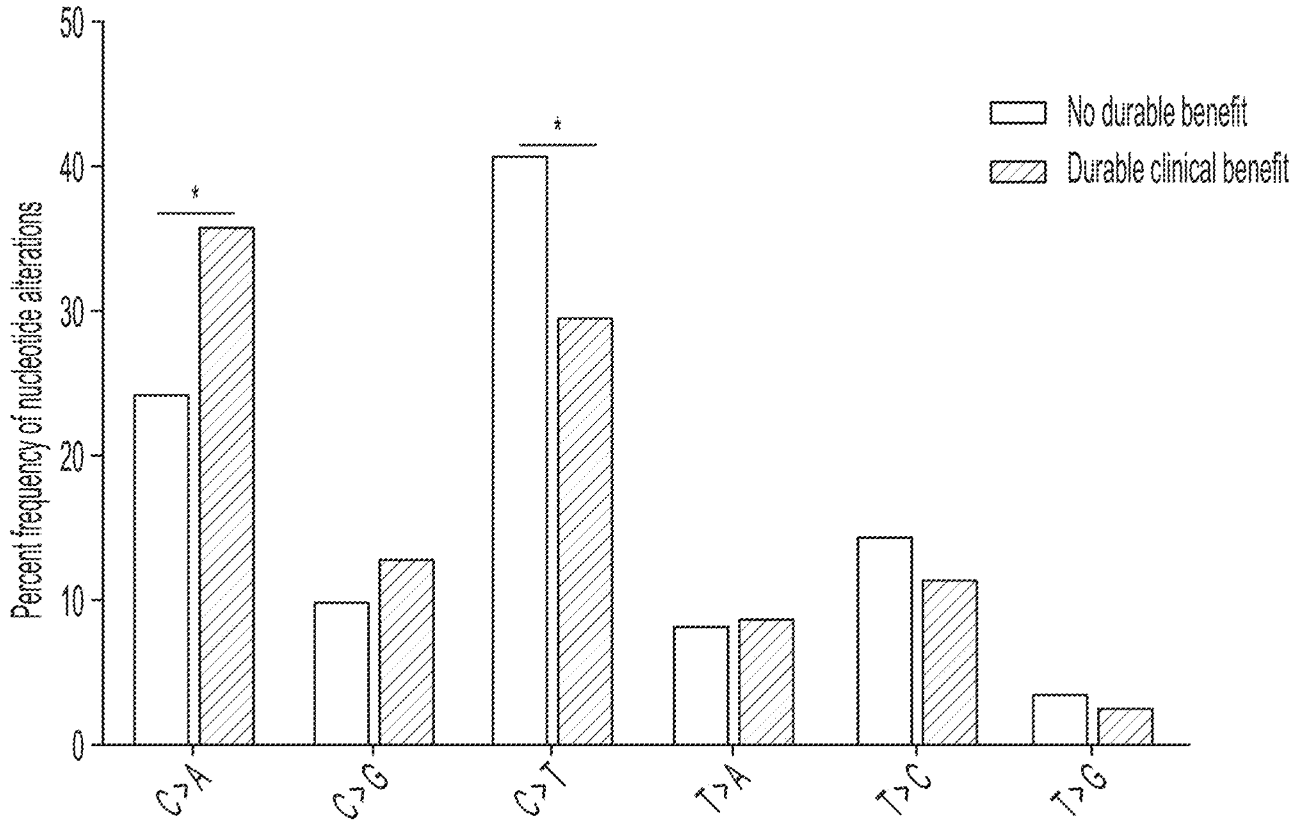

FIG. 9 shows a distribution of nucleotide alterations in nonsynonymous mutations. Across the overall set of sequenced NSCLCs treated with pembrolizumab, C>A transversions are more frequent in those with DCB, while C>T transitions are more frequent in those with NDB (* denotes p=0.01).

Figure 10:
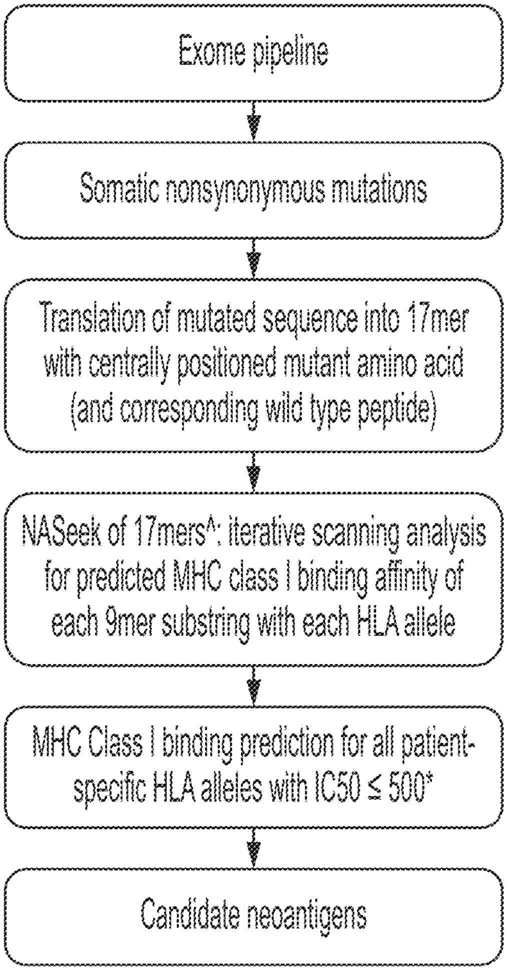

FIG. 10 shows a neoantigen analysis pipeline. ^All steps are executed for predicted wild type and mutant. *MHC Class I prediction by NetMHCv3.4.

Figure 11:
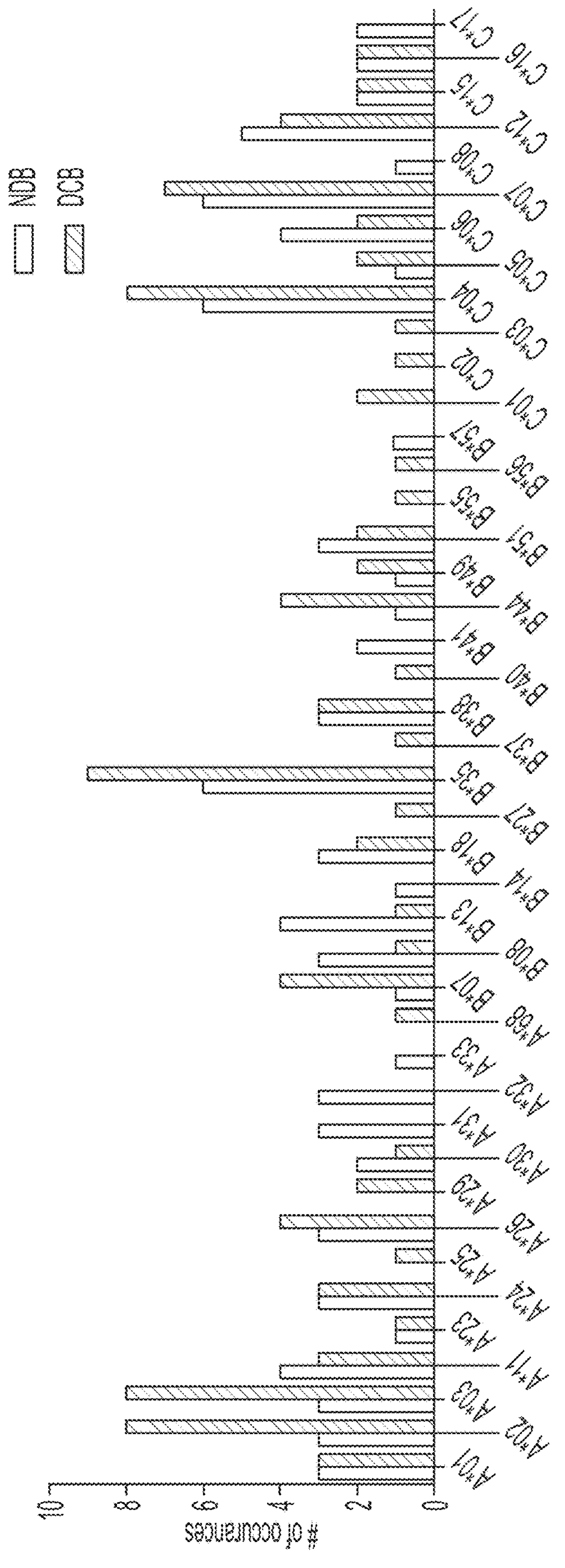

FIG. 11 shows HLA type and benefit to pembrolizumab. There was no evident association between the presence of any specific HLA allele and benefit from pembrolizumab.

Figure 12:
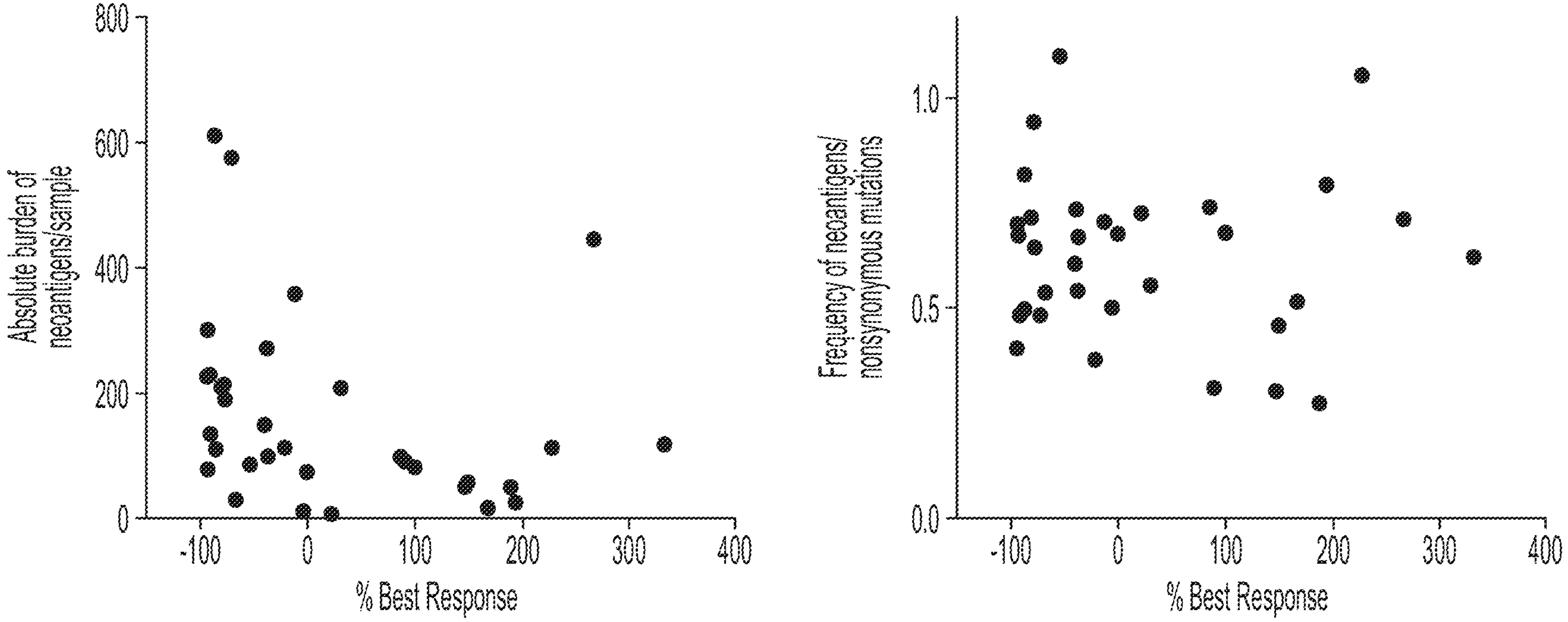

FIG. 12 depicts neoantigens and best objective response. The absolute quantity of predicted neoantigens correlates with best overall response (Spearman ρ −0.43, 95% CI −0.68-−0.10, p=0.01), but the frequency of neoantigens/nonsynonymous mutation does not (Spearman ρ −0.04, 95% CI −0.39-0.30, p=0.78).

Figure 13A:
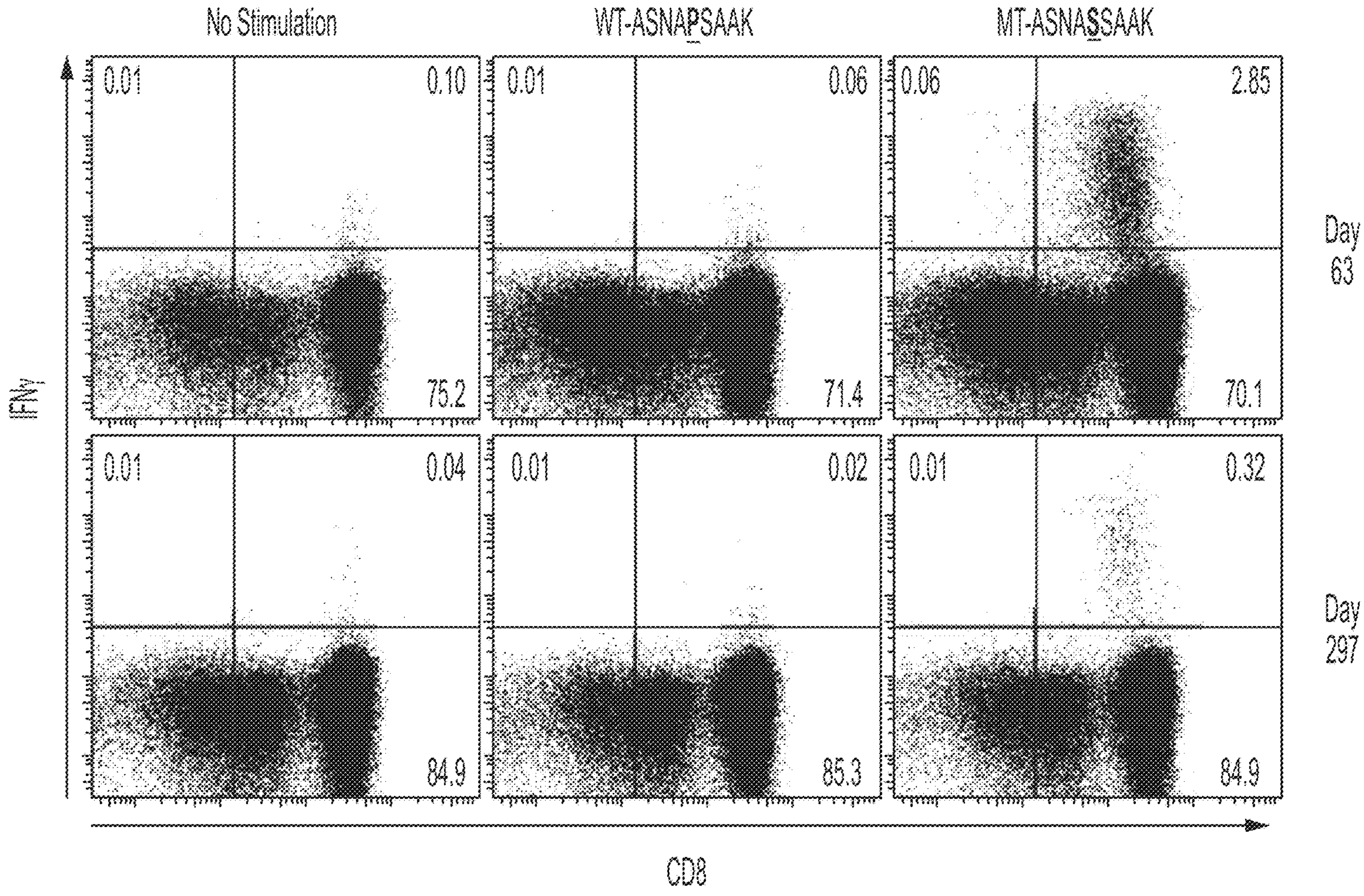
Figure 13B:
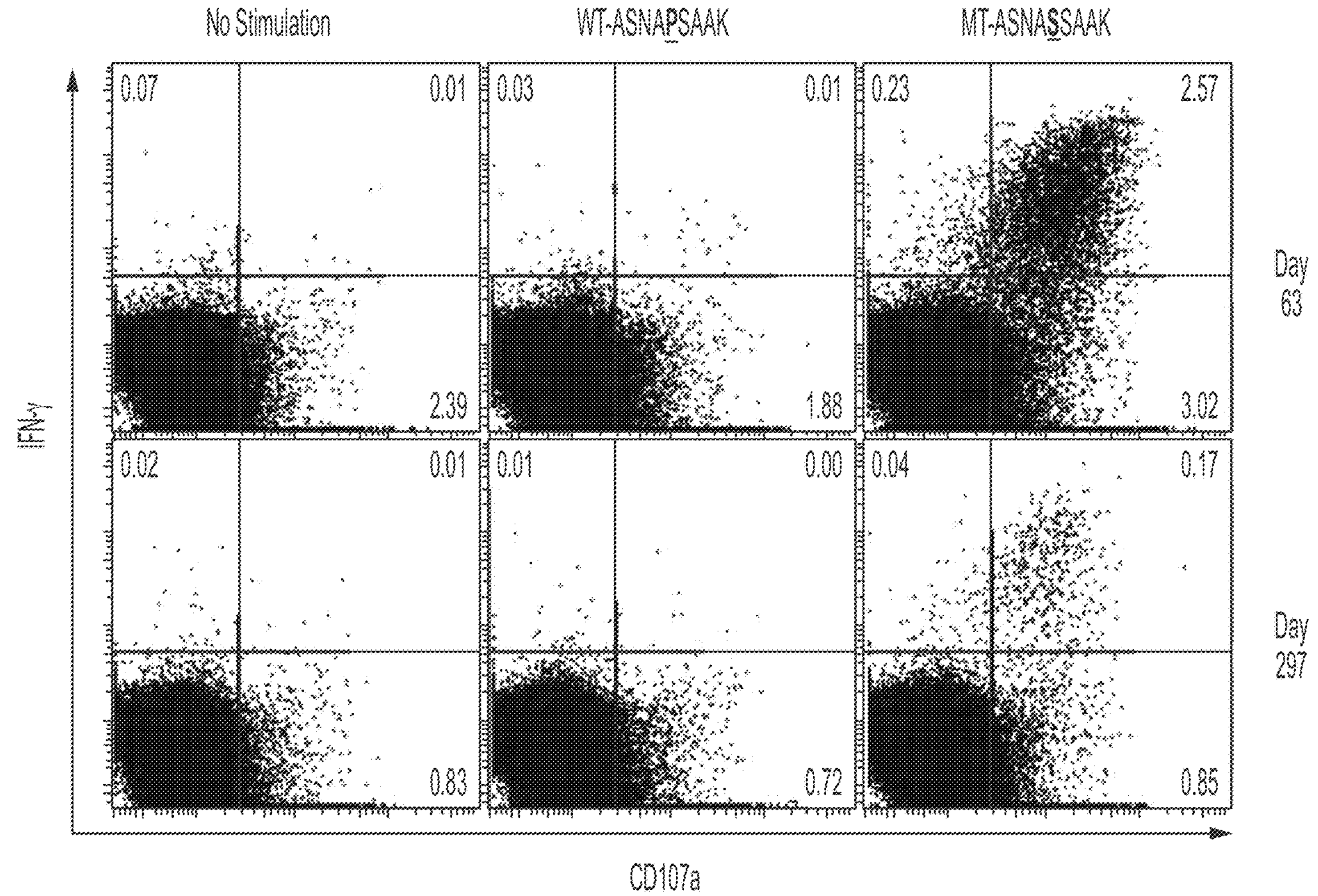
Figure 13C:
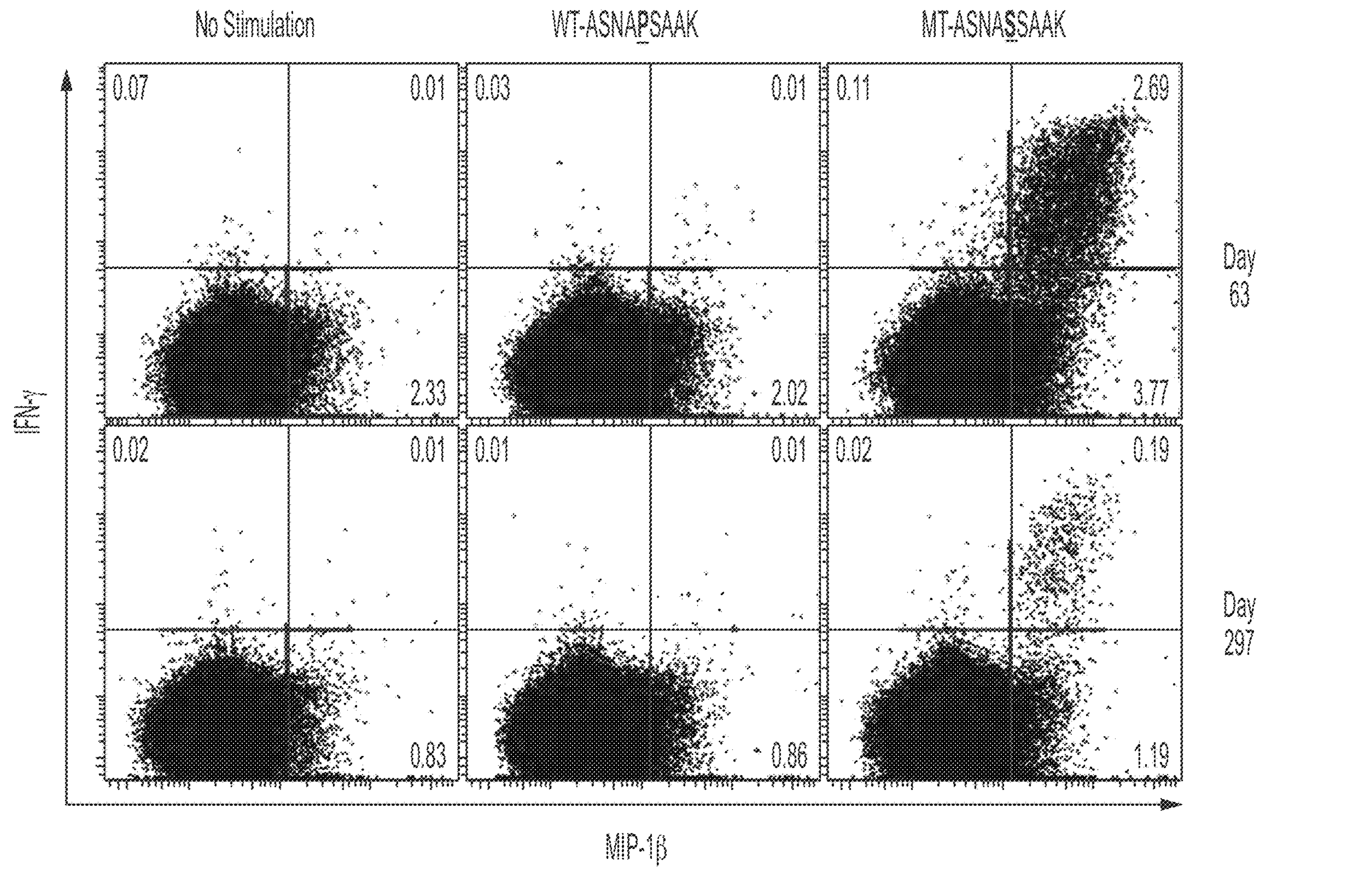
Figure 13D:
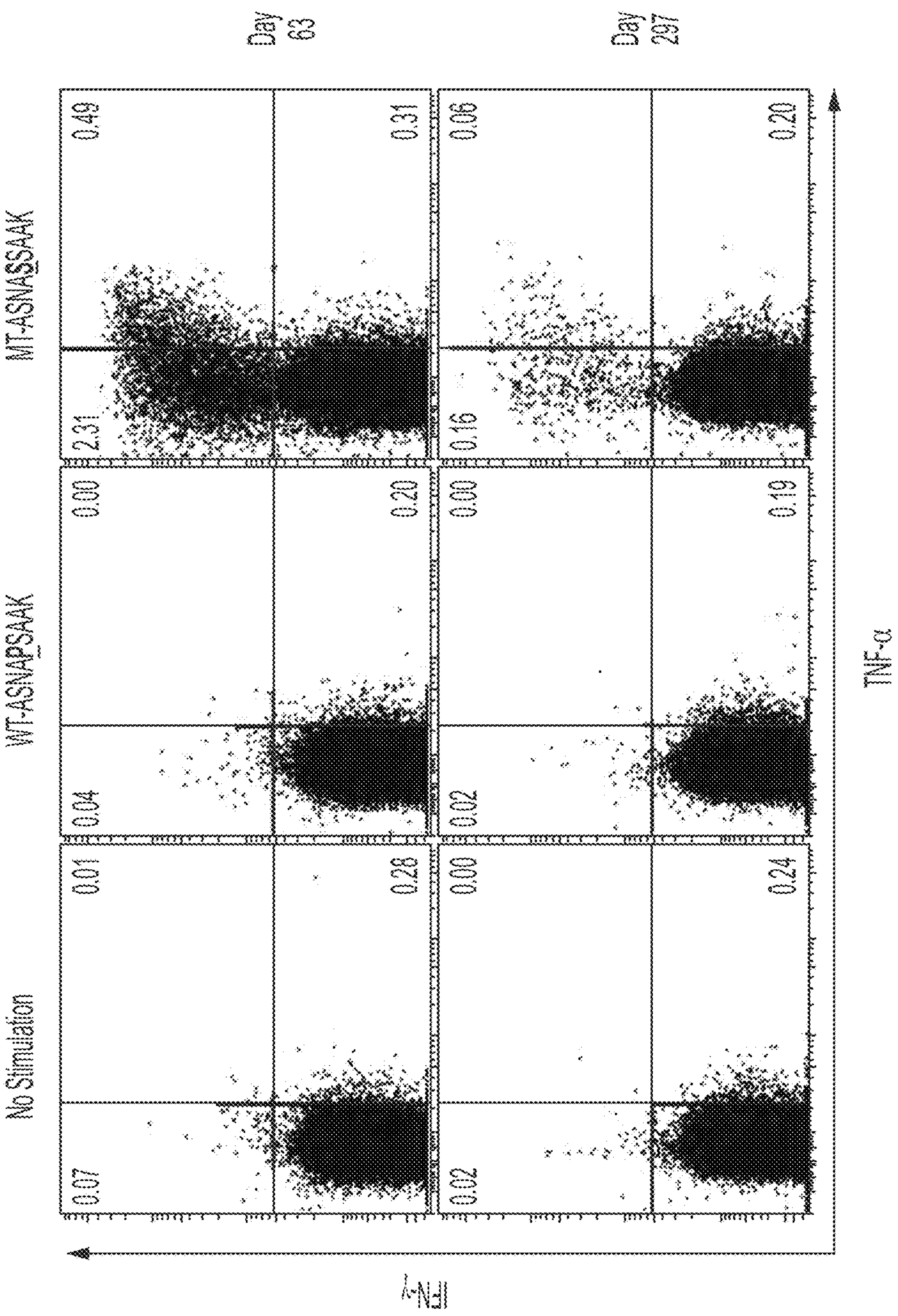

FIGS. 13A-13D demonstrate that following expansion, stimulation of peripheral blood mononuclear cells with wild type (SEQ ID NO: 5925) or mutant (SEQ ID NO: 344) peptide versus no stimulation control shows a polyfunctional CD8+ T cell response to the mutant peptide only. FIG. 13A shows neoantigen-induced IFNγ production by CD3+ CD8+ T-cells at day 63 and day 297 after initiation of therapy. FIG. 13B shows co-staining of CD107a in CD3+ CD8+IFNγ+ cells when stimulated with mutant peptide versus no stimulation or wild type. FIG. 13C shows co-staining of MIP-10 in CD3+CD8+IFNγ+ cells when stimulated with mutant peptide versus no stimulation or wild type. FIG. 13D shows co-staining of TNF-α in CD3+CD8+IFNγ+ cells when stimulated with mutant peptide versus no stimulation or wild type.

Figure 14A:
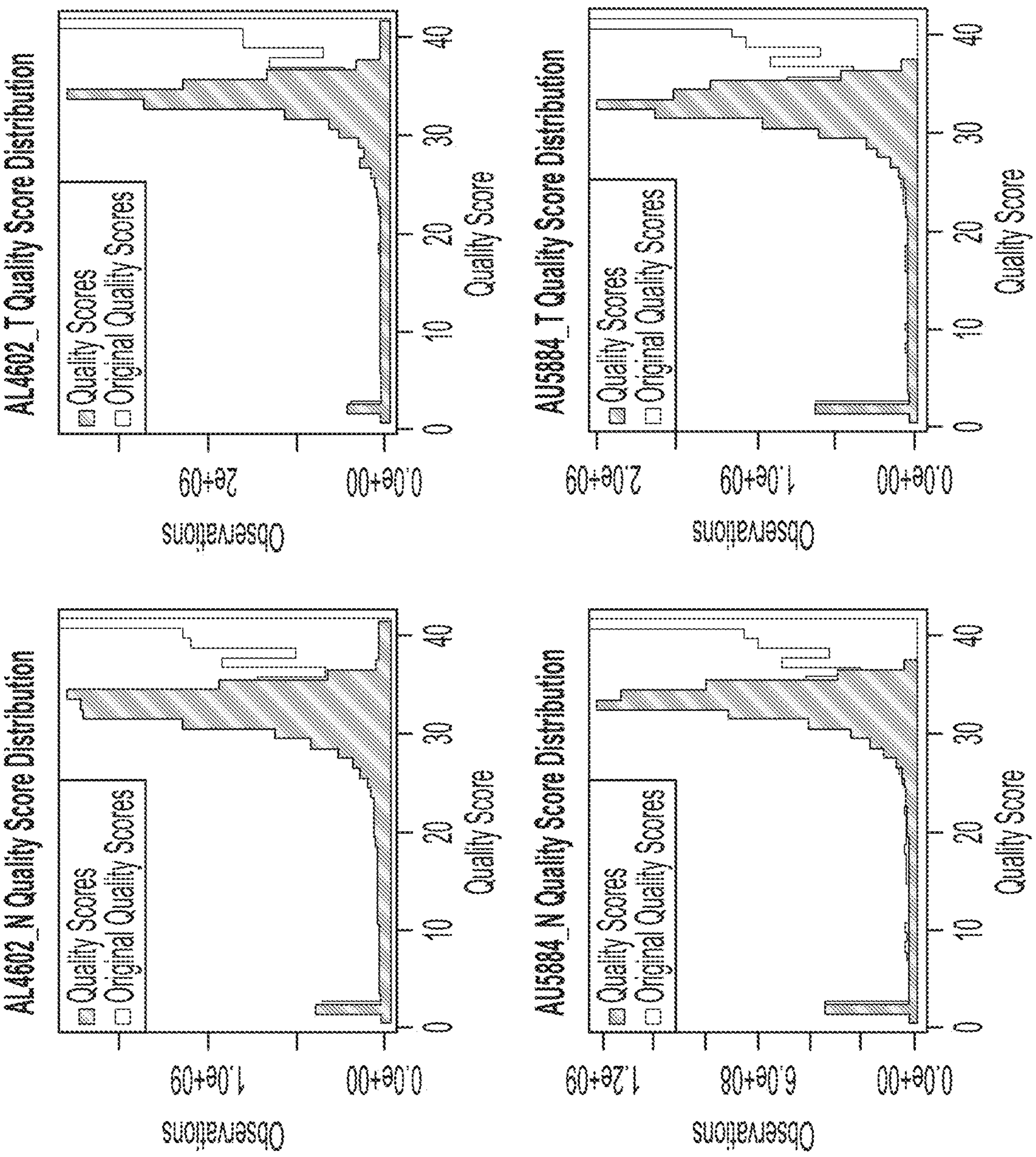
Figure 14B:
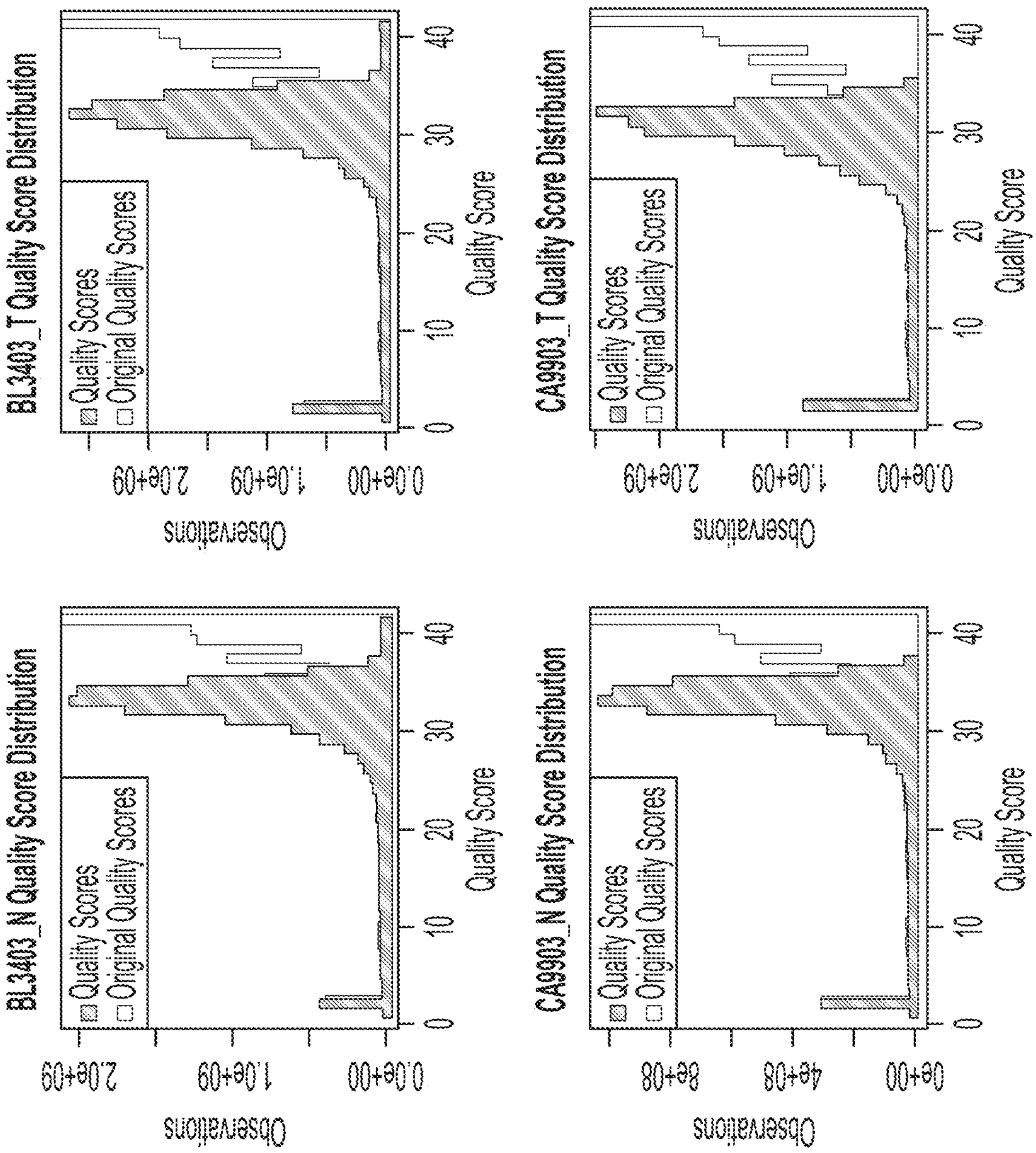
Figure 14C:
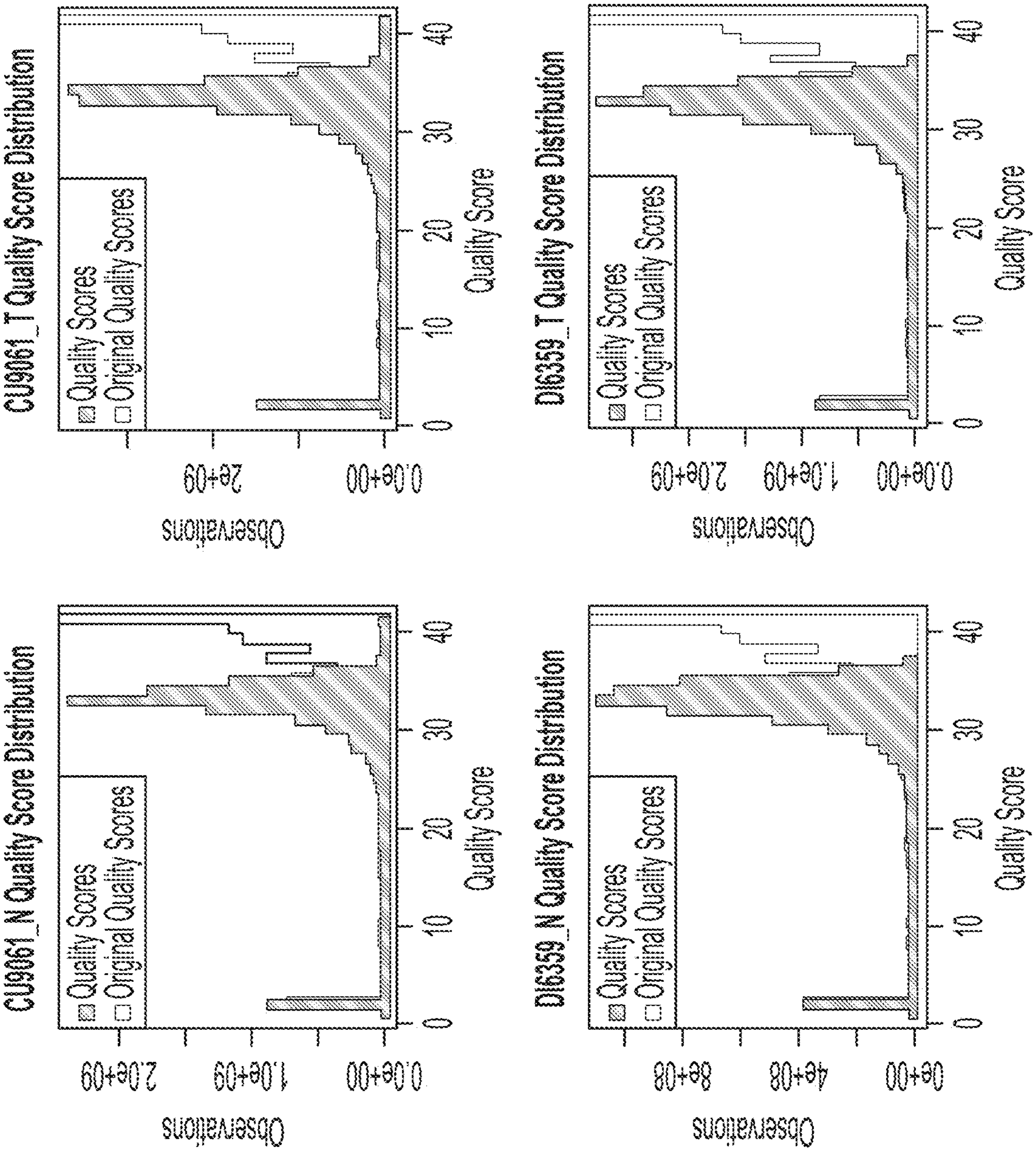
Figure 14D:
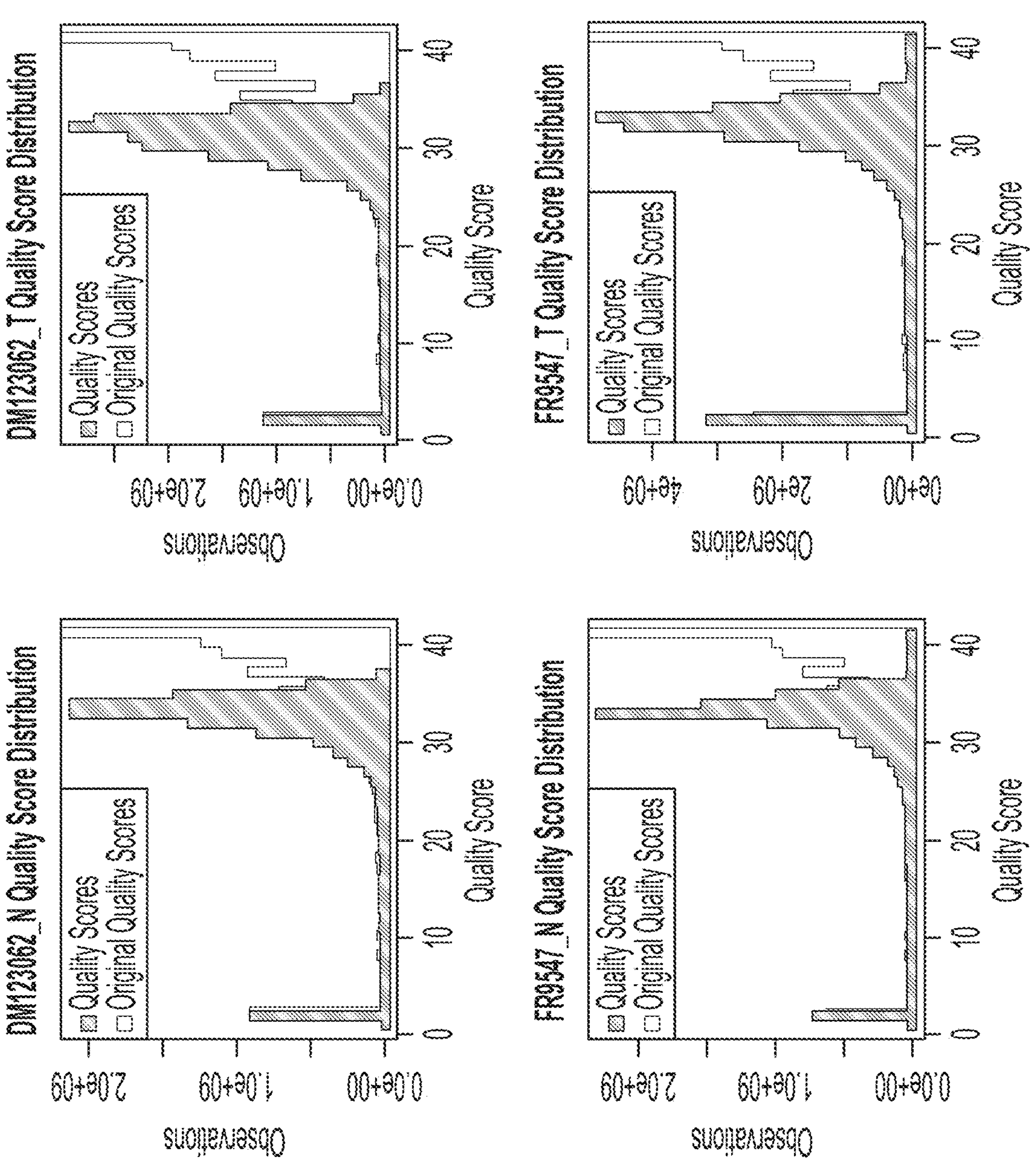
Figure 14E:
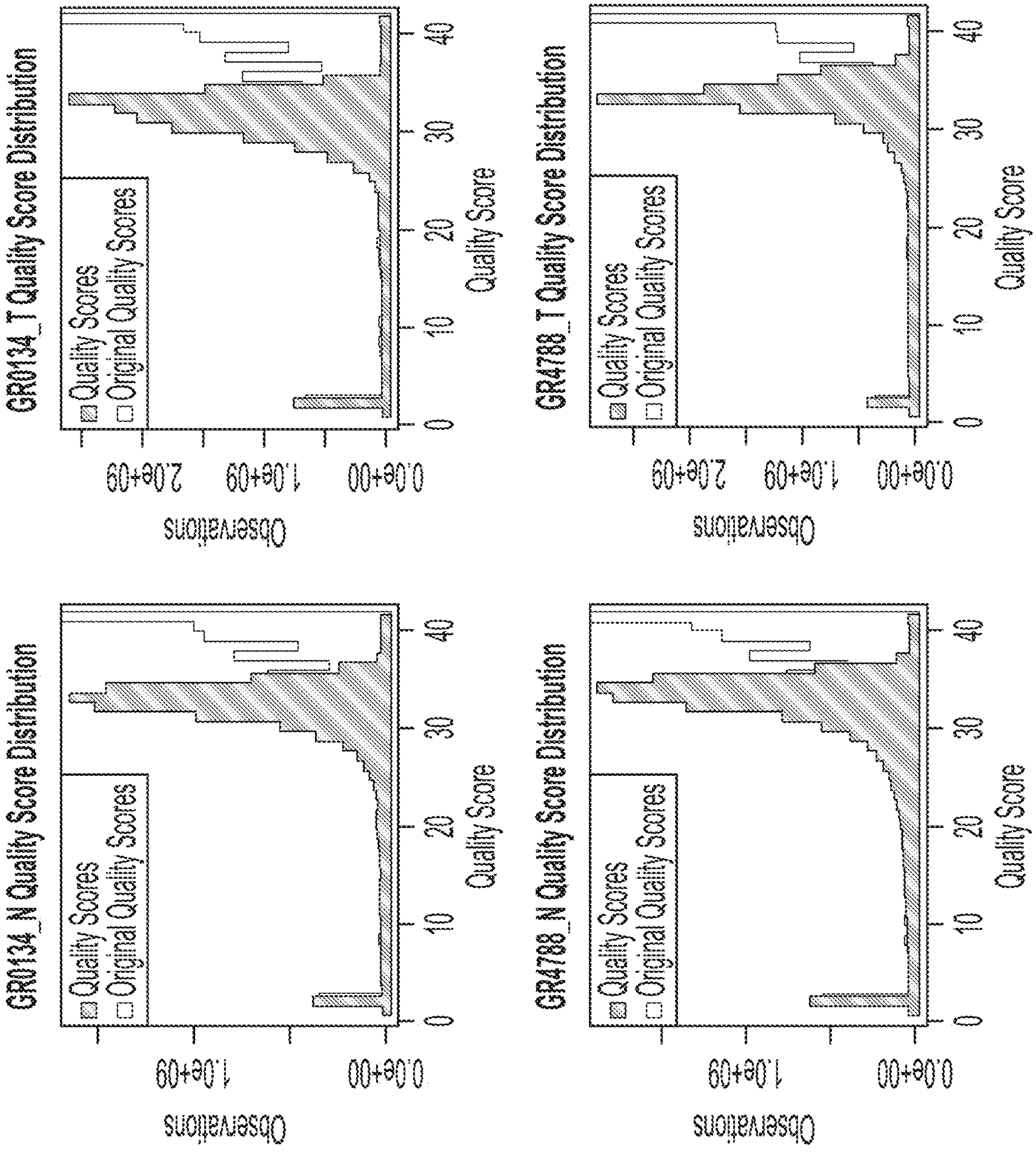
Figure 14F:
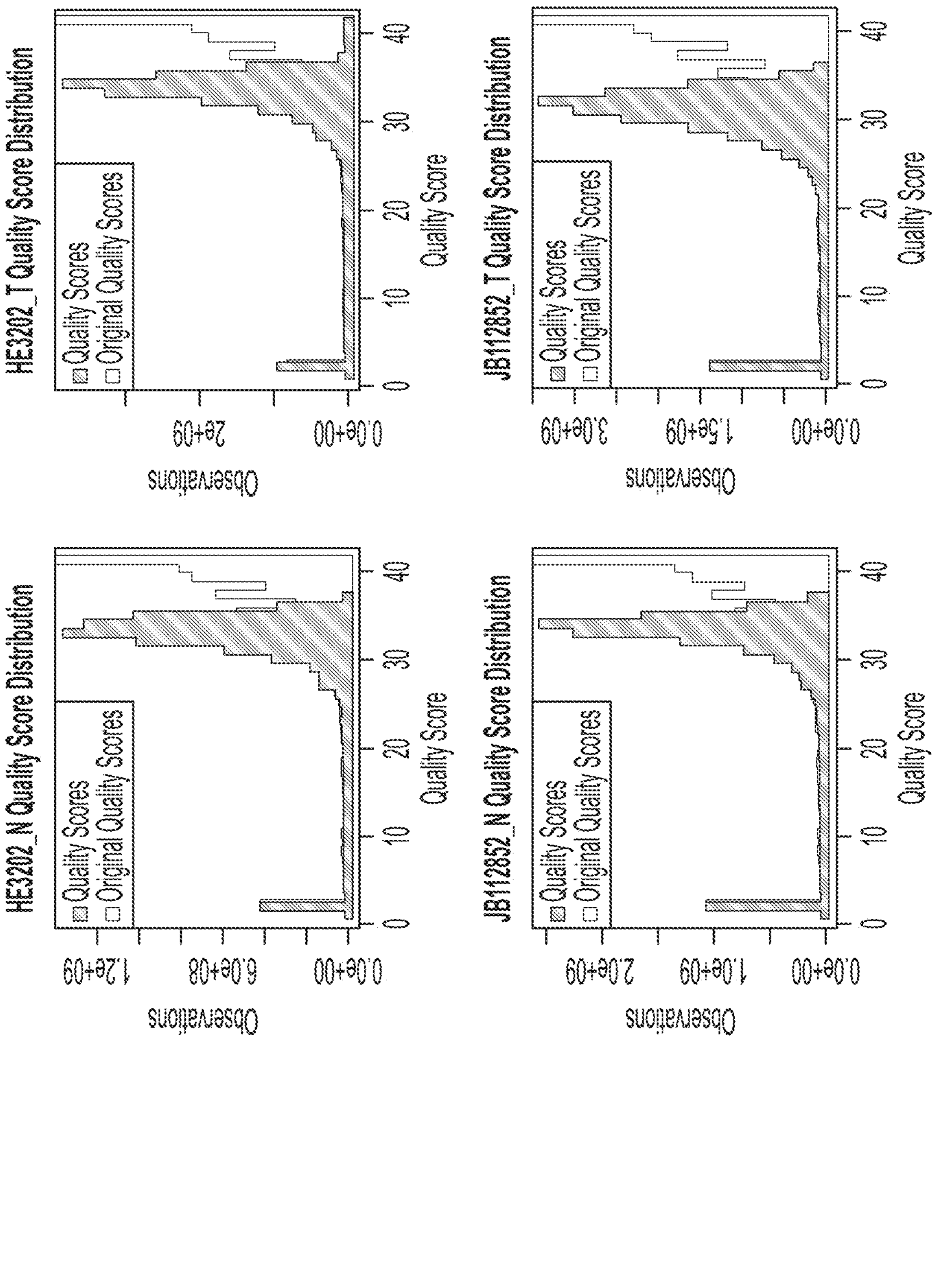
Figure 14G:
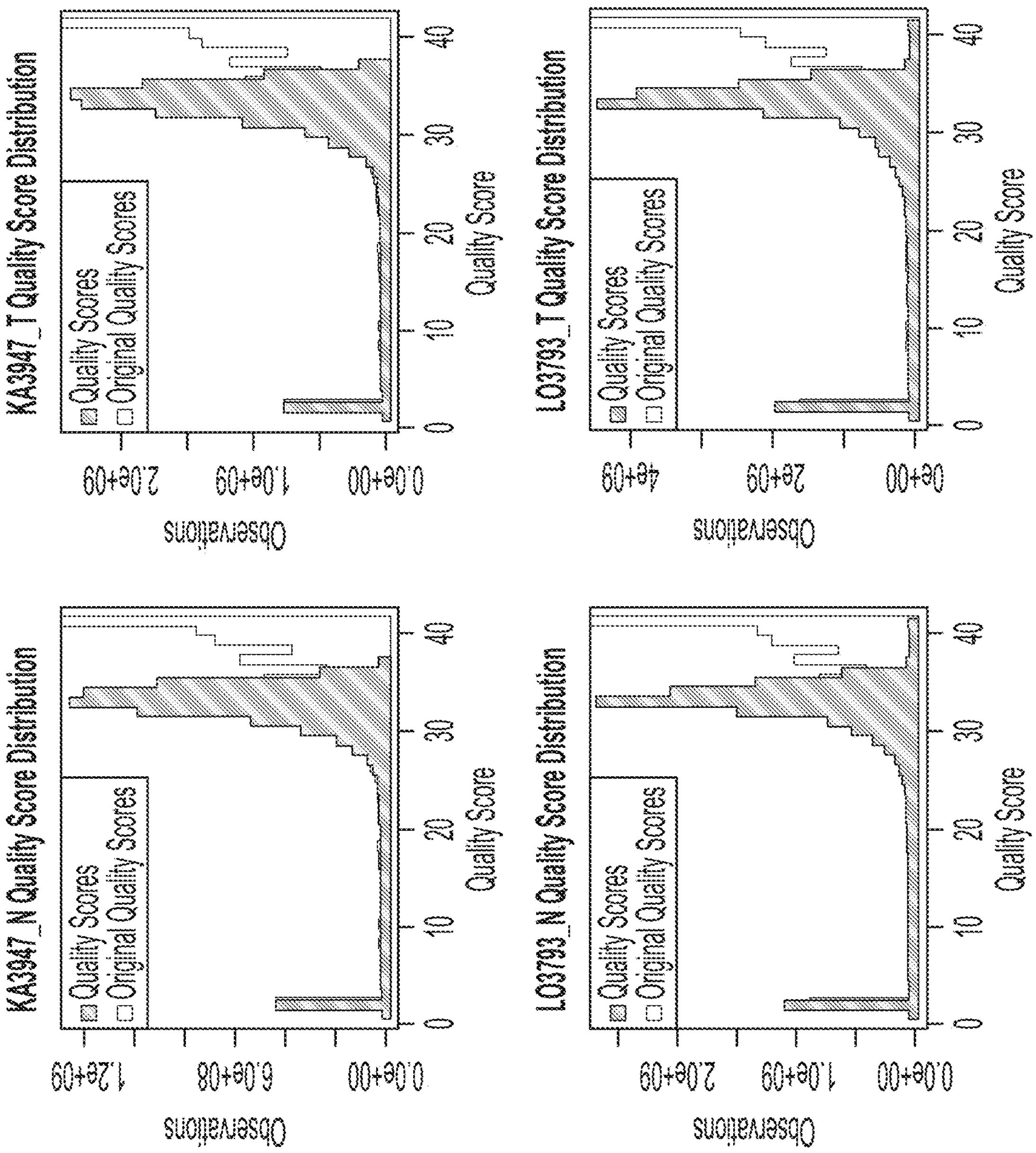
Figure 14H:
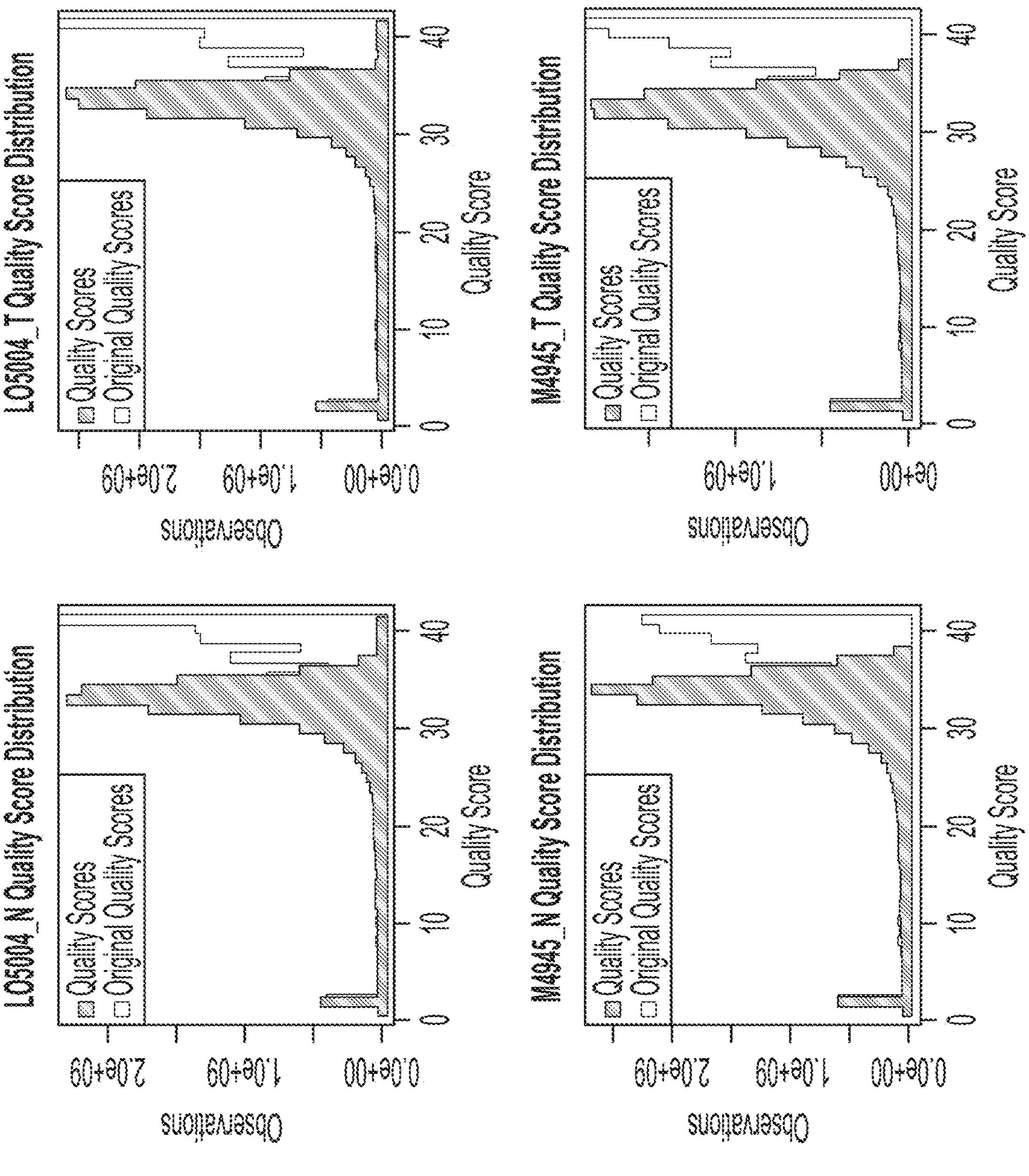
Figure 14I:
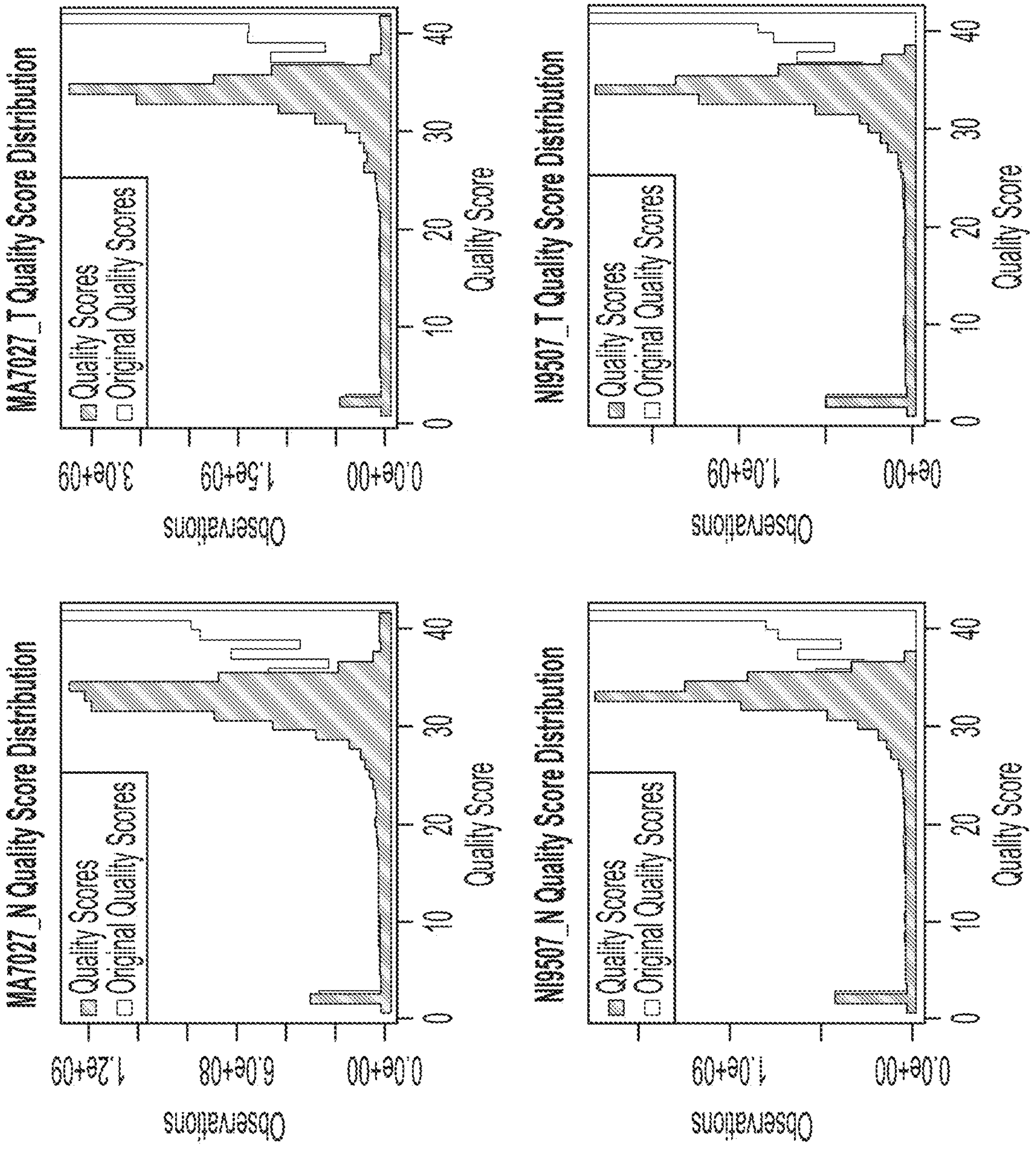
Figure 14J:
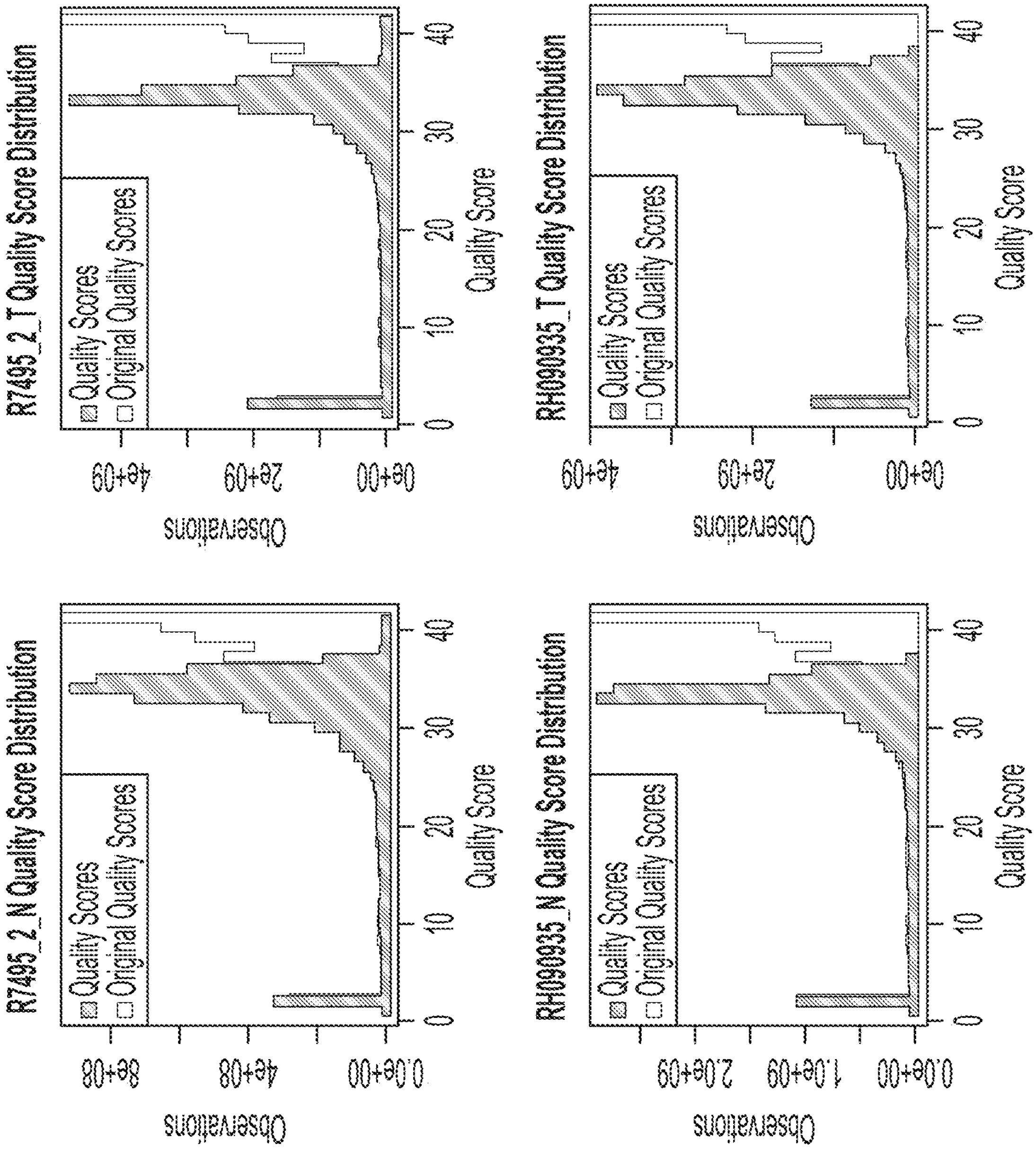
Figure 14K:
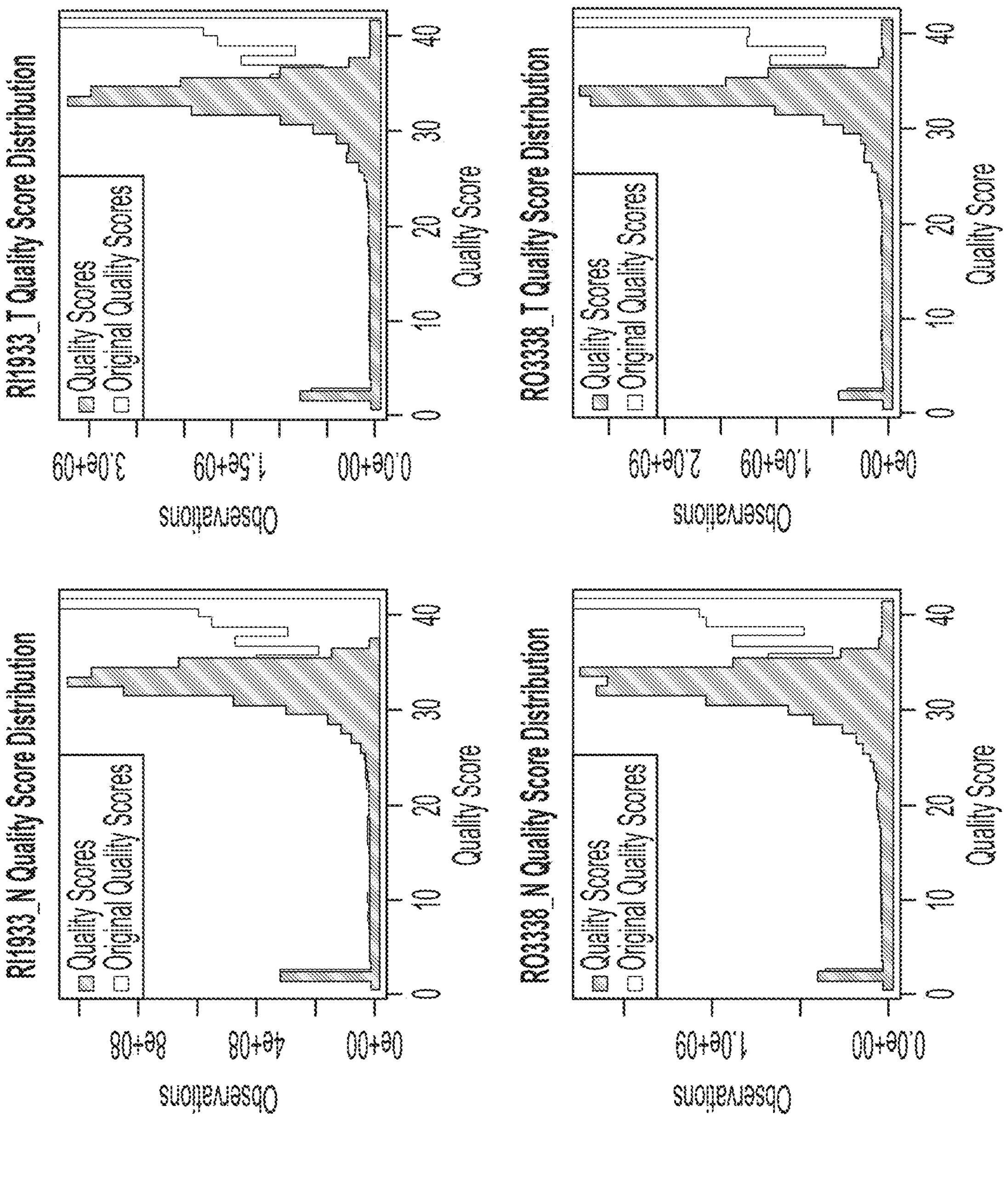
Figure 14L:
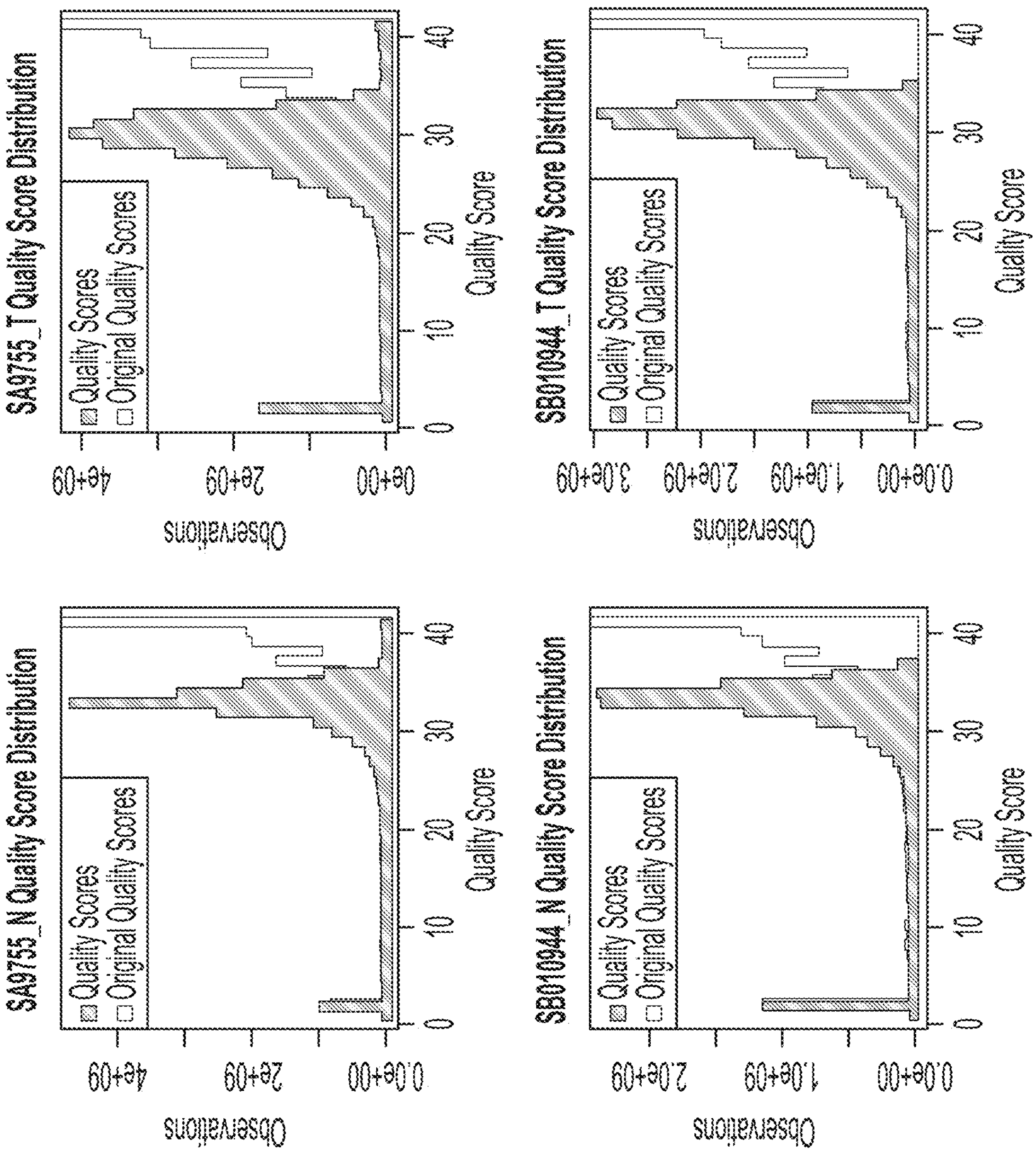
Figure 14M:
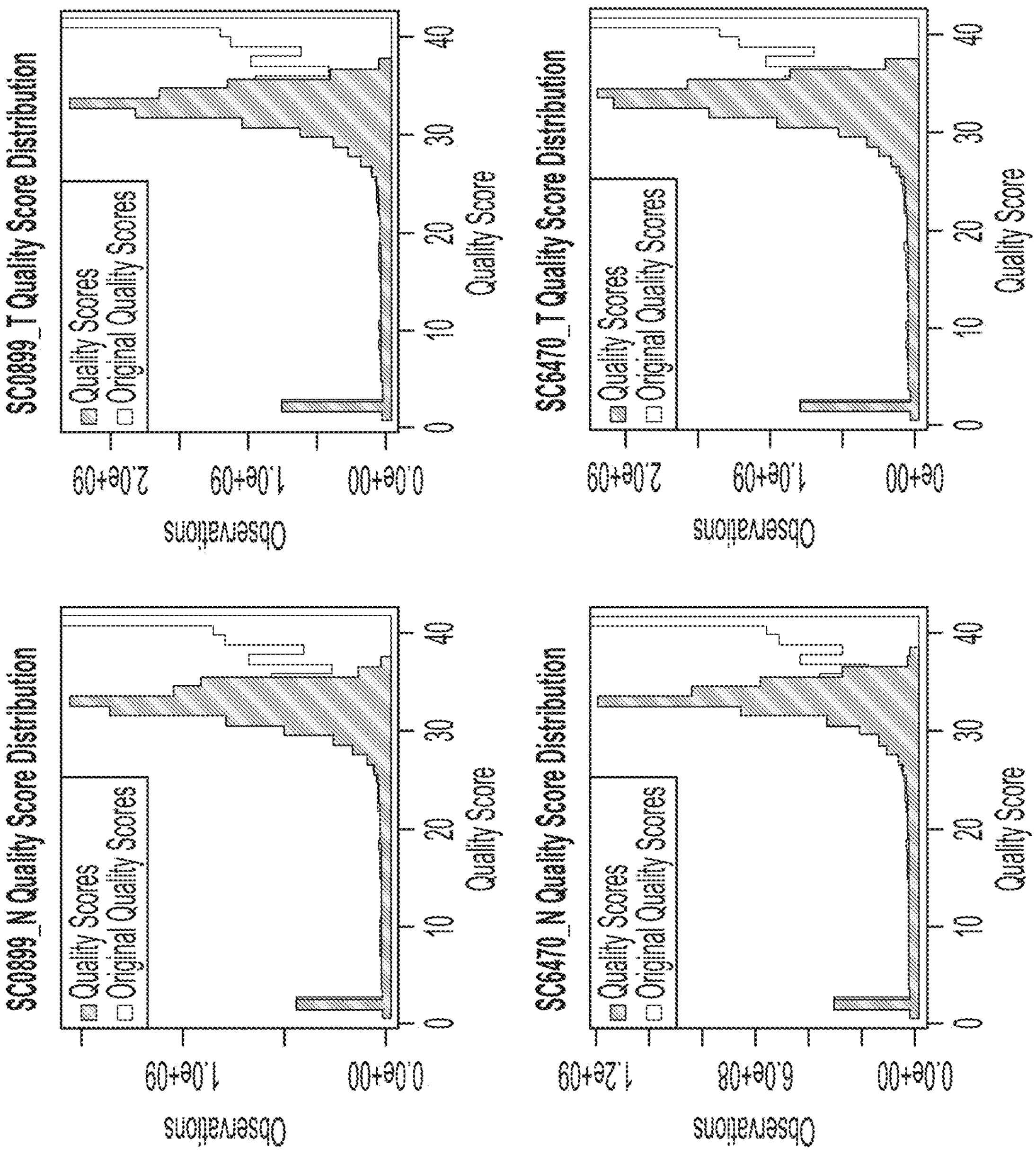
Figure 14N:
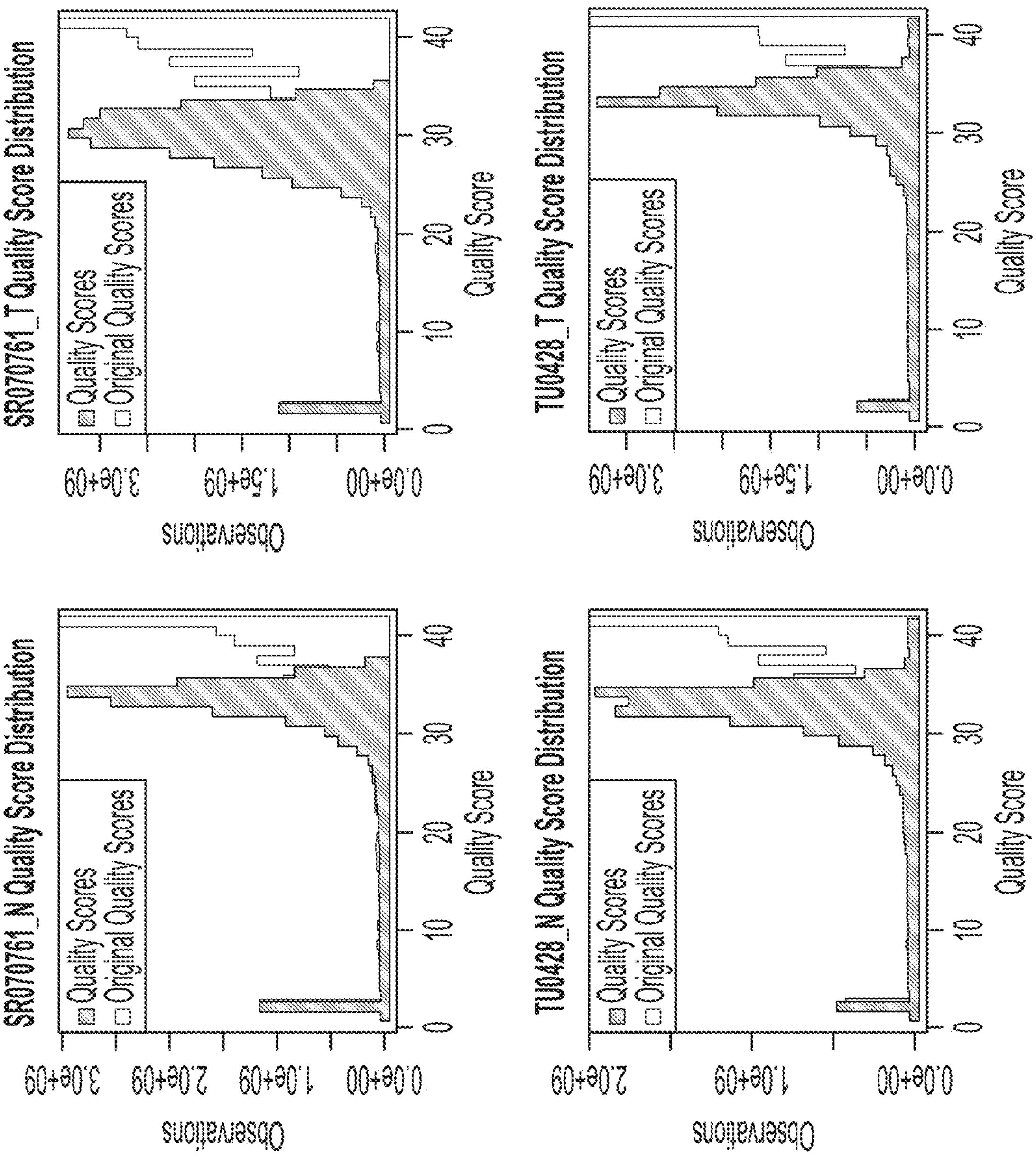
Figure 14O:
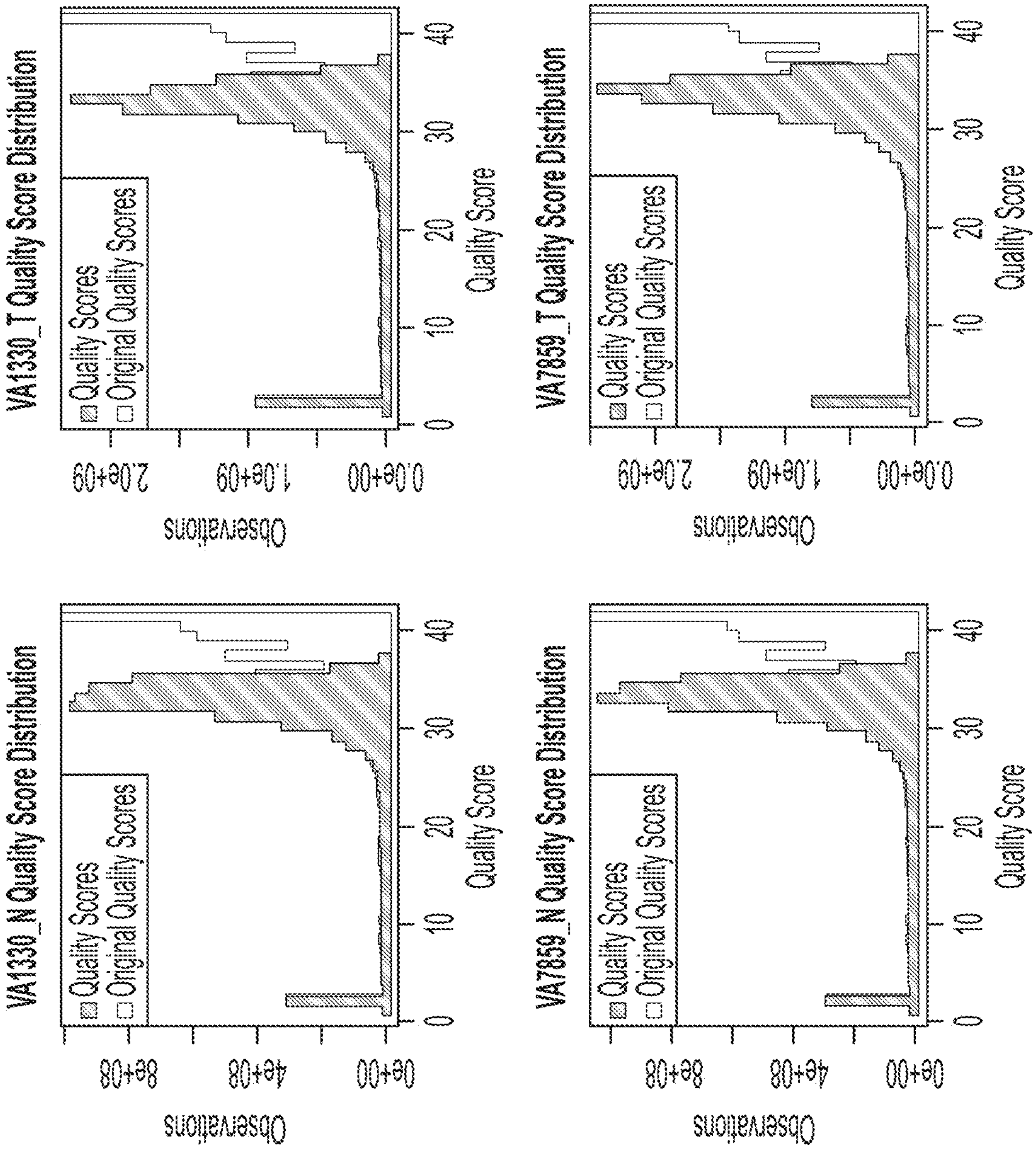
Figure 14P:
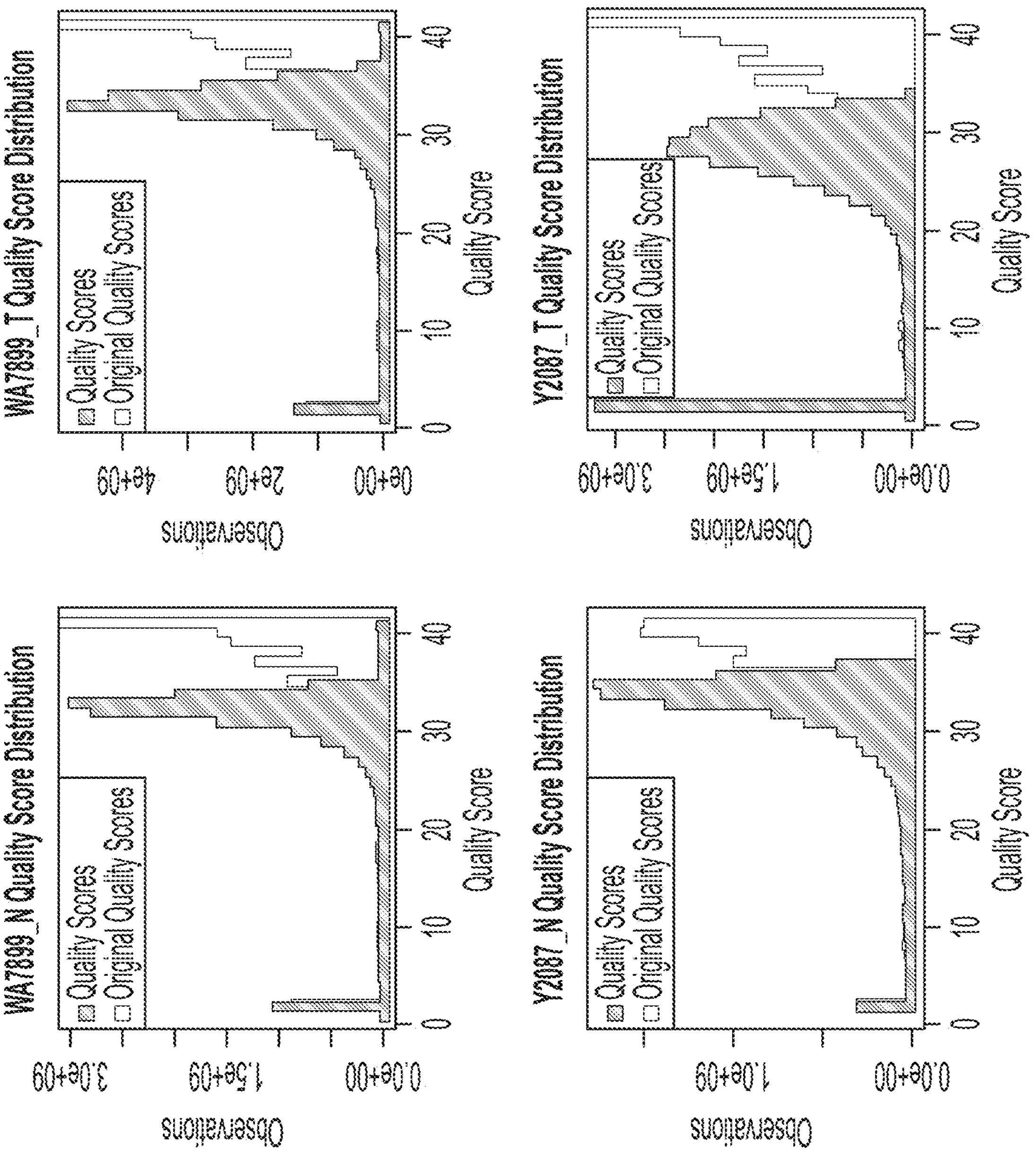
Figure 14Q:
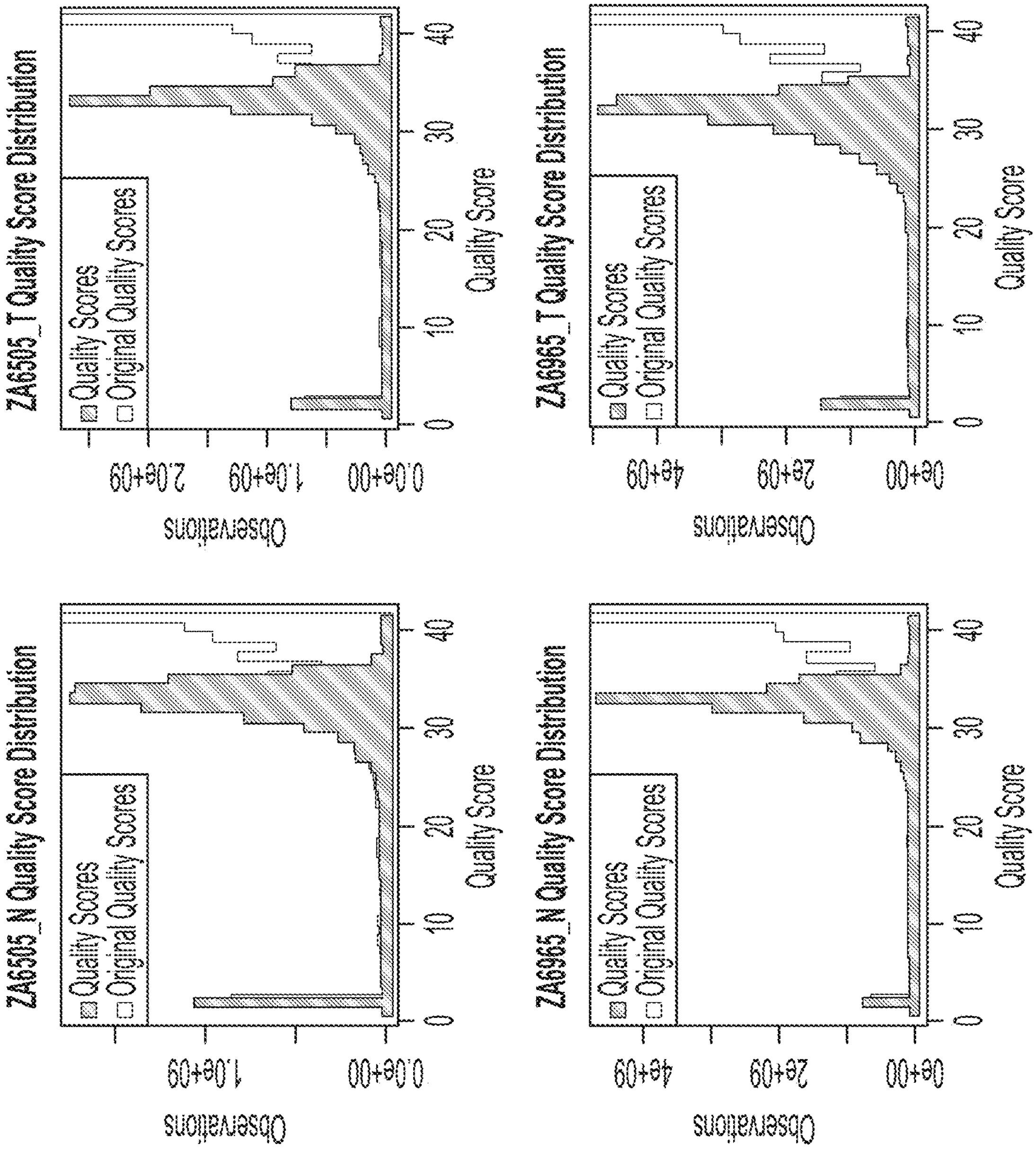

FIGS. 14A-14Q, show the DNA quality metrics.

FIG. 15 depicts a table summarizing clinical and genomic characteristics.

FIG. 16 depicts a table demonstrating nonsynonymous, total exonic mutation burden, and association with clinical efficacy to pembrolizumab. Analyzed independently, nonsynonymous mutation burden significantly correlates with improved confirmed ORR, DCB, and PFS (with the exception of ORR for the validation cohort, p=0.33). Clinical efficacy strongly correlates with nonsynonymous mutation burden in the overall set of sequenced NSCLCs. High total exonic mutation burden less strongly correlates with improved clinical efficacy. ^denotes that three patients are currently undergoing therapy and have not yet reached 6 months of follow-up; as such, these patients are not included in the DCB/NDB calculations and are removed from the numerator and denominator.

FIG. 17 depicts a table of detailed clinical and genomic characteristics of individual patients.

FIG. 18 depicts a table of quality metrics for all samples.

Figure 19A:
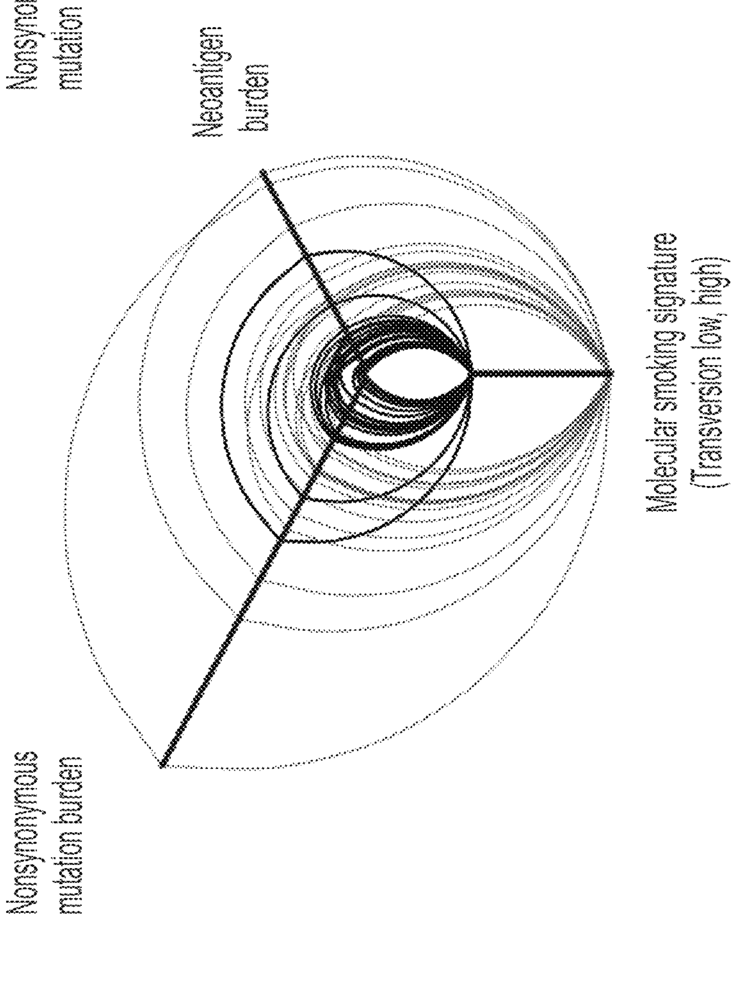
Figure 19B:
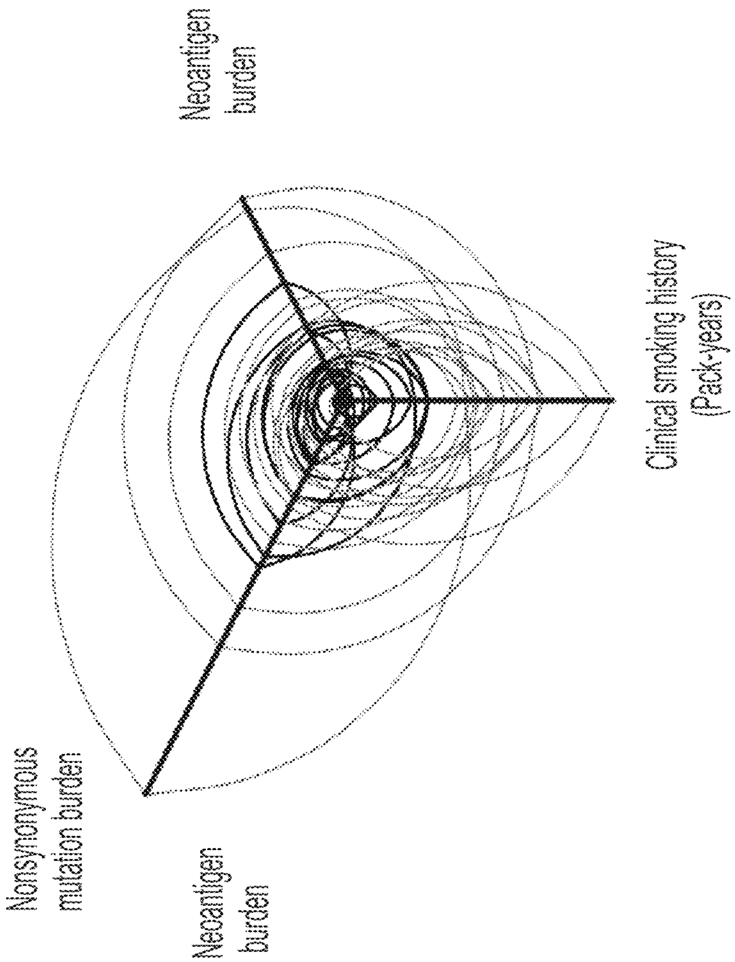

FIG. 19A-19B depict the correlation of molecular smoking signature, nonsynonymous mutation burden, and neoantigen burden. FIG. 19A shows a hive plot that displays the relationship between molecular smoking signature, mutation and neoantigen burden for each tumor. Red lines depict transversion low tumors; blue lines depict transversion high tumors. Transversion low tumors have significantly lower mutation and neoantigen burden compared to transversion high tumors (Mann Whitney p<0.0001 for both). Nonsynonymous mutation burden correlates with neoantigen burden (Spearman ρ 0.91, 95% CI 0.83-0.96, p<0.0001). In FIG. 19B, this hive plot displays the relationship between pack-years of tobacco consumption, mutation and neoantigen burden for each tumor. Red lines depict those who are light/never smokers (≤median pack-years of the cohort, 25); blue lines heavy smokers (>25 pack-years). Modest correlation is seen between pack-years and non-synonymous mutation burden (Spearman ρ 0.31, 95% CI −0.05-0.59, p=0.08) as well as between pack-years and neoantigen burden (Spearman ρ 0.35, 95% CI 0-0.62, p=0.04).

Figure 20:
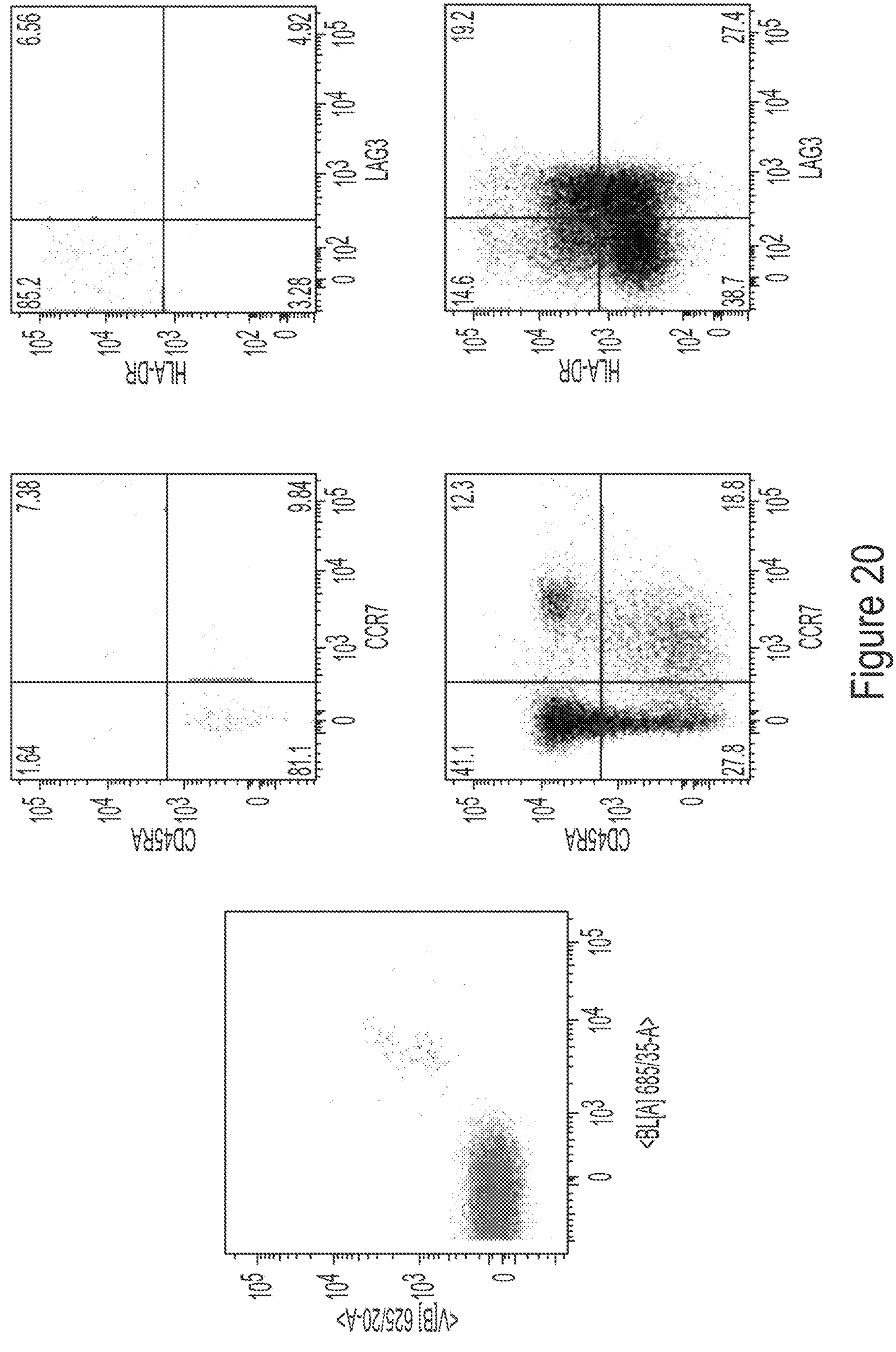

FIG. 20 depicts the immunophenotype of neoantigen-specific T-cells. In the left panel, peripheral blood lymphocytes (PBLs) from day 44 were used to identify HERC1 P3278S neoantigen (ASNASSAAK (SEQ ID NO: 344)) reactive T-cells using two-color MHC multimer staining, as described. Neoantigen-specific T-cells are represented by the events in the double positive position. Flow cytometry dot plots of staining of HERC1 P3278S neoantigen-specific T-cells (Top panels) and bulk CD8+ T-cells (Bottom panels) show expression of indicated phenotypic markers.

FIG. 21 depicts neoepitope sequences. FIG. 21 includes, among other things, a listing of immunogenic mutations, HLA typesm neoantigens and predicted MHC binding. "Mut" peptides disclosed as SEQ ID NOS 1-5581, respectively, in order of appearance, and "WT" peptides disclosed as SEQ ID NOS 5582-11162, respectively, in order of appearance.

DEFINITIONS

In order for the present invention to be more readily understood, certain terms are defined below. Those skilled in the art will appreciate that definitions for certain terms may be provided elsewhere in the specification, and/or will be clear from context.

Administration: As used herein, the term "administration" refers to the administration of a composition to a subject. Administration may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

Affinity: As is known in the art, "affinity" is a measure of the tightness with a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

Amino acid: As used herein, term "amino acid," in its broadest sense, refers to any compound and/or substance that can be incorporated into a polypeptide chain. In some embodiments, an amino acid has the general structure H2N-C(H)(R)—COOH. In some embodiments, an amino acid is a naturally occurring amino acid. In some embodiments, an amino acid is a synthetic amino acid; in some embodiments, an amino acid is a d-amino acid; in some embodiments, an amino acid is an 1-amino acid. "Standard amino acid" refers to any of the twenty standard 1-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Antibody agent: As used herein, the term "antibody agent" refers to an agent that specifically binds to a particular antigen. In some embodiments, the term encompasses any polypeptide with immunoglobulin structural elements sufficient to confer specific binding. Suitable antibody agents include, but are not limited to, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, and antibody fragments. As used herein, the term "antibody agent" also includes intact monoclonal antibodies, polyclonal antibodies, single domain antibodies (e.g., shark single domain antibodies (e.g., IgNAR or fragments thereof)), multispecific antibodies (e.g. bi-specific antibodies) formed from at least two intact antibodies, and antibody fragments so long as they exhibit the desired biological activity. In some embodiments, the term encompasses stapled peptides. In some embodiments, the term encompasses one or more antibody-like binding peptidomimetics. In some embodiments, the term encompasses one or more antibody-like binding scaffold proteins. In come embodiments, the term encompasses monobodies or adnectins. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

Antibody polypeptide: As used herein, the terms "antibody polypeptide" or "antibody", or "antigen-binding fragment thereof", which may be used interchangeably, refer to polypeptide(s) capable of binding to an epitope. In some embodiments, an antibody polypeptide is a full-length antibody, and in some embodiments, is less than full length but includes at least one binding site (comprising at least one, and preferably at least two sequences with structure of antibody "variable regions"). In some embodiments, the term "antibody polypeptide" encompasses any protein having a binding domain which is homologous or largely homologous to an immunoglobulin-binding domain. In particular embodiments, "antibody polypeptides" encompasses polypeptides having a binding domain that shows at least 99% identity with an immunoglobulin binding domain. In some embodiments, "antibody polypeptide" is any protein having a binding domain that shows at least 70%, 80%, 85%, 90%, or 95% identity with an immuglobulin binding domain, for example a reference immunoglobulin binding domain. An included "antibody polypeptide" may have an amino acid sequence identical to that of an antibody that is found in a natural source. Antibody polypeptides in accordance with the present invention may be prepared by any available means including, for example, isolation from a natural source or antibody library, recombinant production in or with a host system, chemical synthesis, etc., or combinations thereof. An antibody polypeptide may be monoclonal or polyclonal. An antibody polypeptide may be a member of any immunoglobulin class, including any of the human classes: IgG, IgM, IgA, IgD, and IgE. In certain embodiments, an antibody may be a member of the IgG immunoglobulin class. As used herein, the terms "antibody polypeptide" or "characteristic portion of an antibody" are used interchangeably and refer to any derivative of an antibody that possesses the ability to bind to an epitope of interest. In certain embodiments, the "antibody polypeptide" is an antibody fragment that retains at least a significant portion of the full-length antibody's specific binding ability. Examples of antibody fragments include, but are not limited to, Fab, Fab', F(ab')2, scFv, Fv, dsFv diabody, and Fd fragments. Alternatively or additionally, an antibody fragment may comprise multiple chains that are linked together, for example, by disulfide linkages. In some embodiments, an antibody polypeptide may be a human antibody. In some embodiments, the antibody polypeptides may be a humanized. Humanized antibody polypeptides include may be chimeric immunoglobulins, immunoglobulin chains or antibody polypeptides (such as Fv, Fab, Fab', F(ab')2 or other antigen-binding subsequences of antibodies) that contain minimal sequence derived from non-human immunoglobulin. In general, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In particular embodiments, antibody polypeptides for use in accordance with the present invention bind to particular epitopes of on immune checkpoint molecules.

Antigen: An "antigen" is a molecule or entity to which an antibody binds. In some embodiments, an antigen is or comprises a polypeptide or portion thereof. In some embodiments, an antigen is a portion of an infectious agent that is recognized by antibodies. In some embodiments, an antigen is an agent that elicits an immune response; and/or (ii) an agent that is bound by a T cell receptor (e.g., when presented by an MHC molecule) or to an antibody (e.g., produced by a B cell) when exposed or administered to an organism. In some embodiments, an antigen elicits a humoral response (e.g., including production of antigen-specific antibodies) in an organism; alternatively or additionally, in some embodiments, an antigen elicits a cellular response (e.g., involving T-cells whose receptors specifically interact with the antigen) in an organism. It will be appreciated by those skilled in the art that a particular antigen may elicit an immune response in one or several members of a target organism (e.g., mice, rabbits, primates, humans), but not in all members of the target organism species. In some embodiments, an antigen elicits an immune response in at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the members of a target organism species. In some embodiments, an antigen binds to an antibody and/or T cell receptor, and may or may not induce a particular physiological response in an organism. In some embodiments, for example, an antigen may bind to an antibody and/or to a T cell receptor in vitro, whether or not such an interaction occurs in vivo. In general, an antigen may be or include any chemical entity such as, for example, a small molecule, a nucleic acid, a polypeptide, a carbohydrate, a lipid, a polymer [in some embodiments other than a biologic polymer (e.g., other than a nucleic acid or amino acid polymer)] etc. In some embodiments, an antigen is or comprises a polypeptide. In some embodiments, an antigen is or comprises a glycan. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some embodiments, antigens utilized in accordance with the present invention are provided in a crude form. In some embodiments, an antigen is or comprises a recombinant antigen.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, %12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Burden: The term "burden" as used herein, for example in reference to mutation burden or neoantigen burden, refers to the number or rate (e.g., of mutations or neoantigens) in a sample or cohort, in some embodiments relative to that observed in an appropriate reference sample or cohort.

Combination therapy: The term "combination therapy", as used herein, refers to those situations in which two or more different pharmaceutical agents are administered in overlapping regimens so that the subject is simultaneously exposed to both agents. When used in combination therapy, two or more different agents may be administered simultaneously or separately. This administration in combination can include simultaneous administration of the two or more agents in the same dosage form, simultaneous administration in separate dosage forms, and separate administration. That is, two or more agents can be formulated together in the same dosage form and administered simultaneously. Alternatively, two or more agents can be simultaneously administered, wherein the agents are present in separate formulations. In another alternative, a first agent can be administered just followed by one or more additional agents. In the separate administration protocol, two or more agents may be administered a few minutes apart, or a few hours apart, or a few days apart.

Comparable: The term "comparable" is used herein to describe two (or more) sets of conditions, circumstances, individuals, or populations that are sufficiently similar to one another to permit comparison of results obtained or phenomena observed. In some embodiments, comparable sets of conditions, circumstances, individuals, or populations are characterized by a plurality of substantially identical features and one or a small number of varied features. Those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied. Those skilled in the art will appreciate that relative language used herein (e.g., enhanced, activated, reduced, inhibited, etc) will typically refer to comparisons made under comparable conditions.

Consensus sequence: As used herein, the term "consensus sequence" refers to a core sequence that elicits or drives a physiological phenomenon (e.g., an immune response). It is to be understood by those of skill in the art that a a cancer cell that shares a "consensus sequence" with an antigen of an infectious agent shares a portion of amino acid sequence that affects the binding affinity of the antigen to an MHC molecule (either directly or allosterically), and/or facilitates recognition by T cell receptors. In some embodiments, a consensus sequence is a tetrapeptide. In some embodiments, a consensus sequence is a nonapeptide. In some embodiments, a consensus sequence is between four and nine amino acids in length. In some embodiments, a consesnsus sequence is greater than nine amino acids in length.

Diagnostic information: As used herein, diagnostic information or information for use in diagnosis is any information that is useful in determining whether a patient has a disease or condition and/or in classifying the disease or condition into a phenotypic category or any category having significance with regard to prognosis of the disease or condition, or likely response to treatment (either treatment in general or any particular treatment) of the disease or condition. Similarly, diagnosis refers to providing any type of diagnostic information, including, but not limited to, whether a subject is likely to have a disease or condition (such as cancer), state, staging or characteristic of the disease or condition as manifested in the subject, information related to the nature or classification of a tumor, information related to prognosis and/or information useful in selecting an appropriate treatment. Selection of treatment may include the choice of a particular therapeutic (e.g., chemotherapeutic) agent or other treatment modality such as surgery, radiation, etc., a choice about whether to withhold or deliver therapy, a choice relating to dosing regimen (e.g., frequency or level of one or more doses of a particular therapeutic agent or combination of therapeutic agents), etc.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, a dosing regimen is or has been correlated with a desired therapeutic outcome, when administered across a population of patients.

Durable clinical benefit: As used herein, the term "durable clinical benefit" (DCB), has its art-understood meaning, referring to a clinical benefit that lasts for a relevant period of time. In some embodiments, such a clinical benefit is or comprises reduction in tumor size, increase in progression free survival, increase in overall survival, decrease in overall tumor burden, decrease in the symptoms caused by tumor growth such as pain, organ failure, bleeding, damage to the skeletal system, and other related sequelae of metastatic cancer and combinations thereof. In some embodiments, the relevant period of time is at least 1 month, 2 months, 3 months, 4 months, 5 months, 6 months, 7 months, 8 months, 9 months, 10 months, 11 months, 1 year, 2 years, 3 years, 4 years, 5 years, or longer. In some particular embodiments, the relevant period of time is 6 months.

Favorable response: As used herein, the term "favorable response" refers to a reduction in frequency and/or intensity of one or more symptoms, reduction in tumor burden, full or partial remission, or other improvement in disease pathophysiology. Symptoms are reduced when one or more symptoms of a particular disease, disorder or condition is reduced in magnitude (e.g., intensity, severity, etc.) and/or frequency. For purposes of clarity, a delay in the onset of a particular symptom is considered one form of reducing the frequency of that symptom. Many cancer patients with smaller tumors have no symptoms. It is not intended that the present invention be limited only to cases where the symptoms are eliminated. The present invention specifically contemplates treatment such that one or more symptoms is/are reduced (and the condition of the subject is thereby "improved"), albeit not completely eliminated. In some embodiments, a favorable response is established when a particular therapeutic regimen shows a statistically significant effect when administered across a relevant population; demonstration of a particular result in a specific individual may not be required. Thus, in some embodiments, a particular therapeutic regimen is determined to have a favorable response when its administration is correlated with a relevant desired effect.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Immune checkpoint modulator: As used herein, the term "immune checkpoint modulator" refers to an agent that interacts directly or indirectly with an immune checkpoint. In some embodiments, an immune checkpoint modulator increases an immune effector response (e.g., cytotoxic T cell response), for example by stimulating a positive signal for T cell activation. In some embodiments, an immune checkpoint modulator increases an immune effector response (e.g., cytotoxic T cell response), for example by inhibiting a negative signal for T cell activation (e.g. disinhibition). In some embodiments, an immune checkpoint modulator interferes with a signal for T cell anergy. In some embodiments, an immune checkpoint modulator reduces, removes, or prevents immune tolerance to one or more antigens.

Long Term Benefit: In general, the term "long term benefit" refers to a desirable clinical outcome, e.g., observed after administration of a particular treatment or therapy of interest, that is maintained for a clinically relevant period of time. To give but one example, in some embodiments, a long term benefit of cancer therapy is or comprises (1) no evidence of disease ("NED", for example upon radiographic assessment) and/or (2) stable or decreased volume of diseases. In some embodiments, a clinically relevant period of time is at least 1 month, at least 2 months, at least 3 months, at least 4 months, at least 5 months or more. In some embodiments, a clinically relevant period of time is at least six months. In some embodiments, a clinically relevant period of time is at least 1 year. Marker: A marker, as used herein, refers to an agent whose presence or level is a characteristic of a particular tumor or metastatic disease thereof. For example, in some embodiments, the term refers to a gene expression product that is characteristic of a particular tumor, tumor subclass, stage of tumor, etc. Alternatively or additionally, in some embodiments, a presence or level of a particular marker correlates with activity (or activity level) of a particular signaling pathway, for example that may be characteristic of a particular class of tumors. The statistical significance of the presence or absence of a marker may vary depending upon the particular marker. In some embodiments, detection of a marker is highly specific in that it reflects a high probability that the tumor is of a particular subclass. Such specificity may come at the cost of sensitivity (i.e., a negative result may occur even if the tumor is a tumor that would be expected to express the marker). Conversely, markers with a high degree of sensitivity may be less specific that those with lower sensitivity. According to the present invention a useful marker need not distinguish tumors of a particular subclass with 100% accuracy.

Modulator: The term "modulator" is used to refer to an entity whose presence in a system in which an activity of interest is observed correlates with a change in level and/or nature of that activity as compared with that observed under otherwise comparable conditions when the modulator is absent. In some embodiments, a modulator is an activator, in that activity is increased in its presence as compared with that observed under otherwise comparable conditions when the modulator is absent. In some embodiments, a modulator is an inhibitor, in that activity is reduced in its presence as compared with otherwise comparable conditions when the modulator is absent. In some embodiments, a modulator interacts directly with a target entity whose activity is of interest. In some embodiments, a modulator interacts indirectly (i.e., directly with an intermediate agent that interacts with the target entity) with a target entity whose activity is of interest. In some embodiments, a modulator affects level of a target entity of interest; alternatively or additionally, in some embodiments, a modulator affects activity of a target entity of interest without affecting level of the target entity. In some embodiments, a modulator affects both level and activity of a target entity of interest, so that an observed difference in activity is not entirely explained by or commensurate with an observed difference in level.

Mutation: As used herein, the term "mutation" refers to permanent change in the DNA sequence that makes up a gene. In some embodiments, mutations range in size from a single DNA building block (DNA base) to a large segment of a chromosome. In some embodiments, mutations can include missense mutations, frameshift mutations, duplications, insertions, nonsense mutation, deletions and repeat expansions. In some embodiments, a missense mutation is a change in one DNA base pair that results in the substitution of one amino acid for another in the protein made by a gene. In some embodiments, a nonsense mutation is also a change in one DNA base pair. Instead of substituting one amino acid for another, however, the altered DNA sequence prematurely signals the cell to stop building a protein. In some embodiments, an insertion changes the number of DNA bases in a gene by adding a piece of DNA. In some embodiments, a deletion changes the number of DNA bases by removing a piece of DNA. In some embodiments, small deletions may remove one or a few base pairs within a gene, while larger deletions can remove an entire gene or several neighboring genes. In some embodiments, a duplication consists of a piece of DNA that is abnormally copied one or more times. In some embodiments, frameshift mutations occur when the addition or loss of DNA bases changes a gene's reading frame. A reading frame consists of groups of 3 bases that each code for one amino acid. In some embodiments, a frameshift mutation shifts the grouping of these bases and changes the code for amino acids. In some embodiments, insertions, deletions, and duplications can all be frameshift mutations. In some embodiments, a repeat expansion is another type of mutation. In some embodiments, nucleotide repeats are short DNA sequences that are repeated a number of times in a row. For example, a trinucleotide repeat is made up of 3-base-pair sequences, and a tetranucleotide repeat is made up of 4-base-pair sequences. In some embodiments, a repeat expansion is a mutation that increases the number of times that the short DNA sequence is repeated.

Neoepitope: A "neoepitope" is understood in the art to refer to an epitope that emerges or develops in a subject after exposure to or occurrence of a particular event (e.g., development or progression of a particular disease, disorder or condition, e.g., infection, cancer, stage of cancer, etc). As used herein, a neoepitope is one whose presence and/or level is correlated with exposure to or occurrence of the event. In some embodiments, a neoepitope is one that triggers an immune response against cells that express it (e.g., at a relevant level). In some embodiments, a neopepitope is one that triggers an immune response that kills or otherwise destroys cells that express it (e.g., at a relevant level). In some embodiments, a relevant event that triggers a neoepitope is or comprises somatic mutation in a cell. In some embodiments, a neoepitope is not expressed in non-cancer cells to a level and/or in a manner that triggers and/or supports an immune response (e.g., an immune response sufficient to target cancer cells expressing the neoepitope). In some embodiments, a neoepitope is a neoantigen.

No Benefit: As used herein, the phrase "no benefit" is used to refer to absence of detectable clinical benefit (e.g., in response to administration of a particular therapy or treatment of interest). In some embodiments, absence of clinical benefit refers to absence of statistically significant change in any particular symptom or characteristic of a particular disease, disorder, or condition. In some embodiments, absence of clinical benefit refers to a change in one or more symptoms or characteristics of a disease, disorder, or condition, that lasts for only a short period of time such as, for example, less than about 6 months, less than about 5 months, less than about 4 months, less than about 3 months, less than about 2 months, less than about 1 month, or less. In some embodiments, no benefit refers to no durable benefit.

Objective Response: As used herein, the phrase "objective response" refers to size reduction of a cancerous mass by a defined amount. In some embodiments, the cancerous mass is a tumor. In some embodiments, confirmed objective response is response confirmed at least four (4) weeks after treatment.

Objective Response Rate: As used herein, the term "objective response rate" ("ORR") has its art-understood meaning referring to the proportion of patients with tumor size reduction of a predefined amount and for a minimum time period. In some embodiments, response duration usually measured from the time of initial response until documented tumor progression. In some embodiments, ORR involves the sum of partial responses plus complete responses.

Patient: As used herein, the term "patient" or "subject" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes cancer, or presence of one or more tumors. In some embodiments, the disorder or condition is metastatic cancer.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Prognostic and predictive information: As used herein, the terms prognostic and predictive information are used interchangeably to refer to any information that may be used to indicate any aspect of the course of a disease or condition either in the absence or presence of treatment. Such information may include, but is not limited to, the average life expectancy of a patient, the likelihood that a patient will survive for a given amount of time (e.g., 6 months, 1 year, 5 years, etc.), the likelihood that a patient will be cured of a disease, the likelihood that a patient's disease will respond to a particular therapy (wherein response may be defined in any of a variety of ways). Prognostic and predictive information are included within the broad category of diagnostic information.

Progression Free Survival: As used herein, the term "progression free survival" (PFS) has its art-understood meaning relating to the length of time during and after the treatment of a disease, such as cancer, that a patient lives with the disease but it does not get worse. In some embodiments, measuring the progression-free survival is utilized as an assessment of how well a new treatment works. In some embodiments, PFS is determined in a randomized clinical trial; in some such embodiments, PFS refers to time from randomization until objective tumor progression and/or death.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids.

Reference: Those of skill in the art will appreciate that, in many embodiments described herein, a determined value or characteristic of interest is compared with an appropriate reference. In some embodiments, a reference value or characteristic is one determined for a comparable cohort, individual, population, or sample. In some embodiments, a reference value or characteristic is tested and/or determined substantially simultaneously with the testing or determination of the characteristic or value of interest. In some embodiments, a reference characteristic or value is or comprises a historical reference, optionally embodied in a tangible medium. Typically, as would be understood by those skilled in the art, a reference value or characteristic is determined under conditions comparable to those utilized to determine or analyze the characteristic or value of interest.

Response: As used herein, the term "response" may refer to an alteration in a subject's condition that occurs as a result of or correlates with treatment. In some embodiments, a response is or comprises a beneficial response. In some embodiments, a beneficial response may include stabilization of the condition (e.g., prevention or delay of deterioration expected or typically observed to occur absent the treatment), amelioration (e.g., reduction in frequency and/or intensity) of one or more symptoms of the condition, and/or improvement in the prospects for cure of the condition, etc. In some embodiments, "response" may refer to response of an organism, an organ, a tissue, a cell, or a cell component or in vitro system. In some embodiments, a response is or comprises a clinical response. In some embodiments, presence, extent, and/or nature of response may be measured and/or characterized according to particular criteria; in some embodiments, such criteria may include clinical criteria and/or objective criteria. In some embodiments, techniques for assessing response may include, but are not limited to, clinical examination, positron emission tomography, chest X-ray CT scan, MRI, ultrasound, endoscopy, laparoscopy, presence or level of a particular marker in a sample, cytology, and/or histology. Where a response of interest is or comprises response of a tumor to therapy, those of ordinary skill will be aware of a variety of established techniques for assessing such response, including, for example, for determining tumor burden, tumor size, tumor stage, etc. For example, certain technologies for assessing response of solid tumors to treatment are discussed in Therasse et. al., "New guidelines to evaluate the response to treatment in solid tumors", European Organization for Research and Treatment of Cancer, National Cancer Institute of the United States, National Cancer Institute of Canada, *J. Natl. Cancer Inst.,* 2000, 92(3):205-216. Those of ordinary skill in the art will be aware of, and/or will appreciate in light of the present disclosure, strategies for determining particular response criteria for individual tumors, tumor types, patient populations or cohorts, etc, as well as for determining appropriate references therefor.

Sample: As used herein, the term "sample" typically refers to a biological sample obtained or derived from a source of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Specific binding: As used herein, the terms "specific binding" or "specific for" or "specific to" refer to an interaction (typically non-covalent) between a target entity (e.g., a target protein or polypeptide) and a binding agent (e.g., an antibody, such as a provided antibody). As will be understood by those of ordinary skill, an interaction is considered to be "specific" if it is favored in the presence of alternative interactions. In many embodiments, an interaction is typically dependent upon the presence of a particular structural feature of the target molecule such as an antigenic determinant or epitope recognized by the binding molecule. For example, if an antibody is specific for epitope A, the presence of a polypeptide containing epitope A or the presence of free unlabeled A in a reaction containing both free labeled A and the antibody thereto, will reduce the amount of labeled A that binds to the antibody. It is to be understood that specificity need not be absolute. For example, it is well known in the art that numerous antibodies cross-react with other epitopes in addition to those present in the target molecule. Such cross-reactivity may be acceptable depending upon the application for which the antibody is to be used. In particular embodiments, an antibody specific for receptor tyrosine kinases has less than 10% cross-reactivity with receptor tyrosine kinase bound to protease inhibitors (e.g., ACT). One of ordinary skill in the art will be able to select antibodies having a sufficient degree of specificity to perform appropriately in any given application (e.g., for detection of a target molecule, for therapeutic purposes, etc.). Specificity may be evaluated in the context of additional factors such as the affinity of the binding molecule for the target molecule versus the affinity of the binding molecule for other targets (e.g., competitors).

Stage of cancer: As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

Subject: As used herein, the term "subject" or "patient" refers to any organism upon which embodiments of the invention may be used or administered, e.g., for experimental, diagnostic, prophylactic, and/or therapeutic purposes.

Typical subjects include animals (e.g., mammals such as mice, rats, rabbits, non-human primates, and humans; insects; worms; etc.).

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, or condition (e.g., a cancer) has been diagnosed with and/or exhibits one or more symptoms of the disease, disorder, or condition. In some embodiments, an individual who is suffering from cancer has cancer, but does not display any symptoms of cancer and/or has not been diagnosed with a cancer.

Susceptible to: An individual who is "susceptible to" a disease, disorder, or condition (e.g., cancer) is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who displays conditions associated with development of the disease, disorder, or condition. In some embodiments, a risk of developing a disease, disorder, and/or condition is a population-based risk.

Target cell or target tissue: As used herein, the terms "target cell" or "target tissue" refer to any cell, tissue, or organism that is affected by a condition described herein and to be treated, or any cell, tissue, or organism in which a protein involved in a condition described herein is expressed. In some embodiments, target cells, target tissues, or target organisms include those cells, tissues, or organisms in which there is a detectable amount of immune checkpoint signaling and/or activity. In some embodiments, target cells, target tissues, or target organisms include those cells, tissues or organisms that display a disease-associated pathology, symptom, or feature.

Therapeutic regimen: As used herein, the term "therapeutic regimen" refers to any method used to partially or completely alleviate, ameliorate, relieve, inhibit, prevent, delay onset of, reduce severity of and/or reduce incidence of one or more symptoms or features of a particular disease, disorder, and/or condition. It may include a treatment or series of treatments designed to achieve a particular effect, e.g., reduction or elimination of a detrimental condition or disease such as cancer. The treatment may include administration of one or more compounds either simultaneously, sequentially or at different times, for the same or different amounts of time. Alternatively, or additionally, the treatment may include exposure to radiation, chemotherapeutic agents, hormone therapy, or surgery. In addition, a "treatment regimen" may include genetic methods such as gene therapy, gene ablation or other methods known to reduce expression of a particular gene or translation of a gene-derived mRNA.

Therapeutic agent: As used herein, the phrase "therapeutic agent" refers to any agent that, when administered to a subject, has a therapeutic effect and/or elicits a desired biological and/or pharmacological effect.

Therapeutically effective amount: As used herein, the term "therapeutically effective amount" refers to an amount of an agent (e.g., an immune checkpoint modulator) that confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic agent or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic agent, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the subject; the time of administration, route of administration, and/or rate of excretion or metabolism of the specific fusion protein employed; the duration of the treatment; and like factors as is well known in the medical arts.

Treatment: As used herein, the term "treatment" (also "treat" or "treating") refers to any administration of a substance (e.g., provided compositions) that partially or completely alleviates, ameliorates, relieves, inhibits, delays onset of, reduces severity of, and/or reduces incidence of one or more symptoms, features, and/or causes of a particular disease, disorder, and/or condition (e.g., cancer). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Wild-type: As used herein, the term "wild-type" has its art-understood meaning that refers to an entity having a structure and/or activity as found in nature in a "normal" (as contrasted with mutant, diseased, altered, etc.) state or context. Those of ordinary skill in the art will appreciate that wild-type genes and polypeptides often exist in multiple different forms (e.g., alleles).

DETAILED DESCRIPTION OF CERTAIN EMBODIMENTS

The present invention encompasses the discovery of particular signatures and/or characteristics that can be detected in certain tumors or tumor samples and that predict or correlate with responsiveness to immune checkpoint modulator therapy. For example, among other things, the present disclosure demonstrates that a high mutational load can correlate with such responsiveness. The present disclosure also particularly demonstrates that presence (e.g., number and/or rate) and/or identity of somatic neoepitopes (e.g., which may result from tumor mutations) can contribute to, and therefore may correlate with, such responsiveness. Among other things, the present disclosure defines certain mutation and/or neoepitope characteristics of relevant tumors that correlate with and/or can be used to predict responsiveness to immune checkpoint modulator therapy. The present disclosure also provides technologies for defining and/or detecting certain mutation "signatures" useful in predicting and/or characterizing such responsiveness.

Furthermore, the overall number and/or rate of mutation and/or of neoepitopes in cancer cells can be predictive of clinical response to immunotherapy, and particularly to immune checkpoint modulator therapy. Thus, in accordance with the present invention, those individuals whose tumors show high mutation burden and/or high neoepitope burden are predisposed to benefit from immunotherapy as described herein compared to those individuals with relatively lower such burdens.

Without wishing to be bound by any particular theory, we note that the present disclosure demonstrates, among other things, that neoepitopes in cancer cells can be associated with increased binding affinity to MHC class I molecules and/or with improved recognition by cytotoxic T cells. In some embodiments, neoepitopes useful in predicting responsiveness to therapy as described herein (e.g., useful for inclusion in a "signature" that can be detected or analyzed in assessing likelihood of response) are those that in fact show increased binding affinity to MHC class I molecules and/or improved recognition by cytotoxic T cells, for example relative to a parent protein that is otherwise identical but lacks the neoepitope.

In general, the present disclosure relates to characterizing tumor responsiveness to immunotherapy, and particularly to immune checkpoint modulator therapy. In some embodiments, such therapy involves blockade of programmed cell death 1 (PD-1). In some particular embodiments, such therapy involves treatment with an agent that interferes with an interaction involving PD-1 (e.g., with PD-L1). In some embodiments, such therapy involves administration of an antibody agent that specifically interacts with PD-1 or with PD-L1. In some embodiments, such therapy involves administration of one or more of nivolumab (BMS-936558, MDX-1106, ONO-4538, a fully human Immunoglobulin G4 (IgG4) monoclonal PD-1 antibody), pembrolizumab (MK-3475, a humanized monoclonal IgG4 anti-PD-1 antibody), BMS-936559 (a fully human IgG4 PD-L1 antibody), MPDL3280A (a humanized engineered IgG1 monoclonal PD-L1 antibody) and/or MEDI4736 (a humanized engineered IgG1 monoclonal PD-L1 antibody).

The present invention provides, among other things, technologies for defining, characterizing, and/or detecting burden (e.g., number, level, and/or rate) of somatic mutations and/or neoepitopes present in cancer cells and/or for defining, characterizing, and/or detecting particular mutation and/or neoepitope "signatures" that predict responsiveness to immunotherapy, and particularly to immune checkpoint modulator therapy. In some embodiments, the present invention provides methods and/or reagents for identifying cancer patients that are likely to respond favorably to treatment with immunotherapy (e.g., with an immune checkpoint modulator) and/or for selecting patients to receive such immunotherapy. Alternatively or additionally, the present invention provides methods and/or reagents for treating patients with an immune checkpoint modulator that have been identified to have cancer harboring a particular mutation burden, neoepitope burden, and/or mutation or neoepitope signature as described herein.

The present invention defines and provides tools and kits for detecting or determining whether a particular cancer patient does or does not have the relevant mutational landscape or signature for responding to immunotherapy (e.g., PD-1 blockade). The present invention demonstrates that certain particular mutational landscapes or signatures are more useful and effective in predicting responsiveness.

The present disclosure demonstrates that high mutational loads can predict responsiveness of cancers to immunotherapy. Furthermore, the disclosure also teaches that high neoepitope loads can predict responsiveness of cancers to immunotherapy. Moreover, the present disclosure demonstrates that particular mutational and/or neoepitope signatures can predict responsiveness of cancers to immunotherapy. Specifically, the present disclosure establishes that signatures including information from DNA repair genes and/or signal transduction genes can predict responsiveness of cancers to immunotherapy. The present disclosure further establishes that signatures that, alternatively or additionally, include characteristics of the established molecular smoking signature, can predict responsiveness of cancers to immunotherapy.

Cancer Cell Mutability

Acquired (or somatic) mutations can occur in the DNA of cells at some time during an individual's life. These changes can be caused by environmental factors such as ultraviolet radiation from the sun, carcinogens in chemicals or cigarette smoke, or can occur if a mistake is made during DNA replication. Cancer cells from cancers such as lung cancer or melanoma, which are often the result of chronic exposure to environmental factor or mutagens, often possess multiple mutations of varying types.

Within tumor types there is a large variability in mutation loads, ranging from tens to thousands of mutations with a cancer cell. In analyzing the tumors of non small cell lung carcinoma (NSCLC) patients, smokers have a much greater mutation burden compared to never-smokers. The present disclosure shows, that in those cancers that are responsive to immunotherapy (e.g., PD-1 blockade), higher mutation loads correlated with better response to immune checkpoint regulators. In some embodiments, highly mutable cancers are more susceptible to attack from the immune system.

Mutations of certain genes correlate with higher (hyper) levels of mutations in cancer cells. The present disclosure demonstrates that mutations in genes associated with DNA repair correlated with cancer cells possessing higher numbers of mutations.

Mutational Load and Susceptibility to Immune System

Among other things, the present disclosure demonstrates a that high mutation load can predict clinical efficacy of immunotherapy treatment for certain cancers. The present disclosure establishes that, in certain cases, individuals with higher somatic mutation loads are more likely to respond positively to immunotherapy than individuals with significantly lower mutation burdens. The present disclosure demonstrates that, for certain cancers, patients with high numbers of mutations are more likely to benefit from treatment with immune checkpoint modulators than those patients with lower mutation loads. In some embodiments, patients with higher numbers of somatic mutations respond better to PD-1 (programmed cell death 1) blockade than those patients with significantly lower overall mutations. In some embodiments, individuals with high numbers of mutations respond better to treatment with anti-PD-1 antibodies than those individuals with low numbers of mutations. In some embodiments, the overall number of mutations has a greater correlation with positive response to immunotherapy than the specific mutational signatures.

In some embodiments, the type of somatic mutation correlates with response to treatment. For example, the present disclosure teaches that individuals with a lower transition to transversion ratio (Ti/Tv) also experienced greater likelihood of positive response to immunotherapy.

Defined Signatures

The present disclosure encompasses the insight that meaningful limits can be imposed on mutational analysis of cancer cells and, moreover, that use of such limits surprisingly defines and/or provides signature formats that effectively predict responsiveness to treatment. In some embodiments, the mutation signatures as described herein correlate with and/or predict response to immunotherapy (e.g., PD-1 blockade). In some embodiments, the genes that are mutated (for example, DNA repair) as well as the exact type of mutation (for example, transversions rather than transitions) correlate with and/or are predictive of positive response to immunotherapy. Moreover, the present disclosure demonstrates that such signatures can be detected and effectively utilized to predict tumor responsiveness.

In some embodiments, as described herein, the present disclosure provides technologies for defining mutation signatures that predict responsiveness to immunotherapy, and particularly to immune checkpoint modulator therapy. In some embodiments, the present disclosure defines one or more characteristics or attributes of useful signatures. In some embodiments, the present disclosure describes and/or establishes effective use of such signatures in predicting therapeutic responsiveness.

Use of Signatures

The present disclosure demonstrates that mutational landscape of particular tumors can predict the likelihood of clinical benefit from immunotherapy (e.g., PD-1 blockade). The disclosure also teaches that high mutation load can predict likelihood of positive response to immunotherapy. Furthermore, the nature of the somatic mutations present can predict response to immunotherapy. As demonstrated herein, in some embodiments, individuals with neoepitope signatures consistent with mutations of genes associated with DNA repair and signaling (e.g., KRAS signaling) also correlated with a positive outcome for immune checkpoint modulation.

The present disclosure particularly demonstrates, surprisingly, that the established "smoking signature" can be effectively utilized to predict responsiveness of certain tumors to immunotherapy, and particularly to immune checkpoint modulator therapy (e.g., PD-1 blockade). In some embodiments, individuals possessing (or whose tumor(s) possess) one or more features of the molecular smoking signature and suffering from a smoking-related cancer are more likely to respond to immunotherapy than are non-smoking individuals and/or individuals that do not posess (or whose tumor(s) do not possess) the one or more features.

Cancer Types

The present disclosure demonstrates that in those cancers that respond to immunotherapy (e.g., immune checkpoint blockade), the tumor mutational landscape of the patient can predict with clinical efficacy. In some embodiments, cancer types to which the present disclosure applied include one or more of lung cancer (e.g., small cell or non-small-cell carcinoma ["NSCLC"), bladder cancer, renal carcinoma, head and neck cancers, and melanoma respond to immunotherapy. In some embodiments, lung cancer responds to PD-1 blockade. In some embodiments, expression of PD-L1 is an indicator of positive response to therapy.

In some embodiments, smoking related cancers are more likely to respond to immunotherapy treatment. The present disclosure demonstrates that those individuals possessing (or whose tumor(s) possess) one or more features or characteristics of the established molecular smoking signature are more likely to respond to immunotherapy treatment. In particular, among other things, the present disclosure establishes that, for those individuals suffering from NSCLC, those with the smoking signature experienced greater clinical benefit from treatment with PD-1 blockade than their non-smoker counterparts.

In some embodiments, a cancer cell comprising a neoepitope is selected from a carcinoma, sarcoma, melanoma, myeloma, leukemia, or lymphoma. In some embodiments, a cancer cell comprising a neoepitope is a melanoma. In some embodiments, a cancer cell comprising a neoepitope is a non-small-cell lung carcinoma.

Relevant Therapeutic Modalities

Teachings of the present disclosure predict responsiveness to immunomodulatory therapeutic modalities or regimens, and particularly to therapeutic modalities or regimens targeting immune checkpoint regulators. The present disclosure demonstrates the mutational landscape of tumors correlates with responsiveness to immune checkpoint regulators. In some embodiments, high somatic mutation load correlates with an increased likelihood of clinical efficacy from immune checkpoint regulators for those cancers responsive to immunotherapy (e.g., PD-1 blockade). In some embodiments, such therapy involves blockade of programmed cell death 1 (PD-1). In some particular embodiments, such therapy involves treatment with an agent that interferes with an interaction involving PD-1 (e.g., with PD-L1). In some embodiments, such therapy involves administration of an antibody agent that specifically interacts with PD-1 or with PD-L1. In some embodiments, such therapy involves administration of one or more of nivolumab (BMS-936558, MDX-1106, ONO-4538, a fully human Immunoglobulin G4 (IgG4) monoclonal PD-1 antibody), pembrolizumab (MK-3475, a humanized monoclonal IgG4 anti-PD-1 antibody), BMS-936559 (a fully human IgG4 PD-L1 antibody), MPDL3280A (a humanized engineered IgG1 monoclonal PD-L1 antibody) and/or MEDI4736 (a humanized engineered IgG1 monoclonal PD-L1 antibody).

Somatic Mutations

Somatic mutations comprise DNA alterations in non-germline cells and commonly occur in cancer cells. It has been discovered herein that certain somatic mutations in cancer cells result in the expression of neoepitopes, that in some embodiments transition a stretch of amino acids from being recognized as "self" to "non-self". According to the present invention, a cancer cell harboring a "non-self" antigen is likely to elicit an immune response against the cancer cell. Immune responses against cancer cells can be enhanced by an immune checkpoint modulator. The present invention teaches that cancers expressing neoepitopes may be more responsive to therapy with immune checkpoint modulator. Among other things, the present invention provides strategies for improving cancer therapy by permitting identification and/or selection of particular patients to receive (or avoid) therapy. The present invention also provides technologies for defining neoepitopes, or sets thereof, whose presence is indicative of a particular clinical outcome of interest (e.g., responsiveness to therapy, for example with a particular immune checkpoint modulator and/or risk of developing a particular undesirable side effect of therapy). The present invention defines and/or permits definition of one or more neoepitope "signatures" associated with beneficial (or undesirable) response to immune checkpoint modulator therapy.

In some embodiments, a somatic mutation results in a neoantigen or neoepitope. Among other things, the present disclosure demonstrates the existence of neoepitopes, arising from somatic mutation, whose presence is associated with a particular response to immune checkpoint modulator therapy. In some embodiments, high numbers of neoepitopes are associated with a positive response to immunotherapy. In some embodiments, a neoepitope is or comprises a tetrapeptide, for example that contributes to increased binding affinity to MHC Class I molecules and/or recognition by cells of the immune system (i.e. T cells) as "non-self". In some embodiments, a neoepitope shares a consensus sequence with an antigen from an infectious agent.

In some embodiments, a neoepitope signature of interest in accordance with the present invention is or comprises a neoepitope or set thereof whose presence in a tumor sample correlates with a particular clinical outcome. In some embodiments, neoepitopes of genes associated with DNA repair correlate with a positive response to immune checkpoint modulation. In some embodiments, neoepitopes of genes associated with signal transduction correlate with a positive response to immune checkpoint therapy. In some embodiments, the present disclosure provides technologies for defining and/or detecting neoepitopes, and particularly those relevant to immune checkpoint modulator therapy.

Among other things, the present disclosure demonstrates definition of neoepitopes and neoepitope signatures associated with a particular response or response feature (e.g., responsiveness to therapy or risk of side effect) of immune checkpoint modulator therapy. In the particular Examples presented herein, such definition is achieved by comparing genetic sequence information from a first plurality of tumor samples, which first plurality contains samples that share a common response feature to immune checkpoint modulator therapy, with that obtained from a second plurality of tumor samples, which second plurality contains samples that do not share the common response feature but are otherwise comparable to those of the first set, so that the comparison defines genetic sequence elements whose presence is associated or correlates with the common response feature. The present disclosure specifically demonstrates that increased mutational burden can correlate with a response feature (e.g., with responsiveness to therapy), but also demonstrates that such increased mutational burden alone may not be sufficient to predict the response feature. The present disclosure demonstrates that, when such somatic mutation generates neoepitopes, a useful neoepitope signature associated with the response feature can be defined. The present disclosure provides specific technologies for defining and utilizing such signatures.

Immune Checkpoint Modulation

Immune checkpoints refer to inhibitory pathways of the immune system that are responsible for maintaining self-tolerance and modulating the duration and amplitude of physiological immune responses.

Certain cancer cells thrive by taking advantage of immune checkpoint pathways as a major mechanism of immune resistance, particularly with respect to T cells that are specific for tumor antigens. For example, certain cancer cells may overexpress one or more immune checkpoint proteins responsible for inhibiting a cytotoxic T cell response. Thus, immune checkpoint modulators may be administered to overcome the inhibitory signals and permit and/or augment an immune attack against cancer cells. Immune checkpoint modulators may facilitate immune cell responses against cancer cells by decreasing, inhibiting, or abrogating signaling by negative immune response regulators (e.g. CTLA4), or may stimulate or enhance signaling of positive regulators of immune response (e.g. CD28).

Immunotherapy agents targeted to immune checkpoint modulators may be administered to encourage immune attack targeting cancer cells. Immunotherapy agents may be or include antibody agents that target (e.g., are specific specific for) immune checkpoint modulators. Examples of immunotherapy agents include antibody agents targeting one or more of CTLA-4, PD-1, PD-L1, GITR, OX40, LAG-3, KIR, TIM-3, CD28, CD40, and CD137.

Specific examples of antibody agents may include monoclonal antibodies. Certain monoclonal antibodies targeting immune checkpoint modulators are available. For instance, ipilumimab targets CTLA-4; tremelimumab targets CTLA-4; pembrolizumab targets PD-1, etc.

Detection of Mutations and/or Neoepitopes

Cancers may be screened to detect mutations and/or neoepitopes (e.g., to detect mutation load/burden and/or neoepitope load/burden, and/or to detect a particular signature) as described herein using any of a variety of known technologies. In some embodiments, particular mutations or neoepitopes, or expression thereof, is/are detected at the nucleic acid level (e.g., in DNA or RNA). In some embodiments, such mutations or neoepitopes, or expression thereof, is detected at the protein level (e.g., in a sample comprising polypeptides from cancer cells, which sample may be or comprise polypeptide complexes or other higher order structures including but not limited to cells, tissues, or organs).

In some particular embodiments, detection involves nucleic acid sequencing. In some embodiments, detection involves whole exome sequencing. In some embodiments, detection involves immunoassay. In some embodiments, detection involves use of a microarray. In some embodiments, detection involves massively parallel exome sequencing sequencing. In some embodiments, mutations and/or neoepitopes may be detected by genome sequencing. In some embodiments, detection involves RNA sequencing. In some embodiments, detection involves standard DNA or RNA sequencing. In some embodiments, detection involves mass spectrometry.

In some embodiments, detection involves next generation sequencing (DNA and/or RNA). In some embodiments, detection involves genome sequencing, genome resequencing, targeted sequencing panels, transcriptome profiling (RNA-Seq), DNA-protein interactions (ChIP-sequencing), and/or epigenome characterization. In some embodiments, re-sequencing of a patient's genome may be utilized, for example to detect genomic variations.

In some embodiments, detection involves using a technique such as ELISA, Western Tranfer, immunoassay, mass spectrometry, microarray analysis, etc.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

Methods of Treatment

In some embodiments, the invention provides methods for identifying cancer patients that are likely to respond favorably to treatment with an immune checkpoint modulator. In some embodiments, the invention provides methods for identifying a cancer patient that is likely to respond favorably to treatment with an immune checkpoint modulator and treating the patient with an immune checkpoint modulator. In some embodiments, the invention provides methods of treating a cancer patient with an immune checkpoint modulator who has previously been identified as likely to respond favorably to treatment with an immune checkpoint modulator. In some embodiments, the invention provides methods for identifying a cancer patient that is not likely to respond favorably to treatment with an immune checkpoint modulator and not treating the patient with an immune checkpoint modulator. In some embodiments, the invention provides methods for identifying a cancer patient who is likely to suffer one or more autoimmune complications if administered an immune checkpoint modulator. In some embodiments, the invention provides methods for treating a cancer patient with an immunosuppressant who has previously identified as likely to suffer one or more autoimmune complications if treated with an immune checkpoint modulator. In some embodiments, the immunosuppressant is administered to the patient prior to or concomitantly with an immune checkpoint modulator.

Administration of Immune Checkpoint Modulators

In accordance with certain methods of the invention, an immune checkpoint modulator is or has been administered to an individual. In some embodiments, treatment with an immune checkpoint modulator is utilized as a sole therapy. In some embodiments, treatment with an immune checkpoint modulator is used in combination with one or more other therapies.

Those of ordinary skill in the art will appreciate that appropriate formulations, indications, and dosing regimens are typically analyzed and approved by government regulatory authorities such as the Food and Drug Administration in the United States. For example, Example 5 presents certain approved dosing information for ipilumimab, an anti-CTL-4 antibody. In many embodiments, an immune checkpoint modulator is administered in accordance with the present invention according to such an approved protocol. However, the present disclosure provides certain technologies for identifying, characterizing, and/or selecting particular patients to whom immune checkpoint modulators may desirably be administered. In some embodiments, insights provided by the present disclosure permit dosing of a given immune checkpoint modulator with greater frequency and/or greater individual doses (e.g., due to reduced susceptibiloity to and/or incidence or intensity of undesirable effects) relative to that recommended or approved based on population studies that include both individuals identified as described herein (e.g., expressing neoepitopes) and other individuals. In some embodiments, insights provided by the present disclosure permit dosing of a given immune checkpoint modulator with reduced frequency and/or reduced individual doses (e.g., due to increased responsiveness) relative to that recommended or approved based on population studies that include both individuals identified as described herein (e.g., expressing neoepitopes) and other individuals.

In some embodiments, an immune system modulator is administered in a pharmaceutical composition that also comprises a physiologically acceptable carrier or excipient. In some embodiments, a pharmaceutical composition is sterile. In many embodiments, a pharmaceutical composition is formulated for a particular mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrrolidone, etc., as well as combinations thereof. A pharmaceutical preparation can, if desired, comprise one or more auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interference with their activity. In some embodiments, a water-soluble carrier suitable for intravenous administration is used.

In some embodiments, a pharmaceutical composition or medicament, if desired, can contain an amount (typically a minor amount) of wetting or emulsifying agents, and/or of pH buffering agents. In some embodiments, a pharmaceutical composition can be a liquid solution, suspension, emulsion, tablet, pill, capsule, sustained release formulation, or powder. In some embodiments, a pharmaceutical composition can be formulated as a suppository, with traditional binders and carriers such as triglycerides. Oral formulation can include standard carriers such as pharmaceutical grades of mannitol, lactose, starch, magnesium stearate, polyvinyl pyrrolidone, sodium saccharine, cellulose, magnesium carbonate, etc.

In some embodiments, a pharmaceutical composition can be formulated in accordance with the routine procedures as a pharmaceutical composition adapted for administration to human beings. For example, in some embodiments, a composition for intravenous administration typically is a solution in sterile isotonic aqueous buffer. Where necessary, a composition may also include a solubilizing agent and a local anesthetic to ease pain at the site of the injection. Generally, ingredients are supplied either separately or mixed together in unit dosage form, for example, as a dry lyophilized powder or water free concentrate in a hermetically sealed container such as an ampule or sachet indicating the quantity of active agent. Where a composition is to be administered by infusion, it can be dispensed with an infusion bottle containing sterile pharmaceutical grade water, saline or dextrose/water. Where a composition is administered by injection, an ampule of sterile water for injection or saline can be provided so that the ingredients may be mixed prior to administration.

In some embodiments, an immune checkpoint modulator can be formulated in a neutral form; in some embodiments it may be formulated in a salt form. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Pharmaceutical compositions for use in accordance with the present invention may be administered by any appropriate route. In some embodiments, a pharmaceutical composition is administered intravenously. In some embodiments, a pharmaceutical composition is administered subcutaneously. In some embodiments, a pharmaceutical composition is administered by direct administration to a target tissue, such as heart or muscle (e.g., intramuscular), or nervous system (e.g., direct injection into the brain; intraventricularly; intrathecally). Alternatively or additionally, in some embodiments, a pharmaceutical composition is administered parenterally, transdermally, or transmucosally (e.g., orally or nasally). More than one route can be used concurrently, if desired.

Immune checkpoint modulators (or a composition or medicament containing an immune checkpoint modulator, can be administered alone, or in conjunction with other immune checkpoint modulators. The term, "in conjunction with," indicates that a first immune checkpoint modulator is administered prior to, at about the same time as, or following another immune checkpoint modulator. For example, a first immune checkpoint modulator can be mixed into a composition containing one or more different immune checkpoint modulators, and thereby administered contemporaneously; alternatively, the agent can be administered contemporaneously, without mixing (e.g., by "piggybacking" delivery of the agent on the intravenous line by which the immune checkpoint modulator is also administered, or vice versa). In another example, the immune checkpoint modulator can be administered separately (e.g., not admixed), but within a short time frame (e.g., within 24 hours) of administration of the immune checkpoint modulator.

In some embodiments, subjects treated with immune checkpoint modulators are administered one or more immunosuppressants. In some embodiments, one or more immunosuppressants are administered to decrease, inhibit, or prevent an undesired autoimmune response (e.g., enterocolitis, hepatitis, dermatitis (including toxic epidermal necrolysis), neuropathy, and/or endocrinopathy), for example, hypothyroidism. Exemplary immunosuppressants include steroids, antibodies, immunoglobulin fusion proteins, and the like. In some embodiments, an immunosuppressant inhibits B cell activity (e.g. rituximab). In some embodiments, an immunosuppressant is a decoy polypeptide antigen.

In some embodiments, immune checkpoint modulators (or a composition or medicament containing immune checkpoint modulators) are administered in a therapeutically effective amount (e.g., a dosage amount and/or according to a dosage regimen that has been shown, when administered to a relevant population, to be sufficient to treat cancer, such as by ameliorating symptoms associated with the cancer, preventing or delaying the onset of the cancer, and/or also lessening the severity or frequency of symptoms of cancer). In some embodiments, long term clinical benefit is observed after treatment with immune checkpoint modulators, including, for example, PD-1 blockers such as pembrolizumab, and/or other agents. Those of ordinary skill in the art will appreciate that a dose which will be therapeutically effective for the treatment of cancer in a given patient may depend, at least to some extent, on the nature and extent of cancer, and can be determined by standard clinical techniques. In some embodiments, one or more in vitro or in vivo assays may optionally be employed to help identify optimal dosage ranges. In some embodiments, a particular dose to be employed in the treatment of a given individual may depend on the route of administration, the extent of cancer, and/or one or more other factors deemed relevant in the judgment of a practitioner in light of patient's circumstances. In some embodiments, effective doses may be extrapolated from dose-response curves derived from in vitro or animal model test systems (e.g., as described by the U.S. Department of Health and Human Services, Food and Drug Administration, and Center for Drug Evaluation and Research in "Guidance for Industry: Estimating Maximum Safe Starting Dose in Initial Clinical Trials for Therapeutics in Adult Healthy Volunteers", Pharmacology and Toxicology, July 2005.

In some embodiments, a therapeutically effective amount of an immune check point modulator can be, for example, more than about 0.01 mg/kg, more than about 0.05 mg/kg, more than about 0.1 mg/kg, more than about 0.5 mg/kg, more than about 1.0 mg/kg, more than about 1.5 mg/kg, more than about 2.0 mg/kg, more than about 2.5 mg/kg, more than about 5.0 mg/kg, more than about 7.5 mg/kg, more than about 10 mg/kg, more than about 12.5 mg/kg, more than about 15 mg/kg, more than about 17.5 mg/kg, more than about 20 mg/kg, more than about 22.5 mg/kg, or more than about 25 mg/kg body weight. In some embodiments, a therapeutically effective amount can be about 0.01-25 mg/kg, about 0.01-20 mg/kg, about 0.01-15 mg/kg, about 0.01-10 mg/kg, about 0.01-7.5 mg/kg, about 0.01-5 mg/kg, about 0.01-4 mg/kg, about 0.01-3 mg/kg, about 0.01-2 mg/kg, about 0.01-1.5 mg/kg, about 0.01-1.0 mg/kg, about 0.01-0.5 mg/kg, about 0.01-0.1 mg/kg, about 1-20 mg/kg, about 4-20 mg/kg, about 5-15 mg/kg, about 5-10 mg/kg body weight. In some embodiments, a therapeutically effective amount is about 0.01 mg/kg, about 0.05 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg about 1.4 mg/kg, about 1.5 mg/kg, about 1.6 mg/kg, about 1.7 mg/kg, about 1.8 mg/kg, about 1.9 mg/kg, about 2.0 mg/kg, about 2.5 mg/kg, about 3.0 mg/kg, about 4.0 mg/kg, about 5.0 mg/kg, about 6.0 mg/kg, about 7.0 mg/kg, about 8.0 mg/kg, about 9.0 mg/kg, about 10.0 mg/kg, about 11.0 mg/kg, about 12.0 mg/kg, about 13.0 mg/kg, about 14.0 mg/kg, about 15.0 mg/kg, about 16.0 mg/kg, about 17.0 mg/kg, about 18.0 mg/kg, about 19.0 mg/kg, about 20.0 mg/kg, body weight, or more. In some embodiments, the therapeutically effective amount is no greater than about 30 mg/kg, no greater than about 20 mg/kg, no greater than about 15 mg/kg, no greater than about 10 mg/kg, no greater than about 7.5 mg/kg, no greater than about 5 mg/kg, no greater than about 4 mg/kg, no greater than about 3 mg/kg, no greater than about 2 mg/kg, or no greater than about 1 mg/kg body weight or less.

In some embodiments, the administered dose for a particular individual is varied (e.g., increased or decreased) over time, depending on the needs of the individual.

In yet another example, a loading dose (e.g., an initial higher dose) of a therapeutic composition may be given at the beginning of a course of treatment, followed by administration of a decreased maintenance dose (e.g., a subsequent lower dose) of the therapeutic composition.

Without wishing to be bound by any theories, it is contemplated that a loading dose may clear out an initial and, in some cases massive, accumulation of undesirable materials (e.g., fatty materials and/or tumor cells, etc) in tissues (e.g., in the liver), and maintenance dosing may delay, reduce, or prevent buildup of fatty materials after initial clearance.

It will be appreciated that a loading dose and maintenance dose amounts, intervals, and duration of treatment may be determined by any available method, such as those exemplified herein and those known in the art. In some embodiments, a loading dose amount is about 0.01-1 mg/kg, about 0.01-5 mg/kg, about 0.01-10 mg/kg, about 0.1-10 mg/kg, about 0.1-20 mg/kg, about 0.1-25 mg/kg, about 0.1-30 mg/kg, about 0.1-5 mg/kg, about 0.1-2 mg/kg, about 0.1-1 mg/kg, or about 0.1-0.5 mg/kg body weight. In some embodiments, a maintenance dose amount is about 0-10 mg/kg, about 0-5 mg/kg, about 0-2 mg/kg, about 0-1 mg/kg, about 0-0.5 mg/kg, about 0-0.4 mg/kg, about 0-0.3 mg/kg, about 0-0.2 mg/kg, about 0-0.1 mg/kg body weight. In some embodiments, a loading dose is administered to an individual at regular intervals for a given period of time (e.g., 1, 2, 3, 4, 5, 6, 7, 8, 9, 10, 11, 12 or more months) and/or a given number of doses (e.g., 1, 2, 3, 4, 5, 6, 7, 8, 9, 10, 15, 20, 25, 30 or more doses), followed by maintenance dosing. In some embodiments, a maintenance dose ranges from 0-2 mg/kg, about 0-1.5 mg/kg, about 0-1.0 mg/kg, about 0-0.75 mg/kg, about 0-0.5 mg/kg, about 0-0.4 mg/kg, about 0-0.3 mg/kg, about 0-0.2 mg/kg, or about 0-0.1 mg/kg body weight. In some embodiments, a maintenance dose is about 0.01, 0.02, 0.04, 0.06, 0.08, 0.1, 0.2, 0.3, 0.4, 0.5, 0.6, 0.7, 0.8, 0.9, 1.0, 1.2, 1.4, 1.6, 1.8, or 2.0 mg/kg body weight. In some embodiments, maintenance dosing is administered for 1, 2, 3, 4, 5, 6, 7, 8, 9, 10, 11, 12 or more months. In some embodiments, maintenance dosing is administered for 1, 2, 3, 4, 5, 6, 7, 8, 9, 10 or more years. In some embodiments, maintenance dosing is administered indefinitely (e.g., for life time).

A therapeutically effective amount of an immune checkpoint modulator may be administered as a one-time dose or administered at intervals, depending on the nature and extent of the cancer, and on an ongoing basis. Administration at an "interval," as used herein indicates that the therapeutically effective amount is administered periodically (as distinguished from a one-time dose). The interval can be determined by standard clinical techniques. In some embodiments, an immune checkpoint modulator is administered bimonthly, monthly, twice monthly, triweekly, biweekly, weekly, twice weekly, thrice weekly, or daily. The administration interval for a single individual need not be a fixed interval, but can be varied over time, depending on the needs and rate of recovery of the individual.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

The invention additionally pertains to a pharmaceutical composition comprising an immune checkpoint modulator, as described herein, in a container (e.g., a vial, bottle, bag for intravenous administration, syringe, etc.) with a label containing instructions for administration of the composition for treatment of cancer.

EXAMPLES

The following examples are provided so as to describe to those of ordinary skill in the art how to make and use methods and compositions of the invention, and are not intended to limit the scope of what the inventors regard as their invention.

Overview

Today, more than a century since the initial observation that the immune system can reject human cancers (1), immune checkpoint inhibitors are demonstrating that adaptive immunity can be harnessed for the treatment of cancer (2-5, 60, 61). In advanced non-small cell lung cancer (NSCLC), anti-PD-1 therapies have demonstrated response rates of 17-21%, with some responses being remarkably durable (3, 6).

Understanding the molecular determinants of response to immunotherapies such as anti-PD-1 therapy is one of the critical challenges in oncology. Among the best responses to date have been seen in both melanomas and NSCLC, cancers largely caused by chronic exposure to mutagens (ultraviolet light (7) and carcinogens in cigarette smoke in lung cancers (8), respectively). However, within tumor types, there is a large variability in mutation burden, ranging from 10 s-1000 s (9-11). This range is particularly broad in patients with NSCLCs as tumors in never-smokers generally have few somatic mutations compared to tumors in smokers (12). We hypothesized that the mutational landscape of NSCLCs may influence how patients respond to anti-PD-1 therapy. To determine how the genomic features of NSCLCs may impact benefit from anti-PD-1 therapy, we sequenced the exomes of NSCLCs from two independent cohorts of patients treated with pembrolizumab, a humanized IgG4-kappa isotype anti-PD-1 antibody (n=16 and n=18, respectively; total n=34) and their matched normal DNA (FIG. 15).

Those skilled in the art, reading the present disclosure will appreciate that particular examples included herein are representative and not limiting. For example, those skilled in the art, reviewing the data for ipilimumab response in melanoma, as provided in detail below, represent proof of concept and establish that neoepitope mutation signatures can be predictive of response to immune checkpoint modulators. Those of ordinary skill in the art, reading the present disclosure, will appreciate and understand that the approach is broadly applicable across cancers and immune checkpoint modulator therapies.

Example 1. Mutational Landscape of Tumors from Patients with Diverse Clinical Outcomes to Pembrolizumab This example illustrates analysis of the mutational landscape of cancer, and demonstrates its effectiveness in defining useful hallmarks of patients that respond favorably or poorly to an immune checkpoint modulator. The example particularly exemplifies analysis of lung cancer patients treated with PD-1 blockade (e.g. pembrolizumab), and defines exemplary mutational characteristics in such patients.

Overall, tumor DNA sequencing generated mean target coverage of 164× and a mean of 94.5% of the target sequence was covered to a depth of at least 10×; coverage and depth were similar between both cohorts as well as between those with or without durable clinical benefit (FIG. 5). We identified a median of 200 (range 11-1192) nonsynonymous mutations per sample (FIG. 6). The median number of total exonic mutations per sample was 327 (range 45-1732). The overall quantity and range of nonsynonymous and exonic mutation burden were similar to published series of NSCLCs (13, 14) (FIG. 7A & 7B). The transition/transversion ratio (Ti/Tv) was 0.74 (FIG. 8), also similar to previously described NSCLCs (13-15). To ensure accuracy of our sequencing data, targeted resequencing with an orthogonal method (Ampliseq) was performed using 376 randomly selected variants and mutations were confirmed in 357 (95%).

Figure 1A:
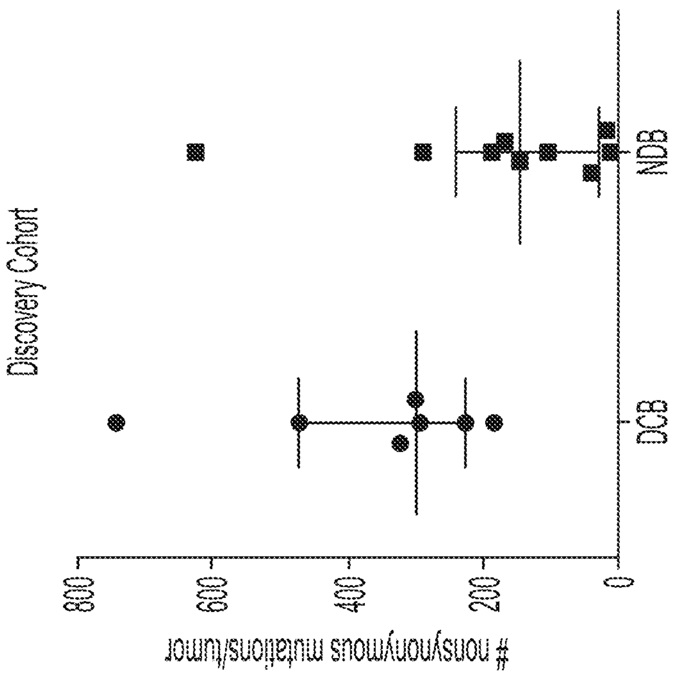
FIGS. 1A-1G shows Nonsynonymous mutation burden predicts clinical benefit with anti-PD-1 therapy. According to FIG. 1A, in the discovery cohort, nonsynonymous mutation burden is greater in tumors with DCB (n=7) compared to those with NDB (n=9) (median 302 vs 148, p=0.02).
Figure 1B:
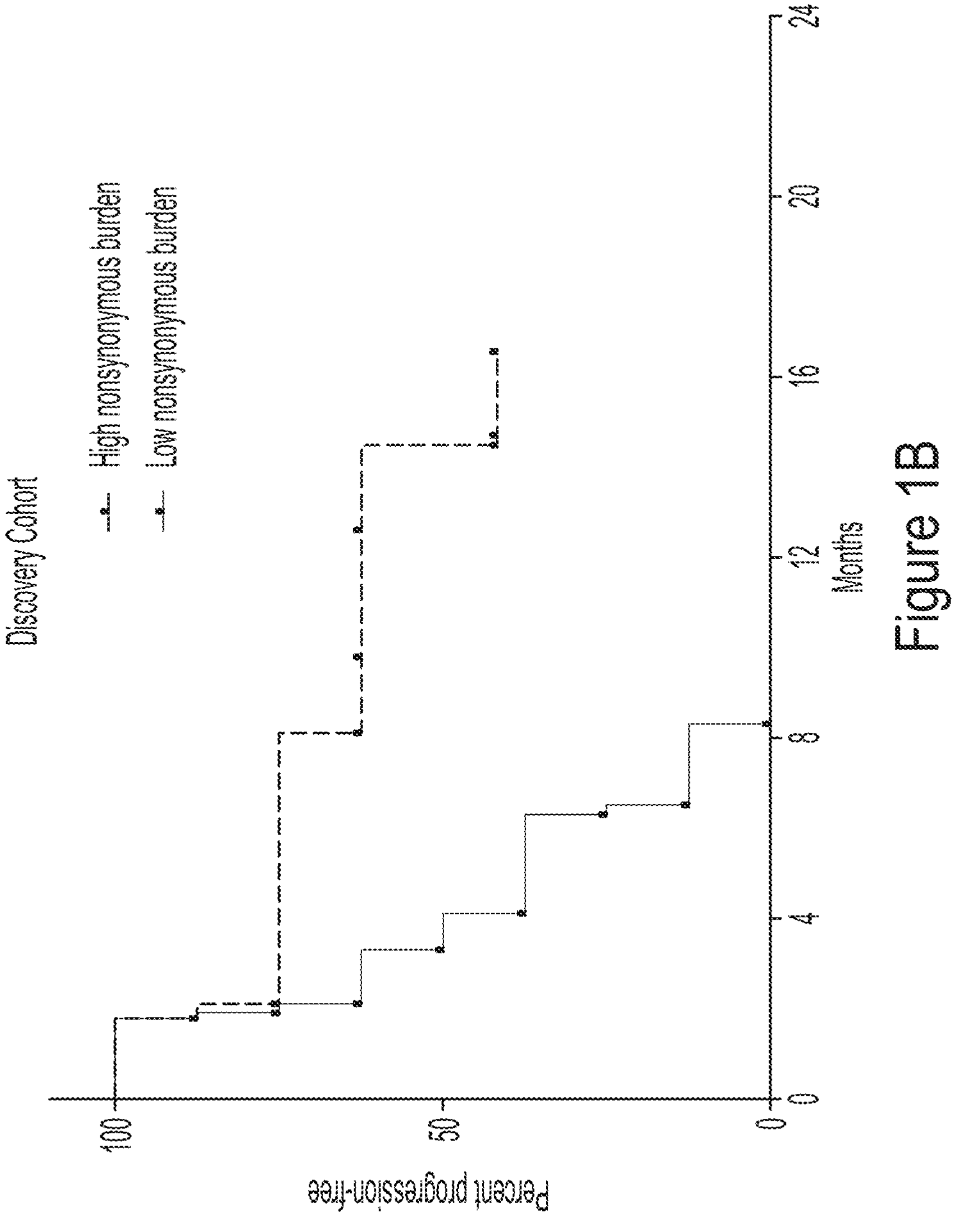

We observed that higher somatic nonsynonymous mutation burden predicted clinical efficacy of anti-PD1 therapy. In the discovery cohort (n=16), the median number of nonsynonymous mutations was 302 in patients with durable clinical benefit (DCB: partial or stable response lasting >6 months) versus 148 with no durable benefit (NDB) (p=0.02) (FIG. 1A). Seventy-three percent of patients with high nonsynonymous burden (defined as above the median burden of the cohort) experienced DCB compared to 13% of those with low mutation burden (p=0.04). Both confirmed objective response rate (ORR) and progression-free survival (PFS) were higher in patients with high nonsynonymous burden (ORR 63% vs. 0%, p=0.03; median PFS 14.5 vs. 3.7 months, p=0.02; HR 0.19, 95% CI 0.05-0.70) (FIG. 1B; FIG. 16).

Figure 1C:
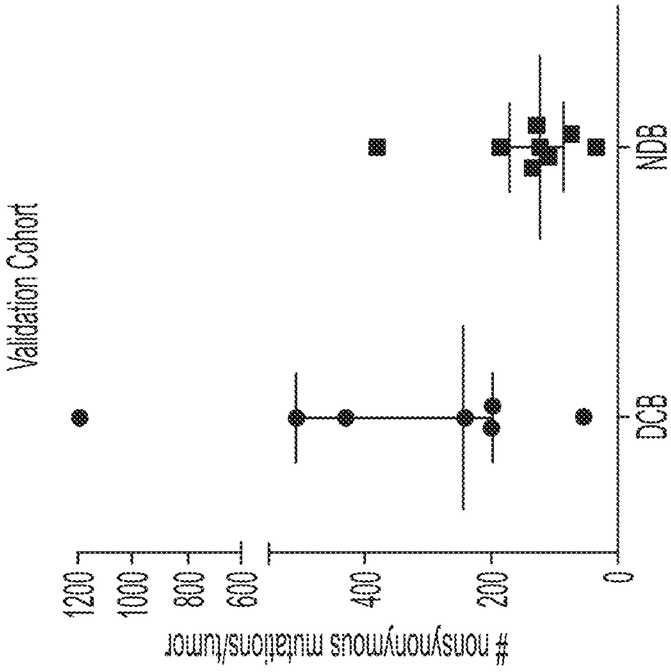
Figure 1D:
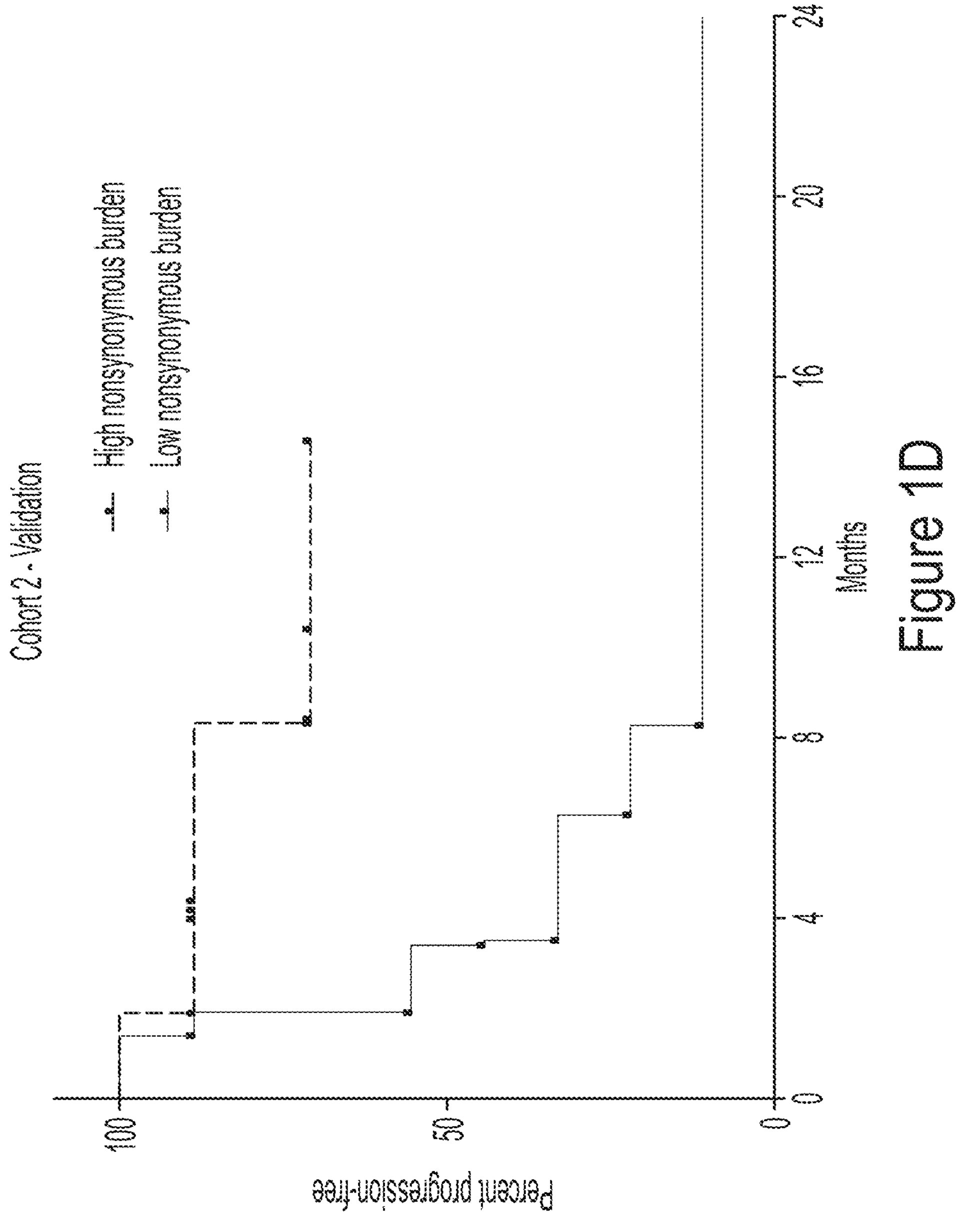

The validation cohort included an independent set of 18 NSCLC samples from patients treated with pembrolizumab; three patients currently on therapy have not yet reached six months of follow up and are therefore not included in calculations of DCB. The clinical characteristics of the validation cohort were similar to the discovery cohort, although there were more never-smokers in the validation cohort (5/18 vs 1/16). The median nonsynonymous mutation burden was 244 in tumors from patients with DCB compared 125 in the NDB group (p=0.04) (FIG. 1C). The rate of DCB and PFS were again both significantly greater in tumors with a nonsynonymous mutation burden above the median (DCB 83% vs 22%, p=0.04; median PFS not reached vs. 3.4 months, log rank p=0.006; HR 0.15, 95% CI 0.04-0.59) (FIG. 1D; FIG. 16).

Figure 1E:
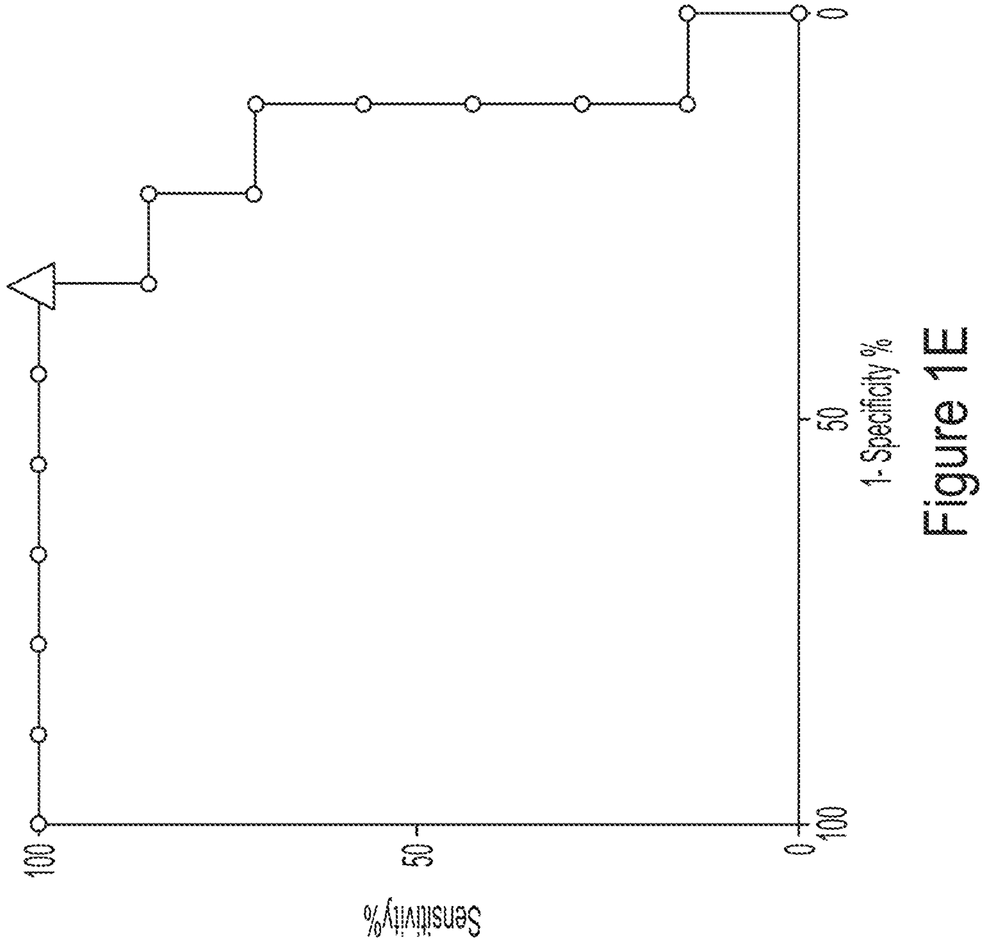

In the discovery cohort, there was high concordance between nonsynonymous mutation burden and DCB, with an area under the receiver operator characteristic curve (AUC) of 87% (FIG. 1E). Patients with nonsynonymous mutation burden≥178, the cut point that combined maximal sensitivity with best specificity, had a likelihood ratio for DCB of 3.0; the sensitivity and specificity of DCB using this cut point was 100% (95% CI 59-100) and 67% (29-93), respectively. Applying this cut point to patients within the validation cohort, the rate of durable benefit in patients with tumors harboring≥178 mutations was 75% compared to 14% in those with <178. This corresponded to a sensitivity of 86% and specificity of 75%.

Figure 1F:
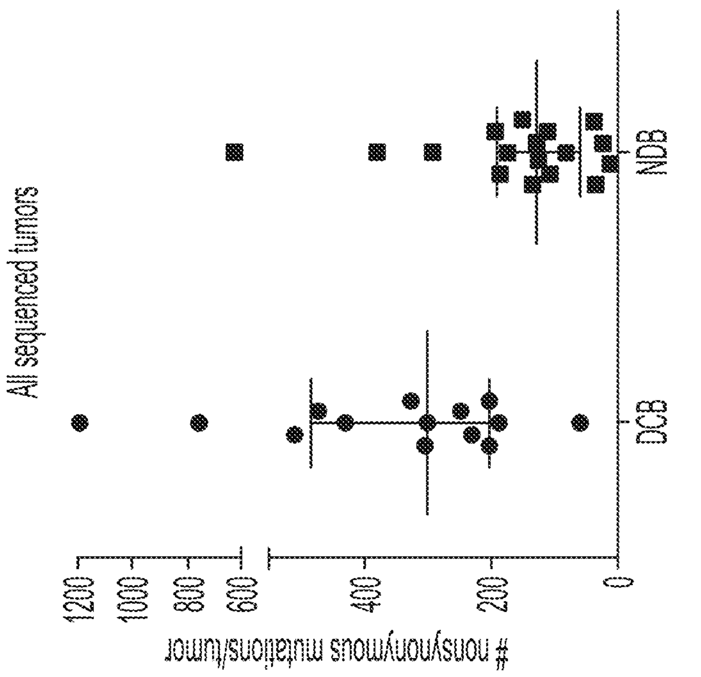
Figure 1G:
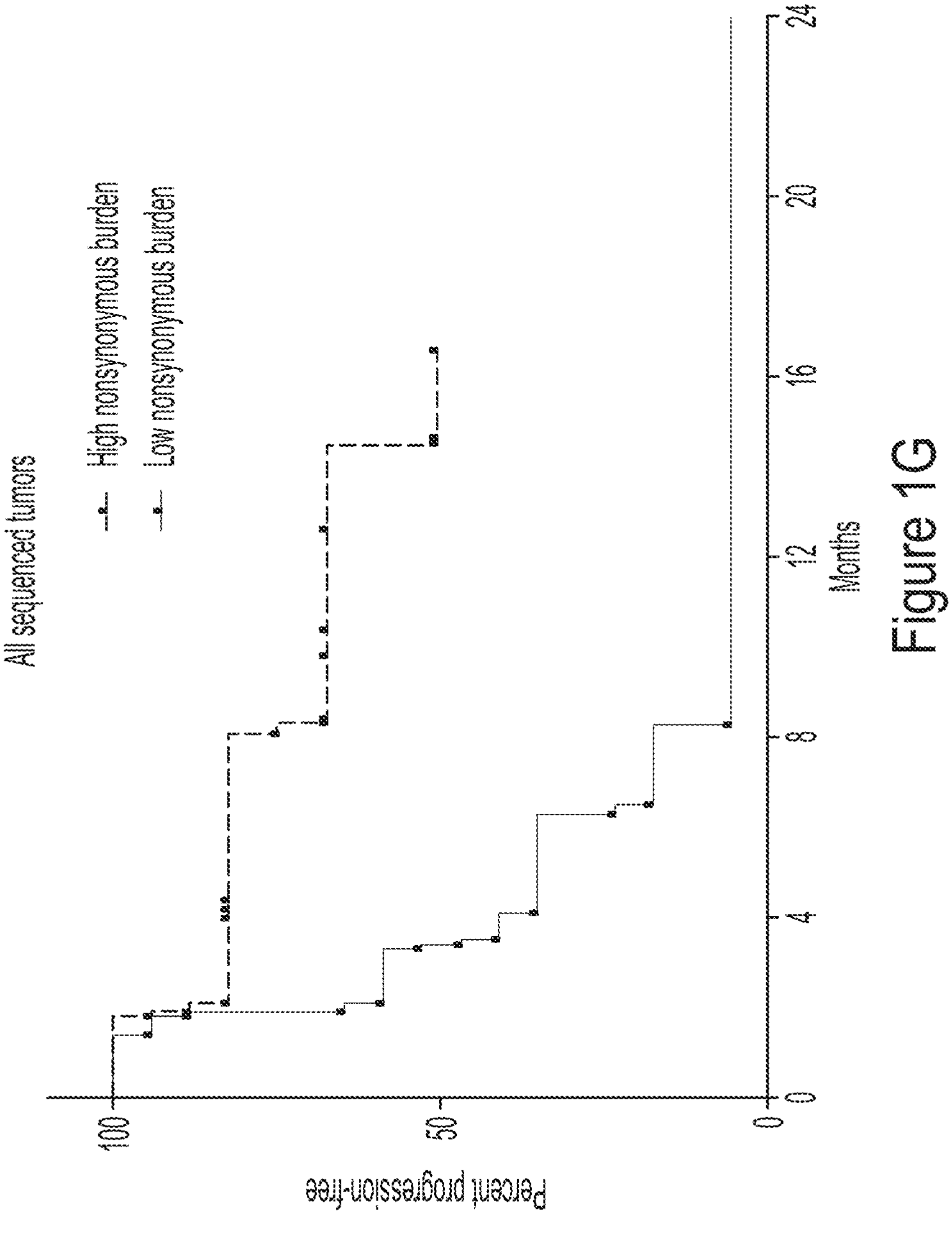

There were few but important exceptions. 5 of 18 tumors with ≥178 nonsynonymous mutations had NDB and one tumor with a very low burden (56 nonsynonymous mutations) had a partial response to pembrolizumab. However, this response was transient, lasting only 8 months. Across both cohorts, this is the only patient with a tumor mutation burden<178 with a confirmed objective response. Notably, although higher nonsynonymous mutation burden was predictive of ORR, DCB, and PFS (FIGS. 1F, 1G), this correlation was less evident when examining total exonic mutation burden (FIG. 16).

Example 2. Somatic Mutation Signatures Associated with Treatment Efficacy

This example demonstrates that certain somatic mutation signatures are associated with efficacy of treatment with an immune checkpoint modulator.

Figure 2A:
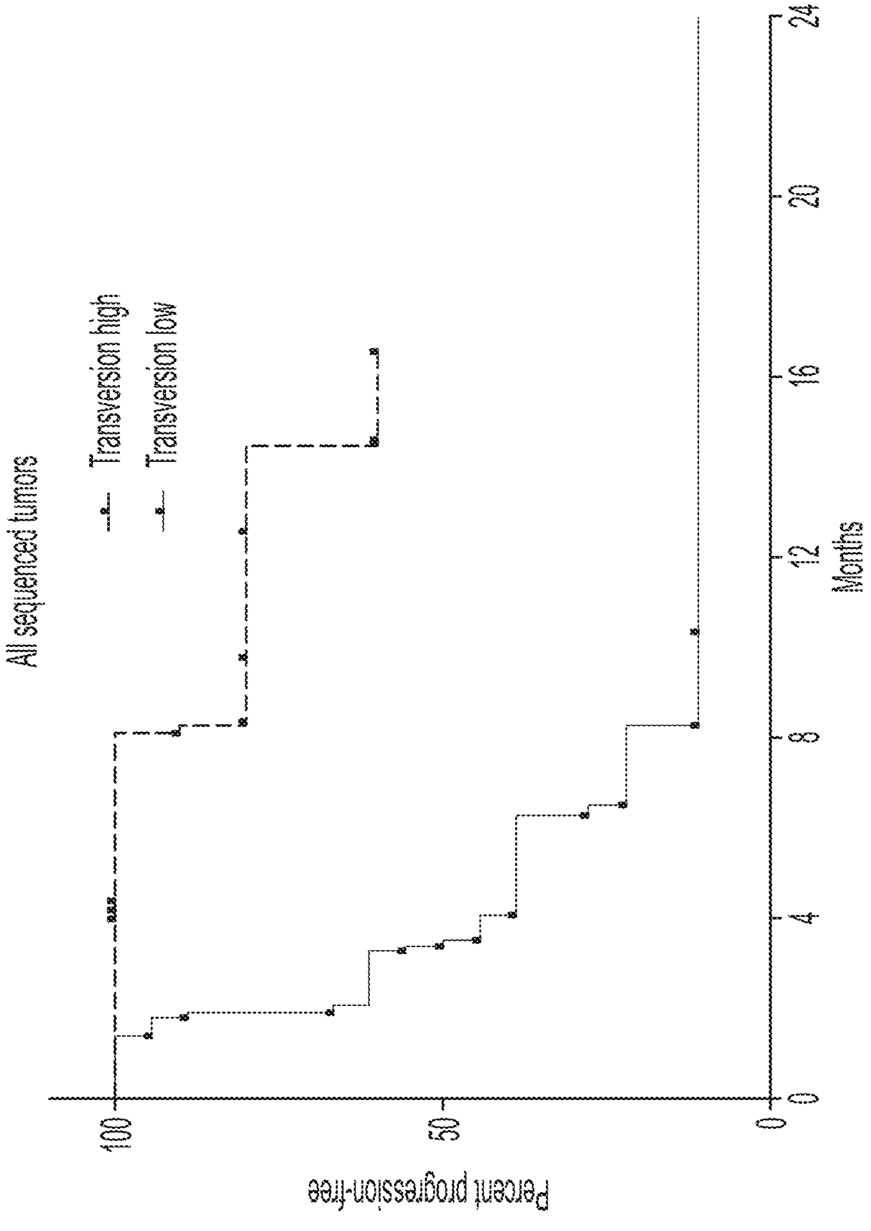
FIGS. 2A-2B show smoking and response to pembrolizumab in NSCLC.
Figure 2B:
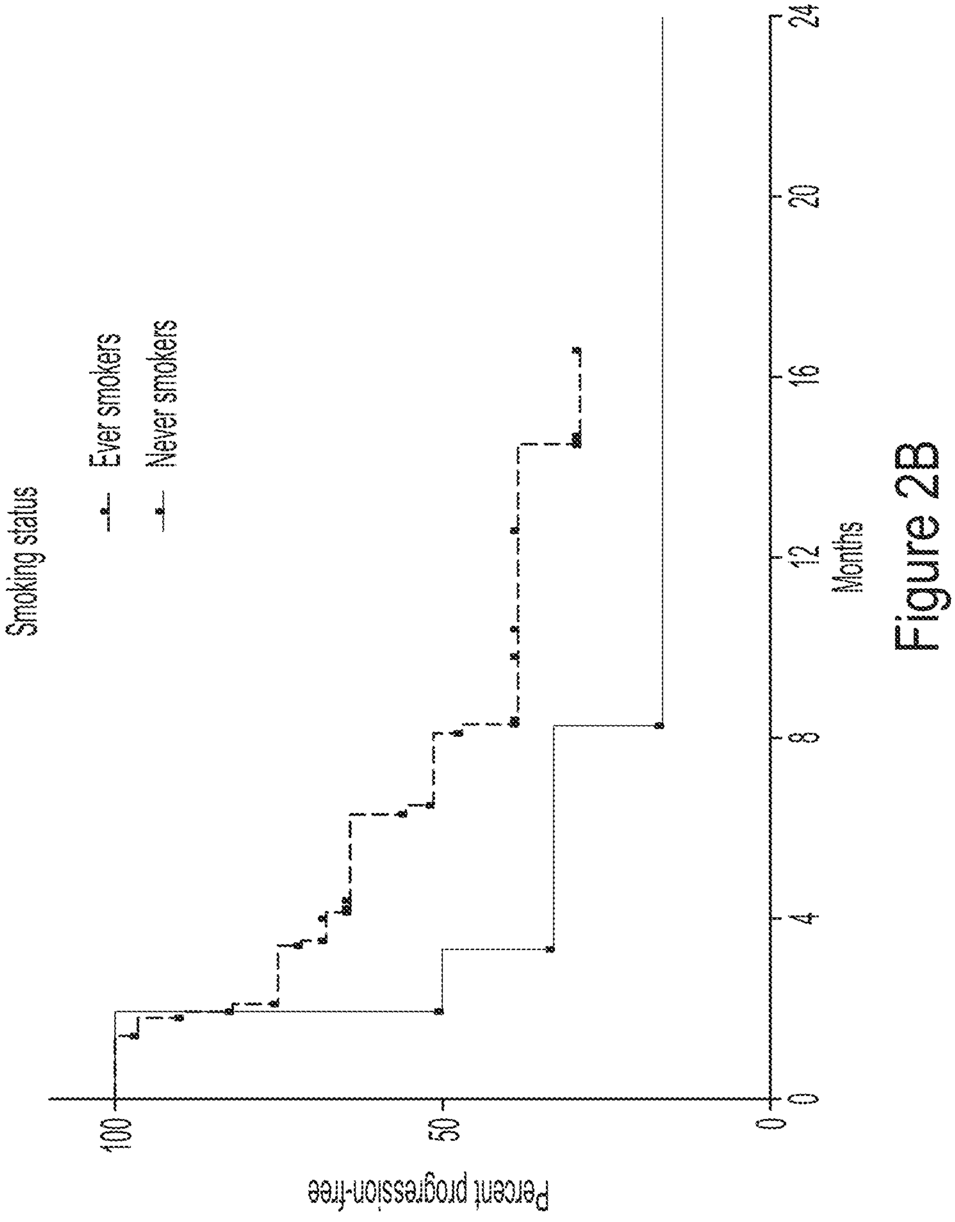

We examined all 34 exomes collectively to determine how patterns of mutational changes associated with response to pembrolizumab. C>A transversions were more frequent and C>T transitions were less frequent in patients with DCB compared to NDB (p=0.01 for both, FIG. 9). A previously validated binary classifier to identify the molecular signature of smoking (14) was applied to differentiate transversion-high (TH, smoking signature) from transversion-low (TL, never smoking signature) cases. Strikingly, patients with tumors harboring the smoking signature were more likely to respond to pembrolizumab. The ORR in TH tumors was 56% vs 17% in TL tumors, p=0.03; the rate of DCB was 77% vs 22%, p=0.004, and the PFS was also significantly longer in TH tumors (median not reached vs 3.5, p=0.0001) (FIG. 2A). Of note, self-reported smoking history did not significantly associate with DCB (never-smokers, 33%, vs. ever smokers, 48%, p=0.66) or PFS (FIG. 2B). Neither the rate of DCB nor PFS were significantly different in ever smokers versus never smokers (Fisher's exact p=0.66 and log-rank p=0.29, respectively) or heavy smokers (greater than median pack-years, 25) versus light/never smokers (≤25 pack-years) (Fisher's exact p=0.08 and log-rank p=0.15, respectively). The molecular smoking signature correlated more significantly with nonsynonymous mutation burden than smoking history (FIG. 19).

Figure 3:
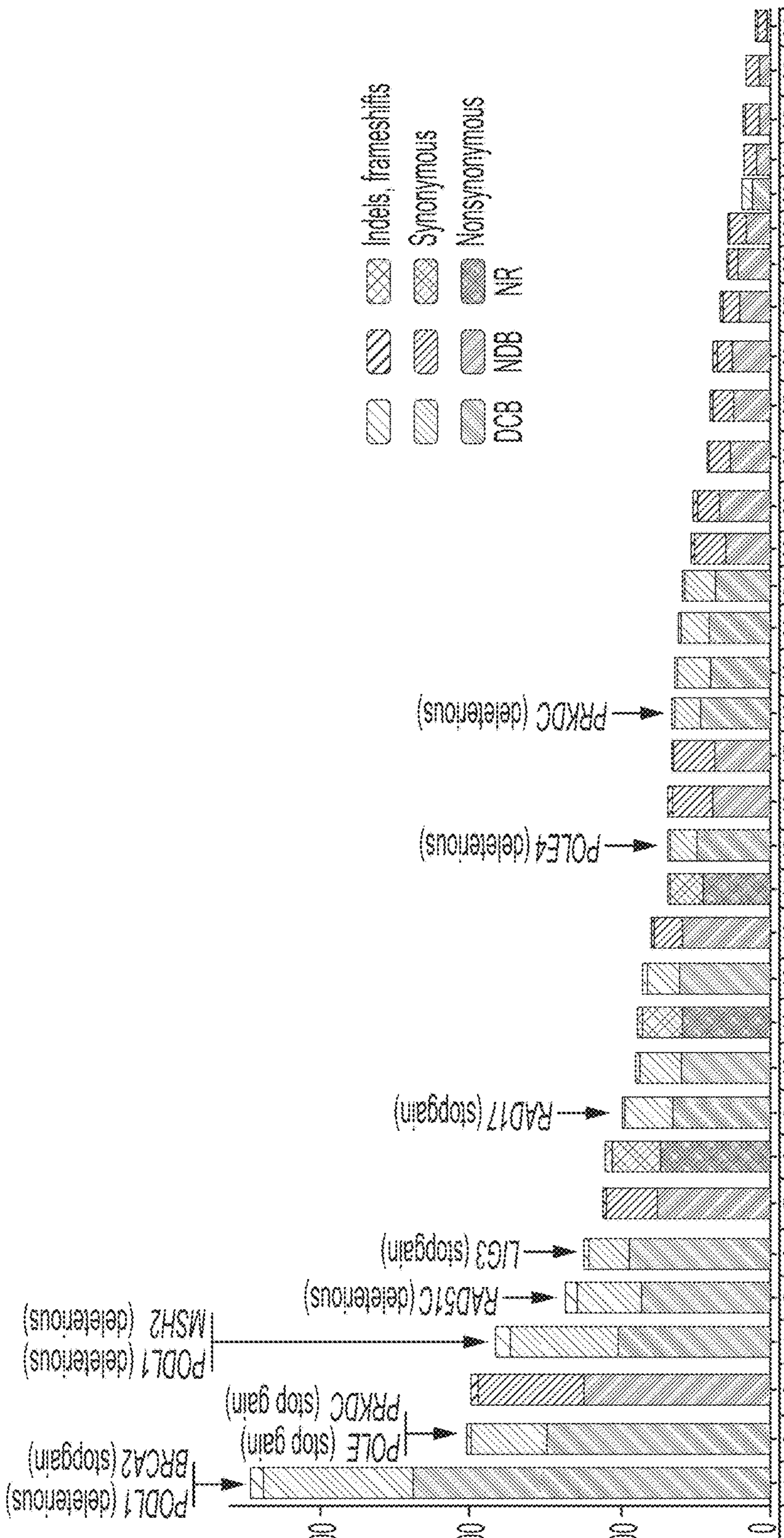
FIG. 3 shows mutation burden, clinical response, and factors contributing to mutation burden. Total exonic mutation burden for each sequenced tumor with nonsynonymous (dark shading), synonymous (medium shading), and indels/ frameshift mutations (light shading) displayed in the histogram. Columns are shaded to indicate durable response (DCB, green; NDB, red; not reached 6 months follow-up (NR), blue). The cohort identification (D, discovery; V, validation), best objective response (PR, partial response; SD, stable disease; POD, progression of disease), and progression-free survival (censored at the time of data lock) are reported in the table. Those with ongoing progression-free survival are labeled with ++. The presence of the molecular smoking signature is displayed with TH cases (purple) and TL cases (orange). The presence of deleterious mutations in specific DNA repair/replication genes is noted by the arrows.

Although the multitude of carcinogens in tobacco smoke are largely responsible for the mutagenesis in lung cancers (16), the wide range of mutation burden within both smokers and never-smokers raises the question of whether additional pathways may also contribute to accumulation of somatic mutations. Interestingly, we found deleterious mutations in a number of genes that are important in DNA repair or are predicted to cause higher mutations rates when mutated. For example, in the three responders with the highest mutation burden, we identified deleterious mutations in polymerase (DNA directed), Delta 1, Catalytic Subunit (POLD1), polymerase (DNA directed), epsilon, catalytic subunit (POLE), and MutS Homolog 2 (MSH2) (FIG. 3). Of particular interest, a POLD1 E374K mutation (SIFT 0.0, POLYPHEN deleterious) was identified in the tumor of a never-smoker with DCB and whose tumor harbored the greatest nonsynonymous mutation burden (n=507) of all never-smokers in our series. POLD1 Glu374 lies in the exonuclease proofreading domain of Pol 6 (17), and mutation of this residue may contribute to low fidelity replication of the lagging DNA strand. Consistent with this hypothesis, the exome of this patient was characterized by a relatively low proportion of C>A transversions (20%) and a predominance of C>T transitions (51%), which is similar to other POLD1 mutant, hypermutated tumors (18) and distinct from smoking-related lung cancers. Another responder, with the greatest mutation burden in our series, had a C284Y mutation in POLD1, which is also located in the exonuclease proofreading domain. Similarly, we observed nonsense mutations in PRKDC, the catalytic subunit of DNA-PK, and RAD17. Both genes are well known to be required for proper DNA repair and maintenance of genomic integrity (19, 20).

In addition to specific DNA repair-associated genes, genes that harbored deleterious mutations common to four or more DCB patients and not present in NDB patients included POLR2A, KEAP1, PAPPA2, PXDNL, RYR1, SCN8A, and SLIT3. Mutations in KRAS were found in 7/14 tumors from patients with DCB compared to 1/17 in the NDB group, a finding that may be explained by the previously reported association between smoking and presence of KRAS mutations in NSCLC (21). There were no mutations or copy number alterations in antigen presentation pathway-associated genes or CD274 (encoding programmed cell death ligand-1, PD-L1) that associated with response or resistance.

How does increased mutation burden affect tumor immunogenicity? The observation that nonsynonymous mutation burden predicts clinical benefit is consistent with the hypothesis that recognition of neoantigens, formed as a consequence of somatic mutations, is important for the activity of anti-PD-1 therapy. We therefore examined the landscape of candidate neoantigens in this tumor set using our previously described computational pipeline (22) (FIG. 10). Briefly, this pipeline identifies mutant nonamers with ≤500 nM binding affinity for patient-specific class I HLA alleles (23, 24), which are considered candidate neoantigens. We identified a median of 112 neoantigens per tumor (range 8-610) and, as expected (25), the quantity of candidate neoantigens per tumor correlated with mutation burden (Spearman ρ 0.91, p<0.0001), similar to the correlation recently reported across cancers (63). Tumors from patients with DCB had significantly higher neoantigen burden compared to those with NDB (median 203 vs 83, p=0.001, FIG. 4A), and high neoantigen burden was associated with improved PFS (median 14.5 vs 3.5 months, p=0.002; HR 0.23, 95% CI 0.09-0.58) (FIG. 4B). The presence of specific HLA alleles did not correlate with clinical efficacy (FIG. 11). The absolute burden of neoantigens, but not the frequency of neoantigens per nonsynonymous mutation, correlated with the degree of response to anti-PD-1 therapy (FIG. 12).

In our study, the goal was not to seek to comprehensively validate all possible candidate neoantigens. Rather, we set out to determine whether anti-PD-1 therapy can alter neoantigen specific T-cell reactivity and whether this can be used for immune monitoring following treatment with anti-PD-1 therapy. To directly test this, candidate neoantigens identified from one patient with a 95% decrease in tumor burden with pembrolizumab were examined. Identified candidate neoantigens were examined in a patient (Study ID #9 in FIG. 3 and FIG. 17) with exceptional response to pembrolizumab and available peripheral blood lymphocytes (PBLs). Predicted HLA-A restricted peptides were synthesized and used to screen for autologous T-cells using a validated high-throughput MHC multimer screening strategy (26, 27) to assess neoantigen-specific reactivity ex vivo in serially collected peripheral blood lymphocytes (PBLs) (Day 0, 21, 44, 63, 256, and 297, where Day 0 is the first date of treatment). This analysis revealed a dominant CD8+ T-cell response against a neoantigen resulting from a HERC1 P3278S mutation (ASNASSAAK (SEQ ID NO: 344)) (FIG. 4C). Notably, this T-cell response was below the level of detection at start of therapy (level of detection of 0.005%), but increased to readily detectable levels within 3 weeks post therapy initiation (0.040% of CD8+ T-cells) and was maintained at Day 44 (0.044% of Cd8+ T-cells). This rapid induction of T cell reactivity correlated with tumor regression and returned to levels just above background in the subsequent months as tumor regression plateaued (FIG. 4D). HERC1 P3278S-multimer reactive T-cells from PBLs collected on day 44 were characterized by a CD45RA-CCR7-HLA-DR+LAG-3− phenotype, consistent with an activated effector population (FIG. 20). These data reveal autologous T-cell responses against cancer neoantigens in the context of a clinical response to anti-PD-1 therapy. To our knowledge, this is first use of cancer exome data to uncover autologous T-cell responses against cancer neoantigens in the context of a clinical response to anti-PD-1 therapy.

Example 3. In Vitro Analyses of Immunogenic Peptides

This example demonstrates the in vitro validation of immunogenic peptides.

To validate the specificity of the neoantigen reactive T-cells, PBLs from day 63 and 297 were expanded in vitro in the presence of the mutant peptide and subsequently re-stimulated with either mutant or wild-type peptide (ASNASSAAK (SEQ ID NO: 344) vs ASNAPSAAK (SEQ ID NO: 5925)), and analyzed by intracellular cytokine staining. At both time points, a substantial population of polyfunctional CD8+ T-cells (characterized by IFNγ, CD107a, MIP10 (the chemokine CCL4), and TNFα production) was detected in response to mutant but not wild-type peptide (FIGS. 4E, 13A-D).

The success of T-cell checkpoint therapies in a number of cancers (2-5) has confirmed the ability to re-establish a tumor-directed effector T-cell response. However, only a subset of patients benefit from these therapies and the determinants and mediators of response are unknown. In the current study, it is shown that in NSCLCs treated with pembrolizumab, elevated nonsynonymous mutation burden is strongly predictive of clinical efficacy and can be used to identify patients with high likelihood of benefit. In addition, clinical efficacy correlates with a molecular signature characteristic of tobacco carcinogen-related mutagenesis, certain DNA repair mutations, and with the burden of neoantigens. Furthermore, we describe an example of using cancer exome data from a lung cancer patient to identify an autologous neoantigen-specific peripheral blood T-cell response that correlated temporally with a rapid and durable response to pembrolizumab.

As expected, mutation burden, smoking signature, and neoantigen burden were closely associated, which limits the capacity for multivariate analysis to distinguish the independent influence of each factor on response to pembrolizumab. Nevertheless, it should be noted that the molecular smoking signature correlated with efficacy while self-reported smoking status did not, highlighting the power of the classifier to identify molecularly-related tumors within a heterogeneous group. Moreover, the correlation between the molecular signature of smoking in the exomes examined and clinical efficacy has important potential implications. As molecular evidence of smoking can be identified by limited genomic assessment (8), it would be interesting to examine whether the molecular smoking signature alone can be used to predict response to anti-PD-1 therapy without the need to sequence the entire exome.

Nearly all tumors in this study (91%) were positive for PD-L1 expression (≥1% membranous staining; clone 22C3, Merck & Co., Inc. (6)). This marker appears to enrich for response (3, 6, 28), but many tumors deemed PD-L1 positive do not respond to anti-PD-1 therapies and responses are also seen in patients with PD-L1 negative tumors (6, 28). Previous studies have reported that pre-treatment PD-L1 expression enriches for response to anti-PD-1 therapies (3, 6, 28), but many tumors deemed PD-L1 positive do not respond and some responses occur in PD-L1 negative tumors (6, 28). Semi-quantitative PD-L1 staining results were available for 30 of 34 patients, where strong staining represented ≥50% PD-L1 expression, weak represented 1-49%, and negative represented <1% (clone 22C3, Merck (6)). As this trial largely enrolled patients with PD-L1 tumor expression, most samples had some degree of PD-L1 expression (24 of 30, 80%, FIG. 17), limiting the capacity to determine relationships between mutation burden and PD-L1 expression. Among those with high nonsynonymous mutation burden (>200, above median of overall cohort) and some degree of PD-L1 expression (weak/strong), the rate of DCB was 91%(10 of 11, 95% CI 59-99%). In contrast, in those with low mutation burden and some degree of PD-L1 expression, the rate of DCB was only 10%(1 of 10, 95% CI 0-44%). When exclusively examining patients with weak PD-L1 expression, high nonsynonymous mutation burden was associated with DCB in 75% (3 of 4, 95% CI 19-99%) while low mutation burden was associated with DCB in 11% (1 of 9, 0%-48%). Large-scale studies are needed to determine the relationship between PD-L1 intensity and mutation burden. Additionally, recent data have demonstrated that the localization of PD-L1 expression within the tumor microenvironment (on infiltrating immune cells (32), at the invasive margin, tumor core, etc. (33)) may affect the use of PD-L1 as a biomarker.

T-cell recognition of cancers relies upon presentation of tumor-specific antigens on MHIC molecules by cancer cells and professional antigen presenting cells (29). A few elegant pre-clinical (30-33, 66-68) and clinical (25, 34-36, 69) reports have demonstrated that neoantigen-specific effector T-cell response can recognize and shrink established tumors (36). Our finding that nonsynonymous mutation burden was more predictive of clinical benefit with anti-PD-1 therapy compared to total exonic mutation burden suggests the importance of neoantigens in dictating response. In support of this, for the first time, the temporal association between the expansion of neoantigen-specific T-cells in peripheral blood with radiographic response to anti-PD-1 therapy is shown. The observation that anti-PD-1-induced neoantigen specific T cell reactivity can be observed within the peripheral blood compartment may open the door to the development of blood-based assays to uncover functional neoantigens and to monitor response following anti-PD-1 therapy. Certain neoantigen sequences are included herein in FIG. 21.

The recent development of T-cell checkpoint inhibitors has begun to transform the treatment landscape for patients with a number of high prevalence malignancies. These findings impact our understanding of response to anti-PD-1 therapy and on its application in the clinic. The ability to identify those patients most likely to benefit from these therapies, as demonstrated here by analysis of nonsynonymous mutation burden, will contribute to maximizing the clinical value of these novel therapies.

Example 4. Materials and Methods for Examples 1-3

The present example provides detailed Materials & Methods for the work presented herein in examples 1-3.

We obtained tumor tissue from lung cancer patients who were treated with pembrolizumab. These samples were from pembrolizumab-treated patients who experienced a long term benefit (LB), or minimal/no benefit (NB). Whole exome sequencing was performed on these tumors and matching normal blood. Somatic mutations and candidate somatic neoantigens generated from these mutations were identified and characterized.

Patients and Clinical Characteristics

All patients had stage IV non-small cell lung cancer (NSCLC) and were treated at Memorial Sloan Kettering Cancer Center (n=29) or the University of California at Los Angeles (n=5) on protocol NCT01295827 (FIG. 17). All patients initiated therapy in 2012-2013 and were treated at 10 mg/kg every 2-3 weeks, except for 5 patients treated at 2 mg/kg every 3 weeks. The overall response rate and progression-free survival are reported to be similar across dose and schedules (6). All patients had consented to Institutional Review Board-approved protocols permitting tissue collection and sequencing. PD-L1 expression was assessed prospectively by immunohistochemistry using a previously validated murine anti-human anti-PD-L1 antibody (clone 22C3, Merck & Co., Inc.). Membranous expression of PD-L1 on tumor cells and infiltrating immune cells were scored. 31 (91%) scored at least 1% positive for PD-L1 expression; 2 patients were PD-L1 negative; and 1 was unknown. Smoking status was evaluated using previously completed self-reported smoking questionnaires executed as standard of care at MSKCC or review of medical records at UCLA. Patients eligible for this analysis all received at least two doses of study therapy and were evaluable for response to pembrolizumab, and did not prematurely discontinue therapy due to toxicity or withdrawal of consent.

Tumor Samples

All tumor tissue used for sequencing was obtained prior to dosing with pembrolizumab, except for one non-responder in whom post-treatment tissue was used (study ID DM123062). Tumor samples used for whole exome sequencing were paraffin-embedded (FFPE). Peripheral blood was collected and DNA isolated from all patients (Nucleospin Blood L, Machery-Nagel). Presence of tumor tissue in the sequenced samples was confirmed by examination of a representative hematoxylin and eosin-stained slide by thoracic pathologists (N.R. or A.M). DNA extraction was performed using the DNEasy kit (Qiagen).

Clinical Efficacy Analysis

Objective response to pembrolizumab was assessed by investigator-assessed immune-related response criteria (irRC) (37) by a study radiologist. Per protocol, CT scans were performed every nine weeks. Partial and complete responses were confirmed by a repeat imaging occurring at least 4 weeks after the initial identification of response; unconfirmed responses were considered stable or progressive disease dependent on results of the second CT scan. Durable clinical benefit (DCB) was defined as stable disease or partial response lasting longer than 6 months (week 27, the time of third protocol-scheduled response assessment). No durable benefit (NDB) was defined as progression of disease≤6 months of beginning therapy. Patients who were still ongoing study therapy at the time of the data lock (Oct. 10, 2014) but who had not yet reached 6 months of follow up were considered "Not reached" (NR). These patients were not included in the analysis of DCB/NDB, but were included in assessments of objective response and progression-free survival. For patients with ongoing response to study therapy, progression free survival was censored at the date of the most recent imaging evaluation. For alive patients, overall survival was censored at the date of last known contact.

Whole Exome Capture and Sequencing

Whole-exome capture libraries were constructed via the Agilent Sure-Select Human All Exon v2.0, 44 Mb baited target with the Broad in-solution hybrid selection process. Enriched exome libraries were sequenced on the HiSeq 2000 platform (Illumina) to generate paired-end reads (2×76 bp) to a goal of 150× mean target coverage (Broad Institute, Cambridge, MA) (FIGS. 14A-14Q, FIG. 18).

HLA Typing

HLA typing was performed at the MSKCC HLA typing lab New York Blood Center by high resolution SeCore HLA sequence-based typing method (HLA-SBT) (Invitrogen). ATHLATES (http://www.broadinstitute.org/scientific-community/science/projects/viral-genomics/athlates) (38) was also used for HLA typing and confirmation.

Exome Analysis Pipeline

Raw sequencing data were aligned to the hg37 genome build using the Burrows-Wheeler Aligner (BWA) version 0.7.10 (39) (FIG. 6). Further indel realignment, base-quality score recalibration and duplicate-read removal were performed using the Genome Analysis Toolkit (GATK) version 3.2.2 (40). Mutations were annotated using SnpEffect version 3.5d (build 2014-03-05) (41). Somatic Sniper version 1.0.0 (42), VarScan version 2.2.3 (43), Strelka version 1.0.13 (44) and MuTect version 1.4 (45) were used to generate single nucleotide variant (SNV) calls using default parameters. VarScan and Strelka were used to generate indel calls. Baseline filters (depth of 7× coverage in tumor specimens, >97% normal allelic fraction, >10% tumor allelic fraction) were chosen. Known single nucleotide polymorphisms (SNPs) were eliminated by comparison to 1000 Genomes Project, ESP6500 (National Heart, Lung and Blood Institute [NHLBI] GO Exome Sequencing Project) and dbSNP132 (46-48). Single nucleotide polymorphisms (SNPs) that were rare in the SNP data bases and present in tumors with an allelic fraction of zero in the normal DNA were manually reviewed using Integrative Genomics Viewer (IGV) and included as somatic SNVs (49). Manual review using IGV was also conducted for all mutations in any of the following additional three categories: (i) called by one caller (ii) coverage between 7×and 35× (iii) tumor allelic frequency less than 10 percent but called by two or more callers. Called SNVs were evaluated as deleterious if denoted as such by snpEff (high), SIFT (50) (score<0.05) or PolyPhen-2 ("D" or "P") (51). SIFT and Polyphen2 prediction scores and GERP++ conservation scores were parsed from dbNSFP version 2.2 (52). Validation resequencing of detected mutations is >97% (53).

Molecular Signature Analysis

The mutation spectrum in each sample was calculated by analyzing nonsynonymous exonic single nucleotide substitutions within their trinucleotide sequence context. That is, for each sample the percentage of each of the six possible single nucleotide changes (C>A:G>T, C>G:G>C, C>T:G>A, T>A:A>T, T>C:A>G, T>G:A>C, with the pyrimidine of the Watson-Crick base pair referenced first) within each of the 16 possible combinations of flanking nucleotides was calculated to generate a 96-feature vector that is used to represent the mutation spectrum for that sample. We utilized a Support Vector Machine (R package e1071) to generate a binary classifier to distinguish transversion low (TL) and transversion high (TH) tumors. Similar to a previously published analysis (14), the classifier was trained using lifelong never smokers and patients with ≥60 pack-years of smoking history as the respective controls. The training set was derived from publicly available exome sequencing and smoking history data from TCGA and previously published results (54). This classifier was applied to all sequenced patients in order to classify all samples as belonging to either the TL or TH categories.

In Silico Neoantigen Pipeline

All nonsynonymous point mutations identified were translated into strings of 17 amino acids with the mutant amino acid situated centrally using a bioinformatic tool called NAseek (22). A sliding window method was used to identify the 9 amino acid substrings within the mutant 17mer that had MHC Class I binding affinity of ≤500 nM to one (or more) of the patient-specific HLA alleles. Binding affinity for the mutant and corresponding wild type nonamer were analyzed using NetMHCv3.4 software (23, 24, 55-57).

Combinatorial Coding and Multimer Screening

HLA-A restricted candidate neoantigens were synthesized in-house (Netherlands Cancer Institute) and HLA-multimers containing these peptides were produced by micro-scale parallel UV-induced peptide exchange reactions as previously described (26, 58). Briefly, peptide-MHC complexes loaded with UV-sensitive peptide were subjected to 366-nm UV light (CAMAG) for one hour at 4° C. in the presence of candidate neoantigen peptide in a 384-well plate. pMHC multimers were generated using a total of 11 different fluorescent streptavidin (SA) conjugates (Invitrogen). For each pMHC monomer, conjugation was performed with two of these fluorochromes. NaN3 (0.02% w/v) and an excess of D-biotin (26.4 mM, Sigma) were added to block residual binding sites. For T cell staining an combinatorial encoding strategy was employed to be able to analyze for reactivity against up to 47 different peptides in parallel (27). The PBMC samples were thawed, treated with DNAse for 1 h and stained with pMHC multimer panels for 15 min at 37C. Subsequently, anti-CD8-AF700 (Invitrogen), anti-CD4-FITC (Invitrogen), anti-CD14-FITC (Invitrogen), anti-CD16-FITC (Invitrogen), anti-CD19-FITC (Invitrogen), and LIVE/DEAD Fixable IR Dead Cell Stain Kit (Invitrogen) were added for additional 20 min on ice. Data acquisition was performed on an LSR II flow cytometer (Becton Dickinson) with FACSDiva 6 software. Cutoff values for the definition of positive responses were ≥0.005% of total CD8+ cells and ≥10 events. For immunophenotypical analysis, day 44 PMLs were stained with HERC1 P3278S MHC multimers in two colors (qdot 625 (Invitrogen) and PerCPe-Fluor710 (ebioscience)) plus anti-CD45RA Ab (Invitrogen), anti-CCR7 Ab (BD Bioscience), anti-HLA-DR Ab (BD Bioscience), and anti-LAG-3 Ab (R&D systems). The immunophenotype of HERC1 P3278S reactive and bulk CD8+ T-cells were analyzed. Data were acquired using an LSR II flow cytometer (Becton Dickson) with FASCDiva 6 software.

Intracellular Cytokine Staining (ICS)

HERC1 P>S mutant and wild type peptides of 9 amino acids in length (Mutant: ASNASSAAK (SEQ ID NO: 344), Wild type: ASNAPSAAK (SEQ ID NO: 5925)) were synthesized (GenScript Piscataway, NJ). 1.5×106 patient PBMCs were cultured with 1.5×106 autologous PBMCs pulsed with HERC1 P>S mutant peptide in RPMI media containing 10% pooled human serum (PHS), 10 mM HEPES, 2 mM L Glutamine, and 50 M P-mercaptoethanol supplemented with IL-15 (10 ng/ml) and IL-2 (10 IU/ml), using methods previously described (59). Cells were harvested at day 12, stained with 3 μL PE-Cy5-CD107a (BD Pharmingen), and either left unstimulated, or stimulated by the addition of (a) mutant peptide or (b) wild type peptide for 2 hours. Cells were then treated with 1× Brefeldin A and monensin (BioLegend) for 4 hours, and subsequently stained with 1 μL Alexa Fluor 405-CD3 (Invitrogen), 3 μL APC-H7-CD8 (BD Bioscience), and 1 μL ECD-CD4 (Beckman Coulter). Upon subsequent washing and permeabilization, the cells were stained with the following antibodies to intracellular cytokines: 3 μL Alexa Fluor 647-IFN-7 (Biolegend), 3 μL PE-MIP-10, and 1 μL PE-Cy7-TNF-α (BD Pharmingen). Data were acquired by flow cytometry (using CYAN flow cytometer, Summit software, Dako Cytomation California Inc., Carpinteria, CA). Analysis was done by FlowJo version 10.1, TreeStar, Inc. CD3+ single cell lymphocytes were gated for analysis (SS vs. FS [low, mid], FS vs. Pulse Width [all, low], and CD3 vs. "dump" channel [high, low]).

Statistics

Mann-Whitney test was used to compare mutation burdens and differences in the frequency of nucleotide changes. The Log-Rank and Mantel-Haenszel tests were used to compare Kaplan-Meier survival curves. The proportion of objective responders/non-responders or DCB/NDB were compared using Fisher's Exact Test. The receiver operator characteristic (ROC) curve was generated by plotting the proportion of all DCB patients with mutation burden above any given cut point (sensitivity) against the proportion of the NDB patients that would also exceed the same cut point (1−specificity). The area under the curve and exact 95% confidence intervals are reported. Correlations between nonsynonymous mutation burden and neoantigen burden, neoantigen burden and best overall response, and frequency of neoantigen burden/nonsynonymous mutation and best overall response were calculated using Spearman correlation formula. Statistical analyses were performed using GraphPad Prism v.6 (Graphpad Prism Software, San Diego, CA).

Example 5. Treatment with Pembrolizumab

This example provides instructions for treatment of a cancer (melanoma) with an antibody immunotherapy (pembrolizumab), as approved by the United States Food & Drug Administration for the treatment of metastatic melanoma. In some embodiments, long term clinical benefit is observed after pembrolizumab treatment.

KEYTRUDA® (pembrolizumab) for injection, for intravenous use Initial U.S.
Approval: 2014

INDICATIONS AND USAGE

KEYTRUDA is a human programmed death receptor-1 (PD-1)-blocking antibody indicated for the treatment of patients with unresectable or metastatic melanoma and disease progression following ipilimumab and, if BRAF V600 mutation positive, a BRAF inhibitor. This indication is approved under accelerated approval based on tumor response rate and durability of response. An improvement in survival or disease-related symptoms has not yet been established. Continued approval for this indication may be contingent upon verification and description of clinical benefit in the confirmatory trials. (1)

DOSAGE AND ADMINISTRATION

Administer 2 mg/kg as an intravenous infusion over 30 minutes every 3 weeks. (2.1)

Reconstitute and dilute prior to intravenous infusion. (2.3)

DOSAGE FORMS AND STRENGTHS

For injection: 50 mg, lyophilized powder in single-use vial for reconstitution (3)

CONTRAINDICATIONS

None. (4)

WARNINGS AND PRECAUTIONS

Immune-mediated adverse reactions: Administer corticosteroids based on the severity of the reaction. (5.1, 5.2, 5.3, 5.4, 5.5, 5.6)

Immune-mediated pneumonitis: Withhold for moderate, and permanently discontinue for severe or life-threatening pneumonitis. (5.1)

Immune-mediated colitis: Withhold for moderate or severe, and permanently discontinue for life-threatening colitis. (5.2)

Immune-mediated hepatitis: Monitor for changes in hepatic function. Based on severity of liver enzyme elevations, withhold or discontinue. (5.3)

Immune-mediated hypophysitis: Withhold for moderate, withhold or discontinue for severe, and permanently discontinue for life-threatening hypophysitis. (5.4)

Immune-mediated nephritis: Monitor for changes in renal function. Withhold for moderate, and permanently discontinue for severe or life-threatening nephritis. (5.5)

Immune-mediated hyperthyroidism and hypothyroidism: Monitor for changes in thyroid function. Withhold for severe and permanently discontinue for life-threatening hyperthyroidism. (5.6)

Embryofetal Toxicity: KEYTRUDA may cause fetal harm. Advise females of reproductive potential of the potential risk to a fetus. (5.8)

ADVERSE REACTIONS

Most common adverse reactions (reported in ≥20% of patients) included fatigue, cough, nausea, pruritus, rash, decreased appetite, constipation, arthralgia, and diarrhea. (6.1)

To report SUSPECTED ADVERSE REACTIONS, contact Merck Sharp & Dohme Corp., a subsidiary of Merck & Co., Inc., at 1-877888-4231 or FDA at 1-800-FDA-1088 or www.fda.gov/medwatch.

USE IN SPECIFIC POPULATIONS

Nursing mothers: Discontinue nursing or discontinue KEYTRUDA. (8.3)

1 Indications and Usage

KEYTRUDA® (pembrolizumab) is indicated for the treatment of patients with unresectable or metastatic melanoma and disease progression following ipilimumab and, if BRAF V600 mutation positive, a BRAF inhibitor [see Clinical Studies (14)].

This indication is approved under accelerated approval based on tumor response rate and durability of response. An improvement in survival or disease-related symptoms has not yet been established. Continued approval for this indication may be contingent upon verification and description of clinical benefit in the confirmatory trials.

2 Dosage and Administration 2.1 Recommended Dosing

The recommended dose of KEYTRUDA is 2 mg/kg administered as an intravenous infusion over 30 minutes every 3 weeks until disease progression or unacceptable toxicity.

2.2 Dose Modifications

Withhold KEYTRUDA for any of the following:

- Grade 2 pneumonitis [see Warnings and Precautions (5.1)]
- Grade 2 or 3 colitis [see Warnings and Precautions (5.2)]
- Symptomatic hypophysitis [see Warnings and Precautions (5.4)]
- Grade 2 nephritis [see Warnings and Precautions (5.5)]
- Grade 3 hyperthyroidism [see Warnings and Precautions (5.6)]
- Aspartate aminotransferase (AST) or alanine aminotransferase (ALT) greater than 3 and up to 5 times upper limit of normal (ULN) or total bilirubin greater than 1.5 and up to 3 times ULN
- Any other severe or Grade 3 treatment-related adverse reaction [see Warnings and Precautions (5.7)]
- Resume KEYTRUDA in patients whose adverse reactions recover to Grade 0-1.
- Permanently discontinue KEYTRUDA for any of the following:
- Any life-threatening adverse reaction
- Grade 3 or 4 pneumonitis [see Warnings and Precautions (5.1)]
- Grade 3 or 4 nephritis [see Warnings and Precautions (5.5)]
- AST or ALT greater than 5 times ULN or total bilirubin greater than 3 times ULN For patients with liver metastasis who begin treatment with Grade 2 AST or ALT, if AST or ALT increases by greater than or equal to 50% relative to baseline and lasts for at least 1 week Grade 3 or 4 infusion-related reactions Inability to reduce corticosteroid dose to 10 mg or less of prednisone or equivalent per day within 12 weeks Persistent Grade 2 or 3 adverse reactions that do not recover to Grade 0-1 within 12 weeks after last dose of KEYTRUDA Any severe or Grade 3 treatment-related adverse reaction that recurs [see Warnings and Precautions (5.7)]

2.3 Preparation and Administration

Preparation

Add 2.3 mL of Sterile Water for Injection, USP by injecting the water along the walls of the vial and not directly on the lyophilized powder (resulting concentration 25 mg/mL).

Slowly swirl the vial. Allow up to 5 minutes for the bubbles to clear. Do not shake the vial.

Visually inspect the reconstituted solution for particulate matter and discoloration prior to administration. Reconstituted KEYTRUDA is a clear to slightly opalescent, colorless to slightly yellow solution. Discard reconstituted vial if extraneous particulate matter other than translucent to white proteinaceous particles is observed.

Withdraw the required volume from the vial(s) of KEYTRUDA and transfer into an intravenous (IV) bag containing 0.9% Sodium Chloride Injection, USP. Mix diluted solution by gentle inversion. The final concentration of the diluted solution should be between 1 mg/mL to 10 mg/mL.

Discard any unused portion left in the vial.

Storage of Reconstituted and Diluted Solutions

The product does not contain a preservative. Store the reconstituted and diluted solutions of KEYTRUDA either:

At room temperature for no more than 4 hours from the time of reconstitution. This includes room temperature storage of reconstituted vials, storage of the infusion solution in the IV bag, and the duration of infusion.

Under refrigeration at 2° C. to 8° C. (36° F. to 46° F.) for no more than 24 hours from the time of reconstitution. If refrigerated, allow the diluted solution to come to room temperature prior to administration.

Do not freeze.

Administration

Administer infusion solution intravenously over 30 minutes through an intravenous line containing a sterile, non-pyrogenic, low-protein binding 0.2 micron to 5 micron in-line or add-on filter.

Do not co-administer other drugs through the same infusion line.

3 Dosage Forms and Strengths

For injection: 50 mg lyophilized powder in a single-use vial for reconstitution

4 Contraindications

None.

5 Warnings and Precautions 5.1 Immune-Mediated Pneumonitis

Pneumonitis occurred in 12 (2.9%) of 411 melanoma patients, including Grade 2 or 3 cases in 8 (1.9%) and 1 (0.2%) patients, respectively, receiving KEYTRUDA in Trial 1. The median time to development of pneumonitis was 5 months (range 0.3 weeks-9.9 months). The median duration was 4.9 months (range 1 week-14.4 months). Five of eight patients with Grade 2 and the one patient with Grade 3 pneumonitis required initial treatment with high-dose systemic corticosteroids (greater than or equal to 40 mg prednisone or equivalent per day) followed by a corticosteroid taper. The median initial dose of high-dose corticosteroid treatment was 63.4 mg/day of prednisone or equivalent with a median duration of treatment of 3 days (range 1-34) followed by a corticosteroid taper. Pneumonitis led to discontinuation of KEYTRUDA in 3 (0.7%) patients. Pneumonitis completely resolved in seven of the nine patients with Grade 2-3 pneumonitis. Monitor patients for signs and symptoms of pneumonitis. Evaluate patients with suspected pneumonitis with radiographic imaging and administer corticosteroids for Grade 2 or greater pneumonitis. Withhold KEYTRUDA for moderate (Grade 2) pneumonitis, and permanently discontinue KEYTRUDA for severe (Grade 3) or life-threatening (Grade 4) pneumonitis [see Dosage and Administration (2.2) and Adverse Reactions (6.1)].

5.2 Immune-Mediated Colitis

Colitis (including microscopic colitis) occurred in 4 (1%) of 411 patients, including Grade 2 or 3 cases in 1 (0.2%) and 2 (0.5%) patients, respectively, receiving KEYTRUDA in Trial 1. The median time to onset of colitis was 6.5 months (range 2.3-9.8). The median duration was 2.6 months (range 0.6 weeks-3.6 months). All three patients with Grade 2 or 3 colitis were treated with high-dose corticosteroids (greater than or equal to 40 mg prednisone or equivalent per day) with a median initial dose of 70 mg/day of prednisone or equivalent; the median duration of initial treatment was 7 days (range 4-41), followed by a corticosteroid taper. One patient (0.2%) required permanent discontinuation of KEYTRUDA due to colitis. All four patients with colitis experienced complete resolution of the event. Monitor patients for signs and symptoms of colitis. Administer corticosteroids for Grade 2 or greater colitis. Withhold KEYTRUDA for moderate (Grade 2) or severe (Grade 3) colitis, and permanently discontinue KEYTRUDA for life threatening (Grade 4) colitis [see Dosage and Administration (2.2) and Adverse Reactions (6.1)].

5.3 Immune-Mediated Hepatitis

Hepatitis (including autoimmune hepatitis) occurred in 2 (0.5%) of 411 patients, including a Grade 4 case in 1 (0.2%) patient, receiving KEYTRUDA in Trial 1. The time to onset was 22 days for the case of Grade 4 hepatitis which lasted 1.1 months. The patient with Grade 4 hepatitis permanently discontinued KEYTRUDA and was treated with high-dose (greater than or equal to 40 mg prednisone or equivalent per day) systemic corticosteroids followed by a corticosteroid taper. Both patients with hepatitis experienced complete resolution of the event. Monitor patients for changes in liver function. Administer corticosteroids for Grade 2 or greater hepatitis and, based on severity of liver enzyme elevations, withhold or discontinue KEYTRUDA [see Dosage and Administration (2.2) and Adverse Reactions (6.1)].

5.4 Immune-Mediated Hypophysitis

Hypophysitis occurred in 2 (0.5%) of 411 patients, consisting of one Grade 2 and one Grade 4 case (0.2% each), in patients receiving KEYTRUDA in Trial 1. The time to onset was 1.7 months for the patient with Grade 4 hypophysitis and 1.3 months for the patient with Grade 2 hypophysitis. Both patients were treated with high-dose (greater than or equal to 40 mg prednisone or equivalent per day) corticosteroids followed by a corticosteroid taper and remained on a physiologic replacement dose. Monitor for signs and symptoms of hypophysitis. Administer corticosteroids for Grade 2 or greater hypophysitis. Withhold KEYTRUDA for moderate (Grade 2) hypophysitis, withhold or discontinue KEYTRUDA for severe (Grade 3) hypophysitis, and permanently discontinue KEYTRUDA for lifethreatening (Grade 4) hypophysitis [see Dosage and Administration (2.2) and Adverse Reactions (6.1)].

5.5 Renal Failure and Immune-Mediated Nephritis

Nephritis occurred in 3 (0.7%) patients, consisting of one case of Grade 2 autoimmune nephritis (0.2%) and two cases of interstitial nephritis with renal failure (0.5%), one Grade 3 and one Grade 4. The time to onset of autoimmune nephritis was 11.6 months after the first dose of KEYTRUDA (5 months after the last dose) and lasted 3.2 months; this patient did not have a biopsy. Acute interstitial nephritis was confirmed by renal biopsy in two patients with Grades 3-4 renal failure. All three patients fully recovered renal function with treatment with high-dose corticosteroids (greater than or equal to 40 mg prednisone or equivalent per day) followed by a corticosteroid taper. Monitor patients for changes in renal function. Administer corticosteroids for Grade 2 or greater nephritis. Withhold KEYTRUDA for moderate (Grade 2) nephritis, and permanently discontinue KEYTRUDA for severe (Grade 3), or life-threatening (Grade 4) nephritis [see Dosage and Administration (2.2) and Adverse Reactions (6.1)].

5.6 Immune-Mediated Hyperthyroidism and Hypothyroidism

Hyperthyroidism occurred in 5 (1.2%) of 411 patients, including Grade 2 or 3 cases in 2 (0.5%) and 1 (0.2%) patients, respectively, receiving KEYTRUDA in Trial 1. The median time to onset was 1.5 months (range 0.5-2.1). The median duration was 2.8 months (range 0.9 to 6.1). One of two patients with Grade 2 and the one patient with Grade 3 hyperthyroidism required initial treatment with high-dose corticosteroids (greater than or equal to 40 mg prednisone or equivalent per day) followed by a corticosteroid taper. One patient (0.2%) required permanent discontinuation of KEYTRUDA due to hyperthyroidism. All five patients with hyperthyroidism experienced complete resolution of the event. Hypothyroidism occurred in 34 (8.3%) of 411 patients, including a Grade 3 case in 1 (0.2%) patient, receiving KEYTRUDA in Trial 1. The median time to onset of hypothyroidism was 3.5 months (range 0.7 weeks-19 months). All but two of the patients with hypothyroidism were treated with long-term thyroid hormone replacement therapy. The other two patients only required short-term thyroid hormone replacement therapy. No patient received corticosteroids or discontinued KEYTRUDA for management of hypothyroidism. Thyroid disorders can occur at any time during treatment. Monitor patients for changes in thyroid function (at the start of treatment, periodically during treatment, and as indicated based on clinical evaluation) and for clinical signs and symptoms of thyroid disorders. Administer corticosteroids for Grade 3 or greater hyperthyroidism, withhold KEYTRUDA for severe (Grade 3) hyperthyroidism, and permanently discontinue KEYTRUDA for life-threatening (Grade 4) hyperthyroidism. Isolated hypothyroidism may be managed with replacement therapy without treatment interruption and without corticosteroids [see Dosage and Administration (2.2) and Adverse Reactions (6.1)].

5.7 Other Immune-Mediated Adverse Reactions

Other clinically important immune-mediated adverse reactions can occur. The following clinically significant, immune-mediated adverse reactions occurred in less than 1% of patients treated with KEYTRUDA in Trial 1: exfoliative dermatitis, uveitis, arthritis, myositis, pancreatitis, hemolytic anemia, partial seizures arising in a patient with inflammatory foci in brain parenchyma, and adrenal insufficiency.

Across clinical studies with KEYTRUDA in approximately 2000 patients, the following additional clinically significant, immune-mediated adverse reactions were reported in less than 1% of patients: myasthenic syndrome, optic neuritis, and rhabdomyolysis.

For suspected immune-mediated adverse reactions, ensure adequate evaluation to confirm etiology or exclude other causes. Based on the severity of the adverse reaction, withhold KEYTRUDA and administer corticosteroids. Upon improvement to Grade 1 or less, initiate corticosteroid taper and continue to taper over at least 1 month. Restart KEYTRUDA if the adverse reaction remains at Grade 1 or less. Permanently discontinue KEYTRUDA for any severe or Grade 3 immune-mediated adverse reaction that recurs and for any life-threatening immune-mediated adverse reaction [see Dosage and Administration (2.2) and Adverse Reactions (6.1)].

5.8 Embryofetal Toxicity

Based on its mechanism of action, KEYTRUDA may cause fetal harm when administered to a pregnant woman. Animal models link the PD-1/PDL-1 signaling pathway with maintenance of pregnancy through induction of maternal immune tolerance to fetal tissue. If this drug is used during pregnancy, or if the patient becomes pregnant while taking this drug, apprise the patient of the potential hazard to a fetus. Advise females of reproductive potential to use highly effective contraception during treatment with KEYTRUDA and for 4 months after the last dose of KEYTRUDA [see Use in Specific Populations (8.1, 8.8)].

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

1. W. B. Coley, The treatment of malignant tumors by repeated inoculations of erysipelas. With a report of ten original cases. 1893. Clinical Orthopaedics and Related Research, 3-11 (1991); published online EpubJan.
2. F. S. Hodi, S. J. O'Day, D. F. McDermott, R. W. Weber, J. A. Sosman, J. B. Haanen, R. Gonzalez, C. Robert, D. Schadendorf, J. C. Hassel, W. Akerley, A. J. van den Eertwegh, J. Lutzky, P. Lorigan, J. M. Vaubel, G. P. Linette, D. Hogg, C. H. Ottensmeier, C. Lebbe, C. Peschel, I. Quirt, J. I. Clark, J. D. Wolchok, J. S. Weber, J. Tian, M. J. Yellin, G. M. Nichol, A. Hoos, W. J. Urba, Improved survival with ipilimumab in patients with metastatic melanoma. The New England Journal of Medicine 363, 711-723 (2010); published online EpubAug 19 (10.1056/NEJMoa1003466).
3. S. L. Topalian, F. S. Hodi, J. R. Brahmer, S. N. Gettinger, D. C. Smith, D. F. McDermott, J. D. Powderly, R. D. Carvajal, J. A. Sosman, M. B. Atkins, P. D. Leming, D. R. Spigel, S. J. Antonia, L. Horn, C. G. Drake, D. M. Pardoll, L. Chen, W. H. Sharfman, R. A. Anders, J. M. Taube, T. L. McMiller, H. Xu, A. J. Korman, M. Jure-Kunkel, S. Agrawal, D. McDonald, G. D. Kollia, A. Gupta, J. M. Wigginton, M. Sznol, Safety, activity, and immune correlates of anti-PD-1 antibody in cancer. The New England Journal of Medicine 366, 2443-2454 (2012); published online EpubJun 28 (10.1056/NEJMoa1200690).

4. J. D. Wolchok, H. Kluger, M. K. Callahan, M. A. Postow, N. A. Rizvi, A. M. Lesokhin, N. H. Segal, C. E. Ariyan, R. A. Gordon, K. Reed, M. M. Burke, A. Caldwell, S. A. Kronenberg, B. U. Agunwamba, X. Zhang, I. Lowy, H. D. Inzunza, W. Feely, C. E. Horak, Q. Hong, A. J. Korman, J. M. Wigginton, A. Gupta, M. Sznol, Nivolumab plus ipilimumab in advanced melanoma. The New England Journal of Medicine 369, 122-133 (2013); published online EpubJul 11 (10.1056/NEJMoa1302369).
5. C. Robert, A. Ribas, J. D. Wolchok, F. S. Hodi, O. Hamid, R. Kefford, J. S. Weber, A. M. Joshua, W. J. Hwu, T. C. Gangadhar, A. Patnaik, R. Dronca, H. Zarour, R. W. Joseph, P. Boasberg, B. Chmielowski, C. Mateus, M. A. Postow, K. Gergich, J. Elassaiss-Schaap, X. N. Li, R. Iannone, S. W. Ebbinghaus, S. P. Kang, A. Daud, Anti-programmed-death-receptor-1 treatment with pembrolizumab in ipilimumab-refractory advanced melanoma: a randomised dose-comparison cohort of a phase 1 trial. Lancet 384, 1109-1117 (2014); published online EpubSep 20 (10.1016/50140-6736(14)60958-2).
6. E. B. Garon, L. Gandhi, N. Rizvi, R. Hui, A. S. Balmanoukian, A. Patnaik, J. P. Eder, G. R. Blumenshein, C. Aggarwal, J.-C. Soria, M. A. Ahn, M. A. Gubens, S. S. Ramalingam, E. Johnson, H. Arkenau, G. M. Lubiniecki, J. Zhang, R. Z. Rutledge, K. Emancipator, N. Leighl, ANTITUMOR ACTIVITY OF PEMBROLIZUMAB (PEMBRO; MK-3475) AND CORRELATION WITH PROGRAMMED DEATH LIGAND 1 (PD-L1) EXPRESSION IN A POOLED ANALYSIS OF PATIENTS (PTS) WITH ADVANCED NON-SMALL CELL LUNG CARCINOMA (NSCLC). Annals of Oncology 25, LBA43 (2014); published online EpubSep. 1, 2014 (10.1093/annonc/mdu438.51).
7. G. P. Pfeifer, Y. H. You, A. Besaratinia, Mutations induced by ultraviolet light. Mutation Research 571, 19-31 (2005); published online EpubApr 1 (10.1016/j.mrfmmm.2004.06.057).
8. G. P. Pfeifer, M. F. Denissenko, M. Olivier, N. Tretyakova, S. S. Hecht, P. Hainaut, Tobacco smoke carcinogens, DNA damage and p53 mutations in smoking-associated cancers. Oncogene 21, 7435-7451 (2002); published online EpubOct 21 (10.1038/sj.onc.1205803).
9. M. S. Lawrence, P. Stojanov, P. Polak, G. V. Kryukov, K. Cibulskis, A. Sivachenko, S. L. Carter, C. Stewart, C. H. Mermel, S. A. Roberts, A. Kiezun, P. S. Hammerman, A. McKenna, Y. Drier, L. Zou, A. H. Ramos, T. J. Pugh, N. Stransky, E. Helman, J. Kim, C. Sougnez, L. Ambrogio, E. Nickerson, E. Shefler, M. L. Cortes, D. Auclair, G. Saksena, D. Voet, M. Noble, D. DiCara, P. Lin, L. Lichtenstein, D. I Heiman, T. Fennell, M. Imielinski, B. Hernandez, E. Hodis, S. Baca, A. M. Dulak, J. Lohr, D. A. Landau, C. J. Wu, J. Melendez-Zajgla, A. Hidalgo-Miranda, A. Koren, S. A. McCarroll, J. Mora, R. S. Lee, B. Crompton, R. Onofrio, M. Parkin, W. Winckler, K. Ardlie, S. B. Gabriel, C. W. Roberts, J. A. Biegel, K. Stegmaier, A. J. Bass, L. A. Garraway, M. Meyerson, T. R. Golub, D. A. Gordenin, S. Sunyaev, E. S. Lander, G. Getz, Mutational heterogeneity in cancer and the search for new cancer-associated genes. Nature 499, 214-218 (2013); published online EpubJul 11 (10.1038/nature12213).
10. L. B. Alexandrov, S. Nik-Zainal, D. C. Wedge, S. A. Aparicio, S. Behjati, A. V. Biankin, G. R. Bignell, N. Bolli, A. Borg, A. L. Borresen-Dale, S. Boyault, B. Burkhardt, A. P. Butler, C. Caldas, H. R. Davies, C. Desmedt, R. Eils, J. E. Eyfjord, J. A. Foekens, M. Greaves, F. Hosoda, B. Hutter, T. Ilicic, S. Imbeaud, M. Imielinski, N. Jager, D. T. Jones, D. Jones, S. Knappskog, M. Kool, S. R. Lakhani, C. Lopez-Otin, S. Martin, N. C. Munshi, H. Nakamura, P. A. Northcott, M. Pajic, E. Papaemmanuil, A. Paradiso, J. V. Pearson, X. S. Puente, K. Raine, M. Ramakrishna, A. L. Richardson, J. Richter, P. Rosenstiel, M. Schlesner, T. N. Schumacher, P. N. Span, J. W. Teague, Y. Totoki, A. N. Tutt, R. Valdes-Mas, M. M. van Buuren, L. van 't Veer, A. Vincent-Salomon, N. Waddell, L. R. Yates, I. Australian Pancreatic Cancer Genome, I. B. C. Consortium, I. M.-S. Consortium, I. PedBrain, J. Zucman-Rossi, P. A. Futreal, U. McDermott, P. Lichter, M. Meyerson, S. M. Grimmond, R. Siebert, E. Campo, T. Shibata, S. M. Pfister, P. J. Campbell, M. R. Stratton, Signatures of mutational processes in human cancer. Nature 500, 415-421 (2013); published online EpubAug 22 (10.1038/nature12477).
11. B. Vogelstein, N. Papadopoulos, V. E. Velculescu, S. Zhou, L. A. Diaz, Jr., K. W. Kinzler, Cancer genome landscapes. Science 339, 1546-1558 (2013); published online EpubMar 29 (10.1126/science.1235122).
12. R. Govindan, L. Ding, M. Griffith, J. Subramanian, N. D. Dees, K. L. Kanchi, C. A. Maher, R. Fulton, L. Fulton, J. Wallis, K. Chen, J. Walker, S. McDonald, R. Bose, D. Ornitz, D. H. Xiong, M. You, D. J. Dooling, M. Watson, E. R. Mardis, R. K. Wilson, Genomic Landscape of Non-Small Cell Lung Cancer in Smokers and Never-Smokers. Cell 150, 1121-1134 (2012); published online EpubSep 14 (DOI 10.1016/j.cell.2012.08.024).
13. P. S. Hammerman, M. S. Lawrence, D. Voet, R. Jing, K. Cibulskis, A. Sivachenko, P. Stojanov, A. McKenna, E. S. Lander, S. Gabriel, G. Getz, C. Sougnez, M. Imielinski, E. Helman, B. Hernandez, N. H. Pho, M. Meyerson, A. Chu, H. J. E. Chun, A. J. Mungall, E. Pleasance, A. G. Robertson, P. Sipahimalani, D. Stoll, M. Balasundaram, I Birol, Y. S. N. Butterfield, E. Chuah, R. J. N. Coope, R. Corbett, N. Dhalla, R. Guin, A. C. Hirst, M. Hirst, R. A. Holt, D. Lee, H. I Li, M. Mayo, R. A. Moore, K. Mungall, K. M. Nip, A. Olshen, J. E. Schein, J. R. Slobodan, A. Tam, N. Thiessen, R. Varhol, T. Zeng, Y. Zhao, S. J. M. Jones, M. A. Marra, G. Saksena, A. D. Cherniack, S. E. Schumacher, B. Tabak, S. L. Carter, N. H. Pho, H. Nguyen, R. C. Onofrio, A. Crenshaw, K. Ardlie, R. Beroukhim, W. Winckler, P. S. Hammerman, G. Getz, M. Meyerson, A. Protopopov, J. H. Zhang, A. Hadjipanayis, S. Lee, R. B. Xi, L. X. Yang, X. J. Ren, H. L. Zhang, S. Shukla, P. C. Chen, P. Haseley, E. Lee, L. Chin, P. J. Park, R. Kucherlapati, N. D. Socci, Y. P. Liang, N. Schultz, L. Borsu, A. E. Lash, A. Viale, C. Sander, M. Ladanyi, J. T. Auman, K. A. Hoadley, M. D. Wilkerson, Y. Shi, C. Liquori, S. W. Meng, L. Li, Y. J. Turman, M. D. Topal, D. H. Tan, S. Waring, E. Buda, J. Walsh, C. D. Jones, P. A. Mieczkowski, D. Singh, J. Wu, A. Gulabani, P. Dolina, T. Bodenheimer, A. P. Hoyle, J. V. Simons, M. G. Soloway, L. E. Mose, S. R. Jefferys, S. Balu, B. D. O'Connor, J. F. Prins, J. Liu, D. Y. Chiang, D. N. Hayes, C. M. Perou, L. Cope, L. Danilova, D. J. Weisenberger, D. T. Maglinte, F. Pan, D. J. den Berg, T. Triche, J. G. Herman, S. B. Baylin, P. W. Laird, G. Getz, M. Noble, D. Voet, G. Saksena, N. Gehlenborg, D. DiCara, J. H. Zhang, H. L. Zhang, C. J. Wu, S. Y. Liu, M. S. Lawrence, L. H. Zou, A. Sivachenko, P. Lin, P. Stojanov, R. Jing, J. Cho, M. D. Nazaire, J. Robinson, H. Thorvaldsdottir, J. Mesirov, P. J. Park, L. Chin, N. Schultz, R. Sinha, G. Ciriello, E. Cerami, B. Gross, A. Jacobsen, J. Gao, B. A. Aksoy, N. Weinhold, R. Ramirez, B. S. Taylor, Y. Antipin, B. Reva, R. L. Shen, Q. Mo, V. Seshan, P. K. Paik, M. Ladanyi, C. Sander, R.

Akbani, N. X. Zhang, B. M. Broom, T. Casasent, A. Unruh, C. Wakefield, R. C. Cason, K. A. Baggerly, J. N. Weinstein, D. Haussler, C. C. Benz, J. M. Stuart, J. C. Zhu, C. Szeto, G. K. Scott, C. Yau, S. Ng, T. Goldstein, P. Waltman, A. Sokolov, K. Ellrott, E. A. Collisson, D. Zerbino, C. Wilks, S. Ma, B. Craft, M. D. Wilkerson, J. T. Auman, K. A. Hoadley, Y. Du, C. Cabanski, V. Walter, D. Singh, J. Y. Wu, A. Gulabani, T. Bodenheimer, A. P. Hoyle, J. V. Simons, M. G. Soloway, L. E. Mose, S. R. Jefferys, S. Balu, J. S. Marron, Y. Liu, K. Wang, J. Liu, J. F. Prins, D. N. Hayes, C. M. Perou, C. J. Creighton, Y. Q. Zhang, W. D. Travis, N. Rekhtman, J. Yi, M. C. Aubry, R. Cheney, S. Dacic, D. Flieder, W. Funkhouser, P. Illei, J. Myers, M. S. Tsao, R. Penny, D. Mallery, T. Shelton, M. Hatfield, S. Morris, P. Yena, C. Shelton, M. Sherman, J. Paulauskis, M. Meyerson, S. B. Baylin, R. Govindan, R. Akbani, I. Azodo, D. Beer, R. Bose, L. A. Byers, D. Carbone, L. W. Chang, D. Chiang, A. Chu, E. Chun, E. Collisson, L. Cope, C. J. Creighton, L. Danilova, L. Ding, G. Getz, P. S. Hammerman, D. N. Hayes, B. Hernandez, J. G. Herman, J. Heymach, C. Ida, M. Imielinski, B. Johnson, I. Jurisica, J. Kaufman, F. Kosari, R. Kucherlapati, D. Kwiatkowski, M. Ladanyi, M. S. Lawrence, C. A. Maher, A. Mungall, S. Ng, W. Pao, M. Peifer, R. Penny, G. Robertson, V. Rusch, C. Sander, N. Schultz, R. L. Shen, J. Siegfried, R. Sinha, A. Sivachenko, C. Sougnez, D. Stoll, J. Stuart, R. K. Thomas, S. Tomaszek, M. S. Tsao, W. D. Travis, C. Vaske, J. N. Weinstein, D. Weisenberger, D. Wheeler, D. A. Wigle, M. D. Wilkerson, C. Wilks, P. Yang, J. J. Zhang, M. A. Jensen, R. Sfeir, A. B. Kahn, A. L. Chu, P. Kothiyal, Z. Wang, E. E. Snyder, J. Pontius, T. D. Pihl, B. Ayala, M. Backus, J. Walton, J. Baboud, D. L. Berton, M. C. Nicholls, D. Srinivasan, R. Raman, S. Girshik, P. A. Kigonya, S. Alonso, R. N. Sanbhadti, S. P. Barletta, J. M. Greene, D. A. Pot, M. S. Tsao, B. Bandarchi-Chamkhaleh, J. Boyd, J. Weaver, D. A. Wigle, I. A. Azodo, S. C. Tomaszek, M. C. Aubry, C. M. Ida, P. Yang, F. Kosari, M. V. Brock, K. Rogers, M. Rutledge, T. Brown, B. Lee, J. Shin, D. Trusty, R. Dhir, J. M. Siegfried, O. Potapova, K. V. Fedosenko, E. Nemirovich-Danchenko, V. Rusch, M. Zakowski, M. V. Iacocca, J. Brown, B. Rabeno, C. Czerwinski, N. Petrelli, Z. Fan, N. Todaro, J. Eckman, J. Myers, W. K. Rathmell, L. B. Thorne, M. Huang, L. Boice, A. Hill, R. Penny, D. Mallery, E. Curley, C. Shelton, P. Yena, C. Morrison, C. Gaudioso, J. S. Bartlett, S. Kodeeswaran, B. Zanke, H. Sekhon, K. David, H. Juhl, X. Van Le, B. Kohl, R. Thorp, N. V. Tien, N. Van Bang, H. Sussman, B. D. Phu, R. Hajek, N. PhiHung, K. Z. Khan, T. Muley, K. R. M. Shaw, M. Sheth, L. Yang, K. Buetow, T. Davidsen, J. A. Demchok, G. Eley, M. Ferguson, L. A. L. Dillon, C. Schaefer, M. S. Guyer, B. A. Ozenberger, J. D. Palchik, J. Peterson, H. J. Sofia, E. Thomson, M. Meyerson, C. G. A. R. Network, Comprehensive genomic characterization of squamous cell lung cancers. Nature 489, 519-525 (2012); published online EpubSep 27 (Doi 10.1038/Nature 11404).

14. The Cancer Genome Atlas Research Network, Comprehensive molecular profiling of lung adenocarcinoma. Nature 511, 543-550 (2014); published online EpubJul 31 (10.1038/nature13385).

15. O. D. Abaan, E. C. Polley, S. R. Davis, Y. J. Zhu, S. Bilke, R. L. Walker, M. Pineda, Y. Gindin, Y. Jiang, W. C. Reinhold, S. L. Holbeck, R. M. Simon, J. H. Doroshow, Y. Pommier, P. S. Meltzer, The exomes of the NCI-60 panel: a genomic resource for cancer biology and systems pharmacology. Cancer Research 73, 4372-4382 (2013); published online EpubJul 15 (10.1158/0008-5472.CAN-12-3342).

16. D. Hoffmann, I. Hoffmann, K. El-Bayoumy, The less harmful cigarette: a controversial issue. a tribute to Ernst L. Wynder. Chemical Research in Toxicology 14, 767-790 (2001); published online EpubJul 17. R. Hindges, U. Hubscher, DNA polymerase delta, an essential enzyme for DNA transactions. Biological Chemistry 378, 345-362 (1997); published online EpubMay 18. C. Palles, J. B. Cazier, K. M. Howarth, E. Domingo, A. M. Jones, P. Broderick, Z. Kemp, S. L. Spain, E. Guarino, I. Salguero, A. Sherborne, D. Chubb, L. G. Carvajal-Carmona, Y. Ma, K. Kaur, S. Dobbins, E. Barclay, M. Gorman, L. Martin, M. B. Kovac, S. Humphray, C. Consortium, W. G. S. Consortium, A. Lucassen, C. C. Holmes, D. Bentley, P. Donnelly, J. Taylor, C. Petridis, R. Roylance, E. J. Sawyer, D. J. Kerr, S. Clark, J. Grimes, S. E. Kearsey, H. J. Thomas, G. McVean, R. S. Houlston, I. Tomlinson, Germline mutations affecting the proofreading domains of POLE and POLD1 predispose to colorectal adenomas and carcinomas. Nature Genetics 45, 136-144 (2013); published online EpubFeb (10.1038/ng.2503).

19. J. F. Goodwin, K. E. Knudsen, Beyond DNA Repair: DNA-PK Function in Cancer. Cancer Discovery 4, 1126-1139 (2014); published online EpubOct (10.1158/2159-8290.CD-14-0358).

20. X. Wang, L. Zou, H. Zheng, Q. Wei, S. J. Elledge, L. Li, Genomic instability and endoreduplication triggered by RAD17 deletion. Genes & Development 17, 965-970 (2003); published online EpubApr 15 (10.1101/gad.1065103).

21. S. Dogan, R. Shen, D. C. Ang, M. L. Johnson, S. P. D'Angelo, P. K. Paik, E. B. Brzostowski, G. J. Riely, M. G. Kris, M. F. Zakowski, M. Ladanyi, Molecular epidemiology of EGFR and KRAS mutations in 3,026 lung adenocarcinomas: higher susceptibility of women to smoking-related KRAS-mutant cancers. Clinical Cancer Research 18, 6169-6177 (2012); published online EpubNov 15 (10.1158/1078-0432.CCR-11-3265).

22. A. S. Charen, V. Makarov, T. Merghoub, L. Walsh, J. Yuan, M. Miller, K. Kannan, M. A. Postow, C. Elipenahli, C. Liu, J. D. Wolchok, T. A. Chan, The neoantigen landscape underlying clinical response to ipilimumab. J Clin Oncol 31, 3003 (2014).

23. M. Nielsen, C. Lundegaard, P. Worning, S. L. Lauemoller, K. Lamberth, S. Buus, S. Brunak, O. Lund, Reliable prediction of T-cell epitopes using neural networks with novel sequence representations. Protein Science 12, 1007-1017 (2003); published online EpubMay (10.1110/ps.0239403).

24. C. Lundegaard, K. Lamberth, M. Harndahl, S. Buus, O. Lund, M. Nielsen, NetMHC-3.0: accurate web accessible predictions of human, mouse and monkey MHC class I affinities for peptides of length 8-11. Nucleic Acids Research 36, W509-512 (2008); published online EpubJul 1 (10.1093/nar/gkn202).

25. M. Rajasagi, S. A. Shukla, E. F. Fritsch, D. B. Keskin, D. DeLuca, E. Carmona, W. Zhang, C. Sougnez, K. Cibulskis, J. Sidney, K. Stevenson, J. Ritz, D. Neuberg, V. Brusic, S. Gabriel, E. S. Lander, G. Getz, N. Hacohen, C. J. Wu, Systematic identification of personal tumor-specific neoantigens in chronic lymphocytic leukemia. Blood 124, 453-462 (2014); published online EpubJul 17 (10.1182/blood-2014-04-567933).

26. B. Rodenko, M. Toebes, S. R. Hadrup, W. J. van Esch, A. M. Molenaar, T. N. Schumacher, H. Ovaa, Generation of peptide-MHC class I complexes through UV-mediated ligand exchange. Nature Protocols 1, 1120-1132 (2006) 10.1038/nprot.2006.121).
27. R. S. Andersen, P. Kvistborg, T. M. Frosig, N. W. Pedersen, R. Lyngaa, A. H. Bakker, C. J. Shu, P. Straten, T. N. Schumacher, S. R. Hadrup, Parallel detection of antigen-specific T cell responses by combinatorial encoding of MHC multimers. Nature Protocols 7, 891-902 (2012); published online EpubMay (10.1038/nprot.2012.037).
28. J. M. Taube, A. Klein, J. R. Brahmer, H. Xu, X. Pan, J. H. Kim, L. Chen, D. M. Pardoll, S. L. Topalian, R. A. Anders, Association of PD-1, PD-1 Ligands, and Other Features of the Tumor Immune Microenvironment with Response to Anti-PD-1 Therapy. Clinical Cancer Research 20, 5064-5074 (2014); published online EpubOct 1 (10.1158/1078-0432.CCR-13-3271).
29. R. D. Schreiber, L. J. Old, M. J. Smyth, Cancer immunoediting: integrating immunity's roles in cancer suppression and promotion. Science 331, 1565-1570 (2011); published online EpubMar 25 (10.1126/science.1203486).
30. T. Matsutake, P. K. Srivastava, The immunoprotective MHC II epitope of a chemically induced tumor harbors a unique mutation in a ribosomal protein. Proceedings of the National Academy of Sciences of the United States of America 98, 3992-3997 (2001); published online EpubMar 27 (10.1073/pnas.071523398).
31. H. Matsushita, M. D. Vesely, D. C. Koboldt, C. G. Rickert, R. Uppaluri, V. J. Magrini, C. D. Arthur, J. M. White, Y. S. Chen, L. K. Shea, J. Hundal, M. C. Wendl, R. Demeter, T. Wylie, J. P. Allison, M. J. Smyth, L. J. Old, E. R. Mardis, R. D. Schreiber, Cancer exome analysis reveals a T-cell-dependent mechanism of cancer immunoediting. Nature 482, 400-404 (2012); published online EpubFeb 16 (10.1038/nature10755).
32. J. C. Castle, S. Kreiter, J. Diekmann, M. Lower, N. van de Roemer, J. de Graaf, A. Selmi, M. Diken, S. Boegel, C. Paret, M. Koslowski, A. N. Kuhn, C. M. Britten, C. Huber, O. Tureci, U. Sahin, Exploiting the mutanome for tumor vaccination. Cancer Research 72, 1081-1091 (2012); published online EpubMar 1 (10.1158/0008-5472.CAN-11-3722).
33. T. Schumacher, L. Bunse, S. Pusch, F. Sahm, B. Wiestler, J. Quandt, O. Menn, M. Osswald, I. Oezen, M. Ott, M. Keil, J. Balss, K. Rauschenbach, A. K. Grabowska, I. Vogler, J. Diekmann, N. Trautwein, S. B. Eichmuller, J. Okun, S. Stevanovic, A. B. Riemer, U. Sahin, M. A. Friese, P. Beckhove, A. von Deimling, W. Wick, M. Platten, A vaccine targeting mutant IDH1 induces antitumour immunity. Nature 512, 324-327 (2014); published online EpubAug 21 (10.1038/nature13387).
34. P. F. Robbins, Y. C. Lu, M. El-Gamil, Y. F. Li, C. Gross, J. Gartner, J. C. Lin, J. K. Teer, P. Cliften, E. Tycksen, Y. Samuels, S. A. Rosenberg, Mining exomic sequencing data to identify mutated antigens recognized by adoptively transferred tumor-reactive T cells. Nature Medicine 19, 747-752 (2013); published online EpubJun (10.1038/nm.3161).
35. N. van Rooij, M. M. van Buuren, D. Philips, A. Velds, M. Toebes, B. Heemskerk, L. J. van Dijk, S. Behjati, H. Hilkmann, D. El Atmioui, M. Nieuwland, M. R. Stratton, R. M. Kerkhoven, C. Kesmir, J. B. Haanen, P. Kvistborg, T. N. Schumacher, Tumor exome analysis reveals neoantigen-specific T-cell reactivity in an ipilimumab-responsive melanoma. J Clin Oncol 31, e439-442 (2013); published online EpubNov 10 (10.1200/JCO.2012.47.7521).
36. E. Tran, S. Turcotte, A. Gros, P. F. Robbins, Y. C. Lu, M. E. Dudley, J. R. Wunderlich, R. P. Somerville, K. Hogan, C. S. Hinrichs, M. R. Parkhurst, J. C. Yang, S. A. Rosenberg, Cancer immunotherapy based on mutation-specific CD4+ T cells in a patient with epithelial cancer. Science 344, 641-645 (2014); published online EpubMay 9 (10.1126/science.1251102).
37. J. D. Wolchok, A. Hoos, S. O'Day, J. S. Weber, O. Hamid, C. Lebbe, M. Maio, M. Binder, O. Bohnsack, G. Nichol, R. Humphrey, F. S. Hodi, Guidelines for the evaluation of immune therapy activity in solid tumors: immune-related response criteria. Clinical Cancer Research 15, 7412-7420 (2009); published online EpubDec 1 (10.1158/1078-0432.CCR-09-1624).
38. C. Liu, X. Yang, B. Duffy, T. Mohanakumar, R. D. Mitra, M. C. Zody, J. D. Pfeifer, ATHLATES: accurate typing of human leukocyte antigen through exome sequencing. Nucleic Acids Research 41, e142 (2013); published online EpubAug (10.1093/nar/gkt481).
39. H. Li, R. Durbin, Fast and accurate short read alignment with Burrows-Wheeler transform. Bioinformatics 25, 1754-1760 (2009); published online EpubJul 15 (10.1093/bioinformatics/btp324).
40. M. A. DePristo, E. Banks, R. Poplin, K. V. Garimella, J. R. Maguire, C. Hartl, A. A. Philippakis, G. del Angel, M. A. Rivas, M. Hanna, A. McKenna, T. J. Fennell, A. M. Kernytsky, A. Y. Sivachenko, K. Cibulskis, S. B. Gabriel, D. Altshuler, M. J. Daly, A framework for variation discovery and genotyping using next-generation DNA sequencing data. Nature Genetics 43, 491-498 (2011); published online EpubMay (10.1038/ng.806).
41. G. De Baets, J. Van Durme, J. Reumers, S. Maurer-Stroh, P. Vanhee, J. Dopazo, J. Schymkowitz, F. Rousseau, SNPeffect 4.0: on-line prediction of molecular and structural effects of protein-coding variants. Nucleic Acids Res 40, D935-939 (2012); published online EpubJan (10.1093/nar/gkr996).
42. D. E. Larson, C. C. Harris, K. Chen, D. C. Koboldt, T. E. Abbott, D. J. Dooling, T. J. Ley, E. R. Mardis, R. K. Wilson, L. Ding, SomaticSniper: identification of somatic point mutations in whole genome sequencing data. Bioinformatics 28, 311-317 (2012); published online EpubFeb 1 (10.1093/bioinformatics/btr665).
43. D. C. Koboldt, Q. Zhang, D. E. Larson, D. Shen, M. D. McLellan, L. Lin, C. A. Miller, E. R. Mardis, L. Ding, R. K. Wilson, VarScan 2: somatic mutation and copy number alteration discovery in cancer by exome sequencing. Genome Res. 22, 568-576 (2012); published online EpubMar (10.1101/gr.129684.111).
44. C. T. Saunders, W. S. Wong, S. Swamy, J. Becq, L. J. Murray, R. K. Cheetham, Strelka: accurate somatic small-variant calling from sequenced tumor-normal sample pairs. Bioinformatics 28, 1811-1817 (2012); published online EpubJul 15 (10.1093/bioinformatics/bts271).
45. K. Cibulskis, M. S. Lawrence, S. L. Carter, A. Sivachenko, D. Jaffe, C. Sougnez, S. Gabriel, M. Meyerson, E. S. Lander, G. Getz, Sensitive detection of somatic point mutations in impure and heterogeneous cancer samples. Nat. Biotechnol. 31, 213-219 (2013); published online EpubMar (10.1038/nbt.2514).

46. S. T. Sherry, M. Ward, K. Sirotkin, dbSNP-database for single nucleotide polymorphisms and other classes of minor genetic variation. Genome Research 9, 677-679 (1999).

47. E. V. Server, NHLBI GO Exome Sequencing Project (ESP). http://evs.qs.washington.edu/EVS 48. M. Via, C. Gignoux, E. G. Burchard, The 1000 Genomes Project: new opportunities for research and social challenges. Genome Medicine 2, 3 (2010)10.1186/gm124).

49. J. T. Robinson, H. Thorvaldsdottir, W. Winckler, M. Guttman, E. S. Lander, G. Getz, J. P. Mesirov, Integrative genomics viewer. Nature Biotechnology 29, 24-26 (2011); published online EpubJan (10.1038/nbt.1754).

50. P. Kumar, S. Henikoff, P. C. Ng, Predicting the effects of coding non-synonymous variants on protein function using the SIFT algorithm. Nat. Protoc. 4, 1073-1081 (2009)10.1038/nprot.2009.86).

51. I. A. Adzhubei, S. Schmidt, L. Peshkin, V. E. Ramensky, A. Gerasimova, P. Bork, A. S. Kondrashov, S. R. Sunyaev, A method and server for predicting damaging missense mutations. Nature Methods 7, 248-249 (2010); published online EpubApr (10.1038/nmeth0410-248).

52. X. Liu, X. Jian, E. Boerwinkle, dbNSFP v2.0: a database of human non-synonymous SNVs and their functional predictions and annotations. Human Mutation 34, E2393-2402 (2013); published online EpubSep (10.1002/humu.22376).

53. A. S. Ho, K. Kannan, D. M. Roy, L. G. Morris, I. Ganly, N. Katabi, D. Ramaswami, L. A. Walsh, S. Eng, J. T. Huse, J. Zhang, I. Dolgalev, K. Huberman, A. Heguy, A. Viale, M. Drobnjak, M. A. Leversha, C. E. Rice, B. Singh, N. G. Iyer, C. R. Leemans, E. Bloemena, R. L. Ferris, R. R. Seethala, B. E. Gross, Y. Liang, R. Sinha, L. Peng, B. J. Raphael, S. Turcan, Y. Gong, N. Schultz, S. Kim, S. Chiosea, J. P. Shah, C. Sander, W. Lee, T. A. Chan, The mutational landscape of adenoid cystic carcinoma. Nature Genetics 45, 791-798 (2013); published online EpubJul (10.1038/ng.2643).

54. M. Imielinski, A. H. Berger, P. S. Hammerman, B. Hernandez, T. J. Pugh, E. Hodis, J. Cho, J. Suh, M. Capelletti, A. Sivachenko, C. Sougnez, D. Auclair, M. S. Lawrence, P. Stojanov, K. Cibulskis, K. Choi, L. de Waal, T. Sharifnia, A. Brooks, H. Greulich, S. Banerji, T. Zander, D. Seidel, F. Leenders, S. Ansen, C. Ludwig, W. Engel-Riedel, E. Stoelben, J. Wolf, C. Goparju, K. Thompson, W. Winckler, D. Kwiatkowski, B. E. Johnson, P. A. Janne, V. A. Miller, W. Pao, W. D. Travis, H. I. Pass, S. B. Gabriel, E. S. Lander, R. K. Thomas, L. A. Garraway, G. Getz, M. Meyerson, Mapping the hallmarks of lung adenocarcinoma with massively parallel sequencing. Cell 150, 1107-1120 (2012); published online EpubSep 14 (10.1016/j.cell.2012.08.029).

55. M. Nielsen, C. Lundegaard, P. Worning, C. S. Hvid, K. Lamberth, S. Buus, S. Brunak, O. Lund, Improved prediction of MHC class I and class II epitopes using a novel Gibbs sampling approach. Bioinformatics 20, 1388-1397 (2004); published online EpubJun 12 (10.1093/bioinformatics/bth100).

56. M. Nielsen, C. Lundegaard, O. Lund, C. Kesmir, The role of the proteasome in generating cytotoxic T-cell epitopes: insights obtained from improved predictions of proteasomal cleavage. Immunogenetics 57, 33-41 (2005); published online EpubApr (10.1007/s00251-005-0781-7).

57. C. Lundegaard, O. Lund, M. Nielsen, Accurate approximation method for prediction of class I MHC affinities for peptides of length 8, 10 and 11 using prediction tools trained on 9mers. Bioinformatics 24, 1397-1398 (2008); published online EpubJun 1 (10.1093/bioinformatics/btn128).

58. M. Toebes, M. Coccoris, A. Bins, B. Rodenko, R. Gomez, N. J. Nieuwkoop, W. van de Kasteele, G. F. Rimmelzwaan, J. B. Haanen, H. Ovaa, T. N. Schumacher, Design and use of conditional MHC class I ligands. Nature Medicine 12, 246-251 (2006); published online EpubFeb (10.1038/nm1360).

59. J. Yuan, S. Gnjatic, H. Li, S. Powel, H. F. Gallardo, E. Ritter, G. Y. Ku, A. A. Jungbluth, N. H. Segal, T. S. Rasalan, G. Manukian, Y. Xu, R. A. Roman, S. L. Terzulli, M. Heywood, E. Pogoriler, G. Ritter, L. J. Old, J. P. Allison, J. D. Wolchok, CTLA-4 blockade enhances polyfunctional NY-ESO-1 specific T cell responses in metastatic melanoma patients with clinical benefit. Proceedings of the National Academy of Sciences of the United States of America 105, 20410-20415 (2008); published online EpubDec 23 (10.1073/pnas.0810114105).

60. T. Powles et al., MPDL3280A (anti-PD-L1) treatment leads to clinical activity in metastatic bladder cancer. Nature 515, 558-562 (2014).

61. S. M. Ansell et al., PD-1 blockade with nivolumab in relapsed or refractory Hodgkin's lymphoma. N Engl J Med 372, 311-319 (2015).

62. A. Snyder et al., Genetic basis for clinical response to CTLA-4 blockade in melanoma. N Engl J Med 371, 2189-2199 (2014).

63. M. S. Rooney, S. A. Shukla, C. J. Wu, G. Getz, N. Hacohen, Molecular and genetic properties of tumors associated with local immune cytolytic activity. Cell 160, 48-61 (2015).

64. R. S. Herbst et al., Predictive correlates of response to the anti-PD-L1 antibody MPDL3280A in cancer patients. Nature 515, 563-567 (2014).

65. P. C. Tumeh et al., PD-1 blockade induces responses by inhibiting adaptive immune resistance. Nature 515, 568-571 (2014).

66. M. M. Gubin et al., Checkpoint blockade cancer immunotherapy targets tumour-specific mutant antigens. Nature 515, 577-581 (2014).

67. M. Yadav et al., Predicting immunogenic tumour mutations by combining mass spectrometry and exome sequencing. Nature 515, 572-576 (2014).

68. F. Duan et al., Genomic and bioinformatic profiling of mutational neoepitopes reveals new rules to predict anticancer immunogenicity. J Exp Med 211, 2231-2248 (2014).

69. C. Linnemann et al., High-throughput epitope discovery reveals frequent recognition of neo-antigens by CD4+ T cells in human melanoma. Nat Med 21, 81-85 (2015).

SEQUENCE LISTING

The patent contains a lengthy sequence listing. A copy of the sequence listing is available in electronic form from the USPTO web site (https://seqdata.uspto.gov/docdetail?docId=US12485162B2). An electronic copy of the sequence listing will also be available from the USPTO upon request and payment of the fee set forth in 37 CFR 1.19(b)(3).

We claim:

1. A method of identifying a subject having cancer as a candidate responsive to a treatment with an antibody agent or antigen binding fragment thereof that interferes with programmed death-1 (PD-1) comprising:

sequencing by whole exome sequencing the exomes in a tumor sample from the subject;

detecting the number of nonsynonymous mutations in the sequenced tumor sample from the subject, wherein the cancer is selected from the group consisting of lung carcinoma, melanoma, renal carcinoma, bladder carcinoma, small cell carcinoma, and head and neck cancer;

comparing the detected number of nonsynonymous mutations with a cut point, wherein the cut point is ≥178 nonsynonymous mutations; and identifying the subject as a candidate responsive to the treatment with the antibody agent when the number of nonsynonymous mutations detected in the tumor sample is at or above the cut point.

2. The method of claim 1, wherein the nonsynonymous mutations are present in a neoepitope recognized by a T cell.

3. The method of claim 2, wherein the neoepitope shares a consensus sequence with an infectious agent.

4. The method of claim 1, wherein the antibody agent or antigen binding fragment thereof is an antibody.

5. The method of claim 4, wherein the antibody target is selected from CTLA-4, PD-1, PD-L1, GITR, OX40, LAG-3, KIR, TIM-3, CD28, CD40, or CD137.

6. The method of claim 5, wherein the antibody targets PD-1.

7. The method of claim 6, wherein the antibody is pembrolizumab.

8. The method of claim 1, wherein the nonsynonymous mutations are selected from missense mutations, frameshift mutations, duplications, insertions, nonsense mutation, deletions or repeat expansions.

* * * * *